United States Patent
Akatsuka et al.

(10) Patent No.: US 8,975,252 B2
(45) Date of Patent: Mar. 10, 2015

(54) MORPHOLINE DERIVATIVE

(75) Inventors: Hidenori Akatsuka, Osaka-fu (JP); Hiroshi Sugama, Osaka-fu (JP); Nobumasa Awai, Osaka-fu (JP); Takayuki Kawaguchi, Osaka-fu (JP); Yoichi Takahashi, Osaka-fu (JP); Toru Iijima, Osaka-fu (JP); Jingkang Shen, Shanghai (CN); Guangxin Xia, Shanghai (CN); Jianshu Xie, Shanghai (CN)

(73) Assignees: Shanghai Pharmaceuticals Holding Co., Ltd., Shanghai (CN); Mitsubishi Tanabe Pharma Corporation, Osaka-Shi (JP)

( * ) Notice: Subject to any disclaimer, the term of this patent is extended or adjusted under 35 U.S.C. 154(b) by 0 days.

(21) Appl. No.: 12/664,637

(22) PCT Filed: Jun. 16, 2008

(86) PCT No.: PCT/JP2008/061004
§ 371 (c)(1),
(2), (4) Date: Dec. 14, 2009

(87) PCT Pub. No.: WO2008/153182
PCT Pub. Date: Dec. 18, 2008

(65) Prior Publication Data
US 2010/0240644 A1 Sep. 23, 2010

(30) Foreign Application Priority Data

Jun. 15, 2007 (JP) ................................ 2007-158892
Sep. 6, 2007 (JP) ................................ 2007-231532

(51) Int. Cl.
| | | |
|---|---|---|
| A61K 31/535 | (2006.01) | |
| C07D 265/30 | (2006.01) | |
| C07D 209/08 | (2006.01) | |
| C07D 209/14 | (2006.01) | |
| C07D 209/30 | (2006.01) | |
| C07D 209/34 | (2006.01) | |
| C07D 209/42 | (2006.01) | |
| C07D 231/56 | (2006.01) | |
| C07D 265/36 | (2006.01) | |
| C07D 403/04 | (2006.01) | |
| C07D 413/04 | (2006.01) | |
| C07D 413/12 | (2006.01) | |
| C07D 413/14 | (2006.01) | |
| C07D 417/14 | (2006.01) | |
| C07D 471/04 | (2006.01) | |

(52) U.S. Cl.
CPC ............ *C07D 265/30* (2013.01); *C07D 209/08* (2013.01); *C07D 209/14* (2013.01); *C07D 209/30* (2013.01); *C07D 209/34* (2013.01); *C07D 209/42* (2013.01); *C07D 231/56* (2013.01); *C07D 265/36* (2013.01); *C07D 403/04* (2013.01); *C07D 413/04* (2013.01); *C07D 413/12* (2013.01); *C07D 413/14* (2013.01); *C07D 417/14* (2013.01); *C07D 471/04* (2013.01)
USPC ...................................................... 514/230.5

(58) Field of Classification Search
None
See application file for complete search history.

(56) References Cited

U.S. PATENT DOCUMENTS

| 3,974,156 A | 8/1976 | Young | |
|---|---|---|---|
| 4,889,857 A * | 12/1989 | Araki et al. ................ | 514/235.2 |
| 5,358,949 A | 10/1994 | Tabusa et al. | |
| 2003/0069418 A1 | 4/2003 | Aquila et al. | |

(Continued)

FOREIGN PATENT DOCUMENTS

| JP | 49-124079 | 11/1974 |
|---|---|---|
| JP | 53-90275 A | 8/1978 |
| JP | 63-301821 A | 12/1988 |

(Continued)

OTHER PUBLICATIONS

STN Search Report Accession No. 1989:553819.*

(Continued)

*Primary Examiner* — Craig Ricci
(74) *Attorney, Agent, or Firm* — Birch, Stewart, Kolasch & Birch, LLP

(57) ABSTRACT

The present invention provides a morpholine derivative of the formula [I];

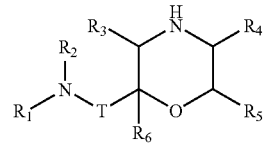

[I]

wherein $R^1$ is a substituted alkyl group, an optionally substituted aryl group, an optionally substituted heterocyclo group, a cycloalkyl group or an alkyl group; $R^2$ is a substituted alkyl group, an optionally substituted aryl group, an optionally substituted heterocyclo group, an optionally substituted alkylcarbonyl group, an optionally substituted arylcarbonyl group, an optionally substituted heterocyclo-substituted carbonyl group or a cycloalkylcarbonyl group; T is a methylene group or a carbonyl group; $R^3$, $R^4$, $R^5$ and $R^6$ are the same or different and a hydrogen atom, an optionally substituted carbamoyl group or an optionally substituted alkyl group;
or pharmaceutically acceptable salts thereof.
These compounds are useful as a renin inhibitor.

26 Claims, No Drawings

(56) References Cited

U.S. PATENT DOCUMENTS

2004/0214832 A1 10/2004 Cai et al.
2004/0220191 A1 11/2004 Schwink et al.

FOREIGN PATENT DOCUMENTS

| JP | 2-115182 A | | 4/1990 | | |
|---|---|---|---|---|---|
| JP | 3-188030 A | | 8/1991 | | |
| JP | 2003-500392 A | | 1/2003 | | |
| JP | 2006 0131559 | * | 5/2005 | .......... | C07D 211/32 |
| JP | 2005-336168 A | | 12/2005 | | |
| JP | 2006-517563 A | | 7/2006 | | |
| JP | 2006-522796 A | | 10/2006 | | |
| JP | 2007-55940 A | | 3/2007 | | |
| JP | 2007-145828 A | | 6/2007 | | |
| WO | WO 03/097618 | * | 11/2003 | .......... | C07D 265/30 |
| WO | WO-03/097618 A1 | | 11/2003 | | |
| WO | WO-2005/042516 A2 | | 5/2005 | | |
| WO | WO-2005/089731 A2 | | 9/2005 | | |
| WO | WO-2005/105778 A2 | | 11/2005 | | |
| WO | WO-2006/005741 A2 | | 1/2006 | | |
| WO | WO 2007/067511 | * | 6/2007 | .......... | A61K 31/5377 |
| WO | WO 2007/067511 A2 | | 6/2007 | | |

OTHER PUBLICATIONS

STN Search Report Accession No. 2003:931345.*
Machine Translation of JP 2006 0131559.*
STN Search Report (Accession No. 2006:489675).*
CAS RN 851748-03-3 (entered into STN Jun. 7, 2005).*
STN Search Report (Accession No. 2007:642442).*
Anderson (Chem and Biol 10:787-797, 2003).*
Thiel (Nature Biotechnol 2:513-519, 2004).*
Corminboeuf et al (Bioorg Med Chem 20:6286-6290, 2010).*
Kato, S et al., "Novel Benzamides as Selective and Potent Gastric Prokinetic Agents. 1. Synthesis and Structure-Activity Relationships of N-[(2-Morpholinyl)alkyl]benzamides", J. Med. Chem. 1990, vol. 33, pp. 1406-1413.
Bulatov et al., "Synthesis of 2-substituted morpholines from dihydroxyalkylsulfamates," Russian Chemical Bulletin, vol. 48, No. 11, pp. 2100-2102, Nov. 1999, XP-002668382.
Supplementary European Search Report for Application No. 08777242.2 dated Feb. 16, 2012.
Yoshiji et al., "Renin-Angiotensin System Inhibitors as Therapeutic Alternatives in the Treatment of Chronic Liver Diseases," Current Medicinal Chemistry, vol. 14, No. 26, pp. 2749-2754, 2007, XP-002668383.

* cited by examiner

MORPHOLINE DERIVATIVE

TECHNICAL FIELD

The present invention relates to morpholine derivatives which are useful as a medicine, especially as a renin inhibitor, pharmaceutically acceptable salts and intermediates thereof.

BACKGROUND ART

Renin inhibitors are expected as a medicine for the prevention and/or treatment of diseases such as hypertension, heart failure, diabetical nephropathy and the like, and 3,4-substituted piperidine derivatives are disclosed for example (Patent Literature 1). But a morpholine derivative is not described in the literature.

Patent Literature 1: WO 06/069788

DISCLOSURE OF INVENTION

Problem To be Solved

The present invention provides novel morpholine derivatives having an excellent activity to inhibit renin.

Means to Solve the Problem

In order to solve the problem, the inventors have extensively studied to find novel morpholine derivatives having an excellent activity to inhibit renin and finally completed the present invention.

The present invention is as follows:

1. A morpholine derivative of the general formula [I]:

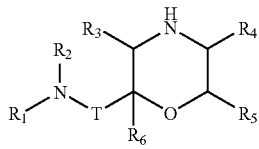

[I]

wherein $R^1$ is A) an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclo group, D) a cycloalkyl group or E) an alkyl group;

$R^2$ is A) an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclo group, D) an optionally substituted alkylcarbonyl group, E) an optionally substituted arylcarbonyl group, F) a carbonyl group substituted with an optionally substituted heterocyclo group or G) a cycloalkylcarbonyl group T is a methylene group or a carbonyl group; and $R^3$, $R^4$, $R^5$ and $R^6$ are same or different and a hydrogen atom, an optionally substituted carbamoyl group or an optionally substituted alkyl group;

or a pharmaceutically acceptable salt thereof; and

2. A morpholine derivative of the general formula (II):

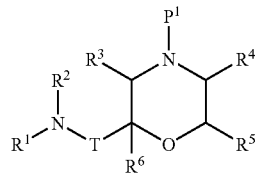

[II]

wherein $R^1$ is A) an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclo group, D) a cycloalkyl group or E) an alkyl group;

$R^2$ is A) an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclo group, D) an optionally substituted alkylcarbonyl group, E) an optionally substituted arylcarbonyl group, F) a carbonyl group substituted with an optionally substituted heterocyclo group or G) a cycloalkylcarbonyl group, T is a methylene group or a carbonyl group;

$R^3$, $R^4$, $R^5$ and $R^6$ are same or different and a hydrogen atom, an optionally substituted carbamoyl group or an optionally substituted alkyl group; and $P^1$ is a protecting group; or a pharmaceutically acceptable salt thereof The compound [I] of the present invention is explained in detail below.

The term "alkyl group" or "alkoxy group" in the present invention is exemplified by a straight or branched group having 1 to 10 carbon atoms, and groups having 1 to 6 carbon atoms are preferable, and groups having 1 to 4 carbon atoms are especially preferable. The term "lower alkyl group" or "lower alkoxy group" is exemplified by a straight or branched group having 1 to 6 carbon atoms, and groups having 1 to 4 carbon atoms are preferable.

The term "lower alkanoyl" is exemplified by a straight or branched group having 2 to 7 carbon atoms, and groups having 2 to 5 carbon atoms are preferable.

The term "cycloalkyl group" is exemplified by a cycloalkyl group having 3 to 8 carbon atoms, groups having 3 to 6 carbon atoms are preferable and groups having 3 to 4 carbon atoms are especially preferable.

The term "halogen atom" means a fluorine atom, a chlorine atom, a bromine atom and an iodine atom, and a fluorine atom, a chlorine atom and a bromine atom are especially preferable.

The term "an aryl group" is exemplified by a phenyl group, a naphthyl group and a tetrahydronaphtyl group.

The term "heterocyclo group" is exemplified by a pyridyl group, a pyrimidyl group, a furyl group, a thienyl group, a quinolyl group, tetrahydroquinolyl group, an isoquinolyl group, a tetrahydroisoquinolyl group, an indolyl group, an indolinyl group, an indazolyl group, a benzofuranyl group, a benzothienyl group, a dihydrobenzofuranyl group, a dihydrocromenyl group, a pyrrolopyridyl group, a benzoxazinyl group, a pyrazolyl group and the like.

An example of substituents of the optionally substituted alkyl group in $R^3$ and $R^6$ includes a hydroxyl group, an optionally substituted alkoxy group, a carboxy group, an optionally substituted carbamoyl group and the like.

An example of substituents of the optionally substituted aryl group, the optionally substituted heterocyclo group, the optionally substituted tetrahydronaphthyl group, the optionally substituted indolyl group, the optionally substituted benzofuranyl group, the optionally substituted benzothienyl group, the optionally substituted quinolyl group, the optionally substituted dihydrocromenyl group, the optionally substituted dihydrobenzofuranyl group, the optionally substituted indazolyl group, the optionally substituted pyrrolopyridinyl group, the optionally substituted benzoxazinyl group, the optionally substituted xanthenyl group, the optionally substituted indolinyl group and the optionally substituted imidazopyridinyl group includes an alkoxy group, an alkoxy group substituted with an alkoxy group, an alkoxy group substituted with an alkylcarbonylamino group, an alkoxy group substituted with an arylcarbonylamino group, an alkoxy group substituted with a heterocyclo-substituted carbonylamino group, an alkoxy group substituted with a cycloalkylcarbonylamino group, an alkoxy group substituted with an alkoxycarbonylamino group, an alkoxy group substituted with an aryl group, a hydroxyl group, an alkyl group, an alkyl group substituted with an alkoxy group, an oxo group, a halogen atom, an alkoxy group substituted with a halogen atom, an aryloxy group, an aryl group, an aryl group substituted with an alkoxy group, a heterocyclic group, a cyano group, a lower alkanoyl group and the like.

An example of substituents of the optionally substituted alkoxy group includes a hydroxyl group, an alkoxy group, a halogen atom, an alkoxy group substituted with a halogen atom, an amino group substituted with an alkylcarbonyl group, an amino group substituted with an arylcarbonyl group, a carbonylamino group substituted with a heterocyclo group, an amino group substituted with a cycloalkylcarbonyl, an amino group substituted with an alkoxycarbonyl group, an aryl group, an aryloxy group and the like.

An example of substituents of the optionally substituted carbamoyl group includes an alkyl group, an alkyl group substituted with a hydroxyl group, an alkyl group substituted with an alkoxy group, an alkyl group substituted with a phenyl group, a cycloalkyl group, a pyrrolidinyl group optionally substituted with a hydroxyalkyl group or an alkoxy-substituted alkyl group and the like.

Among the compounds [I] of the present invention, examples of preferred compound include compounds as follows;

(a1) $R^1$ is A) an alkyl group substituted with a group selected from 1) an optionally substituted alkoxy group, 2) a hydroxyl group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group and 13) an optionally substituted pyrrolopyridinyl group, B) an optionally substituted aryl group, C) an optionally substituted heterocyclo group, D) a cycloalkyl group or E) an alkyl group;

$R^2$ is A) an alkyl group substituted with a group selected from 1) an optionally substituted alkoxy group, 2) a hydroxyl group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group and 13) an optionally substituted pyrrolopyridinyl group, B) an optionally substituted aryl group, C) an optionally substituted heterocyclo group, D) an optionally substituted alkylcarbonyl group, E) an optionally substituted arylcarbonyl group, F) an optionally substituted heterocyclo-substituted carbonyl group or G) a cycloalkylcarbonyl group, T is a methylene group or a carbonyl group, $R^5$ is a hydrogen atom, an optionally substituted carbamoyl group or an optionally substituted alkyl group, $R^3$, $R^4$ and $R^6$ are a hydrogen atom or a pharmaceutically acceptable salt thereof, (a2) the compound of (a1) described above wherein $R^5$ is a hydrogen atom, or a pharmaceutically acceptable salt thereof, (a3) the compound of (a1) or (a2) described above, wherein $R^1$ is a cycloalkyl group or an alkyl group and T is a carbonyl group, or a pharmaceutically acceptable salt thereof, (a4) the compound of any of (a1) to (a3) described above, wherein $R^2$ is an alkyl group substituted with a group selected from 1) an optionally substituted alkoxy group, 2) a hydroxyl group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group and 13) an optionally substituted pyrrolopyridinyl group, or a pharmaceutically acceptable salt thereof, (a5) the compound of any of (a1) to (a4) described above, wherein $R^1$ is a cyclopropyl group, or a pharmaceutically acceptable salt thereof, (a6) the compound of any of (a1) to (a5) described above, wherein $R^2$ is an alkyl group substituted with (1) an aryl group substituted with one or more group(s) selected from an alkoxy group, an alkoxy group substituted with an alkoxy group, an alkoxy group substituted with an alkylcarbonylamino group, an alkoxy group substituted with an alkoxycarbonylamino group, an alkyl group substituted with an alkoxycarbonylamino group, a carbonyl group substituted with an alkoxyalkylamino group, an alkyl group substituted with an alkylcarbonylamino group, and an alkoxy group substituted with an aryl group or (2) a benzooxazinyl group substituted with one or more group(s) selected from an alkyl group substituted with an alkoxy group, an alkyl group and an oxo group.

Examples of the more preferable compound in the present invention include the following compounds;

(b1) a compound [I] wherein $R^2$ is an alkyl group substituted with a group selected from
1) an optionally substituted aryl group,
2) an optionally substituted tetrahydronaphthyl group,
3) an optionally substituted indolyl group,
4) an optionally substituted benzofuranyl group,
5) an optionally substituted benzothienyl group,
6) an optionally substituted quinolyl group,
7) an optionally substituted dihydrocromenyl group,
8) an optionally substituted dihydrobenzofuranyl group
9) an optionally substituted indazolyl group, and
10) an optionally substituted pyrrolopyridinyl group,
$R^1$ is a cycloalkyl group or an alkyl group, T is a carbonyl group, $R^5$ is a hydrogen atom, an optionally substituted carbamoyl group or an optionally substituted alkyl group and $R^3$, $R^4$ and $R^6$ are hydrogen atoms, or a pharmaceutically acceptable salt thereof, (b2) the compound of (b1) described above wherein $R^2$ is selected from
1) a lower alkyl group substituted with an optionally substituted phenyl group,
2) a lower alkyl group substituted with an optionally substituted naphthyl group,
3) a lower alkyl group substituted with an optionally substituted tetrahydronaphthyl group,
4) a lower alkyl group substituted with an optionally substituted indolyl group,
5) a lower alkyl group substituted with an optionally substituted benzofuranyl group,
6) a lower alkyl group substituted with an optionally substituted benzothienyl group,
7) a lower alkyl group substituted with an optionally substituted quinolyl group,
8) a lower alkyl group substituted with an optionally substituted dihydrocromenyl group,
9) a lower alkyl group substituted with an optionally substituted dihydrobenzofuranyl group,
10) a lower alkyl group substituted with an optionally substituted indazolyl group,
11) a lower alkyl group substituted with an optionally substituted pyrrolopyridinyl group, or a pharmaceutically acceptable salt thereof, (b3) the compound of (b1) described above wherein $R^2$ is selected from
1) an optionally substituted phenylmethyl group,
2) an optionally substituted naphthylmethyl group,
3) an optionally substituted tetrahydronaphthylmethyl group,
4) an optionally substituted indolylmethyl group,
5) an optionally substituted benzofuranylmethyl group,
6) an optionally substituted benzothienylmethyl group,
7) an optionally substituted quinolylmethyl group,
8) an optionally substituted dihydrocromenylmethyl group,
9) an optionally substituted dihydrobenzofuranylmethyl group,
10) an optionally substituted indazolylmethyl group,
11) an optionally substituted pyrrolopyridinylmethyl group, or a pharmaceutically acceptable salt thereof, (b4) the compound of (b1) described above wherein $R^2$ is any of 1) to 11) described below;
1) a phenylmethyl group optionally substituted with the same or different, two to four groups selected from a phenyl lower alkoxy group, a halogen atom, a lower alkyl group, a lower alkyl group substituted with a lower alkoxy group, a lower alkoxy group substituted with a lower alkoxy group, an aryl group substituted with a lower alkoxy group, a heterocyclic group, a cyano group, a lower alkoxy group, an alkyl group substituted with an alkoxycarbonylamino group, an alkoxy group substituted with an alkoxycarbonylamino group and a carbonyl group substituted with an alkoxyalkylamino group,
2) a naphthylmethyl group optionally substituted with the same or different, one to six group(s) selected from a trihalogeno lower alkoxy group, a lower alkanoylamino lower alkoxy group, a halogen atom, a lower alkyl group substituted with a lower alkoxy group, a lower alkyl group, a lower alkoxy group substituted with a lower alkoxy group, an aryl group, an aryl group substituted with a lower alkoxy group, a heterocyclic group, a cyano group, a carbonyl group substituted with an alkoxyalkylamino group and a lower alkoxy group,
3) a tetrahydronaphthylmethyl group optionally substituted with the same or different, one to six group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, a carbonyl group substituted with an alkoxyalkylamino group and a lower alkoxy group,
4) a indolylmethyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkyl group substituted with an alkoxycarbonylamino group and a lower alkoxy group,
5) a benzofuranylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group, 6) a benzothienylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group, 7) a quinolylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxyalkylamino group, a carbonyl group substituted with alkoxycarbonylamino group and a lower alkoxy group, 8) a dihydrocromenylmethyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group, 9) a dihydrobenzofuranylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group, 10) a indazolylmethyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group and a lower alkoxy group, 11) a pyrrolopyridinylmethyl group optionally substituted with the same or different, one to three group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkyl group substituted with alkoxycarbonylamino group and a lower alkoxy group, (b5) the compound of (b1) described above wherein $R^2$ is any of 1) to 11) described below;

1) a phenylmethyl group optionally substituted with the same or different, two or three groups selected from a phenyl lower alkoxy group, a halogen atom, a lower alkyl group, a lower alkoxy group substituted with a lower alkoxy group, an alkoxy group substituted with alkoxycarbonylamino group, a carbonyl group substituted with alkoxyalkylamino group and a lower alkoxy group, 2) a naphthylmethyl group optionally substituted with the same or different, one to three group(s) selected from a trihalogeno lower alkoxy group, a lower alkanoylamino lower alkoxy group, a halogen atom, an aryl group, an aryl group substituted with a lower alkoxy group, a heterocyclic group, a lower alkyl group, an alkoxy group substituted with alkoxycarbonylamino group, a carbonyl group substituted with alkoxyalkylamino group and a lower alkoxy group substituted with a lower alkoxy group, 3) a tetrahydronaphthylmethyl group optionally substituted with one or two group(s) selected from a halogen atom, an alkoxy group substituted with alkoxycarbonylamino group, a carbonyl group substituted with alkoxyalkylamino group and a lower alkoxy group substituted with a lower alkoxy group, 4) a indolylmethyl group optionally substituted with the same or different, one to three group(s) selected from a halogen atom, a cyano group, a lower alkoxy group, a lower alkoxy group substituted with an aryl group, a lower alkyl group, an alkyl group substituted with alkoxycarbonylamino group and a lower alkyl group substituted with a lower alkoxy group, 5) a benzofuranylmethyl group optionally substituted with one or three group(s) selected from a halogen atom and a lower alkoxy group substituted with a lower alkoxy group, a lower alkoxy group, a lower alkyl group, a lower alkoxy group substituted with an aryl group, an alkyl group substituted with alkoxycarbonylamino group and a carbonyl group substituted with an alkoxyalkylamino group, 6) a benzothienylmethyl group optionally substituted with a lower alkoxy group substituted with a lower alkoxy group, 7) a quinolylmethyl group optionally substituted with a halogen atom, a lower alkoxy group, a lower alkyl group and a lower alkoxy group substituted with a lower alkoxy group, 8) a dihydrocromenylmethyl group optionally substituted with a lower alkoxy group substituted with a lower alkoxy group, 9) a dihydrobenzofuranylmethyl group optionally substituted with one or two group(s) selected from a halogen atom, a lower alkoxy group, a lower alkyl group and a lower alkoxy group substituted with a lower alkoxy group, 10) a indazolylmethyl group optionally substituted with one or three group(s) selected from a halogen atom, a lower alkyl group substituted with a lower alkoxy group, a lower alkoxy group, a lower alkyl group, a lower alkoxy group substituted with an aryl group and an alkyl group substituted with an alkoxycarbonylamino group, 11) a pyrrolopyridinylmethyl group optionally substituted with one or three group(s) selected from a halogen atom, a lower alkyl group substituted with a lower alkoxy group, a lower alkoxy group, a lower alkyl group, a lower alkoxy group substituted with an aryl group and an alkyl group substituted with an alkoxycarbonylamino group, (b6) the compound of (b1) described above wherein $R^2$ is any of 1) to 11) described below or a pharmaceutically acceptable salt thereof;

1) a phenylmethyl group optionally substituted with two or three groups selected from a phenyl lower alkoxy group, a fluorine atom, a trihalogeno lower alkyl group, a trihalogeno lower alkoxy group, dihalogeno lower alkoxy group, a bromine atom, a chlorine atom, a lower alkyl group, a lower alkoxy group substituted with a lower alkoxy group and a lower alkoxy group, 2) a naphthylmethyl group optionally substituted with the same or different, one to three group(s) selected from a trihalogeno lower alkoxy group, dihalogeno lower alkoxy group, a lower alkanoylamino lower alkoxy group, a fluorine atom, a bromine atom, a chlorine atom, a phenyl group, a phenyl group substituted with a lower alkoxy group, a pyridyl group, a furyl group, a thienyl group, a lower alkyl group and a lower alkoxy group substituted with a lower alkoxy group, 3) a tetrahydronaphthylmethyl group optionally substituted with one or two group(s) selected from a fluorine atom, a chlorine atom, a bromine atom and a lower alkoxy group substituted with a lower alkoxy group,
4) a indolylmethyl group optionally substituted with the same or different, one to three group(s) selected from a fluorine atom, a chlorine atom, a bromine atom, a cyano group, a lower alkoxy group, a lower alkoxy group substituted with a phenyl group, a lower alkyl group, a lower alkyl group substituted with a lower alkoxy group, an alkyl group substituted with an alkoxycarbonylamino group and an alkyl group substituted with an alkylcarbonylamino group,
5) a benzofuranylmethyl group optionally substituted with one to three group(s) selected from a fluorine atom, a chlorine atom, a bromine atom and a lower alkoxy group substituted with a lower alkoxy group,
6) a benzothienylmethyl group optionally substituted with a fluorine atom, a chlorine atom, a bromine atom and a lower alkoxy group substituted with a lower alkoxy group,
7) a quinolylmethyl group optionally substituted with the same or different, one to three group(s) selected from a fluorine atom, a chlorine atom, a lower alkyl group, a lower alkoxy group, an alkoxy group substituted with a lower alkoxycarbonylamino group and a lower alkoxy group substituted with a lower alkoxy group,
8) a dihydrocromenylmethyl group optionally substituted with a lower alkoxy group substituted with a lower alkoxy group,
9) a dihydrobenzofuranylmethyl group optionally substituted with one to three group(s) selected from a chlorine atom a bromine atom and a lower alkoxy group substituted with a lower alkoxy group,
10) a indazolylmethyl group optionally substituted with one to three group(s) selected from a fluorine atom, a chlorine atom, a bromine atom, a lower alkyl group, a trihalogeno lower alkyl group, an alkyl group substituted with an alkoxycarbonylamino group and a lower alkyl group substituted with a lower alkoxy group,
11) a pyrrolopyridinylmethyl group optionally substituted with one to three group(s) selected from a fluorine atom, a chlorine atom, a bromine atom, a lower alkyl group, a trihalogeno lower alkyl group, an alkyl group substituted with an alkoxycarbonylamino group and a lower alkyl group substituted with a lower alkoxy group,
(b7) the compound of (b1) described above wherein $R^2$ is any of 1) to 11) described below or a pharmaceutically acceptable salt thereof;
1) a phenylmethyl group optionally substituted with two or three groups selected from a phenyl group-substituted methoxy group, a phenyl group-substituted ethoxy group, a fluorine atom, a bromine atom, a chlorine atom, a methyl group, a methoxy group-substituted propoxy group and methoxy group,
2) a naphthylmethyl group optionally substituted with the same or different, one to three groups selected from a trifluorobutoxy group, an acetylaminoethoxy group, a fluorine atom, a chlorine atom, a bromine atom, a phenyl group, a methoxy group-substituted phenyl group, a pyridyl group, a furyl group, a thienyl group, a methyl group and a methoxy group-substituted propoxy group,
3) a tetrahydronaphthylmethyl group optionally substituted with one to three groups selected from a chlorine atom, a bromine atom and a methoxy group-substituted propoxy group,
4) an indolylmethyl group optionally substituted with one to three groups selected from a fluorine atom, a chlorine atom, a bromine atom, a cyano group, a methoxy group, a phenyl group-substituted methoxy group, a methyl group and a methoxy group-substituted propyl group,
5) a benzofuranylmethyl group optionally substituted with one to three groups selected from a fluorine atom, a chlorine atom, a bromine atom, a methyl group and a methoxy group-substituted propoxy group,
6) a benzothienylmethyl group optionally substituted with a methoxy group-substituted propoxy group,
7) a quinolylmethyl group optionally substituted with a methoxy group-substituted propoxy group,
8) a dihydrocromenylmethyl group optionally substituted with a methoxy group-substituted propoxy group,
9) a dihydrobenzofuranylmethyl group optionally substituted with one or two groups selected from a chlorine atom, a bromine atom and a methoxy group-substituted propoxy group,
10) a indazolylmethyl group optionally substituted with one or two groups selected from a fluorine atom, a chlorine atom and a methoxy group-substituted propyl group, and
11) a pyrrolopyridinylmethyl group optionally substituted with one or two groups selected from a chlorine atom, a bromine atom and a methoxy group-substituted propyl group,
(b8) the compound of any of (b1) to (b7) described above wherein the indolyl group in $R^2$ is any of the next formulae:

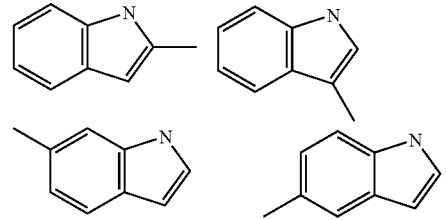

the benzofuranyl group in $R^2$ is any of the next formulae:

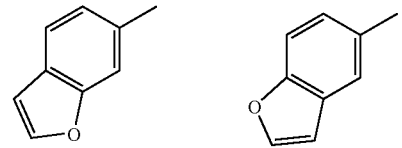

the benzothienyl group in $R^2$ is any of the next formulae:

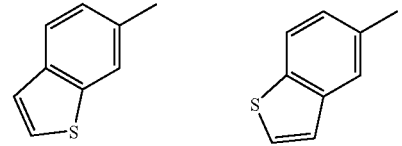

the quinolyl group in $R^2$ is the next formula:

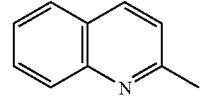

the naphthyl group in $R^2$ is any of the next formulae:

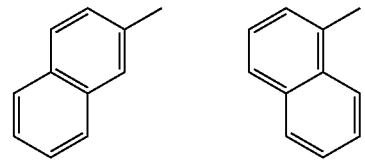

the tetrahydronaphthyl group in R² is any of the next formulae:

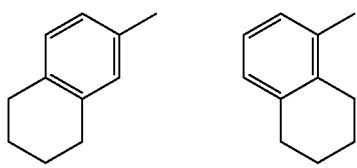

the dihydrocromenyl group in R² is any of the next formulae:

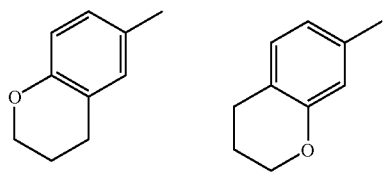

the dihydrobenzofuranyl group in R² is any of the next formulae:

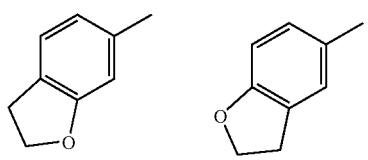

the indazolyl group in R² is any of the next formulae:

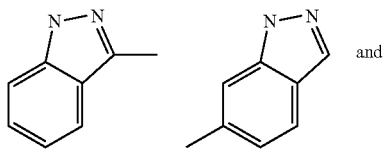

and the pyrrolopyridinyl group in R² is any of the next formulae:

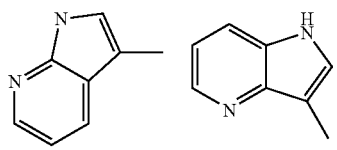

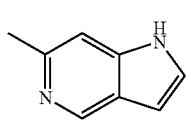

or a pharmaceutically acceptable salt thereof, (b9) the compound of any of (b1) described above wherein R² is any of the next formulae:

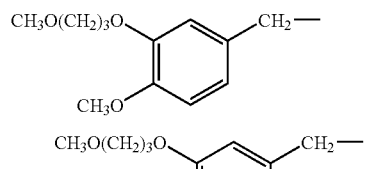

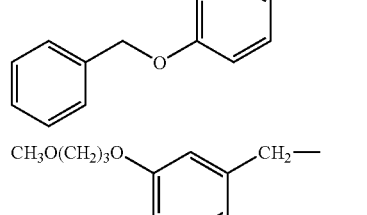

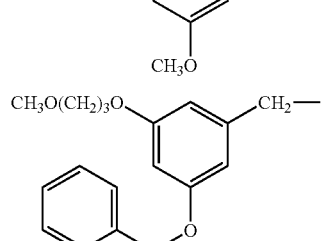

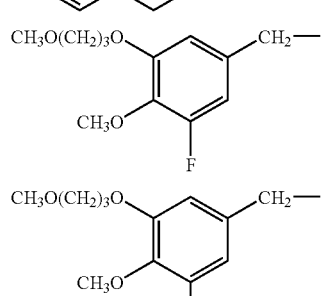

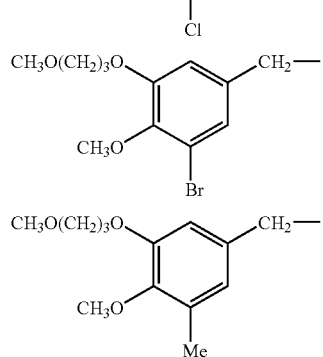

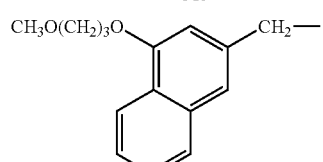

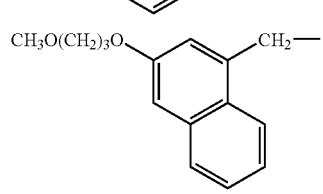

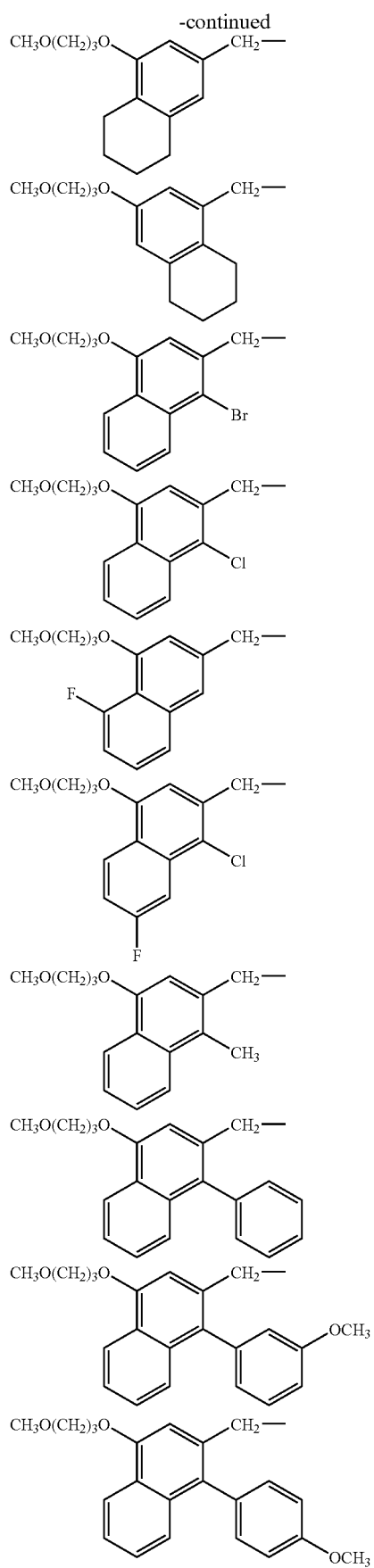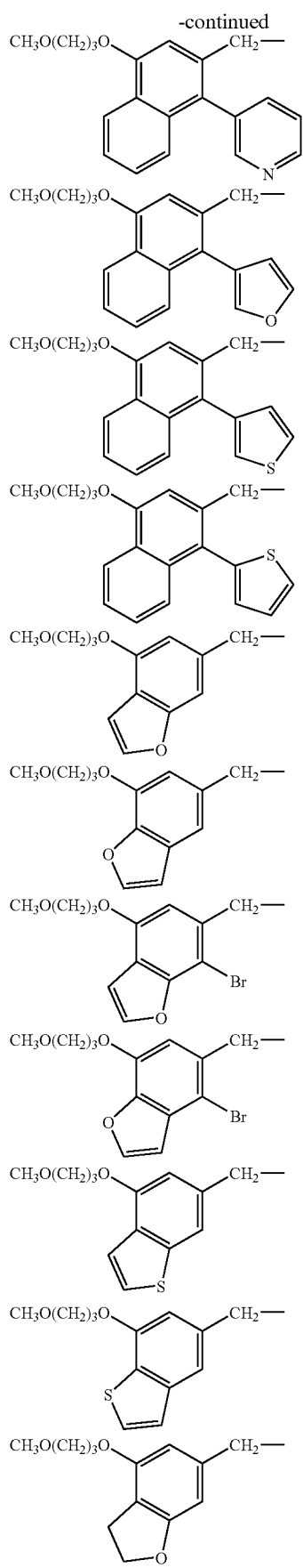

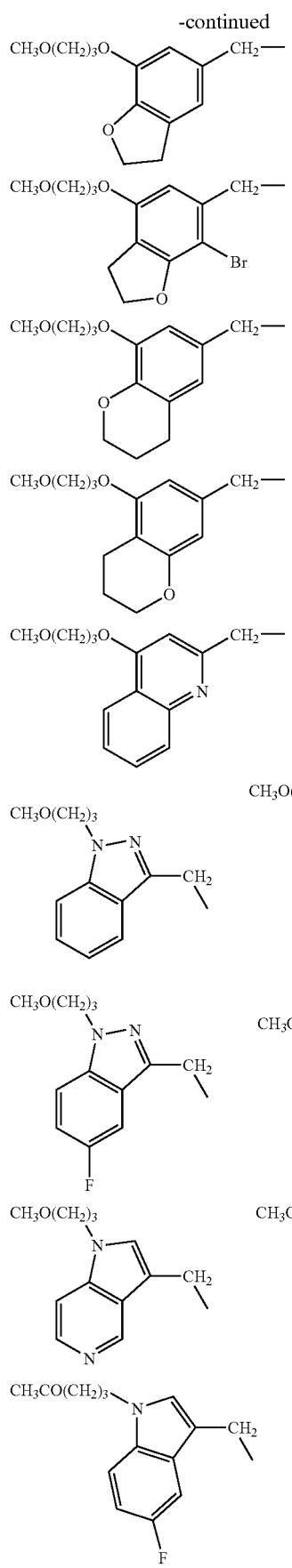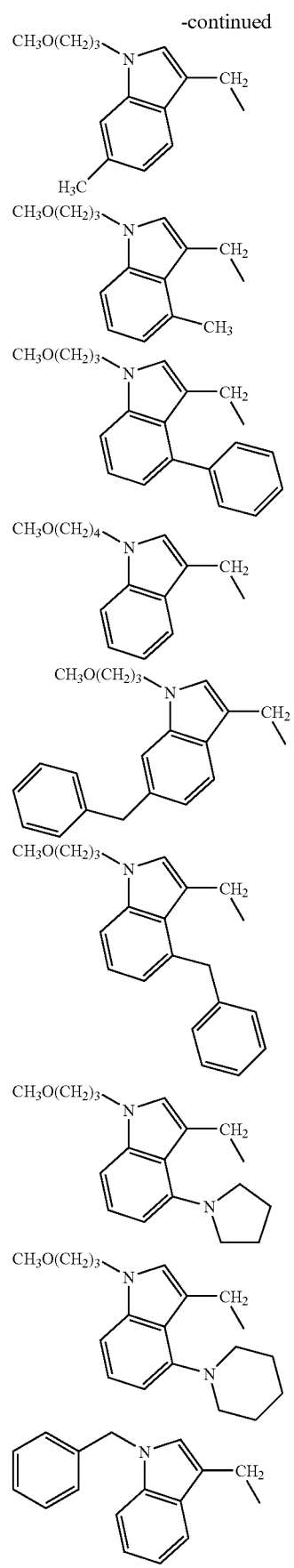

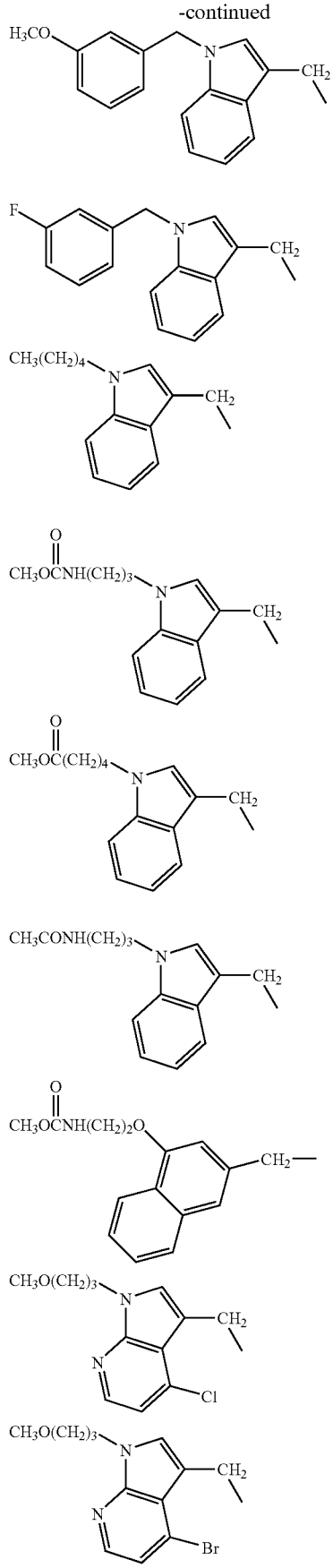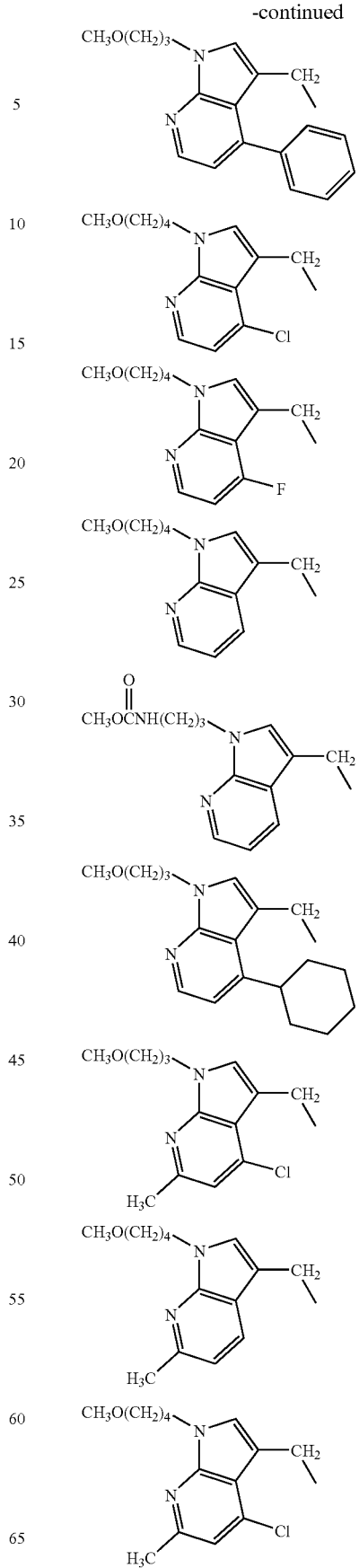

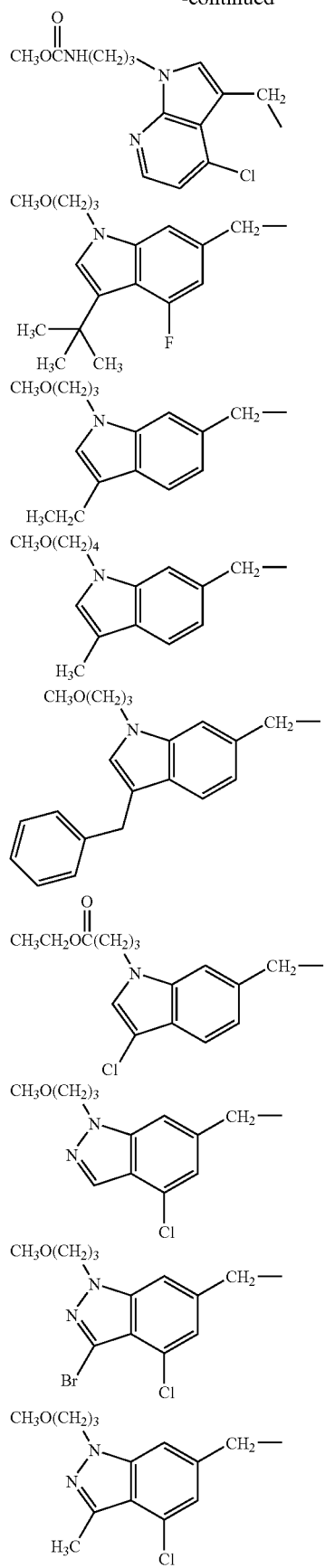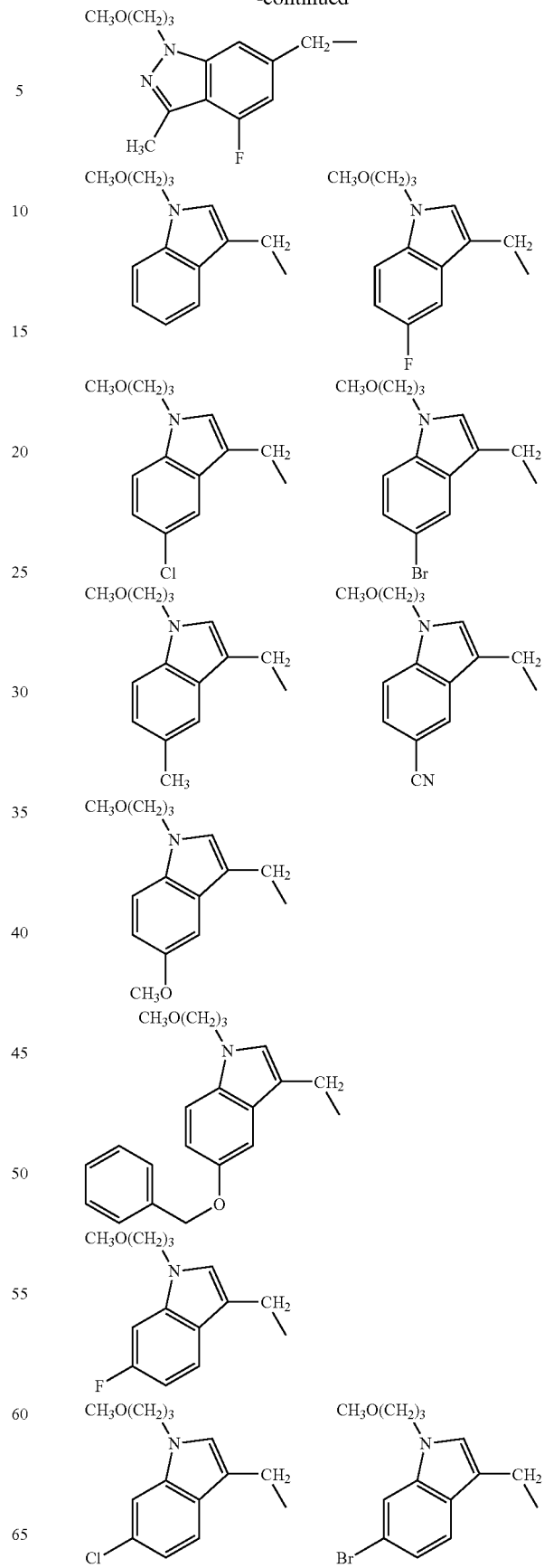

-continued

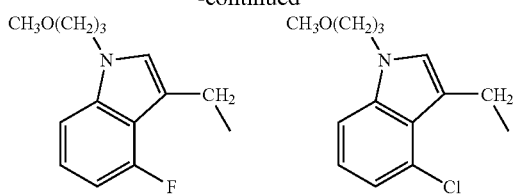
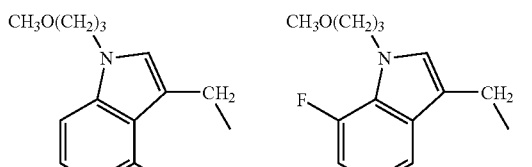
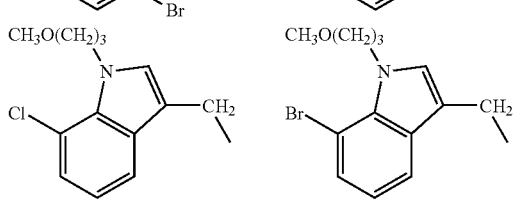
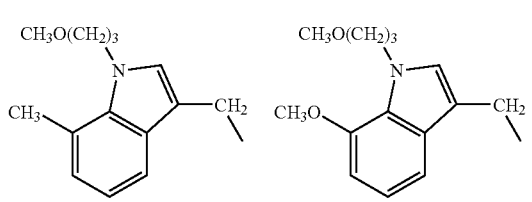
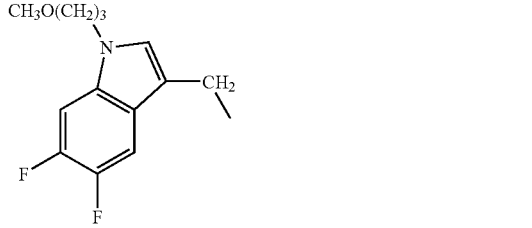
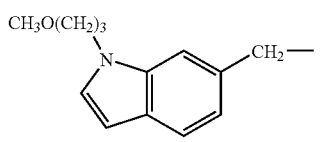
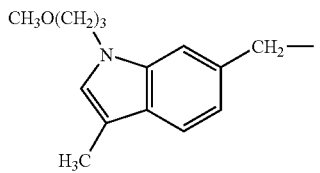
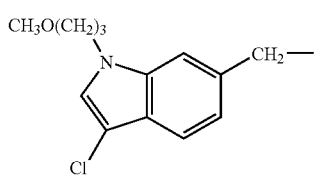
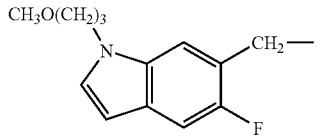

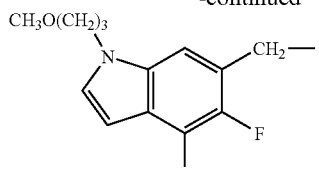
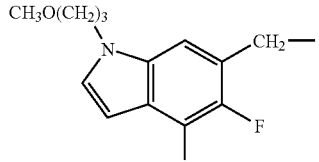
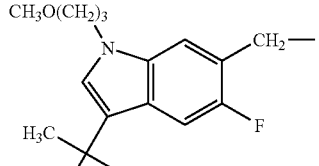
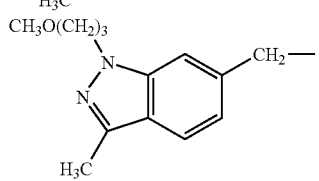

(b10) the compound of any of (b1) to (b9) described above wherein $R^1$ is a $C_{3-8}$ cycloalkyl group, or a pharmaceutically acceptable salt thereof, (b11) the compound of any of (b1) to (b9) described above wherein $R^1$ is a $C_{3-6}$ cycloalkyl group, or a pharmaceutically acceptable salt thereof, (b12) the compound of any of (b1) to (b9) described above wherein $R^1$ is a $C_{3-4}$ cycloalkyl group, or a pharmaceutically acceptable salt thereof, (b13) the compound of any of (b1) to (b9) described above wherein $R^1$ is a cyclopropyl group, or a pharmaceutically acceptable salt thereof, (b14) the compound of any of (b1) to (b13) described above wherein $R^3$ to $R^6$ are any of
1) a hydrogen atom,
2) a carbamoyl group optionally substituted with one or two lower alkyl groups, and
3) a lower alkyl group optionally substituted with a group selected from an amino group optionally substituted with one or two lower alkyl groups, a lower alkanoyl group, a hydroxyl group and a lower alkoxy group, or a pharmaceutically acceptable salt thereof, (b15) the compound of any of (b1) to (b13) described above wherein $R^3$ to $R^6$ are any of
1) a hydrogen atom,
2) a carbamoyl group optionally substituted with one or two methyl groups, and
3) a lower alkyl group optionally substituted with a group selected from an amino group optionally substituted with one or two methyl groups, an acetylamino group, a hydroxyl group and a methoxy group, or a pharmaceutically acceptable salt thereof;

(b16) the compound of any of (b1) to (b13) described above wherein $R^3$ to $R^6$ are any of
1) a hydrogen atom,
2) a carbamoyl group optionally substituted with one or two methyl groups, and 3) a methyl group optionally substituted with a group selected from an amino group optionally substituted with one or two methyl group(s), an acetylamino group, a hydroxyl group and a methoxy group, or a pharmaceutically acceptable salt thereof, (b17) the compound of any of (b1) to (b13) described above wherein $R^3$ to $R^6$ are hydrogen atoms, or a pharmaceutically acceptable salt thereof, (b18) the compound of any of (b1) to (b13) described above wherein $R^5$ is any of
1) a hydrogen atom,
2) a carbamoyl group optionally substituted with one or two lower alkyl groups, and
3) a lower alkyl group optionally substituted with a group selected from an amino group optionally substituted with one or two lower alkyl groups, a lower alkanoylamino group, a hydroxyl group and a lower alkoxy group, or a pharmaceutically acceptable salt thereof, (b19) the compound of any of (b1) to (b13) described above wherein $R^5$ is any of
1) a hydrogen atom,
2) a carbamoyl group optionally substituted with one or two methyl groups, and
3) a lower alkyl group optionally substituted with a group selected from an amino group optionally substituted with one or two methyl groups, an acetylamino group, a hydroxyl group and a methoxy group, or a pharmaceutically acceptable salt thereof, (b20) the compound of any of (b1) to (b13) described above wherein $R^5$ is any of
1) a hydrogen atom,
2) a carbamoyl group optionally substituted with one or two methyl groups, and
3) a methyl group optionally substituted with a group selected from an amino group optionally substituted with one or two methyl groups, an acetylamino group, a hydroxyl group and a methoxy group, or a pharmaceutically acceptable salt thereof, (b21) the compound of any of (b1) to (b13) described above wherein $R^5$ is a hydrogen atom, or a pharmaceutically acceptable salt thereof, Examples of the especially preferred compound in the present invention include a compound wherein
$R^1$ is a cyclopropyl group,
$R^2$ is a lower alkyl group substituted with a 4-methoxy-3-(3-methoxypropoxy)phenyl group, a lower alkyl group substituted with a 4-(3-methoxypropoxy)-2-naphthyl group, a lower alkyl group substituted with a 1-(3-methoxypropyl)indol-3-yl group or a lower alkyl group substituted with a 3-methyl-1-(3-methoxypropyl)-1H-indazol-6-yl group,
T is a carbonyl group and $R^3$ to $R^6$ are hydrogen atoms; and concrete examples of the present invention includes the following compounds;
(2R)—N-cyclopropyl-N-[4-methoxy-3-methoxypropoxy)benzyl]morpholin-2-carboxamide,
(2R)—N-cyclopropyl-N-{[4-(3-methoxypropoxy)-2-naphthyl]methyl}morpholin-2-carboxamide,
(2R)—N-{[1-(3-methoxypropyl)indol-3-yl]methyl}-N-cyclopropylmorpholin-2-carboxamide and
(2R)—N-{[3-methyl-1-(3-methoxypropyl)-1H-indazol-6-yl]methyl}-N-cyclopropylmorpholin-2-carboxamide.

The compound [I] of the present invention can be clinically used either in the free form or in the form of a pharmaceutically acceptable salt thereof. Examples of the pharmaceutically acceptable salt of the compound [I] include a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a carboxyl group(s) and the like in its molecule, examples of the pharmaceutically acceptable salt include, salts with a base such as alkaline metal (e.g., sodium salt, potassium salt) or alkaline earth metal (e.g., calcium salt).

The compound [I] of the present invention also includes a mixture of a stereoisomer such as a geometrical isomer, a tautomer and an enantiomer, and an isolated stereoisomer thereof. When a carbon atom of the morpholine ring having the substituent, T, is an asymmetric carbon in the compound of the present invention, a compound of (R)-configuration is preferable from the view of renin-inhibition.

The present invention also includes an intramolecular salt, a hydrate, a pharmaceutically acceptable solvate and a crystal polymorph of the compound [I]. Additionally it should be understood that the compound [I] of the present invention is not limited to the compounds described in the examples below but includes whole the compounds of the generic formula [I] and pharmaceutically acceptable salts thereof.

The compound of the present invention or the pharmaceutically acceptable salts thereof shows a renin-inhibitory activity. For example, an assay of (2R)—N-cyclopropyl-N-[4-methoxy-3-(3-methoxypropoxy)benzyl]morpholine-2-carboxamide hydrochloride for renin-inhibition showed a value of $IC_{50}$ below 1 μM.

Accordingly the compound of the present invention or the pharmaceutically acceptable salts thereof may be useful as an agent for prevention and/or treatment of hypertension, cardiac failure, diabetical nephropathy and the like, and can be advantageous as a medicine due to its low toxicity.

The compound [I] of the present invention or a pharmaceutically acceptable salt thereof can be either orally or parenterally administered, and can be formulated into a conventional pharmaceutical preparation such as tablets, granules, capsules, powders, injections or inhalants etc.

The dose of the compound [I] of the present invention or a pharmaceutically acceptable salt thereof may vary in accordance with the administration routes, and the ages, body weights and conditions of the patients, but usually it is in the range of about 0.001 to 500 mg/kg, preferably in the range of about 0.1 to 100 mg/kg.

The compound [I] of the present invention can be prepared by the following methods but should not be construed to be limited thereto.

Preparation of the Compound [I]

The compound [I] of the present invention or the pharmaceutically acceptable salt thereof can be prepared by deprotecting $P^1$ of the compound of the generic formula [II];

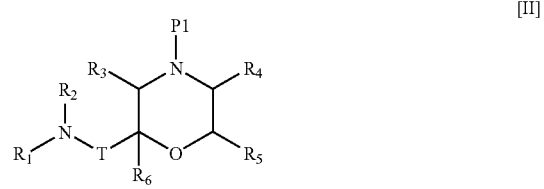

[II]

wherein $P^1$ is a protecting group and the other symbols are the same as defined above, and converting the product to a pharmaceutically acceptable salt thereof, if necessary.

Preparation of the Compound [II]

Among the compound [II], the compound in which T is a carbonyl group can be prepared by reacting the carboxylic acid compound of the generic formula [III]:

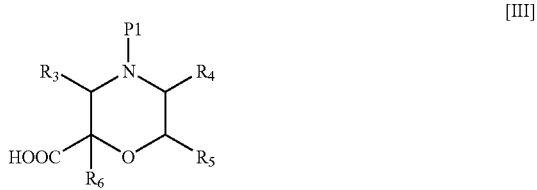
[III]

wherein the symbols are the same as defined above, or an activated derivative thereof with the amine compound of the generic formula [IV];

$R^1R^2NH$ [IV]

wherein the symbols are the same as defined above.

Among the compound [II], the compound in which T is a methylene group can be prepared by reacting the aldehyde compound of the generic formula [V];

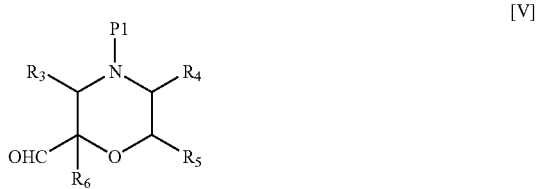
[V]

wherein the symbols are the same as defined above, with the amine compound of the generic formula [VI];

$R^1NH_2$ [VI]

wherein the symbols are the same as defined above, reducing the resulting imino compound to afford the amine compound, and further reacting the amine compound with a compound of the generic formula [VII];

$R^2$—X [VII]

wherein X is a leaving group and the other symbols are the same as defined above.

Reaction of Preparing the Compound [I]

Examples of the protecting group shown as $P^1$ include a usual amino-protecting group such as a tert-butoxycarbonyl group, a benzyloxycarbonyl group, 4-methoxy benzyloxycarbonyl group, a benzyl group, a 4-methoxybenzyl group, an acetyl group, a benzoyl group, a tosyl group and the like.

The protecting group $P^1$ of the compound [II] can be deprotected by a conventional method and usually carried out by treating it with acid or base or catalytic reduction or a deprotecting agent in a suitable solvent or without solvent. As an acid, an inorganic acid such as hydrochloric acid, sulfuric acid and the like, and an organic acid such as acetic acid, trifluoroacetic acid, methanesulfonic acid, p-toluenesulfonic acid and the like can be preferably used As a base, an inorganic base (e.g., an alkali metal hydride such as sodium hydride, an alkali metal carbonate such as sodium carbonates and potassium carbonates, an alkali metal amide such as sodium amides and lithium amide, an alkali metal alkoxide such as sodium methoxide, an alkali metal such as sodium, and an alkali metal hydroxide such as sodium hydroxide, potassium hydroxide etc.) and the like can be preferably used.

As a deprotecting agent, zinc bromide and trimethylsilane trifluoromethanesulfonate etc. can be used. The catalytic reduction can be carried out by preferably using palladium carbon, palladium hydroxide carbon, platinum oxide and the like as a catalyst under hydrogen atmosphere. Examples of the solvent include any solvent which does not disturb the reaction, such as methanol, ethanol, isopropyl alcohol, 1,4-dioxane, diethyl ether, tetrahydrofuran, methylene chloride, chloroform, dichloroethane, ethyl acetate, toluene, and a mixture thereof. The acid or the base described above can be used as the solvent. The reaction can be suitably carried out at from −78° C. to a boiling temperature of the solvent.

Reaction of Preparing the Compound [II]

The compound [II] can be prepared by a condensation reaction of the carboxylic acid compound [III] and the amine compound [IV] in a suitable solvent or without a solvent.

The condensation reaction can be carried out by a conventional condensation reaction in the presence of a condensing agent, or reacting an activated derivative of the compound [III] (e.g., an acid halide, a mixed acid anhydride, an activated ester and the like) with the compound [IV], after the compound [III] is converted to the reactive derivative thereof. Examples of the condensing agent include N,N-dicyclohexylcarbodiimide (DCC), 1-ethyl-3-(3-dimethylaminopropyl) carbodiimide (EDC) or hydrochloride thereof, carbonyldiimidazole (CDI), diphenylphosphoryl azide (DPPA), diethyl cyanophosphonate (DEPC) and the like, and among them DCC, EDC or its hydrochloride is preferable.

When the reactive derivative of the compound [III] is used, the reactive derivative can be reacted with the compound [IV] in a suitable solvent or without a solvent in presence of an acid scavenger if necessary, after the compound [III] is converted to an acid halide using a halogenating agent (e.g., thionyl chloride, thionyl bromide, oxalyl chloride and the like), a mixed acid anhydride using chlorocarbonate ester (e.g., methyl chlorocarbonate, ethyl chlorocarbonate, isobutyl chloroformate and the like) or acid chloride (2,4,6-trichlorobenzoyl chloride and the like), or an activated ester of N-hydroxylamine compound (1-hydroxysuccinimide, 1-hydroxybenzotriazole and the like) or of phenol compound (p-nitrophenol and the like) or a lower alcohol ester(methyl ester, ethyl ester and the like). In a method converting to an acid halide, an addition of catalyst such as dimethylformamide and the like can accelerate the reaction. As an acid scavenger, an inorganic base or an organic base is used when necessary, and examples of an inorganic base include sodium carbonate, potassium carbonate, cesium carbonate, sodium bicarbonate, sodium hydroxide, potassium hydroxide, lithium hydroxide and the like and examples of an organic base include triethylamine, tributylamine, diisopropylethylamine, 1,8-diazabicyclo[5,4,0]undeca-7-ene, N,N-diethylaniline, pyridine, lutidine, colidine and the like. In the present reaction, triethylamine, diisopropylethylamine, pyridine and the like are preferably used as an acid scavenger. When the acid scavenger is used in this reaction, acid scavenger is used as the solvent.

A condensing reaction can be conducted or accelerated by adding 4-aminopyridine and the like in the condensing reaction shown above.

When using a solvent in the condensing reaction above, any inert solvent which does not disturb the reaction can be used and examples of the solvents include chloroform, dichloromethane, dichloroethane, toluene, diethyl ether, tetrahydrofuran, dioxane, 1,2-dimethoxyethane, ethyl acetate, amide-related solvent (N,N-dimethylformamide, N,N-dimethylacetamide, 1,3-dimethyl-2-imidazolidinon etc.), pyridine, 2,6-lutidine, water and the like, and a mixture thereof can be also used. Among them, chloroform, tetrahydrofuran, dioxane, N,N-dimethylformamide, N,N-dimethylacetamide, and a mixture of chloroform and N,N-dimethylformamide etc. are preferred.

Usually the condensation reaction above can be carried out at a temperature from −20° C. to a reflux temperature of the solvent and if necessary, it can be carried out at a lower temperature which is suitably selected.

On the other hand, the reaction of the aldehyde compound [V] with the amino compound [VI] can be carried out by using a conventional reductive amination reaction. For example, it can be conducted if an imine compound, which is obtained by reacting the aldehyde compound [V] with the amino compound [VI] in a suitable solvent, is treated by a suitable reducing agent, or a reaction of the aldehyde compound [V] with the amino compound [VI] is carried out in presence of a suitable reducing agent.

Any reducing agent which does not disturb an amide bond and the like may be used in the reductive amination reaction and examples of the agent include metallic reducing reagents such as sodium borohydride, sodium triacetoxyborohydride, sodium cyanoborohydride and the like.

Also the reduction can be carried out by a catalytic reduction using a metallic catalyst (palladium carbon, platinum carbon, platinum oxide, Raney-Nickel and the like) in place of the reducing agent above.

Any inert solvent which does not disturb the reaction can be used in the reductive amination reaction, and examples of the solvent include chloroform, dichloromethane, 1,2-dichloroethane, tetrahydrofuran, dioxane, 1,2-dimethoxyethane, N,N-dimethylformamide, N,N-dimethylacetamide, 1,3-dimethyl-2-imidazolidinon, toluene, methanol, ethanol, propanol, water and the like, and a mixture of two or more of these solvents may be used. Among them, chloroform, dichloromethane, 1,2-dichloroethane, tetrahydrofuran, 1,2-dimethoxyethane, methanol, ethanol, propanol and the like are preferably used.

The reductive alkylation reaction is usually carried out at a temperature from −10° C. to a reflux temperature of the solvent.

In addition, an organic acid such as acetic acid and the like or a mineral acid such as hydrochloric acid and the like may be added to the reductive alkylation reaction in order to carry out the reaction smoothly.

The subsequent reaction with the compound [VII] can be carried out in a suitable solvent under presence of an acid scavenger. A halogen atom can be preferably used as a leaving group shown as X. Examples of the acid scavenger include potassium phosphate tribasic, sodium carbonate, potassium carbonate, cesium carbonate, sodium bicarbonate, potassium bicarbonate, sodium hydroxide, potassium hydroxide, N,N-diisopropylethylamine, triethylamine, 4-dimethylaminopyridine, triethylenediamine, and 4-methylmorpholine. Any solvent which does not disturb the reaction can be used, and examples of the solvents which are used preferably include N,N-dimethylformamide, 1,4-dioxane, 1,2-dimethoxyethane, methanol, ethanol, tetrahydrofuran, dichloromethane, chloroform, 1,2-dichloroethane, toluene, dimethylsufoxide, pyridine, water and a mixture thereof and the like. The reaction can be preferably carried out at a temperature from room temperature to a boiling point of the solvent.

BEST MODE FOR CARRYING OUT THE INVENTION

Examples of the compounds [I] of the present invention prepared by the methods illustrated above are shown below, but the present invention should not be construed to be limited thereto.

EXAMPLE

Example 1

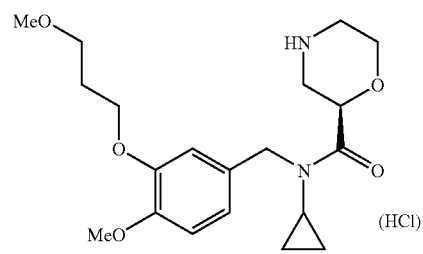

4N HCl/dioxane (1 ml) was added under ice cooling to (2R)-2-({cyclopropyl[4-methoxy-3-(3-methoxypropoxy)benzyl]amino}carbonyl)morpholin-4-carboxylic acid tert-butyl ester (a compound of Reference Example 8, 368 mg) dissolved in chloroform (4 ml), and the mixture was stirred at room temperature for 2 hours. Water was added to the mixture under ice cooling and the organic layer was separated. The aqueous layer was extracted with chloroform after being adjusted to pH 9 by addition of a saturated aqueous solution of sodium bicarbonate. The organic layer was washed with a saturated brine, dried over magnesium sulfate and concentrated in vacuo. The resulting residue was purified by NH-silica gel column chromatography (eluting solvent; n-hexane: ethyl acetate=1:1 to ethyl acetate only) to give (2R)—N-cyclopropyl-N-[4-methoxy-3-(3-methoxypropoxy)benzyl]morpholine-2-carboxamide (230 mg) as a colorless oil.

Next, the compound was dissolved in chloroform (1 ml), 4N HCl/dioxane (185 µl) was added to the solution and the mixture was concentrated in vacuo. The resulting residue was dissolved in water and lyophilized to give (2R)—N-cyclopropyl-N-[4-methoxy-3-(3-methoxypropoxy)benzyl]morpholin-2-carboxamide hydrochloride (198 mg) as a colorless viscous oil.

APCI-MS m/z: 379[M+H]$^+$.

Example 2

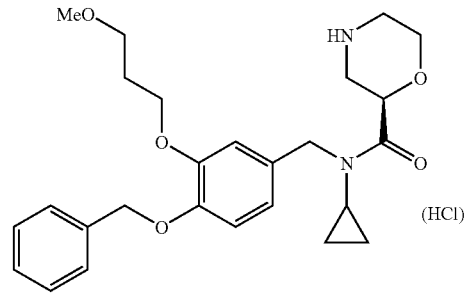

4N HCl/dioxane (1 ml) was added under ice cooling to (2R)-2-{[[4-benzyloxy-3-(3-methoxypropoxy)benzyl](cyclopropyl)amino]carbonyl}morpholine-4-carboxylic acid tert-butyl ester (a compound of Reference Example 9, 217 mg) dissolved in chloroform (1 ml), and the mixture is stirred at room temperature for 2 hours. The mixture was concentrated in vacuo. the residue was added water (1 ml) and diethyl ether (2 ml), and then the mixture was slightly stirred. The layer of diethyl ether was removed by decantation and the resulted residue is lyophilized to give (2R)—N-[4-(benzyloxy)-3-(3-methoxypropoxy)benzyl]-N-cyclopropylmorpholin-2-carboxamide hydrochloride (166 mg) as a colorless powder. APCI-MS m/z: 455[M+H]$^+$.

Example 3

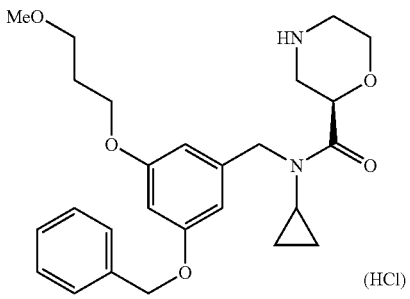

(2R)-2-{[[3-(benzyloxy)-5-(3-methoxypropoxy)benzyl](cyclopropyl)amino]-carbonyl}morpholine-4-carboxylic acid tert-butyl ester (a compound of Reference Example 10, 150 mg) was treated in the same manner as Example 2 to give (2R)—N-[3-(benzyloxy)-5-(3-methoxypropoxy)benzyl]-N-cyclopropylmorpholin-2-carboxamide hydrochloride (107 mg) as a colorless viscous oil.
APCI-MS m/z: 455[M+H]$^+$.

Example 4

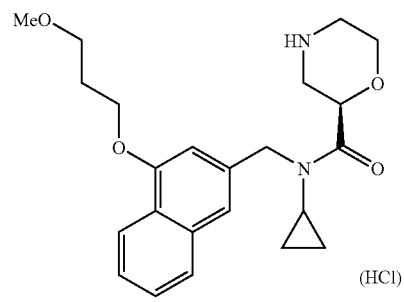

(2R)-2-[(cyclopropyl{[4-(3-methoxypropoxy)-2-naphthyl]methyl}amino]-carbonyl]morpholin-4-carboxylic acid tert-butyl ester (a compound of Reference Example 11, 130 mg) was treated in the same manner as Example 2 to give (2R)—N-cyclopropyl-N-{[4-(3-methoxypropoxy)-2-naphthyl]methyl}morpholin-2-carboxamide hydrochloride (105 mg) as a colorless powder.
APCI-MS m/z: 399[M+H]$^+$.

Example 5-37

Corresponding starting compounds were treated in the same manner as Example 1 or Example 2 to give the following compounds of Table 1.

TABLE 1

| No. of Examples | Structure | Properties |
|---|---|---|
| 5 | ![structure] | Property: colorless foam<br>APCI-MS m/z: 379[M + H]$^+$ |
| 6 | ![structure] | Property: colorless viscous oil<br>APCI-MS m/z: 455[M + H]$^+$ |

TABLE 1-continued
| No. of Examples | Structure | Properties |
|---|---|---|
| 7 | 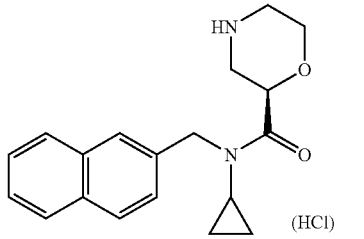 (HCl) | Property: colorless powder<br>APCI-MS m/z: 311[M + H]$^+$ |
| 8 | 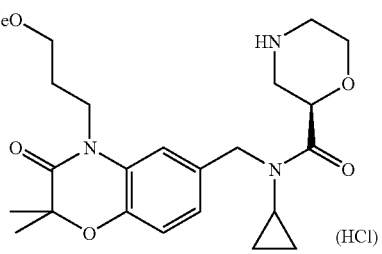 (HCl) | Property: colorless powder<br>APCI-MS m/z: 432[M + H]$^+$ |
| 9 | 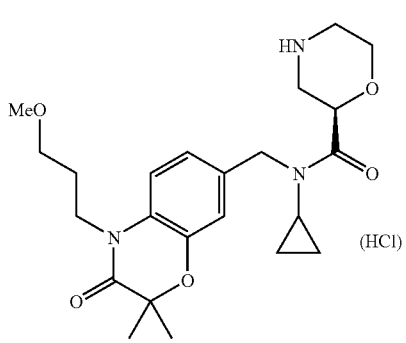 (HCl) | Property: colorless powder<br>APCI-MS m/z: 432[M + H]$^+$ |
| 10 | 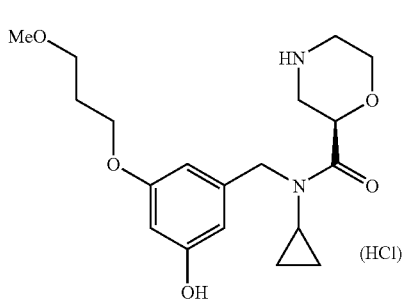 (HCl) | Property: colorless viscous oil<br>APCI-MS m/z: 365[M + H]$^+$ |
| 11 | 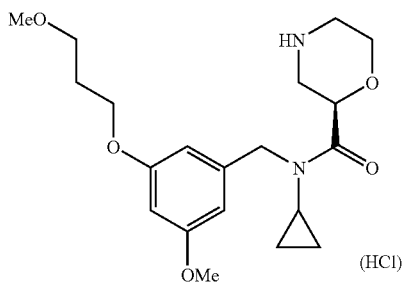 (HCl) | Property: colorless viscous oil<br>APCI-MS m/z: 379[M + H]$^+$ |

TABLE 1-continued

| No. of Examples | Structure | Properties |
|---|---|---|
| 12 | 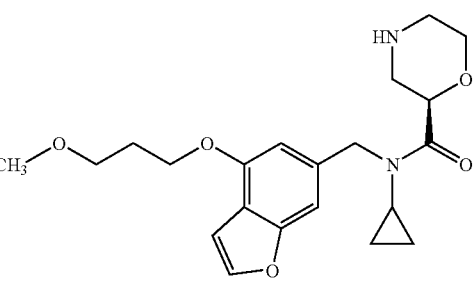 | Hydrochloride<br>Property: colorless powder<br>APCI-MS m/z: 389[M + H]+ |
| 13 | 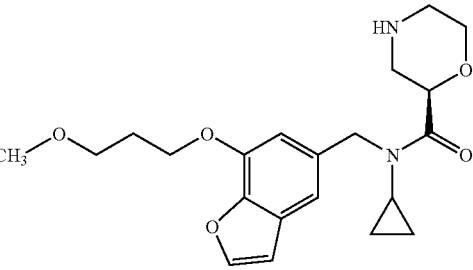 | Hydrochloride<br>Property: colorless powder<br>APCI-MS m/z: 389[M + H]+ |
| 14 | 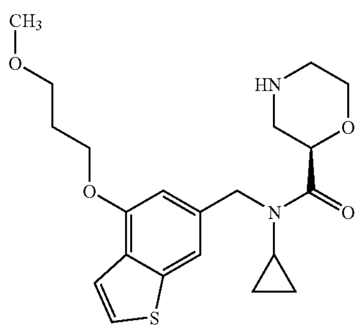 [SMILES: COCCCOc1cc(CN(C(=O)[C@H]2CNCCO2)C2CC2)cc2sccc12] | Hydrochloride<br>Property: colorless powder<br>APCI-MS m/z: 405[M + H]+ |
| 15 | 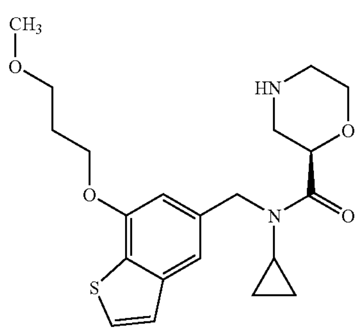 [SMILES: COCCCOc1cc(CN(C(=O)[C@H]2CNCCO2)C2CC2)cc2ccsc12] | Hydrochloride<br>Property: colorless powder<br>APCI-MS m/z: 405[M + H]+ |
| 16 | 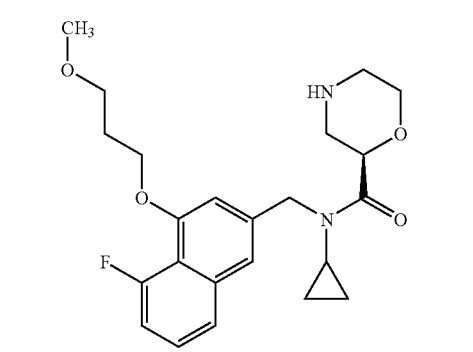 [SMILES: COCCCOc1cc(CN(C(=O)[C@H]2CNCCO2)C2CC2)cc2cccc(F)c12] | Hydrochloride<br>Property: powder<br>APCI-MS m/z: 417[M + H]+ |

TABLE 1-continued

| No. of Examples | Structure | Properties |
|---|---|---|
| 17 | 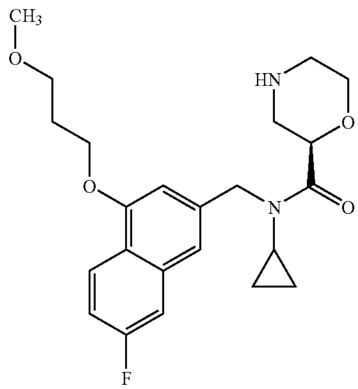 [SMILES: COCCCOc1cc(CN(C(=O)[C@H]2CNCCO2)C2CC2)cc2cc(F)ccc12] | Hydrochloride<br>Property: powder<br>APCI-MS m/z: 417[M + H]$^+$ |
| 18 | 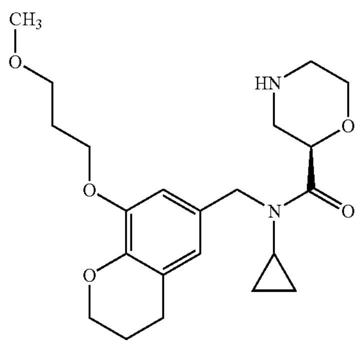 [SMILES: COCCCOc1cc(CN(C(=O)[C@H]2CNCCO2)C2CC2)cc2c1OCCC2] | Hydrochloride<br>Property: colorless powder<br>APCI-MS m/z: 405[M + H]$^+$ |
| 19 | 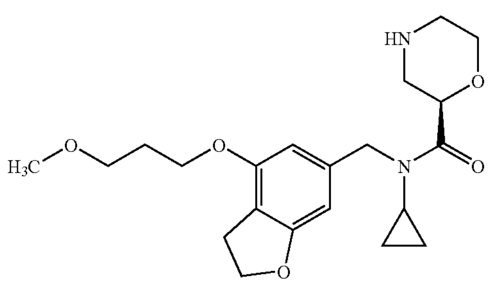 [SMILES: COCCCOc1cc(CN(C(=O)[C@H]2CNCCO2)C2CC2)cc2c1CCO2] | Hydrochloride<br>Property: colorless powder<br>APCI-MS m/z: 391[M + H]$^+$ |
| 20 | 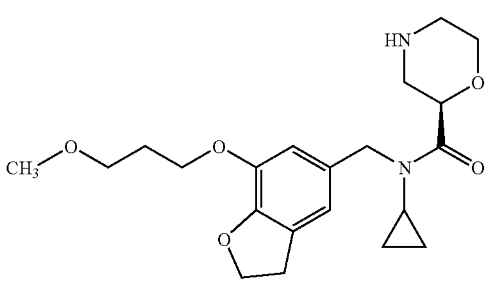 [SMILES: COCCCOc1cc(CN(C(=O)[C@H]2CNCCO2)C2CC2)cc2c1OCC2] | Hydrochloride<br>Property: colorless powder<br>APCI-MS m/z: 391[M + H]$^+$ |

TABLE 1-continued

| No. of Examples | Structure | Properties |
|---|---|---|
| 21 | 3-methoxypropoxy-tetrahydronaphthalene with N-cyclopropyl morpholine-2-carboxamide | Hydrochloride<br>Property:<br>APCI-MS m/z: [M + H]+ |
| 22 | 3-methoxypropoxy-tetrahydronaphthalene with N-cyclopropyl morpholine-2-carboxamide (isomer) | Hydrochloride<br>Property: powder<br>APCI-MS m/z: 403[M + H]+ |
| 23 | 3-methoxypropoxy-naphthalene with N-cyclopropyl morpholine-2-carboxamide | Hydrochloride<br>Property: powder<br>APCI-MS m/z: 399[M + H]+ |
| 24 | 3-methoxypropoxy-methoxy-chloro-phenyl with N-cyclopropyl morpholine-2-carboxamide | Hydrochloride<br>Property: colorless viscous oil<br>APCI-MS<br>m/z: 413/415[M + H]+ |

TABLE 1-continued
| No. of Examples | Structure | Properties |
|---|---|---|
| 25 | 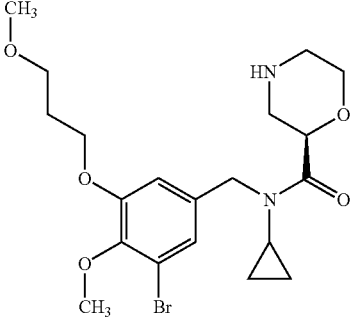 | Hydrochloride<br>Property: colorless viscous oil<br>APCI-MS<br>m/z :457/459[M + H]⁺ |
| 26 | 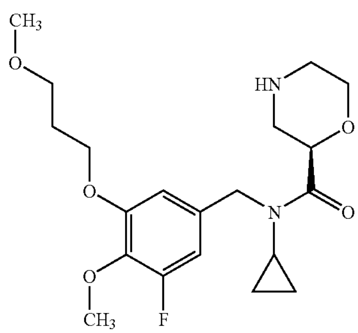 | Hydrochloride<br>Property: colorless viscous oil<br>APCI-MS m/z: 397[M + H]⁺ |
| 27 | 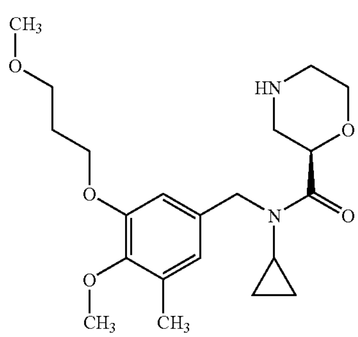 [SMILES: COCCCOc1cc(CN(C(=O)[C@H]2CNCCO2)C2CC2)cc(C)c1OC] | Hydrochloride<br>Property: colorless viscous oil<br>APCI-MS m/z: 393[M + H]⁺ |
| 28 | 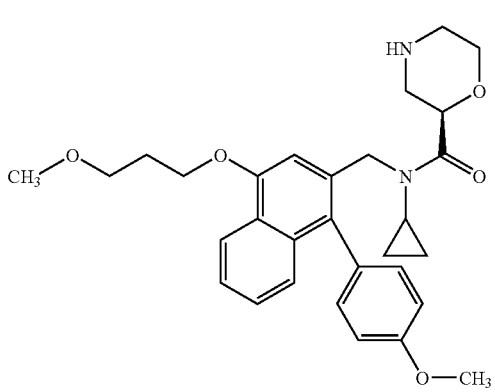 [SMILES: COCCCOc1cc(CN(C(=O)[C@H]2CNCCO2)C2CC2)c(-c2ccc(OC)cc2)c2ccccc12] | Hydrochloride<br>Property: colorless powder<br>APCI-MS m/z: 505[M + H]⁺ |

TABLE 1-continued

| No. of Examples | Structure | Properties |
|---|---|---|
| 29 | 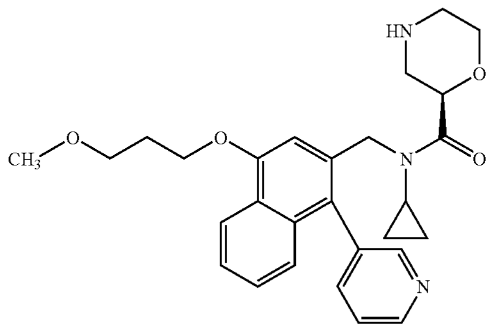 [SMILES: COCCCOc1cc(CN(C(=O)[C@H]2CNCCO2)C2CC2)c(-c2cccnc2)c2ccccc12] | Dihydrochloride<br>Property: pale yellow powder<br>APCI-MS m/z: 476[M + H]$^+$ |
| 30 | 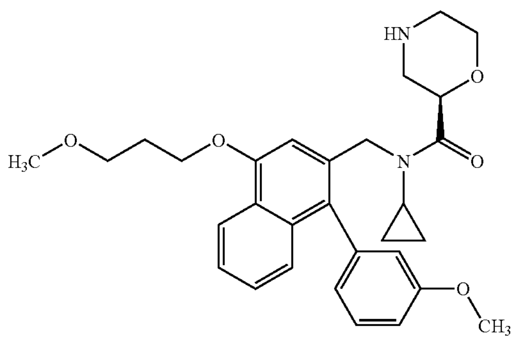 | Hydrochloride<br>Property: colorless powder<br>APCI-MS m/z: 505[M + H]$^+$ |
| 31 | 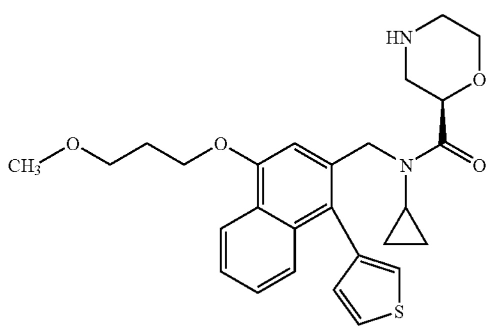 [SMILES: COCCCOc1cc(CN(C(=O)[C@H]2CNCCO2)C2CC2)c(-c2ccsc2)c2ccccc12] | Hydrochloride<br>Property: colorless powder<br>APCI-MS m/z: 481[M + H]$^+$ |
| 32 | 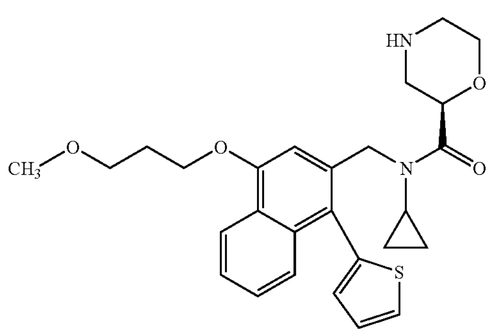 [SMILES: COCCCOc1cc(CN(C(=O)[C@H]2CNCCO2)C2CC2)c(-c2cccs2)c2ccccc12] | Hydrochloride<br>Property: colorless powder<br>APCI-MS m/z: 481[M + H]$^+$ |

TABLE 1-continued
| No. of Examples | Structure | Properties |
|---|---|---|
| 33 | 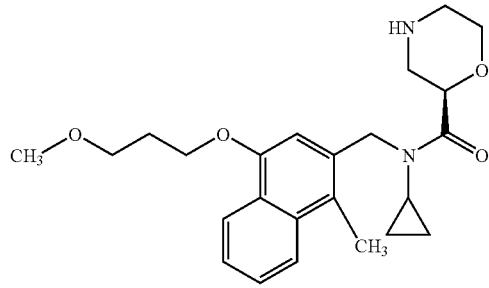 [SMILES: COCCCOc1cc(CN(C(=O)[C@H]2CNCCO2)C2CC2)c(C)c2ccccc12] | Hydrochloride<br>Property: colorless powder<br>APCI-MS m/z: 413[M + H]$^+$ |
| 34 | 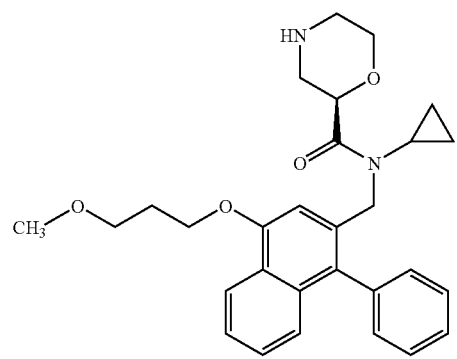 [SMILES: COCCCOc1cc(CN(C(=O)[C@H]2CNCCO2)C2CC2)c(-c2ccccc2)c2ccccc12] | Hydrochloride<br>Property: colorless powder<br>APCI-MS m/z: 475[M + H]$^+$ |
| 35 | 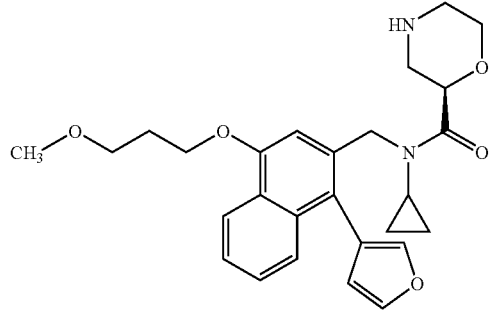 [SMILES: COCCCOc1cc(CN(C(=O)[C@H]2CNCCO2)C2CC2)c(-c2ccoc2)c2ccccc12] | Hydrochloride<br>Property: colorless powder<br>APCI-MS m/z: 465[M + H]$^+$ |
| 36 | 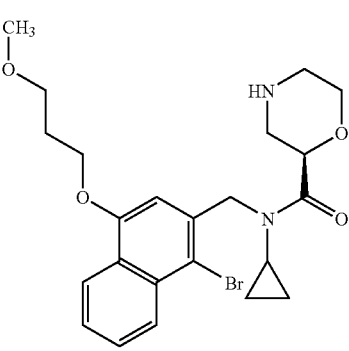 [SMILES: COCCCOc1cc(CN(C(=O)[C@H]2CNCCO2)C2CC2)c(Br)c2ccccc12] | Hydrochloride<br>Property: colorless powder<br>APCI-MS<br>m/z: 477/479[M + H]$^+$ |

TABLE 1-continued

| No. of Examples | Structure | Properties |
|---|---|---|
| 37 | 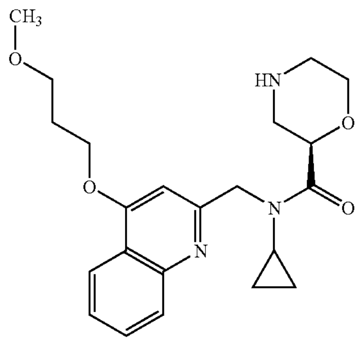 [SMILES: COCCCOc1cc(CN(C(=O)[C@H]2CNCCO2)C2CC2)nc2ccccc12] | Dihydrochloride<br>Property: colorless powder<br>APCI-MS m/z: 400[M + H]$^+$ |

Example 38

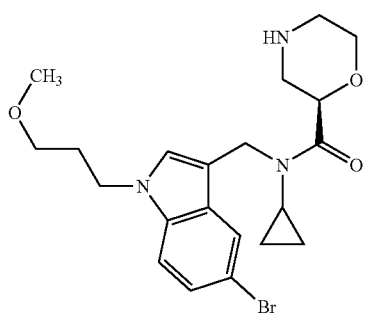 [SMILES: COCCCn1cc(CN(C(=O)[C@H]2CNCCO2)C2CC2)c2cc(Br)ccc21]

Zinc bromide (209 mg) was added to a solution of tert-butyl(2R)-2-{[{[5-bromo-1-(3-methoxypropyl)indol-3-yl]methyl}(cyclopropyl)amino]carbonyl}morpholin-4-carboxylate (a compound of Reference Example 128, 200 mg) in 1,2-dichloroethane (12 ml) and the mixture was stirred at 40° C. for 3 hours. The reaction mixture was poured into a saturated aqueous solution of sodium bicarbonate and extracted with chloroform. The organic layer was washed with water and saturated brine, dried over magnesium sulfate and concentrated in vacuo. The resulted residue was purified with a silica gel column chromatography (eluting solvent: chloroform/methanol=98/2 to 93/7) to give (2R)—N-{[5-bromo-1-(3-methoxypropyl)indol-3-yl]methyl}-N-cyclopropylmorpholin-2-carboxamide (117 mg) as a colorless oil.

APCI-MS m/z: 450/452[M+H]$^+$.

Example 39-50

Corresponding starting compounds were treated in the same manner as Example 38 to give the following compounds of Table 2.

TABLE 2

| 39 | | Property: colorless viscous oil<br>APCI-MS m/z: 372[M + H]$^+$ |
|---|---|---|
| 40 | | Property: colorless viscous oil<br>APCI-MS m/z: 390[M + H]$^+$ |

TABLE 2-continued
| | | |
|---|---|---|
| 41 | 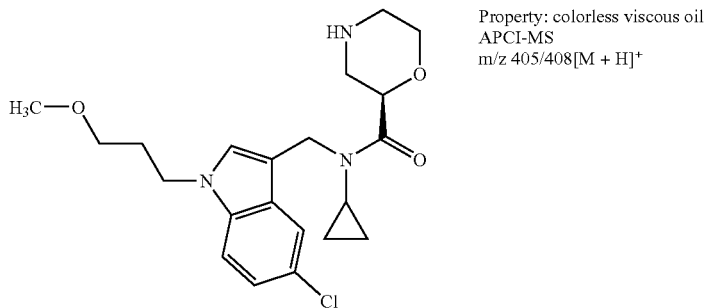 | Property: colorless viscous oil<br>APCI-MS<br>m/z 405/408[M + H]$^+$ |
| 42 | 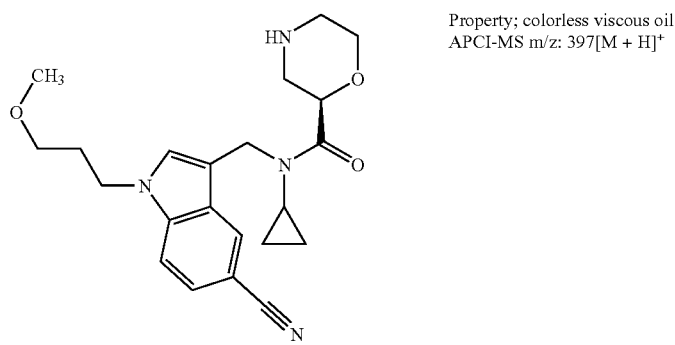 | Property; colorless viscous oil<br>APCI-MS m/z: 397[M + H]$^+$ |
| 43 | 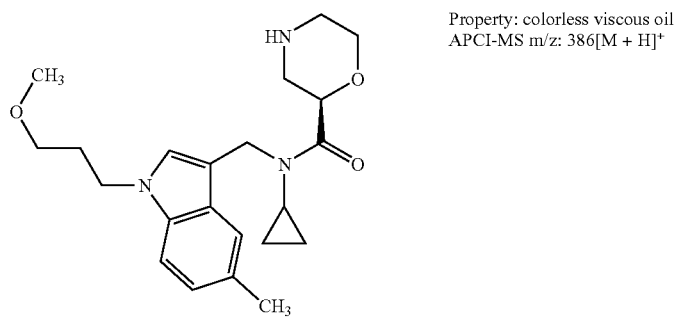 | Property: colorless viscous oil<br>APCI-MS m/z: 386[M + H]$^+$ |
| No. of Examples | Structure | Properties |
|---|---|---|
| 44 | 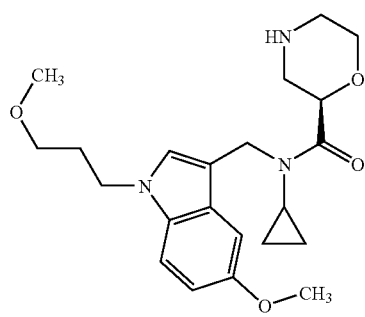 [SMILES: COCCCn1cc(CN(C(=O)[C@H]2CNCCO2)C2CC2)c2cc(OC)ccc21] | Property: colorless viscous oil<br>APCI-MS m/z: 402[M + H]$^+$ |

TABLE 2-continued
| 45 | 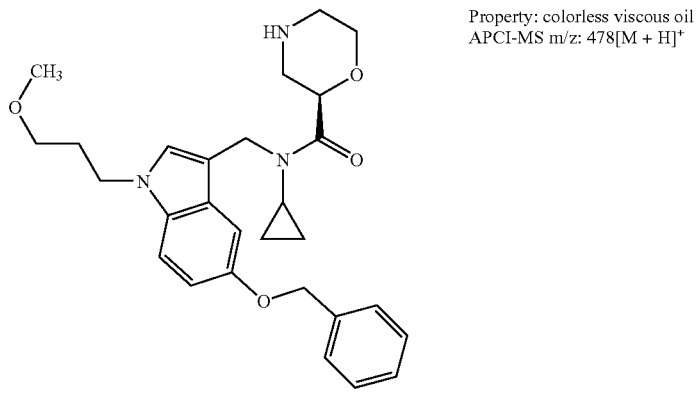 | Property: colorless viscous oil<br>APCI-MS m/z: 478[M + H]+ |
| --- | --- | --- |
| 46 | 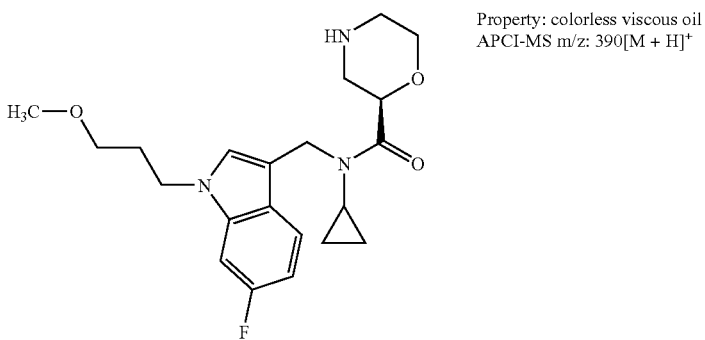 | Property: colorless viscous oil<br>APCI-MS m/z: 390[M + H]+ |
| 47 | 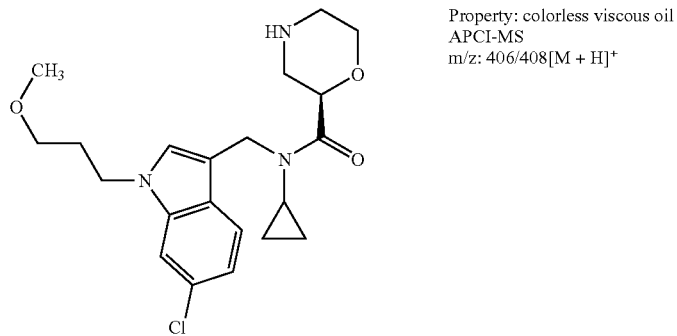 | Property: colorless viscous oil<br>APCI-MS<br>m/z: 406/408[M + H]+ |
| 48 | 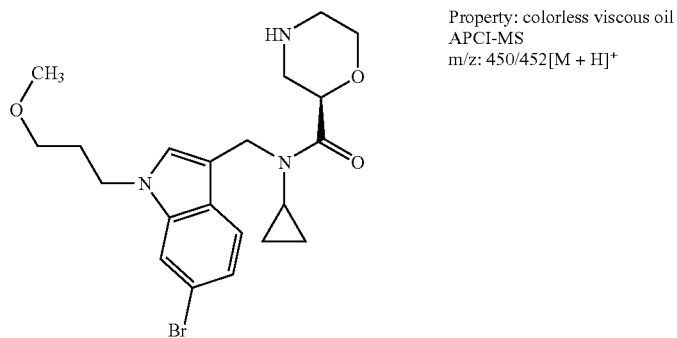 | Property: colorless viscous oil<br>APCI-MS<br>m/z: 450/452[M + H]+ |

TABLE 2-continued

| No. | Structure | Properties |
|---|---|---|
| 49 | 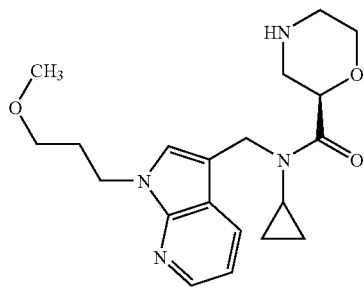 [SMILES: COCCCn1cc(CN(C(=O)[C@H]2CNCCO2)C2CC2)c2cccnc21] | Property: colorless viscous oil<br>APCI-MS m/z: 373[M + H]$^+$ |
| 50 | 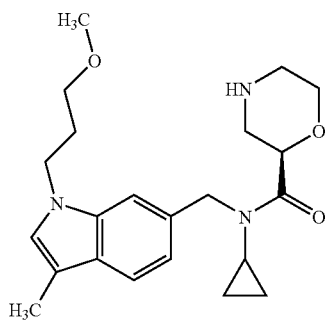 [SMILES: COCCCn1cc(C)c2ccc(CN(C(=O)[C@H]3CNCCO3)C3CC3)cc21] | Property: oil<br>APCI-MS m/z: 386[M + H]$^+$ |

Example 51-53

Corresponding starting compounds were treated in the same manner as Example 2 to give the following compounds of Table 3.

TABLE 3

| No. of Examples | Structure | Properties |
|---|---|---|
| 51 | 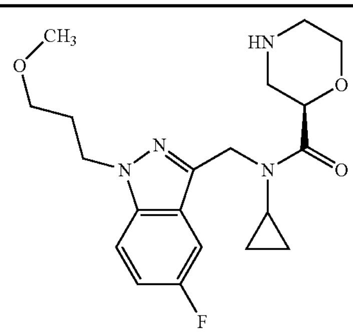 | Hydrochloride<br>Property: colorless powder<br>APCI-MS<br>m/z: 391[M + H]$^+$ |
| 52 | 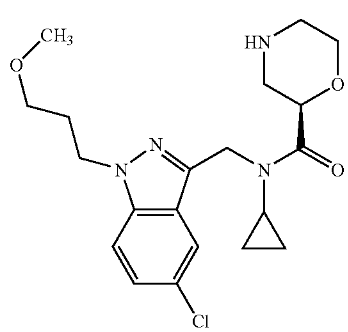 [SMILES: COCCCn1nc(CN(C(=O)[C@H]2CNCCO2)C2CC2)c2cc(Cl)ccc21] | Hydrochloride<br>Property: colorless powder<br>APCI-MS<br>m/z: 407/409[M + H]$^+$ |

TABLE 3-continued

| No. of Examples | Structure | Properties |
|---|---|---|
| 53 | 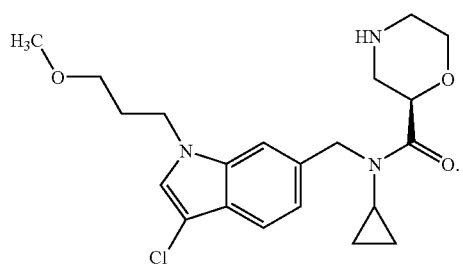 | Hydrochloride<br>Property: colorless viscous oil<br>APCI-MS<br>m/z: 373[M + H]$^+$ |

Example 54

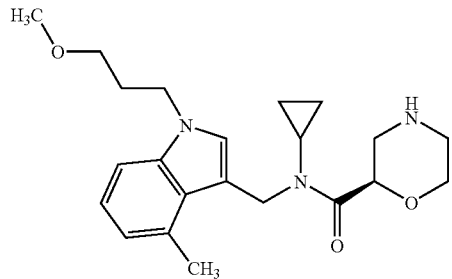 [SMILES: COCCCn1cc(CN(C(=O)[C@H]2CNCCO2)C2CC2)c2c(C)cccc21]

N-Methyl indole (78 mg) and zinc bromide (103 mg) were added to a solution of tert-butyl(2R)-2-{[{[3-chloro-1-(3-methoxypropyl)-1H-indol-6-yl]methyl(cyclopropyl)amino]carbonyl}morpholin}-4-carboxylate (100 mg) in dichloroethane (5 ml) and the mixture was stirred at 40° C. for 6 hours. A saturated aqueous solution of sodium bicarbonate was added to the reaction mixture under ice-cooling and the mixture was extracted with chloroform. The organic layer was washed with saturated brine, dried over magnesium sulfate and concentrated in vacuo. The resulted residue was purified with NH-silica gel column chromatography (eluting solvent: ethyl acetate to ethyl acetate/methanol=10/1) to give (2R)—N-{[3-chloro-1-(3-methoxypropyl)-1H-indol-6-yl]methyl}-N-cyclopropylmorpholin-2-carboxamide (71 mg) as a colorless oil.

APCI-MS m/z: 406/408 [M+H]$^+$.

Example 55

2,6-Lutidine (122 μl) and trimethylsilyl trifluoromethanesulfonate (158 μl) were added successively to a solution of tert-butyl(2R)-2-cyclopropyl{[1-(3-methoxypropyl)-4-methyl-1H-indol-3-yl]methyl}amino}carbonyl]morpholin-4-carboxylate (170 mg) in dichloromethane (5.2 ml) under argon atmosphere and ice-cooling and the mixture was stirred at the same temperature for 30 minutes. A saturated aqueous solution of sodium bicarbonate and methanol were added to the reaction mixture under ice-cooling, the mixture was stirred vigorously for 20 minutes and extracted with chloroform. The organic layer was washed with saturated brine, dried over magnesium sulfate and concentrated in vacuo. The resulted residue was purified with a silica gel column chromatography (eluting solvent: chloroform/methanol=20/1 to 9/1) to give (2R)—N-cyclopropyl-N-{[1-(3-methoxypropyl)-4-methyl-1H-indol-3-yl]methyl}morpholin-2-carboxamide (92.2 mg) as a colorless oil. APCI-MS m/z: 386[M+H]$^+$.

Example 56

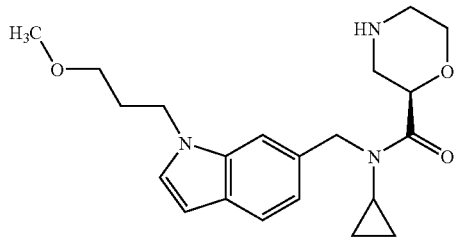 [SMILES: COCCCn1ccc2ccc(CN(C(=O)[C@H]3CNCCO3)C3CC3)cc21]

10% Palladium-carbon (20 mg) was added to a solution of (2R)—N-{[3-chloro-1-(3-methoxypropyl)-1H-indol-6-yl]methyl}-N-cyclopropylmorpholin-2-carboxamide (67 mg) and diisopropylethylamine (43 mg) in ethanol (3 ml) and the mixture was stirred under hydrogen atmosphere at room temperature for 8 hours. Insoluble materials were filtered and the filtrate was concentrated in vacuo. The resulted residue was dissolved in ethyl acetate, washed with a saturated aqueous solution of sodium bicarbonate and saturated brine successively, dried over magnesium sulfate and concentrated in vacuo. The resulted residue was purified with NH-silica gel column chromatography (eluting solvent: ethyl acetate to ethyl acetate/methanol=10/1) to give (2R)—N-cyclopropyl-N-{[1-(3-methoxypropyl)-1H-indol-6-yl]methyl}morpholin-2-carboxamide (53 mg) as a colorless oil.

APCI-MS m/z: 372[M+H]$^+$.

Example 57

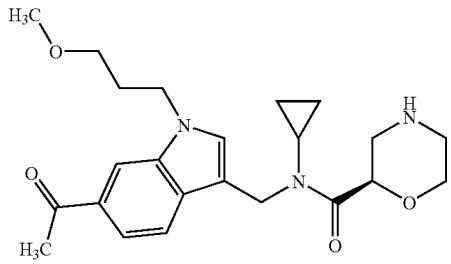 [SMILES: COCCCn1cc(CN(C(=O)[C@H]2CNCCO2)C2CC2)c2ccc(C(C)=O)cc21]

(1) Tri-n-butyl-tin-1-ethoxyvinyl (368 μl) and dichlorobis(triphenylphosphine)palladium(II) (25.5 mg) were added to a solution of tert-butyl(2R)—N-{[{[6-bromo-1-(3-methoxypropyl)-1H-indol-3-yl]methyl}(cyclopropyl)amino]carbonyl}morpholin-4-carboxylate (200 mg) in toluene (5 ml) and the mixture was stirred at 110° C. for 16 hours. The reaction mixture was cooled to room temperature, diluted with ethyl acetate, a saturated aqueous solution of potassium fluoride and the mixture was stirred at room temperature for an hour. The organic layer was washed with water and saturated brine successively, dried over magnesium sulfate and concentrated in vacuo. The resulted residue was purified with a silica gel column chromatography (eluting solvent: chloroform to chloroform/methanol=20/1) to give tert-butyl(2R)-2-[(cyclopropyl{[6-(1-ethoxyvinyl)-1-(3-methoxypropyl)-1H-indol-3-yl]methyl}amino)carbonyl]morpholin-4-carboxylate (98 mg) as a colorless oil.

APCI-MS m/z: 542[M+H]$^+$.

(2) Zinc bromide (209 mg) was added to a solution of the compound obtained in (1) described above (98 mg) in dichloroethane (12 ml) and the mixture was stirred at 40° C. for 24 hours. A saturated aqueous solution of sodium bicarbonate was added to the reaction mixture, the mixture was stirred at room temperature for 30 minutes and extracted with chloroform. The organic layer was washed with water and saturated brine successively, dried over magnesium sulfate and concentrated in vacuo. The resulted residue was purified with a silica gel column chromatography (eluting solvent: chloroform/methanol=20/1 to 10/1) to give (2R)—N-{[6-acetyl-1-(3-methoxypropyl)-1H-indol-3-yl]methyl}-N-cyclopropylmorpholin-2-carboxamide (37 mg) as a pale yellow powder.

APCI-MS m/z: 414[M+H]$^+$.

Example 58

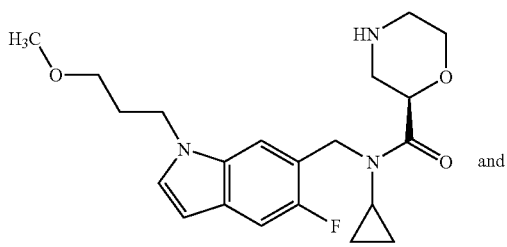
and

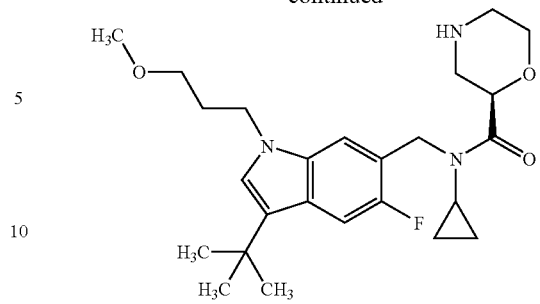

Zinc bromide (160 mg) was added to a solution of tert-butyl(2R)-2-[(cyclopropyl{[5-fluoro-1-(3-methoxypropyl)-1H-indol-6-yl]methyl}amino)carbonyl]morpholin-4-carboxylate (150 mg) in dichloromethane (3 ml) and the mixture was stirred at room temperature for 10 hours. A saturated aqueous solution of sodium bicarbonate was added to the reaction mixture under ice-cooling, and the mixture was extracted with chloroform. The organic layer was washed with saturated brine, dried over magnesium sulfate and concentrated in vacuo. The resulted residue was purified with HPLC MS to give (2R)—N-cyclopropyl-N-{[5-fluoro-1-(3-methoxypropyl)-1H-indol-6-yl]methyl}morpholin-2-carboxamide (50 mg) and (2R)—N-{[3-tert-butyl-5-fluoro-1-methoxypropyl)-1H-indol-6-yl]methyl}-N-cyclopropylmorpholin-2-carboxamide (50 mg) as a colorless oil.

(2R)—N-cyclopropyl-N-{[5-fluoro-1-(3-methoxypropyl)-1H-indol-6-yl]methyl}morpholin-2-carboxamide: APCI-MS m/z: 390[M+H]$^+$ (2R)—N-{[3-tert-butyl-5-fluoro-1-(3-methoxypropyl)-1H-indol-6-yl]methyl}-N-cyclopropylmorpholin-2-carboxamide: APCI-MS m/z: 446[M+H]$^+$

Example 59

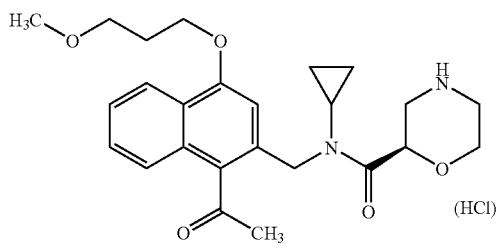

(1) Tri-n-butyl-tin-1-ethoxyvinyl (398 mg) and dichlorobis(triphenylphosphine)palladium(II) (55 mg) were added to a solution of tert-butyl(2R)-2-{[{[1-bromo-4-(3-methoxypropyl)-2-naphthyl]methyl}(cyclopropyl)amino]carbonyl}morpholin-4-carboxylate (227 mg) in toluene (5.0 ml) and the mixture was stirred at 110° C. for 18 hours. Tri-n-butyl-tin-1-ethoxyvinyl (133 mg) and dichlorobis(triphenylphosphine)palladium(II) (55 mg) were further added to the reaction mixture and the mixture was stirred at 110° C. for 6 hours. The reaction mixture was cooled to room temperature, water was added to therein and insoluble materials were filtered through Celite and the residue was washed with ethyl acetate. The organic layer was separated, washed with saturated brine, dried over magnesium sulfate and concentrated in vacuo. The resulted residue was purified with NH-silica gel column chromatography (eluting solvent: n-hexane/ethyl acetate=5/1) to give tert-butyl(2R)-2-[(cyclopropyl){[1-(1-ethoxyvinyl)-4-(3-methoxypropyl)-2-naphthyl]methyl}amino)carbonyl]morpholin-4-carboxylate (70 mg) as a colorless oil.
APCI-MS m/z: 569[M+H]⁺.

(2) A 4N HCl solution of dioxane (500 µl) was added to a solution of the compound obtained in (1) described above (67.5 mg) in chloroform (3 ml) under ice-cooling and the mixture was stirred at room temperature for 4 hours. The reaction mixture was concentrated in vacuo and the resulted residue was triturated in diethyl ether to give (2R)—N-{[1-acetyl-4-(3-methoxypropyl)-2-naphthyl]methyl}-N-cyclopropylmorpholin-2-carboxamide (52.5 mg) as a pale green powder.
APCI-MS m/z: 441[M+H]⁺.

Example 60

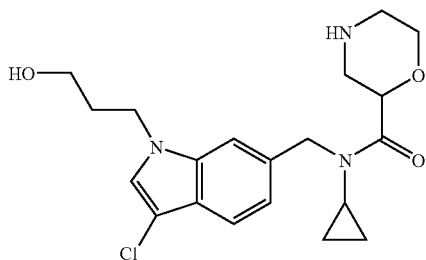 [SMILES: O=C(C1CNCCO1)N(Cc1ccc2c(Cl)cn(CCCO)c2c1)C1CC1]

2,6-Lutidine (108 µl) and trimethylsilyl trifluoromethanesulfonate (139 µl) were added to a solution of tert-butyl(dl)-2-{[({3-chloro-1-[2-(tetrahydro-2H-pyran-2-yloxy)ethyl]-1H-indol-6-yl}methyl)(cyclopropyl)amino]carbonyl}morpholin-4-carboxylate (178 mg) in dichloroethane (5.0 ml) under ice-cooling and the mixture was stirred at the same temperature for 3 hours. A saturated aqueous solution of sodium bicarbonate was added to the reaction mixture under ice-cooling, and the mixture was extracted with chloroform. The organic layer was washed with saturated brine, dried over sodium sulfate and concentrated in vacuo. The resulted residue was purified with a silica gel column chromatography (eluting solvent: chloroform/methanol=6/1) to give (dl)-N-{[3-chloro-1-(3-hydroxypropyl)-1H-indol-6-yl]methyl}-N-cyclopropylmorpholin-2-carboxamide (34.6 mg) as a pale yellow oil.
APCI-MS m/z: 392/394[M+H]⁺.

Example 61

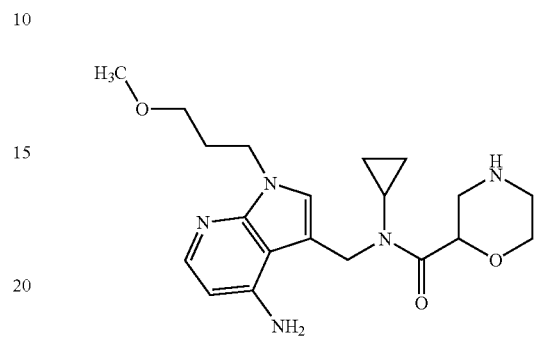

A 4N hydrogen chloride solution of dioxane (0.5 ml) was added to a solution of tert-butyl(dl)-2-{[{[4-(acetylamino)-1-(3-methoxypropyl)-1H-pyrrolo[2,3-b]pyridin-3-yl]methyl}(cyclopropyl)amino]carbonyl}morpholin-4-carboxylate (58 mg) in chloroform (0.5 ml) and the mixture was stirred at room temperature for an hour. The mixture was concentrated in vacuo and the resulted residue was dissolved in water, lyophilized and purified with HPLC MS to give (dl)-N-{[4-amino-1-(3-methoxypropyl)-1H-pyrrolo[2,3-b]pyridin-3-yl]methyl}-N-cyclopropylmorpholin-2-carboxamide (9 mg) as a pale yellow powder.
APCI-MS m/z: 388[M+H]⁺.

Example 62-339

The corresponding starting compounds were treated in the same manner as any of Examples to give compounds listed in the following Table-4.

TABLE 4

| No. of Examples | Structure | Properties |
|---|---|---|
| 62 | 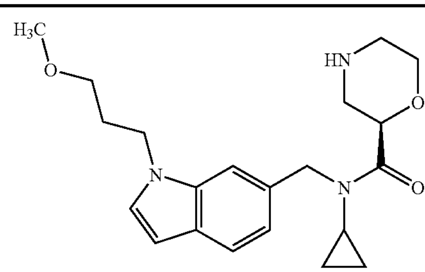 | Property: purified oil<br>APCI-MS m/z: 372[M + H]+ |
| 63 | 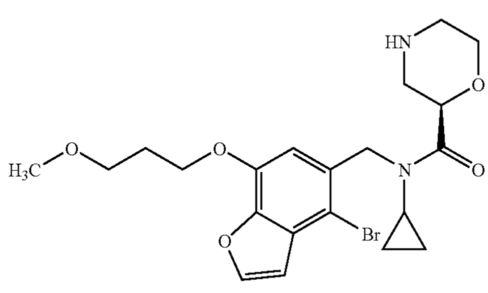 [SMILES: COCCCOc1cc(CN(C(=O)[C@H]2CNCCO2)C2CC2)c(Br)c2ccoc12] | hydrochloride<br>Property: purified powder<br>APCI-MS m/z: 467/469[M + H]+ |

TABLE 4-continued

| No. of Examples | Structure | Properties |
| --- | --- | --- |
| 64 | 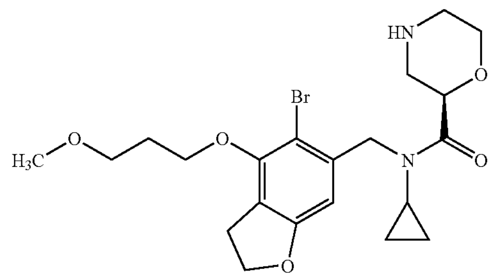 [SMILES: COCCCOc1c(Br)c(CN(C(=O)[C@H]2CNCCO2)C2CC2)cc2c1CCO2] | hydrochloride<br>Property: purified powder<br>APCI-MS m/z: 469/471[M + H]+ |
| 65 | 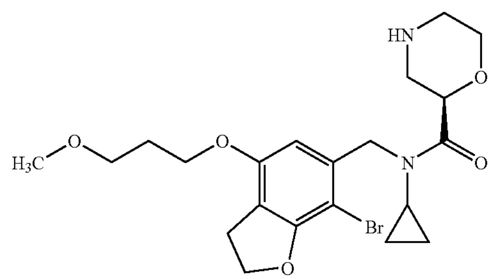 [SMILES: COCCCOc1cc(CN(C(=O)[C@H]2CNCCO2)C2CC2)c(Br)c2c1CCO2] | hydrochloride<br>Property: purified powder<br>APCI-MS m/z: 469/471[M + H]+ |
| 66 | 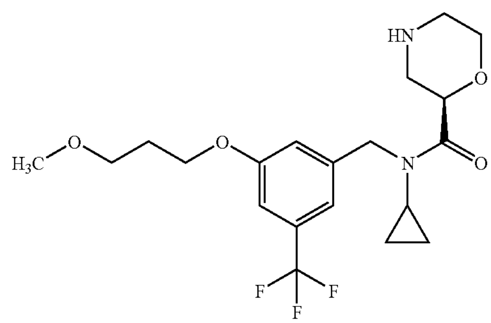 [SMILES: COCCCOc1cc(CN(C(=O)[C@H]2CNCCO2)C2CC2)cc(C(F)(F)F)c1] | hydrochloride<br>Property: purified viscous oil<br>APCI-MS m/z: 417[M + H]+ |
| 67 | 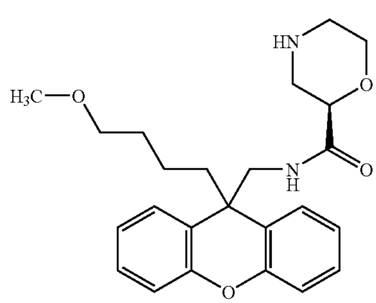 [SMILES: COCCCCC1(CNC(=O)[C@H]2CNCCO2)c2ccccc2Oc2ccccc21] | hydrochloride<br>Property: purified powder<br>APCI-MS m/z: 411[M + H]+ |
| 68 | 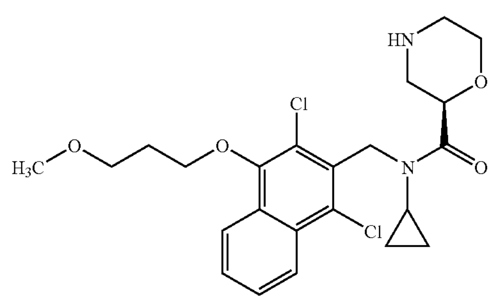 | hydrochloride<br>Property: purified powder<br>APCI-MS m/z: 467/469[M + H]+ |

TABLE 4-continued

| No. of Examples | Structure | Properties |
|---|---|---|
| 69 | 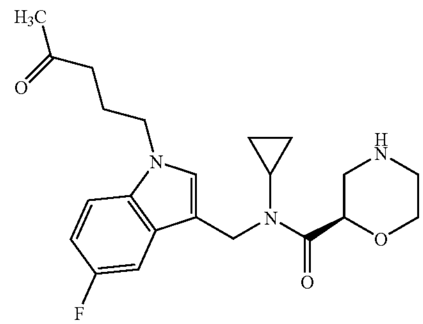 [SMILES: CC(=O)CCCn1cc(CN(C(=O)[C@H]2CNCCO2)C2CC2)c2cc(F)ccc21] | Property: purified viscous oil<br>APCI-MS m/z: 402[M + H]+ |
| 70 | 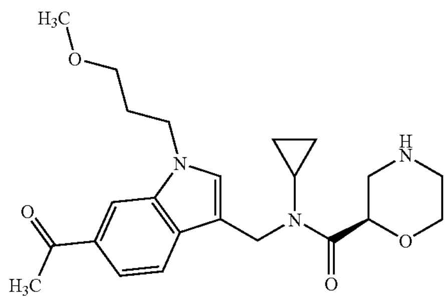 [SMILES: COCCCn1cc(CN(C(=O)[C@H]2CNCCO2)C2CC2)c2ccc(C(C)=O)cc21] | Property: purified viscous oil<br>APCI-MS m/z: 414[M + H]+ |
| 71 | 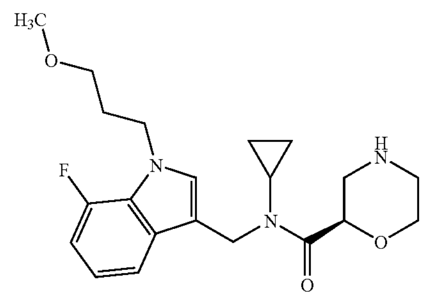 [SMILES: COCCCn1cc(CN(C(=O)[C@H]2CNCCO2)C2CC2)c2cccc(F)c21] | Property: purified viscous oil<br>APCI-MS m/z: 390[M + H]+ |
| 72 | 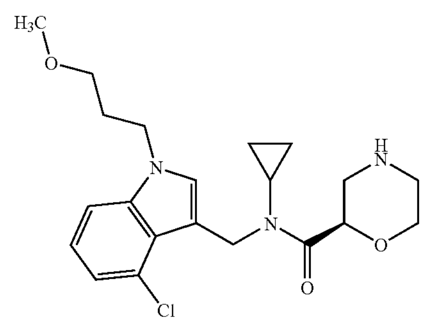 [SMILES: COCCCn1cc(CN(C(=O)[C@H]2CNCCO2)C2CC2)c2c(Cl)cccc21] | Property: purified viscous oil<br>APCI-MS m/z: 406/408[M + H]+ |
| 73 | 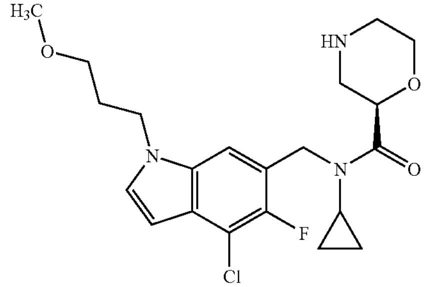 [SMILES: COCCCn1ccc2c(Cl)c(F)c(CN(C(=O)[C@H]3CNCCO3)C3CC3)cc21] | Property: purified oil<br>APCI-MS m/z: 424/426[M + H]+ |

TABLE 4-continued

| No. of Examples | Structure | Properties |
|---|---|---|
| 74 | 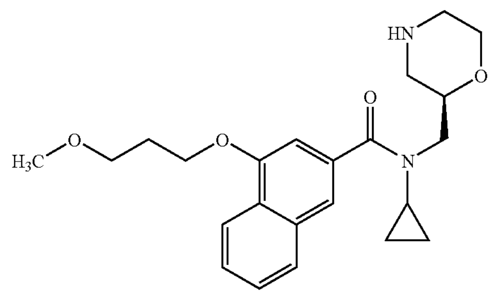 [SMILES: COCCCOc1cc(C(=O)N(C[C@H]2CNCCO2)C2CC2)cc2ccccc12] | hydrochloride<br>Property: purified powder<br>APCI-MS m/z: 399[M + H]+ |
| 75 | 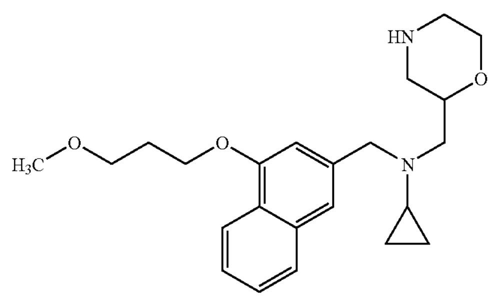 [SMILES: COCCCOc1cc(CN(CC2CNCCO2)C2CC2)cc2ccccc12] | dihydrochloride<br>Property: purified powder<br>APCI-MS m/z: 385[M + H]+ |
| 76 | 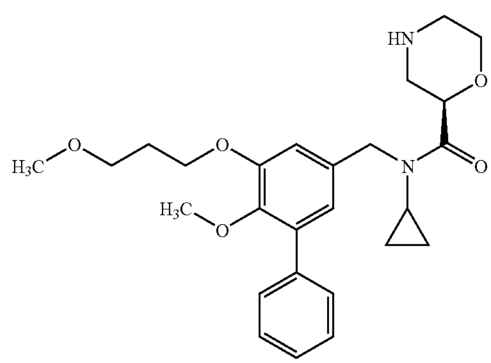 [SMILES: COCCCOc1cc(CN(C(=O)[C@H]2CNCCO2)C2CC2)cc(-c2ccccc2)c1OC] | hydrochloride<br>Property: purified viscous oil<br>APCI-MS m/z: 455[M + H]+ |
| 77 | 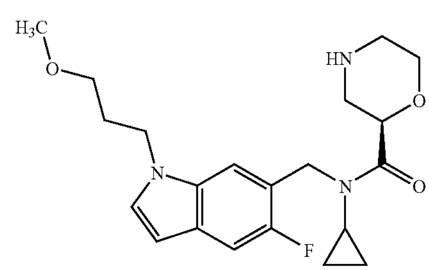 [SMILES: COCCCn1ccc2cc(F)c(CN(C(=O)[C@H]3CNCCO3)C3CC3)cc21] | Property: purified oil<br>APCI-MS m/z: 390[M + H]+ |
| 78 | 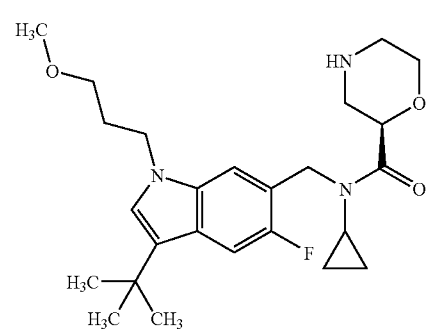 [SMILES: COCCCn1cc(C(C)(C)C)c2cc(F)c(CN(C(=O)[C@H]3CNCCO3)C3CC3)cc21] | Property: purified oil<br>APCI-MS m/z: 446[M + H]+ |

TABLE 4-continued

| No. of Examples | Structure | Properties |
| --- | --- | --- |
| 79 | 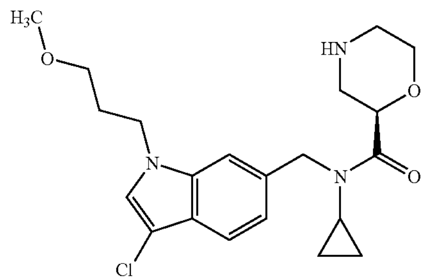 | Property: purified oil<br>APCI-MS m/z: 406/408[M + H]+ |
| 80 | 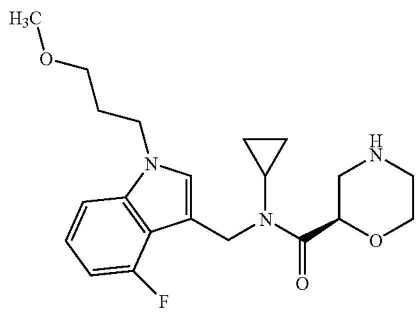 [SMILES: COCCCn1cc(CN(C(=O)[C@H]2CNCCO2)C2CC2)c2c(F)cccc21] | Property: purified viscous oil<br>APCI-MS m/z: 390[M + H]+ |
| 81 | 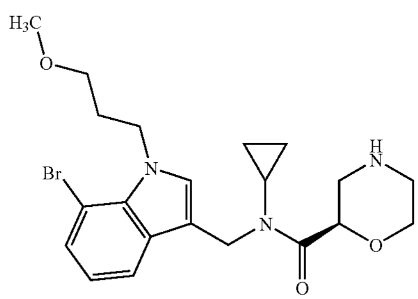 [SMILES: COCCCn1cc(CN(C(=O)[C@H]2CNCCO2)C2CC2)c2cccc(Br)c21] | Property: purified viscous oil<br>APCI-MS m/z: 450/452[M + H]+ |
| 82 | 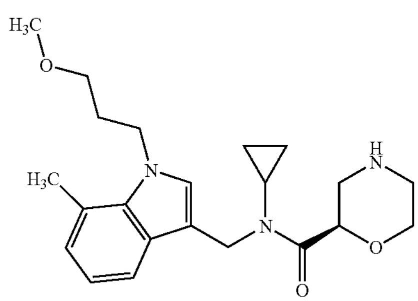 [SMILES: COCCCn1cc(CN(C(=O)[C@H]2CNCCO2)C2CC2)c2cccc(C)c21] | Property: purified viscous oil<br>APCI-MS m/z: 386[M + H]+ |
| 83 | 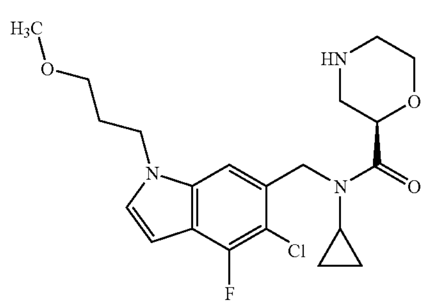 [SMILES: COCCCn1ccc2c(F)c(Cl)c(CN(C(=O)[C@H]3CNCCO3)C3CC3)cc21] | Property: purified oil<br>APCI-MS m/z: 424/426[M + H]+ |

TABLE 4-continued

| No. of Examples | Structure | Properties |
| --- | --- | --- |
| 84 | 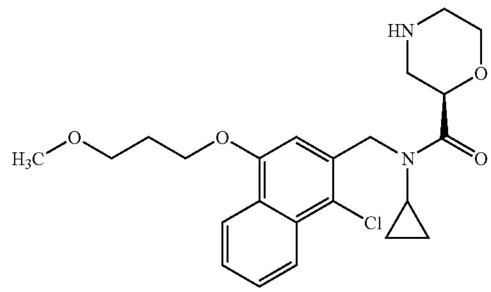 [SMILES: COCCCOc1cc(CN(C(=O)[C@H]2CNCCO2)C2CC2)c(Cl)c2ccccc12] | hydrochloride<br>Property: purified powder<br>APCI-MS m/z: 433/435[M + H]+ |
| 85 | 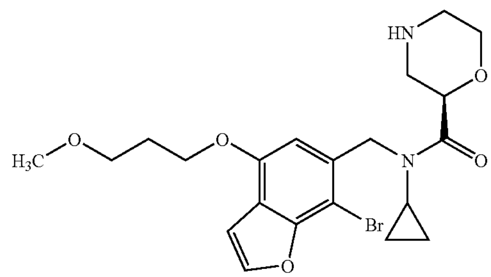 [SMILES: COCCCOc1cc(CN(C(=O)[C@H]2CNCCO2)C2CC2)c(Br)c2occc12] | hydrochloride<br>Property: purified powder<br>APCI-MS m/z: 467/469[M + H]+ |
| 86 | 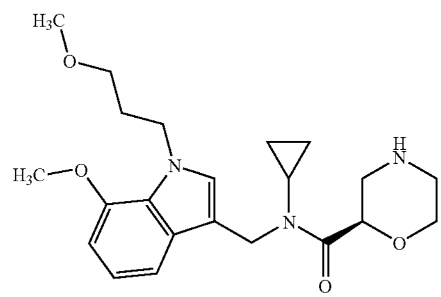 [SMILES: COCCCn1cc(CN(C(=O)[C@H]2CNCCO2)C2CC2)c2cccc(OC)c21] | Property: purified viscous oil<br>APCI-MS m/z: 402[M + H]+ |
| 87 | 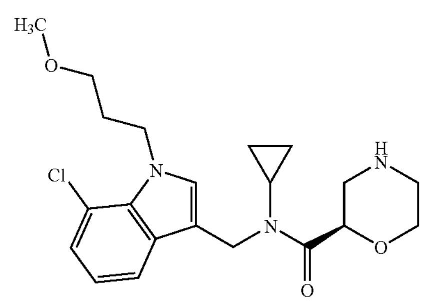 [SMILES: COCCCn1cc(CN(C(=O)[C@H]2CNCCO2)C2CC2)c2cccc(Cl)c21] | Property: purified viscous oil<br>APCI-MS m/z: 406/408[M + H]+ |
| 88 | 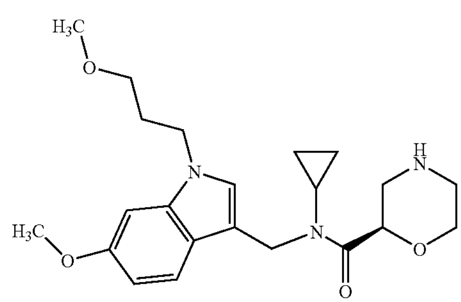 [SMILES: COCCCn1cc(CN(C(=O)[C@H]2CNCCO2)C2CC2)c2ccc(OC)cc21] | Property: purified viscous oil<br>APCI-MS m/z: 402[M + H]+ |

TABLE 4-continued

| No. of Examples | Structure | Properties |
| --- | --- | --- |
| 90 | 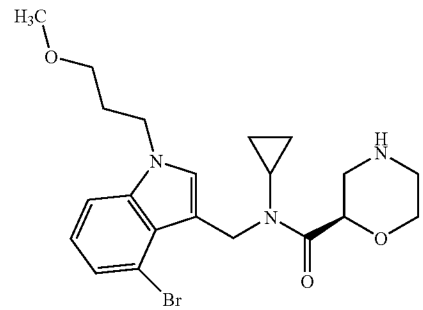 [SMILES: COCCCn1cc(CN(C(=O)[C@H]2CNCCO2)C2CC2)c2c(Br)cccc21] | Property: purified viscous oil<br>APCI-MS m/z: 450/452[M + H]+ |
| 91 | 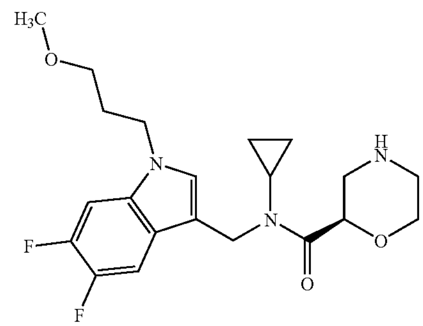 [SMILES: COCCCn1cc(CN(C(=O)[C@H]2CNCCO2)C2CC2)c2cc(F)c(F)cc21] | Property: purified viscous oil<br>APCI-MS m/z: 408[M + H]+ |
| 92 | 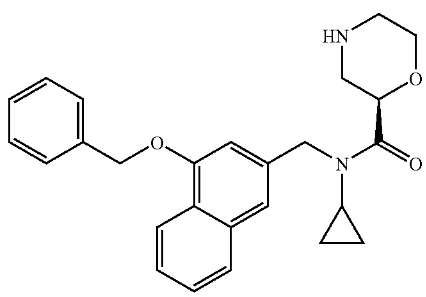 [SMILES: O=C([C@H]1CNCCO1)N(Cc1cc(OCc2ccccc2)c2ccccc2c1)C1CC1] | hydrochloride<br>Property: purified powder<br>APCI-MS m/z: 417[M + H]+ |
| 93 | 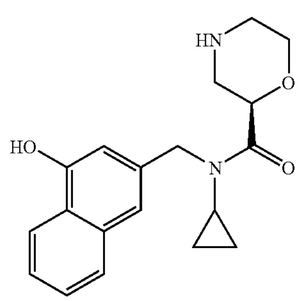 [SMILES: O=C([C@H]1CNCCO1)N(Cc1cc(O)c2ccccc2c1)C1CC1] | hydrochloride<br>Property: purified viscous oil<br>APCI-MS m/z: 327[M + H]+ |
| 94 | 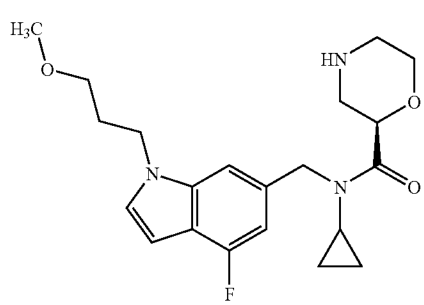 [SMILES: COCCCn1ccc2c(F)cc(CN(C(=O)[C@H]3CNCCO3)C3CC3)cc21] | Property: purified oil<br>APCI-MS m/z: 390[M + H]+ |

TABLE 4-continued

| No. of Examples | Structure | Properties |
|---|---|---|
| 95 | (structure) | Property: purified viscous oil<br>APCI-MS m/z: 446[M + H]+ |
| 96 | (structure) | hydrochloride<br>Property: purified powder<br>APCI-MS m/z: 441[M + H]+ |
| 97 | (structure) | hydrochloride<br>Property: purified viscous oil<br>APCI-MS m/z: 424[M + H]+ |
| 98 | (structure) | Property: purified viscous oil<br>APCI-MS m/z: 386[M + H]+ |
| 99 | (structure) | Property: purified, viscous oil<br>APCI-MS m/z: 397[M + H]+ |

TABLE 4-continued
| No. of Examples | Structure | Properties |
|---|---|---|
| 100 | 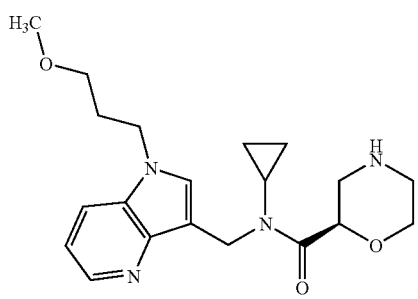 [SMILES: COCCCn1cc(CN(C(=O)[C@H]2CNCCO2)C2CC2)c2ncccc21] | Property: purified viscous oil<br>APCI-MS m/z: 373[M + H]+ |
| 101 | 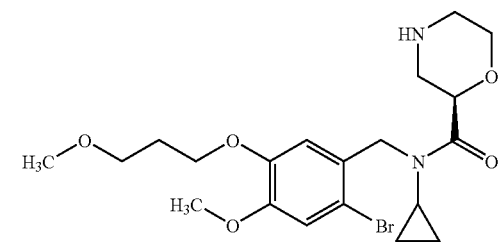 [SMILES: COCCCOc1cc(CN(C(=O)[C@H]2CNCCO2)C2CC2)c(Br)cc1OC] | hydrochloride<br>Property: purified powder<br>APCI-MS m/z: 457/459[M + H]+ |
| 102 | 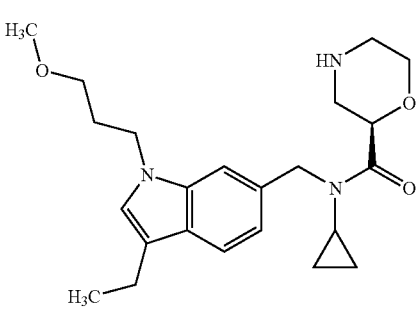 [SMILES: CCc1cn(CCCOC)c2cc(CN(C(=O)[C@H]3CNCCO3)C3CC3)ccc12] | Property: purified oil<br>APCI-MS m/z: 400[M + H]+ |
| 103 | 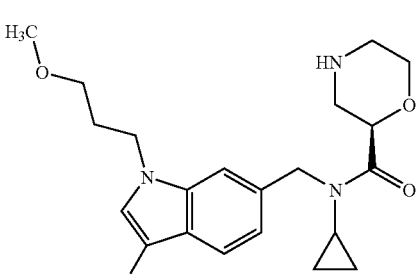 | hydrochloride<br>Property: purified powder<br>APCI-MS m/z: 387[M + H]+ |
| 104 | 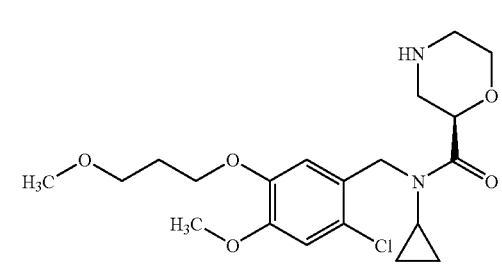 [SMILES: COCCCOc1cc(CN(C(=O)[C@H]2CNCCO2)C2CC2)c(Cl)cc1OC] | hydrochloride<br>Property: purified powder<br>APCI-MS m/z: 413/415[M + H]+ |

TABLE 4-continued

| No. of Examples | Structure | Properties |
|---|---|---|
| 105 | 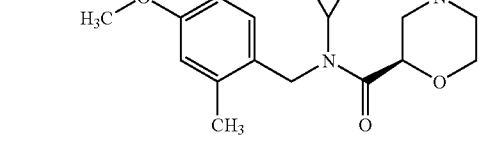 | hydrochloride<br>Property: purified viscous oil<br>APCI-MS m/z: 393[M + H]+ |
| 106 | 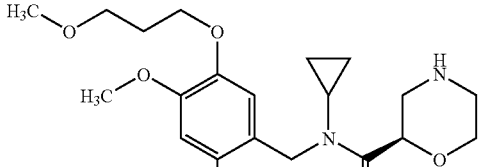 | hydrochloride<br>Property: purified powder<br>APCI-MS m/z: 455[M + H]+ |
| 107 | 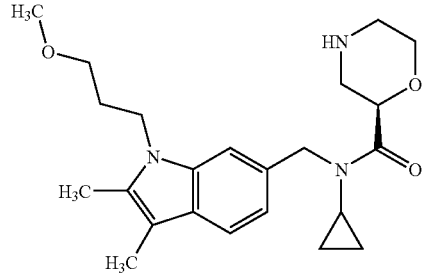 [SMILES: COCCCn1c(C)c(C)c2ccc(CN(C(=O)[C@H]3CNCCO3)C3CC3)cc21] | Property: purified oil<br>APCI-MS m/z: 400[M + H]+ |
| 108 | 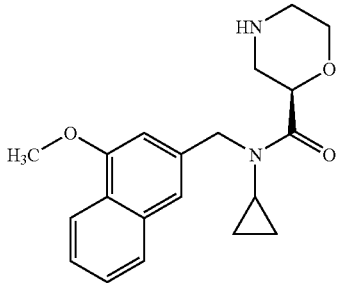 [SMILES: COc1cc(CN(C(=O)[C@H]2CNCCO2)C2CC2)cc2ccccc12] | hydrochloride<br>Property: purified powder<br>APCI-MS m/z: 341[M + H]+ |
| 109 | 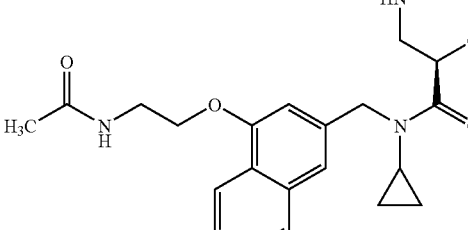 | hydrochloride<br>Property: purified powder<br>APCI-MS m/z: 412[M + H]+ |

TABLE 4-continued

| No. of Examples | Structure | Properties |
|---|---|---|
| 110 | 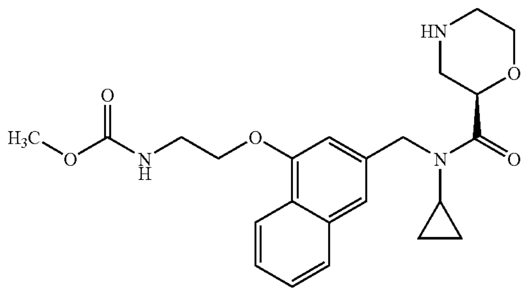 [SMILES: COC(=O)NCCOc1cc(CN(C(=O)[C@H]2CNCCO2)C2CC2)cc2ccccc12] | hydrochloride<br>Property: purified powder<br>APCI-MS m/z: 428[M + H]+ |
| 111 | 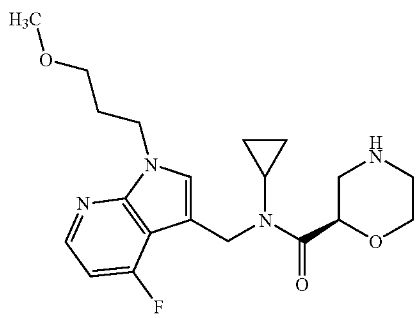 [SMILES: COCCCn1cc(CN(C(=O)[C@H]2CNCCO2)C2CC2)c2c(F)ccnc21] | Property: purified viscous oil<br>APCI-MS m/z: 391[M + H]+ |
| 112 | 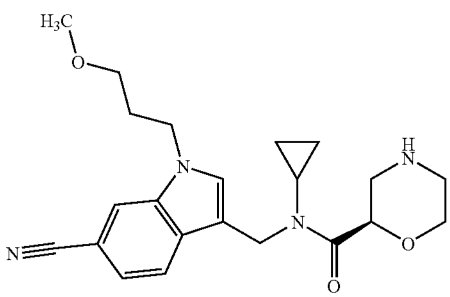 [SMILES: COCCCn1cc(CN(C(=O)[C@H]2CNCCO2)C2CC2)c2ccc(C#N)cc21] | Property: purified powder<br>APCI-MS m/z: 397[M + H]+ |
| 113 | 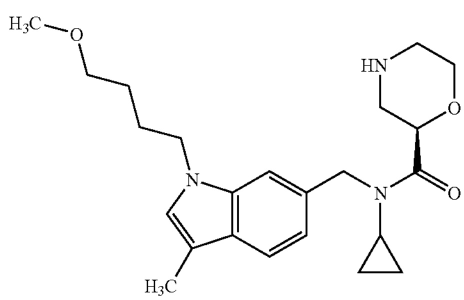 [SMILES: COCCCCn1cc(C)c2ccc(CN(C(=O)[C@H]3CNCCO3)C3CC3)cc21] | Property: purified oil<br>APCI-MS m/z: 400[M + H]+ |
| 114 | 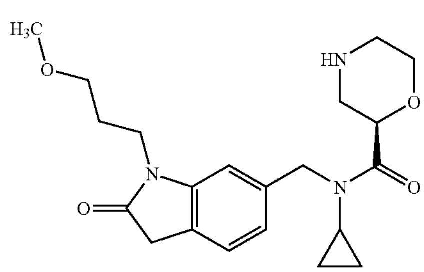 [SMILES: COCCCN1C(=O)Cc2ccc(CN(C(=O)[C@H]3CNCCO3)C3CC3)cc21] | hydrochloride<br>Property: purified powder<br>APCI-MS m/z: 388[M + H]+ |

TABLE 4-continued

| No. of Examples | Structure | Properties |
|---|---|---|
| 115 | 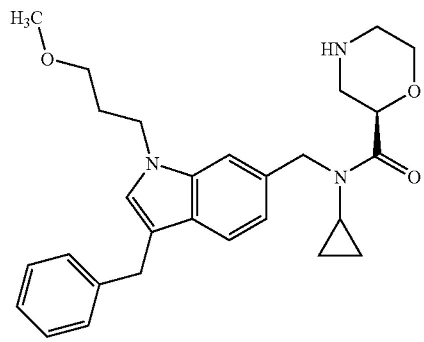 [SMILES: COCCCn1cc(Cc2ccccc2)c2ccc(CN(C(=O)[C@H]3CNCCO3)C3CC3)cc21] | Property: purified oil<br>APCI-MS m/z: 462[M + H]+ |
| 116 | 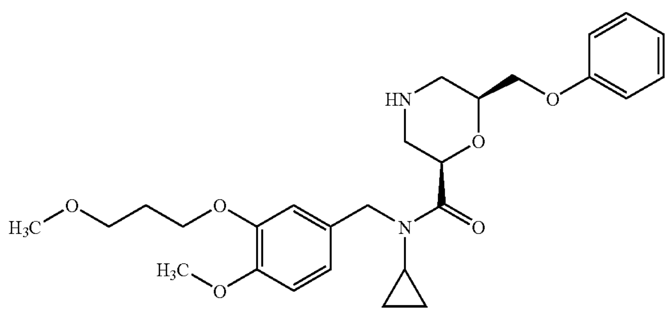 [SMILES: COCCCOc1cc(CN(C(=O)[C@H]2CNC[C@@H](COc3ccccc3)O2)C2CC2)ccc1OC] | hydrochloride<br>Property: purified powder<br>APCI-MS m/z: 485[M + H]+ |
| 117 | 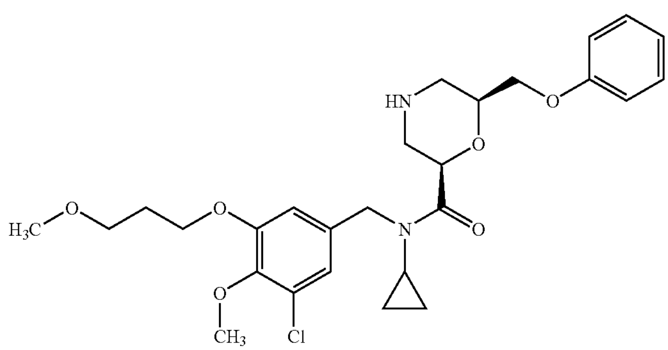 [SMILES: COCCCOc1cc(CN(C(=O)[C@H]2CNC[C@@H](COc3ccccc3)O2)C2CC2)cc(Cl)c1OC] | hydrochloride<br>Property: purified viscous oil<br>APCI-MS m/z: 519/521[M + H]+ |
| 118 | 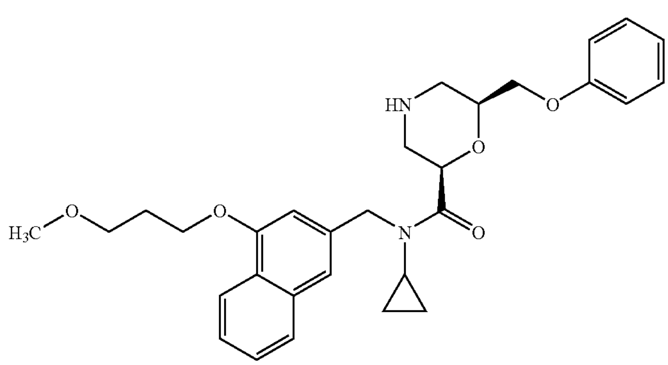 | hydrochloride<br>Property: purified powder<br>APCI-MS m/z: 505[M + H]+ |

TABLE 4-continued

| No. of Examples | Structure | Properties |
|---|---|---|
| 119 | 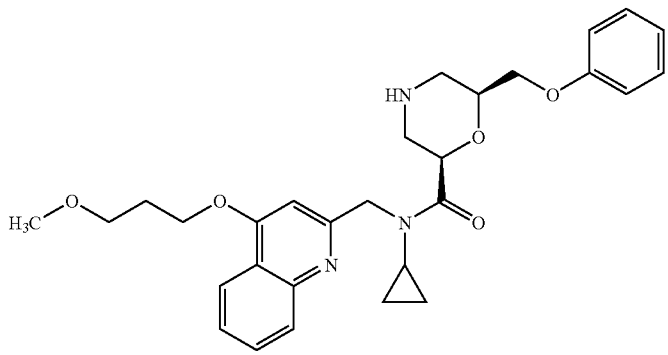 [SMILES: COCCCOc1cc(CN(C(=O)[C@H]2CNC[C@@H](COc3ccccc3)O2)C2CC2)cc2ccccc12] | dihydrochloride<br>Property: purified powder<br>APCI-MS m/z: 506[M + H]+ |
| 120 | 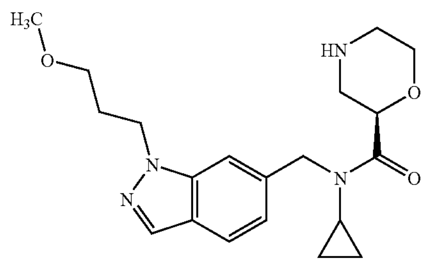 [SMILES: COCCCn1ncc2ccc(CN(C(=O)[C@H]3CNCCO3)C3CC3)cc21] | hydrochloride<br>Property: purified powder<br>APCI-MS m/z: 373[M + H]+ |
| 121 | 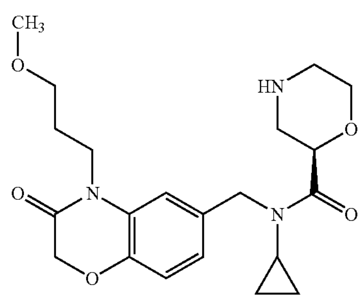 | hydrochloride<br>Property: purified powder<br>APCI-MS m/z: 378[M + H]+ |
| 122 | 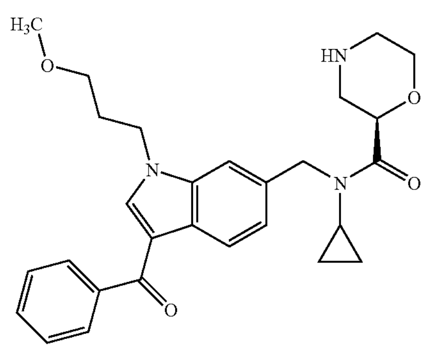 [SMILES: COCCCn1cc(C(=O)c2ccccc2)c2ccc(CN(C(=O)[C@H]3CNCCO3)C3CC3)cc21] | Property: purified viscous oil<br>APCI-MS m/z: 476[M + H]+ |
| 123 | 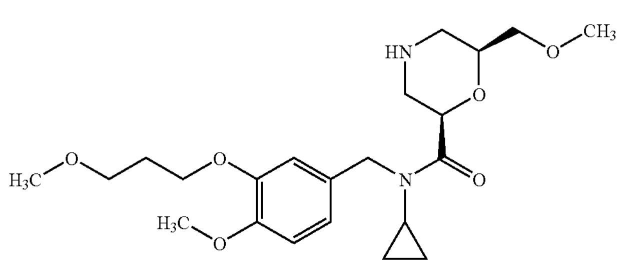 | hydrochloride<br>Property: purified viscous oil<br>APCI-MS m/z: 423[M + H]+ |

TABLE 4-continued

| No. of Examples | Structure | Properties |
|---|---|---|
| 124 | 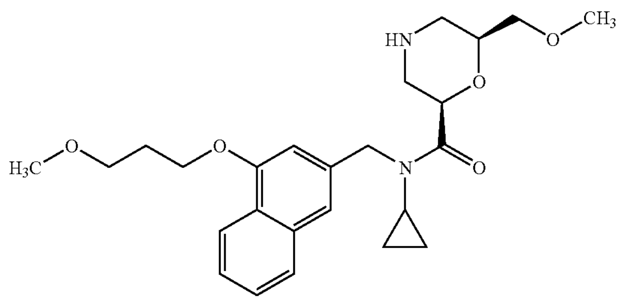 | hydrochloride<br>Property: purified viscous oil<br>APCI-MS m/z: 443[M + H]+ |
| 125 | 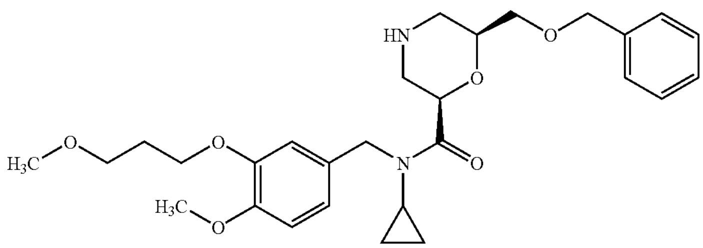 [SMILES: COCCCOc1cc(CN(C(=O)[C@H]2CNC[C@@H](COCc3ccccc3)O2)C2CC2)ccc1OC] | hydrochloride<br>Property: purified viscous oil<br>APCI-MS m/z: 499[M + H]+ |
| 126 | 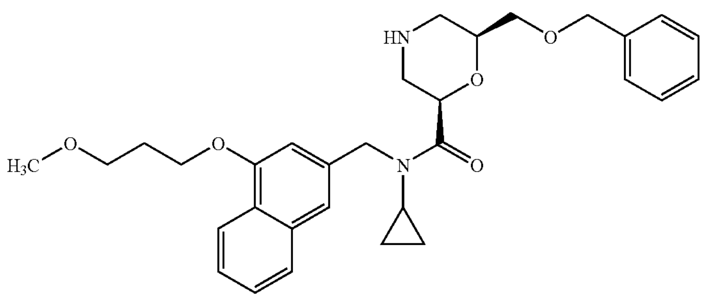 [SMILES: COCCCOc1cc(CN(C(=O)[C@H]2CNC[C@@H](COCc3ccccc3)O2)C2CC2)cc2ccccc12] | hydrochloride<br>Property: purified viscous oil<br>APCI-MS m/z: 519[M + H]+ |
| 127 | 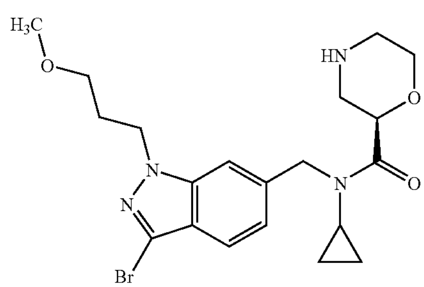 [SMILES: COCCCn1nc(Br)c2ccc(CN(C(=O)[C@H]3CNCCO3)C3CC3)cc21] | hydrochloride<br>Property: purified powder<br>APCI-MS m/z: 451/453[M + H]+ |
| 128 | 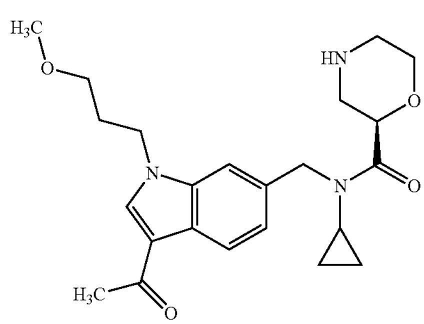 [SMILES: COCCCn1cc(C(C)=O)c2ccc(CN(C(=O)[C@H]3CNCCO3)C3CC3)cc21] | Property: purified oil<br>APCI-MS m/z: 414[M + H]+ |

TABLE 4-continued

| No. of Examples | Structure | Properties |
| --- | --- | --- |
| 129 | 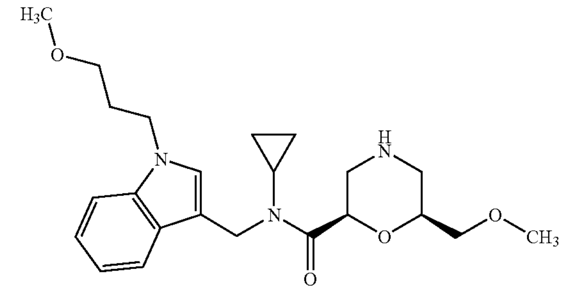 | Property: purified powder<br>APCI-MS m/z: 416[M + H]+ |
| 130 | 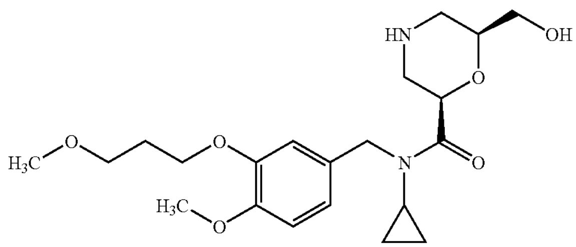 [SMILES: COCCCOc1cc(CN(C(=O)[C@H]2CNC[C@@H](CO)O2)C2CC2)ccc1OC] | hydrochloride<br>Property: purified powder<br>APCI-MS m/z: 409[M + H]+ |
| 131 | 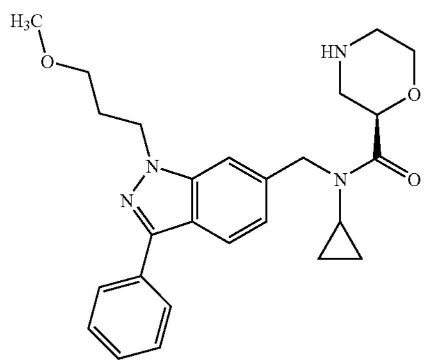 | hydrochloride<br>Property: purified powder<br>APCI-MS m/z: 499[M + H]+ |
| 132 | 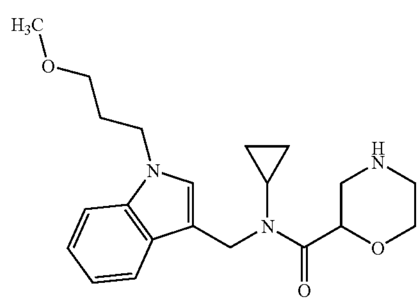 [SMILES: COCCCn1cc(CN(C(=O)C2CNCCO2)C2CC2)c2ccccc21] | Property: purified viscous oil<br>APCI-MS m/z: 372[M + H]+ |
| 133 | 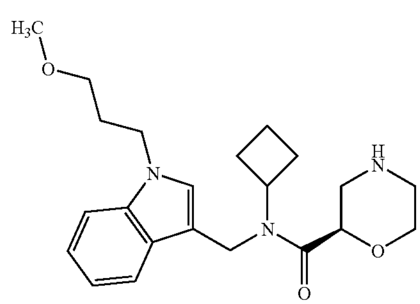 [SMILES: COCCCn1cc(CN(C(=O)[C@H]2CNCCO2)C2CCC2)c2ccccc21] | Property: purified viscous oil<br>APCI-MS m/z: 386[M + H]+ |

TABLE 4-continued

| No. of Examples | Structure | Properties |
| --- | --- | --- |
| 134 | 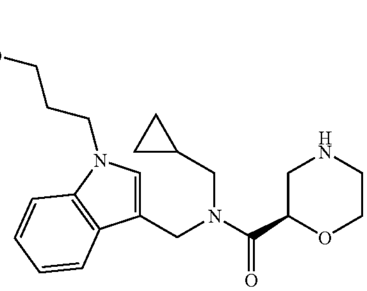 | Property: purified viscous oil<br>APCI-MS m/z: 386[M + H]+ |
| 135 | 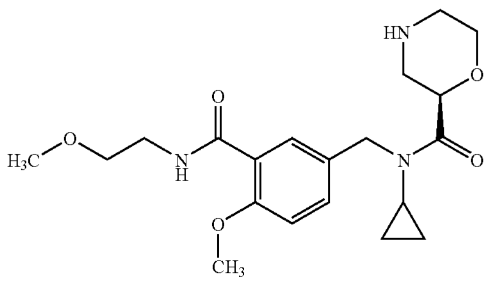 [SMILES: COCCNC(=O)c1cc(CN(C(=O)[C@H]2CNCCO2)C2CC2)ccc1OC] | hydrochloride<br>Property: purified powder<br>APCI-MS m/z: 392[M + H]+ |
| 136 | 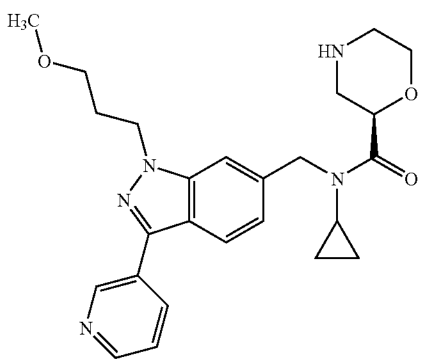 | dihydrochloride<br>Property: purified powder<br>APCI-MS m/z: 450[M + H]+ |
| 137 | 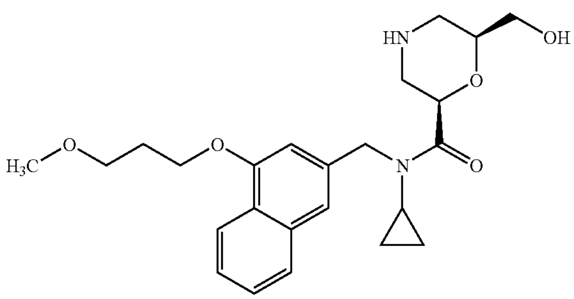 [SMILES: COCCCOc1cc(CN(C(=O)[C@H]2CNC[C@@H](CO)O2)C2CC2)cc2ccccc12] | hydrochloride<br>Property: purified powder<br>APCI-MS m/z: 429[M + H]+ |
| 138 | 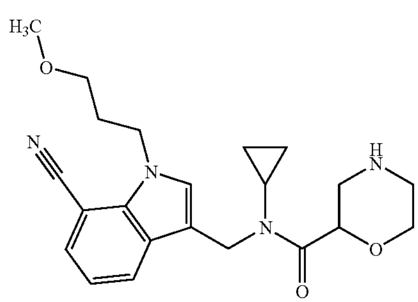 [SMILES: COCCCn1cc(CN(C(=O)C2CNCCO2)C2CC2)c2cccc(C#N)c21] | Property: purified powder<br>APCI-MS m/z: 397[M + H]+ |

TABLE 4-continued
| No. of Examples | Structure | Properties |
|---|---|---|
| 139 | 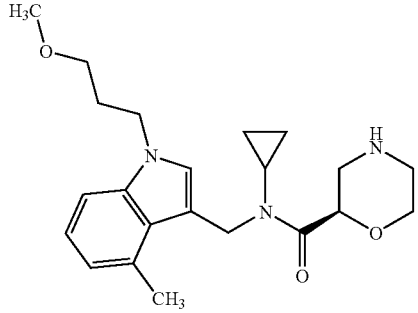 [SMILES: COCCCn1cc(CN(C(=O)[C@H]2CNCCO2)C2CC2)c2c(C)cccc21] | Property: purified viscous oil<br>APCI-MS m/z: 386[M + H]+ |
| 140 | 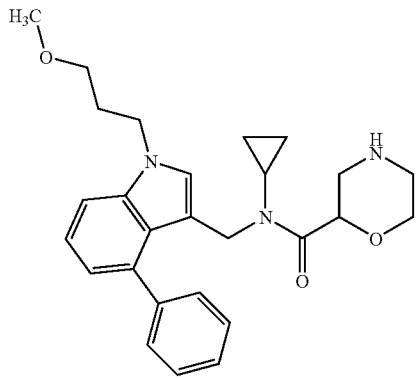 [SMILES: COCCCn1cc(CN(C(=O)C2CNCCO2)C2CC2)c2c(-c3ccccc3)cccc21] | Property: purified viscous oil<br>APCI-MS m/z: 448[M + H]+ |
| 141 | 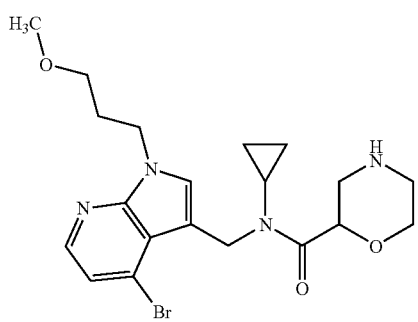 [SMILES: COCCCn1cc(CN(C(=O)C2CNCCO2)C2CC2)c2c(Br)ccnc21] | Property: purified viscous oil<br>APCI-MS m/z: 451/453[M + H]+ |
| 142 | 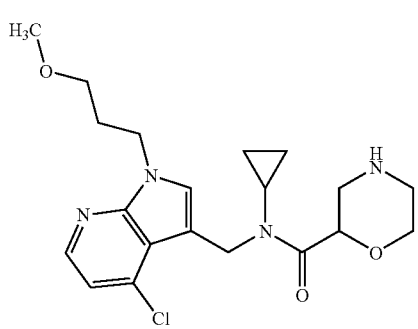 [SMILES: COCCCn1cc(CN(C(=O)C2CNCCO2)C2CC2)c2c(Cl)ccnc21] | Property: purified viscous oil<br>APCI-MS m/z: 407/409[M + H]+ |

TABLE 4-continued

| No. of Examples | Structure | Properties |
| --- | --- | --- |
| 143 | 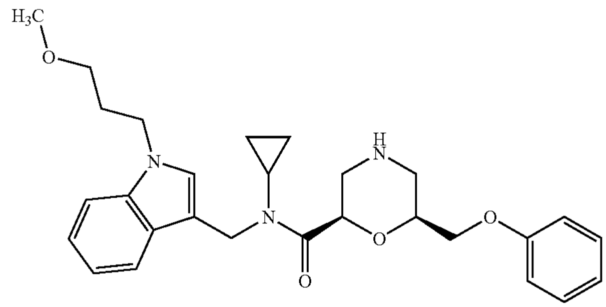 [SMILES: COCCCn1cc(CN(C(=O)[C@H]2CNC[C@@H](COc3ccccc3)O2)C2CC2)c2ccccc21] | Property: purified viscous oil<br>APCI-MS m/z: 478[M + H]+ |
| 144 | 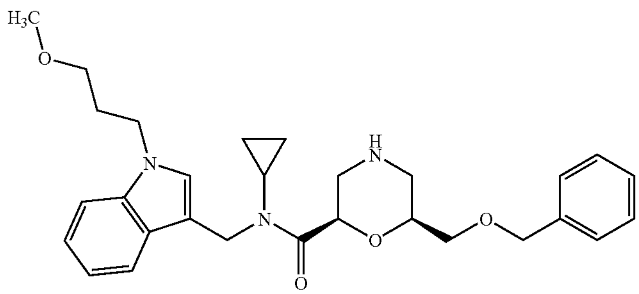 [SMILES: COCCCn1cc(CN(C(=O)[C@H]2CNC[C@@H](COCc3ccccc3)O2)C2CC2)c2ccccc21] | Property: purified viscous oil<br>APCI-MS m/z: 492[M + H]+ |
| 145 | 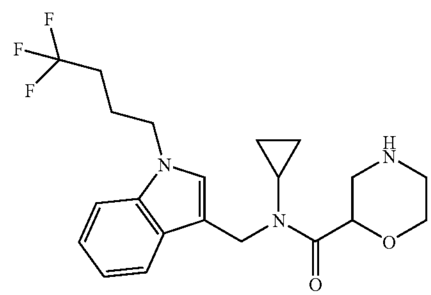 [SMILES: O=C(C1CNCCO1)N(Cc1cn(CCCC(F)(F)F)c2ccccc12)C1CC1] | Property: purified viscous oil<br>APCI-MS m/z: 410[M + H]+ |
| 146 | 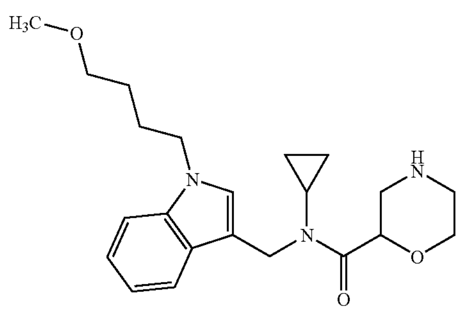 [SMILES: COCCCCn1cc(CN(C(=O)C2CNCCO2)C2CC2)c2ccccc21] | Property: purified viscous oil<br>APCI-MS m/z: 386[M + H]+ |
| 147 | 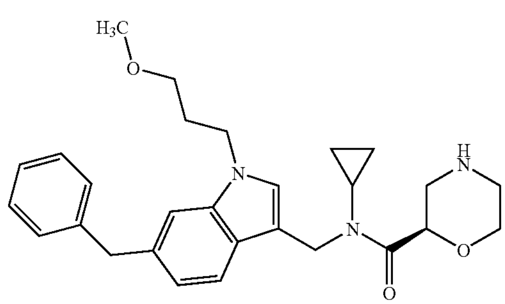 [SMILES: COCCCn1cc(CN(C(=O)[C@H]2CNCCO2)C2CC2)c2ccc(Cc3ccccc3)cc21] | Property: purified viscous oil<br>APCI-MS m/z: 462[M + H]+ |

TABLE 4-continued
| No. of Examples | Structure | Properties |
|---|---|---|
| 148 | 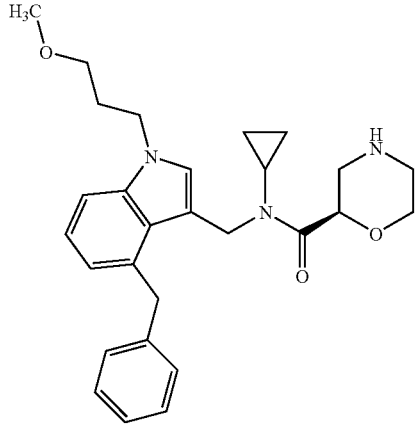 [SMILES: COCCCn1cc(CN(C(=O)[C@H]2CNCCO2)C2CC2)c2c(Cc3ccccc3)cccc21] | Property: purified viscous oil<br>APCI-MS m/z: 462[M + H]+ |
| 149 | 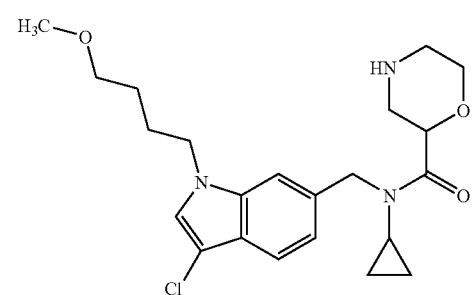 | Property: purified viscous oil<br>APCI-MS m/z: 420/422[M + H]+ |
| 150 | 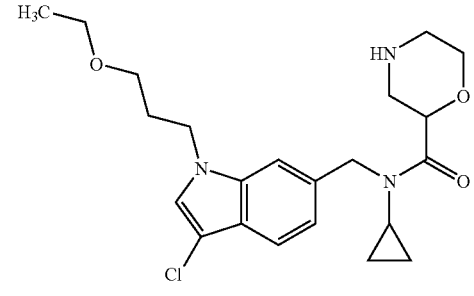 [SMILES: CCOCCCn1cc(Cl)c2ccc(CN(C(=O)C3CNCCO3)C3CC3)cc21] | Property: purified viscous oil<br>APCI-MS m/z: 420/422[M + H]+ |
| 151 | 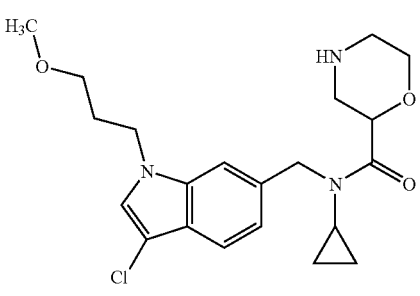 [SMILES: COCCCn1cc(Cl)c2ccc(CN(C(=O)C3CNCCO3)C3CC3)cc21] | Property: purified viscous oil<br>APCI-MS m/z: 406/408[M + H]+ |

TABLE 4-continued

| No. of Examples | Structure | Properties |
|---|---|---|
| 152 | 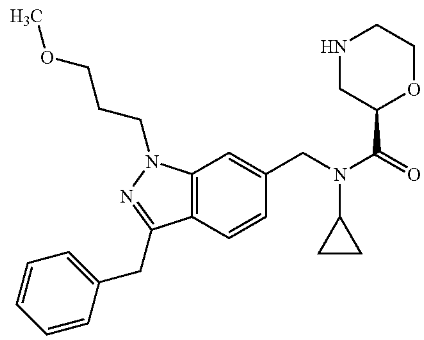 | hydrochloride<br>Property: purified powder<br>APCI-MS m/z: 463[M + H]+ |
| 153 | 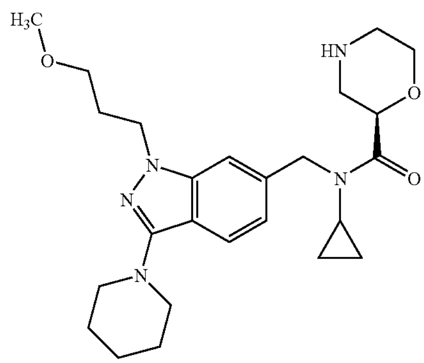 [SMILES: COCCCn1nc(N2CCCCC2)c2ccc(CN(C(=O)[C@H]3CNCCO3)C3CC3)cc21] | dihydrochloride<br>Property: purified powder<br>APCI-MS m/z: 456[M + H]+ |
| 154 | 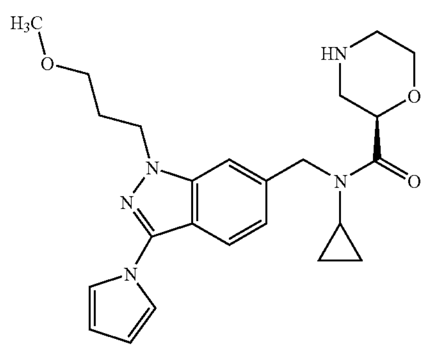 [SMILES: COCCCn1nc(-n2cccc2)c2ccc(CN(C(=O)[C@H]3CNCCO3)C3CC3)cc21] | hydrochloride<br>Property: purified powder<br>APCI-MS m/z: 438[M + H]+ |
| 155 | 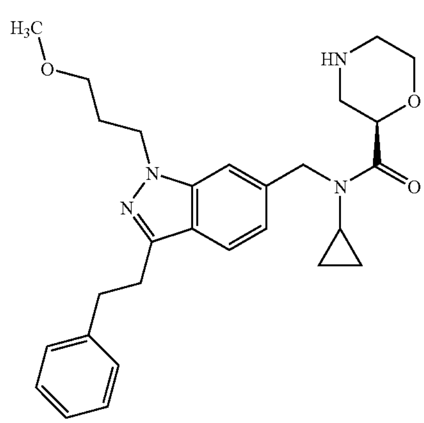 [SMILES: COCCCn1nc(CCc2ccccc2)c2ccc(CN(C(=O)[C@H]3CNCCO3)C3CC3)cc21] | hydrochloride<br>Property: purified, powder<br>APCI-MS m/z: 477[M + H]+ |

TABLE 4-continued

| No. of Examples | Structure | Properties |
|---|---|---|
| 156 | 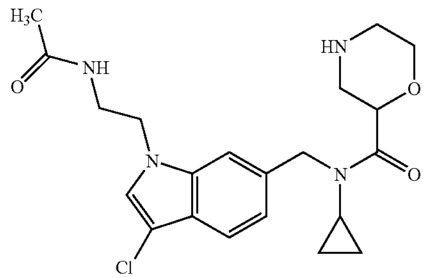 [SMILES: CC(=O)NCCn1cc(Cl)c2ccc(CN(C(=O)C3CNCCO3)C3CC3)cc21] | Property: purified viscous oil<br>APCI-MS m/z: 417/419[M + H]+ |
| 157 | 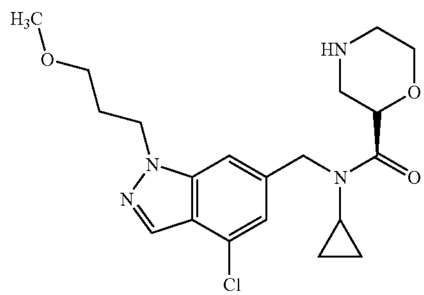 | hydrochloride<br>Property: purified powder<br>APCI-MS m/z: 407/409[M + H]+ |
| 158 | 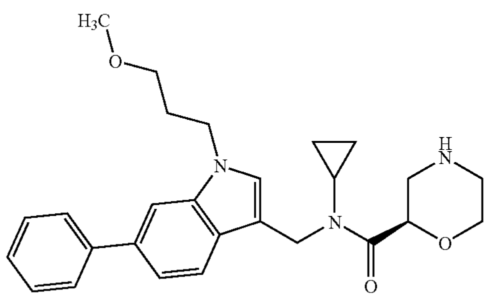 [SMILES: COCCCn1cc(CN(C(=O)[C@H]2CNCCO2)C2CC2)c2ccc(-c3ccccc3)cc21] | Property: purified viscous oil<br>APCI-MS m/z: 448[M + H]+ |
| 159 | 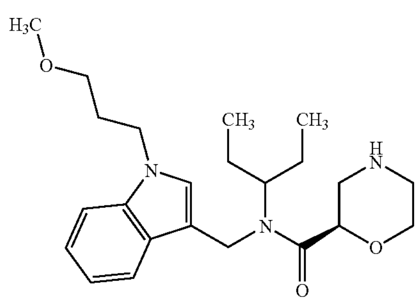 [SMILES: CCC(CC)N(Cc1cn(CCCOC)c2ccccc12)C(=O)[C@H]1CNCCO1] | Property: purified viscous oil<br>APCI-MS m/z: 402[M + H]+ |
| 160 | 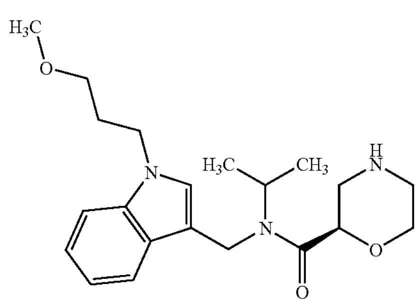 [SMILES: COCCCn1cc(CN(C(=O)[C@H]2CNCCO2)C(C)C)c2ccccc21] | Property: purified viscous oil<br>APCI-MS m/z: 374[M + H]+ |

TABLE 4-continued

| No. of Examples | Structure | Properties |
|---|---|---|
| 161 | 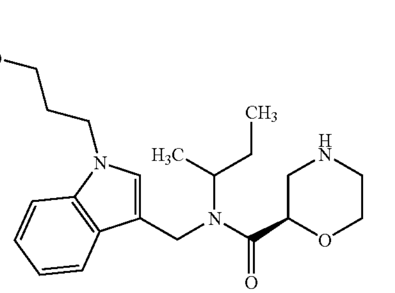 | Property: purified viscous oil<br>APCI-MS m/z: 388[M + H]+ |
| 162 | 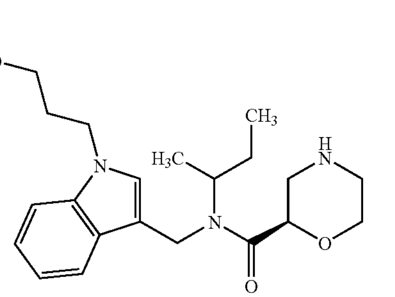 | Property: purified viscous oil<br>APCI-MS m/z: 388[M + H]+ |
| 163 | 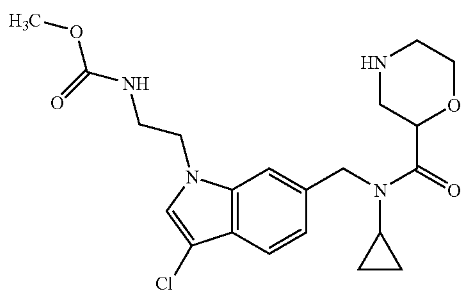 [SMILES: COC(=O)NCCn1cc(Cl)c2ccc(CN(C(=O)C3CNCCO3)C3CC3)cc21] | Property: purified viscous oil<br>APCI-MS m/z: 435/437[M + H]+ |
| 164 | 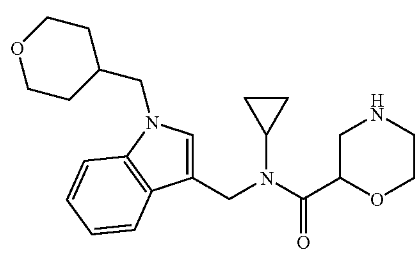 [SMILES: O=C(C1CNCCO1)N(Cc1cn(CC2CCOCC2)c2ccccc12)C1CC1] | Property: purified viscous oil<br>APCI-MS m/z: 398[M + H]+ |
| 165 | 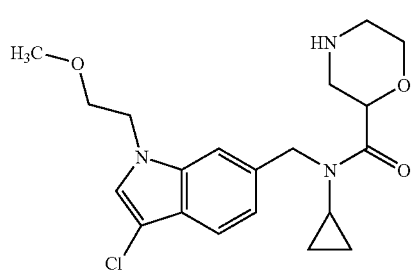 [SMILES: COCCn1cc(Cl)c2ccc(CN(C(=O)C3CNCCO3)C3CC3)cc21] | Property: purified viscous oil<br>APCI-MS m/z: 392/394[M + H]+ |

TABLE 4-continued

| No. of Examples | Structure | Properties |
|---|---|---|
| 166 | 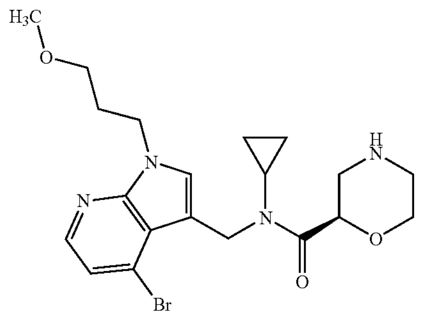 | Property: purified viscous oil<br>APCI-MS<br>m/z: 451/453/449[M + H]+ |
| 167 | 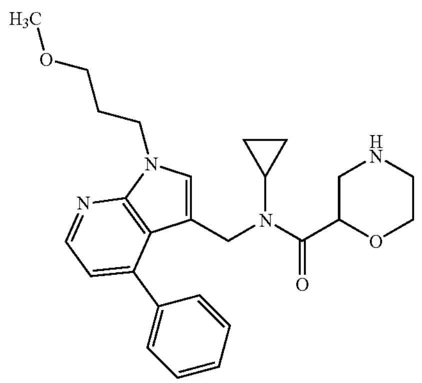 [SMILES: COCCCn1cc(CN(C(=O)C2CNCCO2)C2CC2)c2c(-c3ccccc3)ccnc21] | Property: purified viscous oil<br>APCI-MS m/z: [M + H]+ |
| 168 | 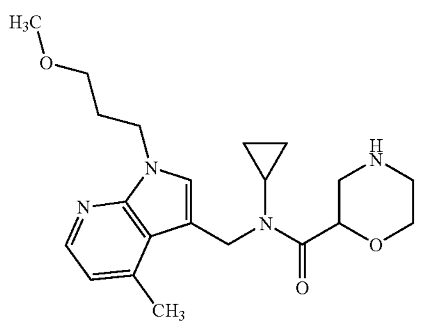 [SMILES: COCCCn1cc(CN(C(=O)C2CNCCO2)C2CC2)c2c(C)ccnc21] | Property: purified viscous oil<br>APCI-MS m/z: 387[M + H]+ |
| 169 | 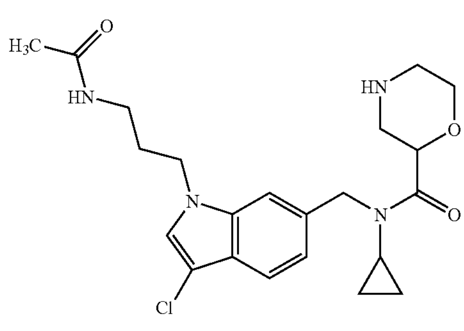 [SMILES: CC(=O)NCCCn1cc(Cl)c2ccc(CN(C(=O)C3CNCCO3)C3CC3)cc21] | Property: purified powder<br>APCI-MS m/z: 433/435[M + H]+ |

TABLE 4-continued

| No. of Examples | Structure | Properties |
|---|---|---|
| 170 | 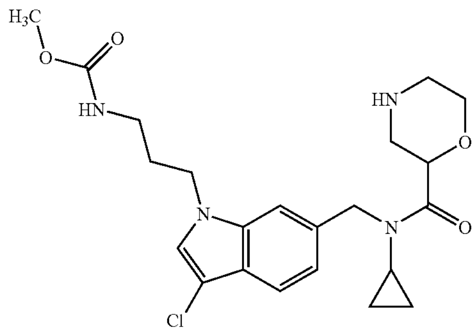 [SMILES: COC(=O)NCCCn1cc(Cl)c2ccc(CN(C(=O)C3CNCCO3)C3CC3)cc21] | Property: purified powder<br>APCI-MS m/z: 449/451[M + H]+ |
| 171 | 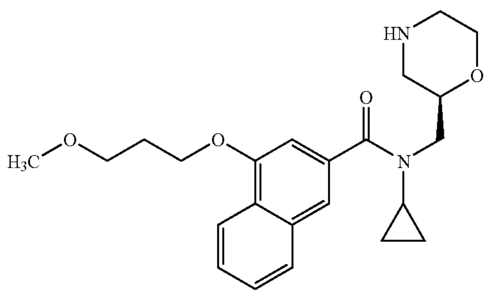 [SMILES: COCCCOc1cc(C(=O)N(C[C@H]2CNCCO2)C2CC2)cc2ccccc12] | hydrochloride<br>Property: purified powder<br>APCI-MS m/z: 399[M + H]+ |
| 172 | 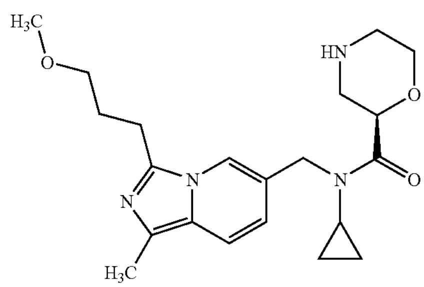 [SMILES: COCCCc1nc(C)c2ccc(CN(C(=O)[C@H]3CNCCO3)C3CC3)cn12] | 2 hydrochloride<br>Property: purified powder<br>APCI-MS m/z: 387[M + H]+ |
| 173 | 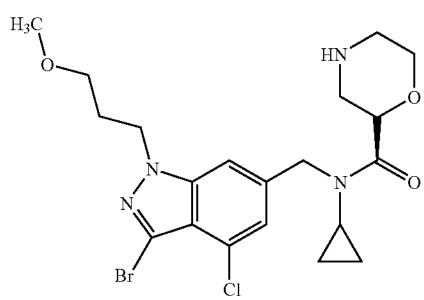 | hydrochloride<br>Property: purified powder<br>APCI-MS m/z: 485/487[M + H]+ |
| 174 | 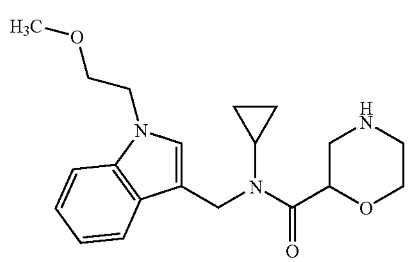 [SMILES: COCCn1cc(CN(C(=O)C2CNCCO2)C2CC2)c2ccccc21] | Property: purified viscous oil<br>APCL-MS m/z: 358[M + H]+ |

| No. of Examples | Structure | Properties |
|---|---|---|
| 175 | 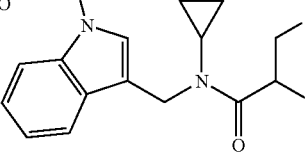 | Property: purified powder<br>APCI-MS m/z: 371[M + H]+ |
| 176 | 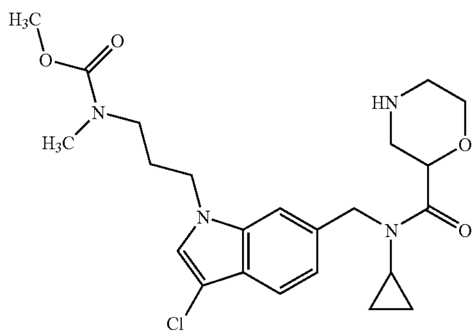 [SMILES: COC(=O)N(C)CCCn1cc(Cl)c2ccc(CN(C(=O)C3CNCCO3)C3CC3)cc21] | Property: purified viscous oil<br>APCI-MS m/z: 463/465[M + H]+ |
| 177 | 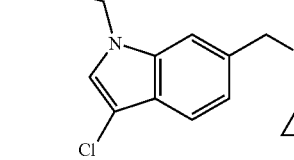 | Property: purified viscous oil<br>APCI-MS m/z: 448/450[M + H]+ |
| 178 | 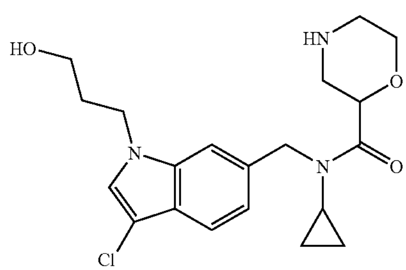 [SMILES: O=C(C1CNCCO1)N(Cc1ccc2c(Cl)cn(CCCO)c2c1)C1CC1] | Property: purified viscous oil<br>APCI-MS m/z: 392/34[M + H]+ |
| 179 | 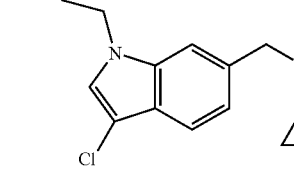 | Property: purified viscous oil<br>APCI-MS m/z: 441[M + H]+ |

TABLE 4-continued
| No. of Examples | Structure | Properties |
|---|---|---|
| 180 | 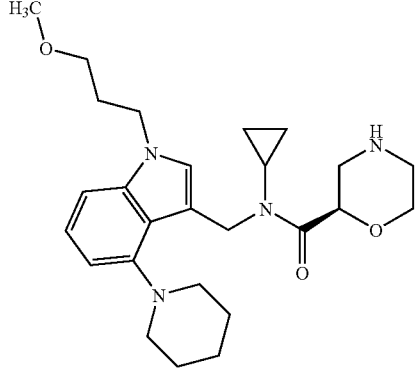 | Property: purified viscous oil<br>APCI-MS m/z: 455[M + H]+ |
| 181 | 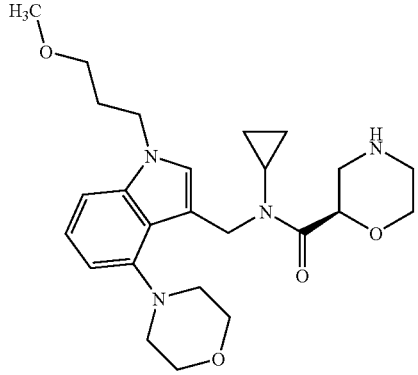 [SMILES: COCCCn1cc(CN(C(=O)[C@H]2CNCCO2)C2CC2)c2c(N3CCOCC3)cccc21] | Property: purified viscous oil<br>APCI-MS m/z: 457[M + H]+ |
| 182 | 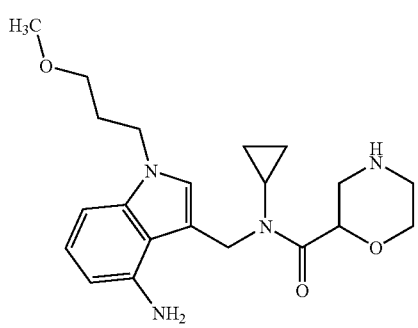 [SMILES: COCCCn1cc(CN(C(=O)C2CNCCO2)C2CC2)c2c(N)cccc21] | Property: purified powder<br>APCI-MS m/z: 388[M + H]+ |
| 183 | 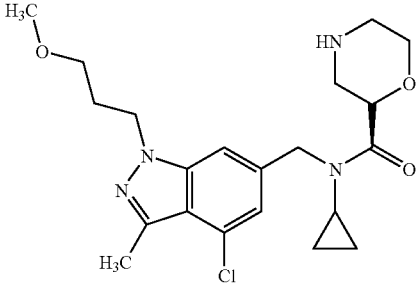 | hydrochloride<br>Property: purified powder<br>APCI-MS m/z: 421/423[M + H]+ |

TABLE 4-continued
| No. of Examples | Structure | Properties |
|---|---|---|
| 184 | 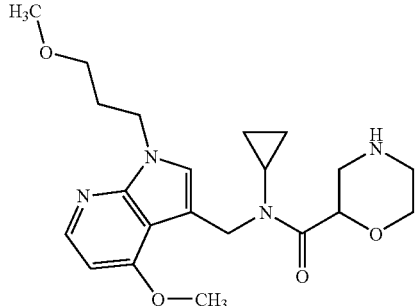 | dihydrochloride<br>Property: purified powder<br>APCI-MS m/z: 403[M + H]+ |
| 185 | 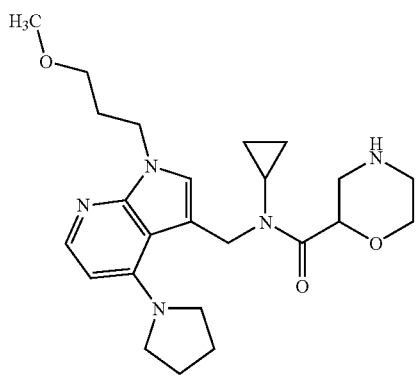 [SMILES: COCCCn1cc(CN(C(=O)C2CNCCO2)C2CC2)c2c(N3CCCC3)ccnc21] | dihydrochloride<br>Property: purified viscous oil<br>APCI-MS m/z: 442[M + H]+ |
| 186 | 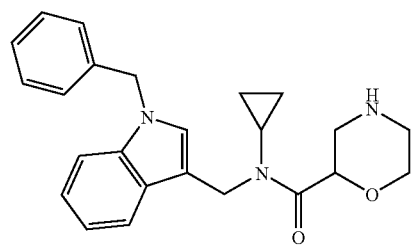 [SMILES: O=C(C1CNCCO1)N(Cc1cn(Cc2ccccc2)c2ccccc12)C1CC1] | Property: purified viscous oil<br>APCI-MS m/z: 390[M + H]+ |
| 187 | 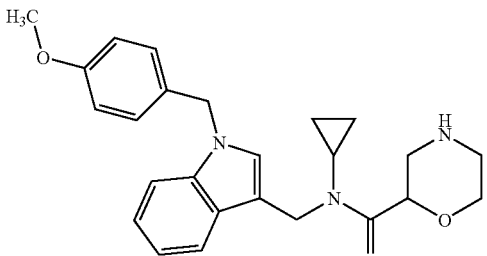 | Property: purified viscous oil<br>APCI-MS m/z: 420[M + H]+ |
| 188 | 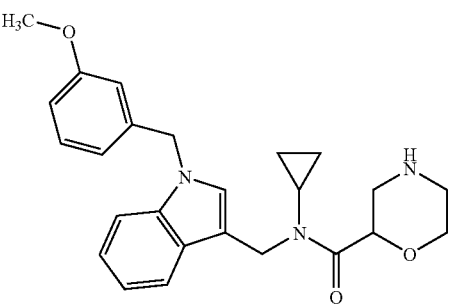 [SMILES: COc1cccc(Cn2cc(CN(C(=O)C3CNCCO3)C3CC3)c3ccccc32)c1] | Property: purified viscous oil<br>APCI-MS m/z: 420[M + H]+ |

TABLE 4-continued
| No. of Examples | Structure | Properties |
|---|---|---|
| 189 | 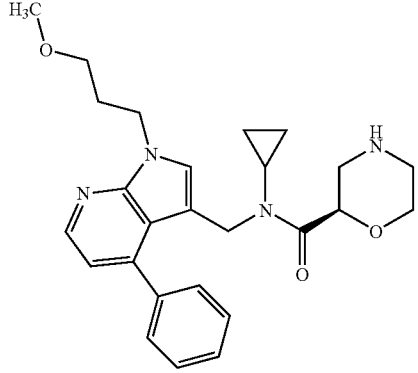 [SMILES: COCCCn1cc(CN(C(=O)[C@H]2CNCCO2)C2CC2)c2c(-c3ccccc3)ccnc21] | Property: purified viscous oil<br>APCI-MS m/z: 449[M + H]+ |
| 190 | 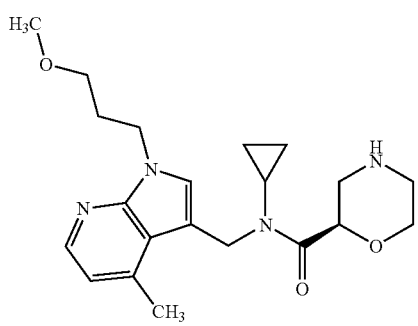 [SMILES: COCCCn1cc(CN(C(=O)[C@H]2CNCCO2)C2CC2)c2c(C)ccnc21] | Property: purified viscous oil<br>APCI-MS m/z: 387[M + H]+ |
| 191 | 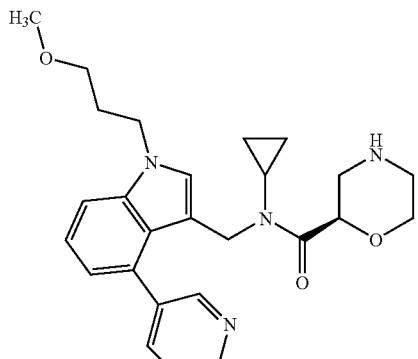 | Property: purified viscous oil<br>APCI-MS m/z: 449[M + H]+ |
| 192 | 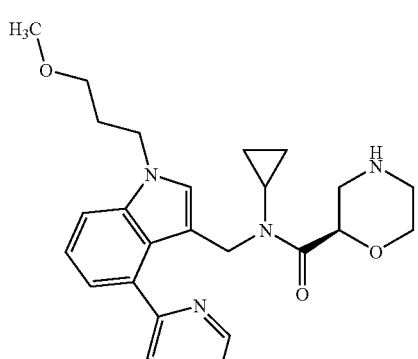 | Property: purified viscous oil<br>APCI-MS m/z: 449[M + H]+ |

TABLE 4-continued

| No. of Examples | Structure | Properties |
|---|---|---|
| 193 | 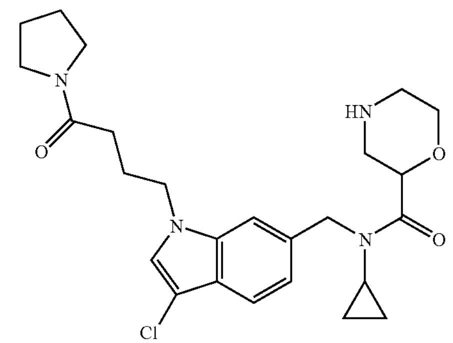 [SMILES: O=C(CCCn1cc(Cl)c2ccc(CN(C(=O)C3CNCCO3)C3CC3)cc21)N1CCCC1] | Property: purified viscous oil<br>APCI-MS m/z: 473/475[M + H]+ |
| 194 | 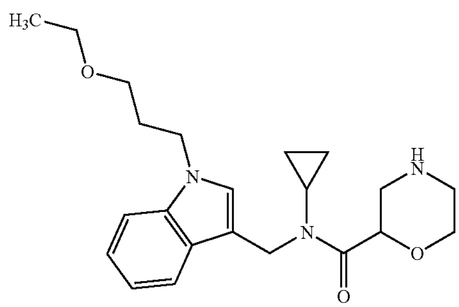 [SMILES: CCOCCCn1cc(CN(C(=O)C2CNCCO2)C2CC2)c2ccccc21] | Property: purified viscous oil<br>APCI-MS m/z: 386[M + H]+ |
| 195 | 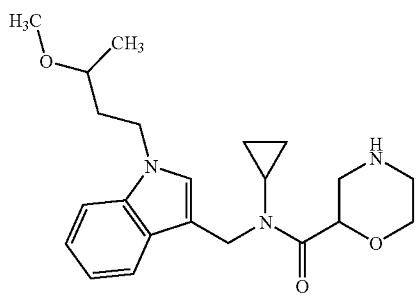 [SMILES: COC(C)CCn1cc(CN(C(=O)C2CNCCO2)C2CC2)c2ccccc21] | Property: purified viscous oil<br>APCI-MS m/z: 386[M + H]+ |
| 196 | 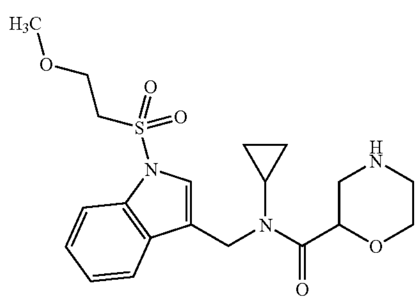 [SMILES: COCCS(=O)(=O)n1cc(CN(C(=O)C2CNCCO2)C2CC2)c2ccccc21] | Property: purified viscous oil<br>APCI-MS m/z: 422[M + H]+ |
| 197 | 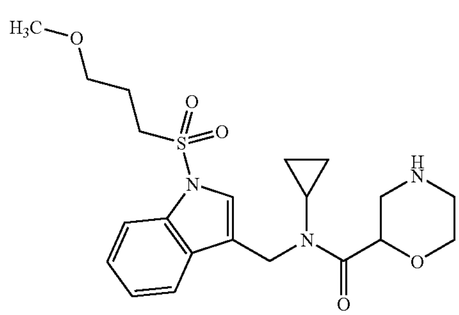 [SMILES: COCCCS(=O)(=O)n1cc(CN(C(=O)C2CNCCO2)C2CC2)c2ccccc21] | Property: purified viscous oil<br>APCI-MS m/z: 436[M + H]+ |

| No. of Examples | Structure | Properties |
|---|---|---|
| 198 | 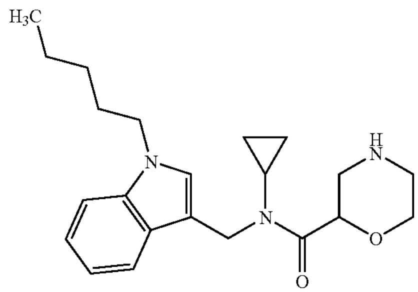 [SMILES: CCCCCn1cc(CN(C(=O)C2CNCCO2)C2CC2)c2ccccc21] | Property: purified viscous oil<br>APCI-MS m/z: 370[M + H]+ |
| 199 | 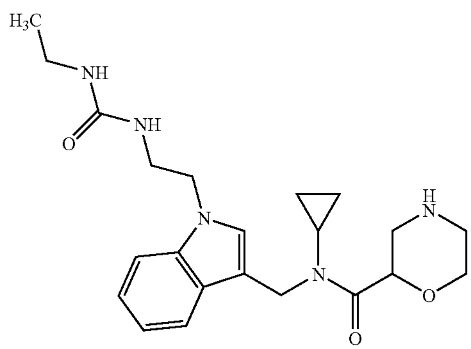 [SMILES: CCNC(=O)NCCn1cc(CN(C(=O)C2CNCCO2)C2CC2)c2ccccc21] | Property: purified powder<br>APCI-MS m/z: 448/450[M + H]+ |
| 200 | 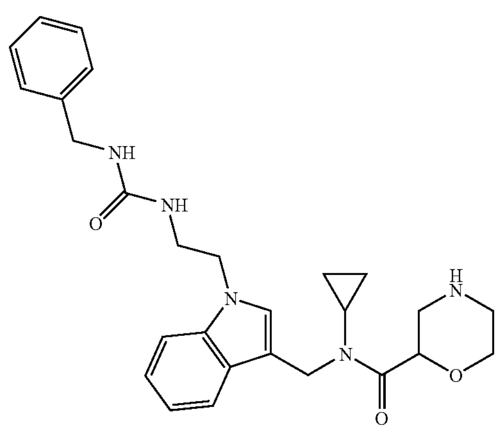 [SMILES: O=C(NCCn1cc(CN(C(=O)C2CNCCO2)C2CC2)c2ccccc21)NCc1ccccc1] | Property: purified powder<br>APCI-MS m/z: 510/512[M + H]+ |
| 201 | 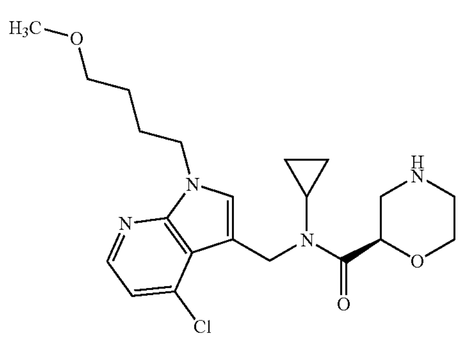 [SMILES: COCCCCn1cc(CN(C(=O)[C@H]2CNCCO2)C2CC2)c2c(Cl)ccnc21] | Property: purified viscous oil<br>APCI-MS: m/z: 421/423[M + H]+ |

TABLE 4-continued

| No. of Examples | Structure | Properties |
| --- | --- | --- |
| 202 | 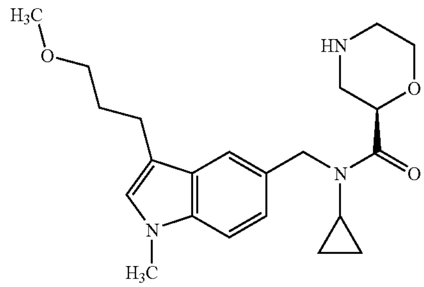 [SMILES: COCCCc1cn(C)c2ccc(CN(C(=O)[C@H]3CNCCO3)C3CC3)cc12] | Property: purified oil<br>APCI-MS m/z: 386[M + H]+ |
| 203 | 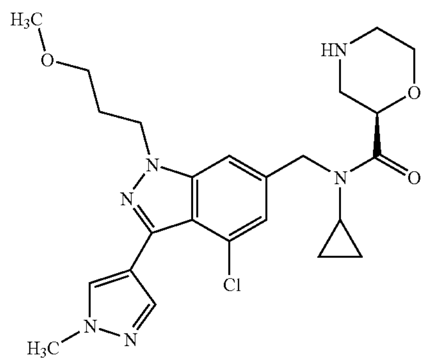 [SMILES: COCCCn1nc(-c2cnn(C)c2)c2c(Cl)cc(CN(C(=O)[C@H]3CNCCO3)C3CC3)cc21] | hydrochloride<br>Property: purified powder<br>APCI-MS m/z: 487/489[M + H]+ |
| 204 | 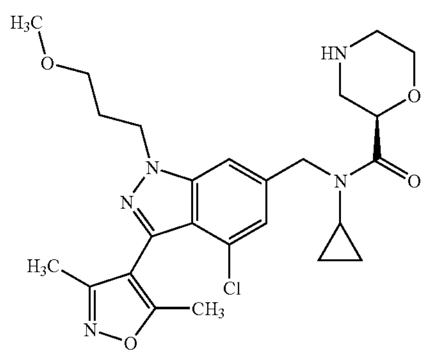 [SMILES: COCCCn1nc(-c2c(C)noc2C)c2c(Cl)cc(CN(C(=O)[C@H]3CNCCO3)C3CC3)cc21] | hydrochloride<br>Property: purified powder<br>APCI-MS m/z: 502/504[M + H]+ |
| 205 | 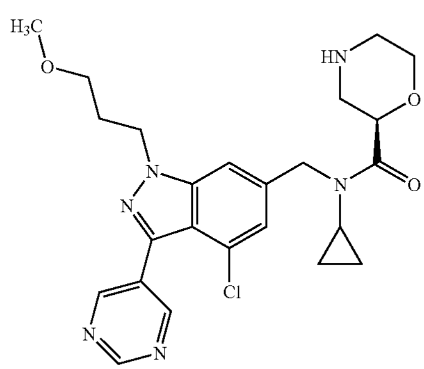 [SMILES: COCCCn1nc(-c2cncnc2)c2c(Cl)cc(CN(C(=O)[C@H]3CNCCO3)C3CC3)cc21] | hydrochloride<br>Property: purified powder<br>APCI-MS m/z: 485/487[M + H]+ |

TABLE 4-continued

| No. of Examples | Structure | Properties |
|---|---|---|
| 206 | 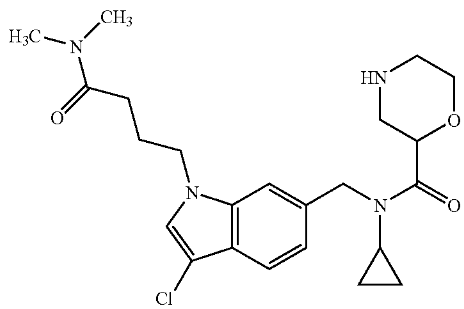 [SMILES: CN(C)C(=O)CCCn1cc(Cl)c2ccc(CN(C(=O)C3CNCCO3)C3CC3)cc21] | Property: purified viscous oil<br>APCI-MS m/z: 447/449[M + H]+ |
| 207 | 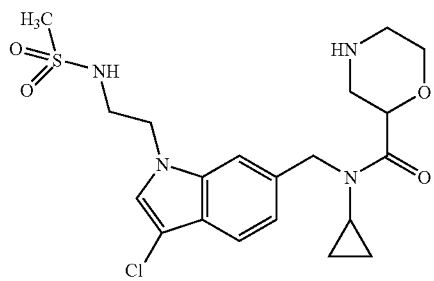 [SMILES: CS(=O)(=O)NCCn1cc(Cl)c2ccc(CN(C(=O)C3CNCCO3)C3CC3)cc21] | Property: purified powder<br>APCI-MS m/z: 455/457[M + H]+ |
| 208 | 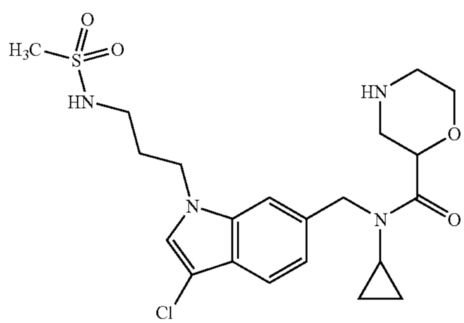 [SMILES: CS(=O)(=O)NCCCn1cc(Cl)c2ccc(CN(C(=O)C3CNCCO3)C3CC3)cc21] | Property: purified viscous oil<br>APCI-MS m/z: 469/471[M + H]+ |
| 209 | 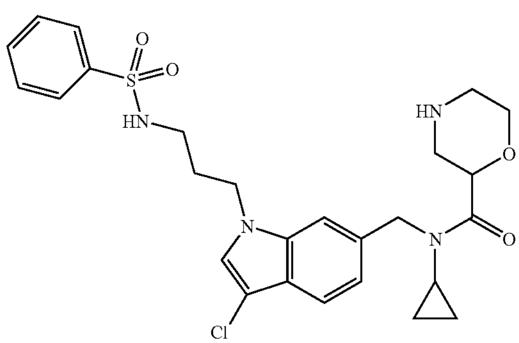 [SMILES: O=C(C1CNCCO1)N(Cc1ccc2c(Cl)cn(CCCNS(=O)(=O)c3ccccc3)c2c1)C1CC1] | Property: purified viscous oil<br>APCI-MS m/z: 531/533[M + H]+ |
| 210 | 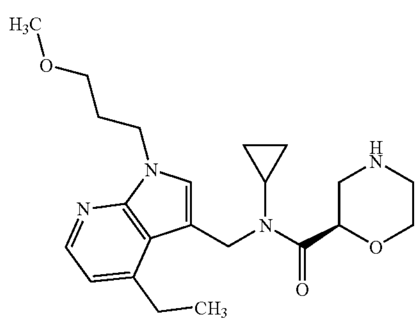 [SMILES: CCc1ccnc2c1c(CN(C(=O)[C@H]1CNCCO1)C1CC1)cn2CCCOC] | Property: purified viscous oil<br>APCI-MS m/z: 401[M + H]+ |

TABLE 4-continued

| No. of Examples | Structure | Properties |
|---|---|---|
| 211 | 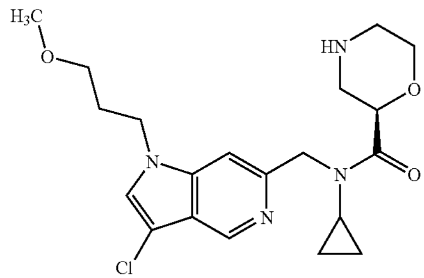 [SMILES: COCCCn1cc(Cl)c2cnc(CN(C(=O)[C@H]3CNCCO3)C3CC3)cc21] | Property: purified oil<br>APCI-MS m/z: 407/409[M + H]+ |
| 212 | 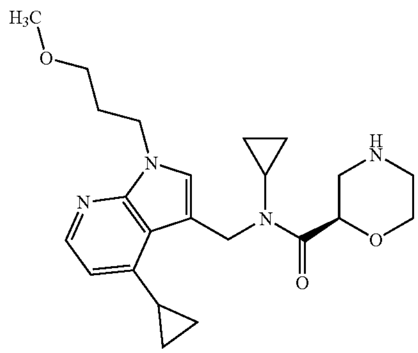 [SMILES: COCCCn1cc(CN(C(=O)[C@H]2CNCCO2)C2CC2)c2c(C3CC3)ccnc21] | Property: purified viscous oil<br>APCL-MS m/z: 413[M + H]+ |
| 213 | 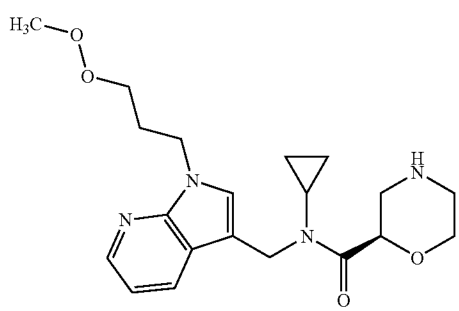 [SMILES: COOCCCn1cc(CN(C(=O)[C@H]2CNCCO2)C2CC2)c2cccnc21] | dihydrochloride<br>Property: purified powder<br>APCI-MS m/z: 387[M + H]+ |
| 214 | 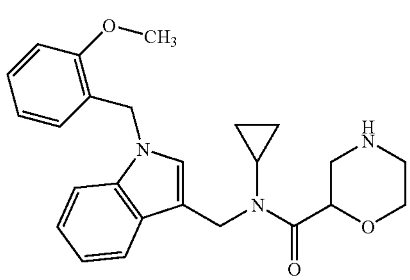 [SMILES: COc1ccccc1Cn1cc(CN(C(=O)C2CNCCO2)C2CC2)c2ccccc21] | Property: purified powder<br>APCI-MS m/z: 420[M + H]+ |
| 215 | 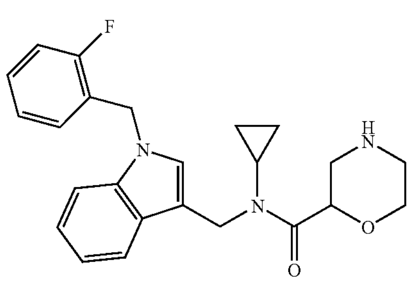 [SMILES: O=C(C1CNCCO1)N(Cc1cn(Cc2ccccc2F)c2ccccc12)C1CC1] | Property: purified viscous oil<br>APCI-MS m/z: 408[M + H]+ |

TABLE 4-continued

| No. of Examples | Structure | Properties |
| --- | --- | --- |
| 216 | 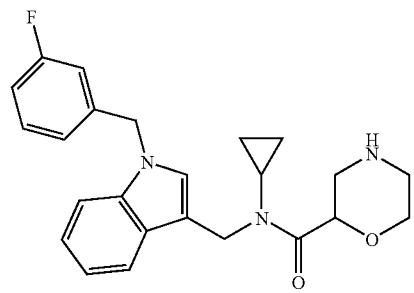 [SMILES: O=C(C1CNCCO1)N(Cc1cn(Cc2cccc(F)c2)c2ccccc12)C1CC1] | Property: purified viscous oil<br>APCI-MS m/z: 408[M + H]+ |
| 217 | 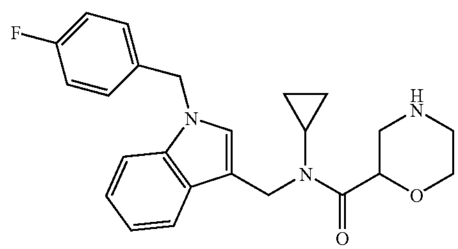 [SMILES: O=C(C1CNCCO1)N(Cc1cn(Cc2ccc(F)cc2)c2ccccc12)C1CC1] | Property: purified viscous oil<br>APCI-MS m/z: 408[M + H]+ |
| 218 | 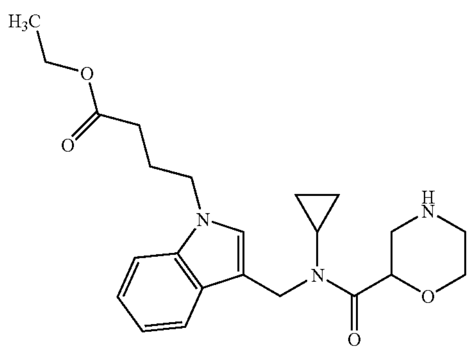 [SMILES: CCOC(=O)CCCn1cc(CN(C(=O)C2CNCCO2)C2CC2)c2ccccc21] | Property: purified viscous oil<br>APCI-MS m/z: 414[M + H]+ |
| 219 | 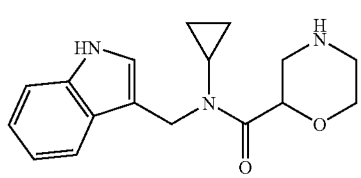 [SMILES: O=C(C1CNCCO1)N(Cc1c[nH]c2ccccc12)C1CC1] | Property: purified powder<br>APCI-MS m/z: 300[M + H]+ |
| 220 | 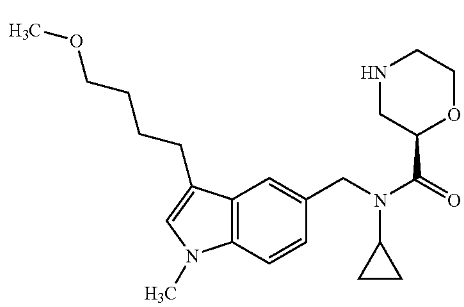 [SMILES: COCCCCc1cn(C)c2ccc(CN(C(=O)[C@H]3CNCCO3)C3CC3)cc12] | Property: purified oil<br>APCI-MS m/z: 400[M + H]+ |

TABLE 4-continued

| No. of Examples | Structure | Properties |
| --- | --- | --- |
| 221 | 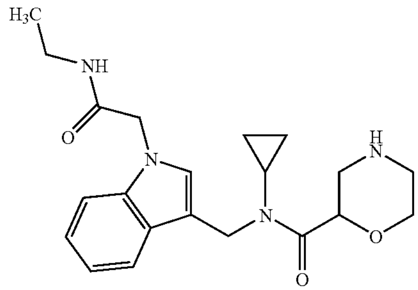 [SMILES: CCNC(=O)Cn1cc(CN(C(=O)C2CNCCO2)C2CC2)c2ccccc21] | Property: purified powder<br>APCI-MS m/z: 385[M + H]+ |
| 222 | 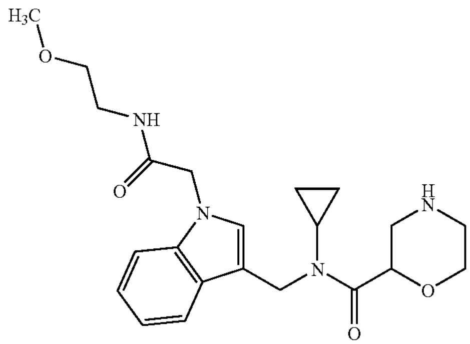 [SMILES: COCCNC(=O)Cn1cc(CN(C(=O)C2CNCCO2)C2CC2)c2ccccc21] | Property: purified viscous oil<br>APCI-MS m/z: 415[M + H]+ |
| 223 | 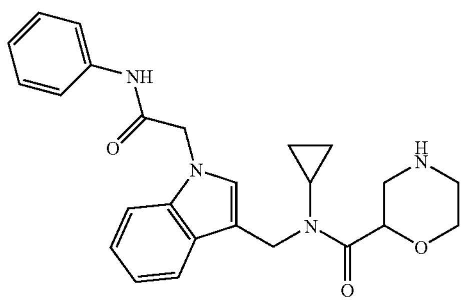 [SMILES: O=C(Cn1cc(CN(C(=O)C2CNCCO2)C2CC2)c2ccccc21)Nc1ccccc1] | Property: purified powder<br>APCI-MS m/z: 433[M + H]+ |
| 224 | 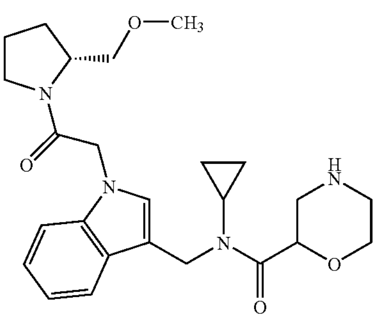 [SMILES: COC[C@H]1CCCN1C(=O)Cn1cc(CN(C(=O)C2CNCCO2)C2CC2)c2ccccc21] | Property: purified viscous oil<br>APCI-MS m/z: 455[M + H]+ |
| 225 | 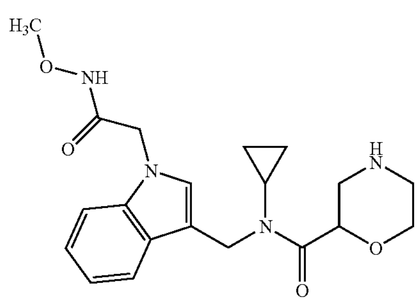 [SMILES: CONC(=O)Cn1cc(CN(C(=O)C2CNCCO2)C2CC2)c2ccccc21] | Property: purified powder<br>APCI-MS m/z: 387[M + H]+ |

TABLE 4-continued

| No. of Examples | Structure | Properties |
|---|---|---|
| 226 | 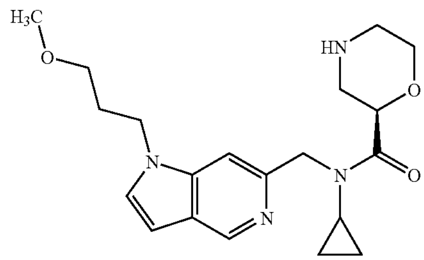 [SMILES: COCCCn1ccc2cnc(CN(C(=O)[C@H]3CNCCO3)C3CC3)cc21] | Property: purified oil<br>APCI-MS m/z: 373[M + H]+ |
| 227 | 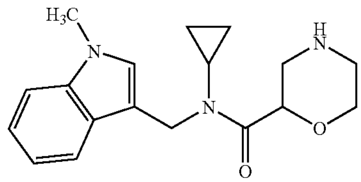 [SMILES: Cn1cc(CN(C(=O)C2CNCCO2)C2CC2)c2ccccc21] | Property: purified viscous oil<br>APCI-MS m/z: 314[M + H]+ |
| 228 | 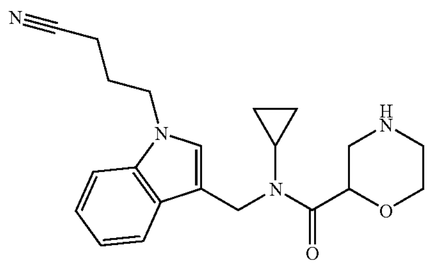 [SMILES: N#CCCCn1cc(CN(C(=O)C2CNCCO2)C2CC2)c2ccccc21] | Property: purified viscous oil<br>APCI-MS m/z: 367[M + H]+ |
| 229 | 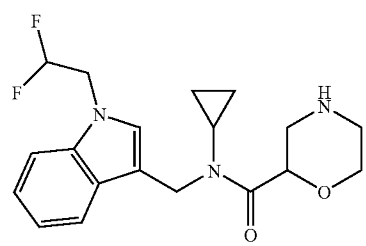 [SMILES: O=C(C1CNCCO1)N(Cc1cn(CC(F)F)c2ccccc12)C1CC1] | Property: purified viscous oil<br>APCI-MS m/z: 364[M + H]+ |
| 230 | 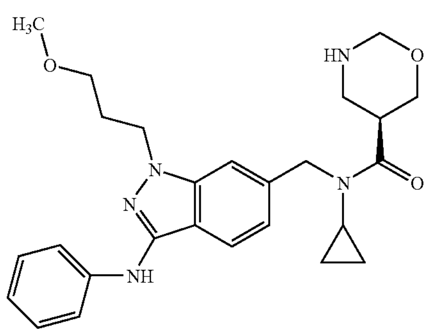 [SMILES: COCCCn1nc(Nc2ccccc2)c2ccc(CN(C(=O)[C@H]3CNCOC3)C3CC3)cc21] | hydrochloride<br>Property: purified powder<br>APCI-MS m/z: 464[M + H]+ |
| 231 | 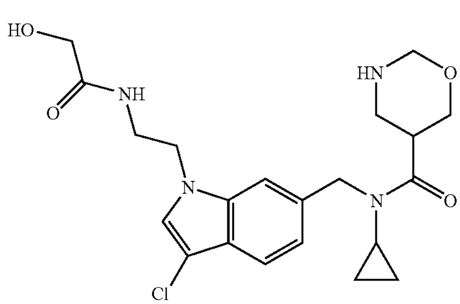 [SMILES: O=C(CO)NCCn1cc(Cl)c2ccc(CN(C(=O)C3CNCOC3)C3CC3)cc21] | Property: purified powder<br>APCI-MS m/z: 435/437[M + H]+ |

TABLE 4-continued
| No. of Examples | Structure | Properties |
|---|---|---|
| 232 | 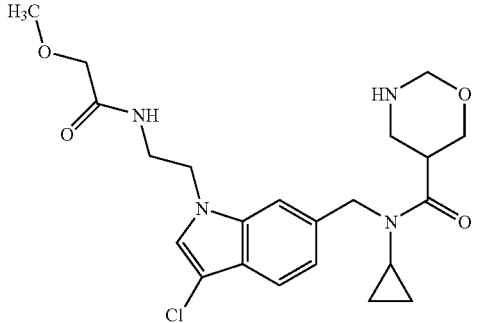 [SMILES: COCC(=O)NCCn1cc(Cl)c2ccc(CN(C(=O)C3CNCOC3)C3CC3)cc21] | Property: purified viscous oil<br>APCI-MS m/z: 449/451[M + H]+ |
| 233 | 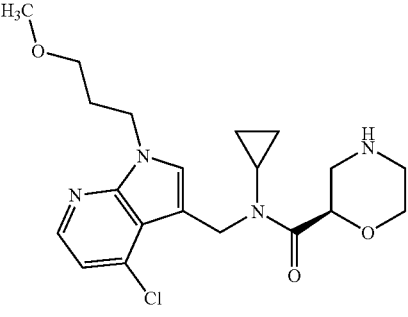 | dihydrochloride<br>Property: purified powder<br>APCI-MS m/z: 407/409[M + H]+ |
| 234 | 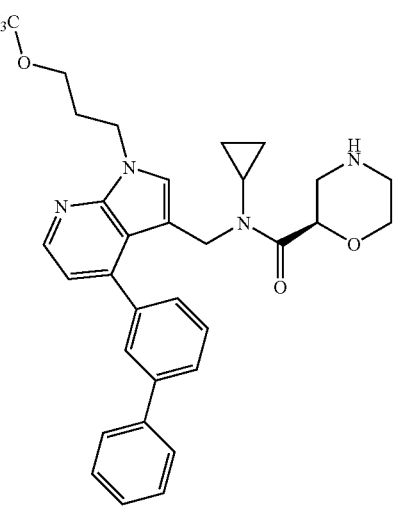 | Property: purified viscous oil<br>APCI-MS m/z: 525[M + H]+ |

TABLE 4-continued
| No. of Examples | Structure | Properties |
|---|---|---|
| 235 | 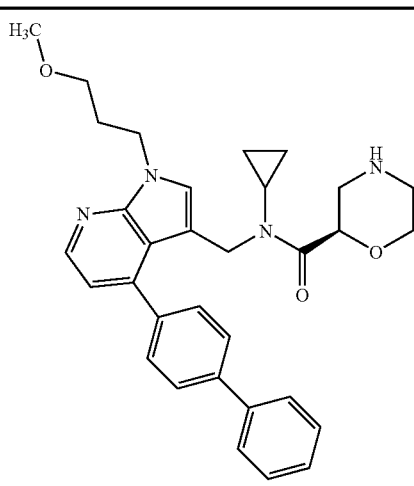 | Property: purified viscous oil<br>APCI-MS m/z: 525[M + H]+ |
| 236 | 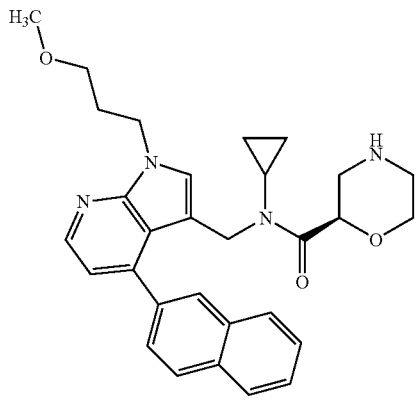 [SMILES: COCCCn1cc(CN(C(=O)[C@H]2CNCCO2)C2CC2)c2c(-c3ccc4ccccc4c3)ccnc21] | Property: purified viscous oil<br>APCI-MS m/z: 499[M + H]+ |
| 237 | 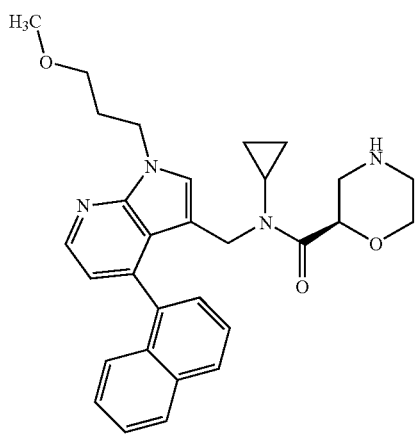 [SMILES: COCCCn1cc(CN(C(=O)[C@H]2CNCCO2)C2CC2)c2c(-c3cccc4ccccc34)ccnc21] | Property: purified viscous oil<br>APCI-MS m/z: 499[M + H]+ |

TABLE 4-continued

| No. of Examples | Structure | Properties |
|---|---|---|
| 239 | 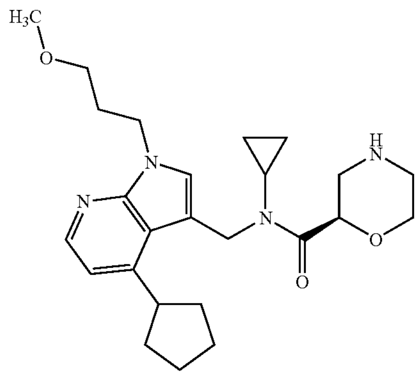 [SMILES: COCCCn1cc(CN(C(=O)[C@H]2CNCCO2)C2CC2)c2c(C3CCCC3)ccnc21] | Property: purified viscous oil<br>APCI-MS m/z: 441[M + H]+ |
| 240 | 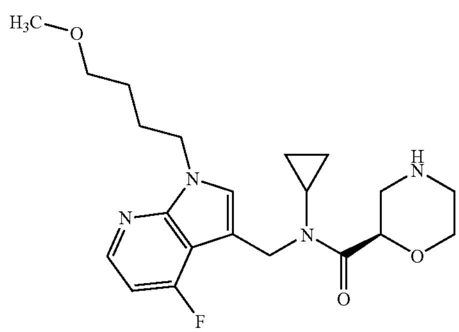 [SMILES: COCCCCn1cc(CN(C(=O)[C@H]2CNCCO2)C2CC2)c2c(F)ccnc21] | Property: purified viscous oil<br>APCI-MS m/z: 405[M + H]+ |
| 241 | 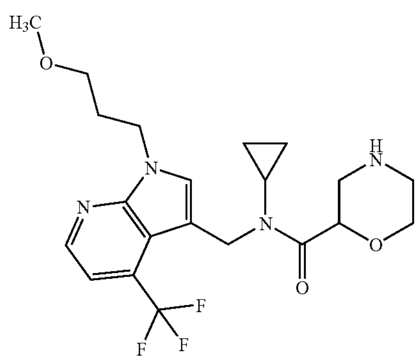 [SMILES: COCCCn1cc(CN(C(=O)C2CNCCO2)C2CC2)c2c(C(F)(F)F)ccnc21] | hydrochloride<br>Property: purified powder<br>APCI-MS m/z: 441[M + H]+ |
| 242 | 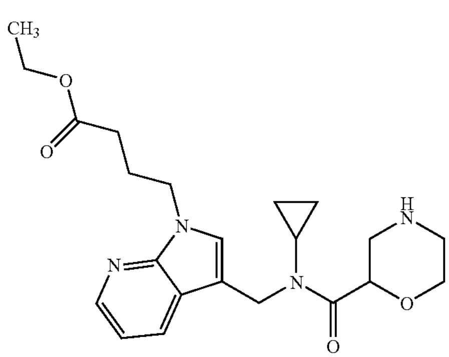 [SMILES: CCOC(=O)CCCn1cc(CN(C(=O)C2CNCCO2)C2CC2)c2cccnc21] | dihydrochloride<br>Property: purified powder<br>APCI-MS m/z: 415[M + H]+ |

TABLE 4-continued

| No. of Examples | Structure | Properties |
|---|---|---|
| 243 | 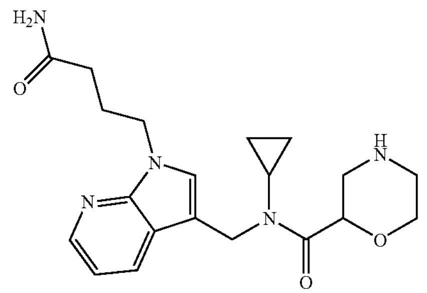 [SMILES: NC(=O)CCCn1cc(CN(C(=O)C2CNCCO2)C2CC2)c2cccnc21] | dihydrochloride<br>Property: purified powder<br>APCI-MS m/z: 386[M + H]+ |
| 244 | 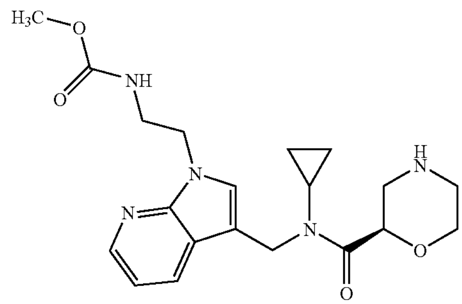 [SMILES: COC(=O)NCCn1cc(CN(C(=O)[C@H]2CNCCO2)C2CC2)c2cccnc21] | dihydrochloride<br>Property: purified powder<br>APCI-MS m/z: 402[M + H]+ |
| 246 | 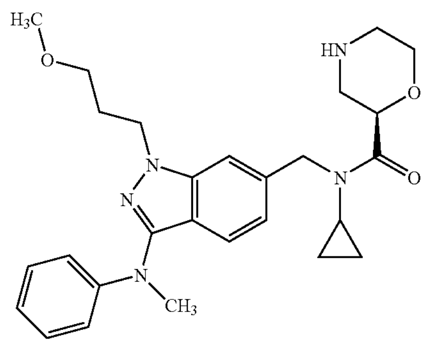 [SMILES: COCCCn1nc(N(C)c2ccccc2)c2ccc(CN(C(=O)[C@H]3CNCCO3)C3CC3)cc21] | hydrochloride<br>Property: purified powder<br>APCI-MS m/z: 478[M + H]+ |
| 247 | 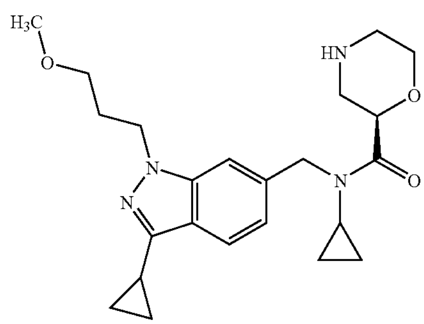 [SMILES: COCCCn1nc(C2CC2)c2ccc(CN(C(=O)[C@H]3CNCCO3)C3CC3)cc21] | hydrochloride<br>Property: purified powder<br>APCI-MS m/z: 413[M + H]+ |
| 248 | 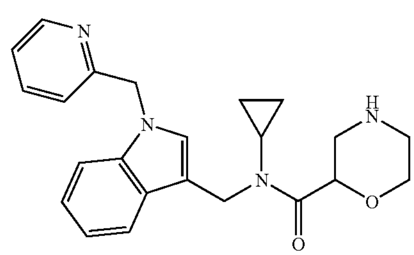 [SMILES: O=C(C1CNCCO1)N(Cc1cn(Cc2ccccn2)c2ccccc12)C1CC1] | Property: purified viscous oil<br>APCI-MS m/z: 391[M + H]+ |

TABLE 4-continued

| No. of Examples | Structure | Properties |
|---|---|---|
| 249 | 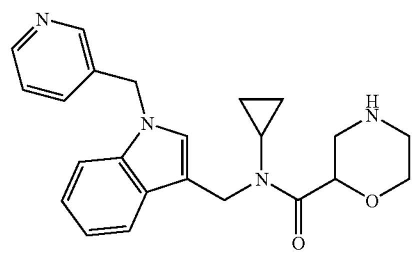 [SMILES: O=C(C1CNCCO1)N(Cc1cn(Cc2cccnc2)c2ccccc12)C1CC1] | Property: purified viscous oil<br>APCI-MS m/z: 391[M + H]+ |
| 250 | 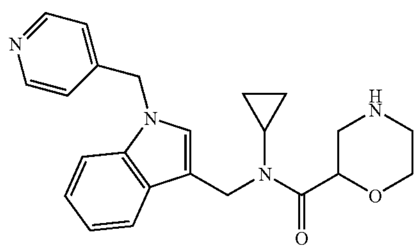 [SMILES: O=C(C1CNCCO1)N(Cc1cn(Cc2ccncc2)c2ccccc12)C1CC1] | Property: purified viscous oil<br>APCI-MS m/z: 391[M + H]+ |
| 251 | 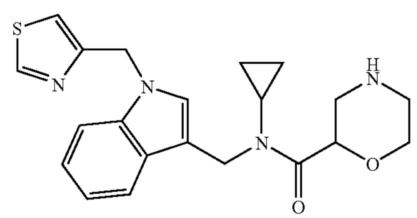 [SMILES: O=C(C1CNCCO1)N(Cc1cn(Cc2cscn2)c2ccccc12)C1CC1] | Property: purified viscous oil<br>APCI-MS m/z: 397[M + H]+ |
| 252 | 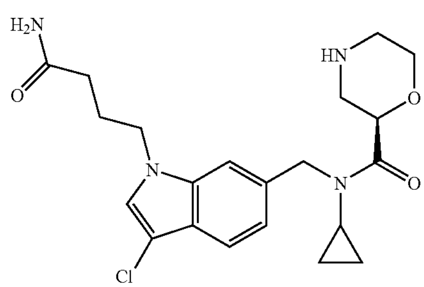 [SMILES: NC(=O)CCCn1cc(Cl)c2ccc(CN(C(=O)[C@H]3CNCCO3)C3CC3)cc21] | Property: purified viscous oil<br>APCI-MS m/z: 433/435[M + H]+ |
| 253 | 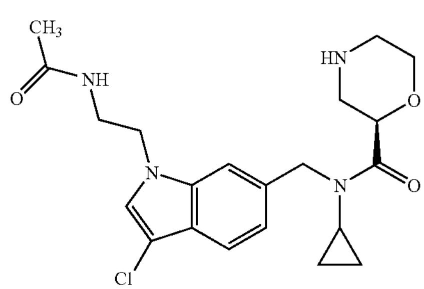 [SMILES: CC(=O)NCCn1cc(Cl)c2ccc(CN(C(=O)[C@H]3CNCCO3)C3CC3)cc21] | Property: purified powder<br>APCI-MS m/z: 419/421[M + H]+ |

TABLE 4-continued

| No. of Examples | Structure | Properties |
|---|---|---|
| 254 | 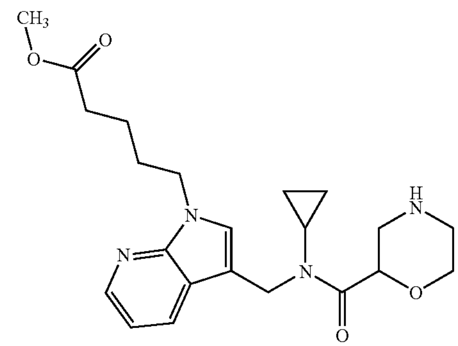 [SMILES: COC(=O)CCCCn1cc(CN(C(=O)C2CNCCO2)C2CC2)c2cccnc21] | dihydrochloride<br>Property: purified powder<br>APCI-MS m/z: 415[M + H]+ |
| 255 | 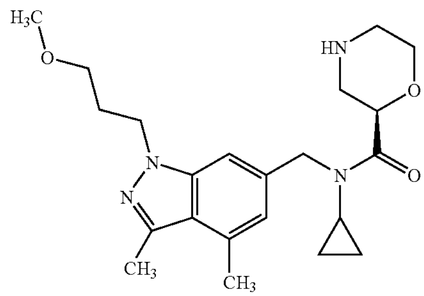 [SMILES: COCCCn1nc(C)c2c(C)cc(CN(C(=O)[C@H]3CNCCO3)C3CC3)cc21] | hydrochloride<br>Property: purified powder<br>APCI-MS m/z: 401[M + H]+ |
| 256 | 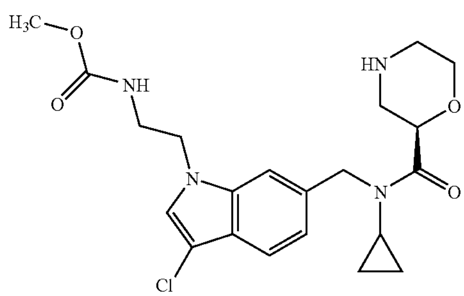 [SMILES: COC(=O)NCCn1cc(Cl)c2ccc(CN(C(=O)[C@H]3CNCCO3)C3CC3)cc21] | Property: purified viscous oil<br>APCI-MS m/z: 435/437[M + H]+ |
| 257 | 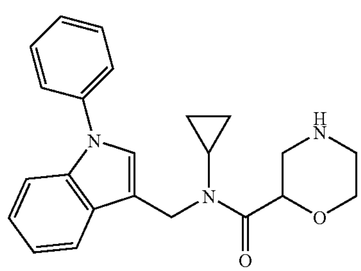 [SMILES: O=C(C1CNCCO1)N(Cc1cn(-c2ccccc2)c2ccccc12)C1CC1] | Property: purified viscous oil<br>APCI-MS m/z: 376[M + H]+ |
| 258 | 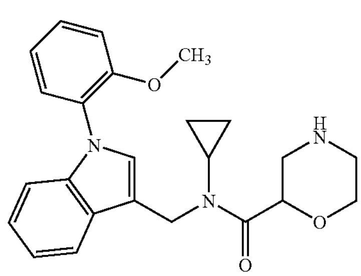 [SMILES: COc1ccccc1-n1cc(CN(C(=O)C2CNCCO2)C2CC2)c2ccccc21] | Property: purified viscous oil<br>APCI-MS m/z: 406[M + H]+ |

TABLE 4-continued
| No. of Examples | Structure | Properties |
|---|---|---|
| 259 | 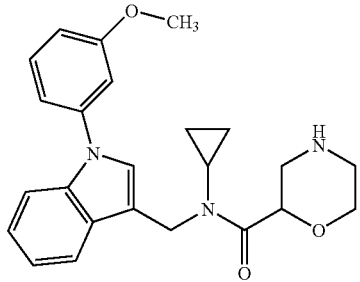 [SMILES: COc1cccc(-n2cc(CN(C(=O)C3CNCCO3)C3CC3)c3ccccc32)c1] | Property: purified viscous oil<br>APCI-MS m/z: 406[M + H]+ |
| 260 | 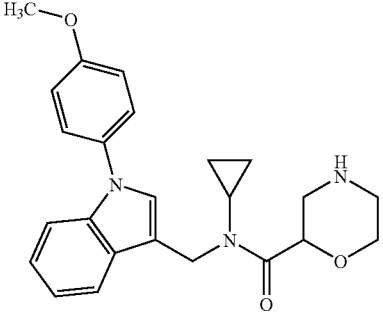 [SMILES: COc1ccc(-n2cc(CN(C(=O)C3CNCCO3)C3CC3)c3ccccc32)cc1] | Property: purified viscous oil<br>APCI-MS m/z: 406[M + H]+ |
| 261 | 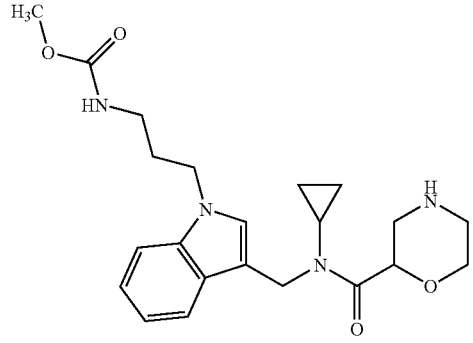 [SMILES: COC(=O)NCCCn1cc(CN(C(=O)C2CNCCO2)C2CC2)c2ccccc21] | Property: purified viscous oil<br>APCI-MS m/z: 415[M + H]+ |
| 262 | 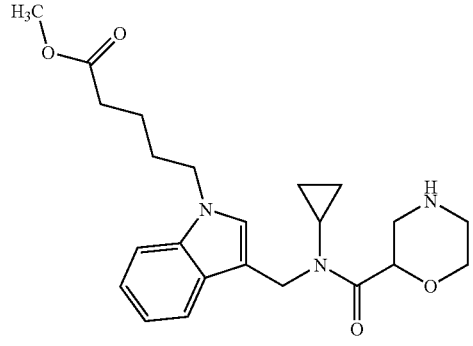 [SMILES: COC(=O)CCCCn1cc(CN(C(=O)C2CNCCO2)C2CC2)c2ccccc21] | Property: purified viscous oil<br>APCI-MS m/z: 414[M + H]+ |

| No. of Examples | Structure | Properties |
|---|---|---|
| 263 | 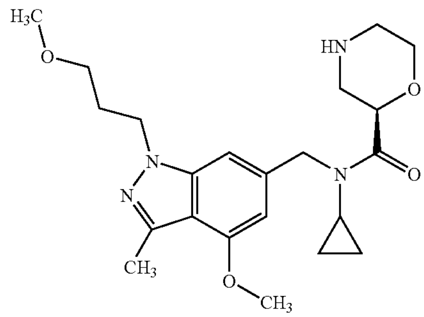 [SMILES: COCCCn1nc(C)c2c(OC)cc(CN(C(=O)[C@H]3CNCCO3)C3CC3)cc21] | hydrochloride<br>Property: purified powder<br>APCI-MS m/z: 417[M + H]+ |
| 264 | 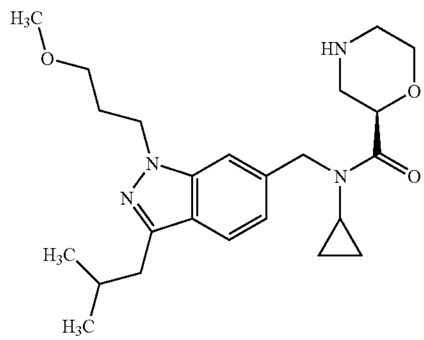 [SMILES: COCCCn1nc(CC(C)C)c2ccc(CN(C(=O)[C@H]3CNCCO3)C3CC3)cc21] | hydrochloride<br>Property: purified powder<br>APCI-MS m/z: 429[M + H]+ |
| 265 | 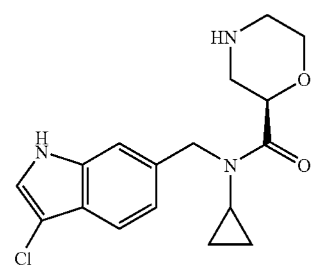 [SMILES: O=C([C@H]1CNCCO1)N(Cc1ccc2c(Cl)c[nH]c2c1)C1CC1] | Property: purified viscous oil<br>APCI-MS m/z: 334/336[M + H]+ |
| 266 | 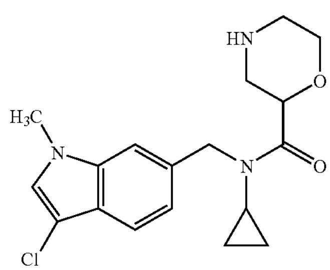 [SMILES: Cn1cc(Cl)c2ccc(CN(C(=O)C3CNCCO3)C3CC3)cc21] | Property: purified viscous oil<br>APCI-MS m/z: 345/350[M + H]+ |
| 267 | 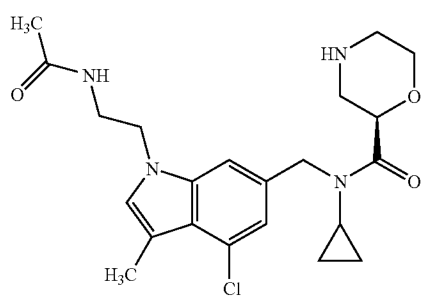 [SMILES: CC(=O)NCCn1cc(C)c2c(Cl)cc(CN(C(=O)[C@H]3CNCCO3)C3CC3)cc21] | Property: purified viscous oil<br>APCI-MS m/z: 434/436[M + H]+ |

TABLE 4-continued

| No. of Examples | Structure | Properties |
|---|---|---|
| 268 | 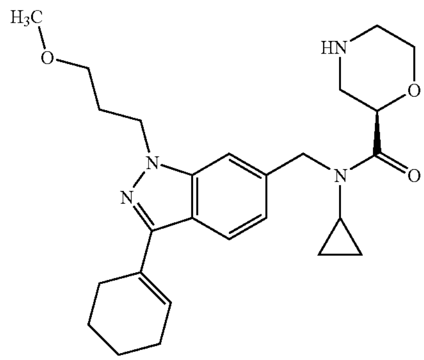 [SMILES: COCCCn1nc(C2=CCCCC2)c2ccc(CN(C(=O)[C@H]3CNCCO3)C3CC3)cc21] | hydrochloride<br>Property: purified powder<br>APCI-MS m/z: 453[M + H]+ |
| 269 | 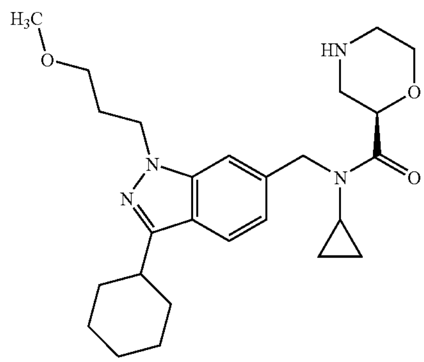 | hydrochloride<br>Property: purified powder<br>APCI-MS m/z: 455[M + H]+ |
| 270 | 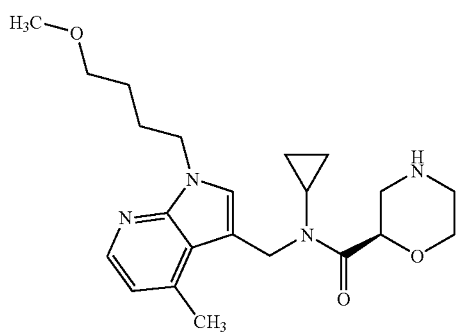 [SMILES: COCCCCn1cc(CN(C(=O)[C@H]2CNCCO2)C2CC2)c2c(C)ccnc21] | dihydrochloride<br>Property: purified powder<br>APCI-MS m/z: 401[M + H]+ |
| 271 | 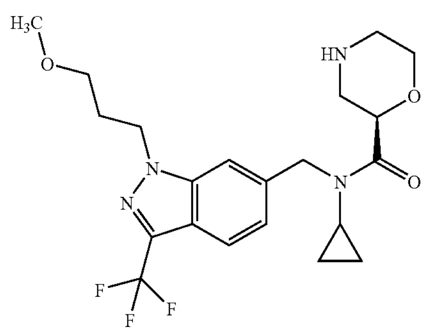 [SMILES: COCCCn1nc(C(F)(F)F)c2ccc(CN(C(=O)[C@H]3CNCCO3)C3CC3)cc21] | hydrochloride<br>Property: purified powder<br>APCI-MS m/z: 441[M + H]+ |

TABLE 4-continued

| No. of Examples | Structure | Properties |
|---|---|---|
| 272 | 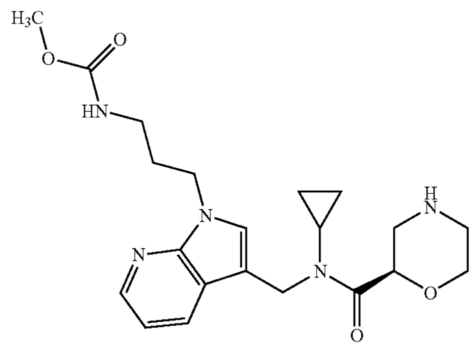 [SMILES: COC(=O)NCCCn1cc(CN(C(=O)[C@H]2CNCCO2)C2CC2)c2cccnc21] | dihydrochloride<br>Property: purified powder<br>APCI-MS m/z: 416[M + H]+ |
| 273 | 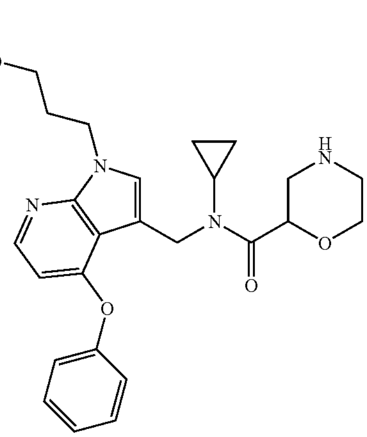 | dihydrochloride<br>Property: purified powder<br>APCI-MS m/z: 465[M + H]+ |
| 274 | 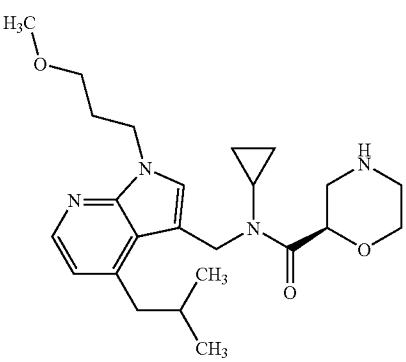 [SMILES: COCCCn1cc(CN(C(=O)[C@H]2CNCCO2)C2CC2)c2c(CC(C)C)ccnc21] | dihydrochloride<br>Property: purified powder<br>APCI-MS m/z: 429[M + H]+ |
| 275 | 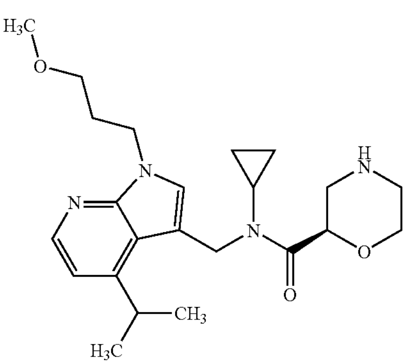 [SMILES: COCCCn1cc(CN(C(=O)[C@H]2CNCCO2)C2CC2)c2c(C(C)C)ccnc21] | dihydrochloride<br>Property: purified powder<br>APCI-MS m/z: 415[M + H]+ |

TABLE 4-continued

| No. of Examples | Structure | Properties |
|---|---|---|
| 276 | 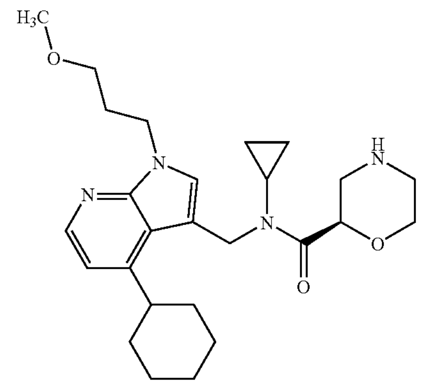 [SMILES: COCCCn1cc(CN(C(=O)[C@H]2CNCCO2)C2CC2)c2c(C3CCCCC3)ccnc21] | dihydrochloride<br>Property: purified powder<br>APCI-MS m/z: 455[M + H]+ |
| 277 | 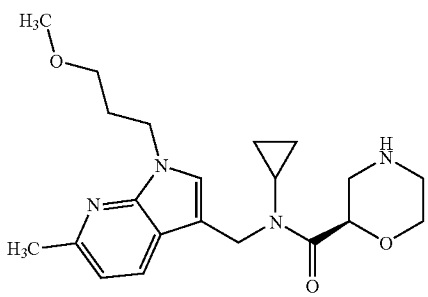 [SMILES: COCCCn1cc(CN(C(=O)[C@H]2CNCCO2)C2CC2)c2ccc(C)nc21] | Property: purified viscous oil<br>APCI-MS m/z: 387[M + H]+ |
| 278 | 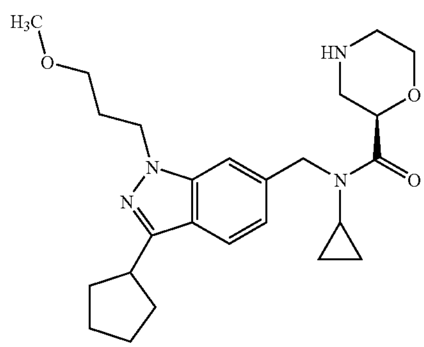 [SMILES: COCCCn1nc(C2CCCC2)c2ccc(CN(C(=O)[C@H]3CNCCO3)C3CC3)cc21] | hydrochloride<br>Property: purified powder<br>APCI-MS m/z: 441[M + H]+ |
| 279 | 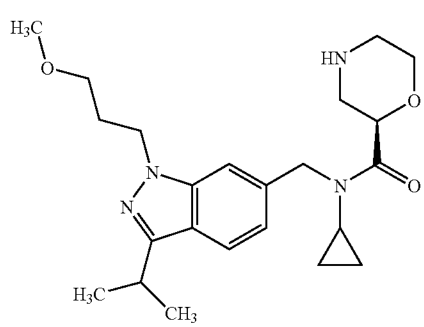 [SMILES: COCCCn1nc(C(C)C)c2ccc(CN(C(=O)[C@H]3CNCCO3)C3CC3)cc21] | hydrochloride<br>Property: purified powder<br>APCI-MS m/z: 415[M + H]+ |

TABLE 4-continued

| No. of Examples | Structure | Properties |
|---|---|---|
| 280 | 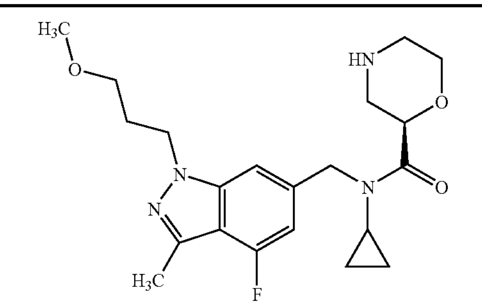 | hydrochloride<br>Property: purified powder<br>APCI-MS m/z: 405[M + H]+ |
| 281 | 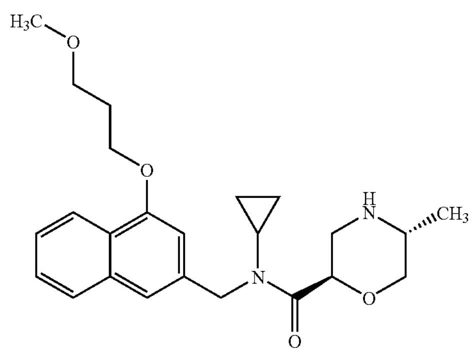 [SMILES: COCCCOc1cc(CN(C(=O)[C@H]2CN[C@H](C)CO2)C2CC2)cc2ccccc12] | hydrochloride<br>Property: purified powder<br>APCI-MS m/z: 413[M + H]+ |
| 282 | 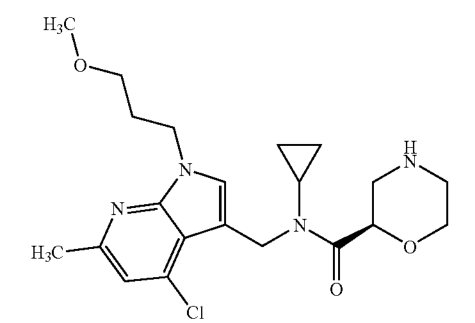 [SMILES: COCCCn1cc(CN(C(=O)[C@H]2CNCCO2)C2CC2)c2c(Cl)cc(C)nc21] | dihydrochloride<br>Property: purified powder<br>APCI-MS m/z: 421/423[M + H]+ |
| 283 | 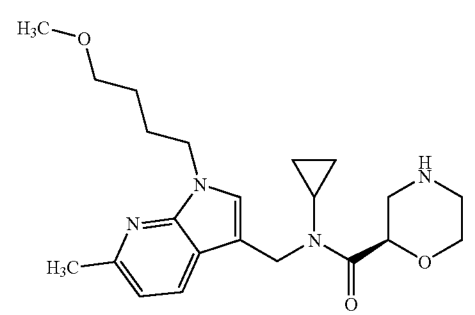 [SMILES: COCCCCn1cc(CN(C(=O)[C@H]2CNCCO2)C2CC2)c2ccc(C)nc21] | dihydrochloride<br>Property: purified powder<br>APCI-MS m/z: 401[M + H]+ |
| 284 | 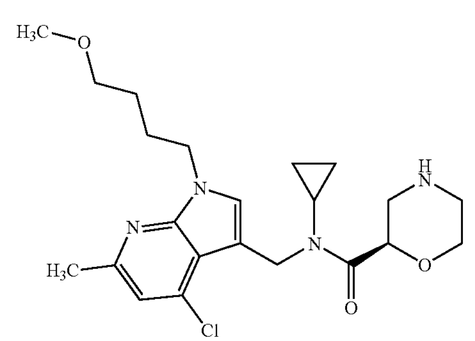 [SMILES: COCCCCn1cc(CN(C(=O)[C@H]2CNCCO2)C2CC2)c2c(Cl)cc(C)nc21] | dihydrochloride<br>Property: purified powder<br>APCI-MS m/z: 435/437[M + H]+ |

TABLE 4-continued

| No. of Examples | Structure | Properties |
|---|---|---|
| 285 | 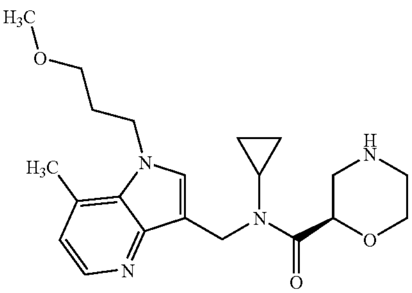 [SMILES: COCCCn1cc(CN(C(=O)[C@H]2CNCCO2)C2CC2)c2nccc(C)c21] | dihydrochloride<br>Property: purified powder<br>APCI-MS m/z: 387[M + H]+ |
| 286 | 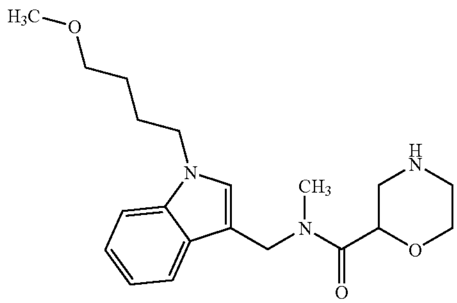 [SMILES: COCCCCn1cc(CN(C)C(=O)C2CNCCO2)c2ccccc21] | Property: purified viscous oil<br>APCI-MS m/z: 360[M + H]+ |
| 287 | 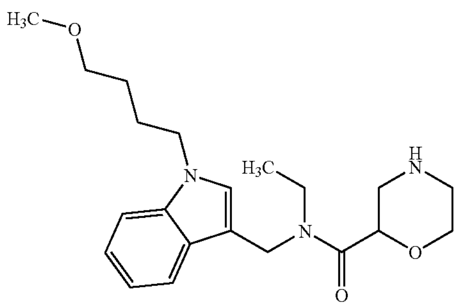 [SMILES: CCN(Cc1cn(CCCCOC)c2ccccc12)C(=O)C1CNCCO1] | Property: purified viscous oil<br>APCI-MS m/z: 374[M + H]+ |
| 288 | 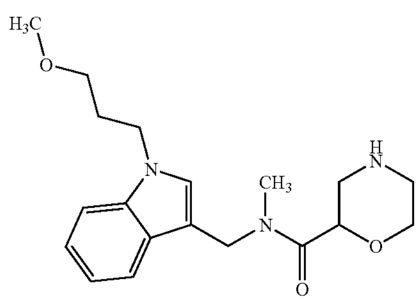 [SMILES: COCCCn1cc(CN(C)C(=O)C2CNCCO2)c2ccccc21] | Property: purified viscous oil<br>APCI-MS m/z: 346[M + H]+ |
| 289 | 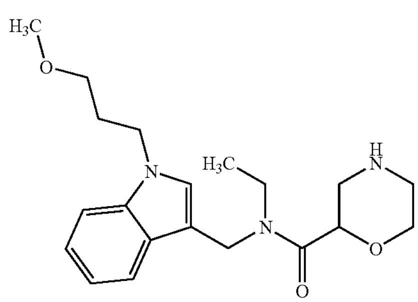 [SMILES: CCN(Cc1cn(CCCOC)c2ccccc12)C(=O)C1CNCCO1] | Property: purified viscous oil<br>APCI-MS m/z: 360[M + H]+ |

TABLE 4-continued
| No. of Examples | Structure | Properties |
|---|---|---|
| 290 | 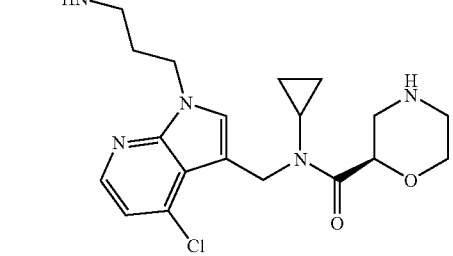 | dihydrochloride<br>Property: purified powder<br>APCI-MS m/z: 434/436[M + H]+ |
| 291 | 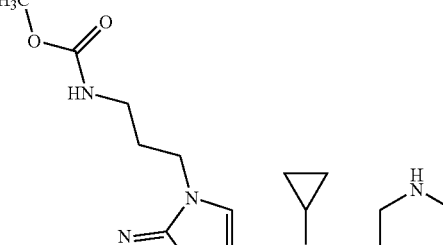 | dihydrochloride<br>Property: purified powder<br>APCI-MS m/z: 450/452[M + H]+ |
| 292 | 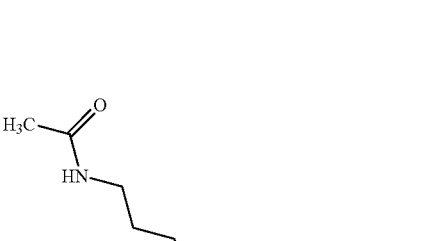 | Property: purified viscous oil<br>APCI-MS m/z: 399[M + H]+ |
| 293 | 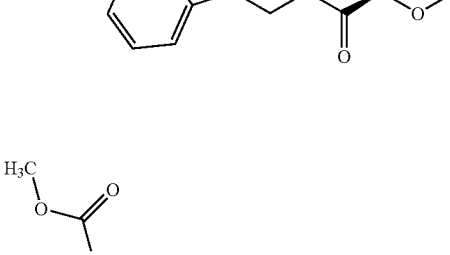 | Property: purified viscous oil<br>APCI-MS m/z: 415[M + H]+ |

TABLE 4-continued

| No. of Examples | Structure | Properties |
|---|---|---|
| 294 | 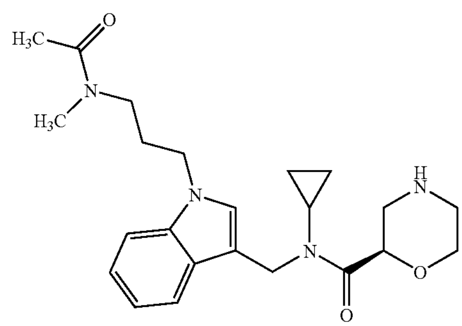 [SMILES: CC(=O)N(C)CCCn1cc(CN(C(=O)[C@H]2CNCCO2)C2CC2)c2ccccc21] | Property: purified viscous oil<br>APCI-MS m/z: 413[M + H]+ |
| 295 | 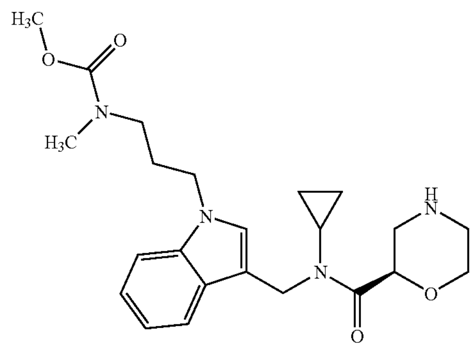 [SMILES: COC(=O)N(C)CCCn1cc(CN(C(=O)[C@H]2CNCCO2)C2CC2)c2ccccc21] | Property: purified viscous oil<br>APCI-MS m/z: 429[M + H]+ |
| 296 | 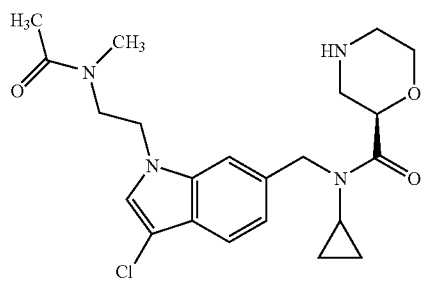 [SMILES: CC(=O)N(C)CCn1cc(Cl)c2ccc(CN(C(=O)[C@H]3CNCCO3)C3CC3)cc21] | Property: purified viscous oil<br>APCI-MS m/z: 433/435[M + H]+ |
| 297 | 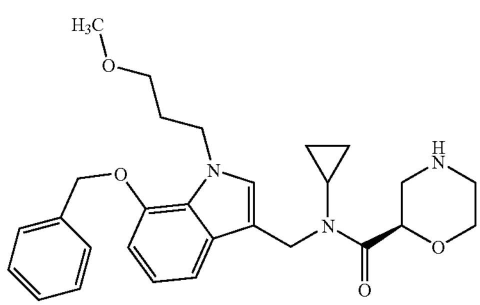 [SMILES: COCCCn1cc(CN(C(=O)[C@H]2CNCCO2)C2CC2)c2cccc(OCc3ccccc3)c21] | Property:<br>ESI-MS m/z: 478[M + H]+ |
| 298 | 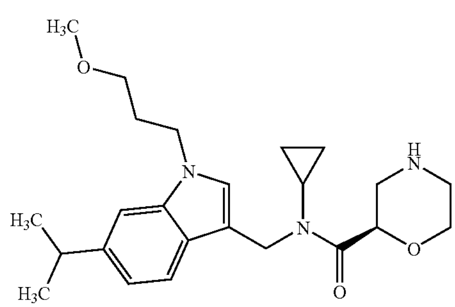 [SMILES: COCCCn1cc(CN(C(=O)[C@H]2CNCCO2)C2CC2)c2ccc(C(C)C)cc21] | Property:<br>ESI-MS m/z: 414[M + H]+ |

TABLE 4-continued
| No. of Examples | Structure | Properties |
|---|---|---|
| 299 | 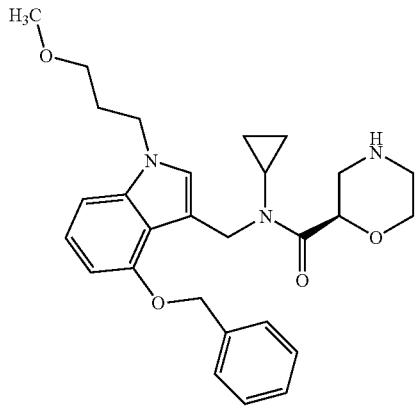 [SMILES: COCCCn1cc(CN(C(=O)[C@H]2CNCCO2)C2CC2)c2c(OCc3ccccc3)cccc21] | Property:<br>ESI-MS m/z: 478[M + H]+ |
| 300 | 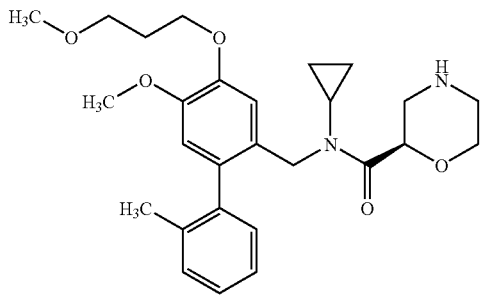 [SMILES: COCCCOc1cc(CN(C(=O)[C@H]2CNCCO2)C2CC2)c(-c2ccccc2C)cc1OC] | hydrochloride<br>Property:<br>ESI-MS m/z: 469[M + H]+ |
| 301 | 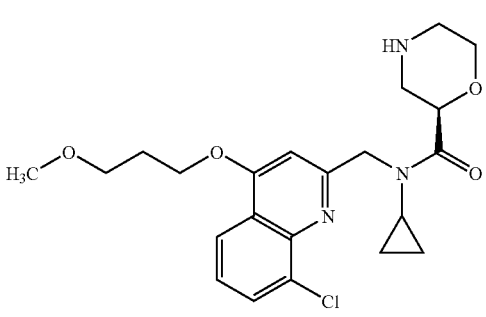 | hydrochloride<br>Property:<br>ESI-MS m/z: 434/436[M + H]+ |
| 302 | 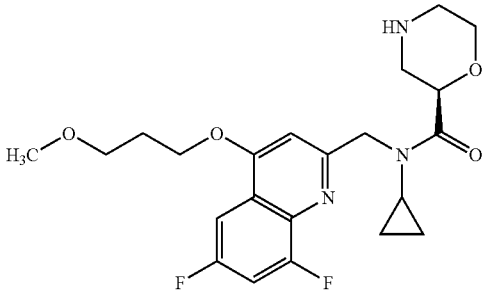 [SMILES: COCCCOc1cc(CN(C(=O)[C@H]2CNCCO2)C2CC2)nc2c(F)cc(F)cc12] | hydrochloride<br>Property:<br>ESI-MS m/z: 436[M + H]+ |

TABLE 4-continued

| No. of Examples | Structure | Properties |
|---|---|---|
| 303 | 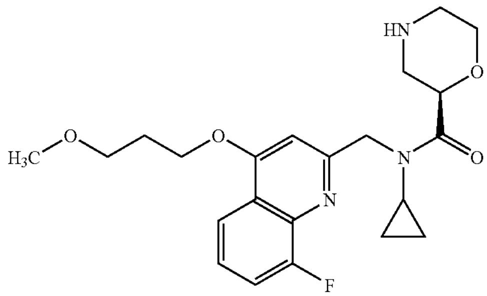 [SMILES: COCCCOc1cc(CN(C(=O)[C@H]2CNCCO2)C2CC2)nc2c(F)cccc12] | hydrochloride<br>Property:<br>ESI-MS m/z: 418[M + H]+ |
| 304 | 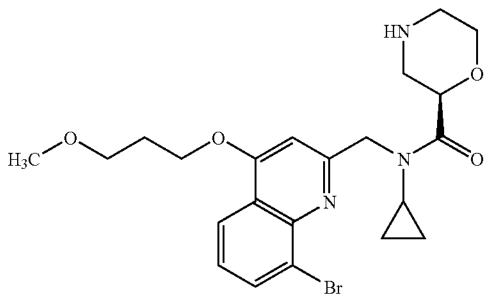 | hydrochloride<br>Property:<br>ESI-MS m/z: 478/480[M + H]+ |
| 305 | 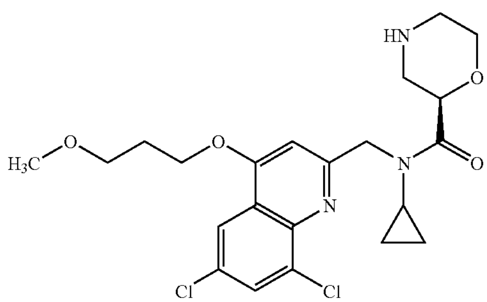 [SMILES: COCCCOc1cc(CN(C(=O)[C@H]2CNCCO2)C2CC2)nc2c(Cl)cc(Cl)cc12] | hydrochloride<br>Property:<br>ESI-MS m/z: 468[M + H]+ |
| 306 | 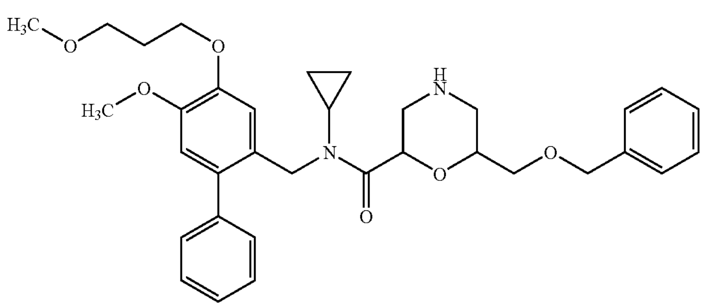 [SMILES: COCCCOc1cc(CN(C(=O)C2CNCC(COCc3ccccc3)O2)C2CC2)c(-c2ccccc2)cc1OC] | Property:<br>ESI-MS m/z: 575[M + H]+ |
| 307 | 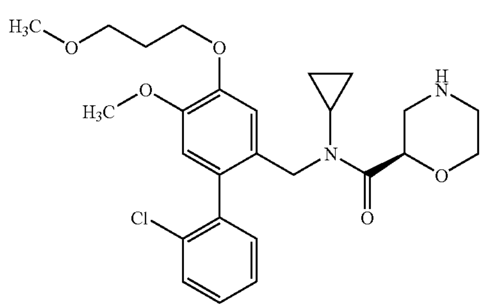 | hydrochloride<br>Property:<br>ESI-MS m/z: 489/491[M + H]+ |

TABLE 4-continued

| No. of Examples | Structure | Properties |
| --- | --- | --- |
| 308 | 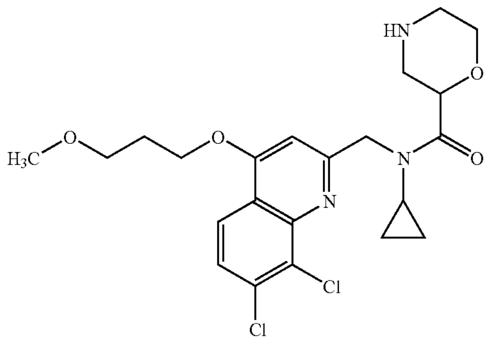 [SMILES: COCCCOc1cc(CN(C(=O)C2CNCCO2)C2CC2)nc2c(Cl)c(Cl)ccc12] | dihydrochloride<br>Property:<br>ESI-MS m/z: 468/470[M + H]+ |
| 309 | 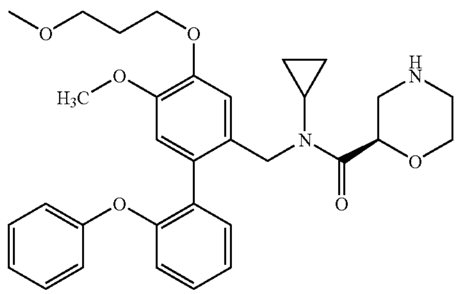 [SMILES: COCCCOc1cc(CN(C(=O)[C@H]2CNCCO2)C2CC2)c(-c2ccccc2Oc2ccccc2)cc1OC] | hydrochloride<br>Property:<br>ESI-MS m/z: 547[M + H]+ |
| 310 | 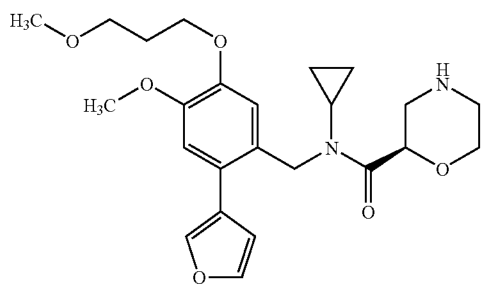 [SMILES: COCCCOc1cc(CN(C(=O)[C@H]2CNCCO2)C2CC2)c(-c2ccoc2)cc1OC] | hydrochloride<br>Property:<br>ESI-MS m/z: 445[M + H]+ |
| 311 | 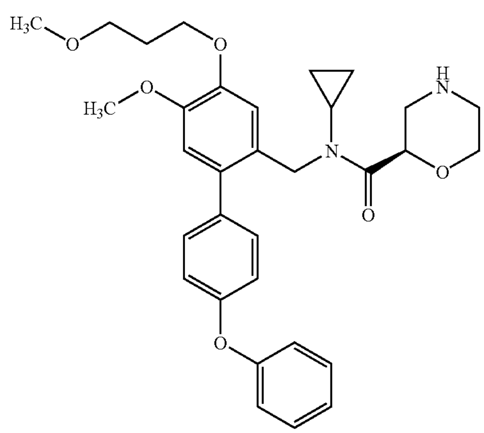 [SMILES: COCCCOc1cc(CN(C(=O)[C@H]2CNCCO2)C2CC2)c(-c2ccc(Oc3ccccc3)cc2)cc1OC] | hydrochloride<br>Property:<br>ESI-MS m/z: 547[M + H]+ |

TABLE 4-continued

| No. of Examples | Structure | Properties |
| --- | --- | --- |
| 312 | 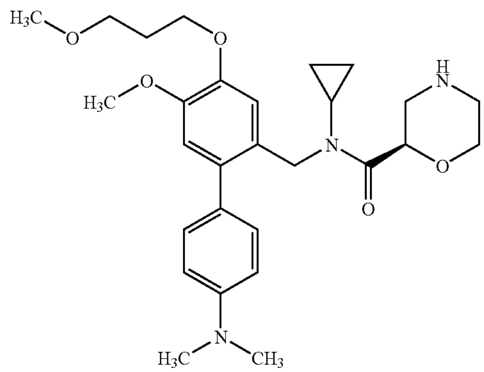 [SMILES: COCCCOc1cc(CN(C(=O)[C@H]2CNCCO2)C2CC2)c(-c2ccc(N(C)C)cc2)cc1OC] | hydrochloride<br>Property:<br>ESI-MS m/z: 498[M + H]+ |
| 313 | 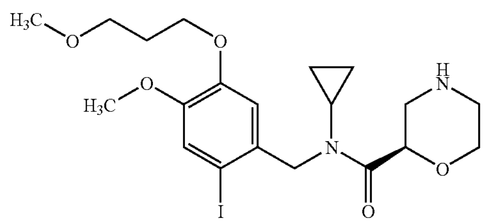 [SMILES: COCCCOc1cc(CN(C(=O)[C@H]2CNCCO2)C2CC2)c(I)cc1OC] | hydrochloride<br>Property:<br>ESI-MS m/z: 505[M + H]+ |
| 314 | 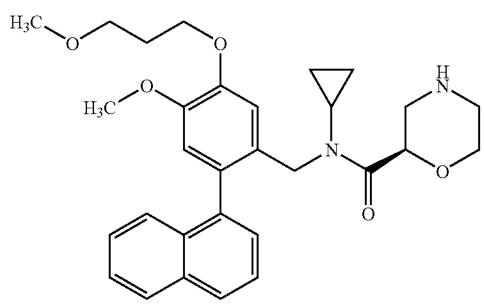 [SMILES: COCCCOc1cc(CN(C(=O)[C@H]2CNCCO2)C2CC2)c(-c2cccc3ccccc23)cc1OC] | hydrochloride<br>Property:<br>ESI-MS m/z: 505[M + H]+ |
| 315 | 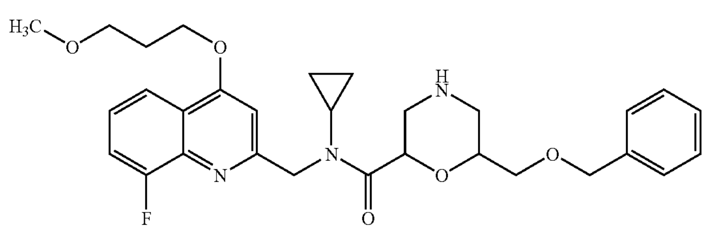 [SMILES: COCCCOc1cc(CN(C(=O)C2CNCC(COCc3ccccc3)O2)C2CC2)nc2c(F)cccc12] | Property:<br>ESI-MS m/z: 538[M + H]+ |
| 316 | 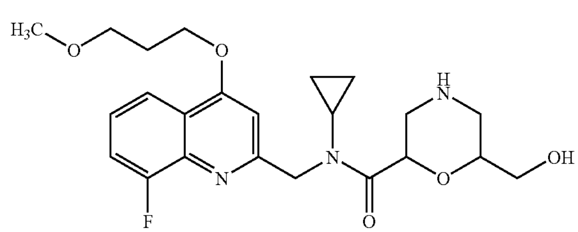 [SMILES: COCCCOc1cc(CN(C(=O)C2CNCC(CO)O2)C2CC2)nc2c(F)cccc12] | Property:<br>ESI-MS m/z: 448[M + H]+ |
| 317 | 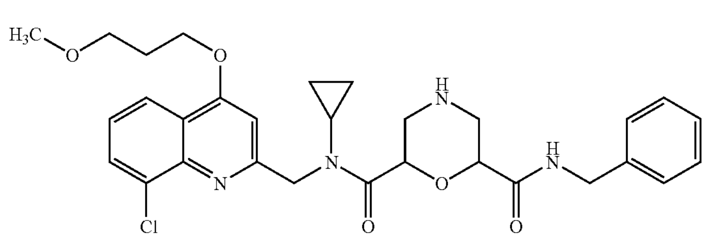 [SMILES: COCCCOc1cc(CN(C(=O)C2CNCC(C(=O)NCc3ccccc3)O2)C2CC2)nc2c(Cl)cccc12] | dihydrochloride<br>Property:<br>ESI-MS m/z: 567[M + H]+ |

TABLE 4-continued

| No. of Examples | Structure | Properties |
|---|---|---|
| 318 | 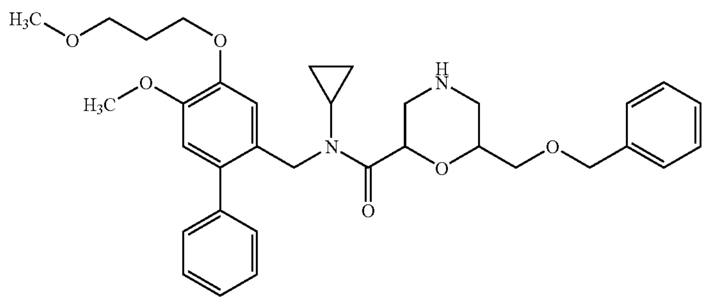 [SMILES: COCCCOc1cc(CN(C(=O)C2CNCC(COCc3ccccc3)O2)C2CC2)c(-c2ccccc2)cc1OC] | Property:<br>ESI-MS m/z: 575[M + H]+ |
| 319 | 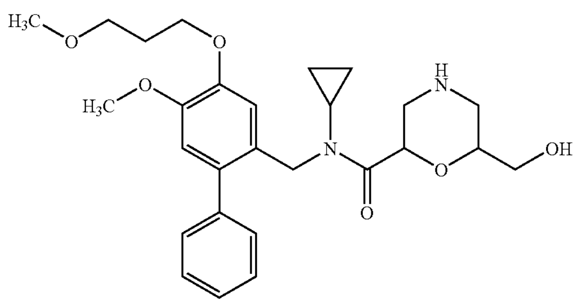 [SMILES: COCCCOc1cc(CN(C(=O)C2CNCC(CO)O2)C2CC2)c(-c2ccccc2)cc1OC] | Property:<br>ESI-MS m/z: 485[M + H]+ |
| 320 | 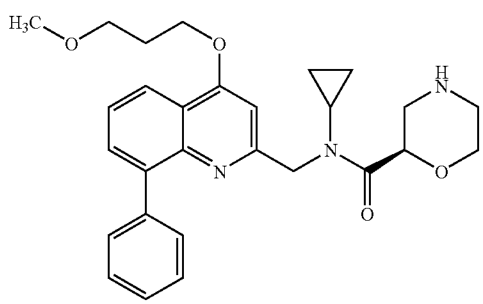 [SMILES: COCCCOc1cc(CN(C(=O)[C@H]2CNCCO2)C2CC2)nc2c(-c3ccccc3)cccc12] | Property:<br>ESI-MS m/z: 476[M + H]+ |
| 321 | 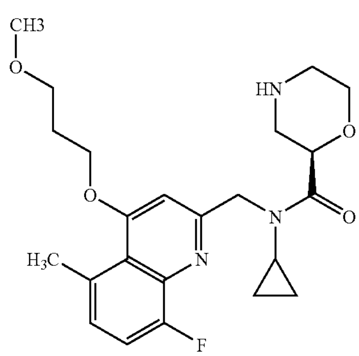 [SMILES: COCCCOc1cc(CN(C(=O)[C@H]2CNCCO2)C2CC2)nc2c(F)ccc(C)c12] | hydrochloride<br>Property:<br>ESI-MS m/z: 432[M + H]+ |
| 322 | 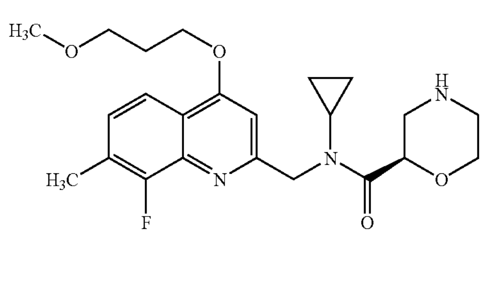 [SMILES: COCCCOc1cc(CN(C(=O)[C@H]2CNCCO2)C2CC2)nc2c(F)c(C)ccc12] | hydrochloride<br>Property:<br>ESI-MS m/z: 432[M + H]+ |

TABLE 4-continued

| No. of Examples | Structure | Properties |
| --- | --- | --- |
| 323 | 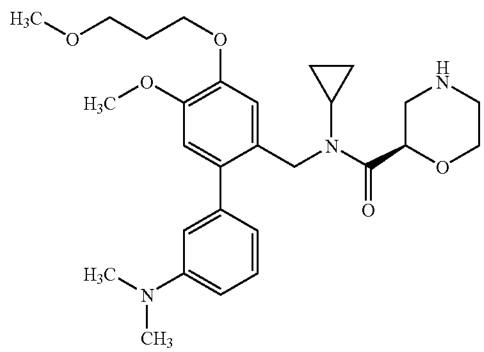 [SMILES: COCCCOc1cc(CN(C(=O)[C@H]2CNCCO2)C2CC2)c(-c2cccc(N(C)C)c2)cc1OC] | dihydrochloride Property: ESI-MS m/z: 498[M + H]+ |
| 324 | 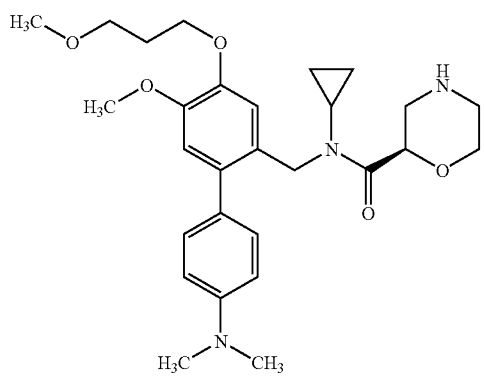 [SMILES: COCCCOc1cc(CN(C(=O)[C@H]2CNCCO2)C2CC2)c(-c2ccc(N(C)C)cc2)cc1OC] | dihydrochloride Property: ESI-MS m/z: 498[M + H]+ |
| 325 | 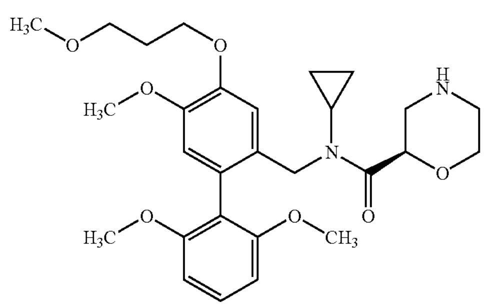 [SMILES: COCCCOc1cc(CN(C(=O)[C@H]2CNCCO2)C2CC2)c(-c2c(OC)cccc2OC)cc1OC] | hydrochloride Property: ESI-MS m/z: 515[M + H]+ |
| 326 | 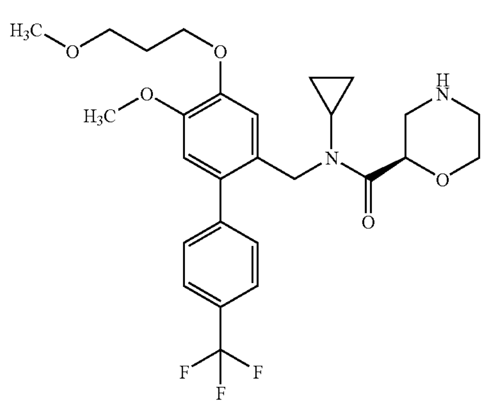 [SMILES: COCCCOc1cc(CN(C(=O)[C@H]2CNCCO2)C2CC2)c(-c2ccc(C(F)(F)F)cc2)cc1OC] | hydrochloride Property: ESI-MS m/z: 523[M + H]+ |

TABLE 4-continued
| No. of Examples | Structure | Properties |
|---|---|---|
| 327 | 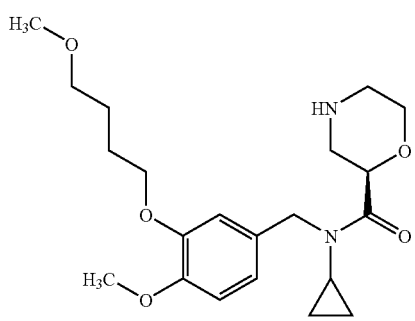 [SMILES: COCCCCOc1cc(CN(C(=O)[C@H]2CNCCO2)C2CC2)ccc1OC] | hydrochloride<br>Property:<br>ESI-MS m/z: 393[M + H]+ |
| 328 | 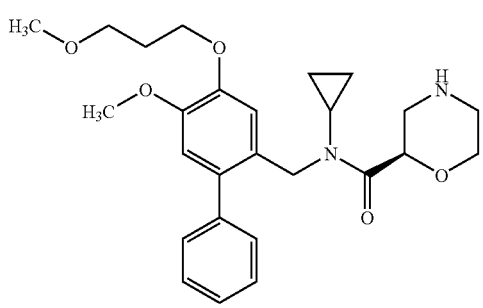 | hydrochloride<br>Property:<br>ESI-MS m/z: 425[M + H]+ |
| 329 | 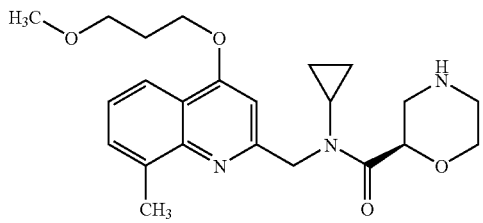 [SMILES: COCCCOc1cc(CN(C(=O)[C@H]2CNCCO2)C2CC2)nc2c(C)cccc12] | dihydrochloride<br>Property:<br>ESI-MS m/z: 414[M + H]+ |
| 330 | 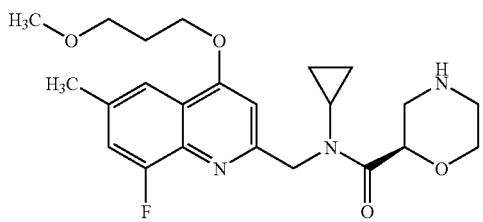 [SMILES: COCCCOc1cc(CN(C(=O)[C@H]2CNCCO2)C2CC2)nc2c(F)cc(C)cc12] | dihydrochloride<br>Property:<br>ESI-MS m/z: 432[M + H]+ |
| 331 | 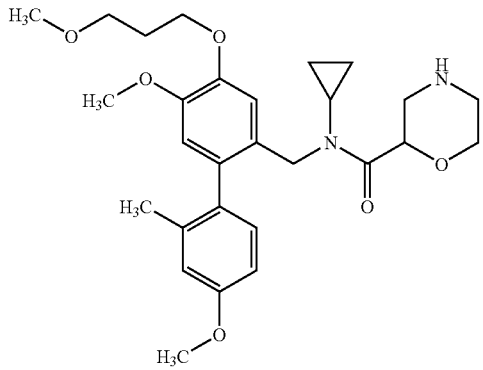 [SMILES: COCCCOc1cc(CN(C(=O)C2CNCCO2)C2CC2)c(-c2ccc(OC)cc2C)cc1OC] | hydrochloride<br>Property:<br>ESI-MS m/z: 499[M + H]+ |

TABLE 4-continued

| No. of Examples | Structure | Properties |
| --- | --- | --- |
| 332 | 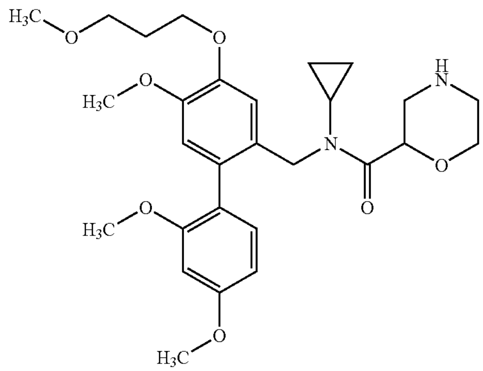 [SMILES: COCCCOc1cc(CN(C(=O)C2CNCCO2)C2CC2)c(-c2ccc(OC)cc2OC)cc1OC] | hydrochloride<br>Property:<br>ESI-MS m/z: 515[M + H]+ |
| 333 | 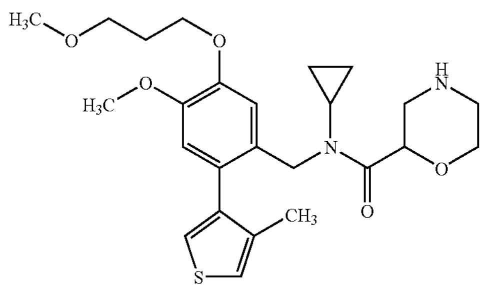 [SMILES: COCCCOc1cc(CN(C(=O)C2CNCCO2)C2CC2)c(-c2cscc2C)cc1OC] | Hydrochloride<br>Property:<br>ESI-MS m/z: 475[M + H]+ |
| 334 | 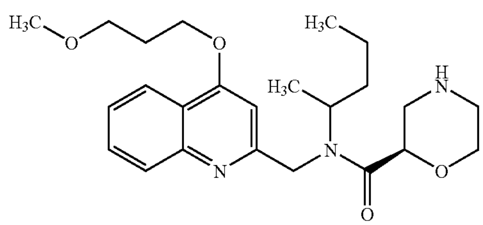 [SMILES: CCCC(C)N(Cc1cc(OCCCOC)c2ccccc2n1)C(=O)[C@H]1CNCCO1] | dihydrochloride<br>Property:<br>ESI-MS m/z: 430[M + H]+ |
| 335 | 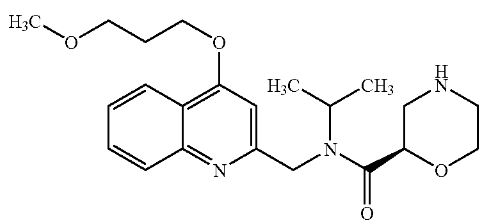 [SMILES: COCCCOc1cc(CN(C(=O)[C@H]2CNCCO2)C(C)C)nc2ccccc12] | dihydrochloride<br>Property:<br>ESI-MS m/z: 402[M + H]+ |
| 336 | 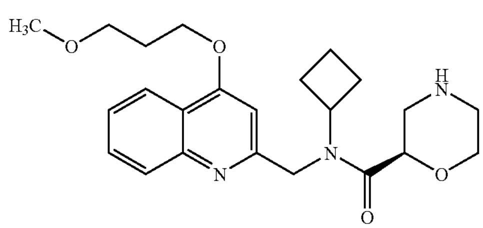 [SMILES: COCCCOc1cc(CN(C(=O)[C@H]2CNCCO2)C2CCC2)nc2ccccc12] | dihydrochloride<br>Property:<br>ESI-MS m/z: 414[M + H]+ |
| 337 | 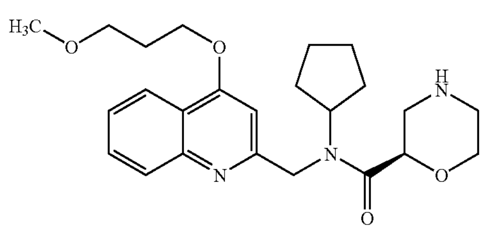 [SMILES: COCCCOc1cc(CN(C(=O)[C@H]2CNCCO2)C2CCCC2)nc2ccccc12] | dihydrochloride<br>Property:<br>ESI-MS m/z: 428[M + H]+ |

TABLE 4-continued
| No. of Examples | Structure | Properties |
|---|---|---|
| 338 | 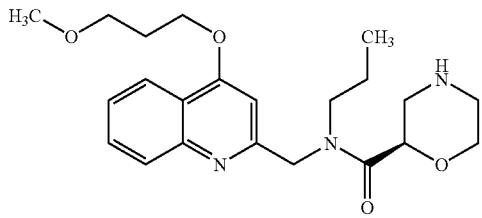 [SMILES: CCCN(Cc1cc(OCCCOC)c2ccccc2n1)C(=O)[C@H]1CNCCO1] | dihydrochloride<br>Property:<br>ESI-MS m/z: 402[M + H]+ |
| 339 | 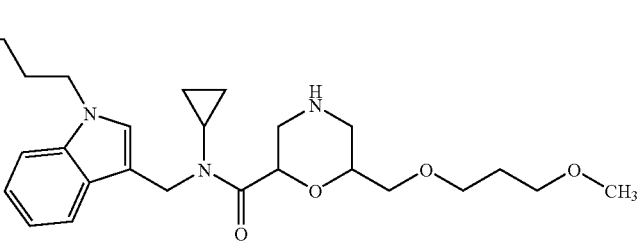 | Property:<br>ESI-MS m/z: 474[M + H]+ |
| 340 | 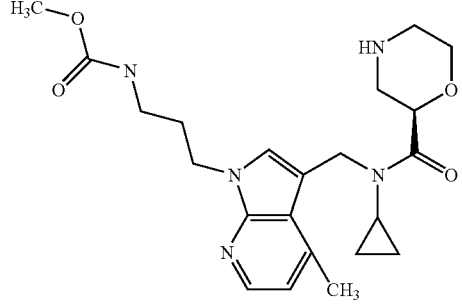 [SMILES: COC(=O)NCCCn1cc(CN(C(=O)[C@H]2CNCCO2)C2CC2)c2c(C)ccnc21] | dihydrochloride<br>Property: purified powder<br>APCI-MS m/z: 430[M + H]+ |
| 341 | 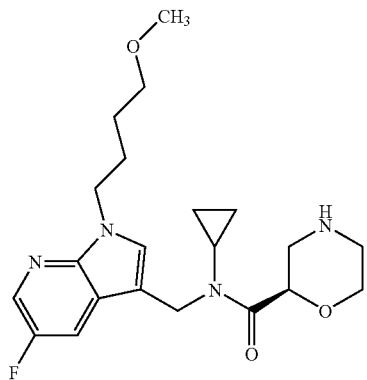 [SMILES: COCCCCn1cc(CN(C(=O)[C@H]2CNCCO2)C2CC2)c2cc(F)cnc21] | Property: purified oil<br>APCI-MS m/z: 405[M + H]+ |
| 342 | 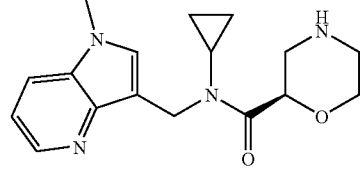 | dihydrochloride<br>Property: purified powder<br>APCI-MS m/z: 387[M + H]+ |

TABLE 4-continued

| No. of Examples | Structure | Properties |
|---|---|---|
| 343 | 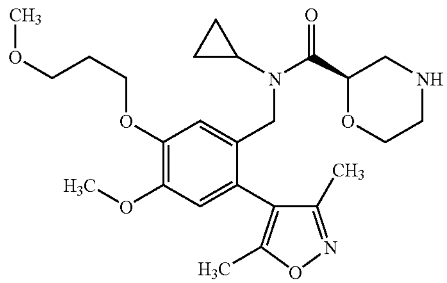 [SMILES: COCCCOc1cc(CN(C(=O)[C@H]2CNCCO2)C2CC2)c(-c2c(C)noc2C)cc1OC] | Hydrochloride<br>Property: purified powder<br>ESI-MS m/z: 474[M + H]+ |
| 344 | 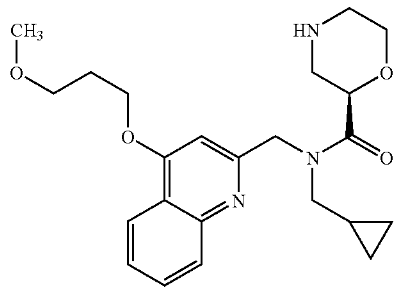 [SMILES: COCCCOc1cc(CN(CC2CC2)C(=O)[C@H]2CNCCO2)nc2ccccc12] | Hydrochloride<br>Property: purified powder<br>ESI-MS m/z: 414[M + H]+ |
| 345 | 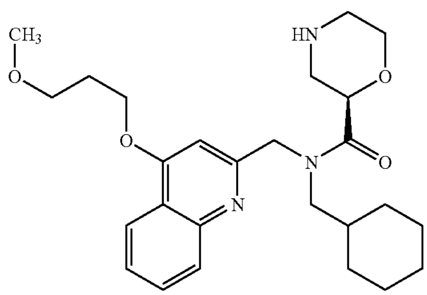 [SMILES: COCCCOc1cc(CN(CC2CCCCC2)C(=O)[C@H]2CNCCO2)nc2ccccc12] | Hydrochloride<br>Property: purified powder<br>ESI-MS m/z: 456[M + H]+ |
| 346 | 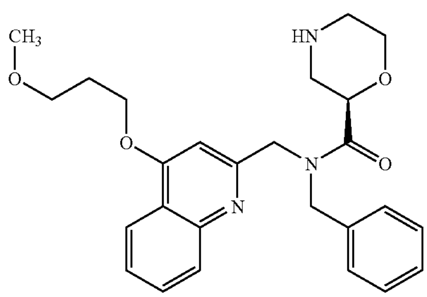 [SMILES: COCCCOc1cc(CN(Cc2ccccc2)C(=O)[C@H]2CNCCO2)nc2ccccc12] | Hydrochloride<br>Property: purified powder<br>ESI-MS m/z: 450[M + H]+ |
| 347 | 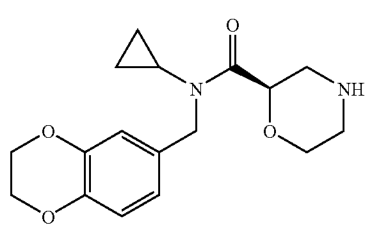 [SMILES: O=C([C@H]1CNCCO1)N(Cc1ccc2c(c1)OCCO2)C1CC1] | Hydrochloride<br>Property: purified powder<br>ESI-MS m/z: 319[M + H]+ |

TABLE 4-continued

| No. of Examples | Structure | Properties |
|---|---|---|
| 348 | 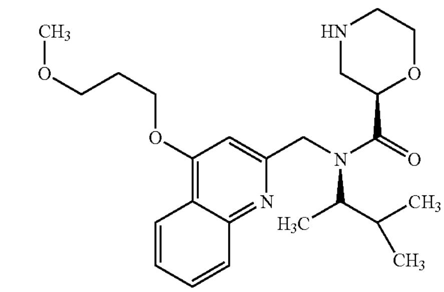 | Hydrochloride<br>Property: purified powder<br>ESI-MS m/z: 430[M + H]+ |
| 349 | 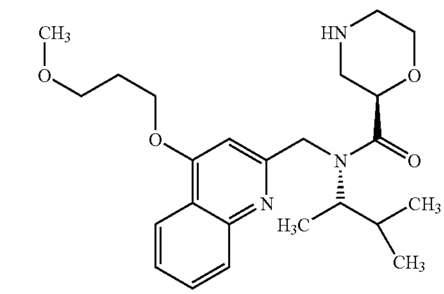 | Hydrochloride<br>Property: purified powder<br>ESI-MS m/z: 430[M + H]+ |
| 350 | 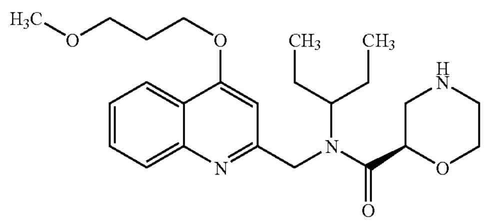 [SMILES: CCC(CC)N(Cc1cc(OCCCOC)c2ccccc2n1)C(=O)[C@H]1CNCCO1] | Hydrochloride<br>Property: purified powder<br>ESI-MS m/z: 430[M + H]+ |

Reference Example 1

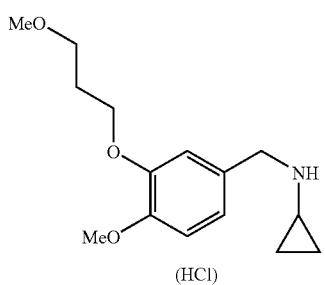

(HCl)

(1) Cyclopropylamine (23.2 ml) was added to a solution of 4-methoxy-3-(3-methoxypropoxy)benzaldehyde (15.00 g) in ethanol (375 ml) and the mixture was heated at 50° C. for 3 hours. The reaction mixture was concentrated in vacuo, the resulted residue was diluted with tetrahydrofuran-ethanol (1:1, 600 ml) and thereto was added sodium borohydride (7.60 g). The mixture was stirred at room temperature overnight, and was further stirred overnight after sodium borohydride (7.60 g) was added. The solvent was evaporated in vacuo, the residue was diluted with ethyl acetate and water and extracted with ethyl acetate. The organic layer was washed with water and saturated brine, dried over sodium sulfate and concentrated in vacuo. The resulted residue was purified with a silica gel column chromatography (eluting solvent: n-hexane/ethyl acetate=1/1 to chloroform/methanol=10/1) to give N-[4-methoxy-3-(3-methoxypropoxy)benzyl]cyclopropanamine (15.83 g) as a pale yellow oil.
APCI-MS m/z: 266[M+H]+.

(2) A 4N HCl-dioxane solution (30 ml) was added to a solution of the compound obtained in (2) described above (15.80 g) in dioxane (30 ml) under ice-cooling and the mixture was stirred at the same temperature for 5 minutes. The mixture was concentrated in vacuo and the resulted residue was triturated in diisopropyl ether to give N-[4-methoxy-3-(3-methoxypropoxy)benzyl]cyclopropan-amine hydrochloride (15.32 g) as a colorless powder.
APCI-MS m/z: 266[M+H]+.

Reference Example 2

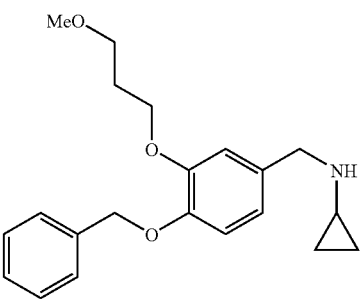 [SMILES: COCCCOc1cc(CNC2CC2)ccc1OCc1ccccc1]

4-(Benzyloxy)-3-(3-methoxypropoxy)benzaldehyde (945 mg) and cyclopropylamine (0.44 ml) were treated in the same manner as Reference Example 1 to give N-[4-(benzyloxy)-3-(3-methoxypropoxy)benzyl]cyclopropanamine (947 mg) as a colorless oil.
APCI-MS m/z: 342[M+H]⁺.

Reference Example 3

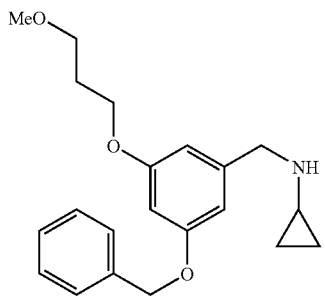 [SMILES: COCCCOc1cc(CNC2CC2)cc(OCc2ccccc2)c1]

(1) A solution of 1-bromo-3-methoxypropane (1.35 g) in acetonitrile (5 ml) and potassium carbonate (1.66 g) were added to a solution of methyl 3-benzyloxy-5-hydroxybenzoate (2.06 g) in acetonitrile (25 ml). After the mixture was heated under reflux for 4 hours, 1-bromo-3-methoxypropane (0.37 g) was added and the mixture was further heated under reflux for 24 hours. After being cooled, the mixture was diluted with ethyl acetate and insoluble materials were filtered through Celite. The filtrate was concentrated in vacuo and the resulted residue was purified with a silica gel column chromatography (eluting solvent: n-hexane/ethyl acetate=9/1 to 7/3) to give methyl 3-(benzyloxy)-5-(3-methoxypropoxy)benzoate (2.67 g) as a colorless oil.
APCI-MS m/z: 331[M+H]⁺.
(2) Lithium aluminium hydride (437 mg) was added little by little to a solution of the compound (1.90 g) obtained in (1) described above in tetrahydrofuran (19 ml) under ice-cooling and the mixture was stirred at the same temperature for an hour. Water (0.44 ml), 10% sodium hydroxide aqueous solution (0.88 ml) and water (1.76 ml) were added successively and the mixture was stirred at room temperature for an hour. Insoluble materials were filtered through Celite, and the insoluble materials were washed with ethyl acetate. The filtrate and the washing were combined, concentrated in vacuo and the resulted residue was purified with a silica gel column chromatography (eluting solvent: n-hexane/ethyl acetate=3/1 to 1/1) to give [3-(benzyloxy)-5-(3-methoxypropoxy)phenyl]methanol (1.74 g) as a colorless oil.
APCI-MS m/z: 303[M+H]⁺.
(3) Bromotrimethylsilane (0.87 ml) was added dropwise to a solution of the compound (1.00 g) obtained in (2) described above in chloroform (20 ml) under ice-cooling and the mixture was stirred at room temperature for 18 hours. The mixture was concentrated in vacuo and the resulted residue was azeotropically distilled with toluene (twice) to give 1-(benzyloxy)-3-(bromomethyl)-5-(3-methoxypropoxy)benzene (1.20 g) as a crude oil, which was used in the next step without further purification.
(4) Cyclopropylamine (2.64 ml) was added to a solution of the compound (1.20 g) obtained in (3) described above in tetrahydrofuran (60 ml) under ice-cooling. After the mixture was stirred at room temperature for 18 hours, it was concentrated in vacuo and the resulted residue was purified with a silica gel column chromatography (eluting solvent: n-hexane/ethyl acetate=2/1 to ethyl acetate) to give N-[3-(benzyloxy)-5-(3-methoxypropoxy)benzyl]cyclopropanamine (0.37 g) as a colorless oil.
APCI-MS m/z: 342[M+H]⁺.

Reference Example 4

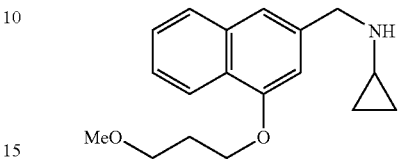

(1) Lithium aluminium hydride (342 mg) was added to a solution of 4-hydroxy-2-naphthalenecarboxylic acid (565 mg) in tetrahydrofuran (10 ml) under ice-cooling and the mixture was stirred at room temperature for 18 hours and at 50° C. for 4 hours. Water (0.35 ml), 2N sodium hydroxide aqueous solution (0.70 ml) and water (0.70 ml) were slowly added successively to the mixture under ice-cooling and the mixture was stirred at room temperature overnight. The mixture was acidified by adding 1N hydrochloric acid, insoluble materials were filtered through Celite and the filtrate was extracted with ethyl acetate. The organic layer was washed with water and saturated brine successively, dried over sodium sulfate and concentrated in vacuo. The resulted residue was purified with a silica gel column chromatography (eluting solvent: chloroform to chloroform/methanol=9/1) to give 3-(hydroxymethyl)-1-naphthol (260 mg) as an orange powder. ESI-MS m/z: 173[M−H]⁻.
(2) The compound obtained in (1) described above (250 mg) was treated in the same manner as Reference Example 3(1) to give [4-(3-methoxypropoxy)-2-naphthyl]methanol (195 mg) as an orange oil.
APCI-MS m/z: 264[M+NH₄]⁺.
(3) The compound obtained in (2) described above (180 mg) was treated in the same manner as Reference Example 3(3) to give 3-(bromomethyl)-1-(3-methoxypropoxy)naphthalene (230 mg) as a crude oil, which was used in the next step without further purification.
(4) The compound obtained in (3) described above (226 mg) was treated in the same manner as Reference Example 3(4) to give N-{[4-(3-methoxypropoxy)-2-naphthyl]methyl}cyclopropanamine (99 mg) as a colorless oil.
APCI-MS m/z: 286[M+H]⁺.

Reference Example 5

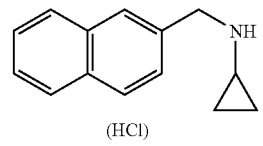

(1) 2-(Bromomethyl)naphthalene (2.21 g) was treated in the same manner as Reference Example 3(4) to give N-(2-naphthylmethyl)cyclopropanamine (1.88 g) as a yellow oil.
APCI-MS m/z: 198[M+H]⁺.
(2) The compound obtained in (1) described above (1.88 g) was treated in the same manner as Reference Example 1(2)

to give N-(2-naphthylmethyl)cyclopropanamine hydrochloride (2.10 g) as a colorless powder.
APCI-MS m/z: 198[M+H]⁺.

Reference Example 6

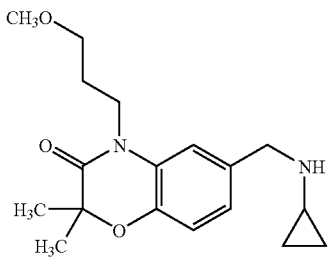

(1) Triphenylphosphine (1.13 g) and N-bromosuccinimide (0.76 g) were added to a solution of 6-(hydroxymethyl)-4-(3-methoxypropyl)-2,2-dimethyl-2H-1,4-benzoxazin-3(4H)-one (1.00 g) in tetrahydrofuran (20 ml) under ice-cooling and the mixture was stirred at room temperature for 3 hours. The mixture was concentrated in vacuo and the resulted residue was purified with a silica gel column chromatography (eluting solvent: n-hexane/ethyl acetate=5/1 to 3/1) to give 6-(bromomethyl)-4-(3-methoxypropyl)-2,2-dimethyl-2H-1,4-benzoxazin-3(4H)-one (1.07 g) as a colorless powder.
APCI-MS m/z: 342/344[M+H]⁺.

(2) The compound obtained in (1) described above (100 mg) was treated in the same manner as Reference Example 3(4) to give 6-[(cyclopropylamino)methyl]-4-(3-methoxypropyl)-2,2-dimethyl-2H-1,4-benzoxazin-3(4H)-one (81 mg).
APCI-MS m/z: 319[M+H]⁺.

Reference Example 7

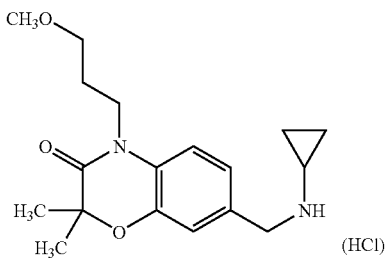

(1) A 1M solution of diisobutyl aluminium hydride in toluene (355 ml) was added to a suspension of methyl 2,2-dimethyl-3-oxo-3,4-dihydro-2H-1,4-benzoxazin-7-carboxylate (20.00 g) in tetrahydrofuran (720 ml) at −40° C., and the reaction mixture was stirred at the same temperature for 2 hours and at −20° C. for 1 hour. The mixture was poured into cooled 6N hydrochloric acid (186 ml) and the organic layer was separated. The aqueous layer was extracted with tetrahydrofuran and the combined organic layer was washed with 1M aqueous solution of sodium/potassium tartrate. The organic layer was dried over sodium sulfate, concentrated in vacuo and the resulted residue was triturated in tert-butylmethyl ether to give 7-(hydroxymethyl)-2,2-dimethyl-2H-1,4-benzoxazin-3(4H)-one (13.15 g) as a colorless powder.
APCI-MS m/z: 208[M+H]⁺.

(2) 1-Bromo-3-methoxypropane (7.75 g), 40% potassium fluoride-alumina (30.3 g) and potassium iodide (0.11 g) were added to a solution of the compound obtained (1) described above (7.00 g) in acetonitrile (560 ml) and the reaction mixture was heated under reflux for 4 hours. Insoluble materials were filtered through Celite, the filtrate was concentrated in vacuo, and the resulted residue was purified with a silica gel column chromatography (eluting solvent: n-hexane/ethyl acetate=1/1) to give 7-(hydroxymethyl)-4-(3-methoxypropyl)-2,2-dimethyl-2H-1,4-benzoxazin-3(4H)-one (7.40 g) as a colorless oil.
APCI-MS m/z: 280[M+H]⁺.

(3) The compound obtained in (2) described above (6.25 g) was treated in the same manner as Reference Example 6(1) to give 7-(bromomethyl)-4-(3-methoxypropyl)-2,2-dimethyl-2H-1,4-benzoxazin-3(4H)-one (7.00 g) as a colorless oil.
APCI-MS m/z: 342/344[M+H]⁺.

(4) The compound obtained in (3) described above (6.00 g) was treated in the same manner as Reference Example 3(4) to give 7-[(cyclopropylamino)methyl]-4-(3-methoxypropyl)-2,2-dimethyl-2H-1,4-benzoxazin-3(4H)-one (5.58 g) as a colorless oil.
APCI-MS m/z: 319[M+H]⁺.

(5) The compound obtained in (4) described above (5.10 g) was treated in the same manner as Reference Example 1(2) to give 7-[(cyclopropylamino)methyl]-4-(3-methoxypropyl)-2,2-dimethyl-2H-1,4-benzoxazin-3(4H)-one hydrochloride (5.00 g) as a colorless powder.
APCI-MS m/z: 319[M+H]⁺.

Reference Example 8

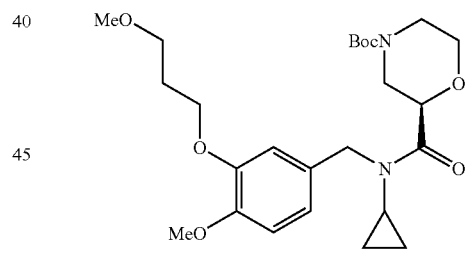

1-Hydroxybenzotriazole (175 mg), triethylamine (145 µl) and 1-ethyl-3-(3-dimethylaminopropyl)carbodiimide hydrochloride (249 mg) were added to a solution of (2R)-(tert-butoxycarbonyl)morpholin-2-carboxylic acid (200 mg) and N-[4-methoxy-3-(3-methoxypropoxy)benzyl]cyclopropanamine hydrochloride (a compound of Reference Example 1(2), 313 mg) in N,N-dimethylformamide (5 ml) successively and the mixture was stirred at room temperature for 3 hours. Water was added to the mixture under ice-cooling and it was extracted with ethyl acetate. The organic layer was washed with a saturated aqueous solution of sodium bicarbonate and saturated brine successively, dried over sodium sulfate and concentrated in vacuo. The resulted residue was purified with a silica gel column chromatography (eluting solvent: n-hexane/ethyl acetate=1/1) to give tert-butyl(2R)-2-({cyclopropyl[4-methoxy-3-(3-methoxypropoxy)benzyl]amino}carbonyl)morpholin-4-carboxylate (368 mg) as a colorless oil.

Reference Example 9

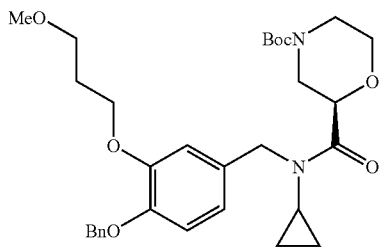

1-Hydroxybenzotriazole (99 mg), and 1-ethyl-3-(3-dimethylaminopropyl)carbodiimide hydrochloride (142 mg) were added to a solution of (2R)-4-(tert-butoxycarbonyl)morpholin-2-carboxylic acid (114 mg) and N-[4-(benzyloxy)-3-(3-methoxypropoxy)benzyl]cyclopropanamine (a compound of Reference Example 2, 202 mg) in chloroform (10 ml) successively and the mixture was stirred at room temperature for 18 hours. A saturated aqueous solution of sodium bicarbonate was poured into the mixture under ice-cooling and it was extracted with ethyl acetate. The organic layer was washed with saturated brine, dried over sodium sulfate and concentrated in vacuo. The resulted residue was purified with a silica gel column chromatography (eluting solvent: n-hexane/ethyl acetate=1/1) to give tert-butyl(2R)-2-{[[4-(benzyloxy)-3-(3-methoxypropoxy)benzyl]cyclopropyl)amino]carbonyl}morpholin-4-carboxylate (222 mg) as a colorless oil.
APCI-MS in/z: 555[M+H]$^+$.

Reference Example 10

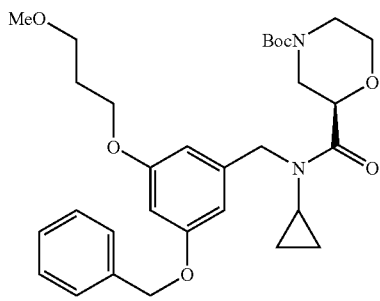

(2R)-4-(tert-Butoxycarbonyl)morpholin-2-carboxylic acid (198 mg) and N-[3-(benzyloxy)-5-(3-methoxypropoxy)benzyl]cyclopropanamine (a compound obtained in Reference Example 3, 351 mg) was treated in the same manner as Reference Example 8 to give tert-butyl(2R)-2-{[[3-(benzyloxy)-5-(3-methoxypropoxy)benzyl]cyclopropyl)amino]carbonyl}morpholin-4-carboxylate (390 mg) as a colorless oil.
APCI-MS m/z: 555[M+H]$^+$.

Reference Example 11

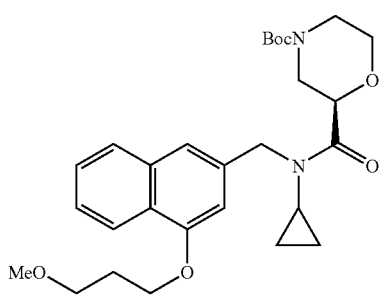

(2R)-4-(tert-Butoxycarbonyl)morpholin-2-carboxylic acid (77 mg) and N-{[4-(3-methoxypropoxy)-2-naphthyl]methyl}cyclopropanamine (a compound obtained in Reference Example 4, 85 mg) were treated in the same manner as Reference Example 9 to give tert-butyl(2R)-2-[cyclopropyl{[4-(3-methoxypropoxy)-2-naphthyl]methyl}amino)carbonyl]morpholin-4-carboxylate (132 mg) as a colorless oil.
APCI-MS m/z: 499[M+H]$^+$.

Reference Example 12

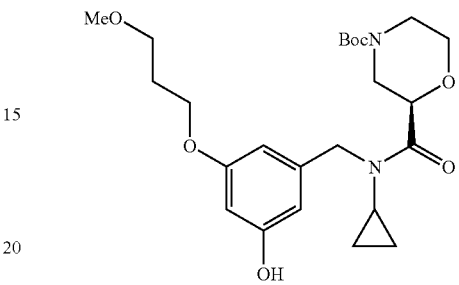

10% Palladium-carbon (containing 50% water, 30 mg) was added to a solution of tert-butyl(2R)-2-{[[3-(benzyloxy)-5-(3-methoxypropoxy)benzyl]cyclopropyl)amino]carbonyl}morpholin-4-carboxylate (a compound obtained in Reference Example 10, 100 mg) in methanol-ethyl acetate (1:1, 2 ml) and the mixture was stirred under normal hydrogen pressure at room temperature for 3 hours. Insoluble materials were filtered and the filtrate was concentrated in vacuo to give tert-butyl(2R)-2-({cyclopropyl[3-hydroxy-5-(3-methoxypropoxy)benzyl]amino}carbonyl)morpholin-4-carboxylate (74 mg) as a pale yellow oil.
APCI-MS m/z: 465[M+H]$^+$.

Reference Example 13

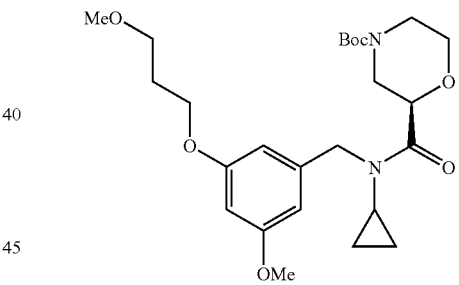

Potassium carbonate (54 mg) and methyl iodide (24 µL) were added to a solution of tert-butyl(2R)-2-({cyclopropyl[3-hydroxy-5-(3-methoxypropoxy)benzyl]amino}carbonyl)morpholin-4-carboxylate (a compound obtained in Reference Example 12, 120 mg) in N,N-dimethylformamide (6 ml) and the mixture was stirred at room temperature for 2 hours. Water was added to the mixture under ice-cooling and it was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=2/1) to give tert-butyl(2R)-2-({cyclopropyl[3-methoxy-5-(3-methoxypropoxy)benzyl]amino}carbonyl)morpholin-4-carboxylate (88 mg) as a colorless oil.
APCI-MS m/z: 479[M+H]$^+$.

Reference Example 14-18

Corresponding starting compounds are treated in the same manner as Reference Example 8 or 9 to give the following compounds.

Reference Example 14

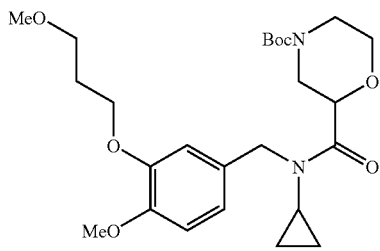 [SMILES: COCCCOc1cc(CN(C(=O)C2CN(C(=O)OC(C)(C)C)CCO2)C2CC2)ccc1OC]

property: colorless oil
APCI-MS m/z: 496[M+NH$_4$]$^+$.

Reference Example 15

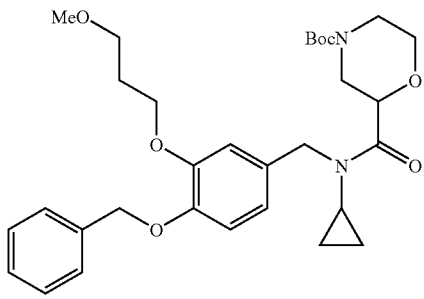 [SMILES: COCCCOc1cc(CN(C(=O)C2CN(C(=O)OC(C)(C)C)CCO2)C2CC2)ccc1OCc1ccccc1]

property: colorless oil
APCI-MS m/z: 572[M+NH$_4$]$^+$

Reference Example 16

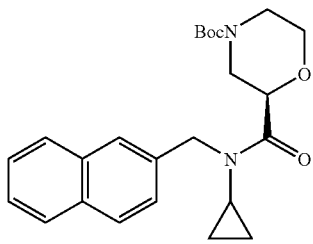

property: colorless oil
APCI-MS m/z: 411[M+H]$^+$

Reference Example 17

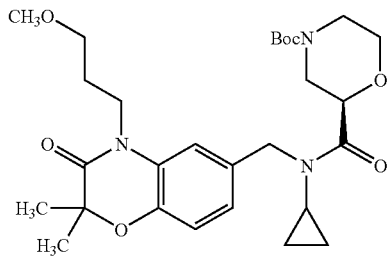

property: colorless oil
APCI-MS m/z: 549[M+NH$_4$]$^+$

Reference Example 18

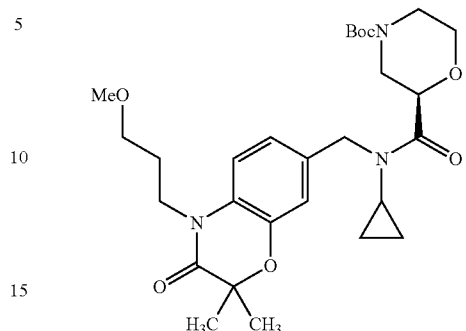

property: colorless viscous oil
APCI-MS m/z: 549[M+NH$_4$]$^+$

Reference Example 19

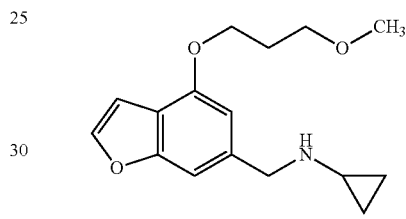

(HCl)

(1) 60% Oily sodium hydride (6.50 g) was washed with n-hexane (100 ml) twice and suspended in tetrahydrofuran (400 ml). A solution of 4-tert-butyl 1-ethyl 2-(diethoxyphosphoryl)succinate (55.0 g) in tetrahydrofuran (100 ml) was added dropwise to the suspension under ice-cooling during 30 minutes and the mixture was stirred at the same temperature for an hour. Next, a solution of 2-furaldehyde (12.8 ml) in tetrahydrofuran (40 ml) was added dropwise during 15 minutes and the mixture was stirred at room temperature for an hour. Water was poured into the reaction solution under ice-cooling and it was extracted with ethyl acetate. The organic layer was washed with saturated brine, dried over sodium sulfate and concentrated in vacuo to give 4-tert-butyl 1-ethyl(2E)-2-(2-furylmethylene)succinate (47 g) as a crude brown oil.

The oil (47 g) was stirred in trifluoroacetic acid (100 ml) at room temperature for an hour, concentrated in vacuo, and the resulted residue was azeotropically distilled with toluene several times to give (3E)-3-(ethoxycarbonyl)-4-(2-furyl)-but-3-ene carboxylic acid (40 g) as a crude brown oil.

The oil (40 g) was dissolved in acetic anhydride (100 ml), thereto was added potassium acetate (19.75 g) and the mixture was heated under reflux for 45 minutes. The reaction mixture was left stand to cool, water (100 ml) was added and concentrated to dryness in vacuo. The resulted residue was purified with a silica gel column chromatography (eluting solvent: n-hexane/ethyl acetate=5/1) to give ethyl 4-(acetyloxy)benzofuran-6-carboxylate (24.66 g) as a pale orange powder.

APCI-MS m/z: 266[M+NH$_4$]$^+$.

(2) Potassium carbonate (42 g) was added to a solution of the compound obtained in (1) described above (24.66 g) in ethanol (150 ml) and the mixture was heated under reflux for 0.5 hour. After the mixture was cooled in ice-water and acidified by adding water and 10% hydrochloric acid, it was extracted with ethyl acetate. The organic layer was washed with saturated brine, dried over sodium sulfate and concentrated in vacuo. The resulted residue was dissolved in dichloromethane and insoluble materials were filtered off. The filtrate was concentrated in vacuo and the resulted residue was dissolved in n-haxene-dichloromethane (5:1) and filtered to give ethyl 4-hydroxybenzofuran-6-carboxylate (19.62 g) as a pale yellow powder.
APCI-MS m/z: 207[M+H]$^+$.

(3) 1-Bromo-3-methoxypropane (8.17 g) and potassium carbonate (9.05 g) were added to a solution of the compound obtained in (2) described above (9.00 g) in acetonitrile (100 ml) and the mixture was heated under reflux for 24 hours. After the mixture was left stand to cool and ice-water was added to the reaction mixture under ice-cooling, it was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=85/15 to 70/30) to give ethyl 4-(3-methoxypropoxy)benzofuran-6-carboxylate (11.25 g) as a yellow oil.
APCI-MS m/z: 279[M+H]$^+$.

(4) A solution of the compound obtained in (3) described above (5.50 g) in tetrahydrofuran (150 ml) was added dropwise to a suspension of lithium aluminium hydride (1.50 g) in tetrahydrofuran (150 ml) under ice-cooling during 10 minutes and the mixture was stirred at the same temperature for an hour. Water (3 ml), 2N sodium hydroxide aqueous solution (6 ml) and water (3 ml) were successively added slowly under ice-cooling and the mixture was stirred at room temperature for 2.5 hours. Insoluble materials were filtered through Celite and the filtrate was concentrated in vacuo. The resulted residue was dissolved in ethyl acetate, dried over sodium sulfate and concentrated in vacuo. The resulted residue was purified with a silica gel column chromatography (eluting solvent: chloroform/methanol=95/15 to 90/10) to give [4-(3-methoxypropoxy)benzofuran-6-yl]methanol (4.68 g) as a pale yellow oil.
APCI-MS m/z: 254[M+NH$_4$]$^+$.

(5) N-Bromosuccinimide (2.10 g) was add in small portions to a solution of the compound obtained in (4) described above (2.00 g) and triphenylphosphine (3.30 g) in dichloromethane (10 ml) under ice-cooling. After stirring of the reaction mixture at room temperature for 0.5 hour, it was purified with a silica gel column chromatography (eluting solvent: n-hexane/ethyl acetate=93/7 to 75/25) to give 6-(bromometnyl)-4-(3-methoxypropoxy)benzofuran (1.57 g) as a pale yellow oil.
APCI-MS m/z: 299/301[M+H]$^+$.

(6) Cyclopropylamine (4.22 ml) was added under ice cooling to a solution of the compound obtained in (5) described above (1.57 g) in tetrahydrofuran (20 ml) and the mixture was stirred at room temperature for 3 hours. After the reaction mixture was concentrated in vacuo, it was diluted with ethyl acetate and washed with a saturated aqueous solution of sodium bicarbonate, water and saturated brine successively. The organic layer was dried over sodium sulfate, concentrated in vacuo and the resulted residue was purified with a silica gel column chromatography (eluting solvent: chloroform/methanol=100/0 to 95/5) to give N-{[4-(3-methoxypropoxy)benzofuran-6-yl]methyl}cyclopropanamine (1.33 g) as a yellow oil.
APCI-MS m/z: 276[M+H]$^+$.

(7) A 4N hydrogen chloride solution in ethyl acetate (2.6 ml) was added under ice-cooling to a solution of the compound obtained in (6) described above (1.33 g) in ethyl acetate (2.6 ml) and the mixture was stirred at the same temperature for 15 minutes. The mixture was concentrated in vacuo, the resulted residue was suspended in diisopropyl ether and filtered to give N-{[4-(3-methoxypropoxy)benzofuran-6-yl]methyl}cyclopropanamine hydrochloride (1.45 g) as a colorless powder.
APCI-MS m/z: 276[M+H]$^+$.

Reference Example 20

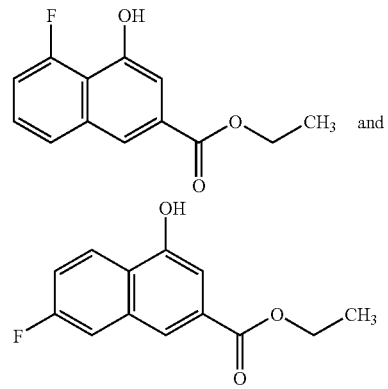

(1) A solution of 4-tert-butyl 1-ethyl 2-(diethoxyphosphoryl)succinate (28.60 g) in tetrahydrofuran (70 ml) was added dropwise to a suspension of 60% oily sodium hydride (3.39 g) in tetrahydrofuran (100 ml) under ice-cooling during 20 minutes, the mixture was stirred at the same temperature for an hour. Next, a solution of 3-fluorobenzaldehyde (10.00 g) in tetrahydrofuran (30 ml) was added thereto and the mixture was stirred at room temperature for 3 hours. Ice-water was added to the reaction mixture under ice-cooling and it was extracted with ethyl acetate. The organic layer was washed with water and saturated brine successively, dried over sodium sulfate and concentrated in vacuo to give 4-tert-butyl 1-ethyl(2E)-2-(3-fluorobenzylidene)succinate (27.7 g) as a crude yellow oil.

Next, the oil (27.7 g) was stirred in trifluoroacetic acid (100 ml) a room temperature for an hour and concentrated in vacuo. The resulted residue was azeotropically distilled with toluene several times to give (3E)-3-(ethoxycarbonyl)-4-(3-fluorophenyl)-but-3-enecarboxylic acid (26.1 g) as a crude yellow oil. Then, the oil (26.1 g) was dissolved in acetic anhydride (200 ml), potassium acetate (12.1 g) was added thereto and the mixture was heated under reflux for 0.5 hour. After the reaction mixture was left stand to cool and water (100 ml) was added, it was extracted with ethyl acetate. The organic layer was washed with a saturated aqueous solution of sodium bicarbonate and saturated brine successively, dried over sodium sulfate and concentrated in vacuo. The resulted residue was purified with a silica gel column chromatography (eluting solvent: n-hexane/ethyl acetate=10/1) to give a mixture of ethyl 4-acetoxy-5-fluoro-2-naphthoate and ethyl 4-acetoxy-7-fluoro-2-naphthoate (15.20 g) as a pale yellow powder.
APCI-MS m/z: 294[M+NH$_4$]$^+$.

(2) Potassium carbonate (12.5 g) was added to a solution of the compound obtained in (1) described above (5.0 g) in ethanol (50 ml) and the mixture was heated under reflux for 0.5 hour. After the reaction mixture was cooled in ice-water and acidified by adding 10% hydrochloric acid and extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=8/1 to 3/1) and each regioisomer was separated. A less polar isomer was triturated in n-hexane-diethyl ether (10:1) to give ethyl 5-fluoro-4-hydroxy-2-naphthoate (0.80 g) as a colorless powder.

ESI-MS m/z: 233[M−H]⁻.

In the same manner, a more polar isomer was treated to give ethyl 7-fluoro-4-hydroxy-2-naphthoate (2.57 g) as a colorless powder.

ESI-MS m/z: 233[M−H]⁻.

Reference Example 21-24

Corresponding starting compounds are treated in the same manner as Reference Example 19(1) to give the following compounds.

Reference Example 21

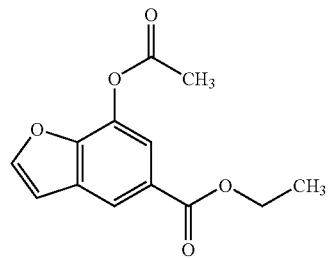 [SMILES: CCOC(=O)c1cc(OC(C)=O)c2occc2c1]

property: pale brown powder
APCI-MS m/z: 266[M+NH$_4$]$^+$

Reference Example 22

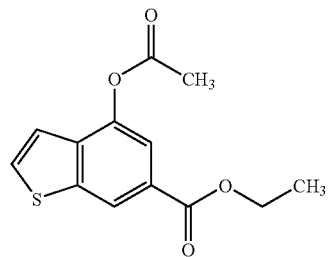 [SMILES: CCOC(=O)c1cc(OC(C)=O)c2ccsc2c1]

property: yellow powder
APCI-MS m/z: 265[M+H]$^+$

Reference Example 23

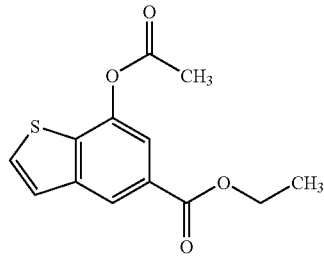

property: yellow viscous oil
APCI-MS m/z: 265[M+H]$^+$

Reference Example 24

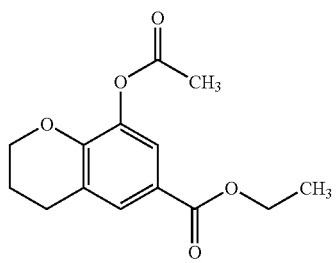 [SMILES: CCOC(=O)c1cc2c(c(OC(C)=O)c1)OCCC2]

property: yellow oil
APCI-MS m/z: 265[M+H]$^+$

Reference Example 25-29

Corresponding starting compounds are treated in the same manner as Reference Example 19(2) to give the following compounds of Table 5.

TABLE 5

| No. of Reference Examples | Structure | Properties |
| --- | --- | --- |
| 25 | OH-benzofuran ethyl ester | Property: pale yellow powder<br>APCI-MS<br>m/z: 207 [M + H]$^+$ |

TABLE 5-continued

| No. of Reference Examples | Structure | Properties |
|---|---|---|
| 26 | 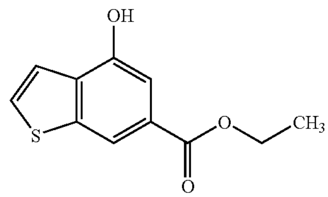 | Property: colorless powder<br>APCI-MS<br>m/z: 223 [M + H]⁺ |
| 27 | 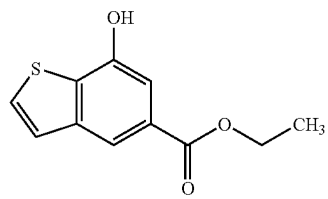 | Property: colorless powder<br>APCI-MS<br>m/z: 223 [M + H]⁺ |
| 28 | 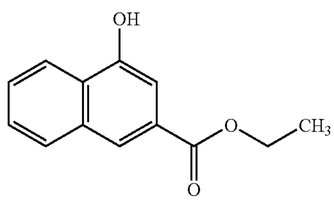 [SMILES: CCOC(=O)c1cc(O)c2ccccc2c1] | Property: pale yellow powder<br>APCI-MS<br>m/z: 217 [M + H]⁺ |
| 29 | 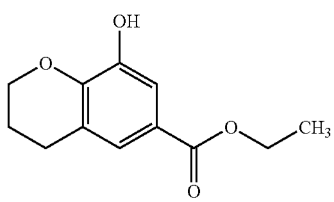 | Property: pale yellow viscous oil<br>APCI-MS<br>m/z: 223 [M + H]⁺ |

Reference Example 30

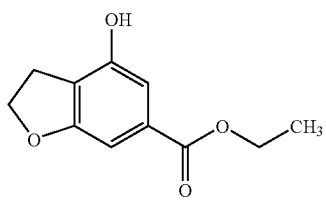

A mixture of ethyl 4-hydroxybenzofuran-6-carboxylate (a compound of Reference Example 19(2), 8.53 g) and 20% palladium hydroxide-carbon (dry, 2.0 g) with ethanol (250 ml) was stirred under normal pressure of hydrogen atmosphere at room temperature for 2 hours. Insoluble materials were filtered through Celite and the residue was washed with ethyl acetate. The filtrate and washing were combined, concentrated in vacuo and the residue was purified with a silica gel column chromatography (eluting solvent: n-hexane/ethyl acetate=80/20 to 50/50) and filtered after being suspended in n-hexane to give ethyl 4-hdroxy-2,3-dihydrobenzofuran-6-carboxylate (7.75 g) as a colorless powder.

APCI-MS m/z: 209[M+H]⁺.

Reference Example 31

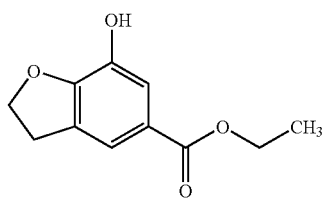

Ethyl 7-hydroxybenzofuran-5-carboxylate (a compound of Reference Example 25, 5.05 g) was treated in the same manner as Reference Example 30 to give ethyl 7-hdroxy-2,3-dihydrobenzofuran-5-carboxylate (5.10 g) as a colorless powder.

APCI-MS m/z: 209[M+H]⁺.

Reference Example 32

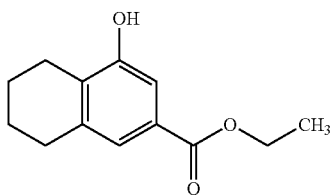 [SMILES: CCOC(=O)c1cc(O)c2c(c1)CCCC2]

Ethyl 4-hydroxy-2-naphthoate (a compound of Reference Example 28, 6.00 g) was treated in the same manner as Reference Example 30 to give ethyl 4-hdroxy-5,6,7,8-tetrahydronaphthalene-2-carboxylate (5.20 g) as a colorless powder.

APCI-MS m/z: 221[M+H]$^+$

Reference Example 33-42

Corresponding starting compounds are treated in the same manner as Reference Example 19(3) to give the following compounds of Table 6.

TABLE 6

| No. of Reference Examples | Structure | Properties |
|---|---|---|
| 33 | 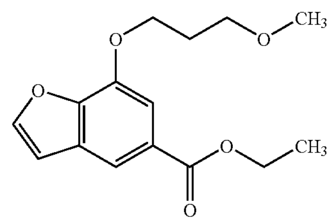 [SMILES: CCOC(=O)c1cc(OCCCOC)c2occc2c1] | Property: colorless powder<br>APCI-MS<br>m/z: 279 [M + H]$^+$ |
| 34 | 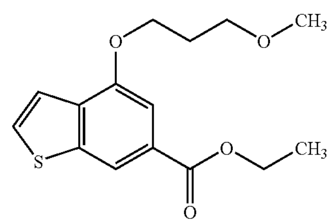 [SMILES: CCOC(=O)c1cc(OCCCOC)c2ccsc2c1] | Property: yellow viscous oil<br>APCI-MS<br>m/z: 295 [M + H]$^+$ |
| 35 | 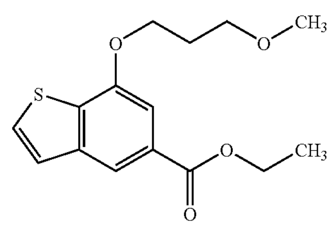 | Property: colorless powder<br>APCI-MS<br>m/z: 295 [M + H]$^+$ |
| 36 | 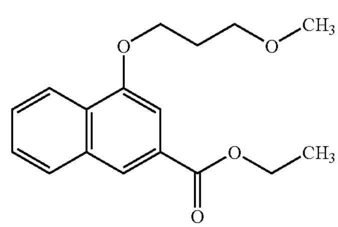 [SMILES: CCOC(=O)c1cc(OCCCOC)c2ccccc2c1] | Property: colorless oil<br>APCI-MS<br>m/z: 306 [M + NH$_4$]$^+$ |
| 37 | 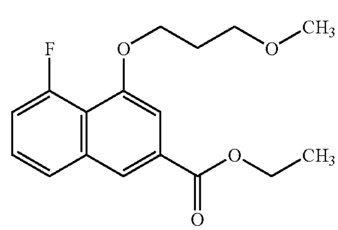 [SMILES: CCOC(=O)c1cc(OCCCOC)c2c(F)cccc2c1] | Property: powder<br>APCI-MS<br>m/z: 307 [M + H]$^+$ |

TABLE 6-continued

| No. of Reference Examples | Structure | Properties |
|---|---|---|
| 38 | 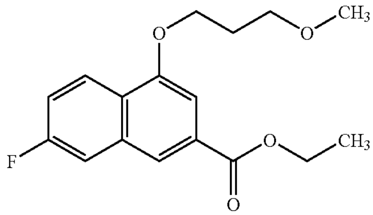 [SMILES: CCOC(=O)c1cc(OCCCOC)c2ccc(F)cc2c1] | Property: oil<br>APCI-MS<br>m/z: 307 [M + H]+ |
| 39 | 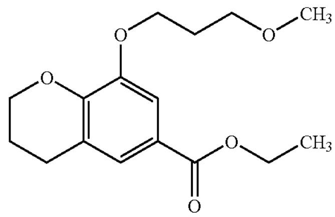 | Property: pale yellow powder<br>APCI-MS<br>m/z: 295 [M + H]+ |
| 40 | 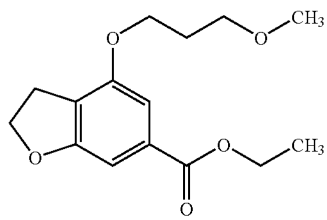 [SMILES: CCOC(=O)c1cc(OCCCOC)c2c(c1)OCC2] | Property: pale yellow powder<br>APCI-MS<br>m/z: 281 [M + H]+ |
| 41 | 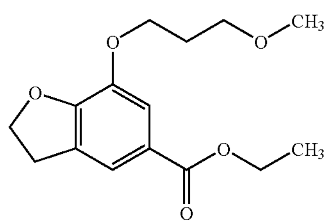 | Property: colorless oil<br>APCI-MS<br>m/z: 281 [M + H]+ |
| 42 | 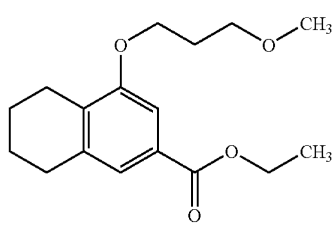 [SMILES: CCOC(=O)c1cc2c(c(OCCCOC)c1)CCCC2] | APCI-MS<br>m/z: 293 [M + H]+ |

Reference Example 43-51

Corresponding starting compounds are treated in the same manner as Reference Example 19(4) to give the following compounds of Table 7.

TABLE 7

| No. of Reference Examples | Structure | Properties |
|---|---|---|
| 43 | 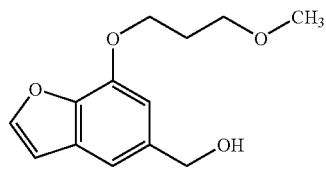 [SMILES: COCCCOc1cc(CO)cc2ccoc12] | Property: colorless powder<br>APCI-MS<br>m/z: 254 [M + NH4]+ |

TABLE 7-continued

| No. of Reference Examples | Structure | Properties |
|---|---|---|
| 44 | 4-(3-methoxypropoxy)-benzothiophene-6-methanol | Property: yellow oil<br>APCI-MS<br>m/z: 270 [M + NH$_4$]$^+$ |
| 45 | 7-(3-methoxypropoxy)-benzothiophene-5-methanol | Property: yellow viscous oil<br>APCI-MS<br>m/z: 270 [M + NH$_4$)$^+$ |
| 46 | 8-fluoro-1-(3-methoxypropoxy)-naphthalene-3-methanol | Property: oil<br>APCI-MS<br>m/z:<br>279 [M + H + MeOH—H$_2$O]$^+$ |
| 47 | 6-fluoro-1-(3-methoxypropoxy)-naphthalene-3-methanol | Property: oil<br>APCI-MS<br>m/z: 282 [M + NH$_4$]$^+$ |
| 48 | 8-(3-methoxypropoxy)-chroman-6-methanol | Property: colorless powder<br>APCI-MS<br>m/z: 270 [M + NH$_4$]$^+$ |
| 49 | 4-(3-methoxypropoxy)-2,3-dihydrobenzofuran-6-methanol | Property: pale yellow viscous oil<br>APCI-MS<br>m/z: 239 [M + H]$^+$ |
| 50 | 7-(3-methoxypropoxy)-2,3-dihydrobenzofuran-5-methanol | Property: colorless oil<br>APCI-MS<br>m/z: 256 [M + NH$_4$]$^+$ |
| 51 | 5-(3-methoxypropoxy)-5,6,7,8-tetrahydronaphthalene-3-methanol | APCI-MS<br>m/z: 268 [M + NH$_4$]$^+$ |

Reference Example 52-58

Corresponding starting compounds are treated in the same manner as Reference Example 19(5) to give the following compounds of Table 8.

TABLE 8

| No. of Reference Examples | Structure | Properties |
|---|---|---|
| 52 | 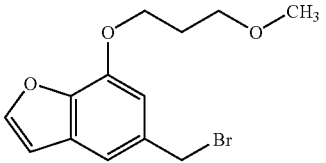 [SMILES: COCCCOc1cc(CBr)cc2ccoc12] | Property: colorless viscous oil<br>APCI-MS<br>m/z: 299/301 [M + H]$^+$ |
| 53 | 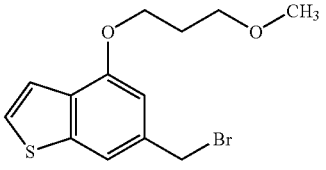 | Property: colorless oil<br>APCI-MS<br>m/z: 235 [M + H − HBr]$^+$ |
| 54 | 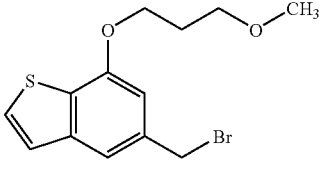 [SMILES: COCCCOc1cc(CBr)cc2ccsc12] | Property: colorless powder<br>APCI-MS<br>m/z: 332/334 [M + NH$_4$]$^+$ |
| 55 | 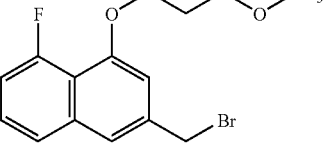 | Property: powder<br>APCI-MS<br>m/z: 327/329 [M + H]$^+$ |
| 56 | 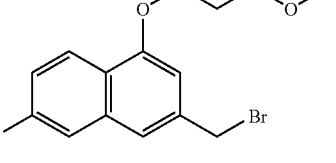 | APCI-M S<br>m/z: 327/329 [M + H]$^+$ |
| 57 | 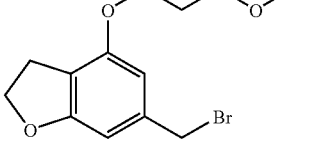 | Property: colorless viscous oil<br>APCI-MS<br>m/z: 301/303 [M + H]$^+$ |
| 58 | 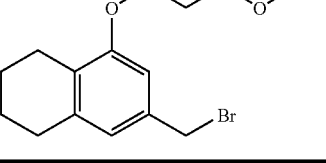 | APCI-MS<br>m/z: 330/332 [M + NH$_4$]$^+$ |

203

Reference Example 59-60

Corresponding starting compounds are treated in the same manner as Reference Example 3(3) to give the following compounds of Table 9.

TABLE 9

| No. of Reference Examples | Structure | Properties |
|---|---|---|
| 59 | 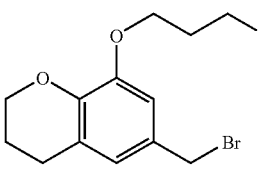 | Property: brown oil |
| 60 | 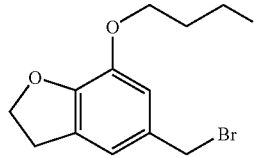 | Used in the next step without purification |

Reference Example 61-69

Corresponding starting compounds are treated in the same manner as Reference Example 19(6) to give the following compounds of Table 10.

TABLE 10

| No. of Reference Examples | Structure | Properties |
|---|---|---|
| 61 | 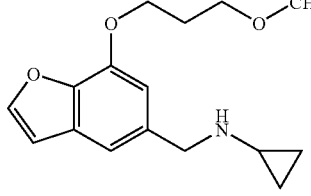 | used in the next step without purification |
| 62 | 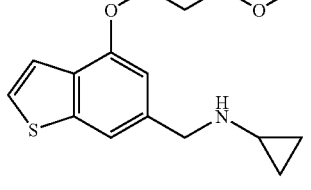 | APCI-MS m/z: 292 [M + H]⁺ |
| 63 | 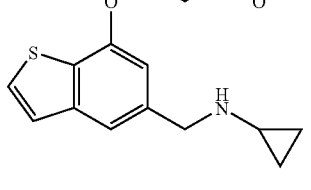 | APCI-MS m/z: 292 [M + H]⁺ |

204

TABLE 10-continued

| No. of Reference Examples | Structure | Properties |
|---|---|---|
| 64 | 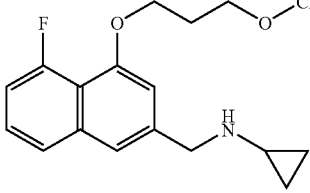 | Property: oil APCI-MS m/z: 304 [M + H]⁺ |
| 65 | 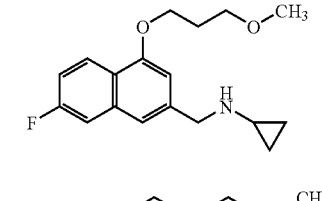 | Property: oil APCI-MS m/z: 304 [M + H]⁺ |
| 66 | 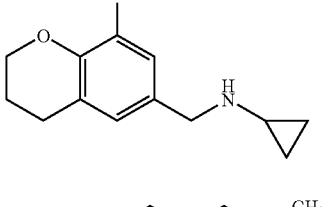 | used in the next step without purification |
| 67 | 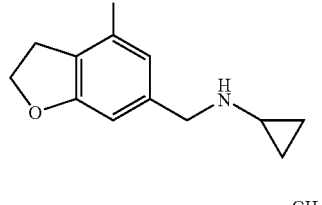 | used in the next step without purification |
| 68 | 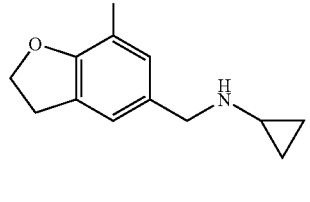 | Property: colorless oil APCI-MS m/z: 278 [M + H]⁺ |
| 69 | 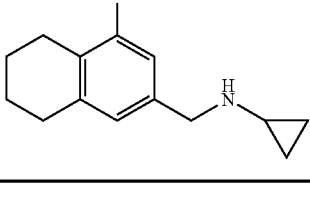 | |

Reference Example 70-77

Corresponding starting compounds are treated in the same manner as Reference Example 19(7) to give the following compounds of Table 11.

TABLE 11

| No. of Reference Examples | Structure | Properties |
|---|---|---|
| 70 | [structure: 7-(3-methoxypropoxy)benzofuran with 5-(cyclopropylaminomethyl)] | Hydrochloride<br>Property: colorless powder<br>APCI-MS m/z: 276[M + H]$^+$ |
| 71 | [structure: 4-(3-methoxypropoxy)benzothiophene with 6-(cyclopropylaminomethyl)] | Hydrochloride<br>Property: colorless powder<br>APCI-MS m/z: 292[M + H]$^+$ |
| 72 | [structure: 7-(3-methoxypropoxy)benzothiophene with 5-(cyclopropylaminomethyl)] | Hydrochloride<br>Property: colorless powder<br>APCI-MS m/z: 292[M + H]$^+$ |
| 73 | [structure: 1,4-disubstituted naphthalene with (3-methoxypropoxy) and (cyclopropylaminomethyl)] | Hydrochloride<br>Property: colorless powder<br>APCI-MS m/z: 286[M + H]$^+$ |
| 74 | [structure: 8-(3-methoxypropoxy)chroman with 6-(cyclopropylaminomethyl)] | Hydrochloride<br>Property: colorless powder<br>APCI-MS m/z: 292[M + H]$^+$ |
| 75 | [structure: 4-(3-methoxypropoxy)-2,3-dihydrobenzofuran with 6-(cyclopropylaminomethyl)] | Hydrochloride<br>Property: colorless powder<br>APCI-MS m/z: 278[M + H]$^+$ |
| 76 | [structure: 7-(3-methoxypropoxy)-2,3-dihydrobenzofuran with 5-(cyclopropylaminomethyl)] | Hydrochloride<br>Property: colorless powder<br>APCI-MS m/z: 278[M + H]$^+$ |

TABLE 11-continued

| No. of Reference Examples | Structure | Properties |
|---|---|---|
| 77 | 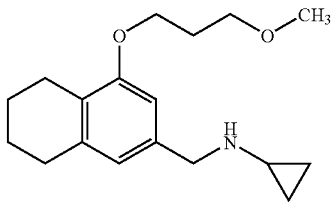 [SMILES: COCCCOc1cc(CNC2CC2)cc2c1CCCC2] | Hydrochloride Property: APCI-MS m/z: [M + H]+ |

Reference Example 78

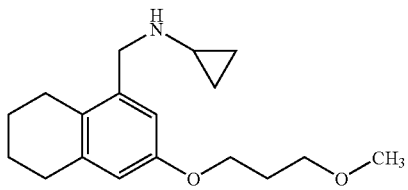 [SMILES: COCCCOc1cc2c(c(CNC3CC3)c1)CCCC2]

(1) 1-Bromo-3-methoxypropane (693 mg) and potassium carbonate (626 mg) were added to a solution of 3-hydroxy-5,6,7,8-tetrahydronaphthalene-1-carboxylic acid (290 mg) in acetonitrile (15 ml) and the mixture was heated under reflux for 8 hours. Ice water was added to the mixture under ice-cooling and it was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=20/1 to 3/1) to give 3-methoxypropyl 3-(3-methoxypropoxy)-5,6,7,8-tetrahydronaphthalen-1-carboxylate (440 mg) as a yellow oil.
APCI-MS m/z: 354[M+NH$_4$]$^+$.

(2) A solution of the compound obtained (1) described above (225 mg) in tetrahydrofuran (3 ml) was added dropwise under ice-cooling to a suspension of lithium aluminium hydride (25.4 mg) in tetrahydrofuran (3 ml) during 5 minutes and the mixture was stirred at the same temperature for 30 minutes. Water (26 μl), 2N aqueous solution of sodium hydroxide (65 μl) and water (78 μl) were added under the same cooling successively, and the mixture was stirred at room temperature for 12 hours. Insoluble materials were filtered through Celite and the filtrate was concentrated in vacuo. The residue was diluted with ethyl acetate, dried over sodium sulfate and concentrated in vacuo to give [3-(3-methoxypropoxy)-5,6,7,8-tetrahydronaphthalen-1-yl]methanol (190 mg) as a pale yellow oil.

(3) N-Bromosuccinimide (197 mg) was added to a solution of the compound obtained (2) described above (185 mg) and triphenylphosphine (291 mg) in tetrahydrofuran (5 ml) under ice-cooling. The reaction mixture was stirred at room temperature for 3 hours, concentrated in vacuo and the resulted residue was purified with a silica gel column chromatography (eluting solvent: n-hexane/ethyl acetate=10/1) to give 5-(bromomethyl)-7-(3-methoxypropoxy)-1,2,3,4-tetrahydronaphthalene (174 mg) as a colorless oil.

(4) Cyclopropylamine (212 μl) was added to a solution of the compound obtained (3) described above (165 mg) in tetrahydrofuran (3 ml) under ice-cooling and the mixture was stirred at room temperature for 5 hours. A saturated aqueous solution of sodium bicarbonate was poured into the reaction mixture and it was extracted with ethyl acetate. The organic layer was washed with saturated brine, dried over sodium sulfate and concentrated in vacuo. The resulted residue was purified with a silica gel column chromatography (eluting solvent: chloroform to chloroform/methanol=10/1) to give N-{[3-(3-methoxypropoxy)-5,6,7,8-tetrahydronaphthalen-1-yl]methyl}cyclopropylamine (145 mg) as a colorless oil.
APCI-MS m/z: 290[M+H]$^+$.

Reference Example 79

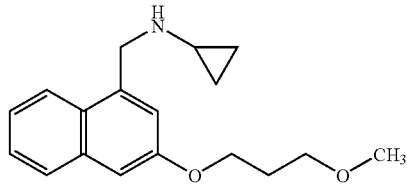 [SMILES: COCCCOc1cc(CNC2CC2)c2ccccc2c1]

(1) 2,3-Dichloro-5,6-dicyano-p-benzoquinone[DDQ] (577 mg) was added to a solution of 3-methoxypropyl 3-(3-methoxypropoxy)-5,6,7,8-tetrahydronaphthalen-1-carboxylate (compound of Reference Example 78(1), 285 mg) in toluene (10 ml) and the mixture was stirred at 60° C. for 3 hours. After being left stand to cool, a saturated aqueous solution of sodium bicarbonate was added to the reaction mixture and the whole mixture was extracted with ethyl acetate. The organic layer was washed with a saturated aqueous solution of sodium bicarbonate and saturated brine successively, dried over sodium sulfate and concentrated in vacuo. The resulted residue was purified with a silica gel column chromatography (eluting solvent: n-hexane to n-hexane/ethyl acetate=2/1) to give 3-methoxypropyl 3-(3-methoxypropoxy)-1-naphthoate (231 mg) as a colorless oil.
APCI-MS m/z: 333[M+H]$^+$.

(2) A compound obtained in (1) described above (180 mg) was treated in the same manner as Reference Example 78(2) to give [3-(3-methoxypropoxy)-1-naphthyl]methanol (142 mg) as a colorless powder.
APCI-MS m/z: 264[M+NH$_4$]$^+$.

(3) A compound obtained in (2) described above (135 mg) was treated in the same manner as Reference Example 78(3) to give 1-(bromomethyl)-3-(3-methoxypropoxy) naphthalene (75 mg) as a colorless viscous oil.
APCI-MS m/z: 309/311[M+H]+.
(4) A compound obtained in (3) described above (70 mg) was treated in the same manner as Reference Example 78(4) to give N-{[3-(3-methoxypropoxy)-1-naphthyl]methyl}cyclopropanamine (61 mg) as a colorless oil.
APCI-MS m/z: 286[M+H]+.

Reference Example 80

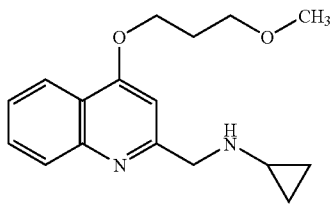 [SMILES: COCCCOc1cc(CNC2CC2)nc2ccccc12]

(1) 1-Bromo-3-methoxypropane (5.00 g) and potassium carbonate (8.90 g) were added to a solution of ethyl 4-hydroxyquinolin-2-carboxylate (5.00 g) in N,N-dimethylformamide (50 ml) and the mixture was stirred at room temperature for 15 hours. The mixture was diluted with ethyl acetate, washed with water and saturated brine successively, dried over sodium sulfate and concentrated in vacuo. The resulted residue was purified with a silica gel column chromatography (eluting solvent: n-hexane/ethyl acetate=50/50) to give ethyl 4-(3-methoxypropoxy)quinolin-2-carboxylate (6.26 g) as a colorless oil.
APCI-MS m/z: 290[M+H]+.
(2) A solution of the compound obtained in (1) described above (5.50 g) in tetrahydrofuran (40 ml) was added dropwise to a suspension of lithium aluminium hydride (0.72 g) in tetrahydrofuran (60 ml) under ice-cooling and the mixture was stirred at room temperature for 5 hours. Water (2 ml) and ammonia-water (4 ml) were added slowly and successively, and the mixture was heated under reflux for 5 hours. Insoluble materials were filtered through Celite, the filtrate was concentrated in vacuo and the resulted residue was purified with a silica gel column chromatography (eluting solvent: ethyl acetate) to give [4-(3-methoxypropoxy)quinolin-2-yl]methanol (4.05 g) as a pale yellow oil.
APCI-MS m/z: 248[M+H]+.
(3) N-Bromosuccinimide (2.89 g) was added portionwise to a solution of the compound obtained (2) described above (3.35 g) and triphenylphosphine (4.26 g) in tetrahydrofuran (70 ml) under ice-cooling. The reaction mixture was stirred at room temperature for 3 hours and cyclopropylamine (10.9 ml) was added thereto under ice-cooling. The reaction mixture was stirred at room temperature for 1.5 hours and then concentrated in vacuo. Ethyl acetate and water were added to the residue and it was extracted with 10% hydrochloric acid. After the aqueous layer was cooled with ice-water and ethyl acetate was added thereto, the mixture was made alkaline (pH 8-9) by adding a saturated aqueous solution of sodium bicarbonate. The ethyl acetate layer was separated, washed with water and saturated brine successively, dried over sodium sulfate and concentrated in vacuo. The resulted residue was purified with a silica gel column chromatography (eluting solvent: n-hexane/ethyl acetate=1/2 to chloroform/methanol=97/3) to give N-{[4-(3-methoxypropoxy)quinolin-2-yl]methyl}cyclopropanamine (2.49 g) as a yellow oil.
APCI-MS m/z: 287[M+H]+.
(4) A 4N hydrogen chloride solution in ethyl acetate (1 ml) was added to a solution of the compound obtained in (3) described above (245 mg) in ethyl acetate (2 ml) under ice-cooling, and the mixture was stirred at room temperature for 10 minutes. The mixture was concentrated in vacuo and the resulted residue was suspended in diisopropyl ether, filtered and recrystallized from ethyl acetate-diisopropyl ether to give N-{[4-(3-methoxypropoxy)quinolin-2-yl]methyl}cyclopropanamine dihydrochloride (1.45 g) as a pale pink powder.
APCI-MS m/z: 287[M+H]+.

Reference Example 81

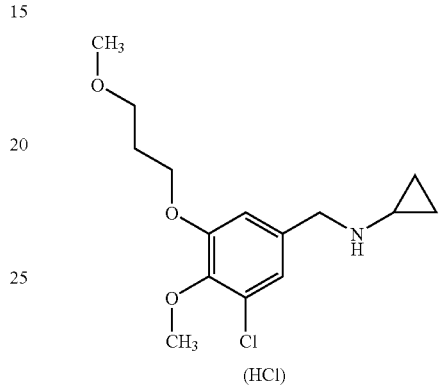

(1) After aluminium chloride (10.22 g) was added portionwise to a solution of 5-chlorovanillin[3-chloro-4-hydroxy-5-methoxybenzaldehyde](10.00 g) in chloroform (100 ml) under ice-cooling, pyridine (19.0 ml) was added dropwise thereto. After being heated under reflux for 18 hours, the reaction mixture was concentrated in vacuo. 3N Hydrochloric acid was added to the residue under ice-cooling and the mixture was stirred at room temperature for 2 hours. The precipitates were filtered, washed with 3N hydrochloric acid and water and recrystallized from ethanol-water to give 3-chloro-4,5-dihydroxybenzaldehyde (8.05 g) as a brown powder.
ESI-MS m/z: 171/173[M−H]−.
(2) Lithium carbonate (5.07 g) and methyl iodide (7.12 ml) were added to a solution of the compound obtained in (1) described above (7.90 g) in N,N-dimethylformamide (100 ml) and the mixture was stirred at 50° C. for 3.5 hours. The reaction mixture was poured into water (500 ml)-conc. hydrochloric acid (15 ml) under ice-cooling and the whole mixture was stirred under ice-cooling for an hour. The precipitates were filtered, washed with water and the resulted crude product was purified with a silica gel column chromatography (eluting solvent: n-hexane/ethyl acetate=9/1 to 4/1) to give 3-chloro-5-hydroxy-4-methoxybenzaldehyde (4.65 g) as a colorless powder.
ESI-MS m/z: 185/187[M−H]−.
(3) 1-Bromo-3-methoxypropane (4.48 g) and potassium carbonate (5.06 g) were added to a solution of the compound obtained in (2) described above (4.55 g) in acetonitrile (46 ml) and the mixture was heated under reflux for 18 hours. Ethyl acetate was added to the mixture under ice-cooling, insoluble materials were filtered through Celite and the filtrate was concentrated in vacuo. The resulted residue was purified with a silica gel column chromatography (eluting solvent: n-hexane/ethyl acetate=9/1 to 4/1) to give 3-chloro-4-methoxy-5-(3-methoxypropoxy)benzaldehyde (6.20 g) as a colorless oil.
APCI-MS m/z: 259/261[M+H]+.

(4) Cyclopropylamine (0.51 ml) was added to a solution of the compound obtained in (3) described above (0.93 g) in ethanol (28 ml) and the mixture was stirred at 50° C. for 3 hours. The mixture was concentrated in vacuo, the resulting residue was dissolved in ethanol (22 ml) and sodium borohydride (0.34 g) was added portionwise under ice-cooling. After stirring at room temperature overnight, sodium borohydride (0.14 g) was further added and the mixture was stirred overnight again. After evaporation of the solvent in vacuo, the residue was diluted with ethyl acetate and water and extracted with ethyl acetate. The organic layer was washed with water and saturated brine successively, dried over sodium sulfate and concentrated in vacuo. The resulted residue was purified with NH-silica gel column chromatography (eluting solvent: n-hexane/ethyl acetate=9/1) to give N-[3-chloro4-methoxy5-(3-methoxypropoxy)benzyl]cyclopropanamine (1.02 g) as a colorless oil. Then, 4N hydrochloric acid solution in dioxane (1.7 ml) was added to a solution of the oil in diethyl ether (10 ml) under ice-cooling. The mixture was stirred at room temperature for 30 minutes and precipitates were filtered, washed with diethyl ether to give N-[3-chloro4-methoxy-5-(3-methoxypropoxy)benzyl]cyclopropanamine hydrochloride (1.05 g) as a colorless powder.
APCI-MS m/z: 300/302[M+H]$^+$.

Reference Example 82

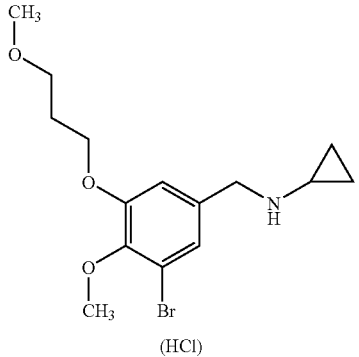

(HCl)

(1) 5-Bromovanillin[3-bromo-4-hydroxy-5-methoxybenzaldehyde] (15.00 g) was treated in the same manner as Reference Example 81(1) to give 3-bromo-4,5-dihydroxybenzaldehyde (9.55 g) as a pale brown powder.
ESI-MS m/z: 215/217[M−H]$^-$.
(2) Lithium carbonate (7.28 g) and methyl iodide (6.13 ml) were added to a solution of the compound obtained in (1) described above (8.55 g) in N,N-dimethylformamide (100 ml) and the mixture was stirred at room temperature for 1.5 hours and at 40° C. for 20 hours. The reaction mixture was poured into a mixture of water (500 ml) and conc. hydrochloric acid (20 ml) under ice-cooling and the whole mixture was stirred at room temperature for 0.5 hour. After filtration of the precipitates, the filtrate was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=9/1 to 4/1) to give 3-bromo-5-hydroxy-4-methoxybenzaldehyde (3.30 g) as a colorless powder.
ESI-MS m/z: 229/231[M−H]$^-$.
(3) The compound obtained in (2) described above (3.25 g) was treated in the same manner as Reference Example 81(3) to give 3-bromo-4-methoxy-5-(3-methoxypropoxy)benzaldehyde (4.10 g) as a colorless oil.
APCI-MS m/z: 303/305[M+H]$^+$.
(4) The compound obtained in (3) described above (1.09 g) was treated in the same manner as Reference Example 81(4) to give N-[3-bromo-4-methoxy-5-(3-methoxypropoxy)benzyl]cyclopropanamine hydrochloride (1.10 g) as a colorless powder.
APCI-MS m/z: 344/346[M+H]$^+$.

Reference Example 83

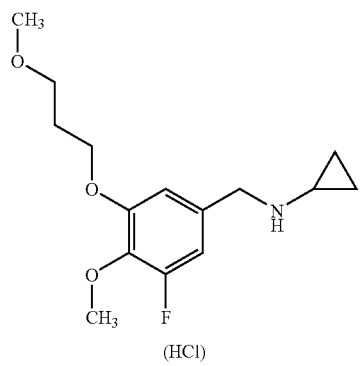

(HCl)

(1) Aluminium chloride (2.24 g) was added portionwise to a solution of 5-fluorovanillin[3-fluoro-4-hydroxy-5-methoxybenzaldehyde] (2.00 g) in chloroform (20 ml) under ice-cooling, and pyridine (4.16 ml) was added dropwise. After being heated under reflux for 18 hours, the mixture was concentrated in vacuo. 3N hydrochloric acid was added to the residue and the mixture was stirred at room temperature for 2 hours. The precipitates were filtered and the filtrate was extracted with ethyl acetate. The organic layer was washed with water and saturated brine successively, dried over sodium sulfate and concentrated in vacuo to give 3-fluoro-4,5-dihydroxybenzaldehyde (0.85 g) as a brown yellow powder.
ESI-MS m/z: 155[M−H]$^-$.
(2) Lithium carbonate (554 mg) and methyl iodide (0.78 ml) were added to a solution of the compound obtained in (1) described above (780 mg) in N,N-dimethylformamide (12 ml) and the mixture was stirred at 40° C. for 7.5 hours. The reaction mixture was poured into 10% hydrochloric acid under ice-cooling and extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=9/1) to give 3-fluoro-5-hydroxy-4-methoxybenzaldehyde (570 mg) as a colorless powder.
ESI-MS m/z: 169[M−H]$^-$.
(3) The compound obtained in (2) described above (520 mg) was treated in the same manner as Reference Example 81(3) to give 3-fluoro-4-methoxy-5-(3-methoxypropoxy)benzaldehyde (720 mg) as a colorless oil.
APCI-MS m/z: 243[M+H]$^+$.
(4) The compound obtained in (3) described above (670 mg) was treated in the same manner as Reference Example 81(4) to give N-[3-fluoro-4-methoxy-5-(3-methoxypropoxy)benzyl]cyclopropanamine hydrochloride (777 mg) as a colorless powder.
APCI-MS m/z: 284[M+H]$^+$.

Reference Example 84

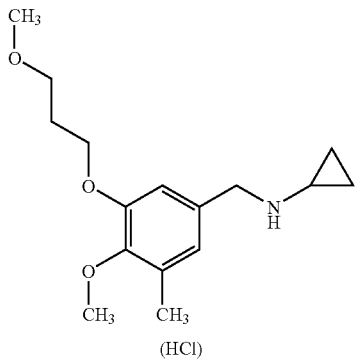

(1) A mixture of 3-fluoro-4-methoxy-5-(3-methoxypropoxy) benzaldehyde [a compound of Reference Example 81(3), 2.00 g], trimethylboroxin (1.61 ml), tris(dibenzylideneacetone)dipalladium (142 mg), 2-dicyclohexylphosphino-2',4',6'-triisopropyl-1,1'-biphenyl(X-Phos) (295 mg) and potassium phosphate (3.28 g) in dioxane (40 ml) was stirred at 100° C. under argon atmosphere for 18 hours. After the reaction mixture was left stand to cool, trimethylboroxin (0.8 ml), tris(dibenzylideneacetone)dipalladium (71 mg) and 2-dicyclohexylphosphino-2',4',6'-triisopropyl-1,1'-biphenyl(X-Phos) (148 mg) were added and the mixture was further stirred at 100° C. for 24 hours. After being stand to cool, ice-water was added to the reaction mixture and it was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=9/10) to give 4-methoxy-3-(3-methoxypropoxy)-5-methylbenzaldehyde (1.61 g) as a yellow oil.
APCI-MS m/z: 239[M+H]⁺.

(2) The compound obtained in (1) described above (1.50 g) was treated in the same manner as Reference Example 81(4) to give N-[4-methoxy-3-(3-methoxypropoxy)-5-methylbenzyl]cyclopropanamine hydrochloride (1.70 g) as a colorless powder.
APCI-MS m/z: 280[M+H]⁺.

Reference Example 85

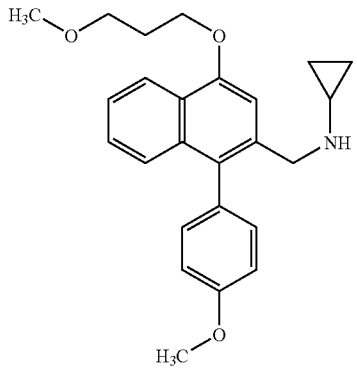 [SMILES: COCCCOc1cc(CNC2CC2)c(-c2ccc(OC)cc2)c2ccccc12]

(1) A solution of di-tert-butyl dicarbonate (1.12 g) in dichloromethane (5 ml) and 4-dimethylaminopyridine (57 mg) were added to a solution of N-{[4-(3-methoxypropoxy))-2-naphthyl]methyl}cyclopropanamine hydrochloride (a compound of Reference Example 73, 1.50 g) and triethylamine (1.3 ml) in dichloromethane (25 ml). After stirring at room temperature for an hour, the reaction mixture was concentrated in vacuo. Ethyl acetate, water and a saturated aqueous solution of sodium bicarbonate were added to the residue and the aqueous layer was separated. The organic layer was washed with water and saturated brine successively, dried over magnesium sulfate and concentrated in vacuo. The resulted residue was purified with a silica gel column chromatography (eluting solvent: n-hexane/ethyl acetate=80/20 to 65/35) to give tert-butyl cyclopropyl{[4-(3-methoxypropoxy)-2-naphthyl]methyl}carbamate (1.78 g) as a colorless oil.
APCI-MS m/z: 403[M+NH₄]⁺

(2) N-Bromosuccinimide (0.91 g) was added to a solution of the compound obtained in (1) described above (1.78 g) in acetonitrile (15 ml) under ice-cooling and the mixture was stirred at room temperature for an hour. The reaction mixture was concentrated in vacuo and the resulted residue was purified with a silica gel column chromatography (eluting solvent: n-hexane/ethyl acetate=80/20 to 50/50) to give tert-butyl{[1-bromo-4-(3-methoxypropoxy)-2-naphthyl]methyl}cyclopropyl carbamate (1.78 g) as a pale yellow oil.
APCI-MS m/z: 481/483 [M+NH₄]⁺.

(3) A mixture of the compound obtained in (2) described above (200 mg), 4-methoxyphenyl boric acid (98 mg), dichlorobis(triphenylphosphine)palladium(II) (60 mg), potassium carbonate (238 mg) and water (0.1 ml) in 1,2-diethoxyethane (5 ml) was stirred at 80° C. for 3 hours. After being left stand to cool, ethyl acetate and water were added to the reaction mixture, insoluble materials were filtered through Celite and the filtrate was extracted with ethyl acetate. The organic layer was washed with water and saturated brine successively, dried over magnesium sulfate and concentrated in vacuo. The resulted residue was treated with activated carbon and purified with a NH-silica gel column chromatography (eluting solvent: n-hexane/ethyl acetate=90/10 to 80/20) to give tert-butyl cyclopropyl{[1-(4-methoxyphenyl)-4-(3-methoxypropoxy)-2-naphthyl]methyl}carbamate (121 mg) as a colorless oil.
APCI-MS m/z: 492[M+H]⁺.

(4) A 4N solution of hydrogen chloride in dioxane (1 ml) was added to a solution of the compound obtained in (3) described above (120 mg) in chloroform (3 ml) under ice-cooling and the mixture was stirred at room temperature for 2 hours. After concentration of the reaction mixture in vacuo, the resulted residue was triturated in diisopropyl ether to give N-{[1-(4-methoxyphenyl)-4-(3-methoxypropoxy)-2-naphthyl]methyl}cyclopropanamine hydrochrolide (100 mg) as a colorless powder.
APCI-MS m/z: 392[M+H]⁺.

Reference Example 86

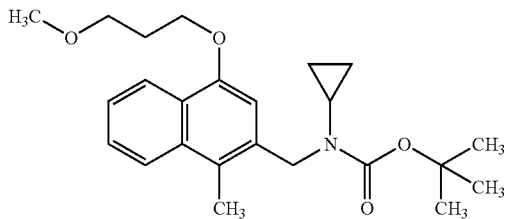 [SMILES: COCCCOc1cc(CN(C(=O)OC(C)(C)C)C2CC2)c(C)c2ccccc12]

A mixture of tert-butyl{[1-bromo-4-(3-methoxypropoxy)-2-naphthyl]methyl}cyclopropylcarbamate (a compound obtained in Reference Example 85(2), 200 mg), trimethyl boroxin (0.09 ml), tris(dibenzylideneacetone)dipalladium (3.94 mg), 2-dicyclohexylphosphino-2',4',6'-triisopropyl-1,1'-biphenyl(X-Phos) (8.2 mg) and potassium phosphate (183 mg) in dioxane (5 ml) was stirred at 100° C. for an hour. After being left stand to cool, trimethyl boroxin (0.03 ml), tris(dibenzylideneacetone)dipalladium (3.94 mg), 2-dicyclohexylphosphino-2',4',6'-triisopropyl-1,1'-biphenyl(X-Phos) (8.2 mg) were added and the mixture was further stirred at 100° C. for an hour. After being left stand to cool, chilled water was added to the reaction mixture and it was extracted with ethyl acetate. The organic layer was washed with water and saturated brine successively, dried over magnesium sulfate and concentrated in vacuo. The resulted residue was purified with a silica gel column chromatography (eluting solvent: n-hexane/ethyl acetate=90/10 to 70/30) to give a crude product of tert-butyl cyclopropyl{[4-(3-methoxypropoxy)-1-methyl-2-naphthyl]methyl}carbamate (163 mg) as a yellow oil.

APCI-MS m/z: 417[M+NH$_4$]$^+$.

Reference Example 87-90

The corresponding starting compounds were treated in the same manner as Reference Example 85(3) to give compounds listed in the following Table 12.

TABLE 12

| No. of Reference Examples | Structure | Properties |
|---|---|---|
| 87 | 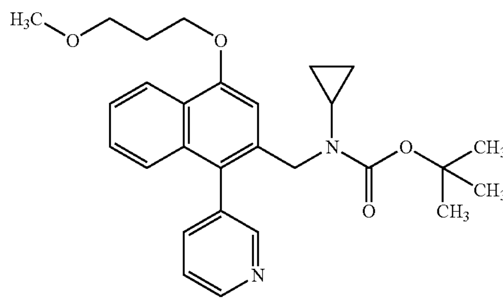 | Property: colorless powder<br>APCI-MS<br>m/z: 463[M + H]$^+$ |
| 88 | 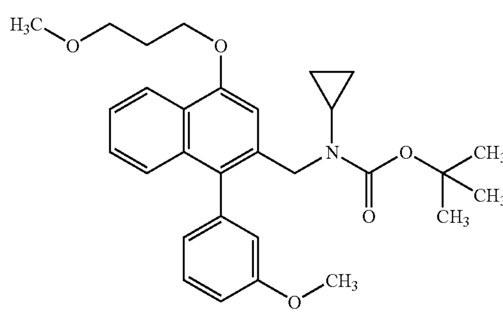 [SMILES: COCCCOc1cc(CN(C(=O)OC(C)(C)C)C2CC2)c(-c2cccc(OC)c2)c2ccccc12] | Property: colorless viscous oil<br>APCI-MS<br>m/z: 492[M + H]$^+$ |
| 89 | 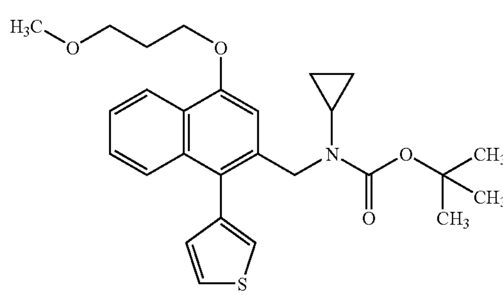 | Property: colorless powder<br>APCI-MS<br>m/z: 468[M + H]$^+$ |

TABLE 12-continued

| No. of Reference Examples | Structure | Properties |
|---|---|---|
| 90 | [structure: 4-(3-methoxypropoxy)-1-(thiophen-2-yl)naphthalen-2-yl)methyl cyclopropyl carbamic acid tert-butyl ester] | Property: colorless viscous oil<br>APCI-MS<br>m/z: 468 [M + H]$^+$ |

Reference Example 91-92

(20)

The corresponding starting compounds were treated in the same manner as Reference Example 86 to give compounds listed in the following Table 13.

TABLE 13

| No. of Reference Examples | Structure | Properties |
|---|---|---|
| 91 | [structure: 4-(3-methoxypropoxy)-1-phenylnaphthalen-2-yl)methyl cyclopropyl carbamic acid tert-butyl ester] | Property: orange viscous oil<br>APCI-MS<br>m/z: 479[M + NH$_4$]$^+$ |
| 92 | [structure: 1-(furan-3-yl)-4-(3-methoxypropoxy)naphthalen-2-yl)methyl cyclopropyl carbamic acid tert-butyl ester] | Property: pale orange powder<br>APCI-MS<br>m/z: 452[M + H]$^+$ |

Reference Example 93-100

The corresponding starting compounds were treated in the same manner as Reference Example 85(4) to give compounds listed in the following Table 14.

TABLE 14

| No. of Reference Examples | Structure | Properties |
| --- | --- | --- |
| 93 | 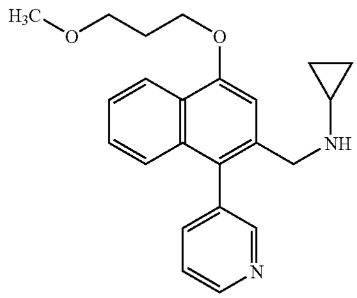 [SMILES: COCCCOc1cc(CNC2CC2)c(-c2cccnc2)c2ccccc12] | Dihydrochloride<br>Property: colorless powder<br>APCI-MS<br>m/z: 363[M + H]$^+$ |
| 94 | 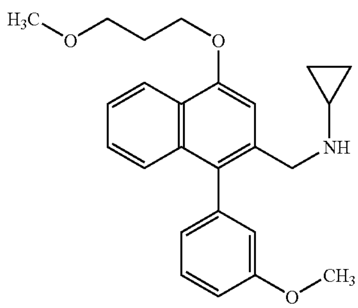 [SMILES: COCCCOc1cc(CNC2CC2)c(-c2cccc(OC)c2)c2ccccc12] | Hydrochloride<br>Property: colorless powder<br>APCI-MS<br>m/z: 392[M + H]$^+$ |
| 95 | 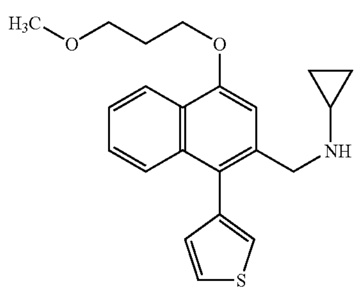 [SMILES: COCCCOc1cc(CNC2CC2)c(-c2ccsc2)c2ccccc12] | Hydrochloride<br>Property: pale yellow powder<br>APCI-MS<br>m/z: 368[M + H]$^+$ |
| 96 | 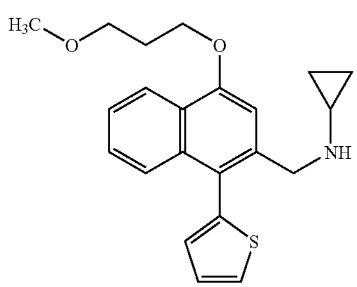 [SMILES: COCCCOc1cc(CNC2CC2)c(-c2cccs2)c2ccccc12] | Hydrochloride<br>Property: colorless powder<br>APCI-MS<br>m/z: 368[M + H]$^+$ |
| 97 | 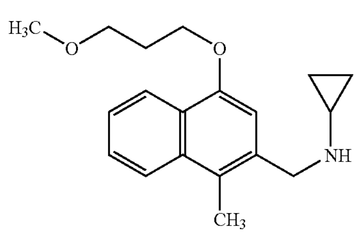 [SMILES: COCCCOc1cc(CNC2CC2)c(C)c2ccccc12] | Hydrochloride<br>used in the next step without purification |

TABLE 14-continued

| No. of Reference Examples | Structure | Properties |
|---|---|---|
| 98 | (structure) | Hydrochloride used in the next step without purification |
| 99 | (structure) | Hydrochloride Property colorless powder APCI-MS m/z: 352[M + H]⁺ |
| 100 | (structure) | Hydrochloride Property: colorless powder APCI-MS m/z: 364/366[M + H]⁺ |

Reference Example 101

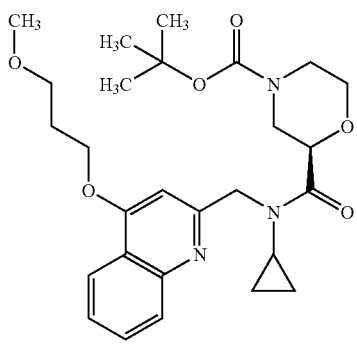 [SMILES: COCCCOc1cc(CN(C(=O)[C@H]2CN(C(=O)OC(C)(C)C)CCO2)C2CC2)nc2ccccc12]

N,N-diisopropylethylamine (165 μL) and 1-ethyl-3-(3-dimethylaminopropyl)carbodiimide hydrochloride (113 mg) were added successively to a solution of N-{[4-(3-methoxypropoxy)quinolin-2-yl]methyl}cyclopropanamine dihydrochloride (a compound of Reference Example 80(4), 170 mg), (2R)-4-(tert-butoxycarbonyl)morpholin-2-carboxylic acid (91 mg) and 1-hydroxybenzotriazole (64 mg) in N,N-dimethylformamide (7 ml) under ice-cooling and the mixture was stirred at room temperature for 4 hours. The mixture was cooled in ice-water, water and a saturated aqueous solution of sodium bicarbonate was added and it was extracted with ethyl acetate. The organic layer was washed with water and saturated brine, dried over sodium sulfate and concentrated in vacuo. The resulted residue was purified with a silica gel column chromatography (eluting solvent: n-hexane/ethyl acetate=1/4) to give tert-butyl(2R)-2-[(cyclopropyl{[4-(3-methoxyprpoxy)quinolin-2-yl]methyl}amino)carbonyl]morpholin-4-carboxylate (177 mg) as a colorless oil.

APCI-MS m/z: 500[M+H]⁺.

Reference Example 102-126

The corresponding starting compounds were treated in the same manner as Reference Example 8, 9 or 101 to give compounds listed in Table 15 below.

TABLE 15

| No. of Reference Examples | Structure | Properties |
|---|---|---|
| 102 | 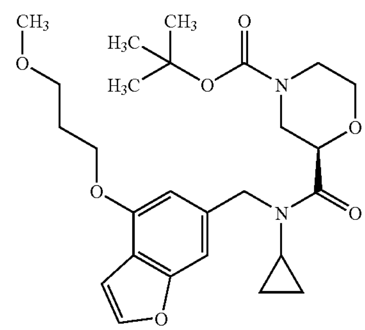 | Property: pale yellow viscous oil<br>APCI-MS m/z: 506[M + NH$_4$]$^+$ |
| 103 | 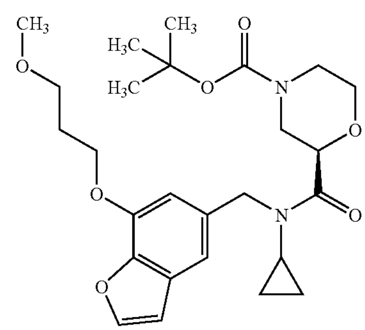 [SMILES: COCCCOc1cc(CN(C(=O)[C@H]2CN(C(=O)OC(C)(C)C)CCO2)C2CC2)cc2ccoc12] | Property: colorless viscous oil<br>APCI-MS m/z: 506[M + NH$_4$]$^+$ |
| 104 | 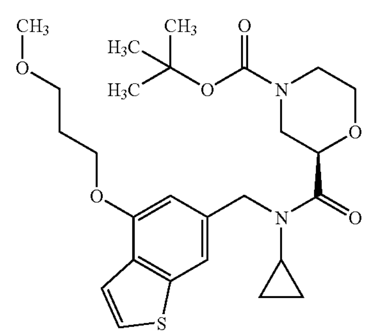 [SMILES: COCCCOc1cc(CN(C(=O)[C@H]2CN(C(=O)OC(C)(C)C)CCO2)C2CC2)cc2sccc12] | Property: colorless viscous oil<br>APCI-MS m/z: 522[M + NH$_4$]$^+$ |
| 105 | 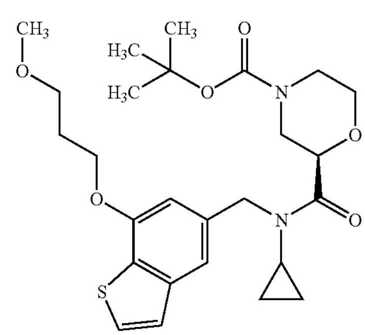 [SMILES: COCCCOc1cc(CN(C(=O)[C@H]2CN(C(=O)OC(C)(C)C)CCO2)C2CC2)cc2ccsc12] | Property: colorless viscous oil<br>APCI-MS m/z: 522[M + NH$_4$]$^+$ |

TABLE 15-continued
| No. of Reference Examples | Structure | Properties |
|---|---|---|
| 106 | 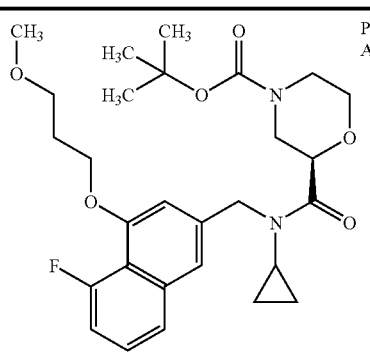 | Property: viscous oil<br>APCI-MS m/z: 534[M + NH$_4$]$^+$ |
| 107 | 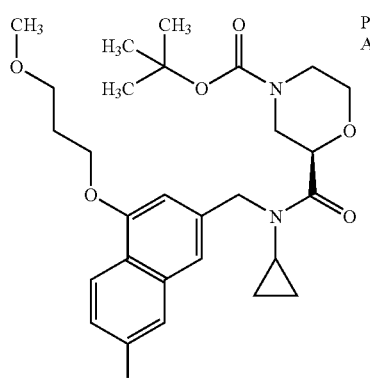 | Property: viscous oil<br>APCI-MS m/z: 517[M + H]$^+$ |
| 108 | 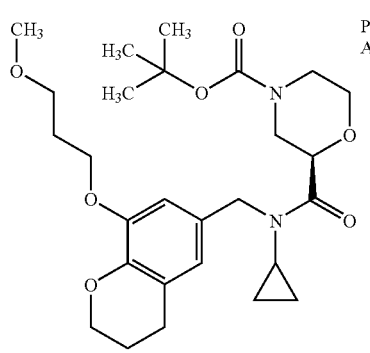 | Property: colorless viscous oil<br>APCI-MS m/z: 505[M + H]$^+$ |
| 109 | 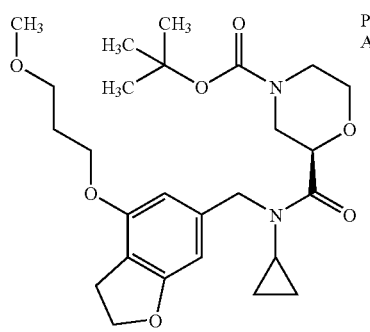 | Property: pale yellow viscous oil<br>APCI-MS m/z: 491[M + H]$^+$ |

TABLE 15-continued
| No. of Reference Examples | Structure | Properties |
|---|---|---|
| 110 | 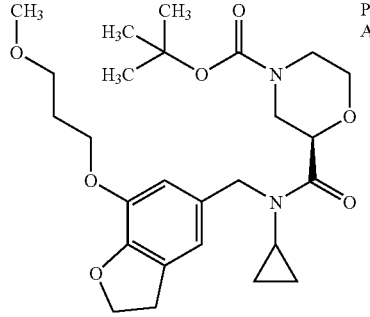 | Property: pale yellow viscous oil<br>APCI-MS m/z: 408[M + NH$_4$]$^+$ |
| 111 | 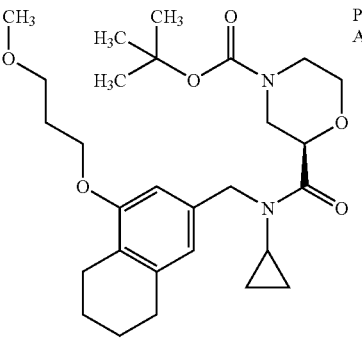 | Property:<br>APCI-MS m/z: [M + H]$^+$ |
| 112 | 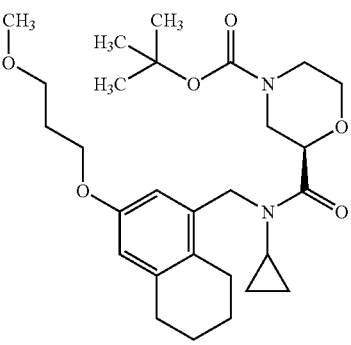 [SMILES: COCCCOc1cc2c(c(CN(C(=O)[C@H]3CN(C(=O)OC(C)(C)C)CCO3)C3CC3)c1)CCCC2] | Property: viscous oil<br>APCI-MS m/z: 503[M + H]$^+$ |
| 113 | 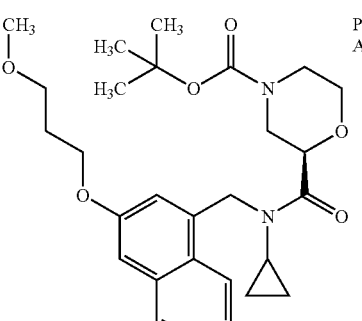 | Property: oil<br>APCI-MS m/z: 499[M + H]$^+$ |

TABLE 15-continued
| No. of Reference Examples | Structure | Properties |
|---|---|---|
| 114 | 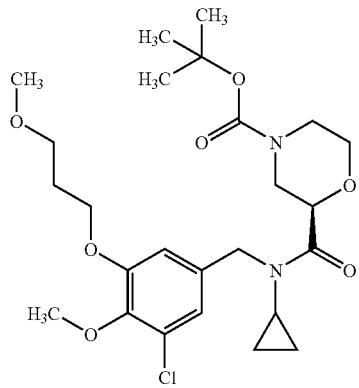 [SMILES: COCCCOc1cc(CN(C(=O)[C@H]2CN(C(=O)OC(C)(C)C)CCO2)C2CC2)cc(Cl)c1OC] | Property: colorless viscous oil<br>APCI-MS<br>m/z: 530/532[M + NH$_4$]$^+$ |
| 115 | 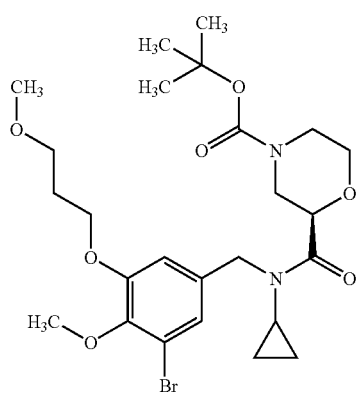 [SMILES: COCCCOc1cc(CN(C(=O)[C@H]2CN(C(=O)OC(C)(C)C)CCO2)C2CC2)cc(Br)c1OC] | Property: colorless viscous oil<br>APCI-MS<br>m/z: 574/576[M + NH$_4$]$^+$ |
| 116 | 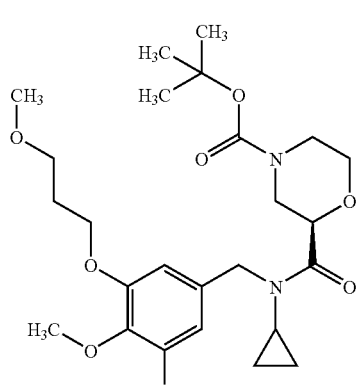 | Property: colorless viscous oil<br>APCI-MS m/z: 514[M + NH$_4$]$^+$ |
| 117 | 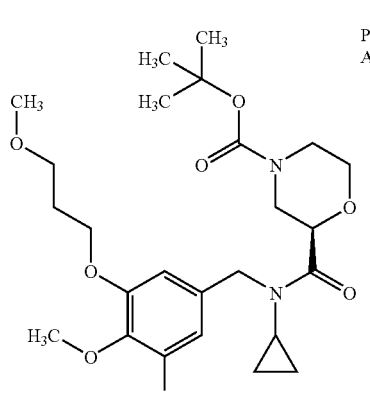 | Property: colorless viscous oil<br>APCI-MS m/z: 510[M + NH$_4$]$^+$ |

TABLE 15-continued
| No. of Reference Examples | Structure | Properties |
|---|---|---|
| 118 | 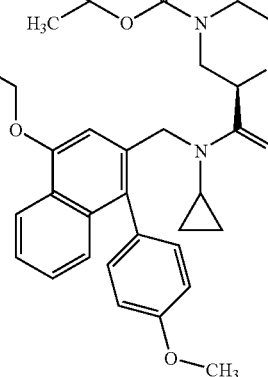 | Property: pale orange viscous oil<br>APCI-MS m/z: 605[M + H]$^+$ |
| 119 | 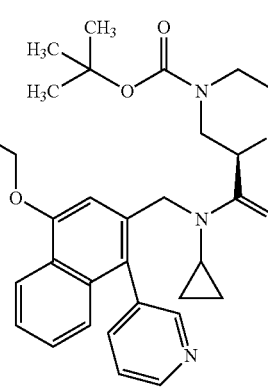 | Property: pale yellow viscous oil<br>APCI-MS m/z: 576[M + H]$^+$ |
| 120 | 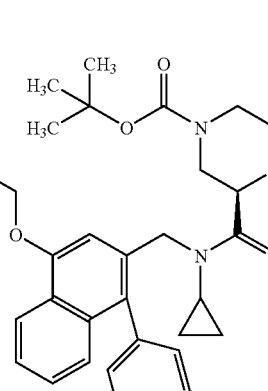 | Property: pale orange viscous oil<br>APCI-MS m/z: 605[M + H]$^+$ |

TABLE 15-continued
| No. of Reference Examples | Structure | Properties |
|---|---|---|
| 121 | 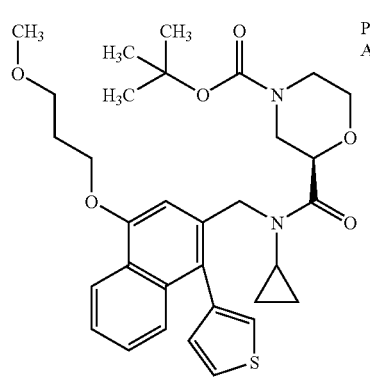 | Property: pale yellow viscous oil<br>APCI-MS m/z: 581[M + H]$^+$ |
| 122 | 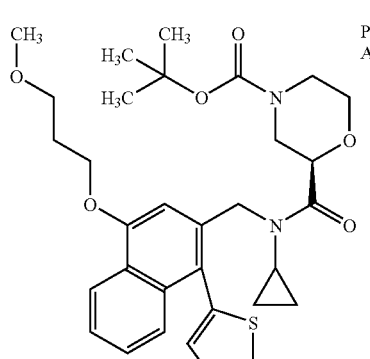 | Property: pale yellow viscous oil<br>APCI-MS m/z: 581[M + H]$^+$ |
| 123 | 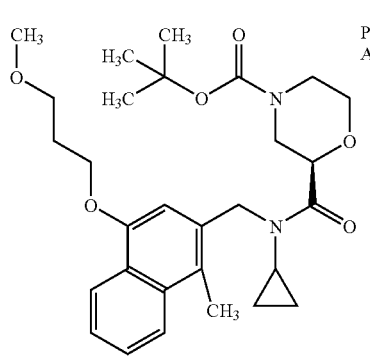 | Property: colorless viscous oil<br>APCI-MS m/z: 530[M + NH$_4$]$^+$ |
| 124 | 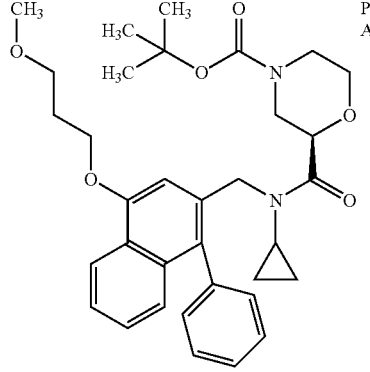 | Property: colorless viscous oil<br>APCI-MS m/z: 575[M + H]$^+$ |

TABLE 15-continued

| No. of Reference Examples | Structure | Properties |
|---|---|---|
| 125 | 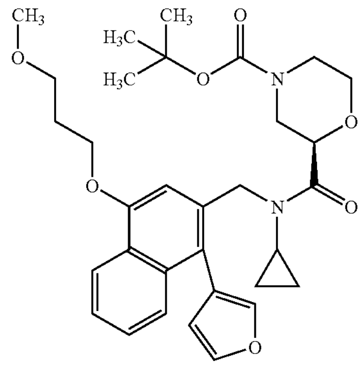 [SMILES: COCCCOc1cc(CN(C(=O)[C@H]2CN(C(=O)OC(C)(C)C)CCO2)C2CC2)c(-c2ccoc2)c2ccccc12] | Property: colorless viscous oil<br>APCI-MS m/z: 565[M + H]$^+$ |
| 126 | 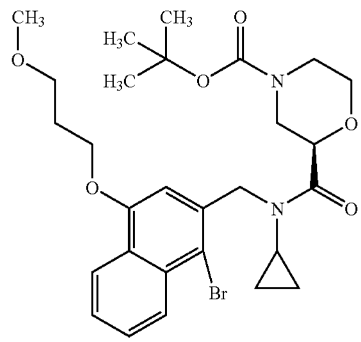 [SMILES: COCCCOc1cc(CN(C(=O)[C@H]2CN(C(=O)OC(C)(C)C)CCO2)C2CC2)c(Br)c2ccccc12] | Property: colorless viscous oil<br>APCI-MS m/z: 577/579[M + H]$^+$ |

Reference Example 127

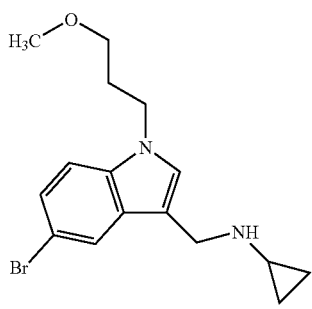

(1) 60% Oily sodium hydride (264 mg) was added to a solution of 5-bromoindol-3-carbaldehyde (1.34 g) in N,N-dimethylformamide (13 ml) and the mixture was stirred at room temperature for 0.5 hour. A solution of 1-bromo-3-methoxypropane (1.10 g) in N,N-dimethylformamide (1 ml) and potassium iodide (990 mg) were added to the mixture and the reaction mixture was stirred at 50° C. for 2 hours. Ice-water was added slowly to the reaction mixture and it was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=70/30 to 20/80) to give 5-bromo-1-(3-methoxypropyl)indol-3-carbaldehyde (1.70 g) as a pale yellow oil.
APCI-MS m/z: 296/298[M+H]$^+$.

(2) Cyclopropylamine (0.80 ml) was added to a solution of the compound obtained in (1) described above (1.69 g) in ethanol (41 ml) and the mixture was stirred at 50° C. for 2 hours. After concentration of the mixture in vacuo, the obtained residue was diluted in toluene and concentrated to dryness in vacuo again. The residue was dissolved in ethanol (32 ml), sodium borohydride (0.54 g) was added thereto and the mixture was stirred at room temperature overnight. Water was added to the reaction mixture and it was extracted with ethyl acetate. The organic layer was washed with water and saturated brine successively, dried over magnesium sulfate and concentrated in vacuo. The resulted residue was purified with a silica gel column chromatography (eluting solvent: chloroform/methanol=100/0 to 96/4) to give N-{[5-bromo-1-(3-methoxypropyl)indol-3-yl]methyl}cyclopropanamine (1.48 g) as a pale yellow oil.
APCI-MS m/z: 280/282[M+H−NH$_2$C$_3$H$_5$]$^+$.

Reference Example 128

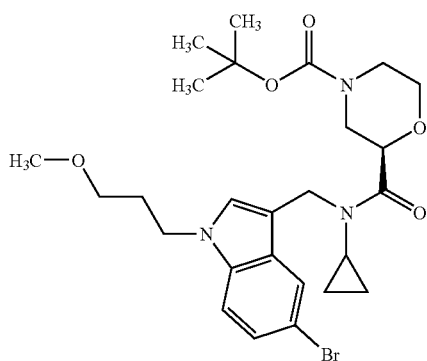 [SMILES: COCCCn1cc(CN(C(=O)[C@H]2CN(C(=O)OC(C)(C)C)CCO2)C2CC2)c2cc(Br)ccc21]

1-Hydroxybenzotriazole (162 mg) and 1-ethyl-3-(3-dimethylaminopropyl)carbodiimide hydrochloride (288 mg) were added successively to a solution of N-{[5-bromo-1-(3-methoxypropyl)indol-3-yl]methyl}cyclopropanamine (a compound of Reference Example 127(2), 405 mg) and (2R)-4-(tert-butoxycarbonyl)morpholin-2-carboxylic acid (231 mg) in N,N-dimethylformamide (12.5 ml) and the mixture was stirred at room temperature overnight. The mixture was diluted with ethyl acetate, washed with water, a saturated aqueous solution of sodium bicarbonate and saturated brine successively and dried over magnesium sulfate. The solvent was evaporated in vacuo and the resulted residue was purified with a silica gel column chromatography (eluting solvent: n-hexane/ethyl acetate=50/50 to 10/90) to give tert-butyl (2R)-2-{[{[5-bromo-1-(3-methoxypropyl)indol-3-yl]methyl}(cyclopropyl)amino]carbonyl}morpholin-4-carboxylate (581 mg) as a colorless oil.

APCI-MS m/z: 550/552[M+H]$^+$.

Reference Example 129

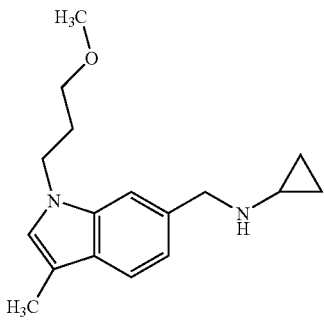 [SMILES: COCCCn1cc(C)c2ccc(CNC3CC3)cc21]

(1) 60% Oily sodium hydride (254 mg) was added to a solution of methyl 3-methylindol-6-carboxylate (1.00 g) in N,N-dimethylformamide (10 ml) under ice-cooling and the mixture was stirred at room temperature for 0.5 hour. A solution of 1-bromo-3-methoxypropane (971 mg) in N,N-dimethylformamide (2 ml) and potassium iodide (1.05 g) were added and the reaction mixture was stirred at room temperature for 3 hours. Ice water was slowly added to the reaction mixture and it was extracted with ethyl acetate. The organic layer was washed with water and saturated brine successively, dried over sodium sulfate and concentrated in vacuo. The resulted residue was purified with a silica gel column chromatography (eluting solvent: chloroform/methanol=20/1 to 3/1) to give methyl 1-(3-methoxypropyl)-3-methylindol-6-carboxylate (1.24 g) as a colorless oil.

APCI-MS m/z: 262[M+H]$^+$.

(2) A solution of the compound obtained in (1) described above (300 mg) in tetrahydrofuran (2 ml) was added dropwise to a suspension of lithium aluminium hydride (43.6 mg) in tetrahydrofuran (2 ml) under ice-cooling and the mixture was stirred at the same temperature for 45 minutes. Water (44 μL), 2N aqueous solution of sodium hydroxide (110 μL) and water (176 μL) were added slowly to the reaction mixture under the same cooling successively, and the mixture was stirred at room temperature for 12 hours. The mixture was diluted with ethyl acetate and dried over sodium sulfate. Insoluble materials were filtered through Celite and the filtrate was concentrated in vacuo to give [1-(3-methoxypropyl)-3-methylindol-6-yl]methanol (280 mg) as a pale brown oil.

APCI-MS m/z: 234[M+H]$^+$.

(3) Manganese dioxide (1.21 g) was added to a solution of the compound obtained in (2) described above (275 mg) in dichloromethane (5 ml) under ice-cooling and the mixture was stirred at room temperature for 20 hours. Insoluble materials were filtered through Celite and the filtrate was concentrated in vacuo to give 1-(3-methoxypropyl)-3-methylindol-6-carbaldehyde (252 mg) as a pale brown oil.

APCI-MS m/z: 232[M+H]$^+$.

(4) Cyclopropylamine (0.15 ml) was added to a solution of the compound obtained in (3) described above (245 mg) in ethanol (5 ml) and the mixture was stirred at 50° C. for 3 hours. The mixture was concentrated in vacuo, the obtained residue was diluted with toluene and concentrated to dryness in vacuo again. The residue was dissolved in ethanol (5 ml), sodium borohydride (100 mg) was added under ice-cooling and the mixture was stirred at room temperature for an hour. Water was added to the reaction mixture under ice-cooling and extracted with ethyl acetate. The organic layer was washed with saturated brine, dried over sodium sulfate and concentrated in vacuo. The resulted residue was purified with a silica gel column chromatography (eluting solvent: chloroform/methanol=100/0 to 5/1) to give N-{[1-(3-methoxypropyl)-3-methylindol-6-yl]methyl}cyclopropanamine (238 mg) as a colorless oil.

APCI-MS m/z: 273 [M+H]$^+$.

Reference Example 130-140

The corresponding starting compounds were treated in the same manner as Reference Example 127(1) to give compounds listed in Table 16 below.

TABLE 16

| No. of Reference Examples | Structure | Properties |
| --- | --- | --- |
| 130 | ![structure] | Property: pale yellow viscous oil<br>APCI-MS m/z: 218[M + H]$^+$ |

TABLE 16-continued

| No. of Reference Examples | Structure | Properties |
| --- | --- | --- |
| 131 | (5-fluoro-1-(3-methoxypropyl)-1H-indole-3-carbaldehyde) | Property: yellow viscous oil<br>APCI-MS m/z: 236[M + H]$^+$ |
| 132 | (5-chloro-1-(3-methoxypropyl)-1H-indole-3-carbaldehyde) | Property: pale yellow viscous oil<br>APCI-MS m/z: 252/254[M + H]$^+$ |
| 133 | (5-cyano-1-(3-methoxypropyl)-1H-indole-3-carbaldehyde) | Property: pale yellow powder<br>APCI-MS m/z: 243[M + H]$^+$ |
| 134 | (1-(3-methoxypropyl)-5-methyl-1H-indole-3-carbaldehyde) | Property: brown viscous oil<br>APCI-MS m/z: 232[M + H]$^+$ |
| 135 | (5-methoxy-1-(3-methoxypropyl)-1H-indole-3-carbaldehyde) | Property: brown viscous oil<br>APCI-MS m/z: 248[M + H]$^+$ |

TABLE 16-continued
| No. of Reference Examples | Structure | Properties |
|---|---|---|
| 136 | 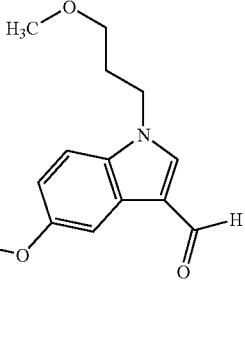 | Property: colorless powder<br>APCI-MS m/z: 324[M + H]⁺ |
| 137 | 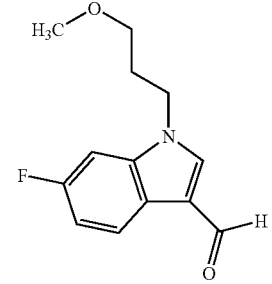 [SMILES: COCCCn1cc(C=O)c2ccc(F)cc21] | Property: brown viscous oil<br>APCI-MS m/z: 236[M + H]⁺ |
| 138 | 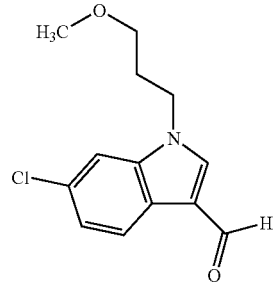 [SMILES: COCCCn1cc(C=O)c2ccc(Cl)cc21] | Property: brown viscous oil<br>APCI-MS<br>m/z: 252/254[M + H]⁺ |
| 139 | 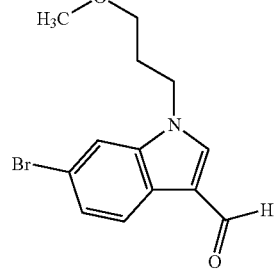 | Property: yellow viscous oil<br>APCI-MS<br>m/z: 296/298[M + H]⁺ |
| 140 | 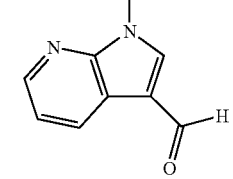 | Property: pale yellow viscous oil<br>APCI-MS m/z: 219[M + H]⁺ |

Reference Example 141-151

The corresponding starting compounds were treated in the same manner as Reference Example 127(2) to give compounds listed in Table 17 below.

TABLE 17

| No. of Reference Examples | Structure | Properties |
|---|---|---|
| 141 | 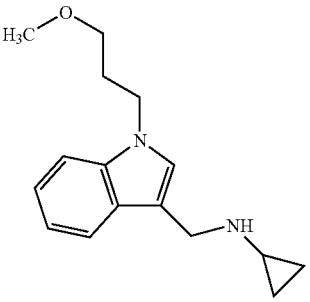 | Property: colorless viscous oil<br>APCI-MS<br>m/z: 202[M + H − $C_3H_7N$]$^+$ |
| 142 | 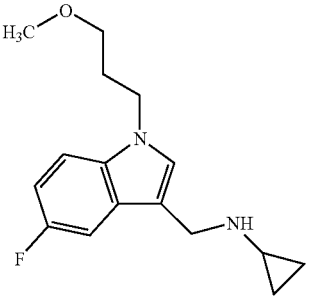 | Property: colorless viscous oil<br>APCI-MS<br>m/z: 220[M + H − $C_3H_7N$]$^+$ |
| 143 | 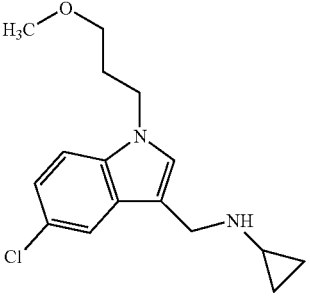 | Property: colorless viscous oil<br>APCI-MS<br>m/z: 236/238[M + H − $C_3H_7N$]$^+$ |
| 144 | 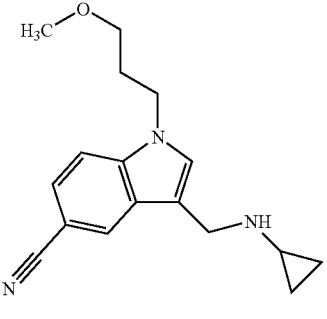 | Property: yellow viscous oil<br>APCI-MS<br>m/z: 227[M + H − $C_3H_7N$]$^+$ |

TABLE 17-continued
| No. of Reference Examples | Structure | Properties |
|---|---|---|
| 145 | 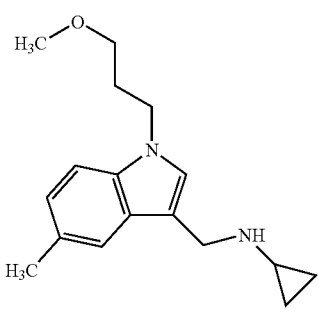 | Property: pale yellow viscous oil<br>APCI-MS<br>m/z: 216[M + H − C$_3$H$_7$N]$^+$ |
| 146 | 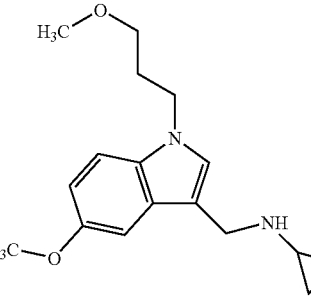 | Property: pale yellow viscous oil<br>APCI-MS<br>m/z: 232[M + H − C$_3$H$_7$N]$^+$ |
| 147 | 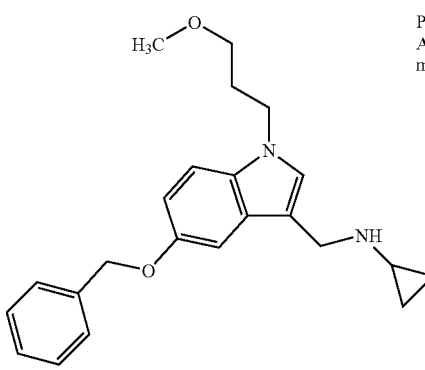 | Property: yellow viscous oil<br>APCI-MS<br>m/z: 308[M + H − C$_3$H$_7$N]$^+$ |
| 148 | 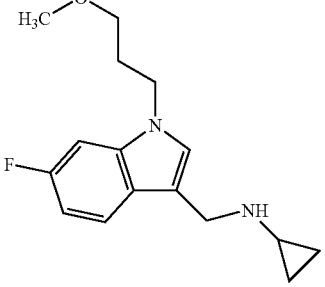 | Property: pale yellow viscous oil<br>APCI-MS<br>m/z: 220[M + H − C$_3$H$_7$N]$^+$ |

TABLE 17-continued

| No. of Reference Examples | Structure | Properties |
|---|---|---|
| 149 | 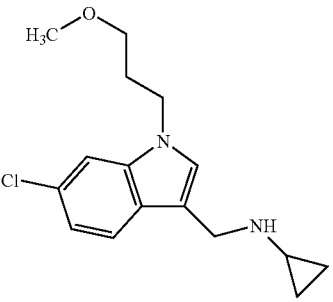 | Property: yellow viscous oil<br>APCI-MS<br>m/z: 236/238[M + H − $C_3H_7N$]$^+$ |
| 150 | 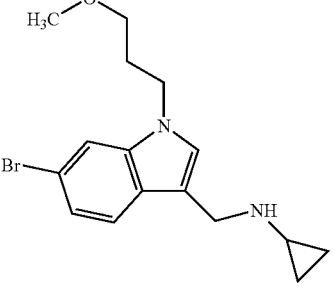 | Property: yellow viscous oil<br>APCI-MS<br>m/z: 280/282[M + H − $C_3H_7N$]$^+$ |
| 151 | 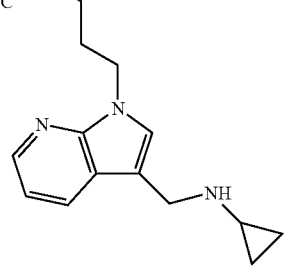 | Property: colorless viscous oil<br>APCI-MS m/z: 260[M + H]$^+$ |

Reference Example 152-163

The corresponding starting compounds were treated in the same manner as Reference Example 128 to give compounds listed in Table 18 below.

TABLE 18

| No. of Reference Examples | Structure | Properties |
|---|---|---|
| 152 | 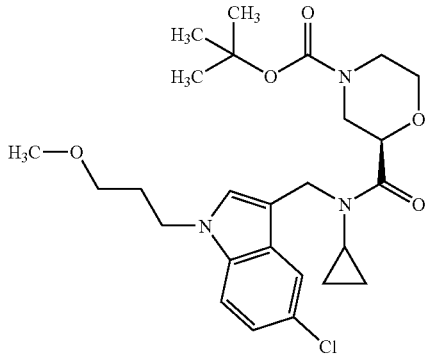 | Property: colorless viscous oil<br>APCI-MS m/z: 472[M + H]$^+$ |

TABLE 18-continued

| No. of Reference Examples | Structure | Properties |
|---|---|---|
| 153 | 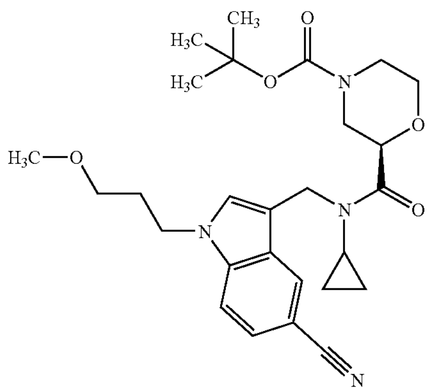 | Property: colorless viscous oil<br>APCI-MS m/z: 490[M + H]⁺ |
| 154 | 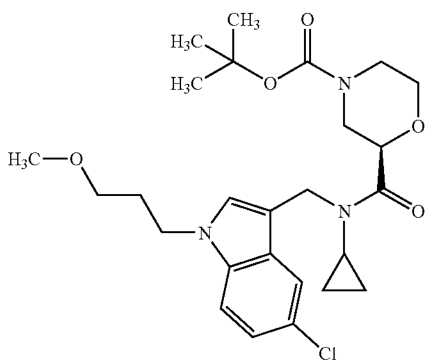 | Property: colorless viscous oil<br>APCI-MS m/z: 506/508[M + H]⁺ |
| 155 | 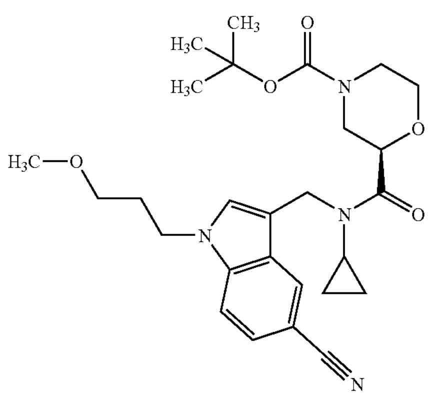 [SMILES: COCCCn1cc(CN(C(=O)[C@H]2CN(C(=O)OC(C)(C)C)CCO2)C2CC2)c2cc(C#N)ccc21] | Property: colorless viscous oil<br>APCI-MS m/z: 497[M + H]⁺ |
| 156 | 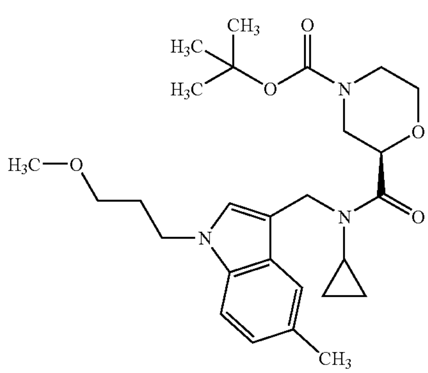 [SMILES: COCCCn1cc(CN(C(=O)[C@H]2CN(C(=O)OC(C)(C)C)CCO2)C2CC2)c2cc(C)ccc21] | Property: colorless viscous oil<br>APCI-MS m/z: 486[M + H]⁺ |

TABLE 18-continued

| No. of Reference Examples | Structure | Properties |
|---|---|---|
| 157 | 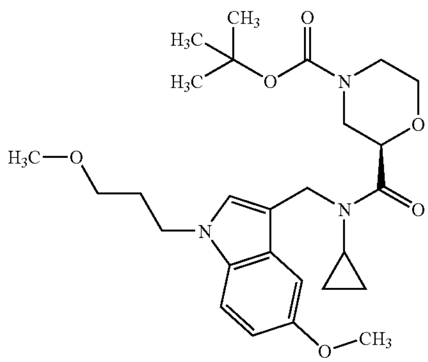 [SMILES: COCCCn1cc(CN(C(=O)[C@H]2CN(C(=O)OC(C)(C)C)CCO2)C2CC2)c2cc(OC)ccc21] | Property: colorless viscous oil<br>APCI-MS m/z: 502[M + H]⁺ |
| 158 | 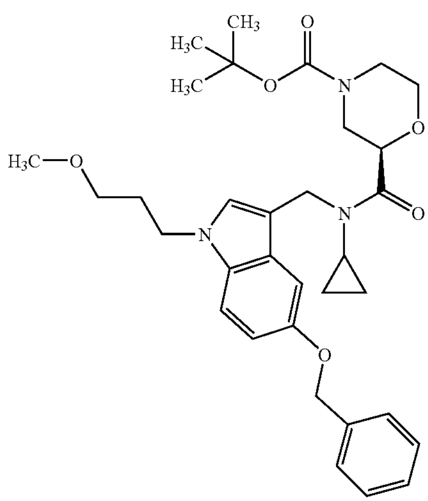 [SMILES: COCCCn1cc(CN(C(=O)[C@H]2CN(C(=O)OC(C)(C)C)CCO2)C2CC2)c2cc(OCc3ccccc3)ccc21] | Property: colorless viscous oil<br>APCI-MS m/z: 578[M + H]⁺ |
| 159 | 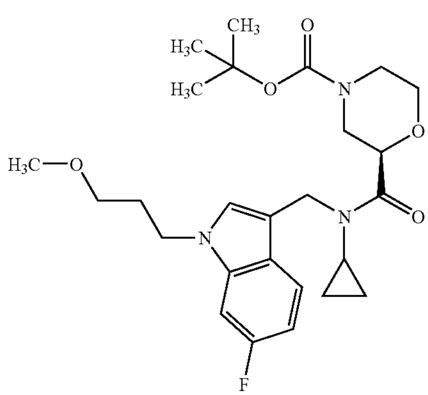 | Property: colorless viscous oil<br>APCI-MS m/z: 506/508[M + H]⁺ |

TABLE 18-continued

| No. of Reference Examples | Structure | Properties |
|---|---|---|
| 160 | 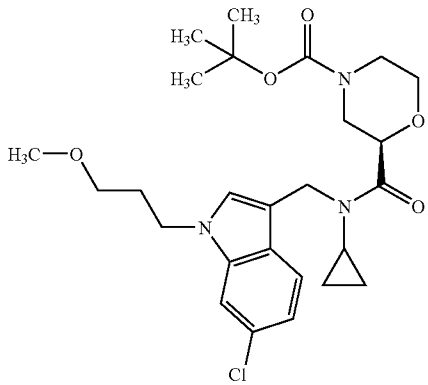 [SMILES: COCCCn1cc(CN(C(=O)[C@H]2CN(C(=O)OC(C)(C)C)CCO2)C2CC2)c2ccc(Cl)cc21] | Property: colorless viscous oil<br>APCI-MS m/z: 506/508[M + H]⁺ |
| 161 | 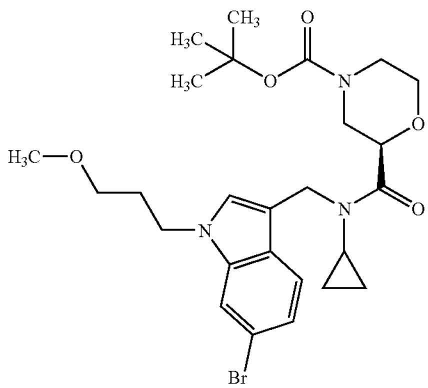 | Property: colorless viscous oil<br>APCI-MS m/z: 550/552[M + H]⁺ |
| 162 | 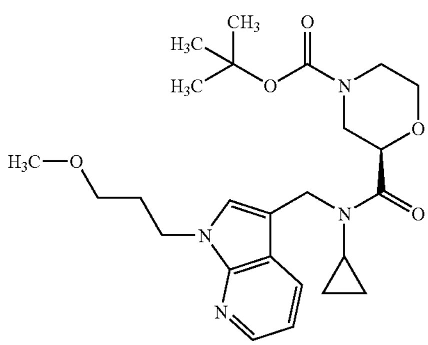 [SMILES: COCCCn1cc(CN(C(=O)[C@H]2CN(C(=O)OC(C)(C)C)CCO2)C2CC2)c2cccnc21] | Property: colorless viscous oil<br>APCI-MS m/z: 473[M + H]⁺ |
| 163 | 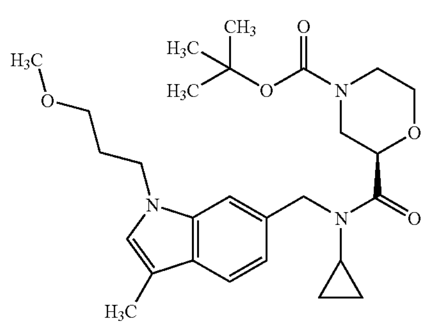 | Property: oil<br>APCI-MS m/z: 486[M + H]⁺ |

Reference Example 164

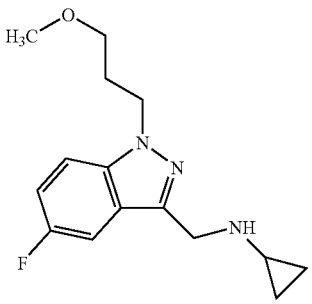

(1) 5-Fluoroisatin (2.00 g) was added to a solution of sodium hydroxide (509 mg) in water (20 ml) and the mixture was stirred at 50° C. The mixture was cooled in ice-salt and sodium nitrite (836 mg) was added therein. Conc. sulfuric acid (2.26 g) was diluted with water (20 ml) and the solution was added dropwise under ice-salt cooling. The mixture was stirred for 15 minutes under the same cooling, and a solution of stannic chloride dihydrate (5.51 g) in conc. hydrochloric acid (10.5 ml) was added dropwise therein. The reaction mixture was stirred at 0° C. for 0.5 hour and at room temperature for 4 hours. The precipitates were filtered, dissolved in ethyl acetate and dried over magnesium sulfate. After evaporation of the solvent in vacuo, the resulted residue was suspended in diisopropyl ether and filtered to give 5-fluoro-1H-indazol-3-carboxylic acid (1.17 g) as a yellow powder.
ESI-MS m/z: 179[M−H]$^-$.

(2) 60% Oily sodium hydride (610 mg) was added to a solution of the compound obtained in (1) described above (1.10 g) in N,N-dimethylformamide (11 ml)-tetrahydrofuran (2 ml) and the mixture was stirred at room temperature for 20 minutes. 1-Bromo-3-methoxypropane (2.34 g) and potassium iodide (1.02 g) were added to the mixture and it was stirred at 50° C. for 24 hours. The reaction mixture was poured into a mixture of ice and 10% hydrochloric acid, and the whole mixture was extracted with ethyl acetate. The organic layer was washed with water and saturated brine, dried over magnesium sulfate, filtered through NH-silica gel pad and the filtrate was concentrated in vacuo. The resulted residue was purified with a silica gel column chromatography (eluting solvent: n-haxane/ethyl acetate=65/35 to 20/80) to give 3-methoxypropyl 5-fluoro-1-(3-methoxypropyl)-1H-indazol-3-carboxylate (0.69 g) as a yellow oil.
APCI-MS m/z: 325[M+H]$^+$.

(3) A solution of the compound obtained in (2) described above (0.69 g) in tetrahydrofuran (4 ml) was added dropwise to a suspension of lithium alminium hydride (118 mg) in tetrahydrofuran (8 ml) under ice-cooling and the mixture was stirred under the same cooling for 2.5 hours. Water was slowly added to the reaction mixture under the same cooling and the mixture was stirred at room temperature for 15 minutes. Insoluble materials were filtered through Celite, the filtrate was concentrated in vacuo and the resulted residue was purified with a silica gel column chromatography (eluting solvent: n-hexane/ethyl acetate=50/50 to 10/90) to give [5-fluoro-1-(3-methoxypropyl)-1H-indazol-3-yl]methanol (0.47 g) as a yellow oil.
APCI-MS m/z: 239[M+H]$^+$.

(4) Manganese dioxide (861 mg) was added to a solution of the compound obtained in (3) described above (472 mg) in toluene (20 ml) and the mixture was stirred at 80° C. for 0.5 hour. After being left stand to cool, insoluble materials were filtered through Celite and the filtrate was concentrated in vacuo. The resulted residue was purified with a silica gel column chromatography (eluting solvent: n-hexane/ethyl acetate=75/25 to 50/50) to give 5-fluoro-1-(3-methoxypropyl)-1H-indazol-3-carbaldehyde (363 mg) as a pale yellow powder.
APCI-MS m/z: 237[M+H]$^+$.

(5) Cyclopropylamine (0.19 ml) was added to a solution of the compound obtained in (4) described above (362 mg) in ethanol (12 ml) and the mixture was stirred at 50° C. for an hour. The mixture was concentrated in vacuo, the obtained residue was diluted with toluene and concentrated to dryness in vacuo again. The residue was dissolved in ethanol (10 ml), sodium borohydride (145 mg) was added under ice-cooling and the mixture was stirred at room temperature for 16 hour. Water was added to the reaction mixture under ice-cooling and extracted with ethyl acetate. The organic layer was washed with water and saturated brine, dried over magnesium sulfate and concentrated in vacuo. The resulted residue was purified with a silica gel column chromatography (eluting solvent:ethyl acetate/methanol=100/0 to 92/8) to give N-{[5-fluoro-1-(3-methoxypropyl)-1H-indazol-3-yl]methyl}cyclopropanamine (280 mg) as a colorless oil.
APCI-MS m/z: 278[M+H]$^+$.

Reference Example 165

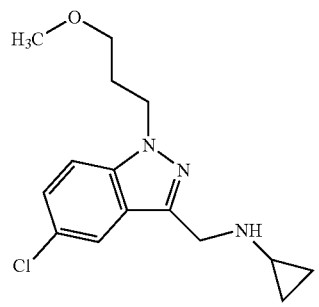 [SMILES: COCCCn1nc(CNC2CC2)c2cc(Cl)ccc21]

(1) 5-Fluoroisatin (2.20 g) was treated in the same manner as Reference Example 164(1) to give 5-chloro-1H-indazol-3-carboxylic acid (1.37 g) as a brown powder.
ESI-MS m/z: 195/197[M−H]$^-$.

(2) The compound obtained in (1) described above (1.20 g) was treated in the same manner as Reference Example 164(2) to give 3-methoxypropyl 5-chloro-1-(3-methoxypropyl)-1H-indazol-3-carboxylate (0.88 g) as a yellow oil.
APCI-MS m/z: 341/343[M+H]$^+$.

(3) The compound obtained in (2) described above (0.88 g) was treated in the same manner as Reference Example 164(3) to give [5-chloro-1-(3-methoxypropyl)-1H-indazol-3-yl]methanol (0.60 g) as a yellow oil.
APCI-MS m/z: 255/257[M+H]$^+$.

(4) The compound obtained in (3) described above (600 mg) was treated in the same manner as Reference Example 164(4) to give 5-chloro-1-(3-methoxypropyl)-1H-indazol-3-carbaldehyde (534 mg) as a pale yellow powder.
APCI-MS m/z: 253/255[M+H]⁺.

(5) The compound obtained in (4) described above (533 mg) was treated in the same manner as Reference Example 164(5) to give N-{[5-chloro-1-(3-methoxypropyl)-1H-indazol-3-yl]methyl}cyclopropanamine (372 mg) as a colorless oil.
APCI-MS m/z: 294/296[M+H]⁺.

Reference Example 166

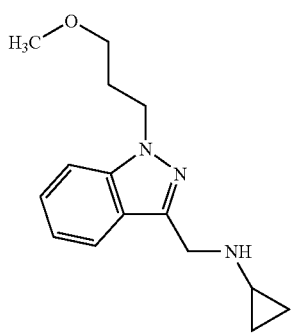 [SMILES: COCCCn1nc(CNC2CC2)c2ccccc21]

(1) 1H-Indazol-3-carboxylic acid (3.24 g) was treated in the same manner as Reference Example 164(2) to give 3-methoxypropyl 1-(3-methoxypropyl)-1H-indazol-3-carboxylate (4.06 g) a an orange oil.
APCI-MS m/z: 307[M+H]⁺.

(2) The compound obtained in (1) described above (3.06 g) was treated in the same manner as Reference Example 164(3) to give [1-(3-methoxypropyl)-1H-indazol-3-yl]methanol (2.17 g) as a colorless oil.
APCI-MS m/z: 221 [M+H]⁺.

(3) The compound obtained in (2) described above (1.00 g) was treated in the same manner as Reference Example 164(4) to give 1-(3-methoxypropyl)-1H-indazol-3-carbaldehyde (0.84 g) as a colorless oil.
APCI-MS m/z: 219[M+H]⁺.

(4) The compound obtained in (3) described above (835 mg) was treated in the same manner as Reference Example 164(5) to give N-{[1-(3-methoxypropyl)-1H-indazol-3-yl]methyl}cyclopropanamine (676 mg) as a colorless oil.
APCI-MS m/z: 260[M+H]⁺.

Reference Example 167-169

The corresponding starting compounds were treated in the same manner as Reference Example 128 to give compounds listed in Table 19 below.

TABLE 19

| No. of Reference Examples | Structure | Properties |
|---|---|---|
| 167 | 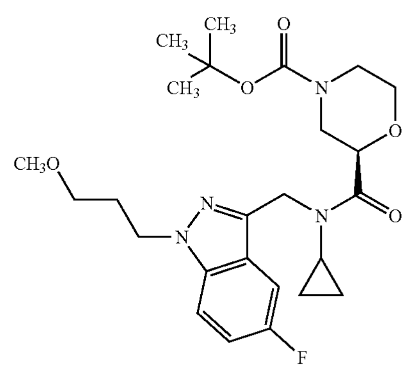 | Property: colorless viscous oil<br>APCI-MS m/z: 491[M + H]⁺ |
| 168 | 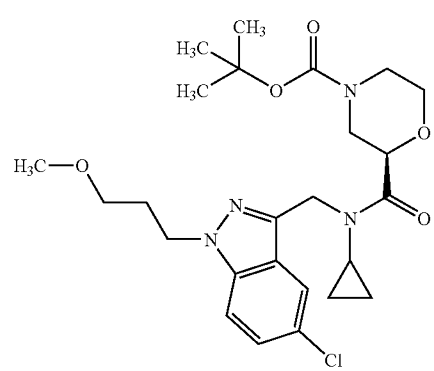 | Property: colorless viscous oil<br>APCI-MS m/z: 507/509[M + H]⁺ |

TABLE 19-continued

| No.of Reference Examples | Structure | Properties |
|---|---|---|
| 169 | 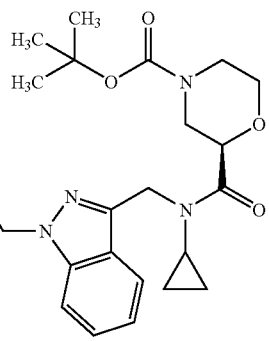 | Property: colorless viscous oil<br>APCI-MS m/z: 473[M + H]$^+$ |

Reference Example 170

(1)

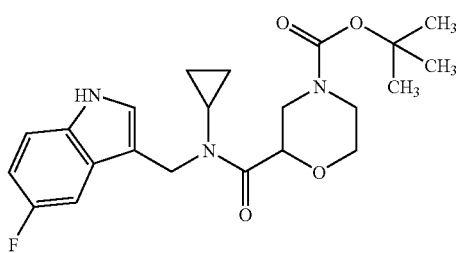 [SMILES: CC(C)(C)OC(=O)N1CCOC(C(=O)N(Cc2c[nH]c3ccc(F)cc23)C2CC2)C1]

1-Hydroxybenzotriazole (486 mg) and 1-ethyl-3-(3-dimethylaminopropyl)carbodiimide hydrochloride (863 mg) were added successively to a solution of N-[(5-fluoro-1H-indol-3-yl)methyl]cyclopropylamine (735 mg) and (dl)-4-(tert-butoxycarbonyl)morpholin-2-carboxylic acid (694 mg) in N,N-dimethylformamide (38 ml) and the mixture was stirred at room temperature for 24 hours. The reaction solution was diluted with an excess of ethyl acetate, washed with water, a saturated aqueous solution of sodium bicarbonate and saturated brine successively and dried over magnesium sulfate. The solvent was evaporated in vacuo and the resulted residue was purified with a silica gel column chromatography (eluting solvent:n-hexane/ethyl acetate=1/1 to 1/4) to give tert-butyl(dl)-2-({cyclopropyl[(5-fluoro-1H-indol-3-yl)methyl]amino}carbonyl)morpholin-4-carboxylate (965 mg) as a pale yellow powder.

APCI-MS m/z: 418 [M+H]$^+$.

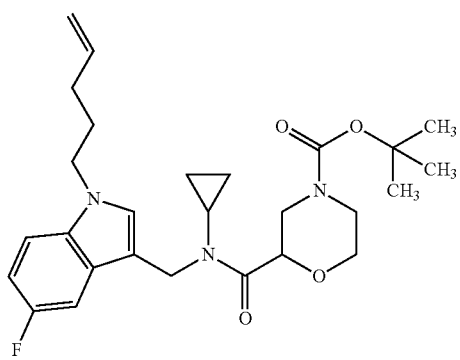 [SMILES: C=CCCCn1cc(CN(C(=O)C2CN(C(=O)OC(C)(C)C)CCO2)C2CC2)c2cc(F)ccc21]

60% Oily sodium hydride (26 mg) was added to a solution of the compound obtained in (1) described above (250 mg) in N,N-dimethylformamide (4 ml) and the mixture was stirred at room temperature for 30 minutes. 5-Bromo-1-penten (78 µg) and potassium iodide (99 mg) were added to the mixture and it was stirred at 50° C. for 3 hours. The reaction mixture was poured into a mixture of ice water and it was extracted with ethyl acetate. The organic layer was washed with water and saturated brine, dried over magnesium sulfate, and concentrated in vacuo. The resulted residue was purified with a silica gel column chromatography (eluting solvent:n-hexane/ethyl acetate=9/1 to 2/3) to give tert-butyl(dl)-2-({cyclopropyl[(5-fluoro-1-pent-4-ene-1-yl-1H-indol-3-yl)methyl]amino}carbonyl)morpholin-4-carboxylate (204 mg) as a colorless oil.

APCI-MS m/z: 486[M+H]$^+$.

(3)

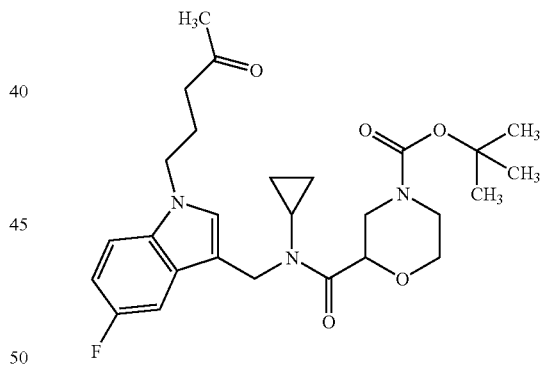

Palladium chloride (7.4 mg) and cuprous chloride(I) (41.4 mg) were added to a mixture of N,N-dimethylformamide (1 ml) and water (1 ml), then, a solution of the compound obtained in (2) described above (203 mg) in N,N-dimethylformamide (2 ml) was added and the mixture was stirred under oxygen atmosphere at room temperature for 20 hours. The reaction mixture was diluted with ethyl acetate and insoluble materials were filtered. The filtrate was washed with water and saturated brine, dried over magnesium sulfate and concentrated in vacuo. The resulted residue was purified with a silica gel column chromatography (eluting solvent: chloroform to chloroform/methanol=20/1) to give tert-butyl (dl)-2-({cyclopropyl[(5-fluoro-1-(4-oxopentyl)-1H-indol-3-yl]methyl}amino)carbonyl]morpholin-4-carboxylate (210 mg) as a colorless oil.

APCI-MS m/z: 502[M+H]$^+$.

Reference Example 171

(1)

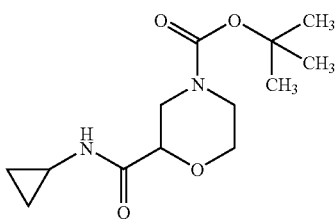 [SMILES: CC(C)(C)OC(=O)N1CCOC(C(=O)NC2CC2)C1]

Cyclopropylamine (222 mg) was added to a solution of (dl)-4-(tert-butoxycarbonyl)morpholin-2-carboxylic acid (600 mg), 1-ethyl-3-(3-dimethylaminopropyl)carbodiimide hydrochloride (596 mg) and 1-hydroxybenzotriazole (420 mg) in chloroform (10 ml) under ice-cooling and the mixture was stirred at room temperature for 15 hours. A saturated aqueous solution of sodium bicarbonate was added to the reaction mixture and it was extracted with chloroform. The organic layer was washed with water and saturated brine successively, dried over sodium sulfate and concentrated in vacuo. The resulted residue was purified with a silica gel column chromatography (eluting solvent: n-hexane/ethyl acetate=4/1 to 2/1) to give tert-butyl(dl)-2-[(cyclopropylamino)carbonyl]morpholin-4-carboxylate (648 mg) as a colorless powder.

APCI-MS m/z: 271[M+H]⁺.

(2)

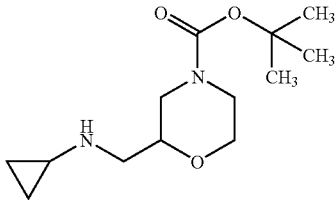 [SMILES: CC(C)(C)OC(=O)N1CCOC(CNC2CC2)C1]

Under argon atmosphere borane dimethylsulfide complex (0.56 ml) was added to a solution of the compound obtained in (1) described above (300 mg) in tetrahydrofuran (10 ml) under ice cooling and the mixture was stirred at room temperature for 3 hours. After methanol (5 ml) was added to the reaction mixture and stirred at room temperature for 1 hour, 5N aqueous solution of sodium hydroxide (10 ml) was added and the mixture was stirred at 50° C. for 12 hours. After being cooled to room temperature, the mixture was extracted with diethyl ether. The organic layer was washed with saturated brine, dried over sodium sulfate and concentrated in vacuo. The resulted residue was purified with a silica gel column chromatography (eluting solvent:chloroform to chloroform/methanol=10/1) to give tert-butyl(dl)-2-[(cyclopropylamino)methyl]morpholin-4-carboxylate (183 mg) as a colorless oil.

APCI-MS m/z: 257[M+H]⁺.

(3)

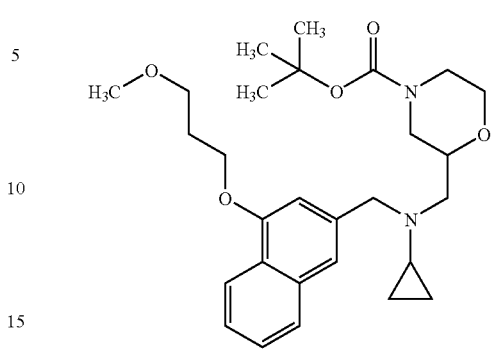

3-(Bromomethyl)-1-(3-methoxypropyl)naphthalene (72 mg) and diisopropylethyl amine (38 mg) were added to a solution of the compound obtained in (2) described above (50 mg) in tetrahydrofuran (2 ml) under ice-cooling and the mixture was stirred at room temperature for 2 hours and at 60° C. for 15 hours. A saturated aqueous solution of sodium bicarbonate was added to the reaction solution under ice-cooling and it was extracted with ethyl acetate. The organic layer was washed with saturated brine, dried over sodium sulfate and concentrated in vacuo. The resulted residue was purified with a silica gel column chromatography (eluting solvent: n-hexane/ethyl acetate=2/1) to give tert-butyl(dl)-2-[(cyclopropyl{[4-(3-methoxypropyl)-2-naphtyl]methyl}amino)carbonyl]morpholin-4-carboxylate (75 mg) as a colorless oil.

APCI-MS m/z: 485[M+H]⁺.

Reference Example 172

(1)

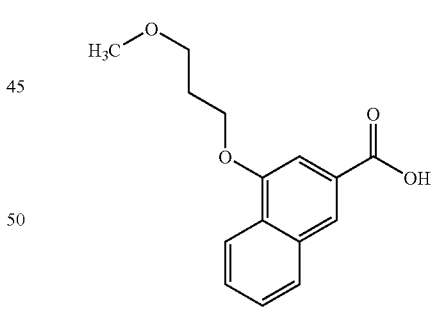

5N Aqueous solution of sodium hydroxide (3.4 ml) was added to a solution of ethyl 4-(3-methoxypropyl)-2-naphthoate (2.41 g) in ethanol and the mixture was stirred at room temperature for 3 hours. The reaction solution was acidified by adding 10% hydrochloric acid under ice-cooling and extracted with ethyl acetate. The organic layer was washed with saturated brine, dried over sodium sulfate and concentrated in vacuo. The resulted residue was triturated in n-hexane to give 4-(3-methoxypropyl)-2-naphthoic acid (2.09 g) as a colorless powder.

ESI-MS m/z: 259[M−H]⁻.

(2)

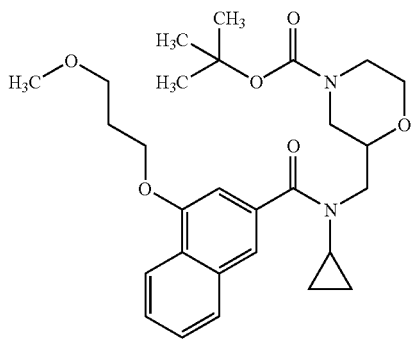 [SMILES: COCCCOc1cc(C(=O)N(CC2CN(C(=O)OC(C)(C)C)CCO2)C2CC2)cc2ccccc12]

Oxalyl chloride (55 mg) and a catalytic amount of N,N-dimethylformamide (a drop) were added to a solution of the compound obtained in (1) described above (75 mg) in chloroform (3 ml) and the mixture was stirred at room temperature for an hour. The reaction mixture was concentrated in vacuo and the residue was dissolved in chloroform (2 ml), which was added to a solution of tert-butyl(dl)-2-[(cyclopropylamino)methyl]morpholin-4-carboxylate (62 mg) and diisopropylethylamine (63 mg) in chloroform (2 ml) under ice cooling and the mixture was stirred at room temperature for 2 hours. Water was added to the reaction mixture under ice-cooling and the mixture was extracted with chloroform. The organic layer was washed with a saturated aqueous solution of sodium bicarbonate and brine successively, dried over sodium sulfate and concentrated in vacuo. The resulted residue was purified with a silica gel column chromatography (eluting solvent: n-hexane to ethyl acetate) to give tert-butyl (dl)-2-({cyclopropyl[4-(3-methoxypropyl)-2-naphthoyl]amino}methyl)morpholin-4-carboxylate (94 mg) as a colorless oil.

APCI-MS m/z: 499[M+H]⁺.

Reference Example 173

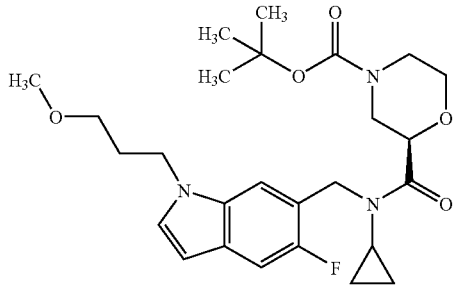 [SMILES: COCCCn1ccc2cc(F)c(CN(C(=O)[C@H]3CN(C(=O)OC(C)(C)C)CCO3)C3CC3)cc21]

10% Palladium-Carbon (80 mg) was added to a solution of tert-butyl(2R)-2-[(cyclopropyl{]5-fluoro-1-(3-methoxypropyl)-1H-indol-6-yl]methyl}amino)carbonyl]morpholin-4-carboxylate carboxylate (180 mg) and diisopropylethylamine (89 mg) in ethanol (5 ml) and the mixture was stirred under normal pressure of hydrogen atmosphere at room temperature for 10 hours. Insoluble materials were filtered through Celite, the filtrate was dissolved in ethyl acetate, washed with water and saturated brine and dried over sodium sulfate. It was concentrated in vacuo to give tert-butyl(2R)-2-[(cyclopropyl{]5-fluoro-1-(3-methoxypropyl)-1H-indol-6-yl]methyl}amino)carbonyl]morpholin-4-carboxylate (157 mg) as a colorless oil.

APCI-MS m/z: 490 [M+H]⁺.

Reference Example 174

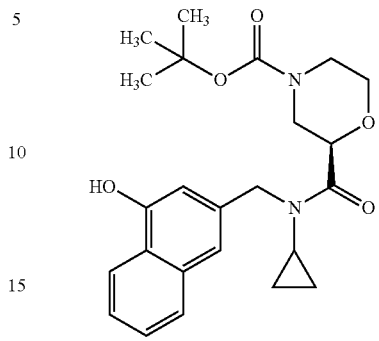

10% Palladium-Carbon (30 mg) was added to a solution of tert-butyl(2R)-2-{[{[4-(benzyloxy)-2-naphthyl]methyl(cyclopropyl)amino]carbonyl}morpholin-4-carboxylate (300 mg) in methanol (3 ml) and the mixture was stirred under normal pressure of hydrogen atmosphere at room temperature for 3 hours. Insoluble materials were filtered through Celite and the filtrate was concentrated in vacuo. The resulted residue was purified with a silica gel column chromatography (eluting solvent: n-hexane/ethyl acetate=4/1 to 1/1) to give tert-butyl(2R)-2-({cyclopropyl[(4-hydroxy-2-naphthyl)methyl]amino}carbonyl)morpholin-4-carboxylate (225 mg) as a colorless oil.

APCI-MS m/z: 427[M+H]⁺.

Reference Example 175

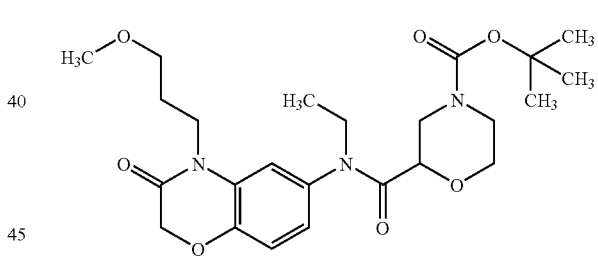

60% Sodium hydride (12 mg) was added to a solution of tert-butyl(dl)-2-({[4-(3-methoxypropyl)-3-oxo-3,4-dihydro-2H-1,4-benzoxazin-6-yl]amino}carbonyl)morpholin-4-carboxylate (100 mg) in N,N-dimethylformamide (3 ml) under ice-cooling and the mixture was stirred at room temperature for 10 minutes. Ethyl iodide (52 mg) was added to the mixture under ice-cooling and the mixture was stirred at room temperature for 2 hours. 60% Sodium hydride (15 mg) was further added to the mixture under ice-cooling and it was stirred at room temperature for 4 hours. Water was added to the reaction mixture under ice-cooling and the mixture was extracted with ethyl acetate. The organic layer was washed with a water and saturated brine successively, dried over sodium sulfate and concentrated in vacuo. The resulted residue was purified with a silica gel column chromatography (eluting solvent: n-hexane to ethyl acetate) to give tert-butyl (dl)-2-({ethyl[4-(3-methoxypropyl)-2-oxo-3,4-dihydro-2H-1,4-benzoxazin-6-yl]amino}carbonyl)morpholin-4-carboxylate (33 mg) as a colorless oil.

APCI-MS m/z: 478[M+H]⁺

Reference Example 176

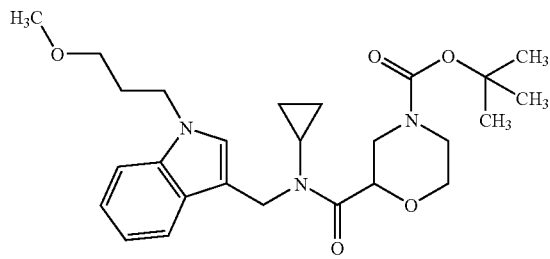 [SMILES: COCCCn1cc(CN(C(=O)C2CN(C(=O)OC(C)(C)C)CCO2)C2CC2)c2ccccc21]

60% Sodium hydride (23 mg) was added to a solution of tert-butyl(dl)-2-{[cyclopropyl(1H-indol-3-ylmethyl)amino]carbonyl}morpholin-4-carboxylate (175 mg) in N,N-dimethylformamide (1 ml) under ice-cooling and the mixture was stirred at room temperature for 30 minutes. A solution of 1-bromo-3-methoxypropane (81 mg) in N,N-dimethylformamide (0.1 ml) and potassium iodide (73 mg) were added to the mixture and the reaction mixture was stirred at room temperature for 3 hours. Water was added to the reaction mixture under ice-cooling and the mixture was extracted with ethyl acetate. The organic layer was washed with a water and saturated brine successively, dried over sodium sulfate and concentrated in vacuo. The resulted residue was purified with a silica gel column chromatography (eluting solvent: chloroform to chloroform/ethyl acetate=1/1) to give tert-butyl(dl)-2-[(cyclopropyl{[1-(3-methoxypropyl)-1H-indol-3-yl]methyl}amino)carbonyl]morpholin-4-carboxylate (100 mg) as a colorless oil.

APCI-MS m/z: 472[M+H]$^+$.

Reference Example 177

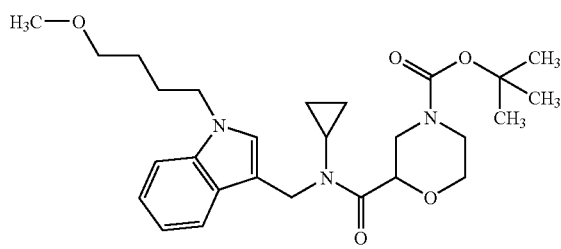 [SMILES: COCCCCn1cc(CN(C(=O)C2CN(C(=O)OC(C)(C)C)CCO2)C2CC2)c2ccccc21]

60% Sodium hydride (11 mg) was added to a solution of tert-butyl(dl)-2-{[cyclopropyl(1H-indol-3-ylmethyl)amino]carbonyl}morpholin-4-carboxylate (100 mg) in N,N-dimethylformamide (0.65 ml) under ice-cooling and the mixture was stirred at room temperature for 15 minutes. 4-Methoxypropyl tosylate (77.5 mg) and potassium iodide (41.5 mg) were added to the reaction mixture and it was stirred at room temperature for an hour. Water was added to the reaction mixture under ice-cooling and the mixture was extracted with ethyl acetate. The organic layer was washed with a water and saturated brine successively, dried over magnesium sulfate and concentrated in vacuo. The resulted residue was purified with a silica gel column chromatography (eluting solvent: chloroform to chloroform/methanol=5/1) to give tert-butyl(dl)-2-[(cyclopropyl{[1-(4-methoxybutyl)-1H-indol-3-yl]methyl}amino)carbonyl]morpholin-4-carboxylate (112 mg) as a colorless oil.

APCI-MS m/z: 486[M+H]$^+$.

Reference Example 178

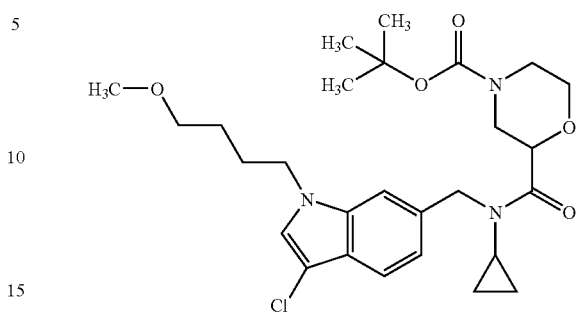

60% Sodium hydride (12.2 mg) was added to a solution of tert-butyl(dl)-2-{[[(3-chloro-1H-indol-6-yl)methyl](cyclopropyl)amino]carbonyl}morpholin-4-carboxylate (100 mg) in N,N-dimethylformamide (3.0 ml) under ice-cooling and the mixture was stirred at room temperature for 15 minutes. 4-Methoxypropyl tosylate (71.5 mg) and potassium iodide (38.3 mg) were added to the reaction mixture and it was stirred at room temperature for 2 hours. Water was added to the reaction mixture under ice-cooling and the mixture was extracted with ethyl acetate. The organic layer was washed with a water and saturated brine successively, dried over sodium sulfate and concentrated in vacuo. The resulted residue was purified with a silica gel column chromatography (eluting solvent: n-hexane/ethyl acetate=1/1) to give tert-butyl(dl)-2-{[[(3-chloro-1-(4-methoxybutyl)-1H-indol-6-yl]methyl}(cyclopropyl)amino]carbonyl}morpholin-4-carboxylate (36.2 mg) as a colorless oil.

APCI-MS m/z: 520/522[M+H]$^+$.

Reference Example 179

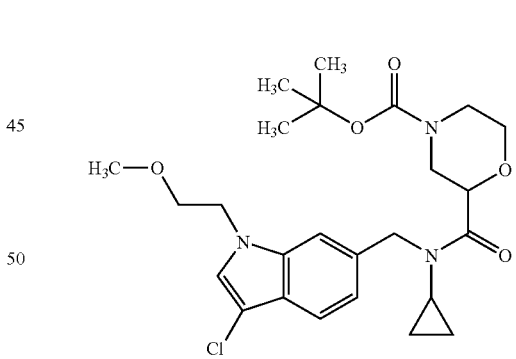

60% Sodium hydride (26.8 mg) was added to a solution of tert-butyl(dl)-2-{[[(3-chloro-1H-indol-6-yl)methyl](cyclopropyl)amino]carbonyl}morpholin-4-carboxylate (242 mg) in N,N-dimethylformamide (7 ml) under ice-cooling and the mixture was stirred at room temperature for 15 minutes. 2-Methoxyethyl bromide (93 µg) and potassium iodide (9.3 mg) were added to the reaction mixture and it was stirred at room temperature for 5 hours. Water was added to the reaction mixture under ice-cooling and the mixture was extracted with ethyl acetate. The organic layer was washed with a water and saturated brine successively, dried over sodium sulfate and concentrated in vacuo. The resulted residue was purified with NH-silica gel column chromatography (eluting solvent: n-hexane/ethyl acetate=1/1 to 1/2) to give tert-butyl(dl)-2-{[{[3-chloro-1-(2-methoxyethyl)-1H-indol-6-yl]methyl}(cyclopropyl)amino]carbonyl}morpholin-4-carboxylate (283 mg) as a colorless oil.

APCI-MS m/z: 492/494[M+H]⁺.

Reference Example 180

(1)

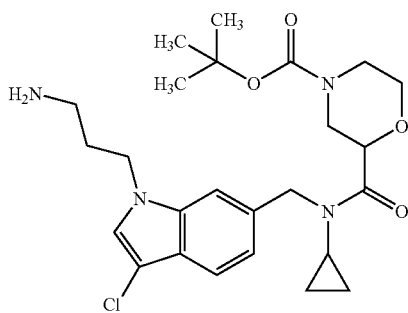 [SMILES: CC(C)(C)OC(=O)N1CCOC(C(=O)N(Cc2ccc3c(Cl)cn(CCCN)c3c2)C2CC2)C1]

Sodium hydroxide (111 mg) and tetrabutylammonium hydrogensulfate (31 mg) were added to a solution of tert-butyl(dl)-2-{[[(3-chloro-1H-indol-6-yl)methyl](cyclopropyl)amino]carbonyl}morpholin-4-carboxylate (400 mg) in acetonitrile (8.0 ml) and the mixture was stirred at room temperature for 15 minutes. 3-Chloropropylamine hydrochloride (180 mg) was added to the reaction mixture and the mixture was heated under reflux for 5 hours. After being cooled to room temperature, insoluble materials were filtered through Celite, water was added to the filtrate and the mixture was extracted with ethyl acetate. The organic layer was washed with saturated brine, dried over magnesium sulfate and concentrated in vacuo. The resulted residue was purified with NH-silica gel column chromatography (eluting solvent: ethyl acetate/methanol=12/1 to 5/1) to give tert-butyl(dl)-2-{[{[1-(3-aminopropyl)-3-chloro-1H-indol-6-yl]methyl(cyclopropyl)amino]carbonyl}morpholin-4-carboxylate (225 mg) as a yellow oil.

APCI-MS m/z: 491/493[M+H]⁺.

(2)

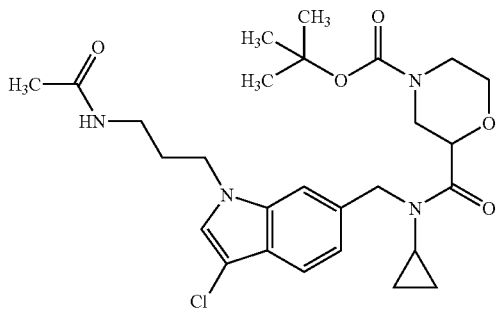 [SMILES: CC(=O)NCCCn1cc(Cl)c2ccc(CN(C(=O)C3CN(C(=O)OC(C)(C)C)CCO3)C3CC3)cc21]

Pyridine (79.0 μg) and acetyl chloride (34.7 μg) were added to a solution of the compound obtained in (1) described above (160 mg) in chloroform (3.0 ml) under ice-cooling and the mixture was stirred at room temperature for an hour. Water was added to the reaction mixture and extracted with chloroform. The organic layer was washed with a saturated aqueous solution of sodium bicarbonate and saturated brine successively, dried over sodium sulfate and concentrated in vacuo. The resulted residue was purified with a silica gel column chromatography (eluting solvent: chloroform/methanol=50/1 to 20/1) to give tert-butyl(dl)-2-{[({1-[3-(acetylamino)propyl]-3-chloro-1H-indol-6-yl}methyl)(cyclopropyl)amino]carbonyl}morpholin-4-carboxylate (155 mg) as a colorless powder.

APCI-MS m/z: 533/535[M+H]⁺.

Reference Example 181

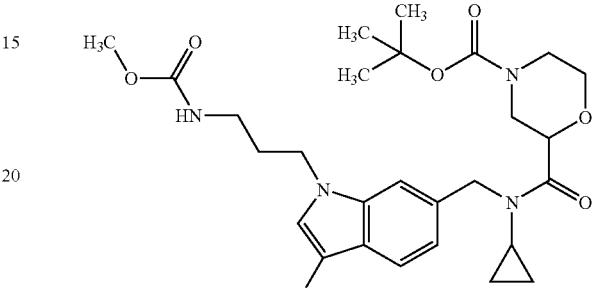

Pyridine (79 μg) and methyl chloroformate (37.7 μg) were added to a solution of the compound obtained in Reference Example 180(1)(160 mg) in chloroform (3 ml) under ice-cooling and the mixture was stirred at room temperature for an hour. Water was added to the reaction mixture and extracted with chloroform. The organic layer was washed with a saturated aqueous solution of sodium bicarbonate and saturated brine successively, dried over sodium sulfate and concentrated in vacuo. The resulted residue was purified with a silica gel column chromatography (eluting solvent: chloroform/methanol=50/1 to 20/1) to give tert-butyl(dl)-2-{[[(3-chloro-1-{3-[(methoxycarbonyl)amino]propyl}-1H-indol-6-yl)methyl](cyclopropyl)amino]carbonyl}morpholin-4-carboxylate (169 mg) as a yellow oil.

APCI-MS m/z: 552/554[M+NH₄]⁺.

Reference Example 182

(1)

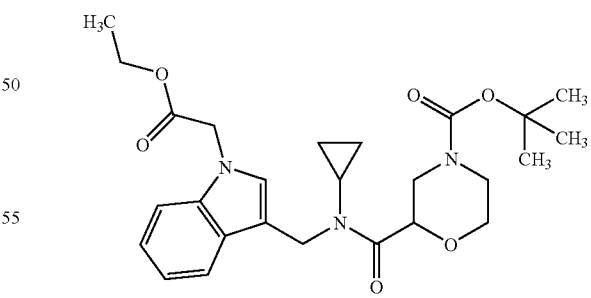

60% Sodium hydride (11 mg) was added to a solution of tert-butyl(dl)-2-{[cyclopropyl(1H-indol-3-ylmethyl)amino]carbonyl}morpholin-4-carboxylate (100 mg) in N,N-dimethylformamide (0.65 ml) under ice-cooling. The reaction mixture was stirred at room temperature for 30 minutes, then cooled in ice-water again and ethyl bromoacetate (33.3 μg) and potassium iodide (41.5 mg) were added. The mixture was warmed up to room temperature and stirred for 20 hours.

Water was added to the reaction mixture and the mixture was extracted with ethyl acetate. The organic layer was washed with water and saturated brine successively, dried over magnesium sulfate and concentrated in vacuo. The residue was purified with a silica gel column chromatography (eluting solvent: n-hexane/ethyl acetate=9/1 to 1/1) to give tert-butyl (dl)-2-[(cyclopropyl{[1-(2-ethoxy-2-oxoethyl)-1H-indol-3-yl]methyl}amino)carbonyl}morpholin-4-carboxylate (44.2 mg).

APCI-MS m/z: 486[M+H]+.

(2)

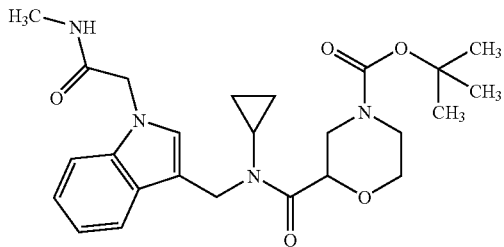 [SMILES: CNC(=O)Cn1cc(CN(C(=O)C2CN(C(=O)OC(C)(C)C)CCO2)C2CC2)c2ccccc21]

2N Aqueous solution of sodium hydroxide (0.45 ml) was added to a solution of the compound obtained in (1) described above (44 mg) in ethanol (0.45 ml). After stirring at room temperature for 10 minutes, chloroform was added to the reaction mixture and it was neutralized by adding 2N hydrochloric acid with vigorously stirring. The organic layer was separated, dried over magnesium sulfate and concentrated in vacuo. The residue was dissolved in N,N-dimethylformamide (1.0 ml) and 2N methylamine solution in tetrahydrofuran (50 μl), 1-hydroxybenzotriazole (14.7 mg) and 1-ethyl-3-(3-dimethylaminopropyl)carbodiimide hydrochloride (20.9 mg) were added successively, and the mixture was stirred at room temperature for an hour. After addition of water, the reaction mixture was extracted with ethyl acetate, the organic layer was washed with water and saturated brine successively, dried over magnesium sulfate and concentrated in vacuo. The residue was purified with a silica gel column chromatography (eluting solvent: chloroform to chloroform/methanol=9/1) to give tert-butyl(dl)-2-{[cyclopropyl({1-[2-(methylamino)-2-oxoethyl]-1H-indol-3-yl)methyl)amino] carbonyl}morpholin-4-carboxylate (29.3 mg) as a colorless powder.

APCI-MS m/z: 471[M+H]+.

Reference Example 183

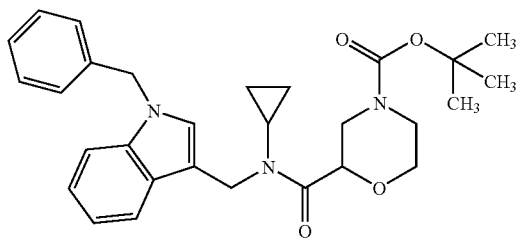 [SMILES: CC(C)(C)OC(=O)N1CCOC(C(=O)N(Cc2cn(Cc3ccccc3)c3ccccc23)C2CC2)C1]

60% Sodium hydride (17 mg) was added to a solution of tert-butyl(dl)-2-{[cyclopropyl(1H-indol-3-ylmethyl)amino]carbonyl}morpholin-4-carboxylate (150 mg) in N,N-dimethylformamide (0.65 ml) under ice-cooling. After stirring at room temperature for 10 minutes, benzyl bromide (53.5 μl) was added and the mixture was stirred at room temperature for an hour. Water was added to the reaction mixture and it was extracted with ethyl acetate. The organic layer was washed with water and saturated brine successively, dried over magnesium sulfate and concentrated in vacuo. The residue was purified with a silica gel column chromatography (eluting solvent: chloroform to chloroform/methanol=20/1) to give tert-butyl(dl)-2-{[[(1-benzyl-1H-indol-3-yl)methyl](cyclopropyl)amino]carbonyl}morpholin-4-carboxylate (176 mg).

APCI-MS m/z: 490[M+H]+.

Reference Example 184

(1)

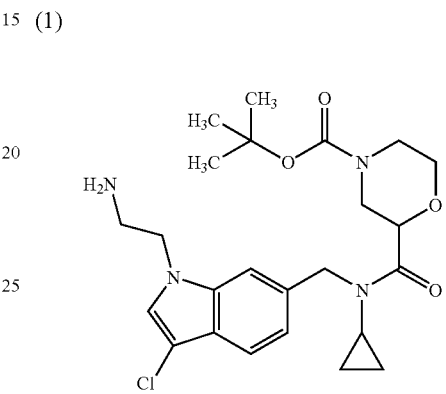

The corresponding starting compounds were treated in the same manner as Reference Example 180(1) to give tert-butyl (dl)-2-{[{[1-(3-aminoethyl)-3-chloro-1H-indol-6-yl]methyl (cyclopropyl)amino]carbonyl}morpholin-4-carboxylate.

APCI-MS m/z: 477/479[M+H]+.

(2)

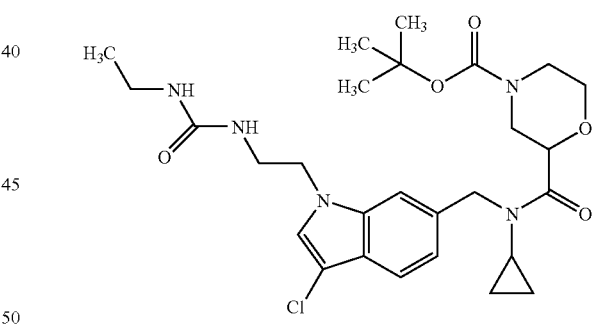

Ethyl isocyanate (37.8 was added to a solution of tert-butyl (dl)-2-{[{[1-(3-aminoethyl)-3-chloro-1H-indol-6-yl]methyl (cyclopropyl)amino]carbonyl}morpholin-4-carboxylate (100 mg) in dichloromethane (2.0 ml) and the mixture was stirred at room temperature for 3 hours. A saturated aqueous solution of sodium bicarbonate was added to the reaction mixture and the mixture was extracted with chloroform. The organic layer was washed with saturated brine, dried over sodium sulfate and concentrated in vacuo. The resulted residue was purified with a silica gel column chromatography (eluting solvent: chloroform to chloroform/methanol=30/1) to give tert-butyl(dl)-2-{[{3-chloro-1-(2-{[(ethylamino)carbonyl]aminoethyl)-1H-indol-6-yl]methyl}((cyclopropyl) amino]carbonyl}morpholin-4-carboxylate (108 mg) as a pale yellow oil.

APCI-MS m/z: 548/550[M+H]+.

Reference Example 185

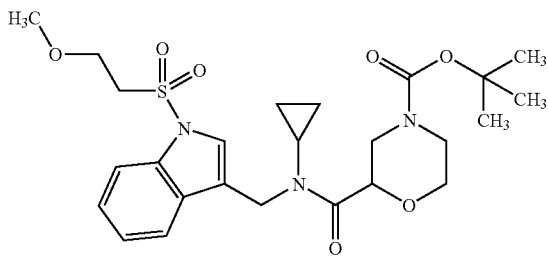 [SMILES: COCCS(=O)(=O)n1cc(CN(C(=O)C2CN(C(=O)OC(C)(C)C)CCO2)C2CC2)c2ccccc21]

60% Sodium hydride (16.5 mg) was added to a solution of tert-butyl(dl)-2-{[cyclopropyl(1H-indol-3-ylmethyl)amino]carbonyl}morpholin-4-carboxylate (150 mg) in N,N-dimethylformamide (1.0 ml) under ice-cooling and the mixture was stirred at room temperature for 5 minutes. 2-Methoxyethylsulfonyl chloride (71.4 mg) was added therein and the mixture was stirred at room temperature for 2 hours. Water was added to the reaction mixture and it was extracted with ethyl acetate. The organic layer was washed with water and saturated brine successively, dried over magnesium sulfate and concentrated in vacuo. The resulted residue was purified with a silica gel column chromatography (eluting solvent: chloroform to chloroform/methanol=25/1) to give tert-butyl(dl)-2-{[cyclopropyl({1-[(2-methoxyethyl)sulfonyl]-1H-indol-6-yl}methyl)amino]carbonyl}morpholin-4-carboxylate (107 mg) as a colorless powder.
APCI-MS m/z: 522[M+H]$^+$.

Reference Example 186

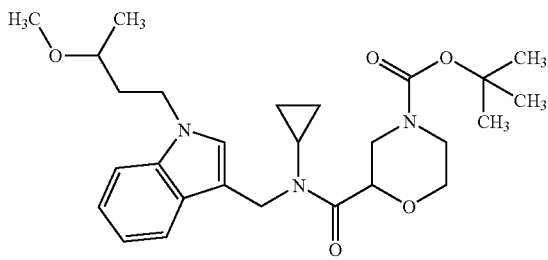 [SMILES: COC(C)CCn1cc(CN(C(=O)C2CN(C(=O)OC(C)(C)C)CCO2)C2CC2)c2ccccc21]

(1) Triethylamine (45 μL) and methanesulfonyl chloride (25 μL) were added to a solution of (dl)-3-methoxy-1-butanol (31 mg) in chloroform (1 ml) under ice cooling and the mixture was stirred at room temperature for 30 minutes. Triethylamine (35 μL) and methanesulfonyl chloride (19 μL) were further added, the mixture was stirred at room temperature for 2 hours and concentrated in vacuo. Toluene was added to the residue, insolble materals were filtered through Celite and the filtrate was concentrated in vacuo.
(2) 60% Sodium hydride (11 mg) was added to a solution of tert-butyl(dl)-2-{[cyclopropyl(1H-indol-3-ylmethyl)amino]carbonyl}morpholin-4-carboxylate (100 mg) in N,N-dimethylformamide (0.65 ml) under ice cooling and the mixture was stirred at room temperature for 30 minutes. The compound obtained in (1) described above (71.4 mg) and potassium iodide (46 mg) were added and the mixture was stirred at room temperature for 15 hours. Water was added to the reaction mixture and it was extracted with ethyl acetate. The organic layer was washed with water and saturated brine successively, dried over magnesium sulfate and concentrated in vacuo. The resulted residue was purified with a silica gel column chromatography (eluting solvent: n-hexane/ethyl acetate=5/1 to 1/2) to give tert-butyl(dl)-2-[(cyclopropyl{[1-(3-methoxybutyl)-1H-indol-3-yl]methyl}amino)carbonyl]morpholin-4-carboxylate (81 mg) as a colorless oil.
APCI-MS m/z: 486[M+H]$^+$.

Reference Example 187

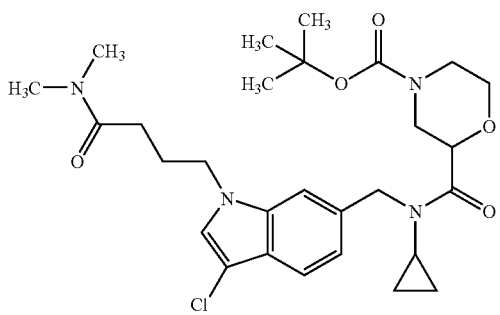 [SMILES: CN(C)C(=O)CCCn1cc(Cl)c2ccc(CN(C(=O)C3CN(C(=O)OC(C)(C)C)CCO3)C3CC3)cc21]

(1) Sodium hydroxide (57.7 mg) and water (2.5 ml) were added to a solution of tert-butyl(dl)-2-{[{[3-chloro-1-(4-ethoxy-4-oxobutyl)-1H-indol-6-yl]methyl}(cyclopropyl)amino]carbonyl}morpholin-4-carboxylate (1.6 g) in ethanol (12.5 ml) and the mixture was refluxed for 30 minutes. The reaction mixture was concentrated in vacuo, the resulted residue was acidified by adding water and 2N hydrochloric acid and the mixture was extracted with chloroform. The organic layer was dried over sodium sulfate and concentrated in vacuo. The resulted residue was purified with a silica gel column chromatography (eluting solvent: chloroform to chloroform/methanol=15/1) to give (dl)-4-(6-{[{[4-(tert-butoxycarbonyl)morpholin-2-yl]carbonyl}(cyclopropyl)amino]methyl}-3-chloro-1H-indol-1-yl)butyric acid (1.48 g) as a pale yellow oil.
ESI-MS m/z: 518/520[M−H]$^−$.
(2) 1-Hydroxybenzotriazole (15 mg) and 1-ethyl-3-(3-dimethylaminopropyl)carbodiimide hydrochloride (20 mg) were added successively to a solution of the compound obtained in (1) described above (50 mg) and dimethylamine hydrochloride (20 mg) in N,N-dimethylformamide (2.0 ml) under ice-cooling and the mixture was stirred at room temperature for 5 hours. Water was added to the reaction mixture under ice-cooling and it was extracted with ethyl acetate. The organic layer was washed with a saturated aqueous solution of sodium bicarbonate, water and saturated brine successively, dried over magnesium sulfate and concentrated in vacuo. The resulted residue was purified with a silica gel column chromatography (eluting solvent: chloroform/methanol=100/1 to 20/1) to give tert-butyl(dl)-2-{[({3-chloro-1-[4-(dimethylamino)-4-oxobutyl]-1H-indol-6-yl}methyl)(cyclopropyl)amino]carbonyl}morpholin-4-carbocylate (35 mg) as a colorless powder.
APCI-MS m/z: 547/549[M+H]$^+$.

Reference Example 188

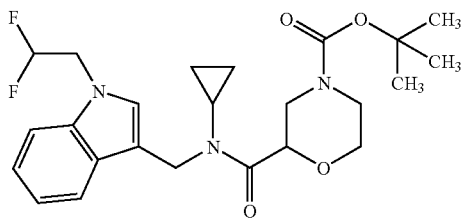 [SMILES: CC(C)(C)OC(=O)N1CCOC(C(=O)N(Cc2cn(CC(F)F)c3ccccc23)C2CC2)C1]

60% Sodium hydride (13.2 mg) was added to a solution of tert-butyl(dl)-2-{[cyclopropyl(1H-indol-3-ylmethyl)amino]carbonyl}morpholin-4-carboxylate (120 mg) in N,N-dimethylformamide (1.0 ml) under ice-cooling and the mixture was stirred at room temperature for 10 minutes. 2,2-Difluoromethyltrifluorosulfonate (77 mg) was added and the mixture was stirred at room temperature for 19 hours. Water was added to the reaction mixture and it was extracted with ethyl acetate. The organic layer was washed with water and saturated brine successively, dried over magnesium sulfate and concentrated in vacuo. The resulted residue was purified with a silica gel column chromatography (eluting solvent: chloroform to chloroform/methanol=20/1) to give tert-butyl(dl)-2-[(cyclopropyl{[1-(2,2-difluoroethyl)-1H-indol-3-yl]methyl}amino)carbonyl]morpholin-4-carboxylate (128 mg).
APCI-MS m/z: 464[M+H]$^+$.

Reference Example 189

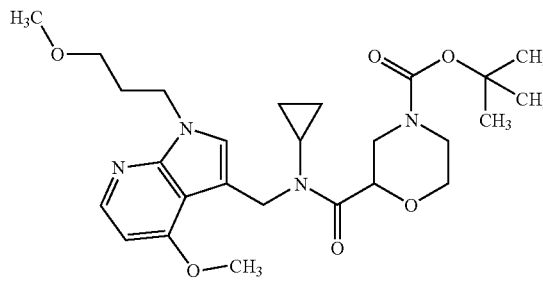

(1) A mixture of tert-butyl(dl)-2-{[{[4-bromo-1-(3-methoxypropyl)-1H-pyrrolo[2,3-b]pyridin-3-yl]methyl}(cyclopropyl)amino]carbonyl}morpholin-4-carboxylate (110 mg), tris(dibenzylideneacetone)dipalladium (4 mg), 2-di-tert-butylphosphino-2',4',6'-triisopropyl-1,1'-biphenyl (tBu X-phos) (7 mg) and potassium hydroxide (34 mg) in dioxane (1 ml)/water (1 ml) was stirred under argon atmosphere at 100° C. for an hour. After being left stand to cool, a saturated aqueous solution of ammonium chloride was poured into the reaction mixture and it was extracted with ethyl acetate. The organic layer was washed with water and saturated brine successively, dried over sodium sulfate and concentrated in vacuo. The resulted residue was a silica gel column chromatography (eluting solvent: ethyl acetate to ethyl acetate/methanol=9/1) to give tert-butyl(dl)-2-[(cyclopropyl{[4-hydroxy-1-(3-methoxypropyl)-1H-pyrrolo[2,3-b]pyridin-3-yl]methyl}amino)carbonyl]morpholin-4-carboxylate (78 mg) as a yellow oil.
APCI-MS m/z: 489[M+H]$^+$.

(2) Potassium carbonate (41 mg) and methyl iodide (25 μL) were added to a solution of the compound obtained in (1) described above (50 mg) in N,N-dimethylformamide (2 ml) and the mixture was stirred at room temperature for 2 hours. Water was added to the reaction mixture and it was extracted with ethyl acetate. The organic layer was washed with water and saturated brine successively, dried over sodium sulfate and concentrated in vacuo. The resulted residue was purified with a silica gel column chromatography (eluting solvent: ethyl acetate to ethyl acetate/methanol=85/15) to give tert-butyl(dl)-2-[(cyclopropyl{[4-methoxy-1-(3-methoxypropyl)-1H-pyrrolo[2,3-b]pyridin-3-yl]methyl}amino)carbonyl]morpholin-4-carboxylate (27 mg) as a yellow oil.
APCI-MS m/z: 503[M+H]$^+$.

Reference Example 190

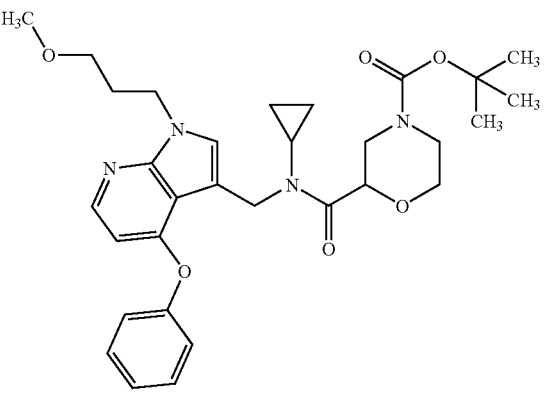 [SMILES: COCCCn1cc(CN(C(=O)C2CN(C(=O)OC(C)(C)C)CCO2)C2CC2)c2c(Oc3ccccc3)ccnc21]

A mixture of tert-butyl(dl)-2-[(cyclopropyl{[4-iodo-1-(3-methoxypropyl)-1H-pyrrolo[2,3-b]pyridin-3-yl]methyl}amino)carbonyl]morpholin-4-carboxylate (300 mg), palladium acetate (5.6 mg), 2-di-tert-butylphosphino-2',4',6'-triisopropyl-1,1'-biphenyl tBu X-phos) (21 mg), phenol (88 μL) and potassium phosphate (318 mg) in toluene (3 ml) was stirred under argon atmosphere at 100° C. for 19 hours. After being left stand to cool, 0.5N aqueous solution of sodium hydroxide was poured into the reaction mixture and the mixture was extracted with ethyl acetate. The organic layer was washed with water and saturated brine successively, dried over sodium sulfate and concentrated in vacuo. The resulted residue was purified with a silica gel column chromatography (eluting solvent: ethyl acetate to ethyl acetate/methanol=9/1) to give tert-butyl (dl)-2-[(cyclopropyl{[1-(3-methoxypropyl)-4-phenoxy-1H-pyrrolo[2,3-b]pyridin-3-yl]methyl}amino)carbonyl]morpholin-4-carboxylate (160 mg, purity 80%) as a yellow oil.
APCI-MS m/z: 565[M+H]$^+$.

Reference Example 191

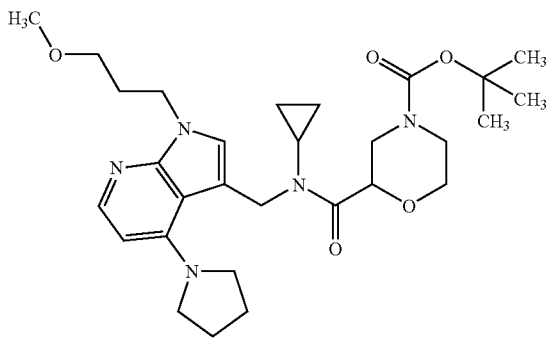 [SMILES: COCCCn1cc(CN(C(=O)C2CN(C(=O)OC(C)(C)C)CCO2)C2CC2)c2c(N3CCCC3)ccnc21]

A mixture of tert-butyl(dl)-2-{[{[4-bromo-1-(3-methoxypropyl)-1H-pyrrolo[2,3-b]pyridin-3-yl]methyl}(cyclopropyl)amino]carbonyl}morpholin-4-carboxylate (73 mg), palladium acetate (0.6 mg), 2-dicyclohexylphosphino-2',4',6'-triisopropyl-1,1'-biphenyl (tBu X-phos) (3.1 mg), pyrrolidine (22 μL) and cesium carbonate (108 mg) in toluene (1.5 ml)/tert-butanol (0.3 ml) was stirred under argon atmosphere at 110° C. for 20 hours. After being left stand to cool, water was poured into the reaction mixture and the mixture was extracted with ethyl acetate. The organic layer was washed with water and saturated brine successively, dried over sodium sulfate and concentrated in vacuo. The resulted residue was purified with a silica gel column chromatography (eluting solvent: ethyl acetate to ethyl acetate/methanol=95/5) to give tert-butyl(dl)-2-[(cyclopropyl{[1-(3-methoxypropyl)-4-pyrrolidin-1-yl-1H-pyrrolo[2,3-b]pyridin-3-yl]methyl}amino)carbonyl]morpholin-4-carboxylate (8.5 mg) as a colorless oil.

APCI-MS m/z: 542[M+H]$^+$.

Reference Example 192

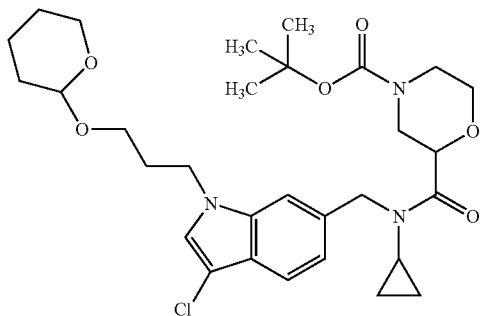 [SMILES: CC(C)(C)OC(=O)N1CCOC(C(=O)N(Cc2ccc3c(Cl)cn(CCCOC4CCCCO4)c3c2)C2CC2)C1]

60% Oily sodium hydride (15.5 mg) was added to a solution of tert-butyl(dl)-2-{[[(3-chloro-1H-indol-6-yl)methyl](cyclopropyl)amino]carbonyl}morpholin-4-carboxylate (140 mg) in N,N-dimethylformamide (5.0 ml) under ice-cooling and the mixture was stirred at room temperature for 15 minutes. 2-(3-Bromopropoxy)tetrahydro-2H-pyrane (65.7 μL) was added to the reaction mixture under ice-cooling and the mixture was stirred at room temperature for 5 hours. Water was poured into the reaction mixture under ice-cooling and the mixture was extracted with chloroform. The organic layer was washed with water and saturated brine successively, dried over sodium sulfate and concentrated in vacuo. The resulted residue was purified with a silica gel column chromatography (eluting solvent: chloroform/methanol=15/1) to give tert-butyl(dl)-2-{[({3-chloro-1-[2-(tetrahydro-2H-pyran-2-yloxy)ethyl]-1H-indol-6-yl}methyl)(cyclopropyl) amino]carbonyl}morpholin-4-carboxylate (181 mg) as a pale yellow oil.

APCI-MS m/z: 576/578[M+H]$^+$.

Reference Example 193

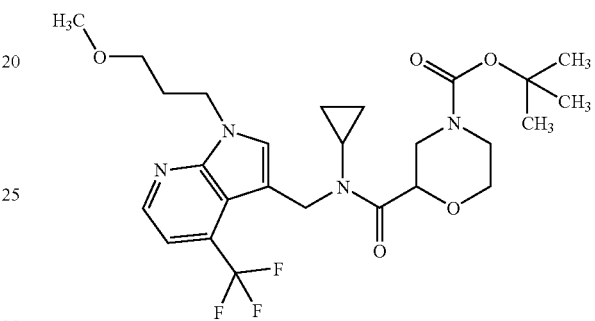

(1) A mixture of tert-butyl(dl)-2-{[{[4-bromo-1-(3-methoxypropyl)-1H-pyrrolo[2,3-b]pyridin-3-yl]methyl}(cyclopropyl)amino]carbonyl}morpholin-4-carboxylate (551 mg), cuprous iodide (10 mg), N,N'-dimethylethylenediamine (11 μL) and sodium iodide (300 mg) in 1,4-dioxane (2 ml) was stirred under argon atmosphere at 110° C. for 20 hours. After being left stand to cool, the reaction mixture was diluted with ethyl acetate, insoluble materials were filtered through Celite and the filtrate was washed with 30% aqueous ammonia solution, water and saturated brine successively, dried over sodium sulfate and concentrated in vacuo. The resulted residue was purified with a silica gel column chromatography (eluting solvent: hexane/ethyl acetate=50/50 to ethyl acetate) to give tert-butyl(dl)-2-[(cyclopropyl{[4-iodo-1-(3-methoxypropyl)-1H-pyrrolo[2,3-b]pyridin-3-yl]methyl}amino)carbonyl]morpholin-4-carboxylate (530 mg) as a yellow oil.

APCI-MS m/z: 599[M+H]$^+$.

(2) A mixture of the compound obtained in (1) described above (18 mg), cuprous iodide (4 mg) and methyl fluorosulfonyldifluoroacetate (51 μL) in 1-methyl-2-pyrrolidone (2 ml) was stirred under argon atmosphere at 120° C. for an hour. After being left stand to cool, 0.5N aqueous solution of sodium bicarbonate was poured into the reaction mixture and it was extracted with ethyl acetate. The organic layer was washed with water and saturated brine successively, dried over sodium sulfate and concentrated in vacuo. The resulted residue was purified with a silica gel column chromatography (eluting solvent: hexane/ethyl acetate=50/50 to ethyl acetate) to give tert-butyl(dl)-2-[(cyclopropyl{[1-(3-methoxypropyl)-4-(trifluoromethyl)-1H-pyrrolo[2,3-b]pyridin-3-yl]methyl}amino)carbonyl] morpholin-4-carboxylate (17 mg) as a yellow oil.

Reference Example 194

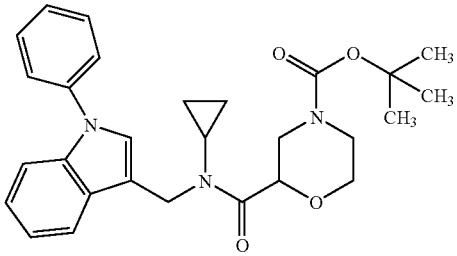 [SMILES: CC(C)(C)OC(=O)N1CCOC(C(=O)N(Cc2cn(-c3ccccc3)c3ccccc23)C2CC2)C1]

A mixture of tert-butyl(dl)-2-{[cyclopropyl(1H-indol-3-ylmethyl)amino]carbonyl}morpholin-4-carboxylate (240 mg), potassium phosphate (223 mg), cuprous iodide (0.95 mg), iodobenzene (56 μl) and cyclohexanediamine (6 μl) in 1,4-dioxane (1.0 ml) was stirred under argon atmosphere at room temperature for 2 hours, and at 50° C. for 16 hours. After being cooled to room temperature, ethyl acetate and NH-silica gel were added to the reaction mixture. Insoluble materials were filtered and the filtrate was concentrated in vacuo. The resulted residue was purified with a silica gel column chromatography (eluting solvent: n-hexane/ethyl acetate=2/1 to 1/3) to give tert-butyl(dl)-2-({cyclopropyl[(1-phenyl-1H-indol-3-yl)methyl]amino}carbonyl)morpholin-4-carboxylate (234 mg) as a yellow oil.

APCI-MS m/z: 476[M+H]$^+$.

Reference Example 195

(1)

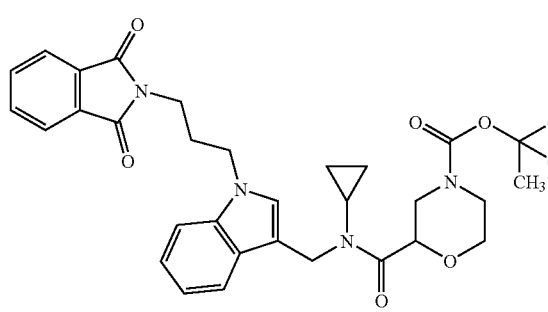

60% Oily sodium hydride (13.2 mg) was added to a solution of tert-butyl(dl)-2-{[cyclopropyl(1H-indol-3-ylmethyl)amino]carbonyl}morpholin-4-carboxylate (200 mg) in N,N-dimethylformamide (1.0 ml) under ice-cooling and the mixture was stirred at room temperature for 10 minutes. N-(3-Bromopropyl)phthalimide (161 mg) was added to the reaction mixture and stirred at room temperature for 3 hours. Water was added to the reaction mixture and it was extracted with ethyl acetate. The organic layer was washed with water and saturated brine successively, dried over magnesium sulfate and concentrated in vacuo. The resulted residue was purified with a silica gel column chromatography (eluting solvent: chloroform to chloroform/methanol=20/1) to give tert-butyl(dl)-2-{[cyclopropyl({1-[3-(1,3-dioxo-1,3-dihydro-2H-isoindol-2-yl)propyl]-1H-indol-3-yl}methyl)amino]carbonyl}morpholin-4-carboxylate (274 mg) as a yellow oil.

APCI-MS m/z: 587[M+H]$^+$.

(2)

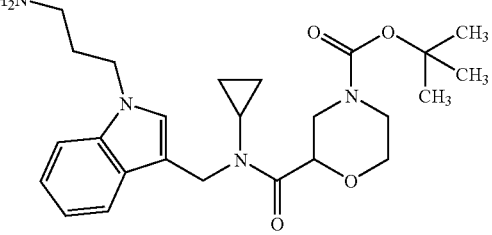

Hyarazine hyarate (55.4 μL) was added to a solution of the compound obtained in (1) described above (164 mg) in ethanol (3.0 ml) and the mixture was stirred at room temperature for 20 hours and at 40° C. for 24 hours. Water was added to to the raction mixture, extracted with chloroform and concentrated in vacuo. The resulted residue was purified with a silica gel column chromatography (eluting solvent: chloroform to chloroform/methanol=20/1) to give tert-butyl(dl)-2-{[{[1-(3-aminopropyl)-1H-indol-3-yl]methyl}(cyclopropyl)amino]carbonyl}morpholin-4-carboxylate (83.8 mg) as a yellow oil.

APCI-MS m/z: 457[M+H]$^+$.

(3)

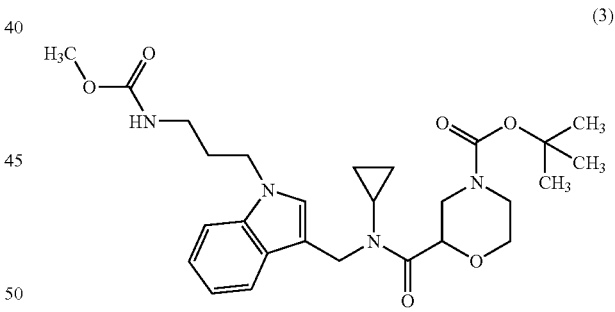

Triethylamine (33.4 μL) and methyl chloroformate (17.1 μL) were added to a solution of the compound obtained in (2) described above (92 mg) in chloroform (1.0 ml) under ice-cooling and the mixture was stirred at room temperature for 3 hours. Water was added to the reaction mixture and it was extracted with chloroform. The organic layer was dried over magnesium sulfate and concentrated in vacuo. The resulted residue was purified with a silica gel column chromatography (eluting solvent: n-hexane/ethyl acetate=7/3 to ethyl acetate) to give tert-butyl(dl)-2-({cyclopropyl[(1-{3-[methoxycarbonyl)amino]propyl}-1H-indol-3-yl)methyl]amino}carbonyl)morpholin-4-carboxylate (64.3 mg) as a yellow oil.

APCI-MS m/z: 515[M+H]$^+$.

Reference Example 196

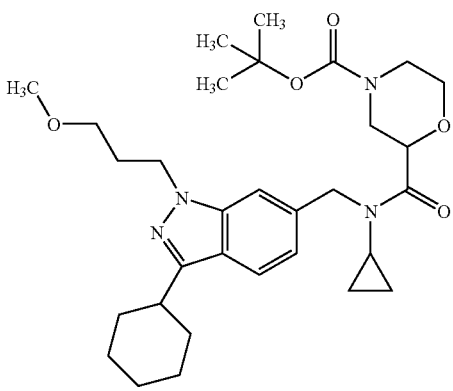 [SMILES: COCCCn1nc(C2CCCCC2)c2ccc(CN(C(=O)C3CN(C(=O)OC(C)(C)C)CCO3)C3CC3)cc21]

10% Palladium-Carbon (30 mg) was added to a solution of tert-butyl(2R)-2-{[{[3-cyclohex-1-ene-1-yl-1-(3-methoxypropyl)-1H-indazol-6-yl]methyl}(cyclopropyl)amino]carbonyl}morpholin-4-carboxylate (300 mg) in ethanol (5 ml) and the mixture was stirred under normal pressure of hydrogen atmosphere at room temperature for 5 hours. Insolble materials were filtered through Celite and the filtrate was concentrated in vacuo. The resulted residue was purified with a silica gel column chromatography (eluting solvent: n-hexane to n-hexane/ethyl acetate=1/2) to give tert-butyl (2R)-2-{[{[3-cyclohexyl-1-(3-methoxypropyl)-1H-indazol-6-yl]methyl}(cyclopropyl)amino]carbonyl}morpholin-4-carboxylate (105 mg) as a colorless oil.

APCI-MS m/z: 555[M+H]$^+$.

Reference Example 197

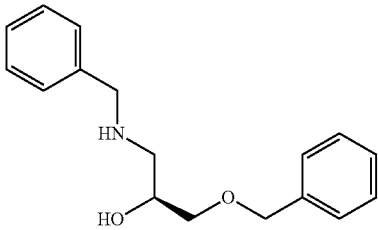 [SMILES: O[C@@H](CNCc1ccccc1)COCc1ccccc1]

Benzyl-(S)-(+)-glycidyl ether (3.28 g) was dissolved in benzylamine (15 ml) and the mixture was stirred at room temperature for 4 days. Excess benzylamine was removed by evaporation in vacuo and the resulted residue was purified with a silica gel column chromatography (eluting solvent: chloroform to chloroform/methanol=9/1) to give (2S)-1-(benzylamino)-3-(benzyloxy)propane-2-ol (4.50 g) as a colorless oil.

APCI-MS m/z: 272[M+H]$^+$.

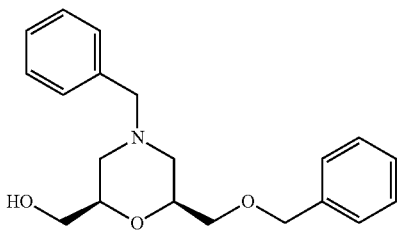 [SMILES: OC[C@H]1CN(Cc2ccccc2)C[C@@H](COCc2ccccc2)O1]

Lithium perchlorate (1.11 g) was added to a solution of the compound obtained in (1) described above (2.17 g) and (S)-(+)-epichlorohydrin (0.83 ml) in toluene (40 ml) at room temperature. After stirring under argon atmosphere at 50° C. for 4 hours, a solution of sodium methylate (1.08 g) in methanol (10 ml) was added dropwise to the reaction mixture. After stirring under argon atmosphere at 50° C. for 4 hours, a saturated aqueous solution of ammonium chloride (20 ml) and water (10 ml) were added to the reaction mixture successively and extracted with ethyl acetate. The ethyl acetate layer was washed with saturated brine, dried over sodium sulfate and concentrated in vacuo. The resulted residue was purified with a silica gel column chromatography (eluting solvent: n-hexane/ethyl acetate=1/1 to ethyl acetate) to give {(2R,6S)-4-benzyl-6-[(benzyloxy)methyl]morpholin-2-yl}methanol (1.89 g) as an colorless oil.

APCI-MS m/z: 328[M+H]$^+$.

(3)

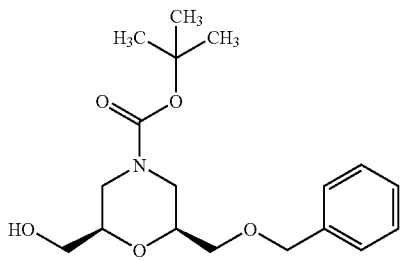 [SMILES: CC(C)(C)OC(=O)N1C[C@@H](COCc2ccccc2)O[C@@H](CO)C1]

A mixture of the compound obtained in (2) described above (1.64 g) and 20% palladium hydroxide-carbon (dry) (0.33 g) in methanol (25 ml) was stirred under normal pressure of hydrogen atmosphere at room temperature for 2.5 hours. 4N Hydrogen chloride in ethyl acetate (2 ml) was added to the reaction mixture under argon atmosphere, insoluble materials were filtered through Celite and the residue was washed with ethyl acetate. The filtrate and the washing was combined and concentrated in vacuo. The resulted residue (1.39 g) was diluted with tetrahydrofuran (8 ml) and water (10 ml), sodium bicarbonate (1.68 g) and a solution of di-tert-butyl dicarbonate (0.92 g) in tetrahydrofuran (2 ml) were added successively and the mixture was stirred at room temperature for 4 hours. The reaction mixture was diluted with water and extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=7/3 to 3/7) to give tert-butyl(2S,6R)-2-[(benzyloxy)methyl]-6-(hydroxymethyl)morpholin-4-carboxylate (0.99 g) as a yellow oil.

APCI-MS m/z: 338[M+H]$^+$.

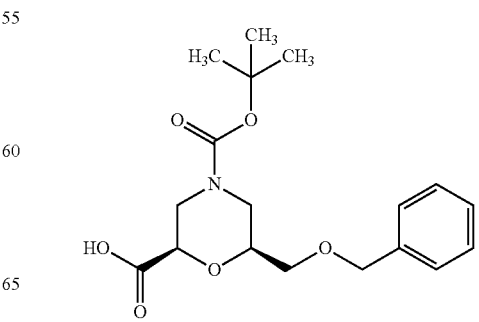

Iodobenzene diacetate (1.61 g) and 2,2,6,6-tetramethyl-1-piperidinyloxy radical (TEMPO) (0.08 g) were added successively to a solution of the compound obtained in (3) described above (0.84 g) in dichloromethane (10 ml)/water (5 ml) and the mixture was stirred under ice-cooling for 5 hours. The reaction mixture was concentrated in vacuo, the resulted residue was diluted with toluene and concentrated to dryness by azeotropical distillation under reduced pressure. The resulted residue was triturated in diisopropyl ether and hexane to give (2R,6S)-6-[(benzyloxy)methyl]-4-(tert-butoxycarbonyl)morpholin-2-carboxylic acid (0.43 g) as a colorless powder.

ESI-MS m/z: 350[M−H]⁻.

(5)

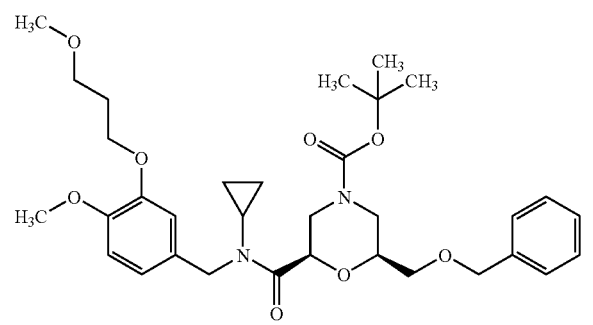 [SMILES: COCCCOc1cc(CN(C(=O)[C@H]2CN(C(=O)OC(C)(C)C)C[C@@H](COCc3ccccc3)O2)C2CC2)ccc1OC]

Diisopropylethylamine (105 μl), 1-hydroxybenzotriazole (81 mg) and 1-ethyl-3-(3-dimethylaminopropyl)carbodiimide hydrochloride (144 mg) were added successively to a solution of N-[4-methoxy-3-(3-methoxypropoxy)benzyl]cyclopropylamine hydrochloride (182 mg) and the carboxylic acid obtained in (4) described above (176 mg) in N,N-dimethylformamide (10 ml) under ice-cooling and the mixture was stirred at room temperature for 16 hours. An aqueous solution of sodium bicarbonate was added to the reaction solution under ice-cooling and the mixture was extracted with ethyl acetate. The organic layer was washed with water, dried over sodium sulfate and concentrated in vacuo.

The resulted residue was purified with a silica gel column chromatography (eluting solvent: n-hexane/ethyl acetate=3/1 to 1/3) to give tert-butyl(2S,6R)-2-[(benzyloxy)methyl]-6-({cyclopropyl[4-methoxy-3-(3-methoxypropoxy)benzyl]amino}carbonyl)morpholin-4-carboxylate (290 mg) as a yellow oil.

APCI-MS m/z: 599[M+H]⁺.

The corresponding starting compounds were treated in the same manner as Reference Example 197 to give the following compounds.

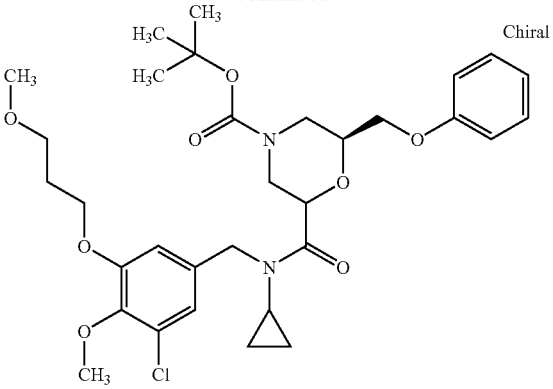

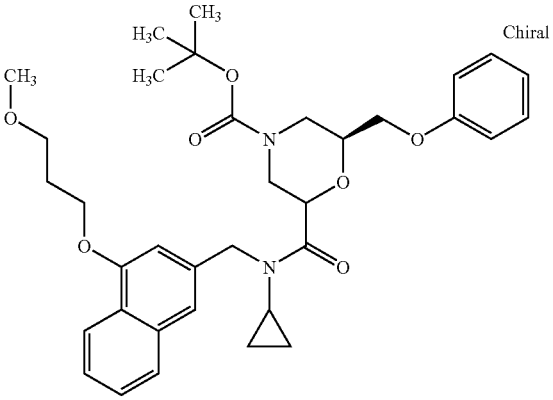

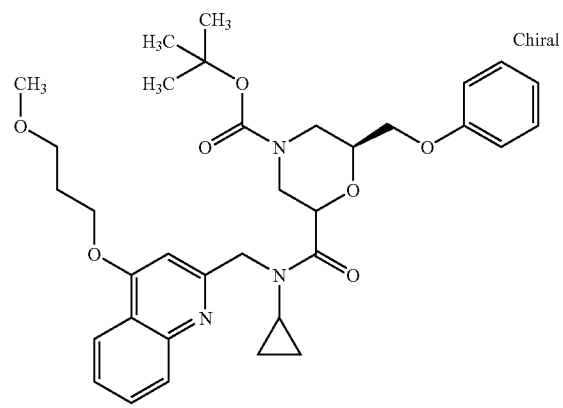

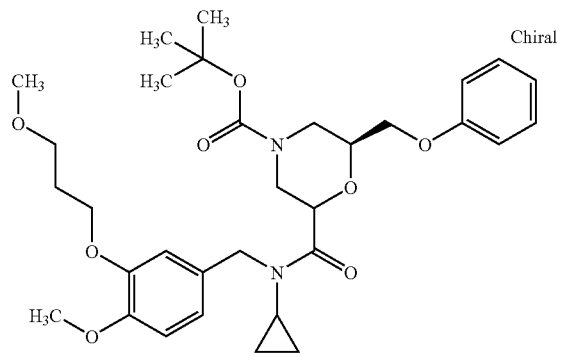

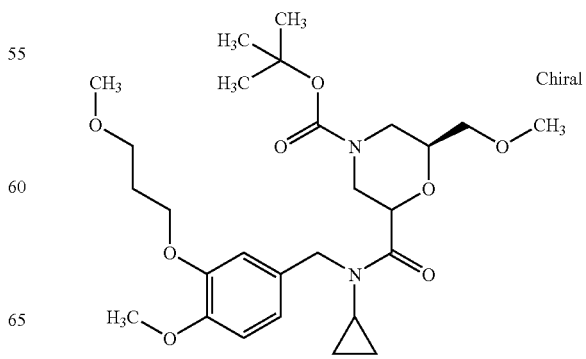

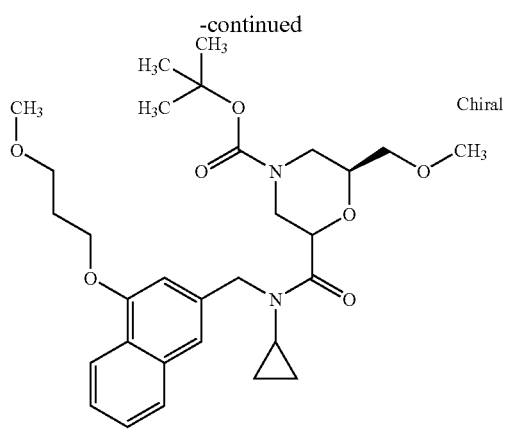

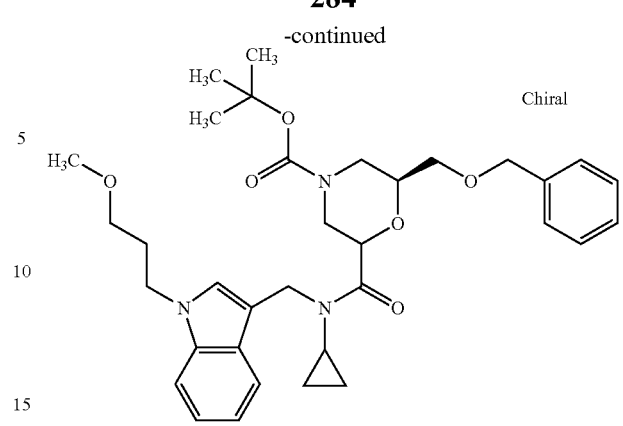

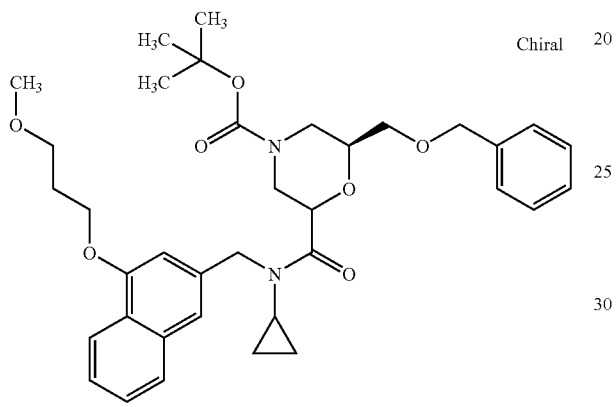

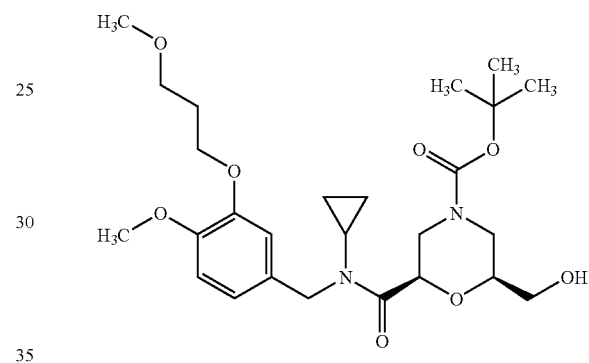

Reference Example 198

20% Palladium hydroxide-carbon (dry) (22 mg) was added to a solution of tert-butyl(2S,6R)-2-[(benzyloxy)methyl]-6-({cyclopropyl[4-methoxy-3-(3-methoxypropoxy)benzyl]amino}carbonyl)morpholin-4-carboxylate (220 mg) in methanol and the mixture was stirred under normal pressure of hydrogen atmosphere at room temperature for 6 hours. After filtration of insoluble materials through Celite, the filtrate was concentrated to give tert-butyl(2R,6S)-2-({cyclopropyl[4-methoxy-3-(3-methoxypropoxy)benzyl]amino}carbonyl)-6-(hydroxymethyl)morpholin-4-carboxylate (200 mg) as a pale yellow oil.

APCI-MS m/z: 509[M+H]$^+$.

The corresponding starting compounds were treated in the same manner as Reference Example 198 to give the following compound.

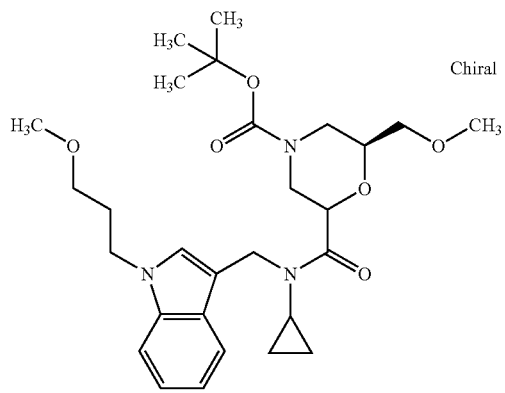

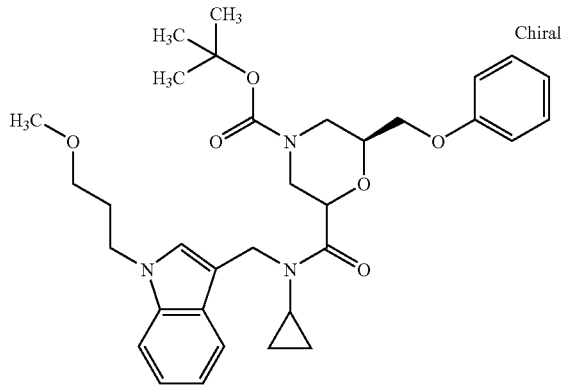

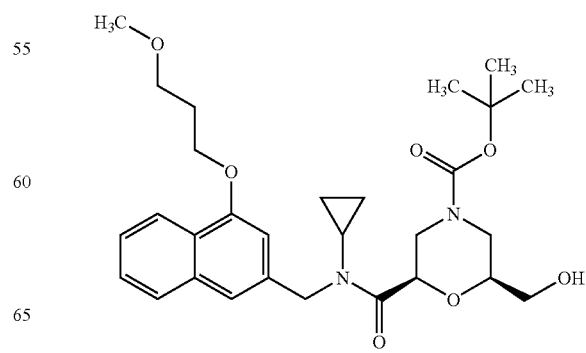

Reference Example 199

(1)

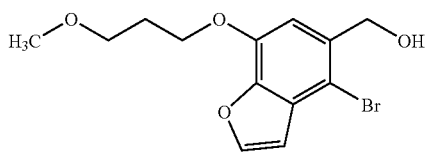 [SMILES: COCCCOc1cc(CO)c(Br)c2ccoc12]

N-Bromosuccinimide (978 mg) was added to a solution of [7-(3-methoxypropoxy)-1-benzofuran-5-yl]methanol (1.18 g) in dichloromethane (30 ml) under ice-cooling and the mixture was stirred at the same temperature for 10 minutes. The reaction mixture was concentrated in vacuo and the resulted residue was purified with a silica gel column chromatography (eluting solvent: n-hexane/ethyl acetate=1/1) to give [4-bromo-7-(3-methoxypropoxy)-1-benzofuran-5-yl] methanol (1.46 g) as a colorless oil.

APCI-MS m/z: 297/299[M+H]$^+$.

(2) The compound obtained in (1) described above was treated with any of Reference Example to give the next compound.

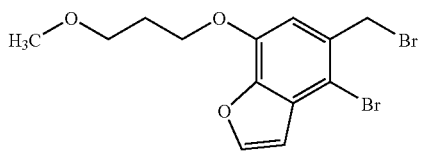 [SMILES: COCCCOc1cc(CBr)c(Br)c2ccoc12]

APCI-MS m/z: 394/396/398[M+NH$_4$]$^+$.

(3) The compound obtained in (2) described above was treated with any of Reference Example to give the next compound.

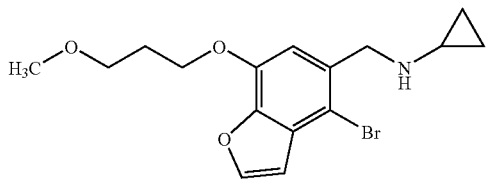 [SMILES: COCCCOc1cc(CNC2CC2)c(Br)c2ccoc12]

Reference Example 200

(1)

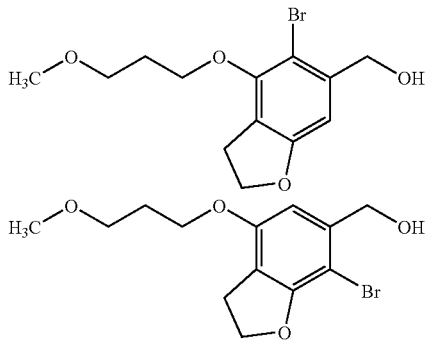

N-Bromosuccinimide (1.04 g) was added to a solution of [4-(3-methoxypropoxy)-2,3-dihydro-1-benzofuran-6-yl] methanol (1.27 g) in dichloromethane (25 ml) under ice-cooling and the mixture was stirred at the same temperature for 30 minutes. The reaction mixture was concentrated in vacuo and the resulted residue was purified with a silica gel column chromatography (eluting solvent: n-hexane/ethyl acetate=3/2) to give [5-bromo-4-(3-methoxypropoxy)-2,3-dihydro-1-benzofuran-6-yl]methanol (860 mg) and [7-bromo-4-(3-methoxypropoxy)-2,3-dihydro-1-benzofuran-6-yl]methanol (540 mg) as a colorless oil.

APCI-MS m/z: 299/301[M+H—H$_2$O]$^+$

APCI-MS m/z: 299/301[M+H—H$_2$O]$^+$.

(2) [5-Bromo-4-(3-methoxypropoxy)-2,3-dihydro-1-benzofuran-6-yl]methanol and [7-bromo-4-(3-methoxypropoxy)-2,3-dihydro-1-benzofuran-6-yl]methanol were treated in the same manner as any of Reference Example to give the next compounds.

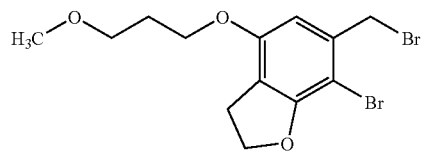 [SMILES: COCCCOc1cc(CBr)c(Br)c2c1CCO2]

APCI-MS m/z: 379/381/383[M+H]$^+$

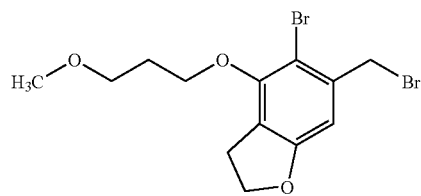 [SMILES: COCCCOc1c(Br)c(CBr)cc2c1CCO2]

APCI-MS m/z: 379/381/383[M+H]$^+$ (3) The compound obtained in (2) described above was treated with any of Reference Example to give the next compound.

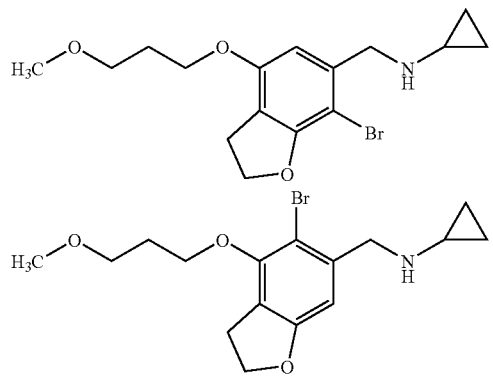

and

Reference Example 201

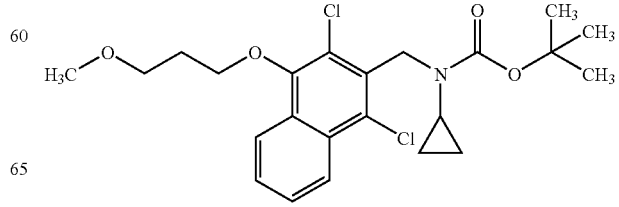

N-Chlorosuccinimide (68.5 mg) was added to a solution of tert-butyl cyclopropyl{[4-(3-methoxypropoxy)-2-naphthyl]methyl}carbamate (180 mg) in acetonitrile (5.0 ml) under ice-cooling and the mixture was stirred at 60° C. for 14 hours, and 75° C. for 6 hours after addition of N-Chlorosuccinimide (137 mg). The reaction mixture was concentrated in vacuo and the resulted residue was purified with a silica gel column chromatography (eluting solvent: n-hexane/ethyl acetate=4/1) to give tert-butyl cyclopropyl{[1,3-dichloro-4-(3-methoxypropoxy)-2-naphthyl]methyl}carbamate (136 mg) as a pale yellow oil.

APCI-MS m/z: 354/356[M+H−Boc]$^+$.

Reference Example 202

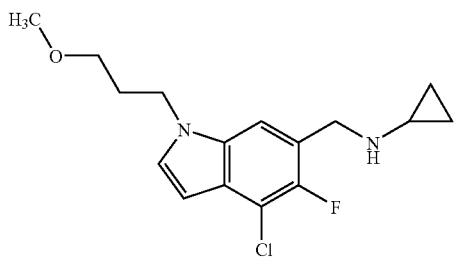 [SMILES: COCCCn1ccc2c(Cl)c(F)c(CNC3CC3)cc21]

(1) 60% Sodium hydride (394 mg) was added to a solution of 4-chloro-5-fluoro-1H indol-6-carboxylic acid (700 mg) in N,N-dimethylformamide (15 ml) under ice-cooling and the mixture was stirred at room temperature for 0.5 hour. 1-Bromo-3-methoxypropane (1.51 g) and potassium iodide (1.63 g) were added to the mixture under ice-cooling and the reaction mixture was stirred at 50-60° C. for 22 hours. Water and ethyl acetate were added to the reaction mixture under ice-cooling and the organic layer was separated. The organic layer was washed with water and saturated brine successively, dried over sodium sulfate and concentrated in vacuo. The resulted residue was purified with a silica gel column chromatography (eluting solvent: n-hexane to n-hexane/ethyl acetate=1/1) to give 3-methoxypropyl 4-chloro-5-fluoro-1-(3-methoxypropyl)-1H-indol-6-carboxylate (882 mg) as a pale yellow oil.

APCI-MS m/z: 358/360 [M+H]$^+$.

(2) A solution of the compound obtained in (1) described above (500 mg) in tetrahydrofuran (6 ml) was added dropwise to a suspension of lithium aluminium hydride (53.1 mg) in tetrahydrofuran (6 ml) under ice-cooling and the mixture was stirred under the same cooling for 45 minutes. Water (55 μL), 2N aqueous solution of sodium hydroxide (138 μL) and water (220 μL) were added slowly to the reaction mixture under the same cooling successively and the mixture was stirred at room temperature for 6 hours. The mixture was diluted with ethyl acetate and dried over sodium sulfate. Insoluble materials were filtered through Celite and the filtrate was concentrated in vacuo to give [4-chloro-5-fluoro-1-(3-methoxypropyl)-1H-indol-6-yl]methanol (410 mg) as a pale brown oil.

APCI-MS m/z: 272/274 [M+H]$^+$.

(3) Manganese dioxide (1.50 g) was added to a solution of the compound obtained in (2) described above (400 mg) in dichloromethane (8 ml) and the mixture was stirred at room temperature for 36 hours. Insoluble materials were filtered through Celite and the filtrate was concentrated in vacuo to give 4-chloro-5-fluoro-1-(3-methoxypropyl)-1H-indol-6-carbaldehyde (352 mg) as a yellow oil.

APCI-MS m/z: 270/272 [M+H]$^+$.

(4) Cyclopropylamine (0.18 ml) was added to a solution of the compound obtained in (3) described above (345 mg) in ethanol (8 ml) and the mixture was stirred at room temperature for 2 hours. The mixture was concentrated in vacuo, the residue was dissolved in toluene and the mixture was again concentrated to dryness in vacuo. The residue was dissolved in ethanol (8 ml), sodium borohydride (145 mg) was added therein under ice-cooling and the mixture was stirred at room temperature for 5 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: ethyl acetate to ethyl acetate/methanol=10/1) to give N-{[4-chloro-5-fluoro-1-(3-methoxypropyl)-1H-indol-6-yl]methyl}cyclopropylamine (143 mg) as a colorless oil.

APCI-MS m/z: 311/313 [M+H]$^+$.

Reference Example 203

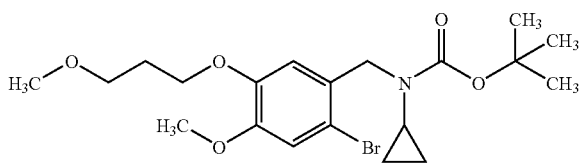

N-Bromosuccinimide (978 mg) was added to a solution of tert-butyl cyclopropyl[4-methoxy-3-(3-methoxypropoxy)benzyl]carbamate (6.36 g) in acetonitrile (50 ml) under ice cooling and the mixture was stirred at room temperature for 3 hours. The reaction mixture was concentrated in vacuo and the resulted residue was purified with a silica gel column chromatography (eluting solvent: n-hexane/ethyl acetate/=4/1 to 3/1) to give tert-butyl [2-bromo-4-methoxy-5-(3-methoxypropoxy)benzyl]cyclopropylcarbamate (3.35 g) as a colorless oil.

APCI-MS m/z: 444/446[M+H]$^+$.

Reference Example 204

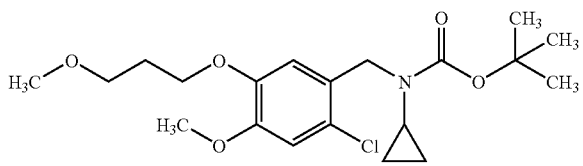 [SMILES: COCCCOc1cc(CN(C(=O)OC(C)(C)C)C2CC2)c(Cl)cc1OC]

N-Chlorosuccinimide (110 mg) was added to a solution of tert-butyl cyclopropyl[4-methoxy-3-(3-methoxypropoxy)benzyl]carbamate (300 mg) in acetonitrile (5.0 ml) under ice cooling and the mixture was stirred at room temperature for an hour and at 75° C. for 5 hours. The reaction mixture was concentrated in vacuo and the resulted residue was purified with a NH-silica gel column chromatography (eluting solvent: n-hexane/ethyl acetate=10/1 to 3/1) to give tert-butyl [2-chloro-4-methoxy-5-(3-methoxypropoxy)benzyl]cyclopropylcarbamate (265 mg) as a colorless oil.

APCI-MS m/z: 400/402[M+H]$^+$.

Reference Example 205

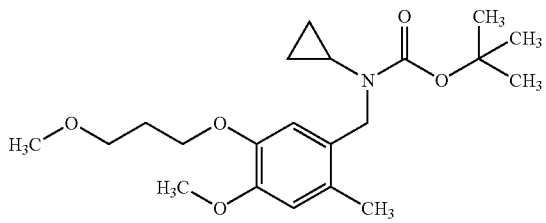 [SMILES: COCCCOc1cc(CN(C(=O)OC(C)(C)C)C2CC2)c(C)cc1OC]

A mixture of tert-butyl [2-bromo-4-methoxy-5-(3-methoxypropoxy)benzyl]cyclopropylcarbamate (200 mg), trimethylboroxin (94 μL), tris(dibenzylideneacetone)dipalladium (8.2 mg), 2-dicyclohexylphosphino-2',4',6'-triisopropyl-1,1'-biphenyl (X-phos) (21.5 mg) and potassium phosphate (191 mg) in dioxane (7.0 ml) was stirred under argon atmosphere at 100° C. for 23 hours. After being stand to cool, water was added to the reaction mixture and the mixture was extracted with ethyl acetate. The organic layer was washed with saturated brine, dried over magnesium sulfate and concentrated in vacuo. The resulted residue was purified with a NH-silica gel column chromatography (eluting solvent: n-hexane/ethyl acetate=10/1 to 3/1) to give tert-butyl cyclopropyl[4-methoxy-5-(3-methoxypropoxy)-2-methylbenzyl]carbamate (103 mg) as a pale yellow oil.
APCI-MS m/z: 380[M+H]$^+$.

Reference Example 206

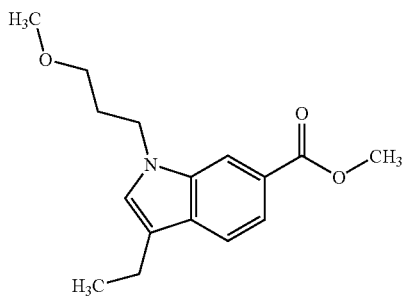

(1) Aluminium chloride (1.29 g) was added portionwise to a solution of acetyl chloride (380 mg) in dichloromethane (20 ml) under ice-cooling and the mixture was stirred at the same cooling for 5 minutes. A solution of methyl 1-(3-methoxypropyl)-1H-indol-6-carboxylate (1.00 g) in dichloromethane (10 ml) was added dropwise therein under ice-cooling and the mixture was stirred at the same cooling for 2 hours. The reaction mixture was poured into ice and the mixture was extracted with ethyl acetate. The organic layer was washed with a saturated aqueous solution of sodium bicarbonate and saturated brine successively, dried over magnesium sulfate and concentrated in vacuo. The resulted residue was triturated in n-hexane to give methyl 3-acetyl-1-(3-methoxypropyl)-1H-indol-6-carboxylate (1.06 g) as a colorless powder.
APCI-MS m/z: 290
(2) A 1M solution of borane tetrahydrofuran in tetrahydrofuran (2.07 ml) was added dropwise to a solution of the compound obtained in (1) described above (200 mg) in tetrahydrofuran (3 ml) under argon atmosphere under ice-cooling and the mixture was stirred at room temperature for an hour. Water was poured into the reaction mixture under ice-cooling, the mixture was stirred at room temperature for a while and extracted with ethyl acetate. The organic layer was washed with saturated brine, dried over sodium sulfate and concentrated in vacuo to give methyl 3-ethyl-1-(3-methoxypropyl)-1H-indol-6-carboxylate (192 mg) as a colorless oil.
APCI-MS m/z: 277[M+11].
(3) The compound obtained in (2) described above was treated in the same manner as any of Reference Example to give a compound of the formula below.

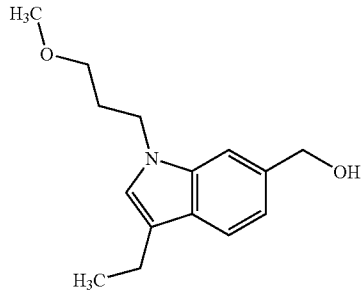 [SMILES: CCc1cn(CCCOC)c2cc(CO)ccc12]

APCI-MS m/z: 248[M+H]$^+$.
(4) The compound obtained in (3) described above was treated in the same manner as any of Reference Example to give a compound of the formula below.

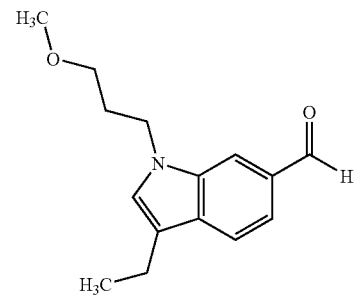 [SMILES: CCc1cn(CCCOC)c2cc(C=O)ccc12]

APCI-MS m/z: 248[M+H]$^+$.
(5) The compound obtained in (4) described above was treated in the same manner as any of Reference Example to give a compound of the formula below.

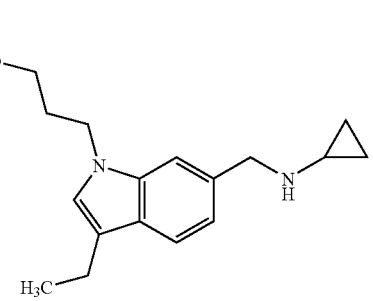

Reference Example 207

(1)

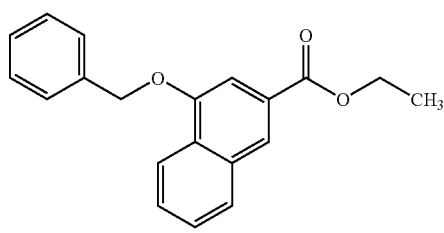 [SMILES: CCOC(=O)c1cc(OCc2ccccc2)c2ccccc2c1]

Potassium carbonate (19.2 g) and benzyl bromide (19.0 g) were added to a solution of ethyl 4-hydroxy-2-naphthoate (20 g) in acetonitrile (200 ml) and the mixture was heated to reflux for 2 hours. After being cooled, the reaction solution was diluted with ethyl acetate and insoluble materials were filtered through Celite. The filtrate was concentrated in vacuo and the resulted residue was purified with a silica gel column chromatography (eluting solvent: n-hexane/ethyl acetate=100/1) to give ethyl 4-(benzyloxy)-2-naphthoate (27.8 g) as a pale yellow oil.

APCI-MS m/z: 307[M+H]$^+$.

(2) The compound obtained in (1) described above was treated in the same manner as any of Reference Example to give a compound of the formula below.

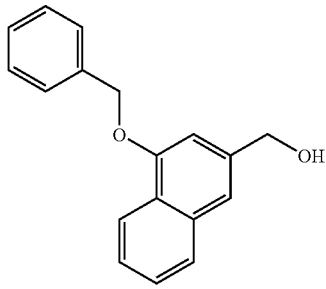 [SMILES: OCc1cc(OCc2ccccc2)c2ccccc2c1]

APCI-MS m/z: 265[M+H]$^+$.

(3) The compound obtained in (2) described above was treated in the same manner as any of Reference Example to give a compound of the formula below.

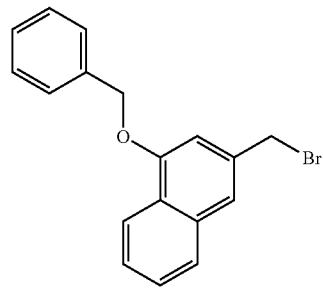 [SMILES: BrCc1cc(OCc2ccccc2)c2ccccc2c1]

(4) The compound obtained in (3) described above was treated in the same manner as any of Reference Example to give a compound of the formula below.

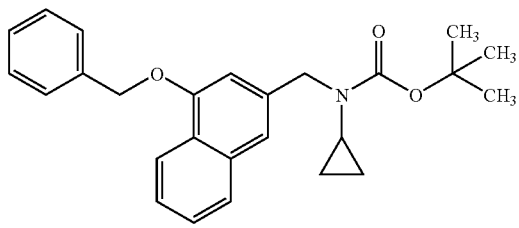 [SMILES: CC(C)(C)OC(=O)N(Cc1cc(OCc2ccccc2)c2ccccc2c1)C1CC1]

Reference Example 208

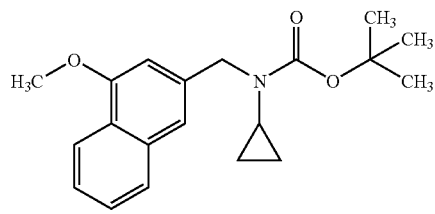 [SMILES: COc1cc(CN(C(=O)OC(C)(C)C)C2CC2)cc2ccccc12]

(1) 10% Palladium-carbon (100 mg) was added to a solution of tert-butyl {[4-(benzyloxy)-2-naphthyl]methyl} cyclopropylcarbamate (1.0 g) in methanol (10 ml) and the mixture was stirred under normal pressure of hydrogen atmosphere at room temperature for 5 hours. Insoluble materials were filtered through Celite, the filtrate was concentrated in vacuio and the resulted residue was purified with a silica gel column chromatography (elutings solvent: n-hexane/ethyl acetate=9/1 to 4/1) to give tert-butyl cyclopropyl[(4-hydroxy-2-naphthyl)methyl]carbamate (680 mg) as a yellow oil.

ESI-MS m/z: 312[M−H]$^-$.

(2) Potassium carbonate (331 mg) and methyl iodide (119 μL) were added to a solution of the compound obtained in (1) described above (500 mg) in N,N-dimethylformamide (5 ml) under ice-cooling and the mixture was stirred at room temperature for 2 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane/ethyl acetate=9/1) to give tert-butyl cyclopropyl[(4-methoxy-2-naphthyl)methyl]carbamate (480 mg) as a pale yellow oil.

APCI-MS m/z: 328[M+H]$^+$.

Reference Example 209

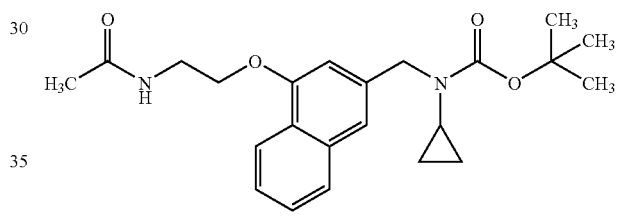

(1) Potassium carbonate (2.65 g) and 1,2-dibromoethane (16.5 ml) were added to a solution of tert-butyl cyclopropyl [(4-hydroxy-2-naphthyl)methyl]carbamate (4.0 g) in acetonitrile (40 ml) and the mixture was heated to reflux for 20 hours. After being cooled, the reaction solution was diluted with ethyl acetate and insoluble materials were filtered through Celite. The filtrate was concentrated in vacuo and the resulted residue was purified with a silica gel column chromatography (eluting solvent: n-hexane/ethyl acetate=100/1 to 10/1) to give tert-butyl {[4-(2-bromoethoxy)-2-naphthyl]methyl}cyclopropylcarbamate (3.8 g) as a colorless oil.

APCI-MS m/z: 420/422[M+H]$^+$.

(2) Sodium azide (2.90 g) was added portionwise to a solution of the compound obtained in (1) described above (3.75 g) in N,N-dimethylformamide (50 ml) under ice-cooling and the mixture was stirred at 60° C. for 2 hours. Water was added to the reaction mixture under ice-cooling and the mixture was extracted with ethyl acetate. The organic layer was washed with water and saturated brine successively, dried over sodium sulfate and concentrated in vacuo. The resulted residue was purified with a silica gel column chromatography (eluting solvent: n-hexane/ethyl acetate=9/1) to give tert-butyl {[4-(2-azidoethoxy)-2-naphthyl] methyl}cyclopropylcarbamate (3.3 g) as a pale yellow oil.

APCI-MS m/z: 383[M+H]$^+$.

(3) 10% Palladium-carbon (330 mg) was added to a solution of the compound obtained in (2) described above (3.30 g) in methanol (33 ml) and the mixture was stirred under normal pressure of hydrogen atmosphere at room temperature for 3 hours. Insoluble materials were filtered through Celite, the filtrate was concentrated in vacuo and the resulted residue was purified with a silica gel column chromatography (eluting solvent: chloroform to chloroform/methanol=9/1) to give tert-butyl {[4-(2-aminoethoxy)-2-naphthyl]methyl}cyclopropylcarbamate (1.20 g) as a pale yellow oil.
APCI-MS m/z: 357[M+H]$^+$.

(4) Pyridine (272 μL) and acetyl chloride (120 μL) were added to a solution of the compound obtained in (3) described above (400 mg) in chloroform (4.0 ml) under ice-cooling and the mixture was stirred at room temperature for an hour. Water was added to the reaction mixture and it was extracted with chloroform. The organic layer was washed with a saturated aqueous solution of sodium bicarbonate and saturated brine successively, dried over sodium sulfate and concentrated in vacuo. The resulted residue was purified with NH-silica gel column chromatography (eluting solvent: n-hexane/ethyl acetate=2/1) to give tert-butyl({4-[2-(acetylamino)ethoxy]-2-naphthyl}methyl)cyclopropylcarbamate (382 mg) as a colorless oil.
APCI-MS m/z: 399 [M+H]$^+$.

Reference Example 210

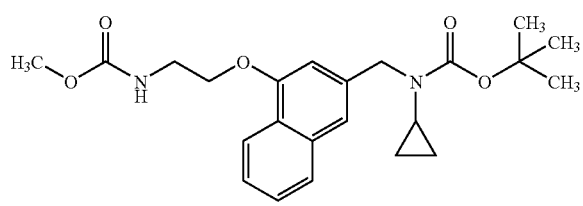 [SMILES: COC(=O)NCCOc1cc(CN(C(=O)OC(C)(C)C)C2CC2)cc2ccccc12]

Pyridine (272 μL) and methyl chloroformate (130 μL) were added to a solution of tert-butyl {[4-(2-aminoethoxy)-2-naphthyl]methyl}cyclopropylcarbamate (400 mg) in chloroform (4.0 ml) under ice-cooling and the mixture was stirred at room temperature for an hour. Water was added to the reaction mixture and it was extracted with chloroform. The organic layer was washed with a saturated aqueous solution of sodium bicarbonate and saturated brine successively, dried over sodium sulfate and concentrated in vacuo. The resulted residue was purified with NH-silica gel column chromatography (eluting solvent: n-hexane to n-hexane/ethyl acetate=2/1) to give methyl {2-[(3-{[(tert-butoxycarbonyl)(cyclopropyl)amino]methyl}-1-naphthyl)oxy]ethyl}carbamate (418 mg) as a colorless oil.
APCI-MS m/z: 415[M+H]$^+$.

Reference Example 211

(1)

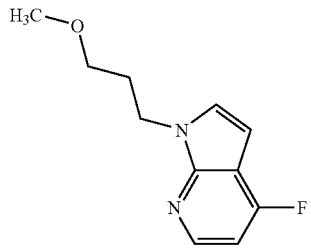

60% Oily sodium hydride (135 mg) was added to a solution of 4-fluoro-1H-pyrrolo[2,3-b]pyridine (384 mg) in N,N-dimethylformamide (6 ml) and the mixture was stirred at room temperature for 1.5 hours. 1-Bromo-3-methoxypropane (518 mg) and potassium iodide (468 mg) were added to the mixture and the reaction mixture was stirred at 50° C. for 1.5 hours. Ice water was added to the reaction mixture slowly and the mixture was extracted with ethyl acetate. The organic layer was washed with water and saturated brine successively, dried over magnesium sulfate and concentrated in vacuo. The resulted residue was purified with a silica gel column chromatography (eluting solvent: n-hexane/ethyl acetate=90/10 to 70/30) to give 4-fluoro-1-(3-methoxypropyl)-1H-pyrrolo[2,3-b]pyridine (520 mg) as a colorless oil.
APCI-MS m/z: 209[M+H]$^+$.

(2)

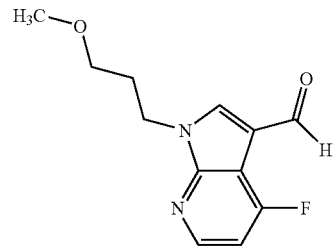 [SMILES: COCCCn1cc(C=O)c2c(F)ccnc21]

A solution of 4-fluoro-1-(3-methoxypropyl)-1H-pyrrolo[2,3-b]pyridine (520 mg) and hexamethylenetetramine (700 mg) in trifluoroacetic acid (9.1 ml) was stirred at 80° C. for 4 hours. After evaporation of the solvent in vacuo, the resulted residue was dissolve in ethyl acetate. The solution was poured slowly into a saturated aqueous solution of sodium bicarbonate and extracted with ethyl acetate. The organic layer was washed with saturated brine, dried over magnesium sulfate and concentrated in vacuo. The resulted residue was purified with a silica gel column chromatography (eluting solvent: n-hexane/ethyl acetate=60/40 to 20/80) to give 4-fluoro-1-(3-methoxypropyl)-1H-pyrrolo[2,3-b]pyridin-3-carbaldehyde (260 mg) as a colorless oil.
APCI-MS m/z: 237[M+H]$^+$.

(3) The compound obtained in (2) described above was treated in the same manner as any of Reference Example to give a compound of the formula below.

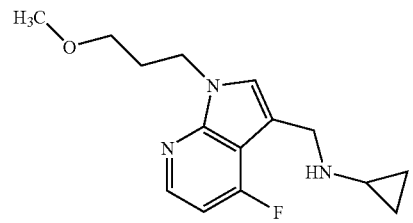 [SMILES: COCCCn1cc(CNC2CC2)c2c(F)ccnc21]

Reference Example 212

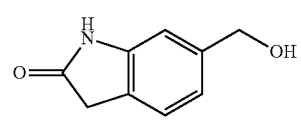 [SMILES: O=C1Cc2ccc(CO)cc2N1]

Lithium borohydride (228 mg) was added to a suspension of methyl 2-oxoindolin-6-carboxylate (1.0 g) in tetrahydrofuran (10 ml) under ice-cooling and the mixture was stirred at 50° C. for 3 hours. Lithium borohydride (456 mg) was further added and the reaction mixture was stirred at 50° C. for 15 hours. Water was added to the reaction mixture under ice-cooling and the mixture was acidified with addition of conc. hydrochloric acid. It was extracted with ethyl acetate, dried over sodium sulfate and concentrated in vacuo. The resulted residue was triturated in methanol to give 6-(hydroxymethyl)-1,3-dihydro-2H-indol-2-one (172 mg) as a colorless powder. The mother liquid was purified with a silica gel column chromatography (eluting solvent: n-hexane/ethyl acetate=10/1 to ethyl acetate) to give the same (242 mg) as a colorless powder.

APCI-MS m/z: 164[M+H]⁺.

(2)

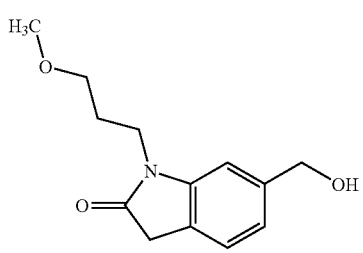 [SMILES: COCCCN1C(=O)Cc2ccc(CO)cc21]

A mixture of 6-(hydroxymethyl)-1,3-dihydro-2H-indol-2-one (150 mg), 1-bromo-3-methoxypropane (211 mg), potassium carbonate (254 mg) and potassium iodide (229 mg) in acetonitrile (6 ml) was refluxed for 15 hours. Further, 1-bromo-3-methoxypropane (70.3 mg) and potassium carbonate (127 mg) were added and the mixture was refluxed for 3 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: chloroform to chloroform/methanol=10/1) to give 6-(hydroxymethyl)-1-(3-methoxypropyl)-1,3-dihydro-2H-indol-2-one (174 mg) as a brown oil.

APCI-MS m/z: 236[M+H]⁺.

(3) The compound obtained in (2) described above was treated in the same manner as any of Reference Example to give a compound of the formula below.

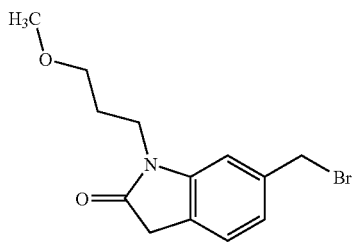 [SMILES: COCCCN1C(=O)Cc2ccc(CBr)cc21]

APCI-MS m/z: 298/300[M+H]⁺.

(4) The compound obtained in (3) described above was treated in the same manner as any of Reference Example to give a compound of the formula below.

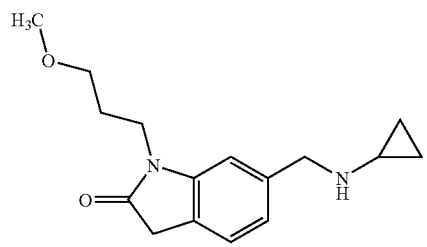 [SMILES: COCCCN1C(=O)Cc2ccc(CNC3CC3)cc21]

Reference Example 213

(1) Concentrated hydrochloric acid (30 ml) and ammonium tetrafluoroborate (21.4 g) were added to a suspension of methyl 3-amino-4-methyl-benzoate (25.3 g) in water (170 ml) and the mixture was cooled to −3° C. A solution of sodium nitrite (10.56 g) in water (24 ml) was added dropwise therein under the same cooling during 30 minutes. The mixture was stirred at −3° C. for an hour and the precipitated crystalline was filtered, washed with water (210 ml), methanol (100 ml) and diethyl ether (100 ml) successively and dried under reduced pressure.

Potassium acetate (6.5 g) and 18-crown-6 (1.01 g) were added to a suspension of the crystalline obtained above in chloroform (340 ml) and the mixture was stirred at room temperature for 70 minutes. Water (800 ml) was added to the reaction mixture and it was extracted with chloroform. The organic layer was washed with water and saturated brine successively, dried over sodium sulfate and concentrated in vacuo. The resulted residue was triturated in n-hexane to give methyl 1H-indazol-6-carboxylate (20.2 g) as a yellow powder.

APCI-MS m/z: 177[M+H]⁺.

(2) The compound obtained in (1) described above (10.0 g) was dissolve in acetic acid (284 ml) and bromine (4.36 ml) was added under light shielding condition at room temperature. After stirring at room temperature for 19 hours, water was added to the reaction mixture, sodium thiosulfate was added and the mixture was stirred at room temperature for 20 minutes. The mixture was extracted with ethyl acetate, the organic layer was washed with water and saturated brine successively, dried over sodium sulfate and concentrated in vacuo. The resulted residue was triturated in isopropyl ether to give methyl 3-bromo-1H-indazol-6-carboxylate (14.4 g) as a pale yellow powder.

APCI-MS m/z: 255/257[M+H]⁺.

(3) 60% Oily sodium hydride (940 mg) was added to a solution of the compound obtained in (2) described above (5.0 g) in N,N-dimethylformamide (34 ml) under ice-cooling and the mixture was stirred at room temperature for 15 minutes. A solution of 1-bromo-3-methoxypropane (3.6 g)

in N,N-dimethylformamide (12 ml) and potassium iodide (650 mg) were added to the mixture under ice-cooling and the mixture was stirred at room temperature for 3 hours. Ethyl acetate and an aqueous solution of ammonium chloride were added to the reaction mixture and the organic layer was separated. The organic layer was washed with water and saturated brine successively, dried over sodium sulfate and concentrated in vacuo. The resulted residue was purified with a silica gel column chromatography (eluting solvent: n-hexane/ethyl acetate=10/1 to 6/1) to give methyl 3-bromo-1-(3-methoxypropyl)-1H-indazol-6-carboxylate (4.3 g) as a yellow powder.

APCI-MS m/z: 327/329[M+H]$^+$.

(4) The compound obtained in (3) described above was treated in the same manner as any of Reference Example to give a compound of the formula below.

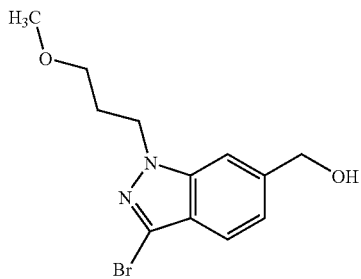 [SMILES: COCCCn1nc(Br)c2ccc(CO)cc21]

APCI-MS m/z: 299/301[M+H]$^+$.

(5) The compound obtained in (4) described above was treated in the same manner as any of Reference Example to give a compound of the formula below.

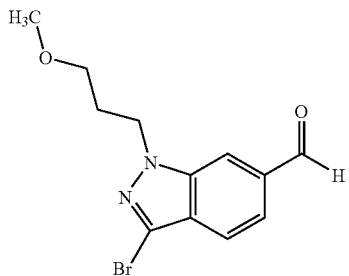 [SMILES: COCCCn1nc(Br)c2ccc(C=O)cc21]

APCI-MS m/z: 297/299[M+H]$^+$.

(6) The compound obtained in (5) described above was treated in the same manner as any of Reference Example to give a compound of the formula below.

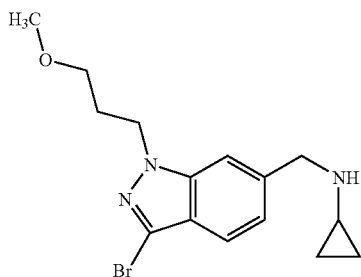 [SMILES: COCCCn1nc(Br)c2ccc(CNC3CC3)cc21]

Reference Example 214

(1)

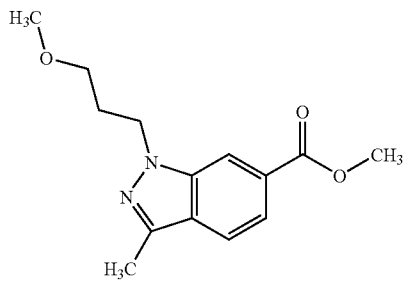

Trimethylboroxin (513 μL), potassium carbonate (1.27 g) and bis(diphenylphosphino)ferrocene dichloropalladium (224 mg) were added to a solution of methyl 3-bromo-1-(3-methoxypropyl)-1H-indazol-6-carboxylate (1.0 g) in 1,4-dioxane (15 ml) under argon atmosphere and the mixture was stirred at 110° C. for 6 hours. Water was added to the reaction mixture under ice-cooling and the mixture was extracted with ethyl acetate. The organic layer was washed with saturated brine, dried over magnesium sulfate and concentrated in vacuo. The resulted residue was purified with a silica gel column chromatography (eluting solvent: n-hexane/ethyl acetate=4/1 to 3/2) to give methyl 1-(3-methoxypropyl)-3-methyl-1H-indazol-6-carboxylate (705 mg) as a yellow powder.

APCI-MS m/z: 263[M+H]$^+$.

(2) The compound obtained in (1) described above was treated in the same manner as any of Reference Example to give a compound of the formula below.

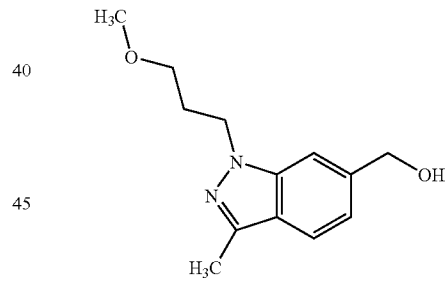

APCI-MS m/z: 235[M+H]$^+$.

(3) The compound obtained in (2) described above was treated in the same manner as any of Reference Example to give a compound of the formula below.

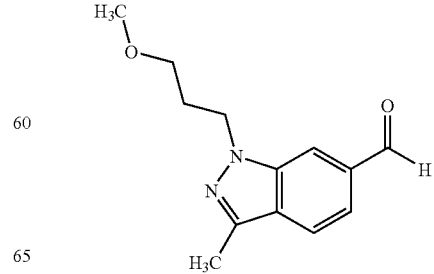

APCI-MS m/z: 233[M+H]$^+$.

(4) The compound obtained in (3) described above was treated in the same manner as any of Reference Example to give a compound of the formula below.

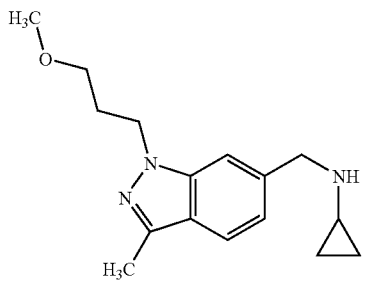 [SMILES: COCCCn1nc(C)c2ccc(CNC3CC3)cc21]

Reference Example 215

(1)

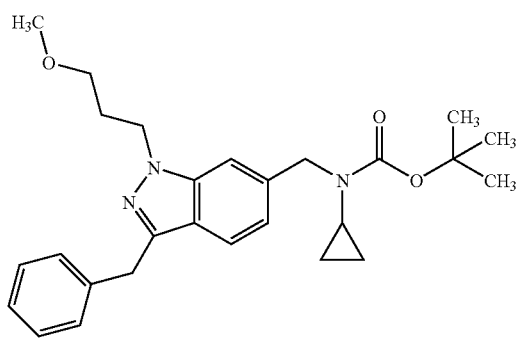 [SMILES: COCCCn1nc(Cc2ccccc2)c2ccc(CN(C(=O)OC(C)(C)C)C3CC3)cc21]

A 0.5M solution of B-benzyl-9-borabicyclo[3,3,1]nonane (BBN) in tetrahydrofuran (1.8 ml) was added to a mixture of tert-butyl {[3-bromo-1-(3-methoxypropyl)-1H-indazol-6-yl]methyl}cyclopropylcarbamate (200 mg), potassium phosphate (290 mg), palladium acetate(II) (4 mg) and 2-dicyclohexylphosphino-2',6'-dimethoxybiphenyl (S-phos) (15 mg) in N,N-dimethylformamide (5 ml) under argon atmosphere and the mixture was stirred at 60° C. for 18 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl {[3-benzyl-1-((3-methoxypropyl)-1H-indazol-6-yl]methyl}cyclopropylcarbamate (198 mg) as a colorless oil.

APCI-MS m/z: 450[M+H]$^+$.

(2)

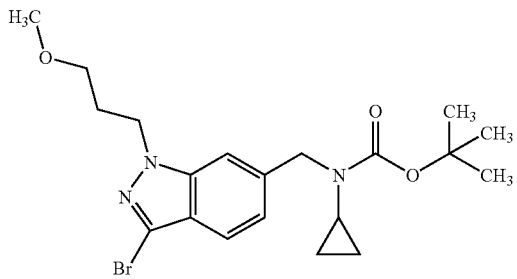 [SMILES: COCCCn1nc(Br)c2ccc(CN(C(=O)OC(C)(C)C)C3CC3)cc21]

A solution of di-tert-butyl dicarbonate in dichloromethane (8 ml) was added to a solution of N-{[3-bromo-1-(3-methoxypropyl)-1H-indazol-6-yl]methyl}cyclopropanamine (1.21 g) in dichloromethane (28 ml) under ice-cooling and the mixture was stirred at room temperature for 19 hours. The reaction mixture was concentrated in vacuo and the resulted residue was purified with a silica gel column chromatography (eluting solvent: n-hexane/ethyl acetate=5/1 to 4/1) to give tert-butyl {[3-bromo-1-(3-methoxypropyl)-1H-indazol-6-yl]methyl}cyclopropylcarbamate (1.53 g) as a colorless powder.

APCI-MS m/z: 438/440[M+H]$^+$.

Reference Example 216

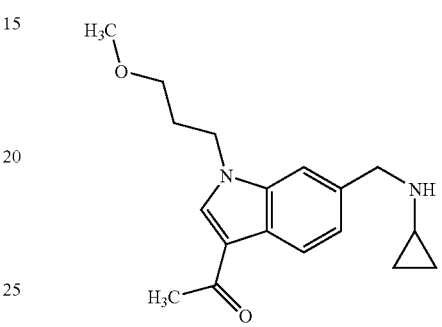

(1) A solution of methyl 3-acetyl-1-(3-methoxypropyl)-1H-indazol-6-carboxylate (285 mg) in tetrahydrofuran (3 ml) was added dropwise to a suspension of lithium aluminium hydride (75 mg) in tetrahydrofuran (3 ml) under ice-cooling and the mixture was stirred under the same cooling for an hour. Water (80 μL), a 2N aqueous solution of sodium hydroxide (200 μL) and water (320 μL) were added slowly to the mixture under the same cooling successively and the mixture was stirred at room temperature for 3 hours. Insoluble materials were filtered through Celite and the filtrate was concentrated in vacuo. The residue was dissolved in ethyl acetate, dried over sodium sulfate and concentrated in vacuo to give 1-[6-(hydroxymethyl)-1-(3-methoxypropyl)-1H-indol-3-yl]ethanol (279 mg) as a colorless oil.

APCI-MS m/z: 246 [M+H]$^+$.

(2) 85% Activated manganese dioxide (1.07 g) was added to a solution of the compound obtained in (1) above (275 mg) in toluene (8 ml) and the mixture was stirred at 60° C. for 5 hours. Insoluble materials were filtered through Celite and the filtrate was concentrated in vacuo to give 3-acetyl-1-(3-methoxypropyl)-1H-indol-6-carbaldehyde (202 mg) as a colorless powder.

APCI-MS m/z: 260 [M+H]$^+$.

(3) Sodium triacetoxy hydride (237 mg) was added to a solution of the compound obtained in (2) above (145 mg) and cyclopropylamine (96 mg) in dichloromethane (6 ml) under ice cooling and the mixture was stirred at room temperature for 2 hours. Cyclopropylamine (64 mg) and sodium triacetoxy hydride (355 mg) were added and the mixture was stirred at room temperature for 14 hours. A solution of sodium bicarbonate was added to the reaction mixture and it was extracted with chloroform. The organic layer was washed with saturated brine, dried over sodium sulfate and concentrated in vacuo. The resulted residue was purified with a silica gel column chromatography (eluting solvent: n-hexane to n-hexane/ethyl acetate=1/1) to give 1-[6-[(cyclopropylamino)methyl)]-1-(3-methoxypropyl)-1H-indol-3-yl]ethanone (145 mg) as a colorless oil.

Reference Example 217

(1)

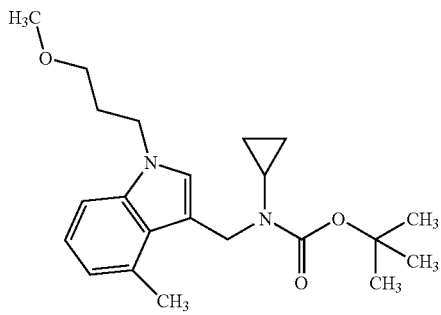 [SMILES: COCCCn1cc(CN(C(=O)OC(C)(C)C)C2CC2)c2c(C)cccc21]

Potassium carbonate (207 mg), trimethylboroxin (175 μL) and bis(diphenylphosphino)ferrocene dichloropalladium (II) (40.8 mg) were added to a solution of tert-butyl {[4-bromo-1-(3-methoxypropyl)-1H-indol-3-yl]methyl}cyclopropylcarbamate (218 mg) in 1,4-dioxane (14.5 ml) and the mixture was stirred at 110° C. under argon atmosphere for 4 hours. After being cooled to room temperature, the reaction mixture was diluted with water and the mixture was extracted with ethyl acetate. The organic layer was washed with a saturated aqueous solution of sodium bicarbonate and saturated brine successively, dried over magnesium sulfate and concentrated in vacuo. The resulted residue was purified with a silica gel column chromatography (eluting solvent: n-hexane to n-hexane/ethyl acetate=1/1 to 1/4) to give tert-butyl cyclopropyl{[1-(3-methoxypropyl)-4-methyl-1H-indol-3-yl]methyl}carbamate (180 mg) as a yellow oil.

APCI-MS m/z: 373[M+H]$^+$.

(2)

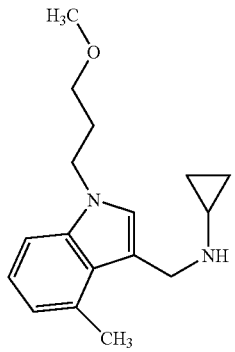 [SMILES: COCCCn1cc(CNC2CC2)c2c(C)cccc21]

Trimethylsilyl trifluoromethanesulfonate (213 μL) was added to a solution of tert-butyl cyclopropyl{[1-(3-methoxypropyl)-4-methyl-1H-indol-3-yl]methyl}carbamate (175 mg and 2,6-lutidine (192 μL) in dichloromethane (7 ml) under ice-cooling and the mixture was stirred at room temperature for 15 minutes. A saturated aqueous solution of sodium bicarbonate and methanol were added successively to the reaction mixture and the mixture was further stirred at the same temperature for 30 minutes. The reaction mixture was extracted with chloroform and the organic layer was washed with saturated brine, dried over magnesium sulfate and concentrated in vacuo. The resulted residue was purified with a silica gel column chromatography (eluting solvent: ethyl acetate/methanol=95/5 to 70/30) to give N-{[1-(3-methoxypropyl)-4-methyl-1H-indol-3-yl]methyl}cyclopropanamine (106 mg) as a colorless oil.

APCI-MS m/z: 216[M+H]$^+$.

Reference Example 218

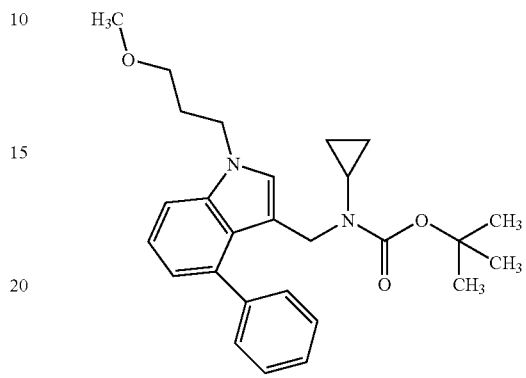

Potassium carbonate (276 mg), phenylboronic acid (122 mg), dichlorobis(triphenylphosphine)palladium(II) (175 mg) and water (132 μl) were added to a solution of tert-butyl {[4-bromo-1-(3-methoxypropyl)-1H-indazol-3-yl]methyl}cyclopropylcarbamate (218 mg) in 1,2-dichloroethane (11 ml) and the mixture was stirred under argon atmosphere at 80° C. for 1.5 hours. The reaction mixture was cooled to room temperature, poured into ice water and extracted with ethyl acetate. The organic layer was washed with a saturated aqueous solution of sodium bicarbonate and saturated brine, dried over magnesium sulfate and concentrated in vacuo. The resulted residue was purified with a silica gel column chromatography (eluting solvent: n-hexane/ethyl acetate=20/1 to 7/3) to give tert-butyl cyclopropyl{[1-(3-methoxypropyl)-4-phenyl-1H-indol-3-yl]methyl}carbamate (212 mg) as a yellow oil.

APCI-MS m/z: 435[M+H]$^+$.

Reference Example 219

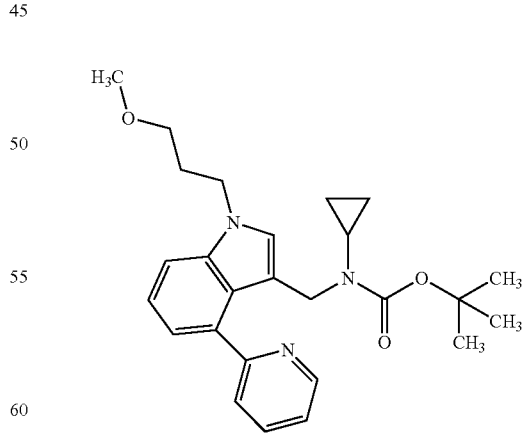

2-Tri-n-butyl-stannylpyridine (480 μl) and dichlorobis(triphenylphosphine)palladium(II) (210 mg) were added to a solution of tert-butyl {[4-bromo-1-(3-methoxypropyl)-1H-indol-3-yl]methyl}cyclopropylcarbamate (219 mg) in toluene (7 ml) and the mixture was stirred under argon atmosphere at 110° C. for 23 hours. The reaction mixture was poured into a saturated solution of potassium fluoride, stirred at room temperature for an hour and extracted with ethyl acetate. The organic layer was washed with water and saturated brine successively, dried over magnesium sulfate and concentrated in vacuo. The resulted residue was purified with a silica gel column chromatography (eluting solvent: n-hexane/ethyl acetate=4/1 to 1/4) to give tert-butyl cyclopropyl {[1-(3-methoxypropyl)-4-pyridin-2-yl-1H-indol-3-yl]methyl}carbamate (76 mg) as a yellow oil.

APCI-MS m/z: 436[M+H]$^+$.

Reference Example 220

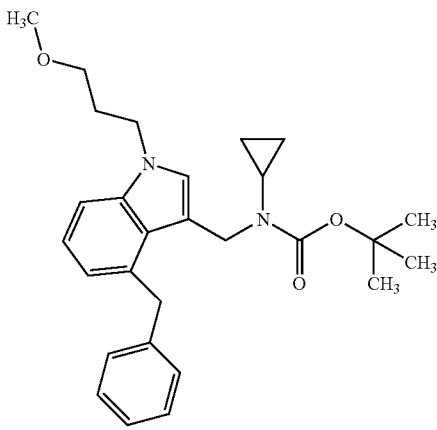 [SMILES: COCCCn1cc(CN(C(=O)OC(C)(C)C)C2CC2)c2c(Cc3ccccc3)cccc21]

Potassium phosphate (498 mg), a 0.5M tetrahydrofuran-solution of B-benzyl-9-BBN (2.8 ml), palladium acetate(II) (21 mg), 2-dicyclohexylphosphino-2',6'-dimethoxybiphenyl (38.5 mg) were added to a solution of tert-butyl {[4-bromo-1-(3-methoxypropyl)-1H-indol-3-yl]methyl}cyclopropylcarbamate (205 mg) in N,N-dimethylformamide (4.3 ml) and the mixture was stirred under argon atmosphere at 80° C. for 3 hours. The reaction mixture was diluted with ethyl acetate, washed with water and saturated brine successively, dried over magnesium sulfate and concentrated in vacuo. The resulted residue was purified with a silica gel column chromatography (eluting solvent: n-hexane/ethyl acetate=20/1 to 2/1) to give tert-butyl {[4-benzyl-1-(3-methoxypropyl)-1H-indol-3-yl]methyl}cyclopropylcarbamate (210 mg) as a yellow oil.

APCI-MS m/z: 449[M+H]$^+$.

Reference Example 221

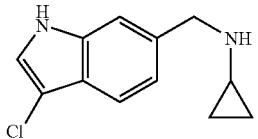 [SMILES: Clc1c[nH]c2cc(CNC3CC3)ccc12]

(1) N-Chlorosuccinimide (3.96 g) was added to a solution of methyl 1H-indol-6-carboxylate (4.94 g) in dichloromethane (100 ml) and the mixture was stirred at room temperature for 1.5 hours. The reaction mixture was concentrated and the resulted residue was purified with a silica gel column chromatography (eluting solvent: n-hexane/ethyl acetate=2/1) to give methyl 3-chloro-1H-indol-6-carboxylate (3.67 g) as a colorless powder.

ESI-MS m/z: 208/210[M–H]$^-$.

(2) A solution of the compound obtained in (1) described above (3.52 g) in tetrahydrofuran (30 ml) was slowly added dropwise to a solution of lithium aluminium hydride (2.23 g) in tetrahydrofuran (60 ml) under ice-cooling and the mixture was stirred at room temperature for 45 minutes. Water (4 ml), a 2N solution of NaOH (8.0 ml) and water (8 ml) were added to the reaction mixture successively under ice-cooling and the mixture was stirred at room temperature for an hour. Insoluble materials were filtered through Celite and the filtrate was dried over magnesium sulfate and concentrated to give (3-chloro-1H-indol-6-yl)methanol (3.72 g) as a colorless powder.

ESI-MS m/z: 182/184[M–H]$^-$.

(3) Manganese dioxide (10.5 g) was added to a solution of the compound obtained in (2) described above (3.72 g) in dichloromethane (100 ml) under ice-cooling and the mixture was stirred at room temperature for 12 hours. Insoluble materials were filtered through Celite and the filtrate was concentrated to give 3-chloro-1H-indol-6-carbaldehyde (2.73 g) as a yellow powder.

ESI-MS m/z: 178/180[M–H]$^-$.

(4) Sodium triacetoxyborohydride (12 g) and acetic acid (2.6 ml) were added to a solution of the compound obtained in (3) described above (4.08 g) and cyclopropylamine (3.2 ml) in dichloroethane (100 ml) and the mixture was stirred at room temperature for 15 hours. After concentration in vauo, a saturated aqueous solution of sodium bicarbonate was added to the reaction solution and the mixture was extracted with ethyl acetate. The organic layer was washed with saturated brine, dried over magnesium sulfate and concentrated in vacuo. The resulted residue was triturated in n-hexane-dichloromethane (1:1) to give N-[3-chloro-1H-indol-6-yl)methyl]cyclopropanamine (3.93 g) as an orange powder. The filtrate was concentrated and the residue was purified with a silica gel column chromatography (eluting solvent: chloroform/methanol=10/1) to give N-[3-chloro-1H-indol-6-yl)methyl]cyclopropanamine (478.3 mg) as a pale orange powder.

APCI-MS m/z: 221/223[M+H]$^+$.

Reference Example 222

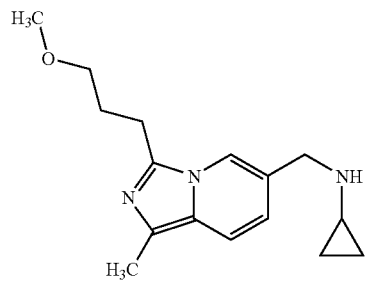 [SMILES: COCCCc1nc(C)c2ccc(CNC3CC3)cn12]

Cycopropylamine (1 ml) was added to a solution of 3-(3-methoxypropyl)-1-methylimidazo[1,5-a]pyridin-6-carbaldehyde (23 mg) in ethanol (5 ml) and the mixture was stirred at 50° C. for 15 hours. The mixture was concentrated in vacuo, the residue was dissolved in ethanol (3 ml) and sodium borohydride (38 mg) was added therein under ice-cooling. After stirring at room temperature for 6 hours, the mixture was diluted with a saturated aqueous solution of sodium bicarbonate and extracted with ethyl acetate. The organic layer was washed with water and saturated brine successively, dried over sodium sulfate and concentrated in vacuo. The resulted residue was purified with a silica gel column chromatography (eluting solvent: ethyl acetate to ethyl acetate/methanol=9/1) to give N-{[3-(3-methoxypropyl)-1-methylimidazo[1,5-a]pyridin-6-yl]methyl}cyclopropanamine (18 mg) as an orange oil.

APCI-MS m/z: 274[M+H]⁺.

Reference Example 223

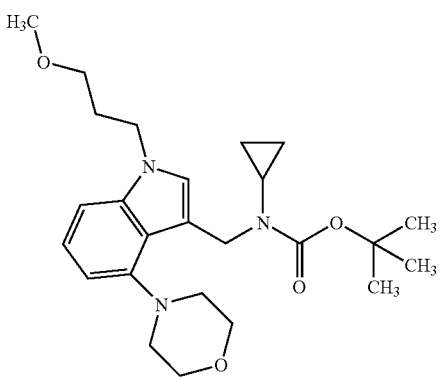 [SMILES: COCCCn1cc(CN(C(=O)OC(C)(C)C)C2CC2)c2c(N3CCOCC3)cccc21]

Morpholine (73.5 μL), cetyltrimethylammoniumbromide (14.6 mg), bis(tri-tert-butylphosphine)palladium(0) (41 mg) and 50% aqueous solution of sodium hydroxide (96 μL) were added to a solution of tert-butyl {[4-bromo-1-(3-methoxypropyl)-1H-indol-3-yl]methy}cyclopropylcarbamate (205 mg) in toluene (3 ml) and the mixture was stirred under argon atmosphere at 90° C. for 23 hours. The reaction mixture was cooled to room temperature, diluted with water and extracted with ethyl acetate. The obtained solution was washed with water and saturated brine successively, dried over magnesium sulfate and concentrated in vacuo. The resulted residue was purified with a silica gel column chromatography (eluting solvent: n-hexane/ethyl acetate=20/1 to 3/2) to give tert-butyl cyclopropyl{[1-(3-methoxypropyl)-4-morpholin-4-yl-1H-indol-3-yl]methy}carbamate (280 mg) as a yellow oil.

APCI-MS m/z: 444[M+H]⁺.

Reference Example 224

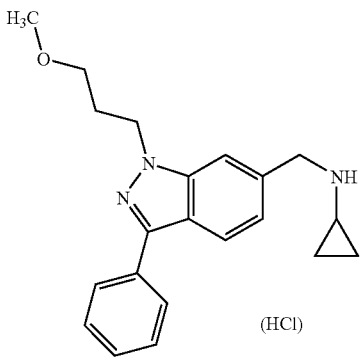 [SMILES: COCCCn1nc(-c2ccccc2)c2ccc(CNC3CC3)cc21 ; "(HCl)"]

(1) tetrakisphenylphosphine palladium(0) (11.9 mg) and a 2M aqueous solution of sodium carbonate were added to a solution of tert-butyl {[3-bromo-1-(3-methoxypropyl)-1H-indazol-6-yl]methy}cyclopropylcarbamate (150 mg) and phenylboric acid (83 mg) in tetrahydrofuran (5 ml) under argon atmosphere at room temperature and the mixture was stirred at 95° C. for 15 hours. Water was added to the reaction solution under ice cooling and extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl cyclopropyl{[1-(3-methoxypropyl)-3-phenyl-4-yl-1H-indazol-6-yl]methy}carbamate (136 mg) as a colorless oil.

APCI-MS m/z: 436[M+H]⁺.

(2) A solution of 4N HCl-dioxane (2 ml) was added to a solution of the compound obtained in (1) described above (130 mg) in chloroform (2 ml), the mixture was stirred at room temperature for 3 hours and concentrated in vacuo to give N-{[1-(3-methoxypropyl)-3-phenyl-4-yl-1H-indazol-6-yl]methyl}cyclopropanamine hydrochloride (112 mg) as a colorless powder.

APCI-MS m/z: 336[M+H]⁺.

Reference Example 225

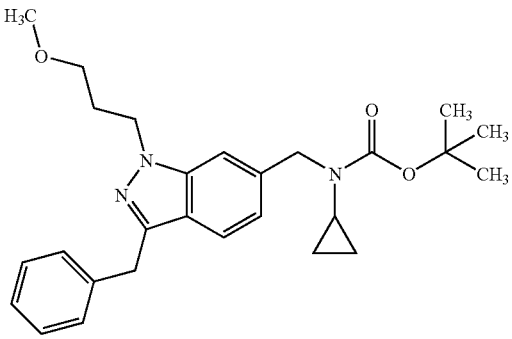 [SMILES: COCCCn1nc(Cc2ccccc2)c2ccc(CN(C(=O)OC(C)(C)C)C3CC3)cc21]

A 0.5M solution of B-benzyl-9-BBN in tetrahydrofuran (1.8 ml) was added to a solution of tert-butyl {[3-bromo-1-(3-methoxypropyl)-1H-indazol-6-yl]methy}cyclopropylcarbamate (200 mg), potassium phosphate (290 mg), palladium acetate(II) (4 mg) and S-Phos (15 mg) in N,N-dimethylformamide (5 ml) under argon atmosphere and the mixture was stirred at 60° C. for 18 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl {[3-benzyl-1-(3-methoxypropyl)-1H-indazol-6-yl]methy}cyclopropylcarbamate (198 mg) as a colorless oil.

APCI-MS m/z: 450[M+H]⁺.

Reference Example 226

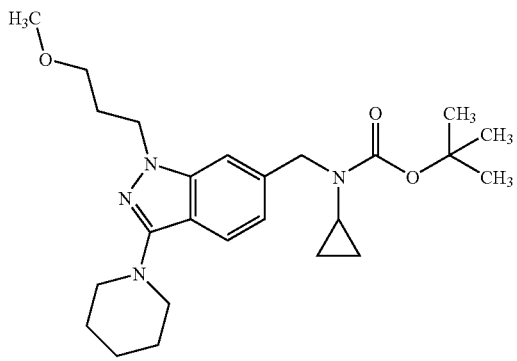 [SMILES: COCCCn1nc(N2CCCCC2)c2ccc(CN(C(=O)OC(C)(C)C)C3CC3)cc21]

A mixture of tert-butyl {[3-bromo1-1-(3-methoxypropyl)-1H-indazol-6-yl]methy}cyclopropylcarbamate (200 mg), piperidine (194 mg), X-Phos (43 mg), cesium carbonate (446 mg) and tris(dibenzylideneacetone)dipalladium (17 mg) in toluene (4 ml)-t-butanol (0.8 ml) was stirred at 95° C. for 18 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl cyclopropyl{[1-(3-methoxypropyl)-3-piperidin-1-yl-1H-indazol-6-yl]methy}carbamate (126 mg) as a yellow oil.

APCI-MS m/z: 443[M+H]$^+$.

Reference Example 227

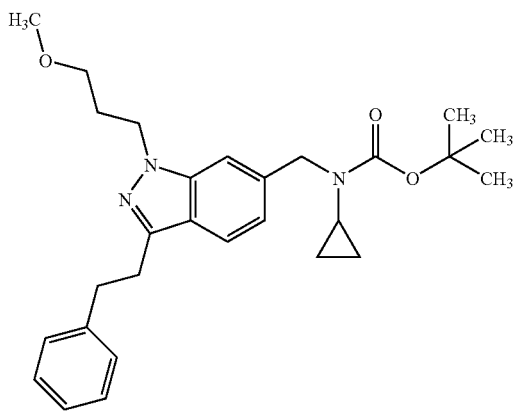 [SMILES: COCCCn1nc(CCc2ccccc2)c2ccc(CN(C(=O)OC(C)(C)C)C3CC3)cc21]

A mixture of tert-butyl {[3-bromo1-1-(3-methoxypropyl)-1H-indazol-6-yl]methy}cyclopropylcarbamate (200 mg), 2-phenylethylboric acid (82.1 mg), potassium carbonate (221 mg) and bis(diphenylphosphino)ferrocene dichloropalladium(II) (50 mg) in 1,4-dioxane (5 ml) was heated to reflux for 25 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl cyclopropyl{[1-(3-methoxypropyl)-3-(2-phenylethyl)-1H-indazol-6-yl]methy}carbamate (108 mg) as a colorless oil.

APCI-MS m/z: 464 [M+H]$^+$.

Reference Example 228

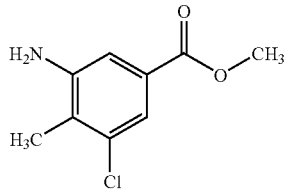

(1) Methyl 3-amino-4-methyl-5-nitro-benzoate (2.54 g) was added portionwise to a mixture of copper chloride(II) (1.95 g), tert-butyl nitrite (1.87 g) in acetonitrile (50 ml) at room temperature and the mixture was stirred at room temperature for 30 minutes. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=20/1) to give methyl 3-chloro-4-methyl-5-nitro-benzoate (1.88 g) as a colorless powder.

(2) Stannic chloride(II) dihydrate (11.2 g) was added to a solution of the compound obtained in (1) described above (2.28 g) in ethyl acetate (45 ml) and stirred at 60° C. for 2 hours. A saturated aqueous solution of sodium bicarbonate was poured into the reaction mixture under ice-cooling and insoluble materials were filtered through Celite. The organic layer was separated, washed with saturated brine, dried over sodium sulfate and concentrated in vacuo. The resulted residue was purified with a silica gel column chromatography (eluting solvent: n-hexane to n-hexane/ethyl acetate=3/2) to give methyl 3-amino-5-chloro-4-methyl-benzoate (1.82 g) as a colorless powder.

APCI-MS m/z: 200/202 [M+H]$^+$.

(3) The compound obtained in (2) described above was treated in the same manner as any of Reference Example to give a compound of the formula below.

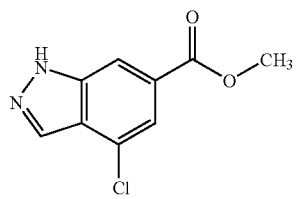

APCI-MS m/z: 211/213 [M+H]$^+$.

(4) The compound obtained in (3) described above was treated in the same manner as any of Reference Example to give a compound of the formula below.

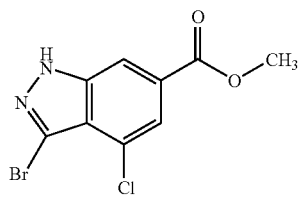

ESI-MS m/z: 287/289/291 [M−H]$^-$.

(5) The compound obtained in (4) described above was treated in the same manner as any of Reference Example to give a compound of the formula below.

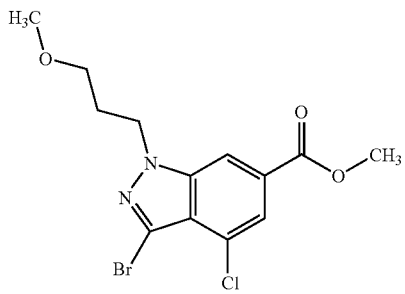

APCI-MS m/z: 361/363/365 [M+H]$^+$.

(6) The compound obtained in (5) described above was treated in the same manner as any of Reference Example to give a compound of the formula below.

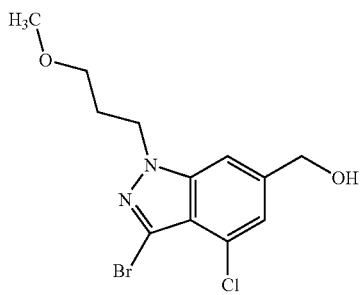 [SMILES: COCCCn1nc(Br)c2c(Cl)cc(CO)cc21]

APCI-MS m/z: 333/335/337 [M+H]$^+$.

(7) The compound obtained in (6) described above was treated in the same manner as any of Reference Example to give a compound of the formula below.

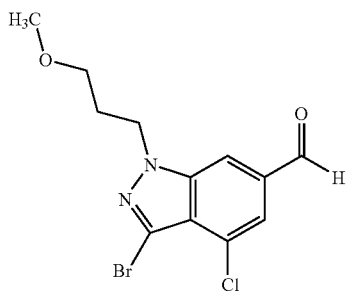 [SMILES: COCCCn1nc(Br)c2c(Cl)cc(C=O)cc21]

APCI-MS m/z: 331/333/335 [M+H]$^+$.

(8) The compound obtained in (7) described above was treated in the same manner as any of Reference Example to give a compound of the formula below.

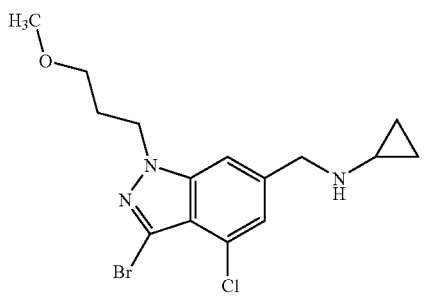 [SMILES: COCCCn1nc(Br)c2c(Cl)cc(CNC3CC3)cc21]

Reference Example 229

(1)

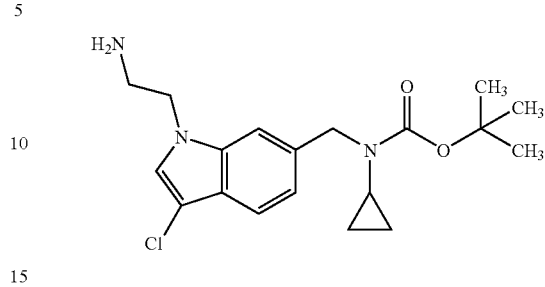

Sodium hydroxide (103 mg) and tetrabutylammonium hydrogensulfate (15 mg) were added to a solution of tert-butyl [(3-chloro-1H-indol-6-yl)methyl]cyclopropylcarbamate (275 mg) in acetonitrile (7.0 ml) and the mixture was stirred at room temperature for 20 minutes. 3-Chloropropylamine hydrochloride (149 mg) was added to the reaction mixture and it was heated under reflux for 16 hours. Sodium hydroxide (103 mg) and 3-Chloropropylamine hydrochloride (149 mg) were added and the mixture was further heated to reflux for 2 hours. The reaction mixture was cooled to room temperature, insoluble materials were filtered through Celite and the filtrate was diluted with water and extracted with ethyl acetate. The organic layer was washed with saturated brine, dried over magnesium sulfate and concentrated in vacuo. The resulted residue was purified with a silica gel column chromatography (eluting solvent: chloroform/methanol=20/1 to 10/1) to give tert-butyl {[1-(2-aminoethyl)-3-chloro-1H-indol-6-yl]methyl}cyclopropylcarbamate (257 mg) as a yellow oil.

APCI-MS m/z: 364/366[M+H]$^+$.

(2)

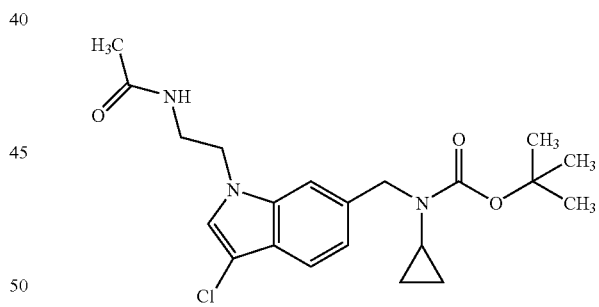

Pyridine (67 μL) and acetyl chloride (29 μL) were added to a solution of the compound obtained in (1) described above (100 mg) in chloroform (3.0 ml) under ice-cooling and the mixture was stirred at room temperature for an hour. Water was added to the reaction mixture and the mixture was extracted with chloroform. The organic layer was washed with a saturated aqueous solution of sodium bicarbonate and saturated brine successively, dried over magnesium sulfate and concentrated in vacuo. The resulted residue was purified with a silica gel column chromatography (eluting solvent: chloroform/methanol=50/1 to 20/1) to give tert-butyl({1-[2-(acetylamino)ethyl]-3-chloro-1H-indol-6-yl}methyl)cyclopropylcarbamate (102 mg) as a pale yellow oil.

APCI-MS m/z: 423/425[M+NH$_4$]$^+$.

(3)

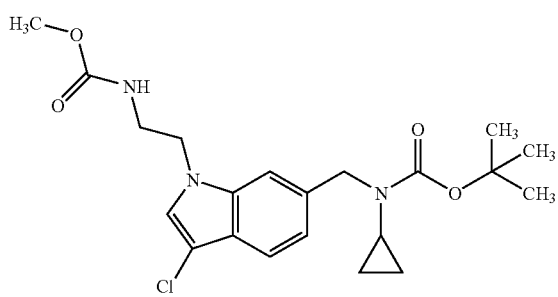 [SMILES: COC(=O)NCCn1cc(Cl)c2ccc(CN(C(=O)OC(C)(C)C)C3CC3)cc21]

Pyridine (80 μL) and methyl chloroformate (38 μL) were added to a solution of tert-butyl {[1-(2-aminoethyl)-3-chloro-1H-indol-6-yl]methyl}cyclopropylcarbamate (120 mg) in chloroform (4.0 ml) under ice-cooling and the mixture was stirred at room temperature for 3 hours. Water was added to the reaction mixture and the mixture was extracted with chloroform. The organic layer was washed with a saturated aqueous solution of sodium bicarbonate and saturated brine successively, dried over sodium sulfate and concentrated in vacuo. The resulted residue was purified with a silica gel column chromatography (eluting solvent: chloroform/methanol=100/1 to 20/1) to give methyl[2-(6-{[(tert-butoxycarbonyl)(cyclopropyl)amino]methyl}-3-chloro-1H-indol-1-yl)ethyl]carbamate (106 mg) as a pale yellow oil.

APCI-MS m/z: 422/424[M+H]$^+$.

Reference Example 230

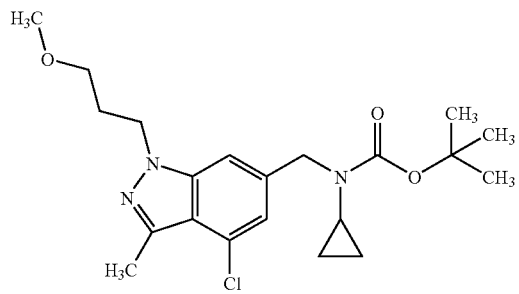 [SMILES: COCCCn1nc(C)c2c(Cl)cc(CN(C(=O)OC(C)(C)C)C3CC3)cc21]

A mixture of tert-butyl {[3-bromo-4-chloro-1-(3-methoxypropyl)-1H-inddazol-6-yl]methyl}cyclopropylcarbamate (180 mg), trimethylboroxin (53 mg), potassium carbonate (158 mg), bis(diphenylphosphino)ferrocene dichloropalladium(II) (29 mg) in 1,4-dioxane (5 ml) was stirred at 110° C. for 4 hours. Water was added to the reaction mixture and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=1/1) to give tert-butyl {[4-chloro-1-(3-methoxypropyl)-3-methyl-1H-inddazol-6-yl]methyl}cyclopropylcarbamate (120 mg) as a colorless oil.

APCI-MS m/z: 408/410 [M+H]$^+$.

Reference Example 231

(1)

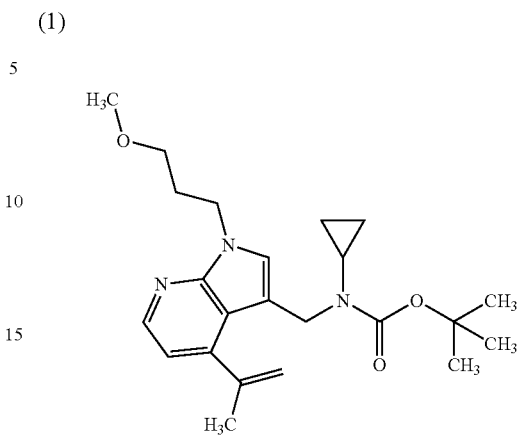

Potassium carbonate (207 mg), isopropenylboric acid pinacol ester (228 μl) and bis(diphenylphosphino)ferrocene dichloropalladium(II) (36.6 mg) were added to a solution of tert-butyl {[4-bromo-1-(3-methoxypropyl)-1H-pyrrolo[2,3-b]pyridin-3-yl]methyl}cyclopropylcarbamate (219 mg) in 1,4-dioxane (14.5 ml) and the mixture was stirred under argon atmosphere at 110° C. for 19 hours. Water was added to the reaction mixture and the mixture was extracted with ethyl acetate. The organic layer was washed with a saturated aqueous solution of sodium bicarbonate and saturated brine successively, dried over magnesium sulfate and concentrated in vacuo. The resulted residue was purified with a silica gel column chromatography (eluting solvent: n-hexane/ethyl acetate=6/1 to 3/7) to give tert-butyl cyclopropyl{[4-isopropenyl-1-(3-methoxypropyl)-1H-pyrrolo[2,3-b]pyridin-3-yl]methyl}carbamate (173 mg) as a pale yellow oil.

APCI-MS m/z: 400[M+H]$^+$.

(2)

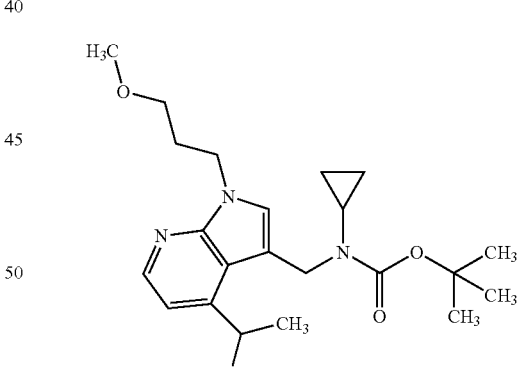

10% Palladium-carbon (50 mg) was added to a solution of the compound obtained in (1) described above (170 mg) in ethyl acetate (12 ml) and the mixture was stirred at room temperature for 6 hours. Insoluble materials were filtered and the filtrate was concentrated in vacuo. The resulted residue was purified with a silica gel column chromatography (eluting solvent: n-hexane/ethyl acetate=6/1 to 3/7) to give tert-butyl cyclopropyl{[4-isopropyl-1-(3-methoxypropyl)-1H-pyrrolo[2,3-b]pyridin-3-yl]methyl}carbamate (81 mg) as a colorless oil.

APCI-MS m/z: 402[M+H]$^+$.

Reference Example 232

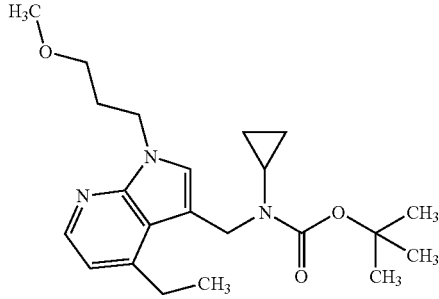 [SMILES: CCc1ccnc2c1c(CN(C(=O)OC(C)(C)C)C1CC1)cn2CCCOC]

Potassium carbonate (207 mg), ethyl boric acid (92.4 mg) and bis(diphenylphosphino)ferrocene dichloropalladium(II) (36.6 mg) were added to a solution of tert-butyl {[4-bromo-1-(3-methoxypropyl)-1H-pyrrolo[2,3-b]pyridin-3-yl]methyl}cyclopropylcarbamate (219 mg) in 1,4-dioxane (14.5 ml) and the mixture was stirred under argon atmosphere at 110° C. for 3 hours. The reaction mixture was cooled to room temperature, water was added therein and extracted with ethyl acetate. The organic layer was washed with a saturated aqueous solution of sodium bicarbonate and saturated brine successively, dried over magnesium sulfate and concentrated in vacuo. The resulted residue was purified with a silica gel column chromatography (eluting solvent: n-hexane/ethyl acetate=4/1 to 1/3) to give tert-butyl cyclopropyl{[4-ethyl-1-(3-methoxypropyl)-1H-pyrrolo[2,3-b]pyridin-3-yl]methyl}carbamate (119 mg) as a pale yellow oil.

APCI-MS m/z: 400[M+H]$^+$.

Reference Example 233

(1)

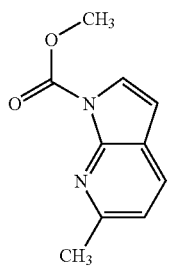

Potassium carbonate (5.03 g), trimethyl boroxin (3.18 ml) and bis(diphenylphosphino)ferrocene dichloropalladium(II) (666 mg) were added to a solution of methyl 6-chloro-1H-pyrrolo[2,3-b]pyridin-1-carboxylate (1.92 g) in 1,4-dioxane (140 ml) and the mixture was stirred at 110° C. for 4 hours under argon atmosphere. The reaction mixture was cooled to room temperature, insoluble materials were filtered and the filtrate was concentrated in vacuo. The residue was diluted with ethyl acetate, washed with water and saturated brine successively, dried over magnesium sulfate and concentrated in vacuo. The resulted residue was purified with a silica gel column chromatography (eluting solvent: n-hexane/ethyl acetate=4/1 to 3/7) to give methyl 6-methyl-1H-pyrrolo[2,3-b]pyridin-1-carboxylate (1.30 g) as a brown powder.

APCI-MS m/z: 191[M+H]$^+$.

(2)

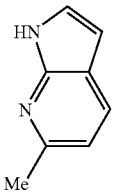

A 1N aqueous solution of sodium hydroxide (9.6 ml) was added to a solution of the compound obtained in (1) described above (183 mg) in methanol (29 ml) and the mixture was stirred at room temperature for 28 hours. The reaction mixture was concentrated in vacuo, the resulted residue was diluted with water and extracted with chloroform. The organic layer was dried over magnesium sulfate and concentrated in vacuo. The resulted residue was purified with a silica gel column chromatography (eluting solvent: n-hexane/ethyl acetate=50/1 to 15/1) to give 6-methyl-1H-pyrrolo[2,3-b]pyridine (107 mg) as a colorless powder.

APCI-MS m/z: 133 [M+H]$^+$.

(3) The compound obtained in (2) described above was treated in the same manner as any of Reference Example to give a compound of the formula below.

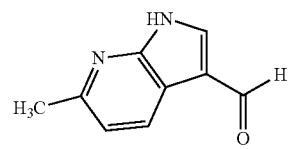

APCI-MS m/z: 161[M+H]$^+$.

(4) The compound obtained in (3) described above was treated in the same manner as any of Reference Example to give a compound of the formula below.

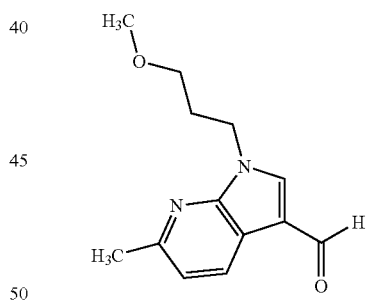

APCI-MS m/z: 233[M+H]$^+$.

(5) The compound obtained in (4) described above was treated in the same manner as any of Reference Example to give a compound of the formula below.

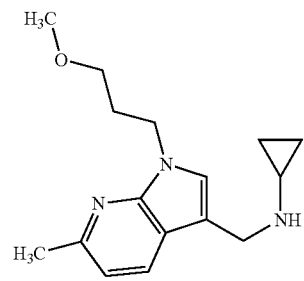 [SMILES: COCCCn1cc(CNC2CC2)c2ccc(C)nc21]

Reference Example 234

(1)

Hexamethylenetetramine (9.63 g) and acetic acid (20 ml) were added to a suspension of 1H-pyrrolo[2,3-b]pyridine (5.91 g) in water (40 ml) and it was stirred at 120° C. for 3 hours. The reaction mixture was cooled to room temperature, water (120 ml) was added and the mixture was stirred at room temperature for an hour. The precipitated crystalline was collected to give 1H-pyrrolo[2,3-b]pyridin-3-carbaldehyde (4.85 g) as a colorless powder.
APCI-MS m/z: 147[M+H]$^+$.

(2) The compound obtained in (1) described above was treated in the same manner as any of Reference Example to give a compound of the formula below.

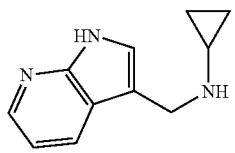 [SMILES: c1cnc2[nH]cc(CNC3CC3)c2c1]

APCI-MS m/z: 188[M+H]$^+$.

(3)

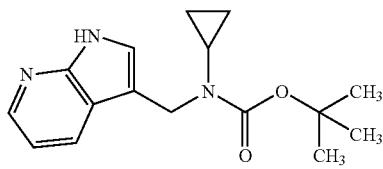 [SMILES: CC(C)(C)OC(=O)N(Cc1c[nH]c2ncccc12)C1CC1]

Potassium carbonate (1.38 g) and a tetrahydrofuran-solution of di-tert-butyl dicarbonate (2 ml) were added to a solution of N-(1H-pyrrolo[2,3-b]pyridin-3-ylmethyl)cyclopropanamine (936 mg) in tetrahydrofuran (10 ml)-water (10 ml) and the mixture was stirred at room temperature for 14 hours. Water was added to the reaction mixture and the mixture was extracted with ethyl acetate. The organic layer was washed with saturated brine, dried over sodium sulfate and concentrated in vacuo. The resulted residue was purified with a silica gel column chromatography (eluting solvent: n-hexane/ethyl acetate=3/1 to 1/2) to give tert-butyl cyclopropyl(1H-pyrrolo[2,3-b]pyridin-3-ylmethyl)carbamate (1.11 g) as a colorless powder.
APCI-MS m/z: 288[M+H]$^+$.

(4)

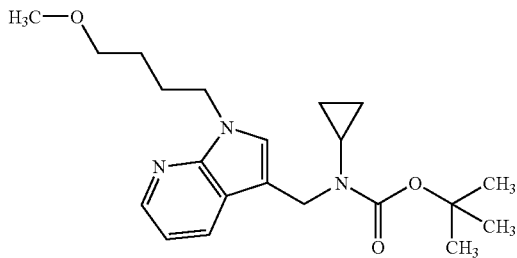 [SMILES: COCCCCn1cc(CN(C(=O)OC(C)(C)C)C2CC2)c2cccnc21]

60% Sodium hydride (88 mg) was added to a solution of the compound obtained in (3) described above (575 mg) in N,N-dimethylformamide (5 ml) under ice-cooling and the mixture was stirred for 10 minutes. A solution of 4-methoxybutyl 4-methylbenzenesulfonate (620 mg) in N,N-dimethylformamide (5 ml) and potassium iodide (33 mg) were added to the mixture and the mixture was stirred at room temperature for 4 hours. Water was added to the reaction mixture and the mixture was extracted with ethyl acetate. The organic layer was washed with water and saturated brine successively, dried over magnesium sulfate and concentrated in vacuo. The resulted residue was purified with a silica gel column chromatography (eluting solvent: n-hexane/ethyl acetate=3/1 to 1/1) to give tert-butyl cyclopropyl{[1-(4-methoxybutyl)-1H-pyrrolo[2,3-b]pyridin-3-yl]methyl}carbamate (636 mg) as a colorless oil.
APCI-MS m/z: 374[M+H]$^+$.

(5) The compound obtained in (4) described above was treated in the same manner as any of Reference Example to give a compound of the formula below.

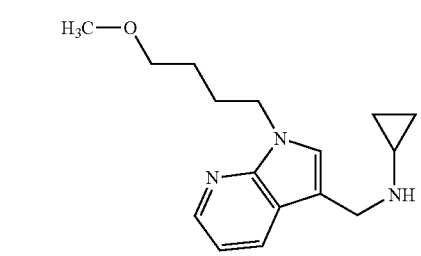 [SMILES: COCCCCn1cc(CNC2CC2)c2cccnc21]

Reference Example 235

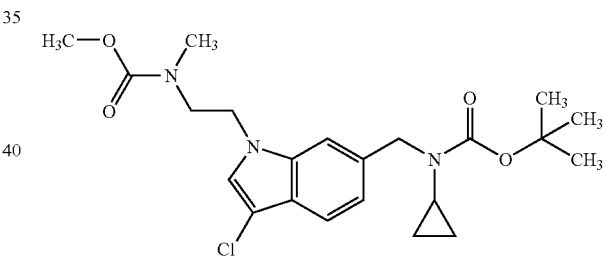

60% Sodium hydride (14.1 mg) was added to a solution of methyl[2-(6-{[(tert-butoxycarbonyl)(cyclopropyl)amino]methyl}-3-chloro-1H-indol-1-yl)ethyl]carbamate (120 mg) in N,N-dimethylformamide (1.5 ml) under ice-cooling and the mixture was stirred at room temperature for 10 minutes. Methyl iodide (27.5 µL) was added to the mixture and it was stirred at room temperature for 30 minutes. Water was added to the reaction mixture under ice-cooling and the mixture was extracted with ethyl acetate. The organic layer was washed with water and saturated brine successively, dried over magnesium sulfate and concentrated in vacuo. The resulted residue was purified with a silica gel column chromatography (eluting solvent: chloroform/methanol=100/1 to 20/1) to give methyl[2-(6-{[(tert-butoxycarbonyl)(cyclopropyl)amino]methyl}-3-chloro-1H-1-indol-1-yl)ethyl]methylcarbamate (101 mg) as a pale yellow oil.
APCI-MS m/z: 420/422[M+H]$^+$.

Reference Example 236

(1) Water (4.2 ml) and hexamethylenetetramine (514 mg) were added to a solution of 7-methyl-1H-pyrrolo[2,3-b]

pyridine (323 mg) in acetic acid (2.3 ml) and the mixture was stirred at 140° C. for 5 hours. The reaction mixture was cooled to room temperature and the solvent was evaporated in vacuo. Water was added to the resulted residue and it was extracted with ethyl acetate. The organic layer was dried over magnesium sulfate and concentrated in vacuo. The resulted residue was purified with a silica gel column chromatography (eluting solvent: chloroform/methanol=50/1 to 15/1) to give 7-methyl-1H-pyrrolo[2,3-b]pyridin-3-carbaldehyde. (197 mg) as a yellow powder.

APCI-MS m/z: 161[M+H]$^+$.

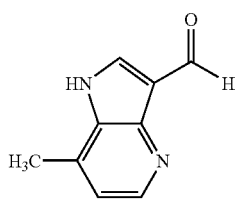

(2) The compound obtained in (1) described above was treated in the same manner as any of Reference Example to give a compound of the formula below.

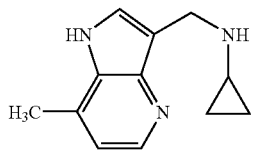

Reference Example 237

(1)

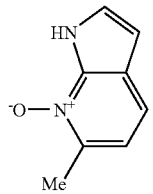

65% m-Chloroperbenzoic acid (1374 mg) was added to a solution of 6-methyl-1H-pyrrolo[2,3-b]pyridine (570 mg) in ethyl acetate (20 ml) under ice-cooling and the mixture was stirred at room temperature for 20 minutes. After concentration of the reaction mixture in vacuo, the resulted residue was diluted with 2% aqueous solution of potassium carbonate and extracted with chloroform. The organic layer was dried over magnesium sulfate and concentrated in vacuo. The resulted residue was purified with a NH-silica gel column chromatography (eluting solvent: chloroform/methanol=30/1 to 9/1) to give 6-methyl-1H-pyrrolo[2,3-b]pyridin-7-oxide (575 mg) as a colorless powder.

APCI-MS m/z: 149[M+H]$^+$.

(2)

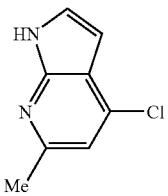

Methanesulfonyl chloride (748 μL) was added to a solution of the compound obtained in (1) described above (573 mg) in N,N-dimethylformamide (15.6 ml) and the mixture was stirred at 75° C. for 21 hours. The reaction mixture was cooled to room temperature, pH of the solution was adjusted to 7 by adding a 5N aqueous solution of sodium hydroxide. The solution was diluted with water and extracted with ethyl acetate. The organic layer was washed with water and saturated brine successively, dried over magnesium sulfate and concentrated in vacuo. The resulted residue was suspended in diisopropyl ether and filtered to give 4-chloro-6-methyl-1H-pyrrolo[2,3-b]pyridine (389 mg) as a pale yellow powder.

APCI-MS m/z: 167/169[M+H]$^+$.

Reference Example 238

(1)

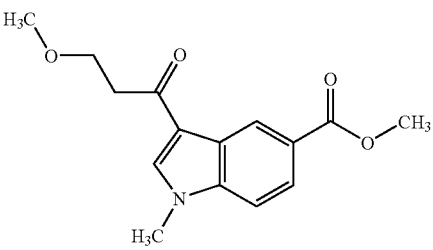

Oxalyl chloride (670 mg) and a catalytic amount of N,N-dimethylformamide (a drop) was added to a solution of 3-methoxypropionic acid (550 mg) in dichloromethane (8 ml) and the mixture was stirred at room temperature for 4 hours. Aluminium chloride (1.06 g) was added portionwise to the reaction mixture under ice-cooling and the mixture was stirred at the same temperature for 5 minutes. A solution of methyl 1-methyl-1H-indol-5-carboxylate (500 mg) in dichloromethane (4 ml) was added dropwise to the reaction mixture under ice-cooling and the mixture was stirred at room temperature for 3 hours. The reaction mixture was added to ice and it was extracted with chloroform. The organic layer was washed with a saturated aqueous solution of sodium bicarbonate and saturated brine successively, dried over sodium sulfate and concentrated in vacuo. The resulted residue was purified with a silica gel column chromatography (eluting solvent: n-hexane to ethyl acetate) to give methyl 3-(3-methoxypropanoyl)-1-methyl-1-indol-5-carboxylate (679 mg) as a colorless powder.

APCI-MS m/z: 276[M+H]$^+$.

(2)

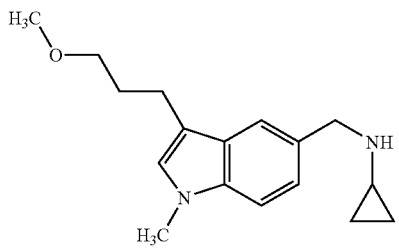 [SMILES: COCCCc1cn(C)c2ccc(CNC3CC3)cc12]

A 1M tetrahydrofuran-solution of borane tetrahydrofuran (2.62 ml) was added dropwise to a solution of 1-{5-[(cyclopropylamino)methyl]-1-methyl-1H-indol-3-yl}-3-methoxy propan-1-one (150 mg) in tetrahydrofuran (2.5 ml) under ice-cooling and the mixture was stirred at room temperature for 15 hours. A 5N aqueous solution of sodium hydroxide (2.5 ml) and methanol (1.25 ml) were added to the reaction mixture and it was stirred at 50° C. for 24 hours. The reaction mixture was cooled to room temperature, extracted with diethyl ether. The organic layer was washed with saturated brine, dried over sodium sulfate and concentrated in vacuo. The resulted residue was purified with a silica gel column chromatography (eluting solvent: chloroform to chloroform/methanol=5/1) to give N-{[3-(3-methoxypropyl)-1-methyl-1H-indol-5-yl]methyl}cyclopropanamine (107 mg) as a colorless oil.

APCI-MS m/z: 273[M+H]$^+$.

Reference Example 239

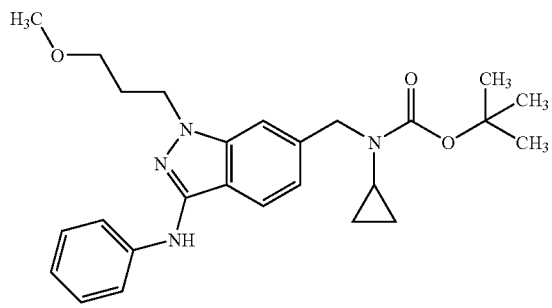 [SMILES: COCCCn1nc(Nc2ccccc2)c2ccc(CN(C(=O)OC(C)(C)C)C3CC3)cc21]

A mixture of tert-butyl {[3-bromo-1-(3-methoxypropyl)-1H-indazol-6-yl]methyl}cyclopropylcarbamate (200 mg), aniline (64 mg), 2-dicyclohexylphosphino-2',4',6'-triisopropyl-1,1'-biphenyl (X-Phos) (8.7 ml), potassium carbonate (88 mg) and tris(dibenzylideneacetone)dipalladium (4.2 mg) in tert-butanol (3 ml) was stirred at 100° C. for 24 hours under argon atmosphere. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl {[3-anilino-1-(3-methoxypropyl)-1H-indazol-6-yl]methyl}cyclopropylcarbamate (162 mg) as a yellow oil.

APCI-MS m/z: 451[M+H]$^+$.

Reference Example 240

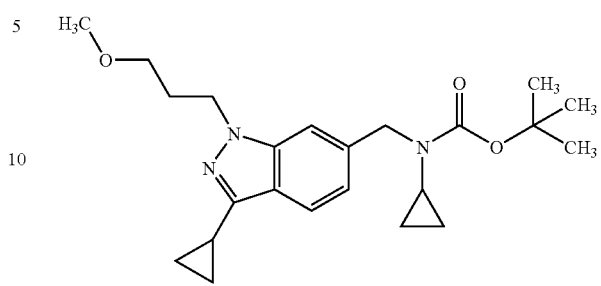

Tetrakis(triphenylphosphine)palladium(0) (20 mg) was added to a solution of tert-butyl {[3-bromo-1-(3-methoxypropyl)-1H-indazol-6-yl]methyl}cyclopropylcarbamate (150 mg), potassium cyclopropyltrifluoroborate (73 mg) and potassium phosphate (254 mg) in toluene (3 ml)-water (1 ml) under argon atmosphere and the mixture was stirred at 100° C. for 24 hours. Potassium cyclopropyltrifluoroborate (24 mg), potassium phosphate (73 mg) and tetrakis(triphenylphosphine)palladium(0) (20 mg) were added to the reaction mixture and it was stirred further at 100° C. for 24 hours. Water was added to the reaction mixture under ice-cooling, the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl cyclopropyl{[3-cyclopropyl-1-(3-methoxypropyl)-1H-indazol-6-yl]methyl}carbamate (57 mg) as a colorless oil.

APCI-MS m/z: 400[M+H]$^+$.

Reference Example 241

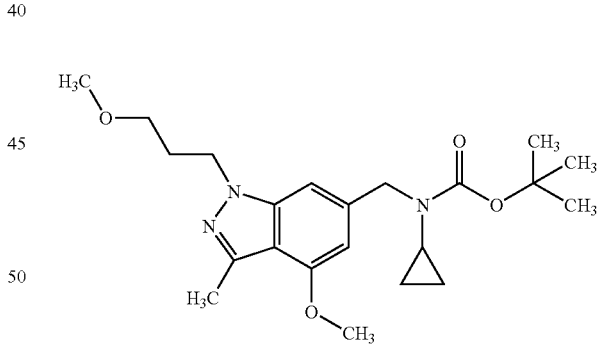

A solution of potassium hydroxide (41 mg) in water (1 ml) was added to a mixture of tert-butyl {[4-chloro-1-(3-methoxypropyl)-3-methyl-1H-indazol-6-yl]methyl}cyclopropylcarbamate (100 mg), 2-di-tert-butylphosphino-2',4',6'-triisopropyl-1,1'-biphenyl (tBu X-Phos) (8.3 mg), tris(dibenzylideneacetone)dipalladium(0) (9.0 mg) in 1,4-dioxane (1 ml) under argon atmosphere and the mixture was stirred at 100° C. for 90 minutes. A 1N solution of HCl (0.8 ml) and water were added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=1/2) to give tert-butyl cyclopropyl{[4-hydroxy-1-(3-methoxypropyl)-3-methyl-1H-indazol-6-yl]methyl}carbamate (91 mg) as a pale brown oil.

APCI-MS m/z: 390[M+H]$^+$.

(2) Methyl iodide (62 mg) was added to a mixture of the compound obtained in (1) described above (85 mg) and potassium carbonate (90 mg) in N,N-dimethylformamide (2 ml) under ice-cooling and the mixture was stirred at room temperature for 2 hours. Water was added to the reaction mixture and the mixture was extracted with ethyl acetate. The organic layer was washed with water and saturated brine successively, dried over sodium sulfate and concentrated in vacuo. The resulted residue was purified with a silica gel column chromatography (eluting solvent: n-hexane to n-hexane/ethyl acetate=1/1) to give tert-butyl cyclopropyl{[4-methoxy-1-(3-methoxypropyl)-3-methyl-1H-indazol-6-yl]methyl}carbamate (76 mg) as a pale brown oil.

APCI-MS m/z: 404[M+H]$^+$.

Reference Example 242

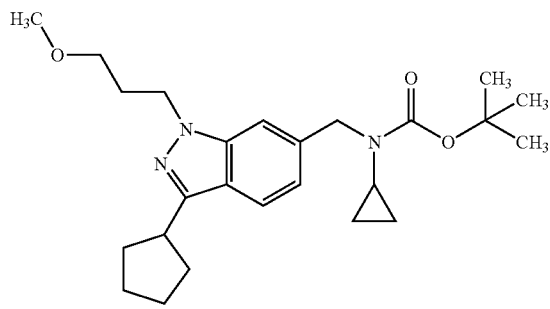 [SMILES: COCCCn1nc(C2CCCC2)c2ccc(CN(C(=O)OC(C)(C)C)C3CC3)cc21]

(1) A mixture of tert-butyl {[3-bromo-1-(3-methoxypropyl)-1H-indazol-6-yl]methyl}cyclopropylcarbamate (150 mg), cyclopenten-1-yl boric acid (57 mg), potassium carbonate (142 mg) and bis(diphenylphosphino)ferrocene dichloropalladium(II) (25 mg) in 1,4-dioxane (4 ml) was stirred at 110° C. for 18 hours under argon atmosphere. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=2/1) to give tert-butyl {[3-cyclopent-1-ene-1-yl-1-(3-methoxypropyl)-1H-indazol-6-yl]methyl}cyclopropylcarbamate (130 mg) as a colorless oil.

APCI-MS m/z: 426 [M+H]$^+$.

(2) 10% Palladium-carbon (35 mg) was added to a solution of the compound obtained in (1) described above (123 mg) in ethanol (5 ml) and the mixture was stirred under hydrogen atmosphere at room temperature for 4 hours. Insoluble materials were filtered and the filtrate was concentrated in vacuo. The resulted residue was purified with a silica gel column chromatography (eluting solvent: n-hexane to n-hexane/ethyl acetate=2/1) to give tert-butyl {[3-cyclopentyl-1-(3-methoxypropyl)-1H-indazol-6-yl]methyl}cyclopropylcarbamate (95 mg) as a colorless oil.

APCI-MS m/z: 428[M+H]$^+$.

Reference Example 243

(1)

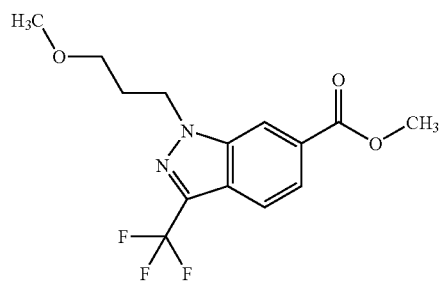

A mixture of methyl 3-iodo-1-(3-methoxypropyl)-1H-indazol-6-carboxylate (500 mg), methyl fluorosulfonyldifluoroacetate (1.29 g), hexamethylphosphoramide (1.20 g) and cuprous iodide(I) (306 mg) in N,N-dimethylformamide (4 ml) was stirred at 75° C. for 6 hours, and at 100° C. for 2 hours under argon atmosphere. Water and ethyl acetate were added to the reaction mixture under ice-cooling, and insoluble materials were filtered through Celite. The organic layer was separated, washed with water and saturated brine successively, dried over sodium sulfate and concentrated in vacuo. The resulted residue was purified with a silica gel column chromatography (eluting solvent: n-hexane to n-hexane/ethyl acetate=1/1) to give methyl 1-(3-methoxypropyl)-3-(trifluoromethyl)-1H-indazol-6-carboxylate (355 mg) as a colorless oil.

APCI-MS m/z: 317[M+H]$^+$.

(2) The compound obtained in (1) described above was treated in the same manner as any of Reference Example to give a compound of the formula below.

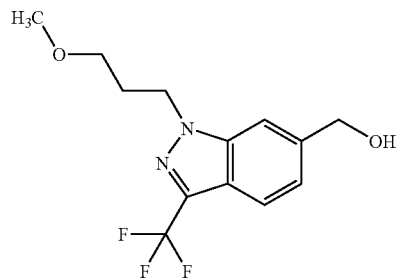 [SMILES: COCCCn1nc(C(F)(F)F)c2ccc(CO)cc21]

APCI-MS m/z: 289[M+H]$^+$.

(3) The compound obtained in (2) described above was treated in the same manner as any of Reference Example to give a compound of the formula below.

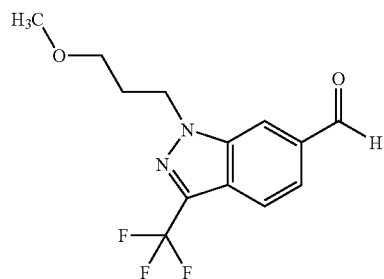 [SMILES: COCCCn1nc(C(F)(F)F)c2ccc(C=O)cc21]

APCI-MS m/z: 287[M+H]$^+$.

(4) The compound obtained in (3) described above was treated in the same manner as any of Reference Example to give a compound of the formula below.

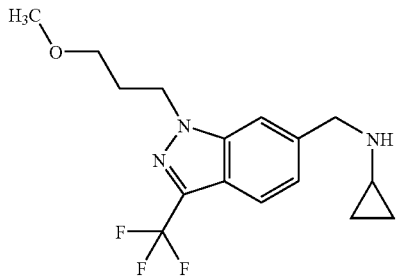 [SMILES: COCCCn1nc(C(F)(F)F)c2ccc(CNC3CC3)cc21]

Reference Example 244

(1)

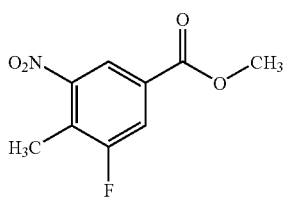

A solution of methyl 3-amino-4-methyl-5-nitrobanzoate (500 mg) in o-dichlorobenzene (7 ml)-dichloromethane (10 ml) was added dropwise to a suspension of nitorosyl tetrafluoroborate (334 mg) in o-dichlorobenzene (3 ml) under ice-cooling, and the mixture was stirred at the same temperature for 45 minutes. Then, the mixture was heated up to 100° C. and stirred at the same temperature for 3 hours. Water was added to the reaction mixture under ice-cooling and the mixture was extracted with ethyl acetate. The organic layer was washed with saturated brine, dried over sodium sulfate and concentrated in vacuo. The resulted residue was purified with a silica gel column chromatography (eluting solvent: n-hexane to n-hexane/ethyl acetate=5/1) to give methyl 3-fluoro-4-methyl-5-nitrobenzoate (291 mg) as a pale yellow powder.

(2) The compound obtained in (1) described above was treated in the same manner as any of Reference Example to give a compound of the formula below.

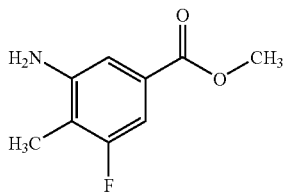

APCI-MS m/z: 184[M+H]$^+$.

(3) The compound obtained in (2) described above was treated in the same manner as any of Reference Example to give a compound of the formula below.

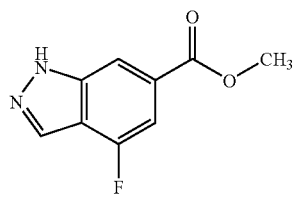

APCI-MS m/z: 195[M+H]$^+$.

(4) The compound obtained in (3) described above was treated in the same manner as any of Reference Example to give a compound of the formula below.

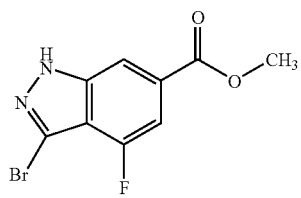

ESI-MS m/z: 271/273[M+H]$^+$.

(5) The compound obtained in (4) described above was treated in the same manner as any of Reference Example to give a compound of the formula below.

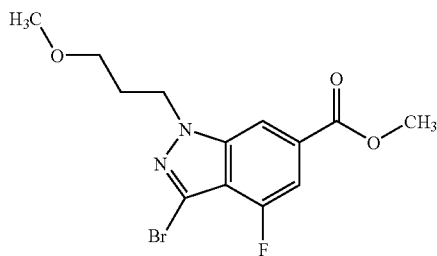

APCI-MS m/z: 345/347[M+H]$^+$.

(6) The compound obtained in (5) described above was treated in the same manner as any of Reference Example to give a compound of the formula below.

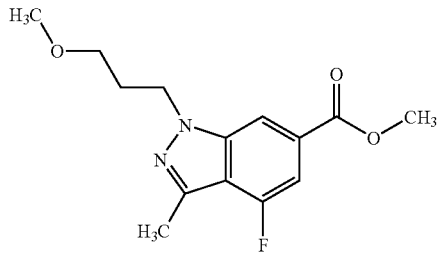

APCI-MS m/z: 281[M+H]$^+$.

(7) The compound obtained in (6) described above was treated in the same manner as any of Reference Example to give a compound of the formula below.

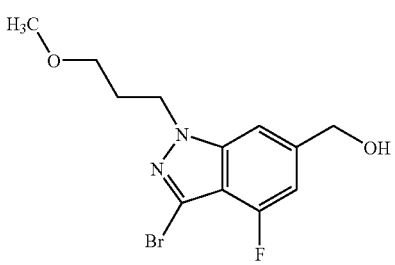 [SMILES: COCCCn1nc(Br)c2c(F)cc(CO)cc21]

APCI-MS m/z: 253[M+H]+.

(8) The compound obtained in (7) described above was treated in the same manner as any of Reference Example to give a compound of the formula below.

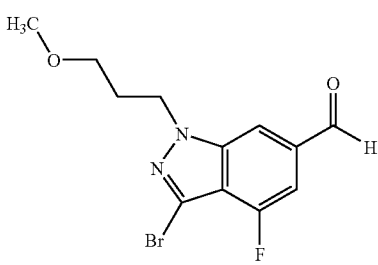 [SMILES: COCCCn1nc(Br)c2c(F)cc(C=O)cc21]

APCI-MS m/z: 251[M+H]+.

(9) The compound obtained in (8) described above was treated in the same manner as any of Reference Example to give a compound of the formula below.

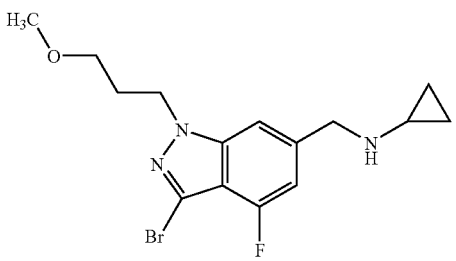 [SMILES: COCCCn1nc(Br)c2c(F)cc(CNC3CC3)cc21]

Reference Example 245

(1)

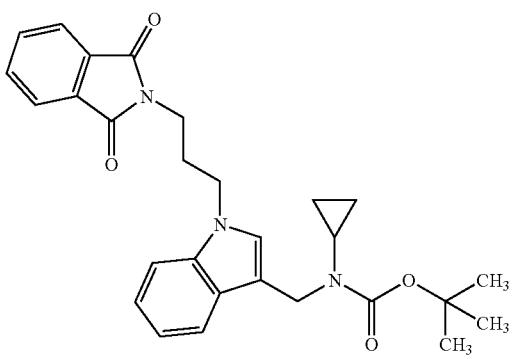 [SMILES: CC(C)(C)OC(=O)N(Cc1cn(CCCN2C(=O)c3ccccc3C2=O)c2ccccc12)C1CC1]

60% Sodium hydride (616 mg) was added to a solution of tert-butyl cyclopropyl-(1H-indol-3yl-methyl)carbamate (4.0 g) in N,N-dimethylformamide (1.0 ml) under ice-cooling and the mixture was stirred at room temperature for 10 minutes. N-(3-bromopropyl)phthalimide (4.5 g) was added to the reaction mixture and stirred at room temperature for 3 hours. Water was added to the reaction mixture and the mixture was extracted with ethyl acetate.

The organic layer was washed with water and saturated brine successively, dried over magnesium sulfate and concentrated in vacuo. The resulted residue was purified with a silica gel column chromatography (eluting solvent: n-hexane/ethyl acetate=10/1 to 2/3) to give tert-butyl cyclopropyl({1-[3-(1,3-dioxo-1,3-dihydro-2H-isoindol-2-yl)propyl]-1H-indol-3-yl}methyl)carbamate (5.55 g) as a yellow oil.

APCI-MS m/z: 474[M+H]+.

(2)

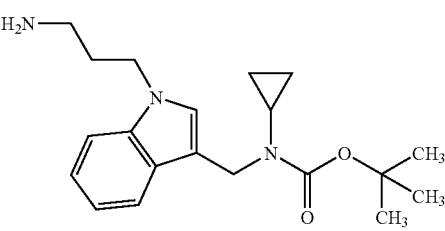 [SMILES: CC(C)(C)OC(=O)N(Cc1cn(CCCN)c2ccccc12)C1CC1]

Hydrazine hydrate (2.25 ml) was added to a solution of the compound obtained in (1) described above (5.51 g) in ethanol (120 ml) and the mixture was stirred at 40° C. for 11 hours. Water was added to the reaction mixture and it was extracted with chloroform. The organic layer was washed with saturated brine, dried over sodium sulfate and concentrated in vacuo. The resulted residue was purified with a silica gel column chromatography (eluting solvent: chloroform to chloroform/methanol=30/1) to give tert-butyl {[1-(3-amino-propyl)-1H-indol-3-yl]methyl}cyclopropylcarbamate (2.68 g) as a yellow oil.

APCI-MS m/z: 344[M+H]+.

(3)

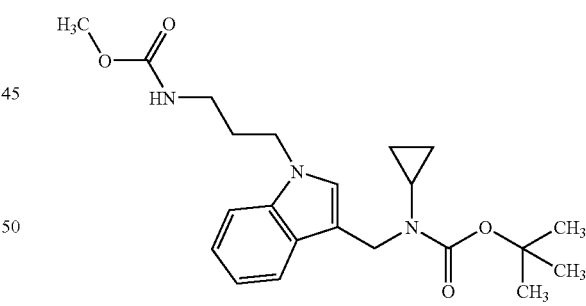

Triethylamine (483 µl) and methyl chloroformate (247 µl) were added to a solution of the compound obtained in (2) described above (1.0 g) in chloroform (15 ml) under ice-cooling and the mixture was stirred at the same temperature for 5 minutes. Water was added to the reaction mixture and it was extracted with chloroform. The organic layer was dried over magnesium sulfate and concentrated in vacuo. The resulted residue was purified with a silica gel column chromatography (eluting solvent: n-hexane-ethyl acetate=4/1 to 1/2) to give methyl[3-(3-{[(tert-butoxycarbonyl)(cyclopropyl)aminomethyl}-1H-indol-1-yl)propyl]carbamate (1.00 g) as a yellow viscous oil.

APCI-MS m/z: 419[M+NH4]+.

(4) The compound obtained in (3) described above was treated in the same manner as any of Reference Example to give a compound of the formula below.

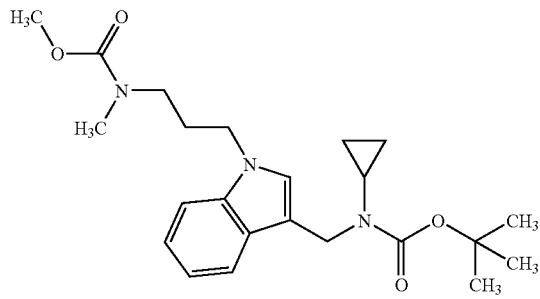 [SMILES: COC(=O)N(C)CCCn1cc(CN(C(=O)OC(C)(C)C)C2CC2)c2ccccc21]

APCI-MS m/z: 433[M+NH$_4$]$^+$.

(3-2)

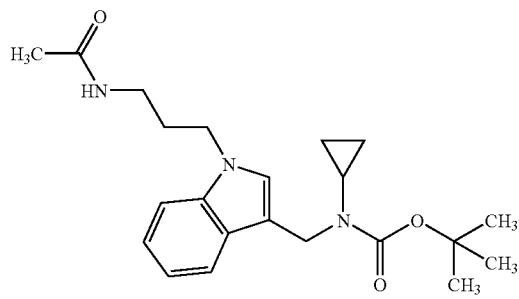 [SMILES: CC(=O)NCCCn1cc(CN(C(=O)OC(C)(C)C)C2CC2)c2ccccc21]

Triethylamine (483 μl) and acetyl chloride (228 μl) were added to a solution of the compound obtained in (2) described above (1.0 g) in chloroform (15 ml) under ice-cooling and the mixture was stirred at the same temperature for 5 minutes. Water was added to the reaction mixture and it was extracted with chloroform. The organic layer was dried over magnesium sulfate and concentrated in vacuo. The resulted residue was purified with a NH-silica gel column chromatography (eluting solvent: n-hexane/chloroform=1/2 to chloroform) to give tert-butyl({1-[3-(acetylamino)propyl]-1H-indol-3-yl}methyl)cyclopropylcarbamate (958 mg) as a yellow viscous oil.

APCI-MS m/z: 386[M+H]$^+$.

(4-2) The compound obtained in (3-2) described above was treated in the same manner as any of Reference Example to give a compound of the formula below.

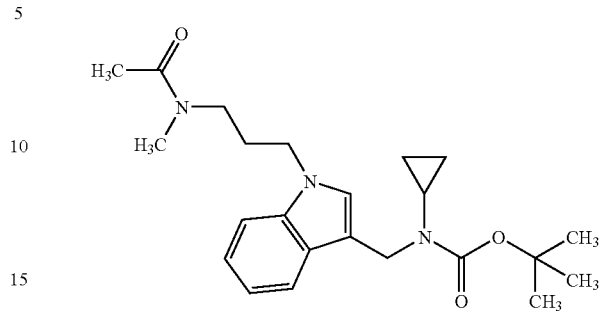

APCI-MS m/z: 400[M+H]$^+$.

Reference Example 246

N-Chlorosuccinimide (514 mg) was added to a solution of tert-butyl 1H-pyrrolo[3,2-c]pyridin-6-carboxylate (800 mg) in dichloromethane (16 ml) at room temperature and the mixture was stirred at the room temperature for 3 hours. The reaction mixture was concentrated in vacuo and the resulted residue was dissolved in tetrahydrofuran. The organic layer was washed with saturated brine, dried over sodium sulfate and concentrated in vacuo to give a crude product of tert-butyl 3-chloro-1H-pyrrolo[3,2-c]pyridin-6-carboxylate (1.06 g) as an orange powder.

APCI-MS m/z: 253/255[M+H]$^+$.

Reference Example 247-586

The corresponding starting compounds were treated in the same manner as any of Reference Examples to give compounds listed in the following Table 20.

TABLE 20

| No of Ref. Example | Structure | Properties |
|---|---|---|
| 247 | 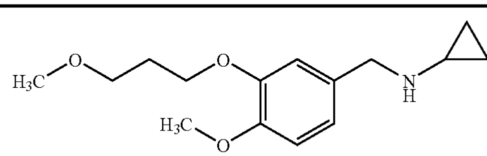 | Property: purified oil<br>APCI-MS m/z: 266[M + H]$^+$ |
| 248 | 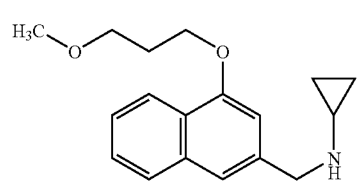 [SMILES: COCCCOc1cc(CNC2CC2)cc2ccccc12] | Property: purified viscous oil<br>APCI-MS m/z: 286[M + H]$^+$ |

TABLE 20-continued

| No of Ref. Example | Structure | Properties |
|---|---|---|
| 249 | 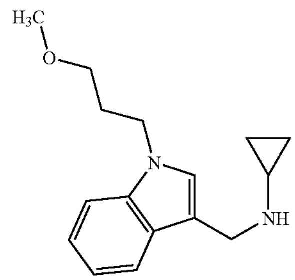 | Property: purified viscous oil<br>APCI-MS m/z: 202[M + H]+ |
| 250 | 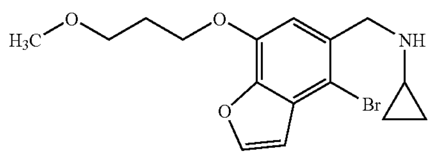 [SMILES: COCCCOc1cc(CNC2CC2)c(Br)c2ccoc12] | hydrochloride<br>Property: purified powder<br>APCI-MS m/z: 354/356[M + H]+ |
| 251 | 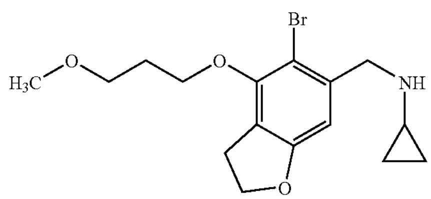 [SMILES: COCCCOc1c(Br)c(CNC2CC2)cc2c1CCO2] | hydrochloride<br>Property: purified powder<br>APCI-MS m/z: 356/358[M + H]+ |
| 252 | 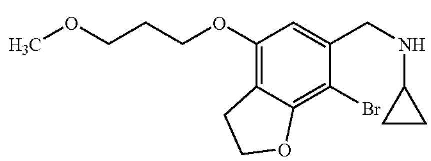 [SMILES: COCCCOc1cc(CNC2CC2)c(Br)c2c1CCO2] | hydrochloride<br>Property: purified powder<br>APCI-MS m/z: 356/358[M + H]+ |
| 253 | 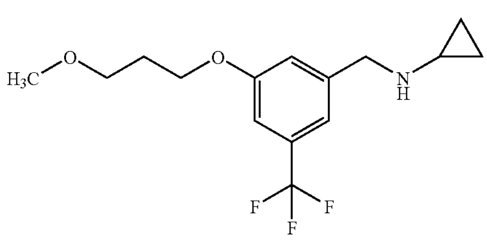 [SMILES: COCCCOc1cc(CNC2CC2)cc(C(F)(F)F)c1] | hydrochloride<br>Property: purified powder<br>APCI-MS m/z: 304[M + H]+ |
| 254 | 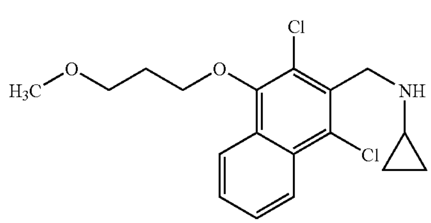 [SMILES: COCCCOc1c(Cl)c(CNC2CC2)c(Cl)c2ccccc12] | hydrochloride<br>Property: purified powder<br>APCI-MS m/z: 354/356[M + H]+ |

TABLE 20-continued

| No of Ref. Example | Structure | Properties |
|---|---|---|
| 255 | 1-(3-methoxypropyl)-4-chloro-3-((cyclopropylamino)methyl)indole | Property: purified viscous oil<br>APCI-MS m/z: 236/238[M + H]+ |
| 256 | 1-(3-methoxypropyl)-7-fluoro-3-((cyclopropylamino)methyl)indole | Property: purified viscous oil<br>APCI-MS m/z: 220[M + H]+ |
| 257 | 1-(3-methoxypropyl)-7-bromo-3-((cyclopropylamino)methyl)indole | Property: purified viscous oil<br>APCI-MS m/z: 280/282[M + H]+ |
| 258 | 1-(3-methoxypropyl)-4-fluoro-3-((cyclopropylamino)methyl)indole | Property: purified viscous oil<br>APCI-MS m/z: 220[M + H]+ |
| 259 | 1-(3-methoxypropyl)-7-methyl-3-((cyclopropylamino)methyl)indole | Property: purified viscous oil<br>APCI-MS m/z: 216[M + H]+ |

TABLE 20-continued

| No of Ref. Example | Structure | Properties |
|---|---|---|
| 260 | 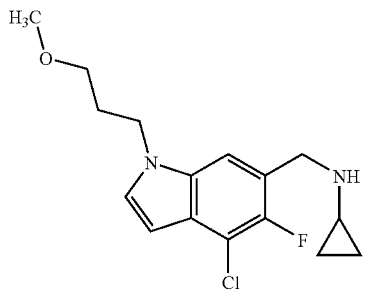 [SMILES: COCCCn1ccc2c(Cl)c(F)c(CNC3CC3)cc21] | Property: purified oil<br>APCI-MS m/z: 311/313[M + H]+ |
| 261 | 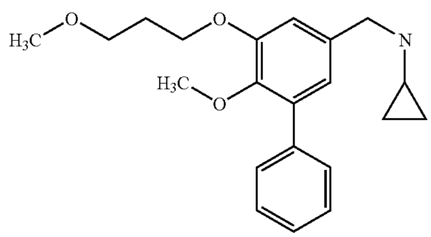 [SMILES: COCCCOc1cc(CNC2CC2)cc(-c2ccccc2)c1OC] | hydrochloride<br>Property: purified viscous oil<br>APCI-MS m/z: 342[M + H]+ |
| 262 | 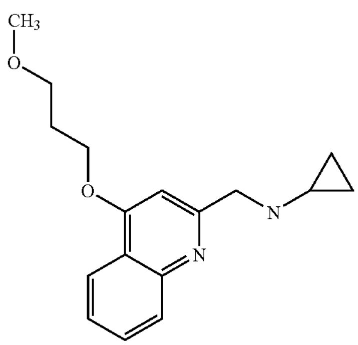 [SMILES: COCCCOc1cc(CNC2CC2)nc2ccccc12] | dihydrochloride<br>Property: purified powder<br>APCI-MS m/z: 287[M + H]+ |
| 263 | 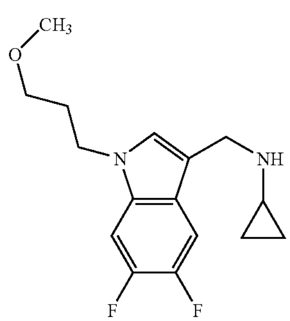 | Property: purified viscous oil<br>APCI-MS m/z: 238[M + H]+ |
| 264 | 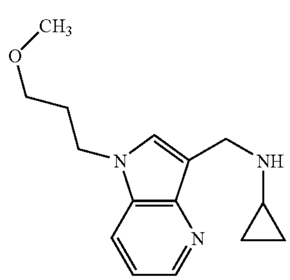 [SMILES: COCCCn1cc(CNC2CC2)c2ncccc21] | Property: purified viscous oil<br>APCI-MS m/z: 260[M + H]+ |

TABLE 20-continued

| No of Ref. Example | Structure | Properties |
|---|---|---|
| 265 | 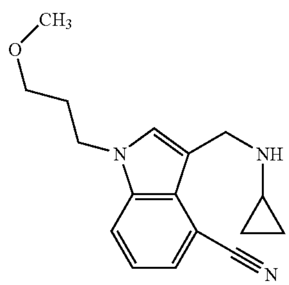 [SMILES: COCCCn1cc(CNC2CC2)c2c(C#N)cccc21] | Property: purified viscous oil<br>APCI-MS m/z: 284[M + H]+ |
| 266 | 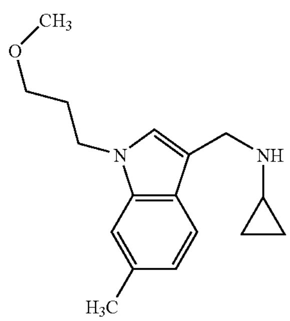 | Property: purified viscous oil<br>APCI-MS m/z: 216[M + H]+ |
| 267 | 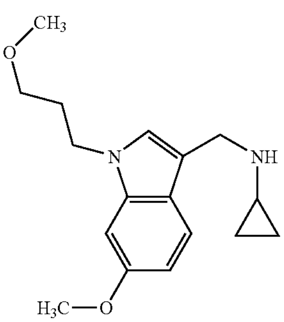 | Property: purified viscous oil<br>APCI-MS m/z: 232[M + H]+ |
| 268 | 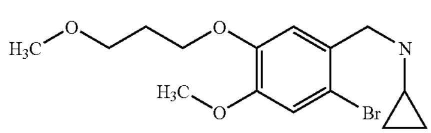 | hydrochloride<br>Property: purified powder<br>APCI-MS m/z: 344/346[M + H]+ |
| 269 | 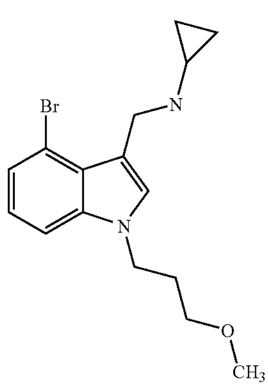 [SMILES: COCCCn1cc(CNC2CC2)c2c(Br)cccc21] | Property: purified viscous oil<br>APCI-MS m/z: 337/339[M + H]+ |

TABLE 20-continued

| No of Ref. Example | Structure | Properties |
|---|---|---|
| 270 | 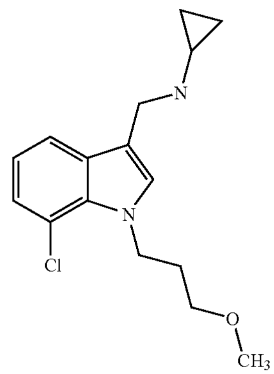 | Property: purified viscous oil<br>APCI-MS m/z: 236/238[M + H]+ |
| 271 | 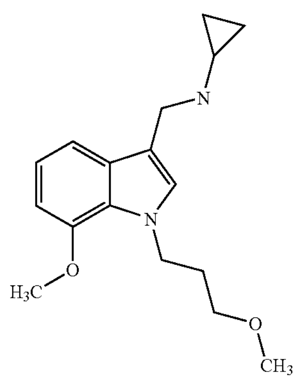 | Property: purified viscous oil<br>APCI-MS m/z: 232[M + H]+ |
| 272 | 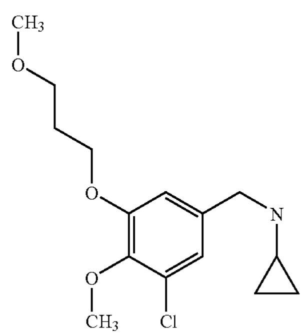 [SMILES: COCCCOc1cc(CNC2CC2)cc(Cl)c1OC] | hydrochloride<br>Property: purified powder<br>APCI-MS m/z: 300/302[M + H]+ |
| 273 | 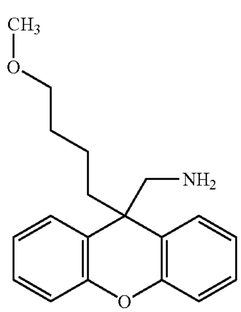 [SMILES: COCCCCC1(CN)c2ccccc2Oc2ccccc21] | Property: purified oil<br>APCI-MS m/z: 298[M + H]+ |

TABLE 20-continued

| No of Ref. Example | Structure | Properties |
|---|---|---|
| 274 | 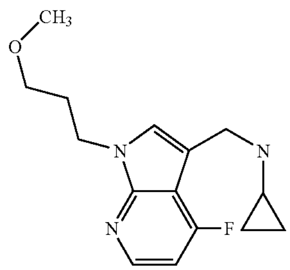 [SMILES: COCCCn1cc(CNC2CC2)c2c(F)ccnc21] | Property: purified viscous oil<br>APCI-MS m/z: 278[M + H]+ |
| 275 | 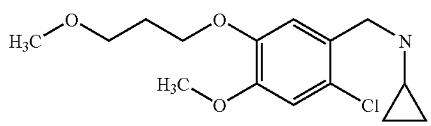 [SMILES: COCCCOc1cc(CNC2CC2)c(Cl)cc1OC] | hydrochloride<br>Property: purified powder<br>APCI-MS m/z: 300/302[M + H]+ |
| 276 | 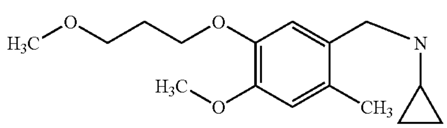 [SMILES: COCCCOc1cc(CNC2CC2)c(C)cc1OC] | hydrochloride<br>Property: purified powder<br>APCI-MS m/z: 280[M + H]+ |
| 277 | 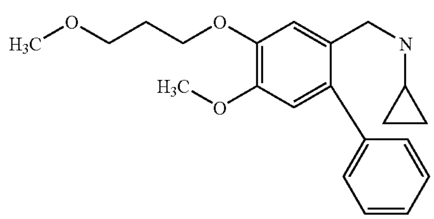 [SMILES: COCCCOc1cc(CNC2CC2)c(-c2ccccc2)cc1OC] | hydrochloride<br>Property: purified powder<br>APCI-MS m/z: 342[M + H]+ |
| 278 | 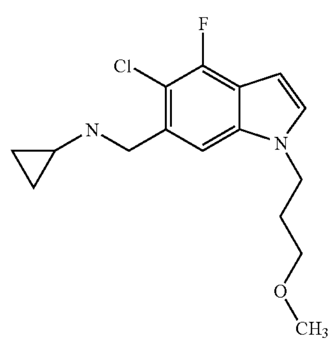 [SMILES: COCCCn1ccc2c(F)c(Cl)c(CNC3CC3)cc21] | Property: purified oil<br>APCI-MS m/z: 311/313[M + H]+ |
| 279 | 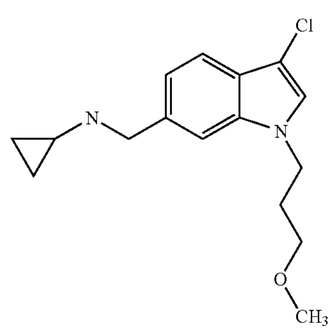 [SMILES: COCCCn1cc(Cl)c2ccc(CNC3CC3)cc21] | Property: purified oil<br>APCI-MS m/z: 293/295[M + H]+ |

TABLE 20-continued

| No of Ref. Example | Structure | Properties |
|---|---|---|
| 280 | 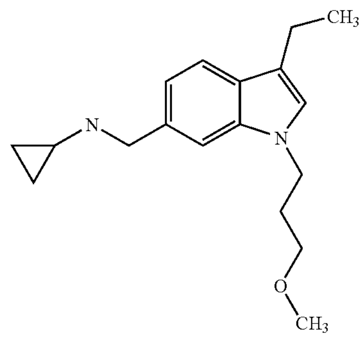 [SMILES: CCc1cn(CCCOC)c2cc(CNC3CC3)ccc12] | Property: purified oil<br>APCI-MS m/z: 287[M + H]+ |
| 281 | 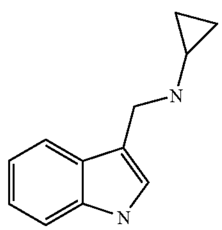 [SMILES: c1ccc2c(CNC3CC3)c[nH]c2c1] | Property: purified powder<br>APCI-MS m/z: 187[M + H]+ |
| 282 | 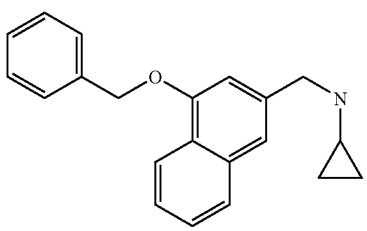 [SMILES: c1ccc(COc2cc(CNC3CC3)cc3ccccc23)cc1] | Property: purified oil<br>APCI-MS m/z: 304[M + H]+ |
| 283 | 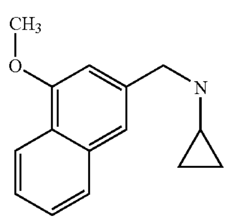 [SMILES: COc1cc(CNC2CC2)cc2ccccc12] | hydrochloride<br>Property: purified powder<br>APCI-MS m/z: 228[M + H]+ |
| 284 | 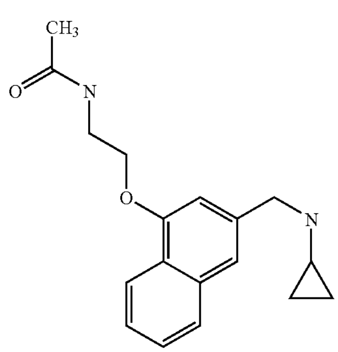 [SMILES: CC(=O)NCCOc1cc(CNC2CC2)cc2ccccc12] | hydrochloride<br>Property: purified powder<br>APCI-MS m/z: 299[M + H]+ |

TABLE 20-continued

| No of Ref. Example | Structure | Properties |
|---|---|---|
| 285 | 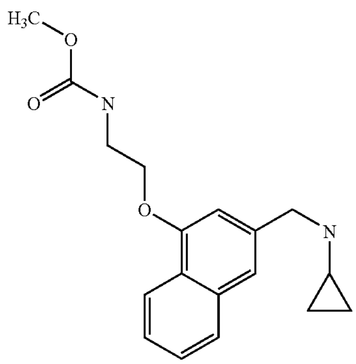 [SMILES: COC(=O)NCCOc1cc(CNC2CC2)cc2ccccc12] | hydrochloride<br>Property: purified powder<br>APCI-MS m/z: 315[M + H]+ |
| 286 | 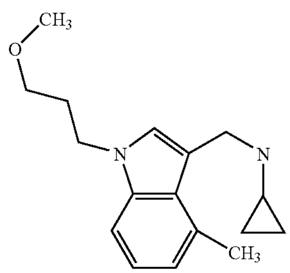 | Property: purified viscous oil<br>APCI-MS m/z: 216[M + H]+ |
| 287 | 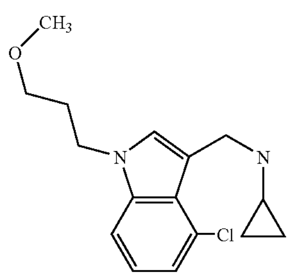 [SMILES: COCCCn1cc(CNC2CC2)c2c(Cl)cccc21] | Property: purified viscous oil<br>APCI-MS m/z: 294/296[M + H]+ |
| 288 | 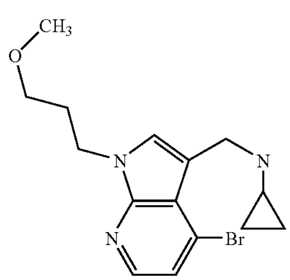 [SMILES: COCCCn1cc(CNC2CC2)c2c(Br)ccnc21] | Property: purified viscous oil<br>APCI-MS m/z: 338/340[M + H]+ |
| 289 | 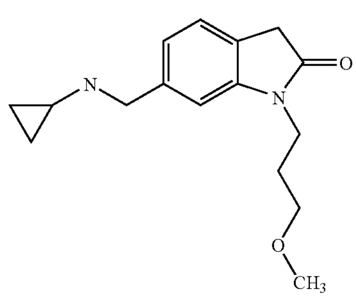 [SMILES: COCCCN1C(=O)Cc2ccc(CNC3CC3)cc21] | Property: purified oil<br>APCI-MS m/z: 275[M + H]+ |

TABLE 20-continued

| No of Ref. Example | Structure | Properties |
|---|---|---|
| 290 | 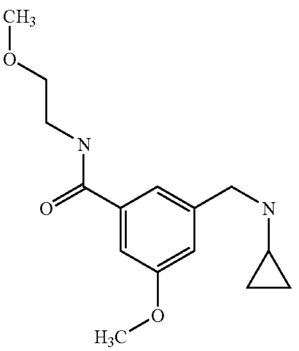 [SMILES: COCCNC(=O)c1cc(CNC2CC2)cc(OC)c1] | Property: purified oil<br>APCI-MS m/z: 279[M + H]+ |
| 291 | 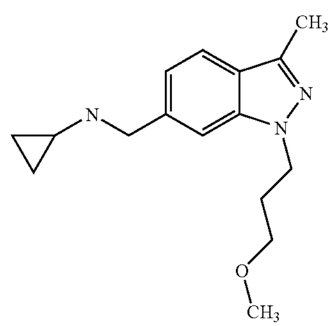 [SMILES: COCCCn1nc(C)c2ccc(CNC3CC3)cc21] | Property: purified oil<br>APCI-MS m/z: 274[M + H]+ |
| 292 | 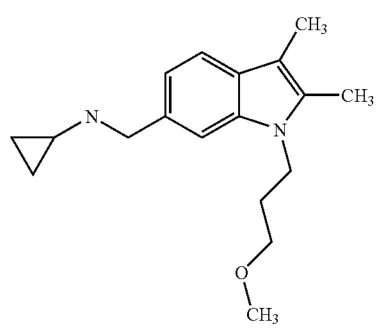 [SMILES: COCCCn1c(C)c(C)c2ccc(CNC3CC3)cc21] | Property: purified oil<br>APCI-MS m/z: 287[M + H]+ |
| 293 | 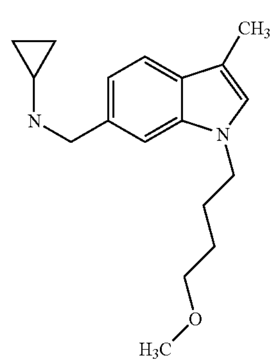 [SMILES: COCCCCn1cc(C)c2ccc(CNC3CC3)cc21] | Property: purified oil<br>APCI-MS m/z: 287[M + H]+ |

TABLE 20-continued
| No of Ref. Example | Structure | Properties |
|---|---|---|
| 294 | 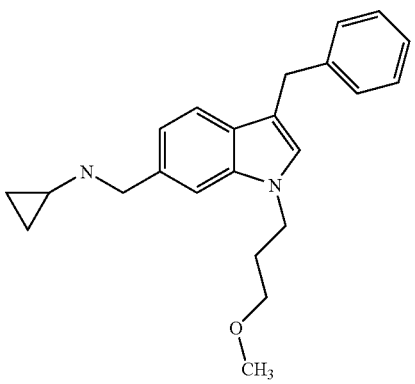 | Property: purified oil<br>APCI-MS m/z: 349[M + H]+ |
| 295 | 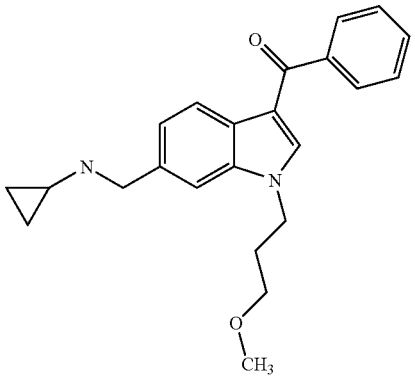 [SMILES: COCCCn1cc(C(=O)c2ccccc2)c2ccc(CNC3CC3)cc21] | Property: purified oil<br>APCI-MS m/z: 363[M + H]+ |
| 296 | 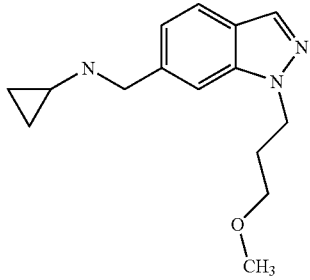 [SMILES: COCCCn1ncc2ccc(CNC3CC3)cc21] | Property: purified oil<br>APCI-MS m/z: 260[M + H]+ |
| 297 | 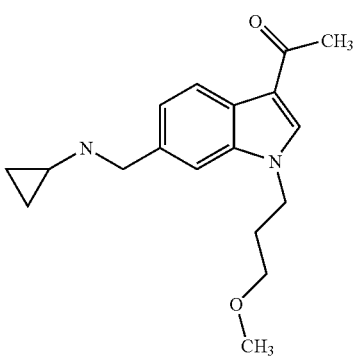 [SMILES: COCCCn1cc(C(C)=O)c2ccc(CNC3CC3)cc21] | Property: purified oil<br>APCI-MS m/z: 301[M + H]+ |

TABLE 20-continued

| No of Ref. Example | Structure | Properties |
|---|---|---|
| 298 | 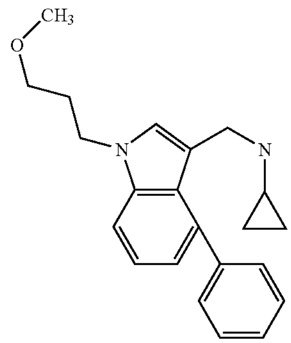 [SMILES: COCCCn1cc(CNC2CC2)c2c(-c3ccccc3)cccc21] | Property: purified viscous oil<br>APCI-MS m/z: 335[M + H]$^+$ |
| 299 | 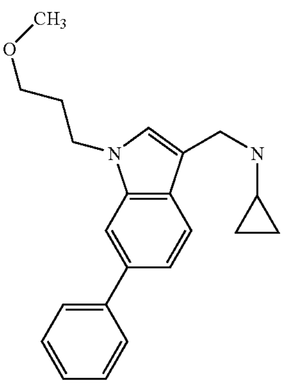 | Property: purified viscous oil<br>APCI-MS m/z: 278[M + H]$^+$ |
| 300 | 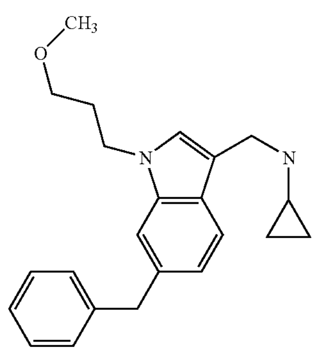 | Property: purified viscous oil<br>APCI-MS m/z: 292[M + H]$^+$ |
| 301 | 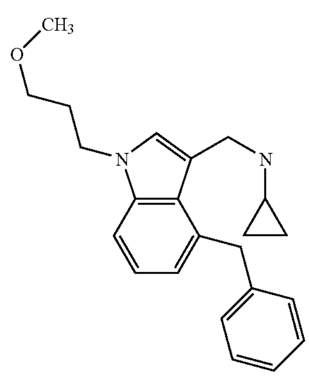 [SMILES: COCCCn1cc(CNC2CC2)c2c(Cc3ccccc3)cccc21] | Property: purified viscous oil<br>APCI-MS m/z: 349[M + H]$^+$ |

TABLE 20-continued

| No of Ref. Example | Structure | Properties |
|---|---|---|
| 302 | 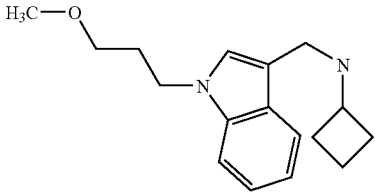 | Property: purified viscous oil<br>APCI-MS m/z: 202[M + H]$^+$ |
| 303 | 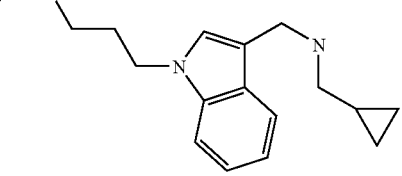 | Property: purified viscous oil<br>APCI-MS m/z: 202[M + H]$^+$ |
| 304 | 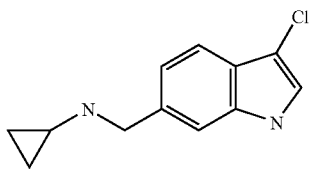 [SMILES: Clc1c[nH]c2cc(CNC3CC3)ccc12] | Property: purified powder<br>APCI-MS m/z: 221/223[M + H]$^+$ |
| 305 | 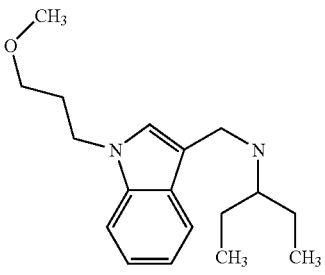 [SMILES: CCC(CC)NCc1cn(CCCOC)c2ccccc12] | Property: purified viscous oil<br>APCI-MS m/z: 289[M + H]$^+$ |
| 306 | 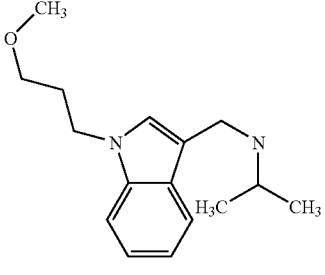 | Property: purified viscous oil<br>APCI-MS m/z: 202[M + H]$^+$ |
| 307 | 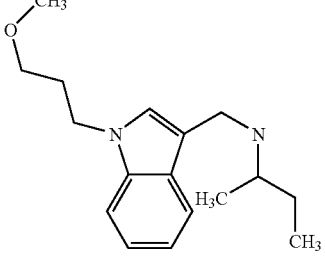 | Property: purified viscous oil<br>APCI-MS m/z: 202[M + H]$^+$ |

TABLE 20-continued

| No of Ref. Example | Structure | Properties |
|---|---|---|
| 308 | 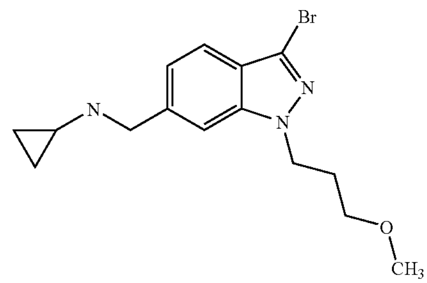 [SMILES: COCCCn1nc(Br)c2ccc(CNC3CC3)cc21] | Property: purified oil<br>APCI-MS m/z: 338/340[M + H]+ |
| 309 | 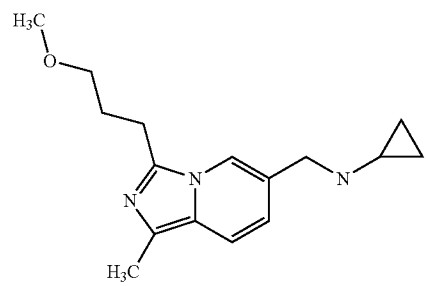 [SMILES: COCCCc1nc(C)c2ccc(CNC3CC3)cn12] | Property: purified viscous oil<br>APCI-MS m/z: 274[M + H]+ |
| 310 | 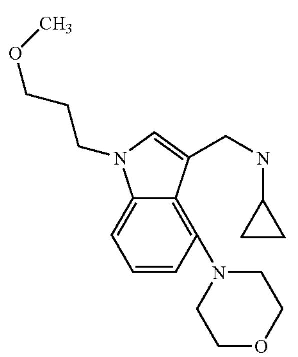 [SMILES: COCCCn1cc(CNC2CC2)c2c(N3CCOCC3)cccc21] | Property: purified viscous oil<br>APCI-MS m/z: 344[M + H]+ |
| 311 | 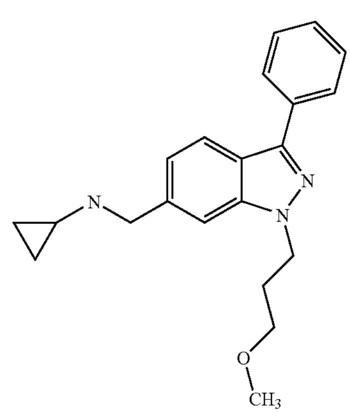 [SMILES: COCCCn1nc(-c2ccccc2)c2ccc(CNC3CC3)cc21] | hydrochloride<br>Property: purified powder<br>APCI-MS m/z: 336[M + H]+ |

TABLE 20-continued
| No of Ref. Example | Structure | Properties |
|---|---|---|
| 312 | 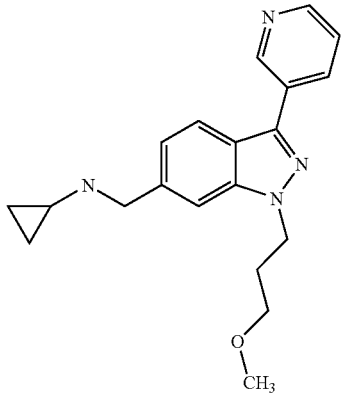 [SMILES: COCCCn1nc(-c2cccnc2)c2ccc(CNC3CC3)cc21] | dihydrochloride<br>Property: purified powder<br>APCI-MS m/z: 337[M + H]$^+$ |
| 313 | 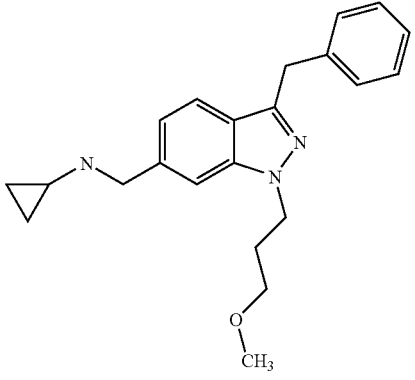 [SMILES: COCCCn1nc(Cc2ccccc2)c2ccc(CNC3CC3)cc21] | hydrochloride<br>Property: purified oil<br>APCI-MS m/z: 350[M + H]$^+$ |
| 314 | 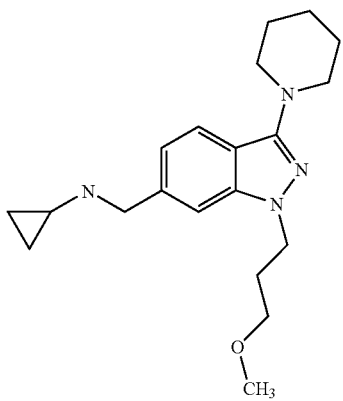 [SMILES: COCCCn1nc(N2CCCCC2)c2ccc(CNC3CC3)cc21] | dihydrochloride<br>Property: purified oil<br>APCI-MS m/z: 343[M + H]$^+$ |

TABLE 20-continued
| No of Ref. Example | Structure | Properties |
|---|---|---|
| 315 | 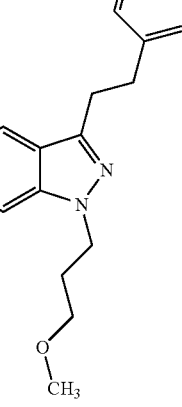 | hydrochloride<br>Property: purified powder<br>APCI-MS m/z: 364[M + H]$^+$ |
| 316 | 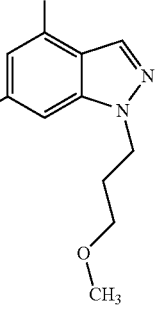 | Property: purified oil<br>APCI-MS m/z: 294/296[M + H]$^+$ |
| 317 | 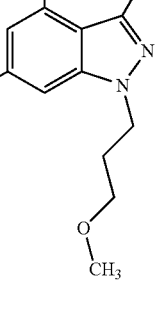 | Property: purified oil<br>APCI-MS m/z: 372/374[M + H]$^+$ |
| 318 | 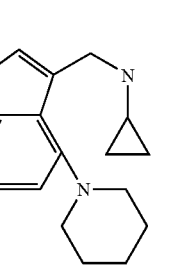 | Property: purified viscous oil<br>APCI-MS m/z: 342[M + H]$^+$ |

TABLE 20-continued
| No of Ref. Example | Structure | Properties |
|---|---|---|
| 319 | 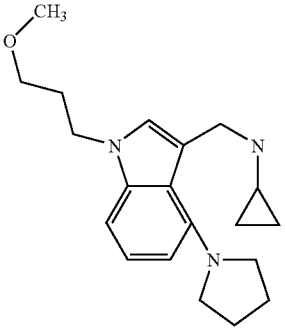 | Property: purified viscous oil<br>APCI-MS m/z: 328[M + H]+ |
| 320 | 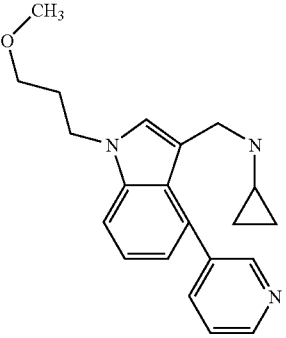 [SMILES: COCCCn1cc(CNC2CC2)c2c(-c3cccnc3)cccc21] | Property: purified viscous oil<br>APCI-MS m/z: 336[M + H]+ |
| 321 | 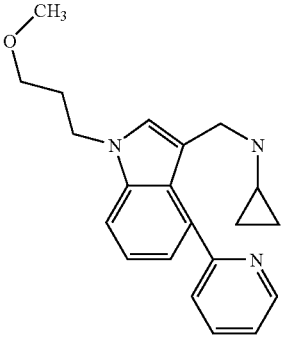 [SMILES: COCCCn1cc(CNC2CC2)c2c(-c3ccccn3)cccc21] | Property: purified viscous oil<br>APCI-MS m/z: 336[M + H]+ |
| 322 | 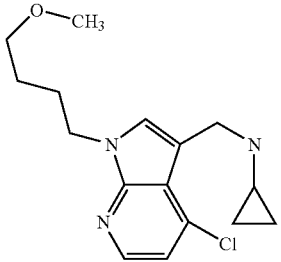 [SMILES: COCCCCn1cc(CNC2CC2)c2c(Cl)ccnc21] | Property: purified viscous oil<br>APCI-MS m/z: 308/310[M + H]+ |

TABLE 20-continued
| No of Ref. Example | Structure | Properties |
|---|---|---|
| 323 | 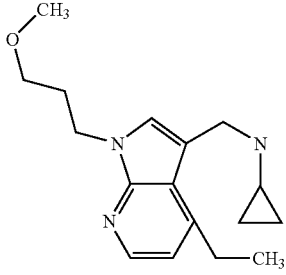 [SMILES: CCc1ccnc2c1c(CNC1CC1)cn2CCCOC] | Property: purified viscous oil<br>APCI-MS m/z: 288[M + H]⁺ |
| 324 | 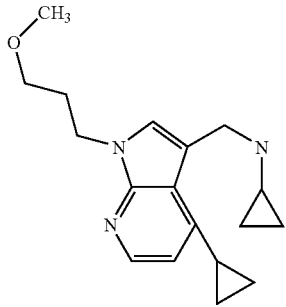 [SMILES: COCCCn1cc(CNC2CC2)c2c(C3CC3)ccnc21] | Property: purified viscous oil<br>APCI-MS m/z: 300[M + H]⁺ |
| 325 | 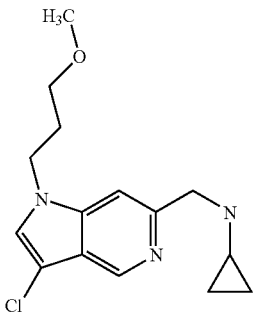 [SMILES: COCCCn1cc(Cl)c2cnc(CNC3CC3)cc21] | Property: purified oil<br>APCI-MS m/z: 294/296[M + H]⁺ |
| 326 | 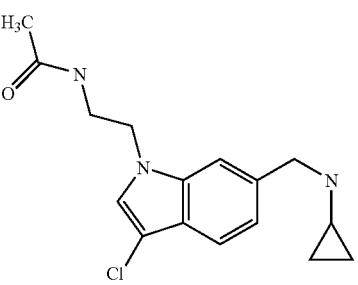 [SMILES: CC(=O)NCCn1cc(Cl)c2ccc(CNC3CC3)cc21] | Property: purified viscous oil<br>APCI-MS m/z: 306/308[M + H]⁺ |
| 327 | 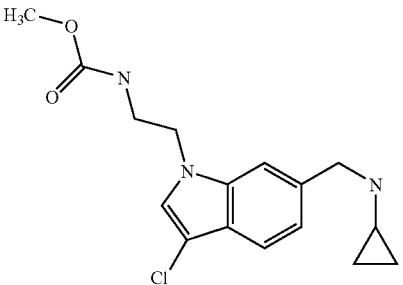 [SMILES: COC(=O)NCCn1cc(Cl)c2ccc(CNC3CC3)cc21] | Property: purified viscous oil<br>APCI-MS m/z: 322/324[M + H]⁺ |

TABLE 20-continued
| No of Ref. Example | Structure | Properties |
|---|---|---|
| 328 | 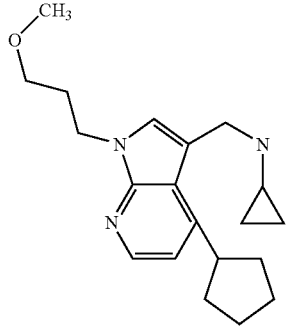 [SMILES: COCCCn1cc(CNC2CC2)c2c(C3CCCC3)ccnc21] | Property: purified viscous oil<br>APCI-MS m/z: 328[M + H]⁺ |
| 329 | 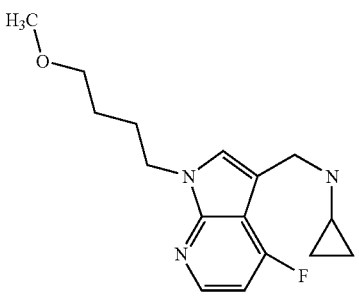 [SMILES: COCCCCn1cc(CNC2CC2)c2c(F)ccnc21] | Property: purified viscous oil<br>APCI-MS m/z: 292[M + H]⁺ |
| 330 | 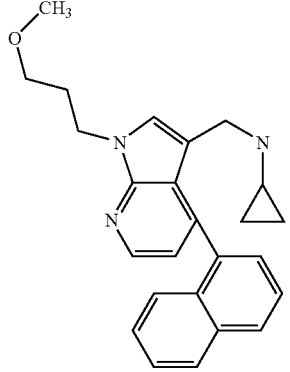 [SMILES: COCCCn1cc(CNC2CC2)c2c(-c3cccc4ccccc34)ccnc21] | Property: purified viscous oil<br>APCI-MS m/z: 386[M + H]⁺ |
| 331 | 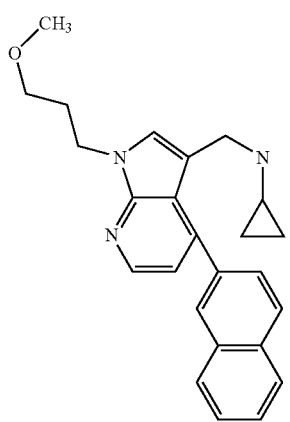 [SMILES: COCCCn1cc(CNC2CC2)c2c(-c3ccc4ccccc4c3)ccnc21] | Property: purified viscous oil<br>APCI-MS m/z: 386[M + H]⁺ |

TABLE 20-continued
| No of Ref. Example | Structure | Properties |
|---|---|---|
| 332 | 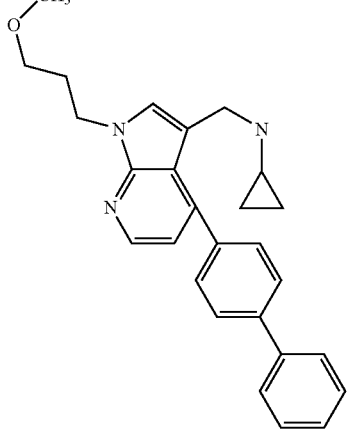 | Property: purified viscous oil<br>APCI-MS m/z: 412[M + H]$^+$ |
| 333 | 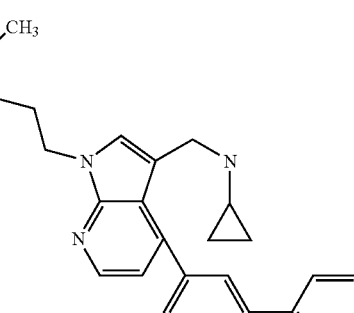 | Property: purified viscous oil<br>APCI-MS m/z: 412[M + H]$^+$ |
| 334 | 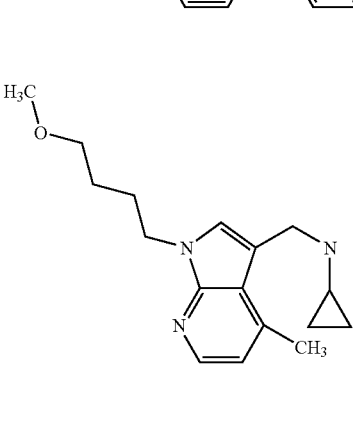 | Property: purified viscous oil<br>APCI-MS m/z: 288[M + H]$^+$ |
| 335 | 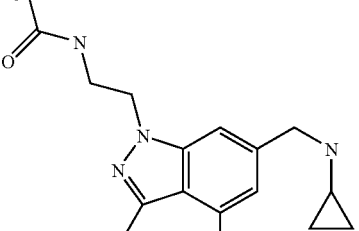 | Property: purified powder<br>APCI-MS m/z: 321/323[M + H]$^+$ |

TABLE 20-continued

| No of Ref. Example | Structure | Properties |
|---|---|---|
| 336 | 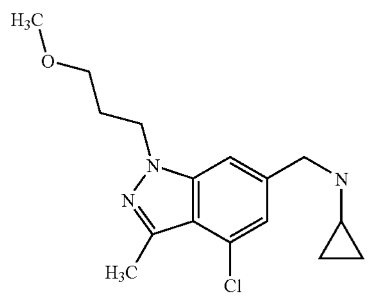 [SMILES: COCCCn1nc(C)c2c(Cl)cc(CNC3CC3)cc21] | hydrochloride<br>Property: purified powder<br>APCI-MS m/z: 308/310[M + H]⁺ |
| 337 | 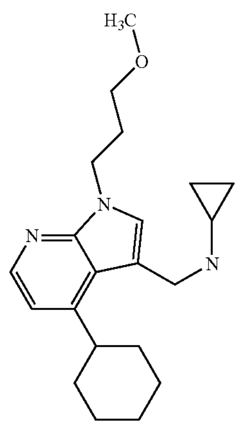 [SMILES: COCCCn1cc(CNC2CC2)c2c(C3CCCCC3)ccnc21] | Property: purified viscous oil<br>APCI-MS m/z: 342[M + H]⁺ |
| 338 | 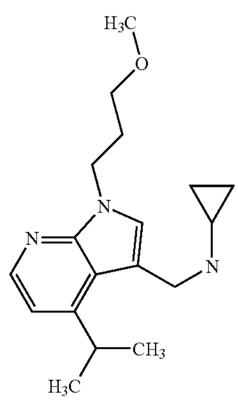 [SMILES: COCCCn1cc(CNC2CC2)c2c(C(C)C)ccnc21] | Property: purified viscous oil<br>APCI-MS m/z: 302[M + H]⁺ |
| 339 | 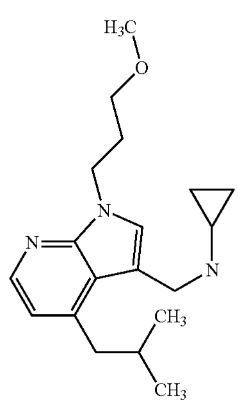 [SMILES: COCCCn1cc(CNC2CC2)c2c(CC(C)C)ccnc21] | Property: purified viscous oil<br>APCI-MS m/z: 316[M + H]⁺ |

TABLE 20-continued
| No of Ref. Example | Structure | Properties |
|---|---|---|
| 340 | 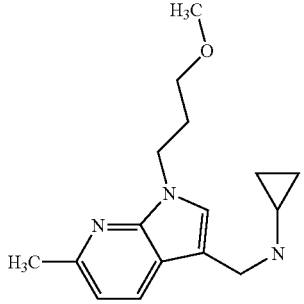 [SMILES: COCCCn1cc(CNC2CC2)c2ccc(C)nc21] | Property: purified viscous oil<br>APCI-MS m/z: 274[M + H]$^+$ |
| 341 | 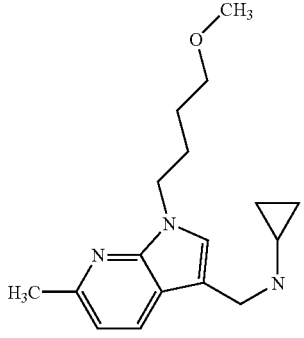 [SMILES: COCCCCn1cc(CNC2CC2)c2ccc(C)nc21] | Property: purified viscous oil<br>APCI-MS m/z: 288[M + H]$^+$ |
| 342 | 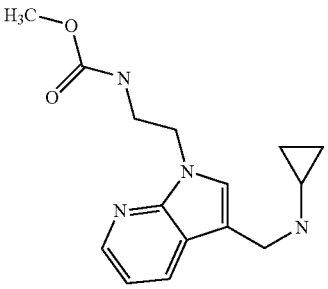 [SMILES: COC(=O)NCCn1cc(CNC2CC2)c2cccnc21] | dihydrochloride<br>Property: purified powder<br>APCI-MS m/z: 289[M + H]$^+$ |
| 343 | 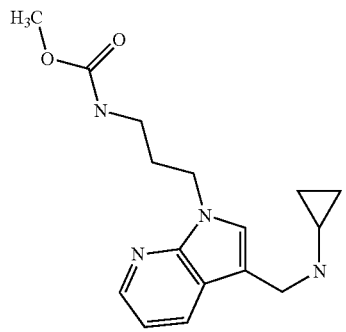 [SMILES: COC(=O)NCCCn1cc(CNC2CC2)c2cccnc21] | dihydrochloride<br>Property: purified powder<br>APCI-MS m/z: 303[M + H]$^+$ |

TABLE 20-continued

| No of Ref. Example | Structure | Properties |
|---|---|---|
| 344 | 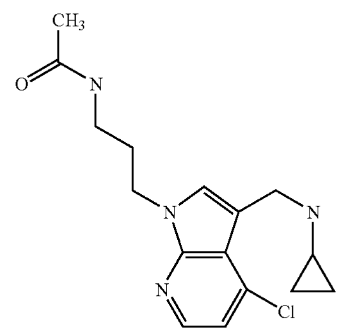 [SMILES: CC(=O)NCCCn1cc(CNC2CC2)c2c(Cl)ccnc21] | hydrochloride<br>Property: purified viscous oil<br>APCI-MS m/z: 321/323[M + H]⁺ |
| 345 | 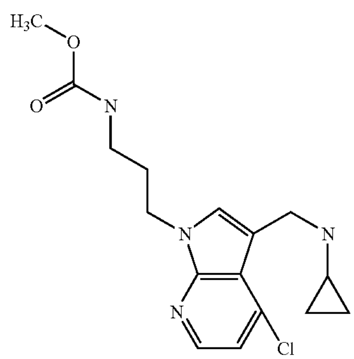 [SMILES: COC(=O)NCCCn1cc(CNC2CC2)c2c(Cl)ccnc21] | hydrochloride<br>Property: purified powder<br>APCI-MS m/z: 337/339[M + H]⁺ |
| 346 | 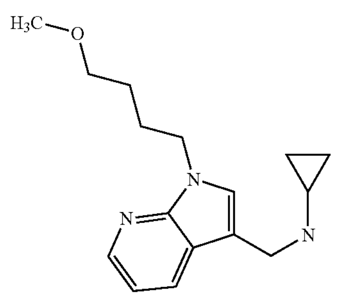 [SMILES: COCCCCn1cc(CNC2CC2)c2cccnc21] | dihydrochloride<br>Property: purified powder<br>APCI-MS m/z: 274[M + H]⁺ |
| 347 | 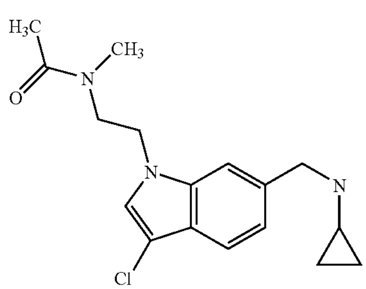 [SMILES: CC(=O)N(C)CCn1cc(Cl)c2ccc(CNC3CC3)cc21] | Property: purified viscous oil<br>APCI-MS m/z: 320/322[M + H]⁺ |

TABLE 20-continued
| No of Ref. Example | Structure | Properties |
|---|---|---|
| 348 | 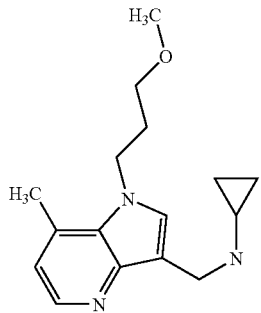 [SMILES: COCCCn1cc(CNC2CC2)c2nccc(C)c21] | Property: purified viscous oil<br>APCI-MS m/z: 274[M + H]⁺ |
| 349 | 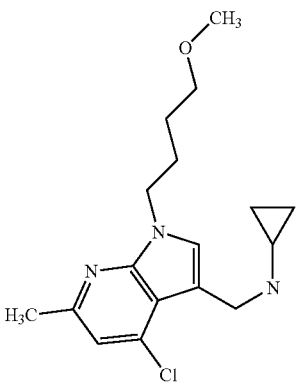 [SMILES: COCCCCn1cc(CNC2CC2)c2c(Cl)cc(C)nc21] | Property: purified viscous oil<br>APCI-MS m/z: 321/323[M + H]⁺ |
| 350 | 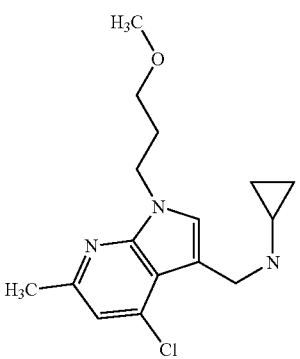 [SMILES: COCCCn1cc(CNC2CC2)c2c(Cl)cc(C)nc21] | Property: purified viscous oil<br>APCI-MS m/z: 308/310[M + H]⁺ |
| 351 | 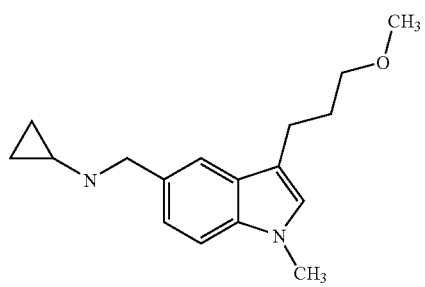 [SMILES: COCCCc1cn(C)c2ccc(CNC3CC3)cc12] | Property: purified oil<br>APCI-MS m/z: 273[M + H]⁺ |

TABLE 20-continued
| No of Ref. Example | Structure | Properties |
|---|---|---|
| 352 | 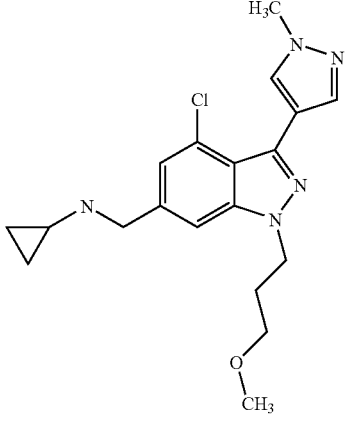 [SMILES: COCCCn1nc(-c2cnn(C)c2)c2c(Cl)cc(CNC3CC3)cc21] | hydrochloride<br>Property: purified powder<br>APCI-MS m/z: 374/378[M + H]$^+$ |
| 353 | 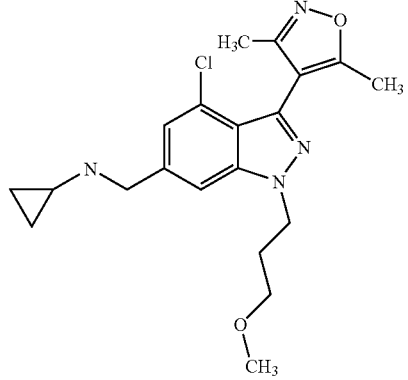 [SMILES: COCCCn1nc(-c2c(C)noc2C)c2c(Cl)cc(CNC3CC3)cc21] | hydrochloride<br>Property: purified powder<br>APCI-MS m/z: 389/391[M + H]$^+$ |
| 354 | 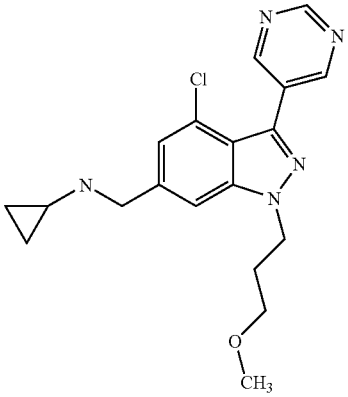 [SMILES: COCCCn1nc(-c2cncnc2)c2c(Cl)cc(CNC3CC3)cc21] | hydrochloride<br>Property: purified powder<br>APCI-MS m/z: 371/373[M + H]$^+$ |
| 355 | 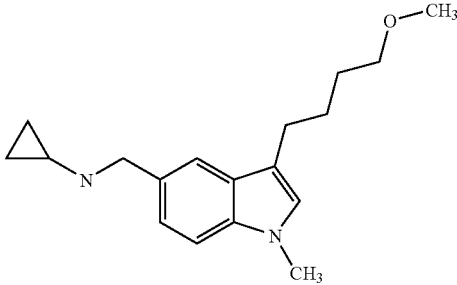 [SMILES: COCCCCc1cn(C)c2ccc(CNC3CC3)cc12] | Property: purified oil<br>APCI-MS m/z: 287[M + H]$^+$ |

TABLE 20-continued
| No of Ref. Example | Structure | Properties |
|---|---|---|
| 356 | 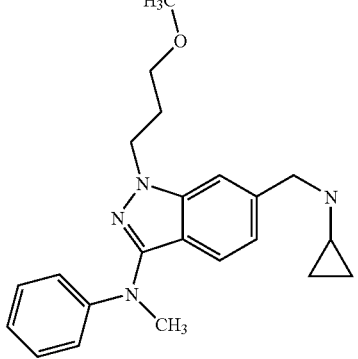 | hydrochloride<br>Property: purified oil<br>APCI-MS m/z: 365[M + H]$^+$ |
| 357 | 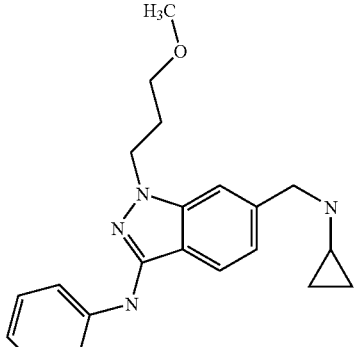 | hydrochloride<br>Property: purified powder<br>APCI-MS m/z: 351[M + H]$^+$ |
| 358 | 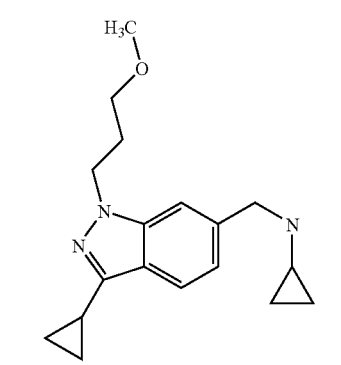 [SMILES: COCCCn1nc(C2CC2)c2ccc(CNC3CC3)cc21] | hydrochloride<br>Property: purified powder<br>APCI-MS m/z: 300[M + H]$^+$ |
| 359 | 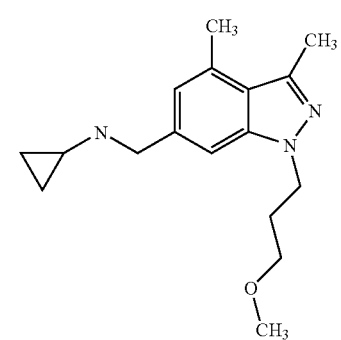 [SMILES: COCCCn1nc(C)c2c(C)cc(CNC3CC3)cc21] | hydrochloride<br>Property: purified powder<br>APCI-MS m/z: 288[M + H]$^+$ |

TABLE 20-continued

| No of Ref. Example | Structure | Properties |
|---|---|---|
| 360 | 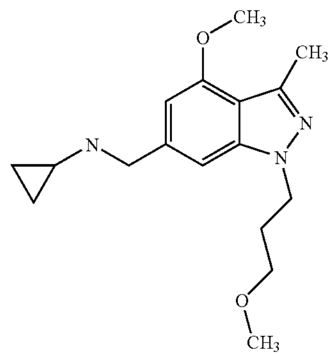 [SMILES: COCCCn1nc(C)c2c(OC)cc(CNC3CC3)cc21] | hydrochloride<br>Property: purified powder<br>APCI-MS m/z: 304[M + H]⁺ |
| 361 | 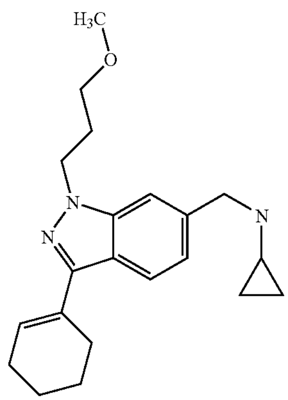 [SMILES: COCCCn1nc(C2=CCCCC2)c2ccc(CNC3CC3)cc21] | hydrochloride<br>Property: purified powder<br>APCI-MS m/z: 340[M + H]⁺ |
| 362 | 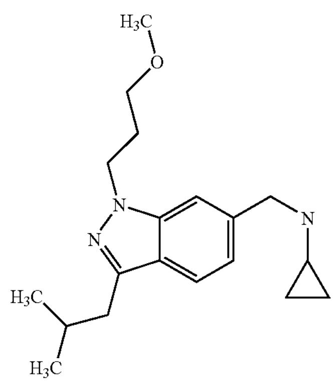 [SMILES: COCCCn1nc(CC(C)C)c2ccc(CNC3CC3)cc21] | hydrochloride<br>Property: purified viscous oil<br>APCI-MS m/z: 316[M + H]⁺ |
| 363 | 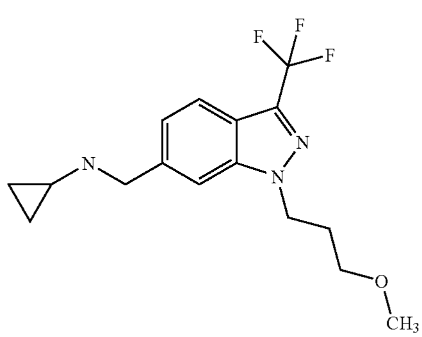 [SMILES: COCCCn1nc(C(F)(F)F)c2ccc(CNC3CC3)cc21] | Property: purified oil<br>APCI-MS m/z: 328[M + H]⁺ |

TABLE 20-continued

| No of Ref. Example | Structure | Properties |
|---|---|---|
| 364 | 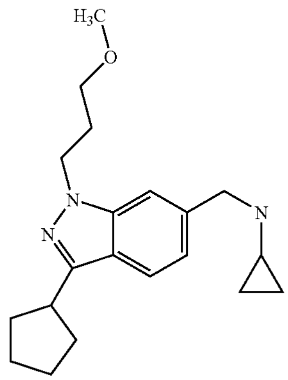 [SMILES: COCCCn1nc(C2CCCC2)c2ccc(CNC3CC3)cc21] | hydrochloride<br>Property: purified powder<br>APCI-MS m/z: 328[M + H]$^+$ |
| 365 | 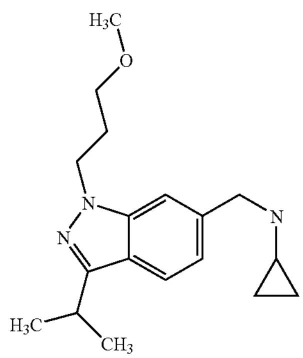 [SMILES: COCCCn1nc(C(C)C)c2ccc(CNC3CC3)cc21] | hydrochloride<br>Property: purified powder<br>APCI-MS m/z: 302[M + H]$^+$ |
| 366 | 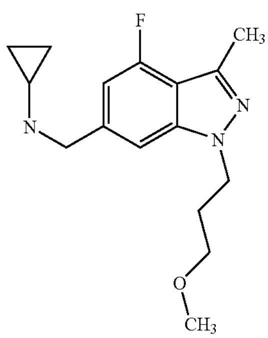 [SMILES: COCCCn1nc(C)c2c(F)cc(CNC3CC3)cc21] | Property: purified oil<br>APCI-MS m/z: 292[M + H]$^+$ |
| 367 | 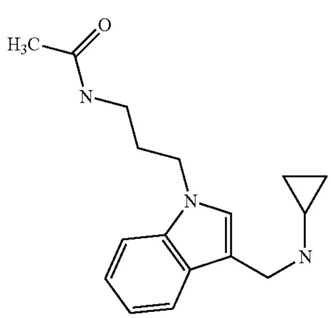 [SMILES: CC(=O)NCCCn1cc(CNC2CC2)c2ccccc21] | Property: purified oil<br>APCI-MS m/z: 286[M + H]$^+$ |

TABLE 20-continued

| No of Ref. Example | Structure | Properties |
|---|---|---|
| 368 | 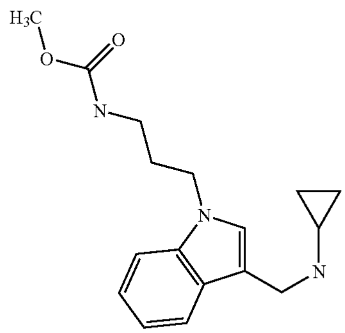 [SMILES: COC(=O)NCCCn1cc(CNC2CC2)c2ccccc21] | Property: purified oil<br>APCI-MS m/z: 302[M + H]+ |
| 369 | 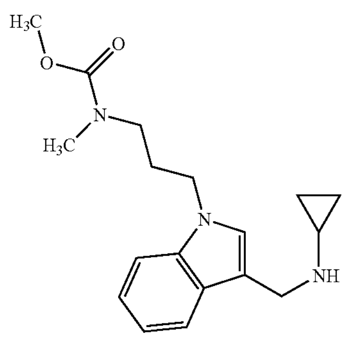 [SMILES: COC(=O)N(C)CCCn1cc(CNC2CC2)c2ccccc21] | Property: purified liquid<br>APCI-MS m/z: 316[M + H]+ |
| 370 | 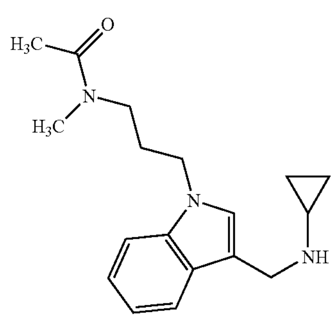 [SMILES: CC(=O)N(C)CCCn1cc(CNC2CC2)c2ccccc21] | Property: purified liquid<br>APCI-MS m/z: 300[M + H]+ |
| 371 | 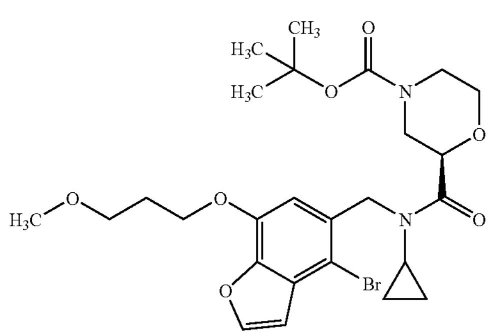 [SMILES: COCCCOc1cc(CN(C(=O)[C@H]2CN(C(=O)OC(C)(C)C)CCO2)C2CC2)c(Br)c2ccoc12] | Property: purified viscous oil<br>APCI-MS m/z: 567/569[M + H]+ |

TABLE 20-continued
| No of Ref. Example | Structure | Properties |
|---|---|---|
| 372 | 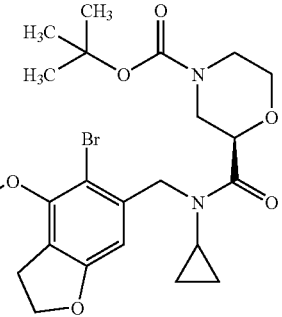 | Property: purified viscous oil<br>APCI-MS m/z: 569/571[M + H]+ |
| 373 | 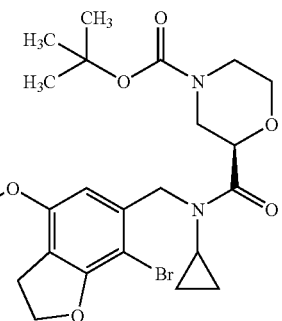 | Property: purified viscous oil<br>APCI-MS m/z: 569/571[M + H]+ |
| 374 | 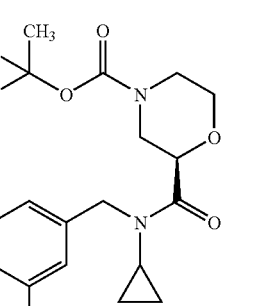 | Property: purified viscous oil<br>APCI-MS m/z: 517[M + H]+ |
| 375 | 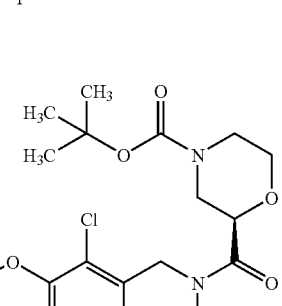 | Property: purified viscous oil<br>APCI-MS m/z: 567/569[M + H]+ |

TABLE 20-continued

| No of Ref. Example | Structure | Properties |
|---|---|---|
| 376 | 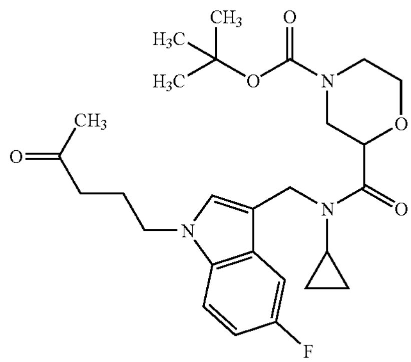 [SMILES: CC(=O)CCCn1cc(CN(C(=O)C2CN(C(=O)OC(C)(C)C)CCO2)C2CC2)c2cc(F)ccc21] | Property: purified viscous oil<br>APCI-MS m/z: 502[M + H]⁺ |
| 377 | 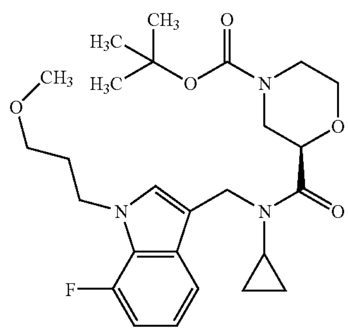 [SMILES: COCCCn1cc(CN(C(=O)[C@H]2CN(C(=O)OC(C)(C)C)CCO2)C2CC2)c2cccc(F)c21] | Property: purified viscous oil<br>APCI-MS m/z: 490[M + H]⁺ |
| 378 | 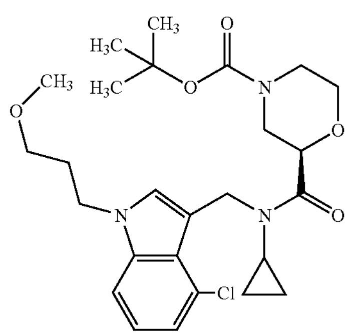 | Property: purified viscous oil<br>APCI-MS m/z: 506/508[M + H]⁺ |
| 379 | 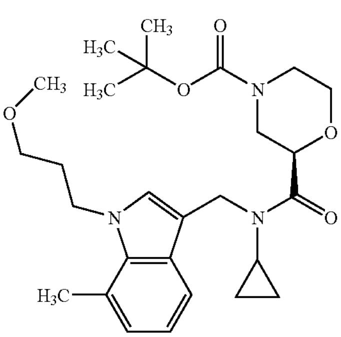 [SMILES: COCCCn1cc(CN(C(=O)[C@H]2CN(C(=O)OC(C)(C)C)CCO2)C2CC2)c2cccc(C)c21] | Property: purified viscous oil<br>APCI-MS m/z: 486[M + H]⁺ |

TABLE 20-continued
| No of Ref. Example | Structure | Properties |
|---|---|---|
| 380 | 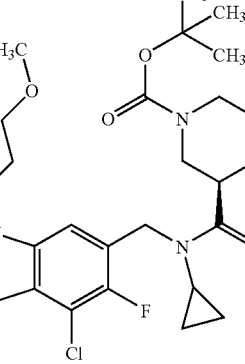 | Property: purified liquid<br>APCI-MS m/z: 524/526[M + H]+ |
| 381 | 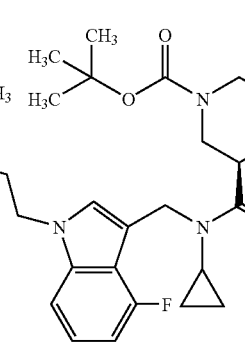 | Property: purified viscous oil<br>APCI-MS m/z: 490[M + H]+ |
| 382 | 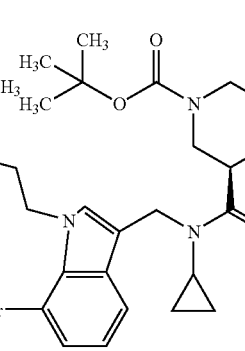 | Property: purified viscous oil<br>APCI-MS m/z: 550/552[M + H]+ |
| 383 | 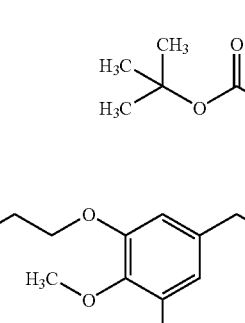 | Property: purified viscous oil<br>APCI-MS m/z: 555[M + H]+ |

TABLE 20-continued
| No of Ref. Example | Structure | Properties |
|---|---|---|
| 384 | 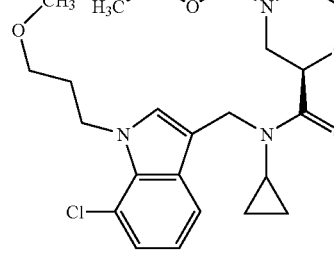 | Property: purified viscous oil<br>APCI-MS m/z: 506/508[M + H]$^+$ |
| 385 | 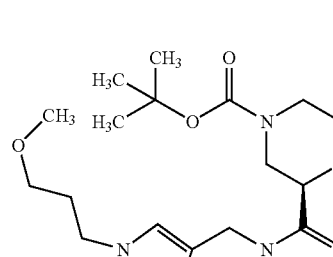 | Property: purified viscous oil<br>APCI-MS m/z: 502[M + H]$^+$ |
| 386 | 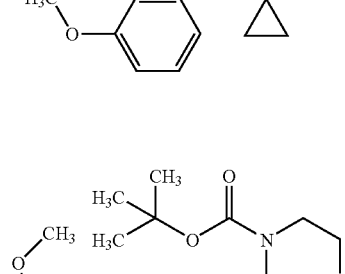 | Property: purified viscous oil<br>APCI-MS m/z: 550/552[M + H]$^+$ |
| 387 | 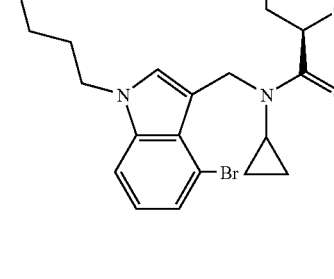 | Property: purified viscous oil<br>APCI-MS m/z: 508[M + H]$^+$ |

TABLE 20-continued

| No of Ref. Example | Structure | Properties |
|---|---|---|
| 388 | 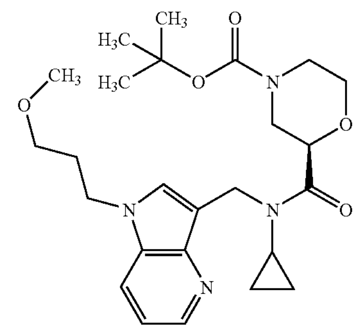 [SMILES: COCCCn1cc(CN(C(=O)[C@H]2CN(C(=O)OC(C)(C)C)CCO2)C2CC2)c2ncccc21] | Property: purified viscous oil<br>APCI-MS m/z: 473[M + H]⁺ |
| 389 | 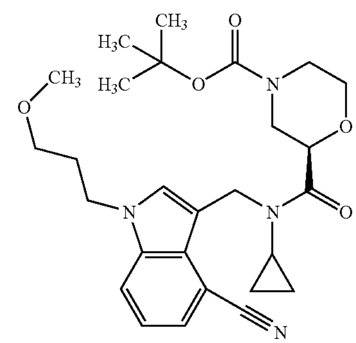 [SMILES: COCCCn1cc(CN(C(=O)[C@H]2CN(C(=O)OC(C)(C)C)CCO2)C2CC2)c2c(C#N)cccc21] | Property: purified viscous oil<br>APCI-MS m/z: 497[M + H]⁺ |
| 390 | 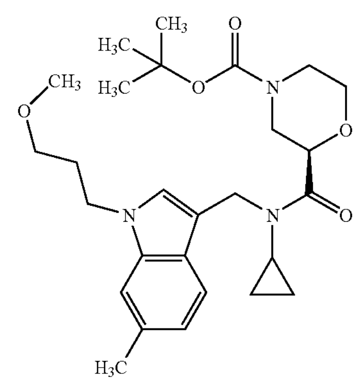 [SMILES: COCCCn1cc(CN(C(=O)[C@H]2CN(C(=O)OC(C)(C)C)CCO2)C2CC2)c2ccc(C)cc21] | Property: purified viscous oil<br>APCI-MS m/z: 486[M + H]⁺ |
| 391 | 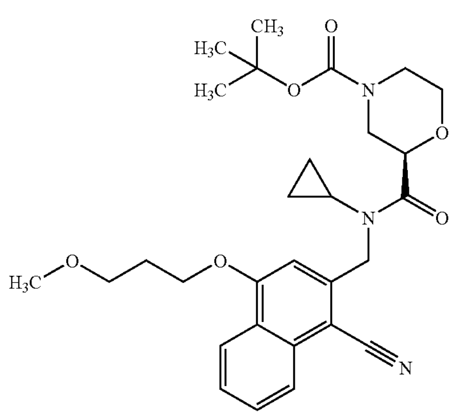 [SMILES: COCCCOc1cc(CN(C(=O)[C@H]2CN(C(=O)OC(C)(C)C)CCO2)C2CC2)c(C#N)c2ccccc12] | Property: purified viscous oil<br>APCI-MS m/z: 524[M + H]⁺ |

TABLE 20-continued
| No of Ref. Example | Structure | Properties |
|---|---|---|
| 392 | 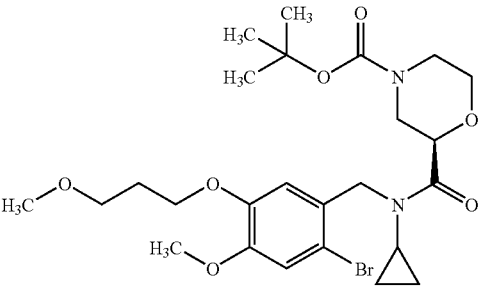 | Property: purified viscous oil<br>APCI-MS m/z: 557/559[M + H]$^+$ |
| 393 | 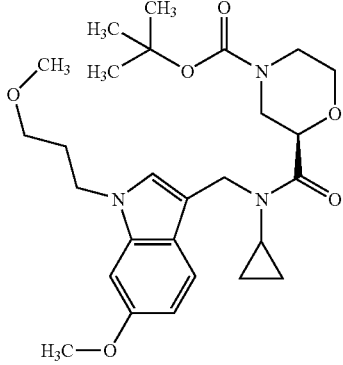 [SMILES: COCCCn1cc(CN(C(=O)[C@H]2CN(C(=O)OC(C)(C)C)CCO2)C2CC2)c2ccc(OC)cc21] | Property: purified viscous oil<br>APCI-MS m/z: 502[M + H]$^+$ |
| 394 | 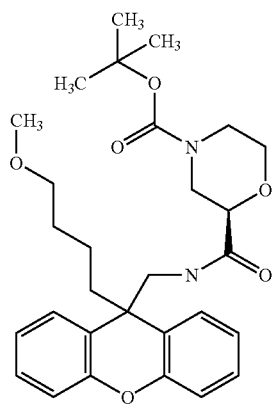 [SMILES: COCCCCC1(CNC(=O)[C@H]2CN(C(=O)OC(C)(C)C)CCO2)c2ccccc2Oc2ccccc21] | Property: purified viscous oil<br>APCI-MS m/z: 511[M + H]$^+$ |
| 395 | 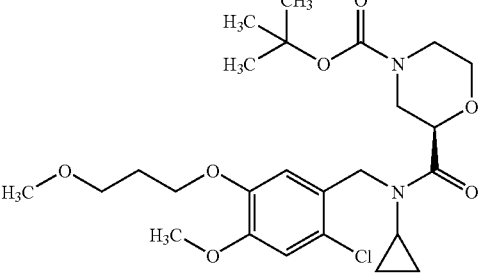 | Property: purified viscous oil<br>APCI-MS m/z: 513/515[M + H]$^+$ |

TABLE 20-continued
| No of Ref. Example | Structure | Properties |
|---|---|---|
| 396 | 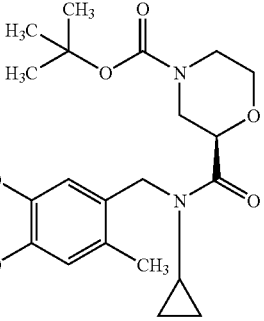 | Property: purified viscous oil<br>APCI-MS m/z: 493[M + H]$^+$ |
| 397 | 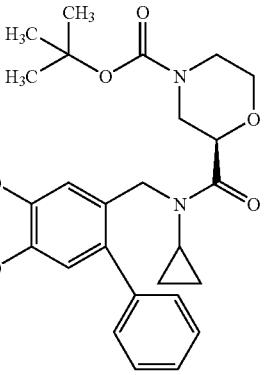 | Property: purified viscous oil<br>APCI-MS m/z: 555[M + H]$^+$ |
| 398 | 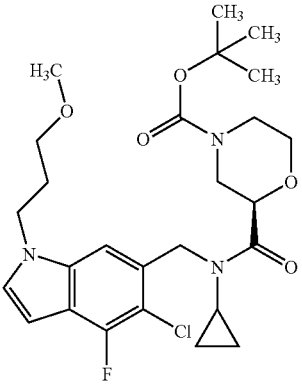 [SMILES: COCCCn1ccc2c(F)c(Cl)c(CN(C(=O)[C@H]3CN(C(=O)OC(C)(C)C)CCO3)C3CC3)cc21] | Property: purified liquid<br>APCI-MS m/z: 524/526[M + H]$^+$ |
| 399 | 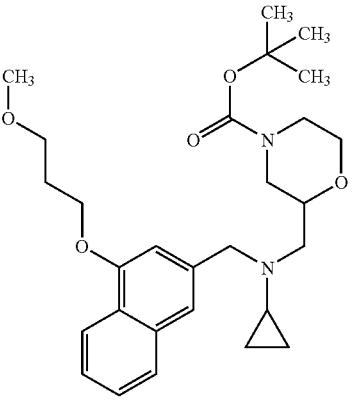 [SMILES: COCCCOc1cc(CN(CC2CN(C(=O)OC(C)(C)C)CCO2)C2CC2)cc2ccccc12] | Property: purified liquid<br>APCI-MS m/z: 485[M + H]$^+$ |

TABLE 20-continued

| No of Ref. Example | Structure | Properties |
|---|---|---|
| 400 | 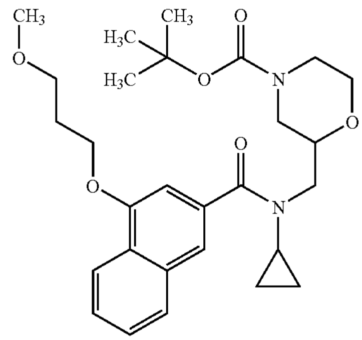 [SMILES: COCCCOc1cc(C(=O)N(CC2CN(C(=O)OC(C)(C)C)CCO2)C2CC2)cc2ccccc12] | Property: purified liquid<br>APCI-MS m/z: 516[M + H]+ |
| 401 | 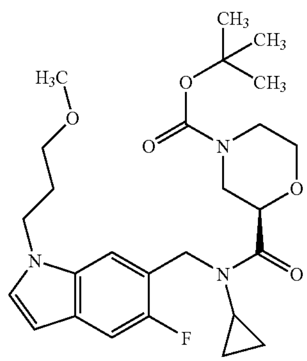 [SMILES: COCCCn1ccc2cc(F)c(CN(C(=O)[C@H]3CN(C(=O)OC(C)(C)C)CCO3)C3CC3)cc21] | Property: purified liquid<br>APCI-MS m/z: 490[M + H]+ |
| 402 | 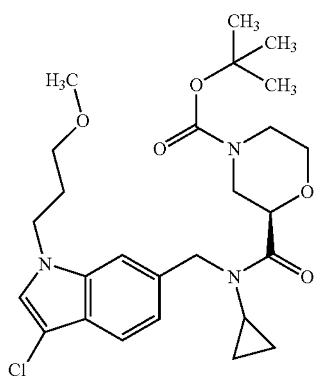 [SMILES: COCCCn1cc(Cl)c2ccc(CN(C(=O)[C@H]3CN(C(=O)OC(C)(C)C)CCO3)C3CC3)cc21] | Property: purified liquid<br>APCI-MS m/z: 506/508[M + H]+ |
| 403 | 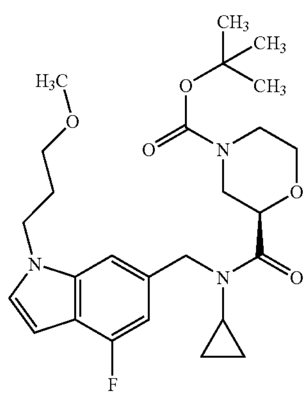 [SMILES: COCCCn1ccc2c(F)cc(CN(C(=O)[C@H]3CN(C(=O)OC(C)(C)C)CCO3)C3CC3)cc21] | Property: purified liquid<br>APCI-MS m/z: 490[M + H]+ |

TABLE 20-continued

| No of Ref. Example | Structure | Properties |
|---|---|---|
| 404 | 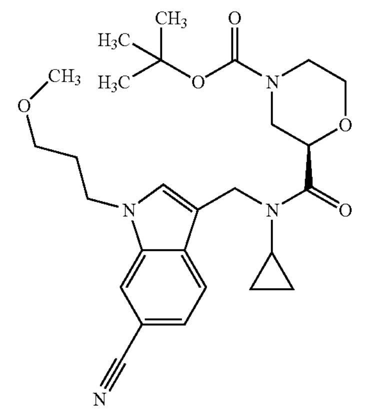 [SMILES: COCCCn1cc(CN(C(=O)[C@H]2CN(C(=O)OC(C)(C)C)CCO2)C2CC2)c2ccc(C#N)cc21] | Property: purified powder<br>APCI-MS m/z: 497[M + H]⁺ |
| 405 | 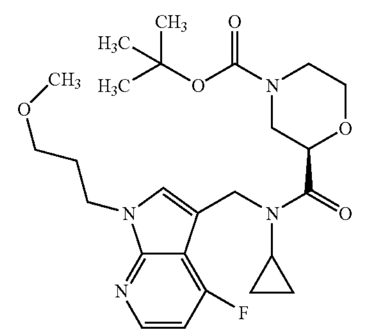 [SMILES: COCCCn1cc(CN(C(=O)[C@H]2CN(C(=O)OC(C)(C)C)CCO2)C2CC2)c2c(F)ccnc21] | Property: purified viscous oil<br>APCI-MS m/z: 491[M + H]⁺ |
| 406 | 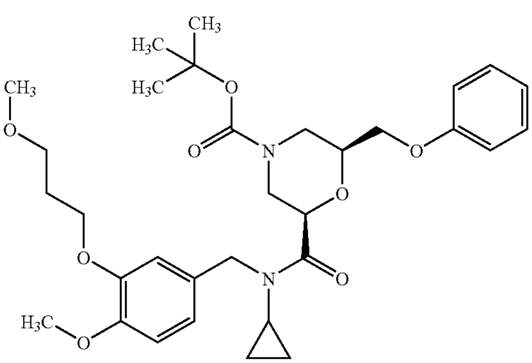 [SMILES: COCCCOc1cc(CN(C(=O)[C@H]2CN(C(=O)OC(C)(C)C)C[C@@H](COc3ccccc3)O2)C2CC2)ccc1OC] | Property: purified viscous oil<br>APCI-MS m/z: 585[M + H]⁺ |
| 407 | 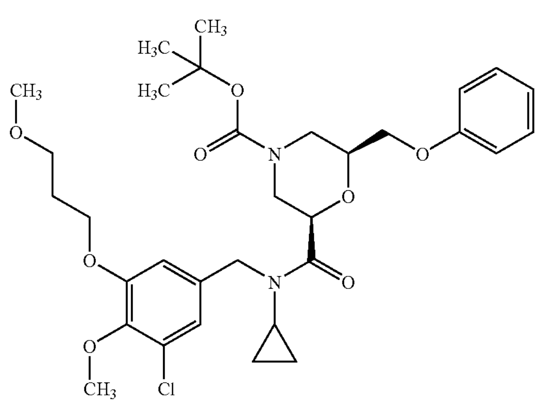 [SMILES: COCCCOc1cc(CN(C(=O)[C@H]2CN(C(=O)OC(C)(C)C)C[C@@H](COc3ccccc3)O2)C2CC2)cc(Cl)c1OC] | Property: purified viscous oil<br>APCI-MS m/z: 619/621[M + H]⁺ |

TABLE 20-continued
| No of Ref. Example | Structure | Properties |
|---|---|---|
| 408 | 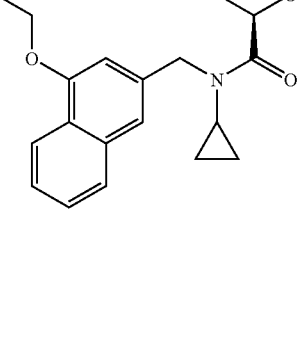 | Property: purified viscous oil<br>APCI-MS m/z: 605[M + H]$^+$ |
| 409 | 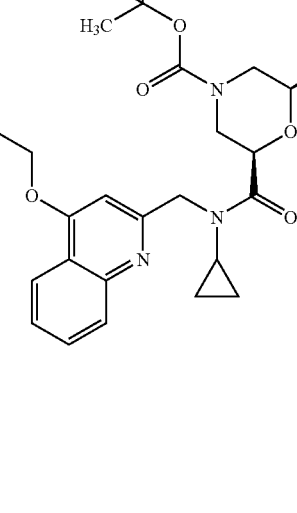 | Property: purified viscous oil<br>APCI-MS m/z: 606[M + H]$^+$ |
| 410 | 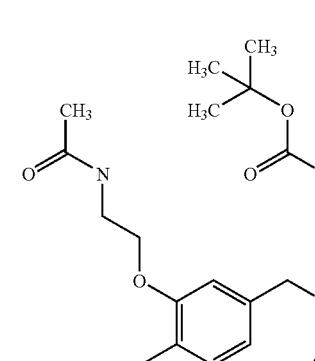 | Property: purified viscous oil<br>APCI-MS m/z: 512[M + H]$^+$ |

TABLE 20-continued
| No of Ref. Example | Structure | Properties |
|---|---|---|
| 411 | 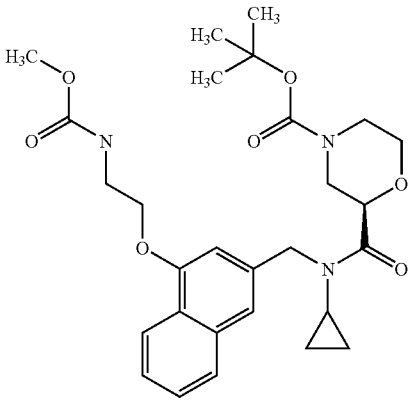 [SMILES: COC(=O)NCCOc1cc(CN(C(=O)[C@H]2CN(C(=O)OC(C)(C)C)CCO2)C2CC2)cc2ccccc12] | Property: purified powder<br>APCI-MS m/z: 528[M + H]$^+$ |
| 412 | 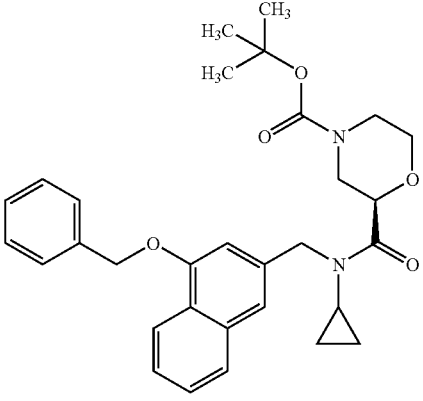 [SMILES: CC(C)(C)OC(=O)N1CCO[C@@H](C(=O)N(Cc2cc(OCc3ccccc3)c3ccccc3c2)C2CC2)C1] | Property: purified viscous oil<br>APCI-MS m/z: 517[M + H]$^+$ |
| 413 | 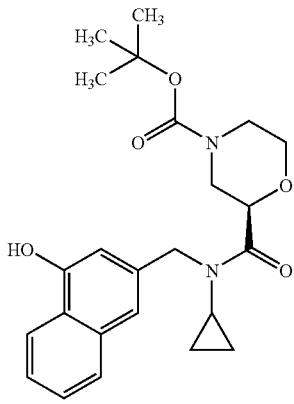 [SMILES: CC(C)(C)OC(=O)N1CCO[C@@H](C(=O)N(Cc2cc(O)c3ccccc3c2)C2CC2)C1] | Property: purified powder<br>APCI-MS m/z: 427[M + H]$^+$ |

TABLE 20-continued
| No of Ref. Example | Structure | Properties |
|---|---|---|
| 414 | 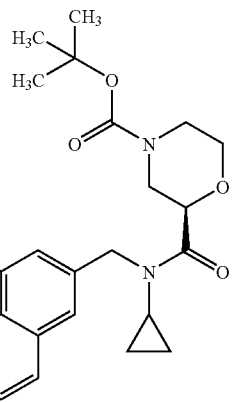 | Property: purified viscous oil<br>APCI-MS m/z: 441[M + H]$^+$ |
| 415 | 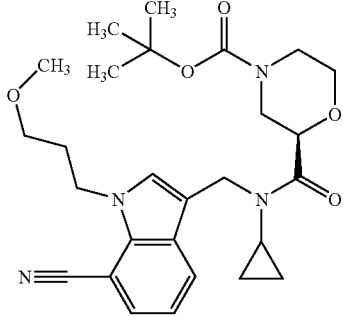 [SMILES: COCCCn1cc(CN(C(=O)[C@H]2CN(C(=O)OC(C)(C)C)CCO2)C2CC2)c2cccc(C#N)c21] | Property: purified viscous oil<br>APCI-MS m/z: 497[M + H]$^+$ |
| 416 | 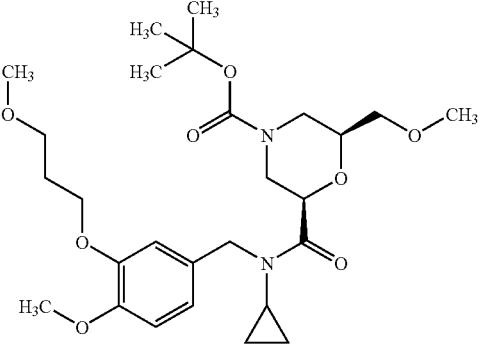 [SMILES: COCCCOc1cc(CN(C(=O)[C@H]2CN(C(=O)OC(C)(C)C)C[C@@H](COC)O2)C2CC2)ccc1OC] | Property: purified viscous oil<br>APCI-MS m/z: 540[M + NH4]+ |
| 417 | 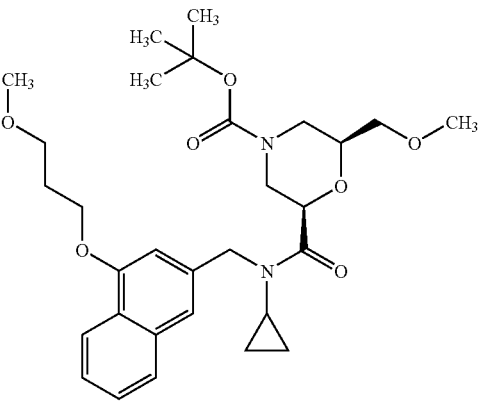 [SMILES: COCCCOc1cc(CN(C(=O)[C@H]2CN(C(=O)OC(C)(C)C)C[C@@H](COC)O2)C2CC2)cc2ccccc12] | Property: purified viscous oil<br>APCI-MS m/z: 560[M + NH4]$^+$ |

TABLE 20-continued
| No of Ref. Example | Structure | Properties |
|---|---|---|
| 418 | 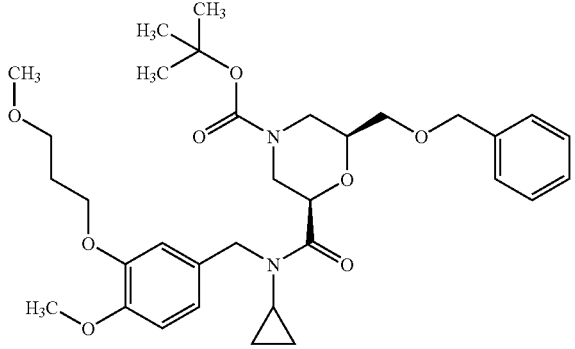 [SMILES: COCCCOc1cc(CN(C(=O)[C@H]2CN(C(=O)OC(C)(C)C)C[C@@H](COCc3ccccc3)O2)C2CC2)ccc1OC] | Property: purified viscous oil<br>APCI-MS m/z: 616[M + NH4]$^+$ |
| 419 | 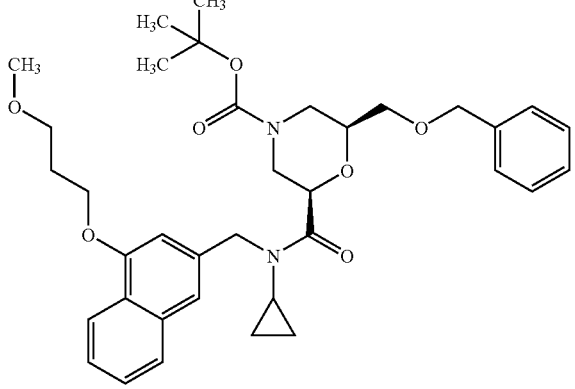 | Property: purified viscous oil<br>APCI-MS m/z: 636[M + NH4]$^+$ |
| 420 | 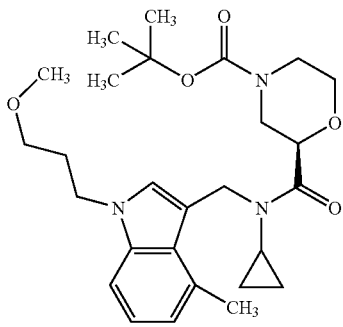 [SMILES: COCCCn1cc(CN(C(=O)[C@H]2CN(C(=O)OC(C)(C)C)CCO2)C2CC2)c2c(C)cccc21] | Property: purified viscous oil<br>APCI-MS m/z: 503[M + NH4]$^+$ |
| 421 | 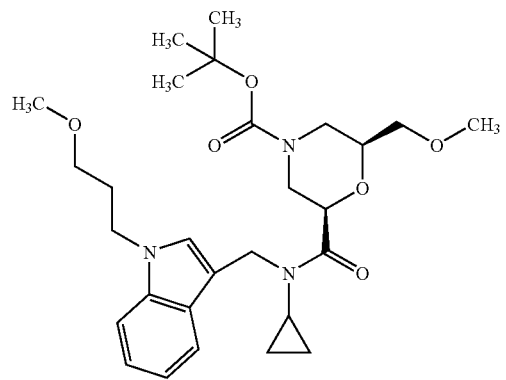 | Property: purified viscous oil<br>APCI-MS m/z: 516[M + H]$^+$ |

TABLE 20-continued

| No of Ref. Example | Structure | Properties |
|---|---|---|
| 422 | 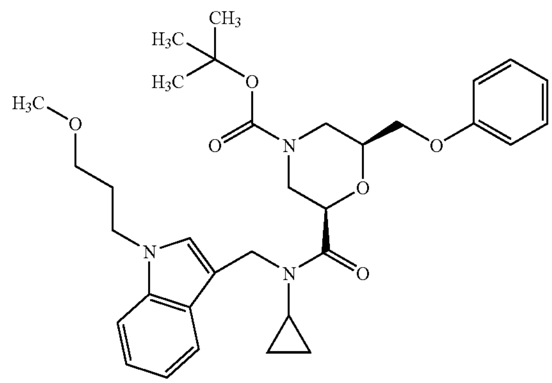 [SMILES: COCCCn1cc(CN(C(=O)[C@H]2CN(C(=O)OC(C)(C)C)C[C@@H](COc3ccccc3)O2)C2CC2)c2ccccc21] | Property: purified viscous oil<br>APCI-MS m/z: 578[M + H]+ |
| 423 | 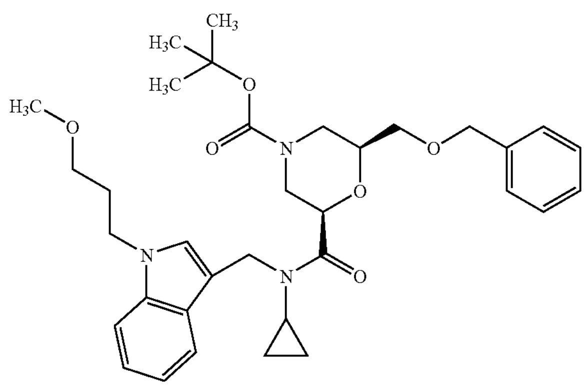 [SMILES: COCCCn1cc(CN(C(=O)[C@H]2CN(C(=O)OC(C)(C)C)C[C@@H](COCc3ccccc3)O2)C2CC2)c2ccccc21] | Property: purified viscous oil<br>APCI-MS m/z: 609[M + NH4]+ |
| 424 | 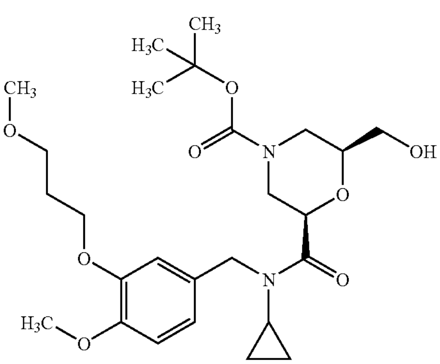 [SMILES: COCCCOc1cc(CN(C(=O)[C@H]2CN(C(=O)OC(C)(C)C)C[C@@H](CO)O2)C2CC2)ccc1OC] | Property: purified viscous oil<br>APCI-MS m/z: 526[M + NH4]+ |
| 425 | 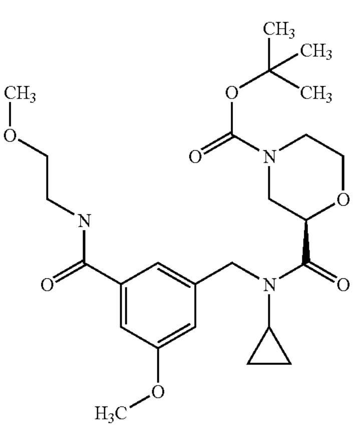 [SMILES: COCCNC(=O)c1cc(CN(C(=O)[C@H]2CN(C(=O)OC(C)(C)C)CCO2)C2CC2)cc(OC)c1] | Property: purified liquid<br>APCI-MS m/z: 509[M + NH4]+ |

TABLE 20-continued

| No of Ref. Example | Structure | Properties |
|---|---|---|
| 426 | 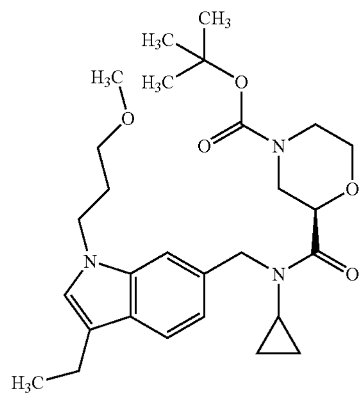 [SMILES: CCc1cn(CCCOC)c2cc(CN(C(=O)[C@H]3CN(C(=O)OC(C)(C)C)CCO3)C3CC3)ccc12] | Property: purified liquid<br>APCI-MS m/z: 500[M + H]+ |
| 427 | 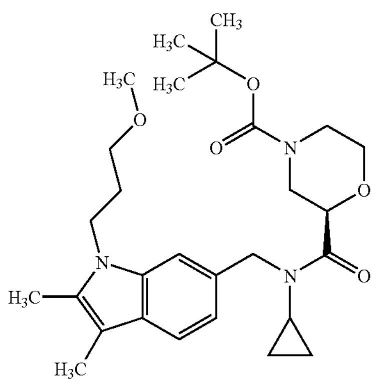 [SMILES: COCCCn1c(C)c(C)c2ccc(CN(C(=O)[C@H]3CN(C(=O)OC(C)(C)C)CCO3)C3CC3)cc21] | Property: purified liquid<br>APCI-MS m/z: 500[M + H]+ |
| 428 | 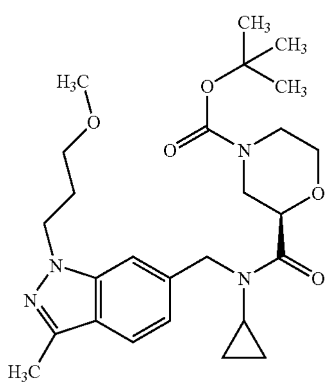 [SMILES: COCCCn1nc(C)c2ccc(CN(C(=O)[C@H]3CN(C(=O)OC(C)(C)C)CCO3)C3CC3)cc21] | Property: purified liquid<br>APCI-MS m/z: 487[M + H]+ |
| 429 | 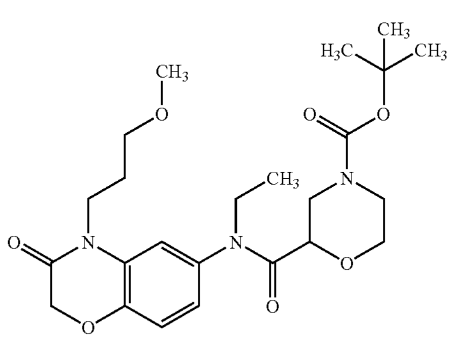 [SMILES: CCN(C(=O)C1CN(C(=O)OC(C)(C)C)CCO1)c1ccc2c(c1)N(CCCOC)C(=O)CO2] | Property: purified liquid<br>APCI-MS m/z: 478[M + H]+ |

TABLE 20-continued
| No of Ref. Example | Structure | Properties |
|---|---|---|
| 430 | 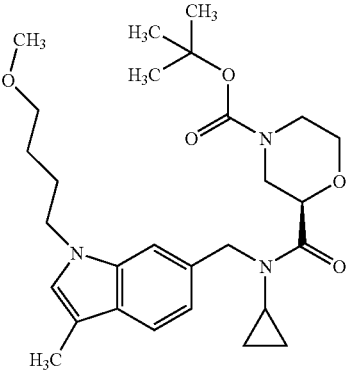 [SMILES: COCCCCn1cc(C)c2ccc(CN(C(=O)[C@H]3CN(C(=O)OC(C)(C)C)CCO3)C3CC3)cc21] | Property: purified liquid<br>APCI-MS m/z: 500[M + H]$^+$ |
| 431 | 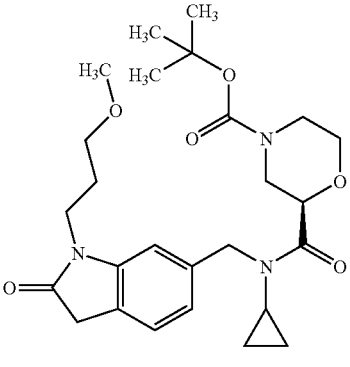 [SMILES: COCCCN1C(=O)Cc2ccc(CN(C(=O)[C@H]3CN(C(=O)OC(C)(C)C)CCO3)C3CC3)cc21] | Property: purified liquid<br>APCI-MS m/z: [M + H]$^+$ |
| 432 | 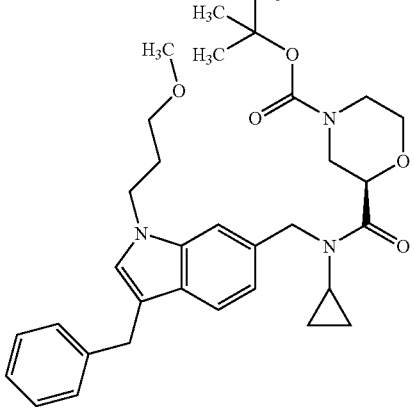 | Property: purified liquid<br>APCI-MS m/z: 562[M + H]$^+$ |
| 433 | 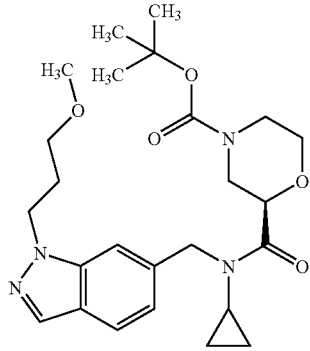 [SMILES: COCCCn1ncc2ccc(CN(C(=O)[C@H]3CN(C(=O)OC(C)(C)C)CCO3)C3CC3)cc21] | Property: purified liquid<br>APCI-MS m/z: 473[M + H]$^+$ |

TABLE 20-continued

| No of Ref. Example | Structure | Properties |
|---|---|---|
| 434 | 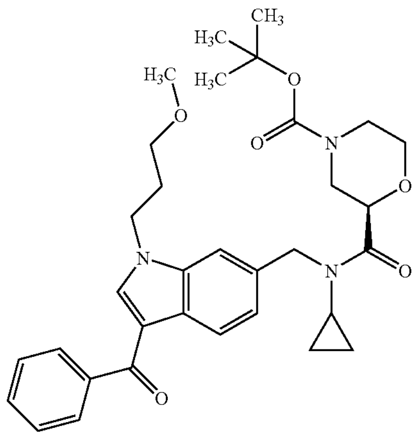 [SMILES: COCCCn1cc(C(=O)c2ccccc2)c2ccc(CN(C(=O)[C@H]3CN(C(=O)OC(C)(C)C)CCO3)C3CC3)cc21] | Property: purified powder<br>APCI-MS m/z: 593[M + NH4]+ |
| 435 | 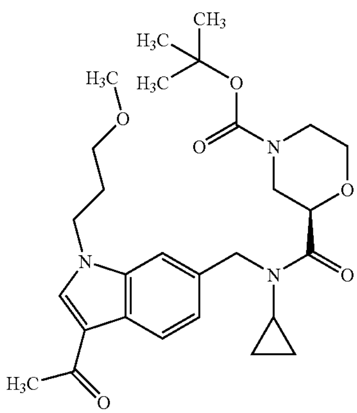 [SMILES: COCCCn1cc(C(C)=O)c2ccc(CN(C(=O)[C@H]3CN(C(=O)OC(C)(C)C)CCO3)C3CC3)cc21] | Property: purified liquid<br>APCI-MS m/z: 514[M + H]+ |
| 436 | 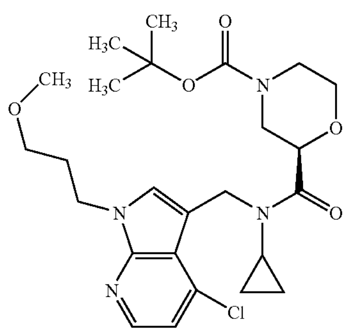 | Property: purified powder<br>APCI-MS m/z: 507/509[M + H]+ |
| 437 | 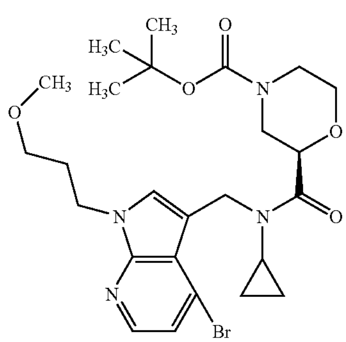 [SMILES: COCCCn1cc(CN(C(=O)[C@H]2CN(C(=O)OC(C)(C)C)CCO2)C2CC2)c2c(Br)ccnc21] | Property: purified powder<br>APCI-MS m/z: 551/553[M + H]+ |

TABLE 20-continued
| No of Ref. Example | Structure | Properties |
|---|---|---|
| 438 | 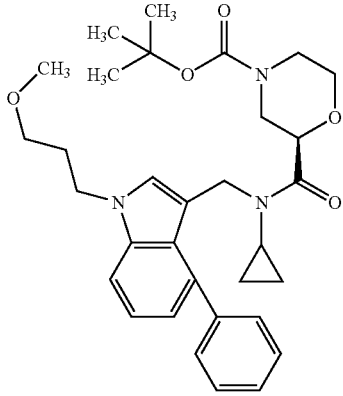 [SMILES: COCCCn1cc(CN(C(=O)[C@H]2CN(C(=O)OC(C)(C)C)CCO2)C2CC2)c2c(-c3ccccc3)cccc21] | Property: purified viscous oil<br>APCI-MS m/z: 548[M + H]+ |
| 439 | 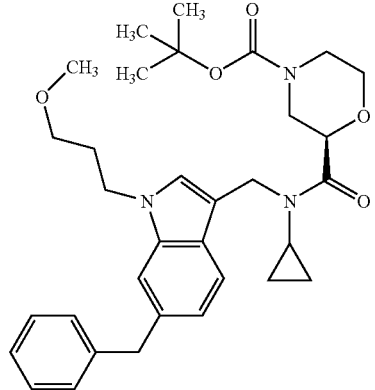 [SMILES: COCCCn1cc(CN(C(=O)[C@H]2CN(C(=O)OC(C)(C)C)CCO2)C2CC2)c2ccc(Cc3ccccc3)cc21] | Property: purified viscous oil<br>APCI-MS m/z: 562[M + H]+ |
| 440 | 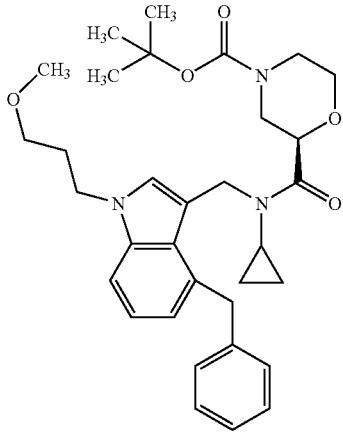 [SMILES: COCCCn1cc(CN(C(=O)[C@H]2CN(C(=O)OC(C)(C)C)CCO2)C2CC2)c2c(Cc3ccccc3)cccc21] | Property: purified viscous oil<br>APCI-MS m/z: 562[M + H]+ |

TABLE 20-continued

| No of Ref. Example | Structure | Properties |
|---|---|---|
| 441 | 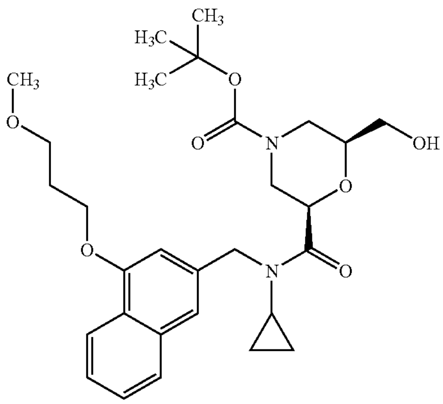 [SMILES: COCCCOc1cc(CN(C(=O)[C@H]2CN(C(=O)OC(C)(C)C)C[C@@H](CO)O2)C2CC2)cc2ccccc12] | Property: purified viscous oil<br>APCI-MS m/z: 529[M + H]⁺ |
| 442 | 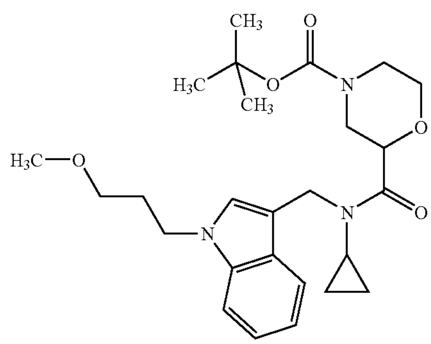 | Property: purified viscous oil<br>APCI-MS m/z: 472[M + H]⁺ |
| 443 | 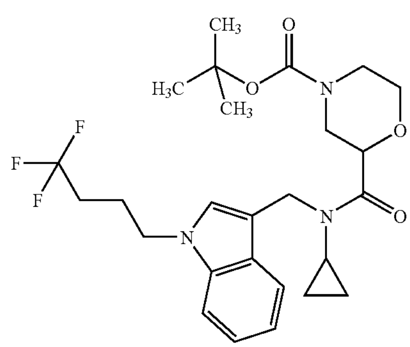 [SMILES: CC(C)(C)OC(=O)N1CCOC(C(=O)N(Cc2cn(CCCC(F)(F)F)c3ccccc23)C2CC2)C1] | Property: purified viscous oil<br>APCI-MS m/z: 510[M + H]⁺ |
| 444 | 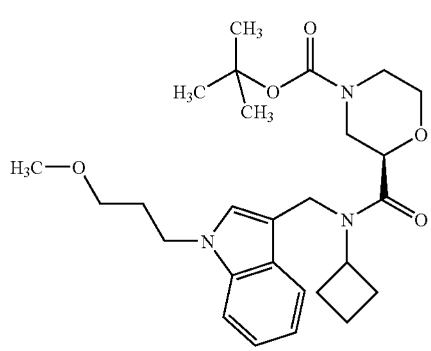 [SMILES: COCCCn1cc(CN(C(=O)[C@H]2CN(C(=O)OC(C)(C)C)CCO2)C2CCC2)c2ccccc21] | Property: purified viscous oil<br>APCI-MS m/z: 486[M + H]⁺ |

TABLE 20-continued
| No of Ref. Example | Structure | Properties |
|---|---|---|
| 445 | 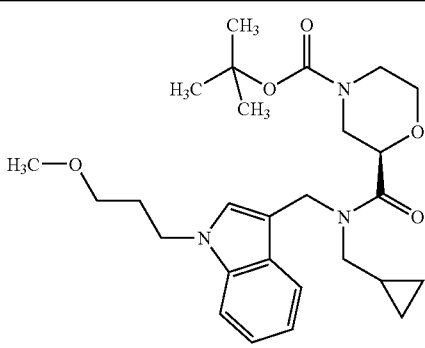 | Property: purified viscous oil<br>APCl-MS m/z: 486[M + H]⁺ |
| 446 | 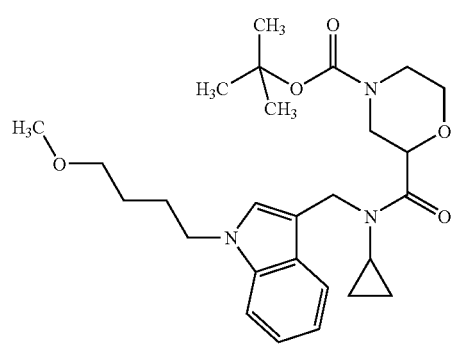 [SMILES: COCCCCn1cc(CN(C(=O)C2CN(C(=O)OC(C)(C)C)CCO2)C2CC2)c2ccccc21] | Property: purified viscous oil<br>APCI-MS m/z: 486[M + H]⁺ |
| 447 | 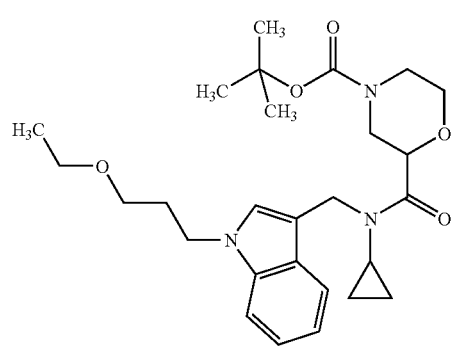 [SMILES: CCOCCCn1cc(CN(C(=O)C2CN(C(=O)OC(C)(C)C)CCO2)C2CC2)c2ccccc21] | Property: purified viscous oil<br>APCI-MS m/z: 486[M + H]⁺ |
| 448 | 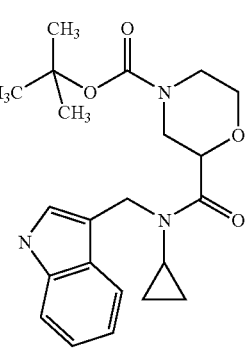 | Property: purified powder<br>APCI-MS m/z: 400[M + H]⁺ |

TABLE 20-continued

| No of Ref. Example | Structure | Properties |
|---|---|---|
| 449 | 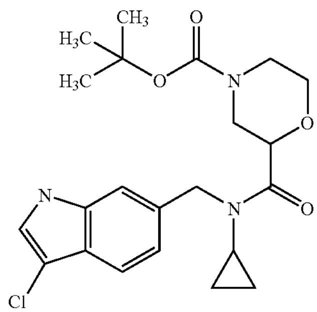 [SMILES: CC(C)(C)OC(=O)N1CCOC(C(=O)N(Cc2ccc3c(Cl)c[nH]c3c2)C2CC2)C1] | Property: purified viscous oil<br>APCI-MS m/z: 434/436[M + H]+ |
| 450 | 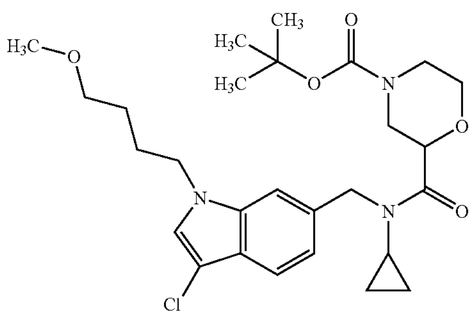 [SMILES: COCCCCn1cc(Cl)c2ccc(CN(C(=O)C3CN(C(=O)OC(C)(C)C)CCO3)C3CC3)cc21] | Property: purified viscous oil<br>APCI-MS m/z: 537/539[M + NH4]+ |
| 451 | 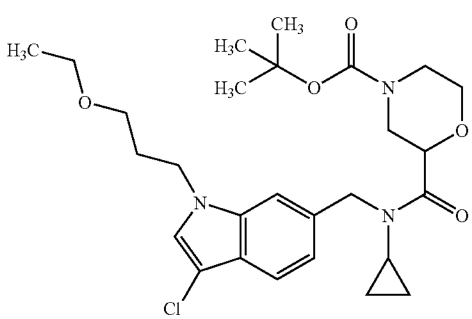 [SMILES: CCOCCCn1cc(Cl)c2ccc(CN(C(=O)C3CN(C(=O)OC(C)(C)C)CCO3)C3CC3)cc21] | Property: purified viscous oil<br>APCI-MS m/z: 520/522[M + H]+ |
| 452 | 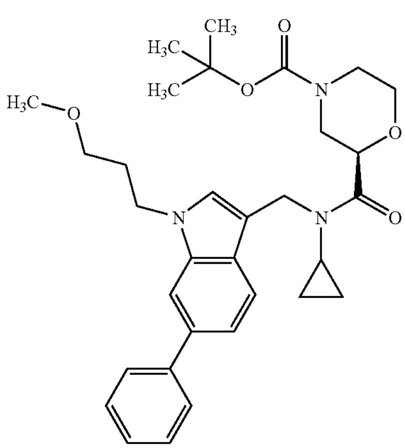 [SMILES: COCCCn1cc(CN(C(=O)[C@H]2CN(C(=O)OC(C)(C)C)CCO2)C2CC2)c2ccc(-c3ccccc3)cc21] | Property: purified viscous oil<br>APCI-MS m/z: 548[M + H]+ |

TABLE 20-continued

| No of Ref. Example | Structure | Properties |
|---|---|---|
| 453 | 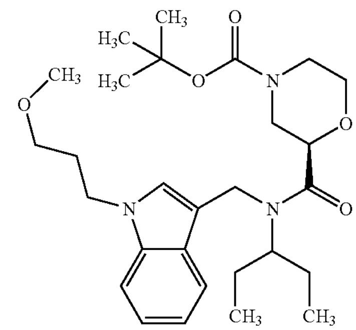 [SMILES: CCC(CC)N(Cc1cn(CCCOC)c2ccccc12)C(=O)[C@H]1CN(C(=O)OC(C)(C)C)CCO1] | Property: purified viscous oil<br>APCI-MS m/z: 502[M + H]+ |
| 454 | 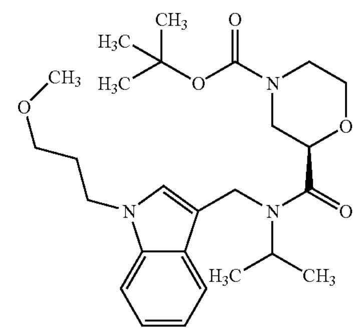 [SMILES: COCCCn1cc(CN(C(=O)[C@H]2CN(C(=O)OC(C)(C)C)CCO2)C(C)C)c2ccccc21] | Property: purified viscous oil<br>APCI-MS m/z: 474[M + H]+ |
| 455 | 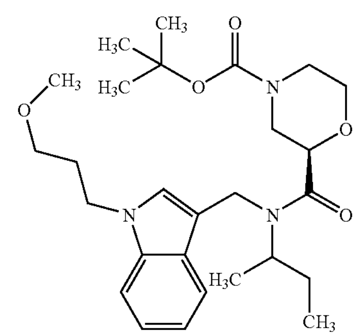 [SMILES: CCC(C)N(Cc1cn(CCCOC)c2ccccc12)C(=O)[C@H]1CN(C(=O)OC(C)(C)C)CCO1] | Property: purified viscous oil<br>APCI-MS m/z: 488[M + H]+ |
| 456 | 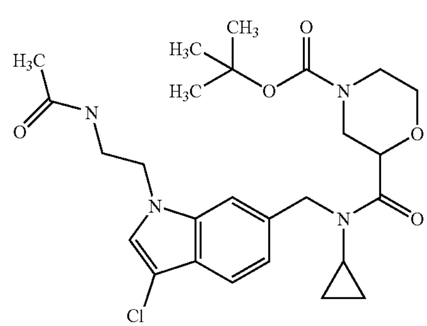 [SMILES: CC(=O)NCCn1cc(Cl)c2ccc(CN(C(=O)C3CN(C(=O)OC(C)(C)C)CCO3)C3CC3)cc21] | Property: purified viscous oil<br>APCI-MS m/z: 519/521[M + H]+ |

| No of Ref. Example | Structure | Properties |
|---|---|---|
| 457 | 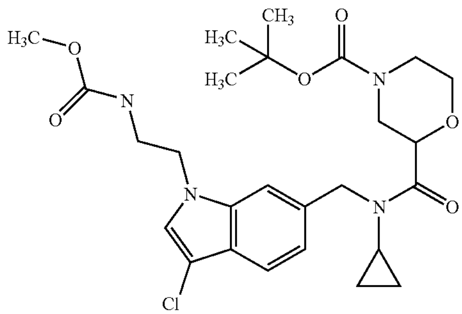 [SMILES: COC(=O)NCCn1cc(Cl)c2ccc(CN(C(=O)C3CN(C(=O)OC(C)(C)C)CCO3)C3CC3)cc21] | Property: purified viscous oil<br>APCI-MS m/z: 552/554[M + NH4]$^+$ |
| 458 | 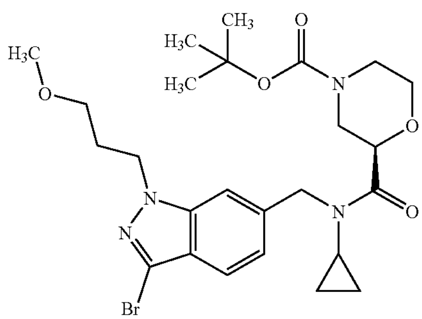 [SMILES: COCCCn1nc(Br)c2ccc(CN(C(=O)[C@H]3CN(C(=O)OC(C)(C)C)CCO3)C3CC3)cc21] | Property: purified liquid<br>APCI-MS m/z: 551/553[M + H]$^+$ |
| 459 | 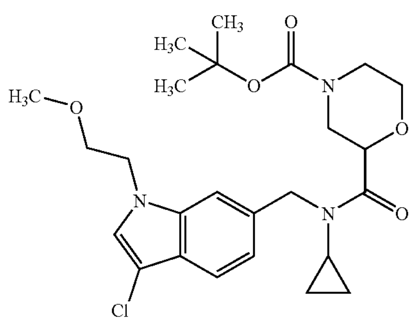 [SMILES: COCCn1cc(Cl)c2ccc(CN(C(=O)C3CN(C(=O)OC(C)(C)C)CCO3)C3CC3)cc21] | Property: purified viscous oil<br>APCI-MS m/z: 492/494[M + H]$^+$ |
| 460 | 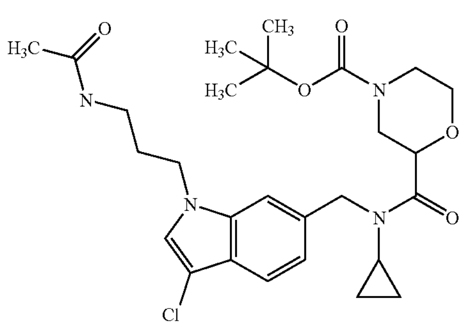 [SMILES: CC(=O)NCCCn1cc(Cl)c2ccc(CN(C(=O)C3CN(C(=O)OC(C)(C)C)CCO3)C3CC3)cc21] | Property: purified powder<br>APCI-MS m/z: 533/535[M + H]$^+$ |

TABLE 20-continued

| No of Ref. Example | Structure | Properties |
|---|---|---|
| 461 | 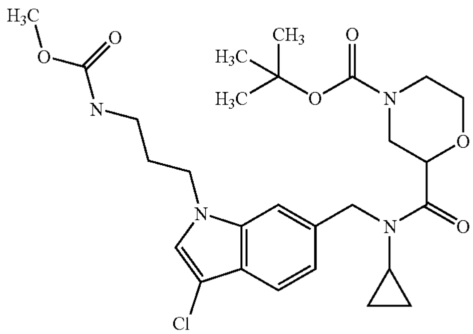 [SMILES: COC(=O)NCCCn1cc(Cl)c2ccc(CN(C(=O)C3CN(C(=O)OC(C)(C)C)CCO3)C3CC3)cc21] | Property: purified viscous oil<br>APCI-MS m/z: 566/568[M + NH4]+ |
| 462 | 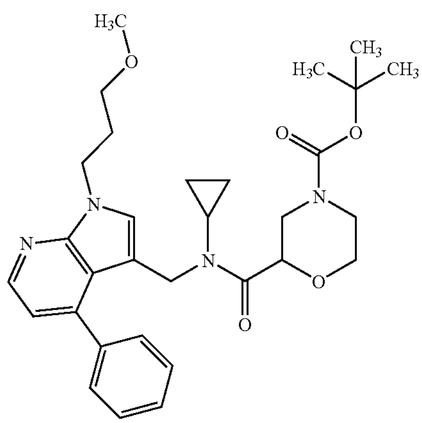 [SMILES: COCCCn1cc(CN(C(=O)C2CN(C(=O)OC(C)(C)C)CCO2)C2CC2)c2c(-c3ccccc3)ccnc21] | Property: ☆purified viscous oil<br>APCI-MS m/z: 549[M + H]+ |
| 463 | 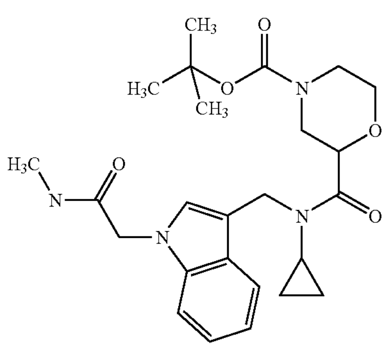 [SMILES: CNC(=O)Cn1cc(CN(C(=O)C2CN(C(=O)OC(C)(C)C)CCO2)C2CC2)c2ccccc21] | Property: purified viscous oil<br>APCI-MS m/z: 488[M + H]+ |
| 464 | 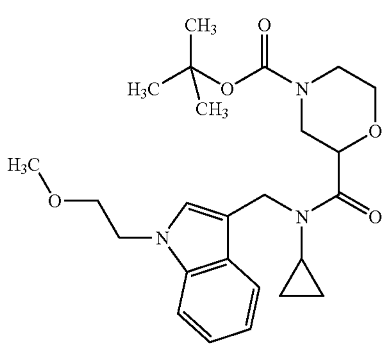 [SMILES: COCCn1cc(CN(C(=O)C2CN(C(=O)OC(C)(C)C)CCO2)C2CC2)c2ccccc21] | Property: purified viscous oil<br>APCI-MS m/z: 458[M + H]+ |

TABLE 20-continued

| No of Ref. Example | Structure | Properties |
|---|---|---|
| 465 | 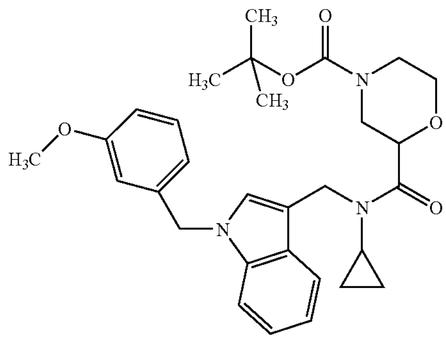 [SMILES: COc1cccc(Cn2cc(CN(C(=O)C3CN(C(=O)OC(C)(C)C)CCO3)C3CC3)c3ccccc32)c1] | Property: purified viscous oil<br>APCI-MS m/z: 520[M + H]+ |
| 466 | 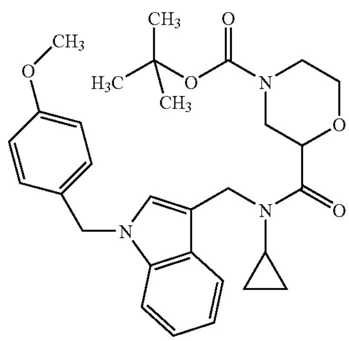 [SMILES: COc1ccc(Cn2cc(CN(C(=O)C3CN(C(=O)OC(C)(C)C)CCO3)C3CC3)c3ccccc32)cc1] | Property: purified viscous oil<br>APCI-MS m/z: 520[M + H]+ |
| 467 | 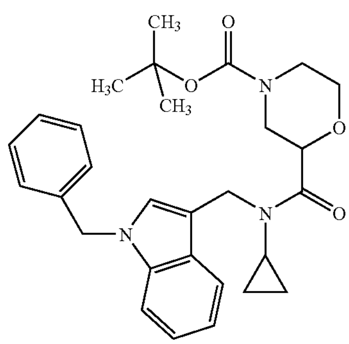 [SMILES: CC(C)(C)OC(=O)N1CCOC(C(=O)N(Cc2cn(Cc3ccccc3)c3ccccc23)C2CC2)C1] | Property: purified viscous oil<br>APCI-MS m/z: 490[M + H]+ |
| 468 | 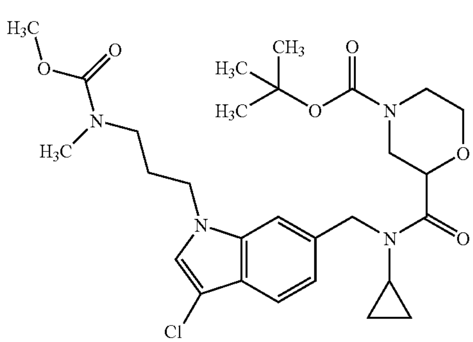 [SMILES: COC(=O)N(C)CCCn1cc(Cl)c2ccc(CN(C(=O)C3CN(C(=O)OC(C)(C)C)CCO3)C3CC3)cc21] | Property: purified viscous oil<br>APCI-MS m/z: 580/582[M + NH4]+ |

TABLE 20-continued

| No of Ref. Example | Structure | Properties |
|---|---|---|
| 469 | 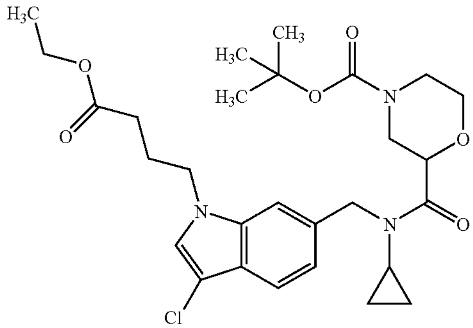 [SMILES: CCOC(=O)CCCn1cc(Cl)c2ccc(CN(C(=O)C3CN(C(=O)OC(C)(C)C)CCO3)C3CC3)cc21] | Property: purified viscous oil<br>APCI-MS m/z: 565/667[M + NH4]+ |
| 470 | 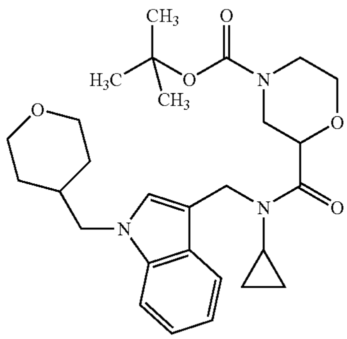 | Property: purified viscous oil<br>APCI-MS m/z: 627[M + H]+ |
| 471 | 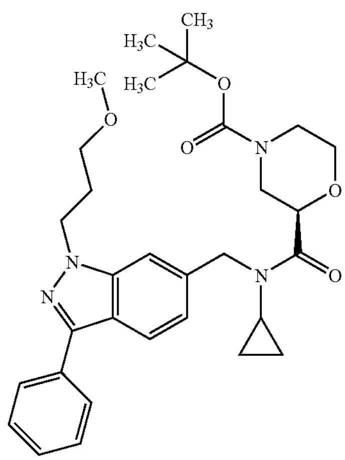 [SMILES: COCCCn1nc(-c2ccccc2)c2ccc(CN(C(=O)[C@H]3CN(C(=O)OC(C)(C)C)CCO3)C3CC3)cc21] | Property: purified liquid<br>APCI-MS m/z: 549[M + H]+ |
| 472 | 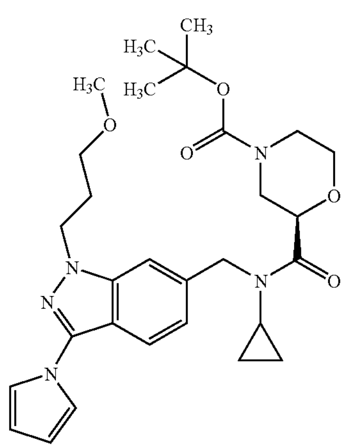 [SMILES: COCCCn1nc(-n2cccc2)c2ccc(CN(C(=O)[C@H]3CN(C(=O)OC(C)(C)C)CCO3)C3CC3)cc21] | Property: purified liquid<br>APCI-MS m/z: 538[M + H]+ |

TABLE 20-continued
| No of Ref. Example | Structure | Properties |
|---|---|---|
| 473 | 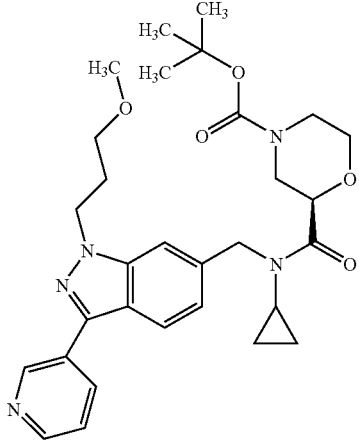 [SMILES: COCCCn1nc(-c2cccnc2)c2ccc(CN(C(=O)[C@H]3CN(C(=O)OC(C)(C)C)CCO3)C3CC3)cc21] | Property: purified liquid<br>APCI-MS m/z: 550[M + H]$^+$ |
| 474 | 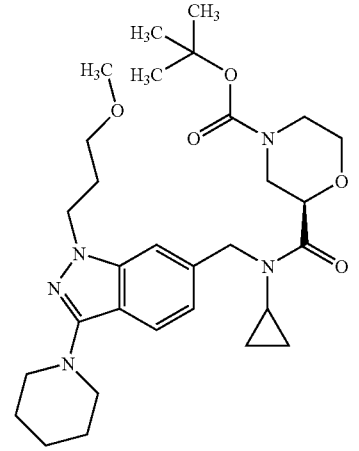 [SMILES: COCCCn1nc(N2CCCCC2)c2ccc(CN(C(=O)[C@H]3CN(C(=O)OC(C)(C)C)CCO3)C3CC3)cc21] | Property: purified liquid<br>APCI-MS m/z: 556[M + H]$^+$ |
| 475 | 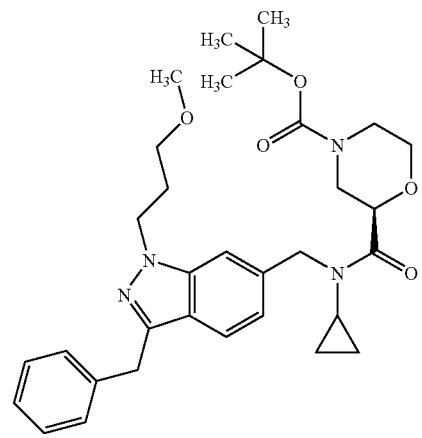 [SMILES: COCCCn1nc(Cc2ccccc2)c2ccc(CN(C(=O)[C@H]3CN(C(=O)OC(C)(C)C)CCO3)C3CC3)cc21] | Property: purified liquid<br>APCI-MS m/z: 563[M + H]$^+$ |

TABLE 20-continued
| No of Ref. Example | Structure | Properties |
|---|---|---|
| 476 | 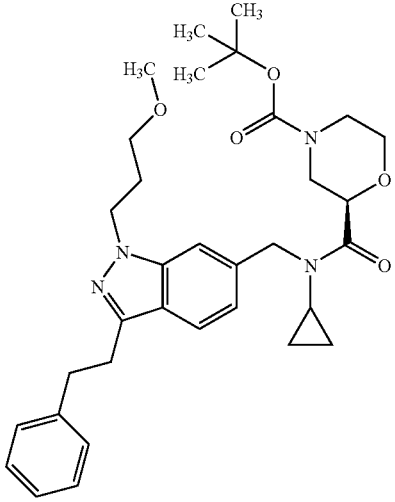 [SMILES: COCCCn1nc(CCc2ccccc2)c2ccc(CN(C(=O)[C@H]3CN(C(=O)OC(C)(C)C)CCO3)C3CC3)cc21] | Property: purified liquid<br>APCI-MS m/z: 577[M + H]+ |
| 477 | 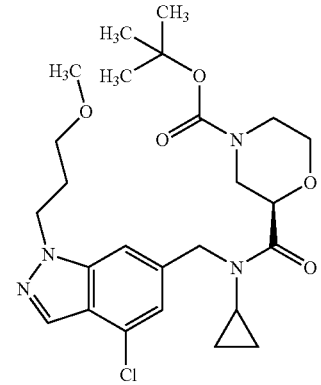 [SMILES: COCCCn1ncc2c(Cl)cc(CN(C(=O)[C@H]3CN(C(=O)OC(C)(C)C)CCO3)C3CC3)cc21] | Property: purified liquid<br>APCI-MS m/z: 507/509[M + H]+ |
| 478 | 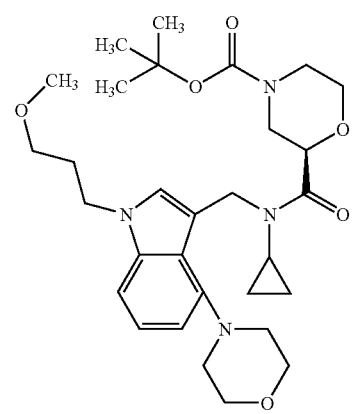 [SMILES: COCCCn1cc(CN(C(=O)[C@H]2CN(C(=O)OC(C)(C)C)CCO2)C2CC2)c2c(N3CCOCC3)cccc21] | Property: purified viscous oil<br>APCI-MS m/z: 557[M + H]+ |

TABLE 20-continued

| No of Ref. Example | Structure | Properties |
|---|---|---|
| 479 | 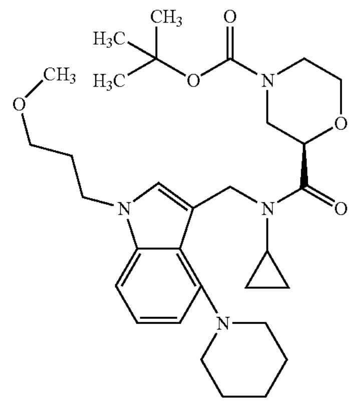 [SMILES: COCCCn1cc(CN(C(=O)[C@H]2CN(C(=O)OC(C)(C)C)CCO2)C2CC2)c2c(N3CCCCC3)cccc21] | Property: purified viscous oil<br>APCI-MS m/z: 555[M + H]+ |
| 480 | 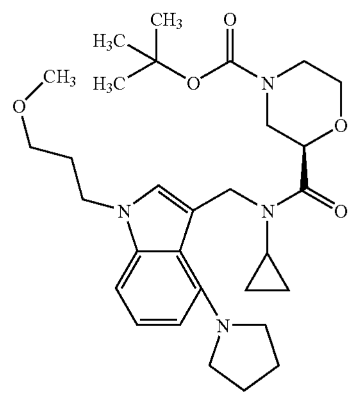 [SMILES: COCCCn1cc(CN(C(=O)[C@H]2CN(C(=O)OC(C)(C)C)CCO2)C2CC2)c2c(N3CCCC3)cccc21] | Property: purified viscous oil<br>APCI-MS m/z: 541[M + H]+ |
| 481 | 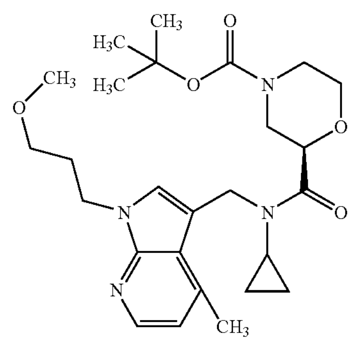 [SMILES: COCCCn1cc(CN(C(=O)[C@H]2CN(C(=O)OC(C)(C)C)CCO2)C2CC2)c2c(C)ccnc21] | Property: purified viscous oil<br>APCI-MS m/z: 487[M + H]+ |
| 482 | 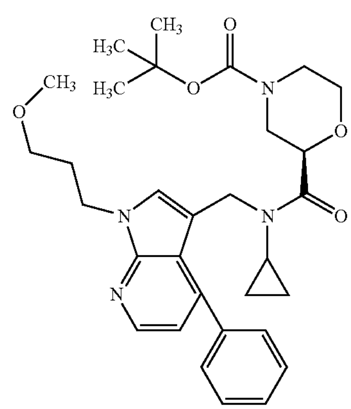 | Property: purified powder<br>APCI-MS m/z: 549[M + H]+ |

TABLE 20-continued

| No of Ref. Example | Structure | Properties |
|---|---|---|
| 483 | 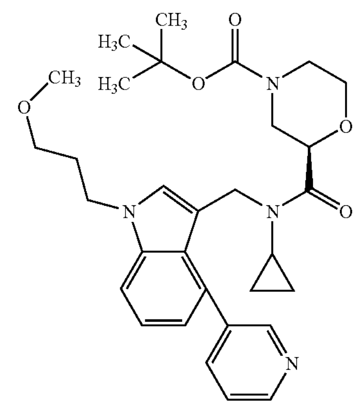 [SMILES: COCCCn1cc(CN(C(=O)[C@H]2CN(C(=O)OC(C)(C)C)CCO2)C2CC2)c2c(-c3cccnc3)cccc21] | Property: purified viscous oil<br>APCI-MS m/z: 549[M + H]+ |
| 484 | 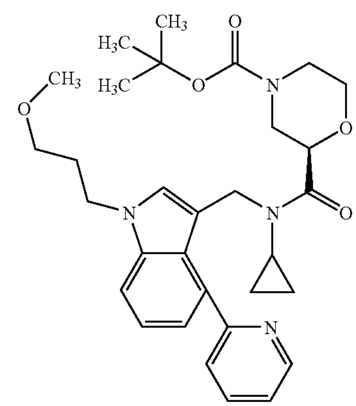 [SMILES: COCCCn1cc(CN(C(=O)[C@H]2CN(C(=O)OC(C)(C)C)CCO2)C2CC2)c2c(-c3ccccn3)cccc21] | Property: purified powder<br>APCI-MS m/z: 549[M + H]+ |
| 485 | 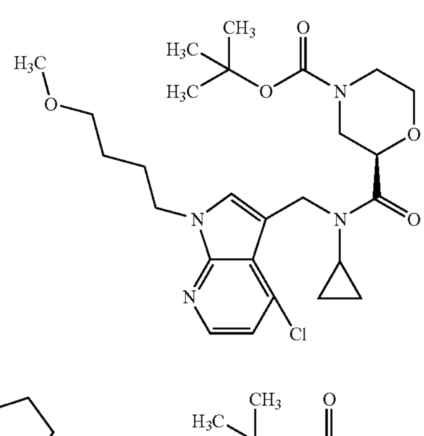 | Property: purified viscous oil<br>APCI-MS m/z: 521/523[M + H]+ |
| 486 | 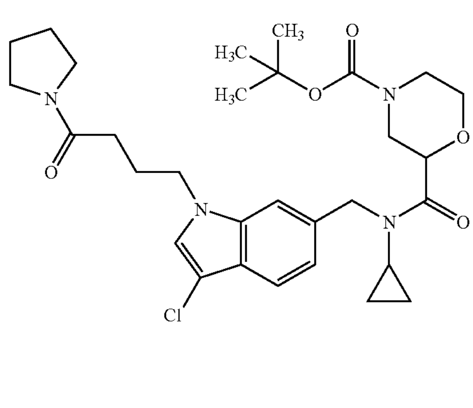 [SMILES: CC(C)(C)OC(=O)N1CCOC(C(=O)N(Cc2ccc3c(Cl)cn(CCCC(=O)N4CCCC4)c3c2)C2CC2)C1] | Property: purified viscous oil<br>APCI-MS m/z: 573/575[M + H]+ |

TABLE 20-continued
| No of Ref. Example | Structure | Properties |
|---|---|---|
| 487 | 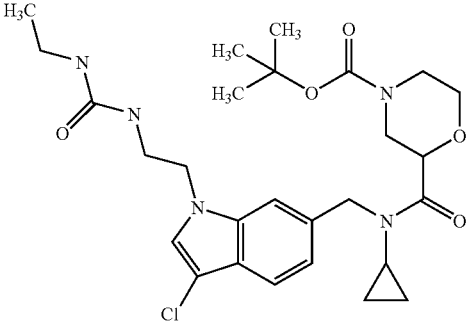 | Property: purified viscous oil<br>APCI-MS m/z: 548/550[M + H]$^+$ |
| 488 | 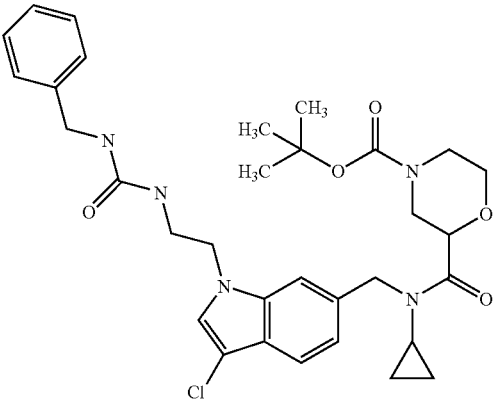 [SMILES: CC(C)(C)OC(=O)N1CCOC(C(=O)N(Cc2ccc3c(Cl)cn(CCNC(=O)NCc4ccccc4)c3c2)C2CC2)C1] | Property: purified viscous oil<br>APCI-MS m/z: 610/612[M + H]$^+$ |
| 489 | 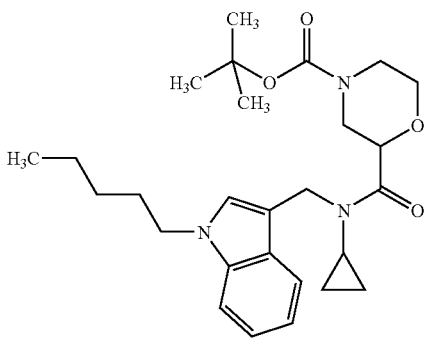 [SMILES: CCCCCn1cc(CN(C(=O)C2CN(C(=O)OC(C)(C)C)CCO2)C2CC2)c2ccccc21] | Property: purified viscous oil<br>APCI-MS m/z: 470[M + H]$^+$ |
| 490 | 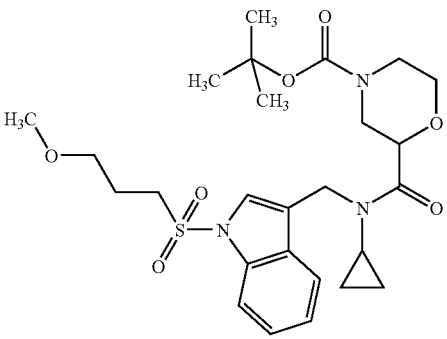 [SMILES: COCCCS(=O)(=O)n1cc(CN(C(=O)C2CN(C(=O)OC(C)(C)C)CCO2)C2CC2)c2ccccc21] | Property: purified viscous oil<br>APCI-MS m/z: 553[M + NH4]$^+$ |

TABLE 20-continued

| No of Ref. Example | Structure | Properties |
|---|---|---|
| 491 | 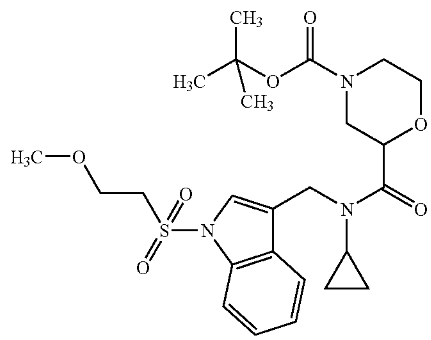 [SMILES: COCCS(=O)(=O)n1cc(CN(C(=O)C2CN(C(=O)OC(C)(C)C)CCO2)C2CC2)c2ccccc21] | Property: purified viscous oil<br>APCI-MS m/z: 539[M + NH4]+ |
| 492 | 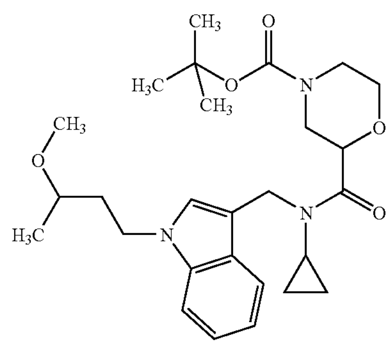 [SMILES: COC(C)CCn1cc(CN(C(=O)C2CN(C(=O)OC(C)(C)C)CCO2)C2CC2)c2ccccc21] | Property: purified viscous oil<br>APCI-MS m/z: 486[M + H]+ |
| 493 | 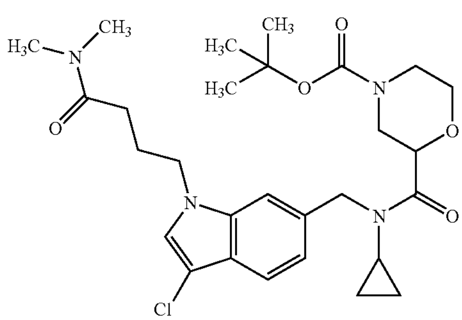 [SMILES: CN(C)C(=O)CCCn1cc(Cl)c2ccc(CN(C(=O)C3CN(C(=O)OC(C)(C)C)CCO3)C3CC3)cc21] | Property: purified viscous oil<br>APCI-MS m/z: 564/566[M + NH4]+ |
| 494 | 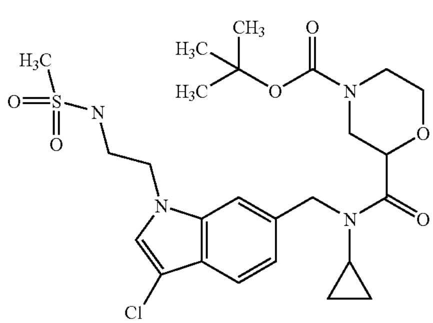 [SMILES: CC(C)(C)OC(=O)N1CCOC(C(=O)N(Cc2ccc3c(Cl)cn(CCNS(C)(=O)=O)c3c2)C2CC2)C1] | Property: purified viscous oil<br>APCI-MS m/z: 555/557[M + H]+ |

TABLE 20-continued
| No of Ref. Example | Structure | Properties |
|---|---|---|
| 495 | 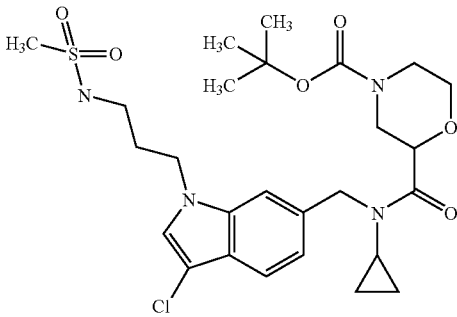 [SMILES: CC(C)(C)OC(=O)N1CCOC(C(=O)N(Cc2ccc3c(Cl)cn(CCCNS(C)(=O)=O)c3c2)C2CC2)C1] | Property: purified powder<br>APCI-MS m/z: 586/588[M + NH4]+ |
| 496 | 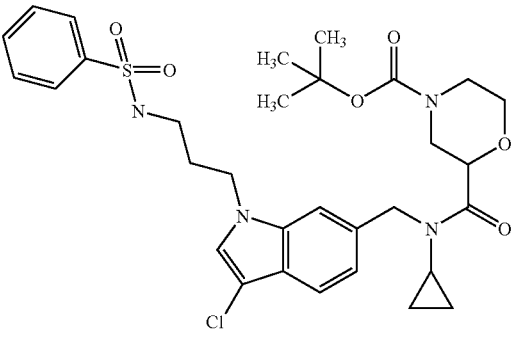 [SMILES: CC(C)(C)OC(=O)N1CCOC(C(=O)N(Cc2ccc3c(Cl)cn(CCCNS(=O)(=O)c4ccccc4)c3c2)C2CC2)C1] | Property: purified powder<br>APCI-MS m/z: 631/633[M + H]+ |
| 497 | 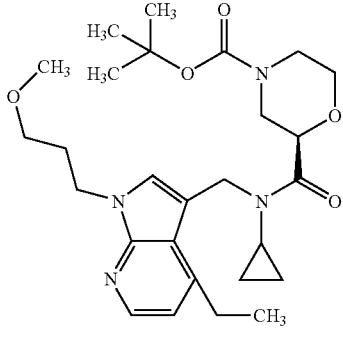 [SMILES: CCc1ccnc2c1c(CN(C(=O)[C@H]1CN(C(=O)OC(C)(C)C)CCO1)C1CC1)cn2CCCOC] | Property: purified viscous oil<br>APCI-MS m/z: 501[M + H]+ |
| 498 | 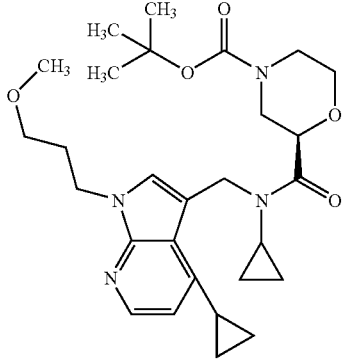 [SMILES: COCCCn1cc(CN(C(=O)[C@H]2CN(C(=O)OC(C)(C)C)CCO2)C2CC2)c2c(C3CC3)ccnc21] | Property: purified viscous oil<br>APCI-MS m/z: 513[M + H]+ |

TABLE 20-continued

| No of Ref. Example | Structure | Properties |
|---|---|---|
| 499 | 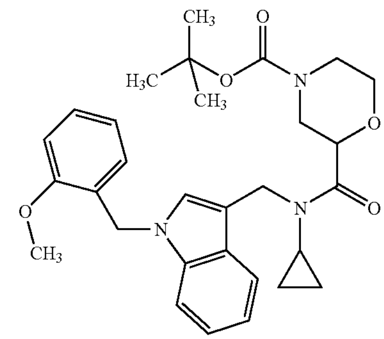 [SMILES: COc1ccccc1Cn1cc(CN(C(=O)C2CN(C(=O)OC(C)(C)C)CCO2)C2CC2)c2ccccc21] | Property: purified viscous oil<br>APCI-MS m/z: 520[M + H]+ |
| 500 | 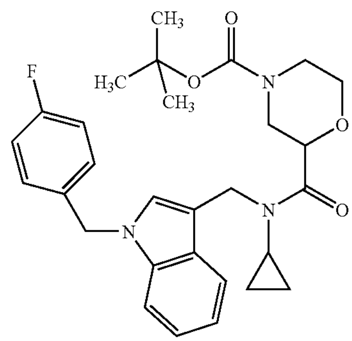 [SMILES: CC(C)(C)OC(=O)N1CCOC(C(=O)N(Cc2cn(Cc3ccc(F)cc3)c3ccccc23)C2CC2)C1] | Property: purified viscous oil<br>APCI-MS m/z: 508[M + H]+ |
| 501 | 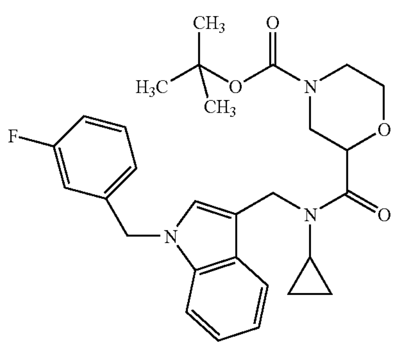 [SMILES: CC(C)(C)OC(=O)N1CCOC(C(=O)N(Cc2cn(Cc3cccc(F)c3)c3ccccc23)C2CC2)C1] | Property: purified viscous oil<br>APCI-MS m/z: 508[M + H]+ |
| 502 | 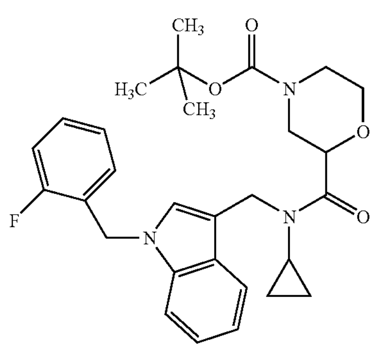 [SMILES: CC(C)(C)OC(=O)N1CCOC(C(=O)N(Cc2cn(Cc3ccccc3F)c3ccccc23)C2CC2)C1] | Property: purified viscous oil<br>APCI-MS m/z: 508[M + H]+ |

TABLE 20-continued

| No of Ref. Example | Structure | Properties |
|---|---|---|
| 503 | 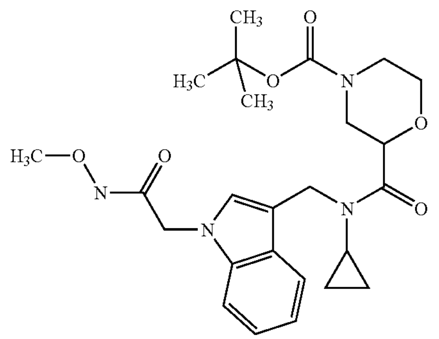 [SMILES: CONC(=O)Cn1cc(CN(C(=O)C2CN(C(=O)OC(C)(C)C)CCO2)C2CC2)c2ccccc21] | Property: purified powder<br>APCI-MS m/z: 504[M + NH4]+ |
| 504 | 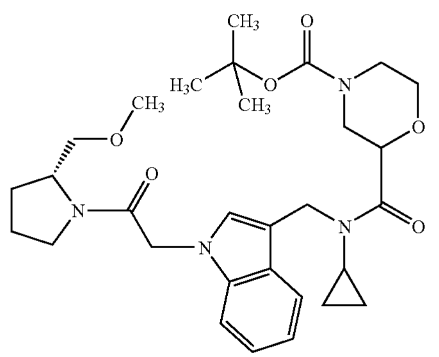 [SMILES: COC[C@H]1CCCN1C(=O)Cn1cc(CN(C(=O)C2CN(C(=O)OC(C)(C)C)CCO2)C2CC2)c2ccccc21] | Property: purified viscousoil<br>APCI-MS m/z: 572[M + NH4]+ |
| 505 | 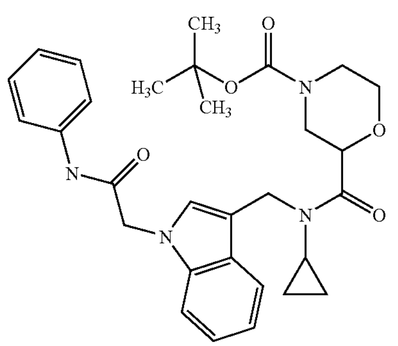 [SMILES: CC(C)(C)OC(=O)N1CCOC(C(=O)N(Cc2cn(CC(=O)Nc3ccccc3)c3ccccc23)C2CC2)C1] | Property: purified powder<br>APCI-MS m/z: 550[M + NH4]+ |
| 506 | 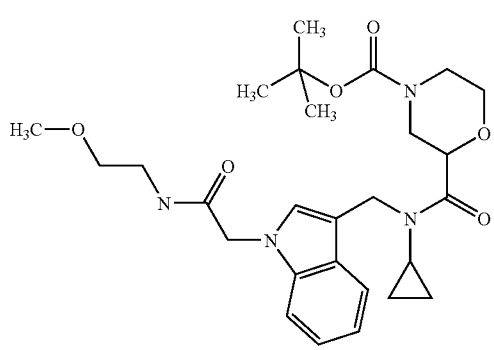 [SMILES: COCCNC(=O)Cn1cc(CN(C(=O)C2CN(C(=O)OC(C)(C)C)CCO2)C2CC2)c2ccccc21] | Property: purified viscous oil<br>APCI-MS m/z: 532[M + NH4]+ |

| No of Ref. Example | Structure | Properties |
|---|---|---|
| 507 | 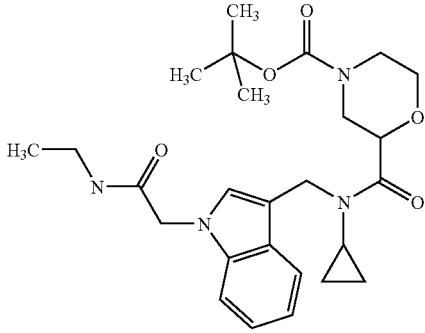 [SMILES: CCNC(=O)Cn1cc(CN(C(=O)C2CN(C(=O)OC(C)(C)C)CCO2)C2CC2)c2ccccc21] | Property: purified powder<br>APCI-MS m/z: 502[M + NH4]$^+$ |
| 508 | 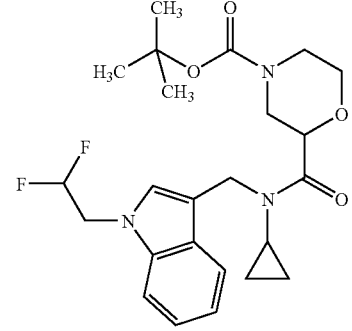 [SMILES: CC(C)(C)OC(=O)N1CCOC(C(=O)N(Cc2cn(CC(F)F)c3ccccc23)C2CC2)C1] | Property: purified powder<br>APCI-MS m/z: 464[M + H]$^+$ |
| 509 | 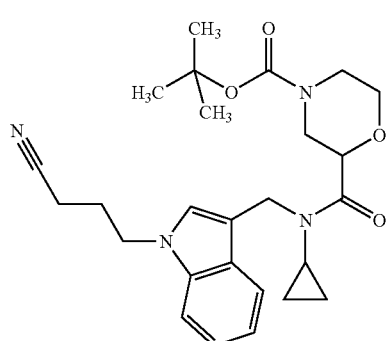 | Property: purified viscous oil<br>APCI-MS m/z: 467[M + H]$^+$ |
| 510 | 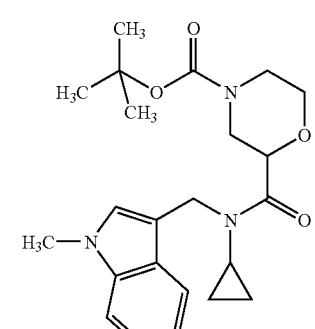 | Property: purified powder<br>APCI-MS m/z: 414[M + H]$^+$ |

TABLE 20-continued
| No of Ref. Example | Structure | Properties |
|---|---|---|
| 511 | 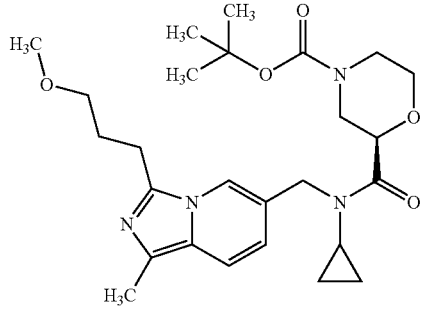 [SMILES: COCCCc1nc(C)c2ccc(CN(C(=O)[C@H]3CN(C(=O)OC(C)(C)C)CCO3)C3CC3)cn12] | Property purified viscous oil<br>APCI-MS m/z: 487[M + H]$^+$ |
| 512 | 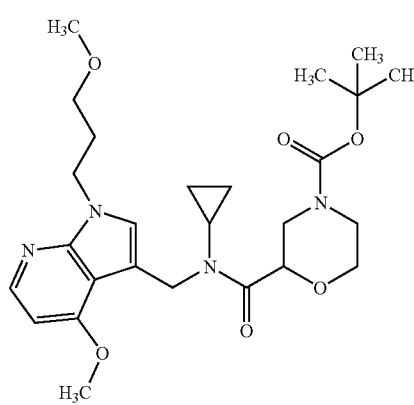 | Property: purified viscous oil<br>APCI-MS m/z: 503[M + H]$^+$ |
| 513 | 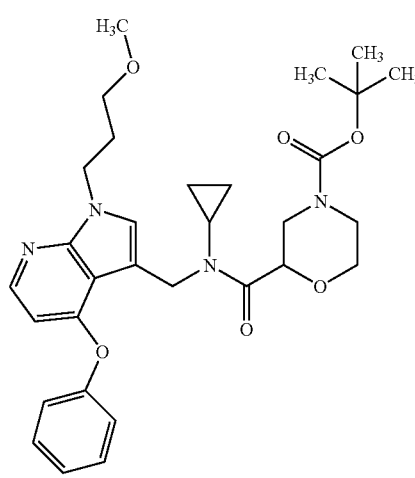 | Property: ✻purified viscous oil<br>APCI-MS m/z: 565[M + H]$^+$ |

TABLE 20-continued

| No of Ref. Example | Structure | Properties |
|---|---|---|
| 514 | 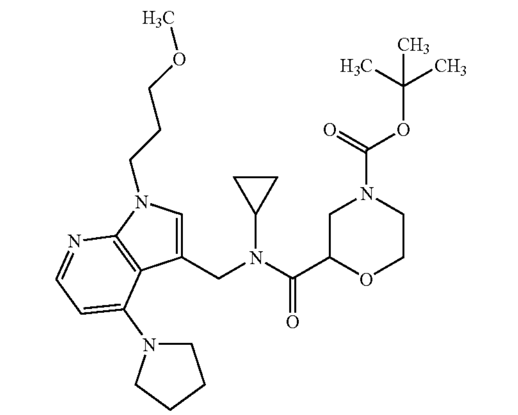 [SMILES: COCCCn1cc(CN(C(=O)C2CN(C(=O)OC(C)(C)C)CCO2)C2CC2)c2c(N3CCCC3)ccnc21] | Property: purified viscous oil<br>APCI-MS m/z: 542[M + H]+ |
| 515 | 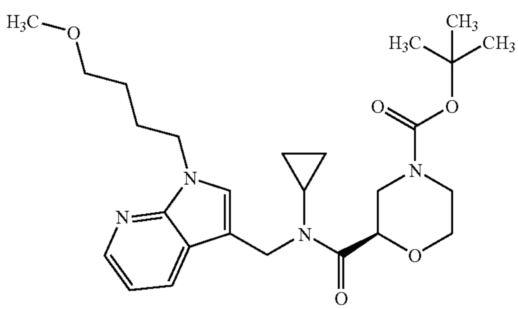 | Property: purified viscous oil<br>APCI-MS m/z: 437[M + H]+ |
| 516 | 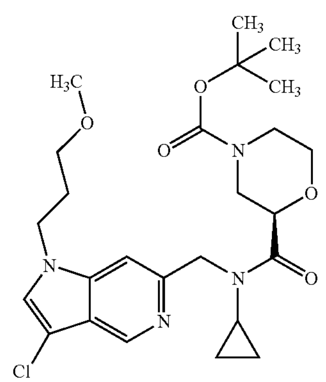 [SMILES: COCCCn1cc(Cl)c2cnc(CN(C(=O)[C@H]3CN(C(=O)OC(C)(C)C)CCO3)C3CC3)cc21] | Property: purified liquid<br>APCI-MS m/z: 507/509[M + H]+ |
| 517 | 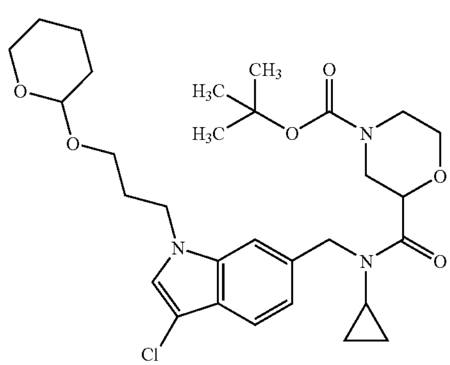 [SMILES: CC(C)(C)OC(=O)N1CCOC(C(=O)N(Cc2ccc3c(Cl)cn(CCCOC4CCCCO4)c3c2)C2CC2)C1] | Property: purified viscous oil<br>APCI-MS m/z: 593/595[M + NH4]+ |

TABLE 20-continued

| No of Ref. Example | Structure | Properties |
|---|---|---|
| 518 | 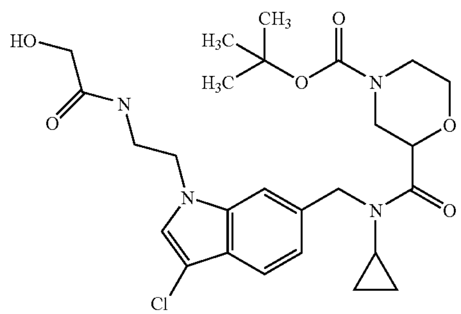 [SMILES: CC(C)(C)OC(=O)N1CCOC(C(=O)N(Cc2ccc3c(Cl)cn(CCNC(=O)CO)c3c2)C2CC2)C1] | Property: purified viscous oil<br>APCI-MS m/z: 552/554[M + NH4]+ |
| 519 | 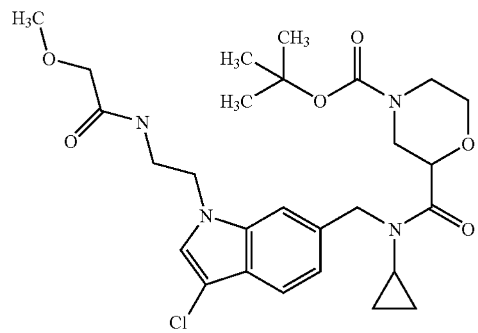 | Property: purified viscous oil<br>APCI-MS m/z: 566/568[M + NH4]+ |
| 520 | 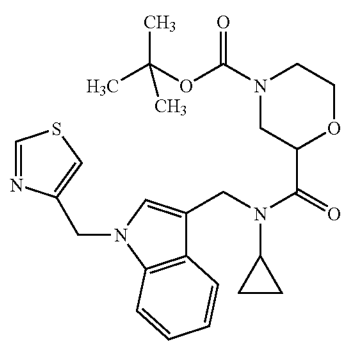 [SMILES: CC(C)(C)OC(=O)N1CCOC(C(=O)N(Cc2cn(Cc3cscn3)c3ccccc23)C2CC2)C1] | Property: purified powder<br>APCI-MS m/z: 514[M + NH4]+ |
| 521 | 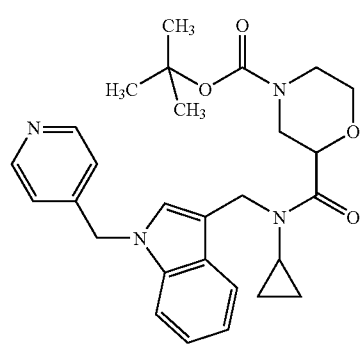 [SMILES: CC(C)(C)OC(=O)N1CCOC(C(=O)N(Cc2cn(Cc3ccncc3)c3ccccc23)C2CC2)C1] | Property: purified powder<br>APCI-MS m/z: 491[M + H]+ |

TABLE 20-continued

| No of Ref. Example | Structure | Properties |
|---|---|---|
| 522 | 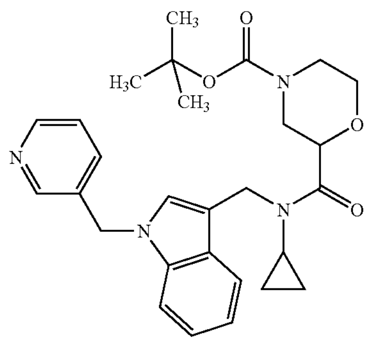 [SMILES: CC(C)(C)OC(=O)N1CCOC(C(=O)N(Cc2cn(Cc3cccnc3)c3ccccc23)C2CC2)C1] | Property: purified powder<br>APCI-MS m/z: 491[M + H]+ |
| 523 | 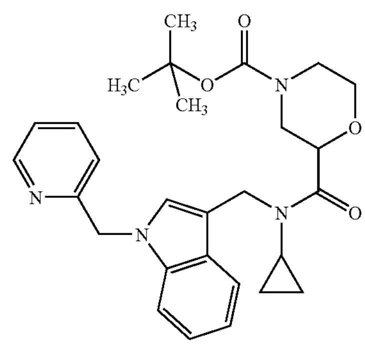 [SMILES: CC(C)(C)OC(=O)N1CCOC(C(=O)N(Cc2cn(Cc3ccccn3)c3ccccc23)C2CC2)C1] | Property: purified powder<br>APCI-MS m/z: 491[M + H]+ |
| 524 | 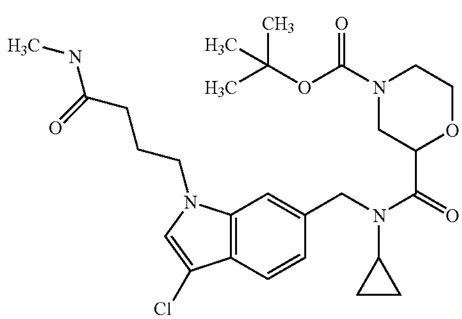 [SMILES: CNC(=O)CCCn1cc(Cl)c2ccc(CN(C(=O)C3CN(C(=O)OC(C)(C)C)CCO3)C3CC3)cc21] | Property: purified viscous oil<br>APCI-MS m/z: 533/535[M + H]+ |
| 525 | 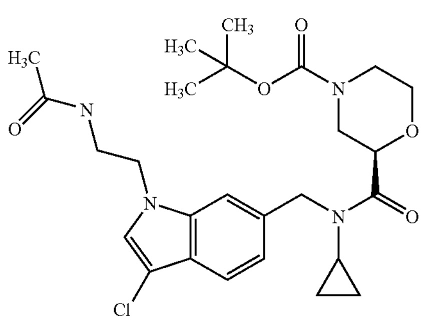 [SMILES: CC(=O)NCCn1cc(Cl)c2ccc(CN(C(=O)[C@H]3CN(C(=O)OC(C)(C)C)CCO3)C3CC3)cc21] | Property: purified viscous oil<br>APCI-MS m/z: 519/521[M + H]+ |

TABLE 20-continued
| No of Ref. Example | Structure | Properties |
|---|---|---|
| 526 | 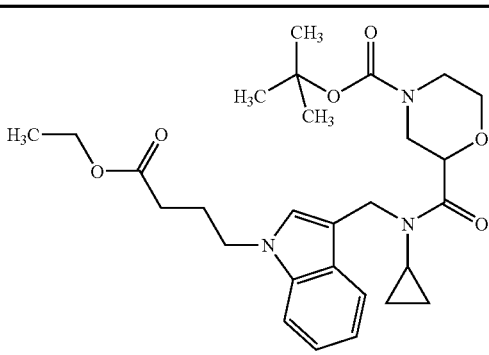 | Property: purified viscous oil<br>APCI-MS m/z: 514[M + H]$^+$ |
| 527 | 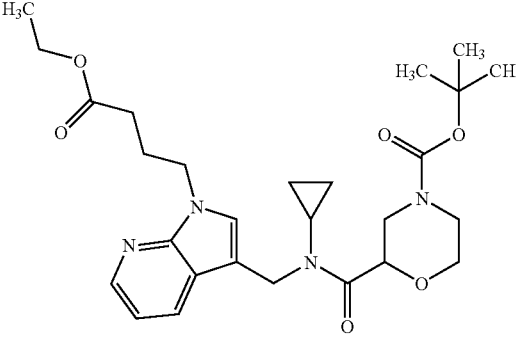 | Property: purified viscous oil<br>APCI-MS m/z: 515[M + H]$^+$ |
| 528 | 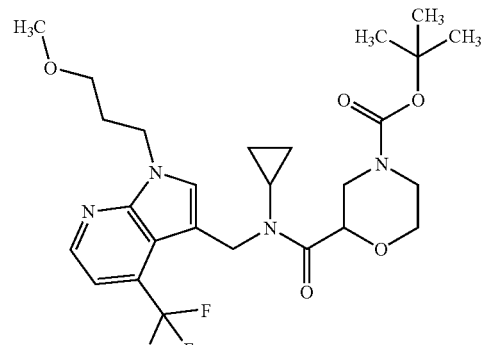 | Property: purified viscous oil<br>APCI-MS m/z: 541[M + H]$^+$ |
| 529 | 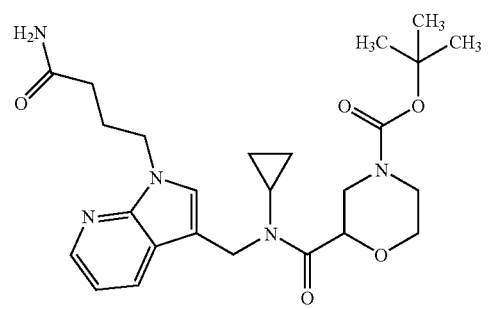 [SMILES: CC(C)(C)OC(=O)N1CCOC(C(=O)N(Cc2cn(CCCC(N)=O)c3ncccc23)C2CC2)C1] | Property: purified viscous oil<br>APCI-MS m/z: 486[M + H]$^+$ |

TABLE 20-continued

| No of Ref. Example | Structure | Properties |
|---|---|---|
| 530 | 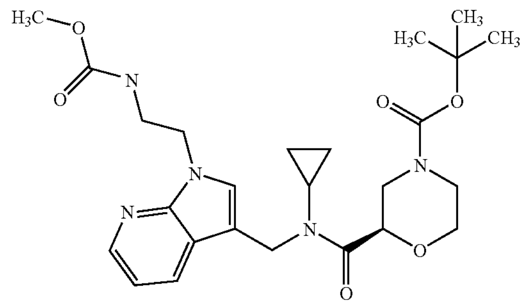 [SMILES: COC(=O)NCCn1cc(CN(C(=O)[C@H]2CN(C(=O)OC(C)(C)C)CCO2)C2CC2)c2cccnc21] | Property: purified viscous oil<br>APCI-MS m/z: 502[M + H]+ |
| 531 | 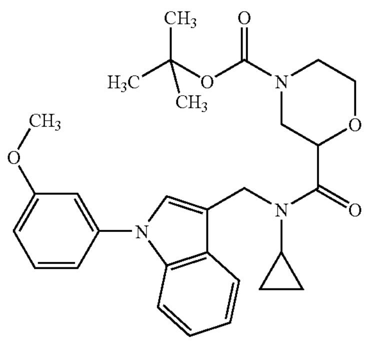 [SMILES: COc1cccc(-n2cc(CN(C(=O)C3CN(C(=O)OC(C)(C)C)CCO3)C3CC3)c3ccccc32)c1] | Property: purified powder<br>APCI-MS m/z: 506[M + H]+ |
| 532 | 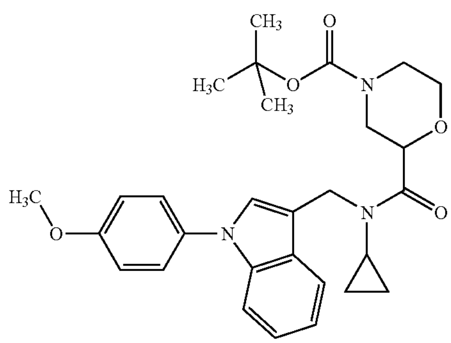 [SMILES: COc1ccc(-n2cc(CN(C(=O)C3CN(C(=O)OC(C)(C)C)CCO3)C3CC3)c3ccccc32)cc1] | Property: purified powder<br>APCI-MS m/z: 506[M + H]+ |
| 533 | 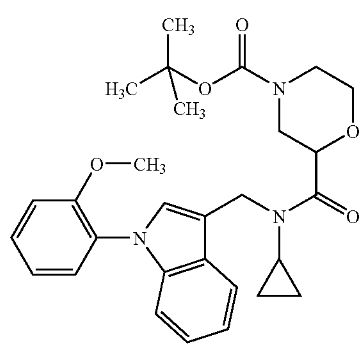 [SMILES: COc1ccccc1-n1cc(CN(C(=O)C2CN(C(=O)OC(C)(C)C)CCO2)C2CC2)c2ccccc21] | Property: purified powder<br>APCI-MS m/z: 506[M + H]+ |

TABLE 20-continued

| No of Ref. Example | Structure | Properties |
|---|---|---|
| 534 | 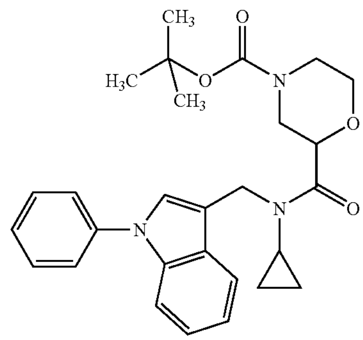 [SMILES: CC(C)(C)OC(=O)N1CCOC(C(=O)N(Cc2cn(-c3ccccc3)c3ccccc23)C2CC2)C1] | Property: purified powder<br>APCI-MS m/z: 476[M + H]+ |
| 535 | 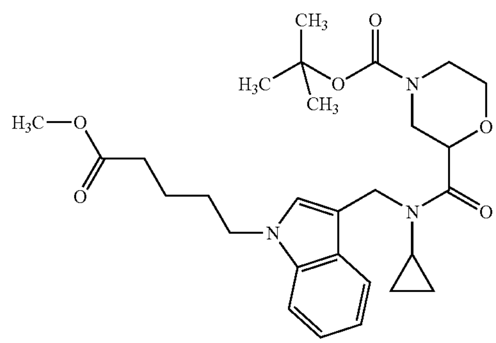 [SMILES: COC(=O)CCCCn1cc(CN(C(=O)C2CN(C(=O)OC(C)(C)C)CCO2)C2CC2)c2ccccc21] | Property: purified viscous oil<br>APCI-MS m/z: 531[M + NH4]+ |
| 536 | 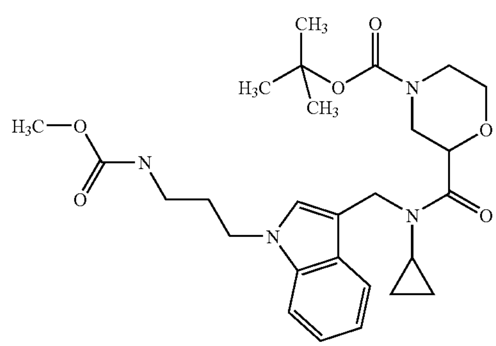 | Property: purified viscous oil<br>APCI-MS m/z: 532[M + NH4]+ |
| 537 | 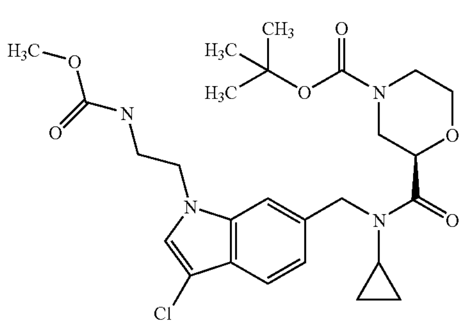 [SMILES: COC(=O)NCCn1cc(Cl)c2ccc(CN(C(=O)[C@H]3CN(C(=O)OC(C)(C)C)CCO3)C3CC3)cc21] | Property: purified viscous oil<br>APCI-MS m/z: 552/554[M + NH4]+ |

TABLE 20-continued
| No of Ref. Example | Structure | Properties |
|---|---|---|
| 538 | 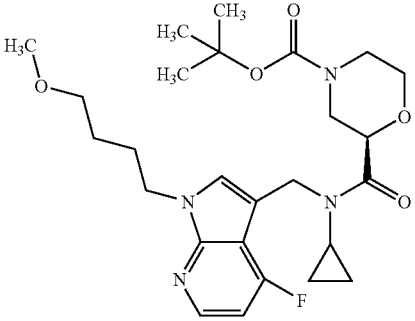 [SMILES: COCCCCn1cc(CN(C(=O)[C@H]2CN(C(=O)OC(C)(C)C)CCO2)C2CC2)c2c(F)ccnc21] | Property: purified viscous oil<br>APCI-MS m/z: 505[M + H]$^+$ |
| 539 | 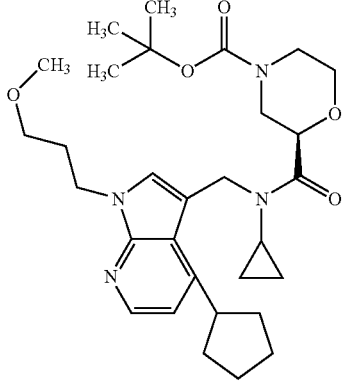 [SMILES: COCCCn1cc(CN(C(=O)[C@H]2CN(C(=O)OC(C)(C)C)CCO2)C2CC2)c2c(C3CCCC3)ccnc21] | Property: purified viscous oil<br>APCI-MS m/z: 541[M + H]$^+$ |
| 540 | 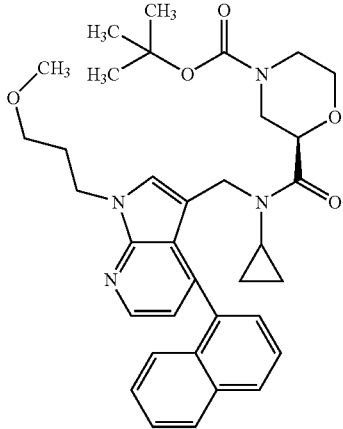 [SMILES: COCCCn1cc(CN(C(=O)[C@H]2CN(C(=O)OC(C)(C)C)CCO2)C2CC2)c2c(-c3cccc4ccccc34)ccnc21] | Property: purified viscous oil<br>APCI-MS m/z: 599[M + H]$^+$ |

TABLE 20-continued

| No of Ref. Example | Structure | Properties |
|---|---|---|
| 541 | 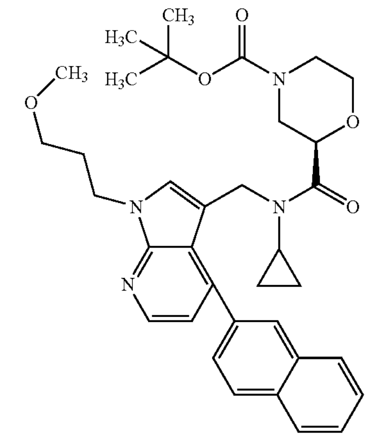 [SMILES: COCCCn1cc(CN(C(=O)[C@H]2CN(C(=O)OC(C)(C)C)CCO2)C2CC2)c2c(-c3ccc4ccccc4c3)ccnc21] | Property: purified viscous oil<br>APCI-MS m/z: 599[M + H]+ |
| 542 | 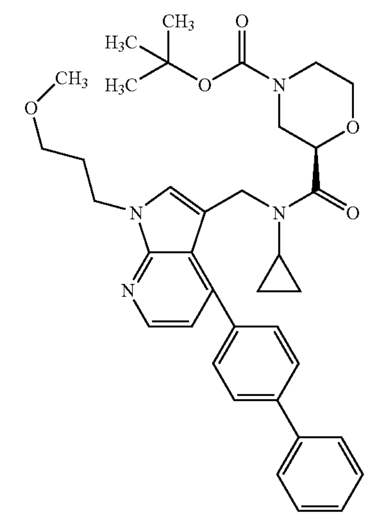 [SMILES: COCCCn1cc(CN(C(=O)[C@H]2CN(C(=O)OC(C)(C)C)CCO2)C2CC2)c2c(-c3ccc(-c4ccccc4)cc3)ccnc21] | Property: purified viscous oil<br>APCI-MS m/z: 625[M + H]+ |
| 543 | 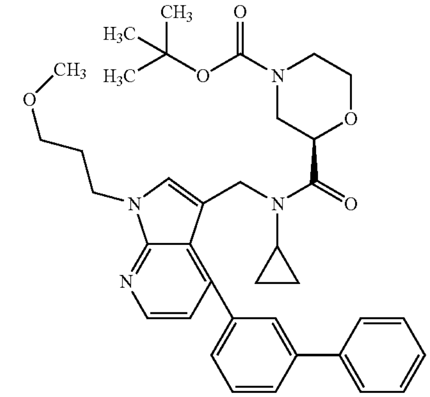 [SMILES: COCCCn1cc(CN(C(=O)[C@H]2CN(C(=O)OC(C)(C)C)CCO2)C2CC2)c2c(-c3cccc(-c4ccccc4)c3)ccnc21] | Property: purified viscous oil<br>APCI-MS m/z: 625[M + H]+ |

TABLE 20-continued

| No of Ref. Example | Structure | Properties |
|---|---|---|
| 544 | 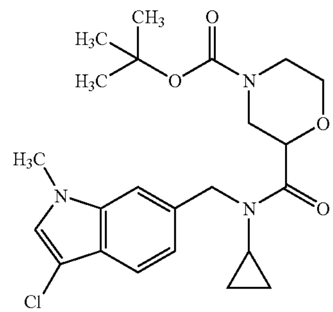 [SMILES: Cn1cc(Cl)c2ccc(CN(C(=O)C3CN(C(=O)OC(C)(C)C)CCO3)C3CC3)cc21] | Property: purified viscous oil<br>APCI-MS m/z: 448/440[M + H]+ |
| 545 | 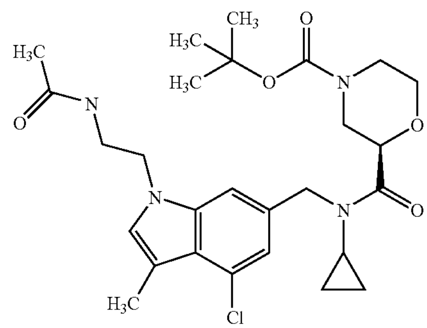 [SMILES: CC(=O)NCCn1cc(C)c2c(Cl)cc(CN(C(=O)[C@H]3CN(C(=O)OC(C)(C)C)CCO3)C3CC3)cc21] | Property: purified powder<br>APCI-MS m/z: 534/536[M + H]+ |
| 546 | 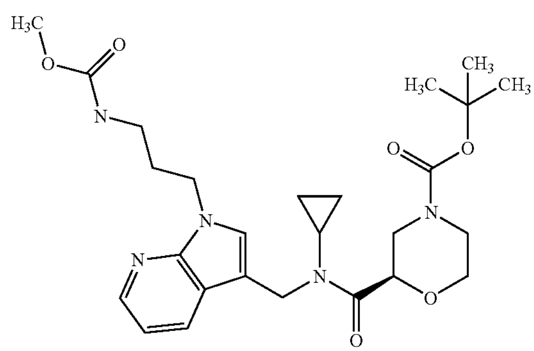 [SMILES: COC(=O)NCCCn1cc(CN(C(=O)[C@H]2CN(C(=O)OC(C)(C)C)CCO2)C2CC2)c2cccnc21] | Property: purified viscous oil<br>APCI-MS m/z: 516[M + H]+ |
| 547A | 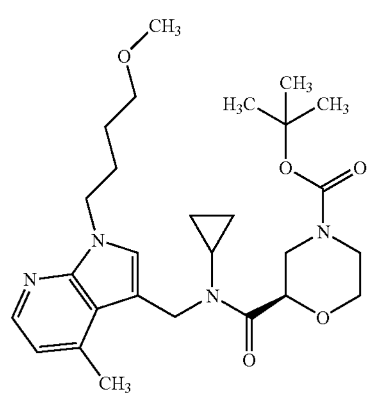 [SMILES: COCCCCn1cc(CN(C(=O)[C@H]2CN(C(=O)OC(C)(C)C)CCO2)C2CC2)c2c(C)ccnc21] | Property: purified viscous oil<br>APCI-MS m/z: 501[M + H]+ |

TABLE 20-continued
| No of Ref. Example | Structure | Properties |
|---|---|---|
| 547B | 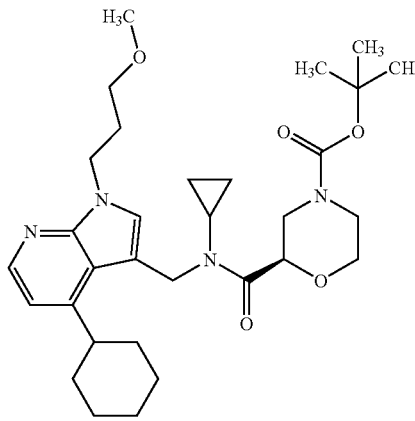 | Property: purified viscous oil<br>APCI-MS m/z: 555[M + H]$^+$ |
| 548 | 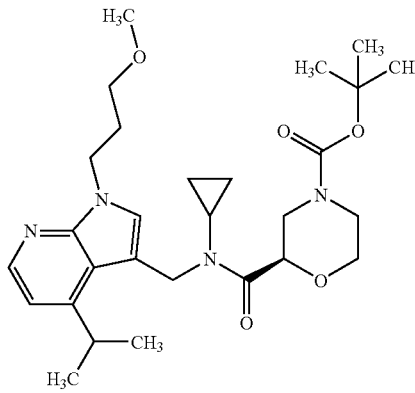 | Property: purified viscous oil<br>APCI-MS m/z: 515[M + H]$^+$ |
| 549 | 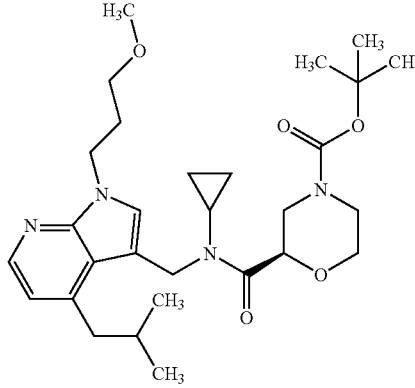 | Property: purified viscous oil<br>APCI-MS m/z: 529[M + H]$^+$ |
| 550 | 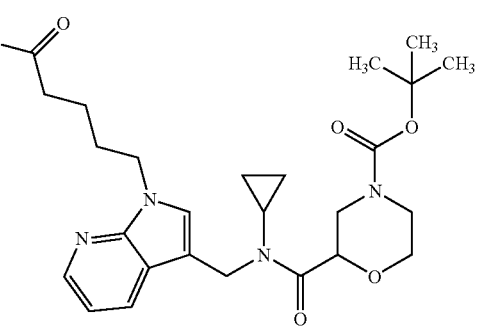 | Property: purified viscous oil<br>APCI-MS m/z: 515[M + H]$^+$ |

TABLE 20-continued

| No of Ref. Example | Structure | Properties |
|---|---|---|
| 551 | 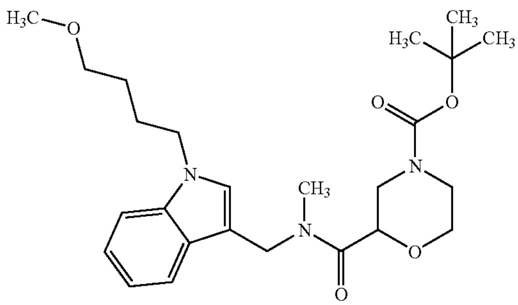 [SMILES: COCCCCn1cc(CN(C)C(=O)C2CN(C(=O)OC(C)(C)C)CCO2)c2ccccc21] | Property: purified viscous oil<br>APCI-MS m/z: 460[M + H]+ |
| 552 | 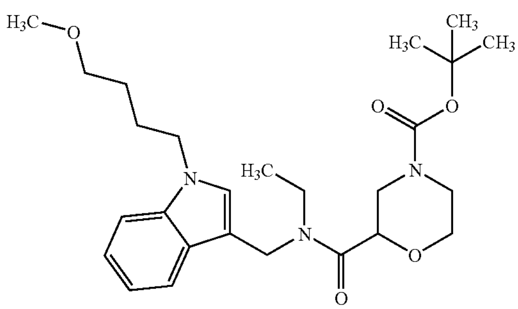 [SMILES: CCN(Cc1cn(CCCCOC)c2ccccc12)C(=O)C1CN(C(=O)OC(C)(C)C)CCO1] | Property: purified viscous oil<br>APCI-MS m/z: 474[M + H]+ |
| 553 | 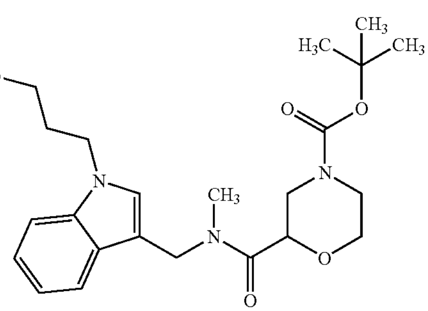 | Property: purified viscous oil<br>APCI-MS m/z: 446[M + H]+ |
| 554 | 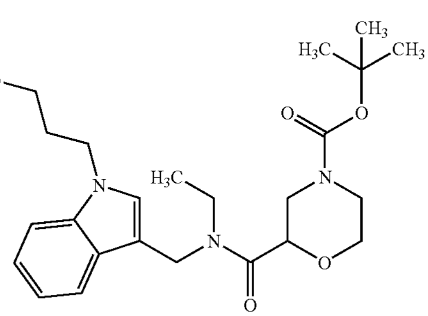 | Property: purified viscous oil<br>APCI-MS m/z: 460[M + H]+ |

TABLE 20-continued
| No of Ref. Example | Structure | Properties |
|---|---|---|
| 555 | 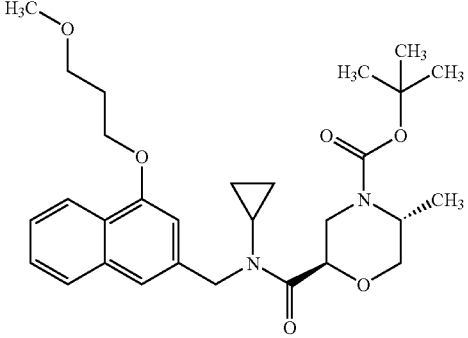 [SMILES: COCCCOc1cc(CN(C(=O)[C@H]2CN(C(=O)OC(C)(C)C)[C@H](C)CO2)C2CC2)cc2ccccc12] | Property: purified viscous oil<br>APCI-MS m/z: 513[M + H]+ |
| 556 | 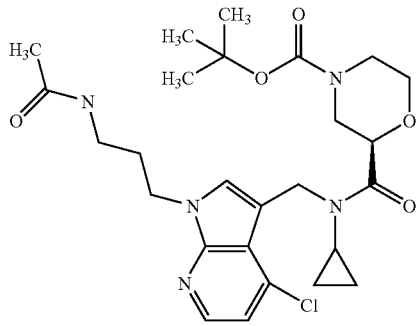 [SMILES: CC(=O)NCCCn1cc(CN(C(=O)[C@H]2CN(C(=O)OC(C)(C)C)CCO2)C2CC2)c2c(Cl)ccnc21] | Property: purified viscous oil<br>APCI-MS m/z: 534/536[M + H]+ |
| 557 | 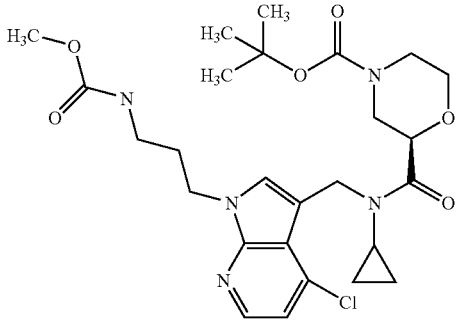 [SMILES: COC(=O)NCCCn1cc(CN(C(=O)[C@H]2CN(C(=O)OC(C)(C)C)CCO2)C2CC2)c2c(Cl)ccnc21] | Property: purified powder<br>APCI-MS m/z: 550/552[M + H]+ |
| 558 | 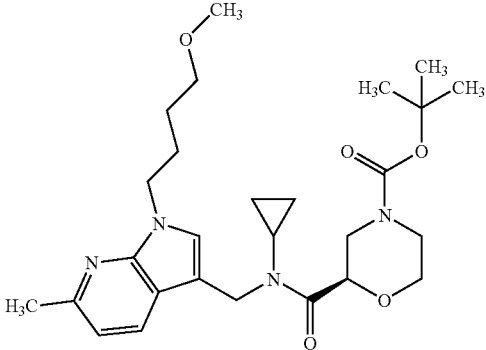 [SMILES: COCCCCn1cc(CN(C(=O)[C@H]2CN(C(=O)OC(C)(C)C)CCO2)C2CC2)c2ccc(C)nc21] | Property: purified viscous oil<br>APCI-MS m/z: 501[M + H]+ |

TABLE 20-continued

| No of Ref. Example | Structure | Properties |
|---|---|---|
| 559 | 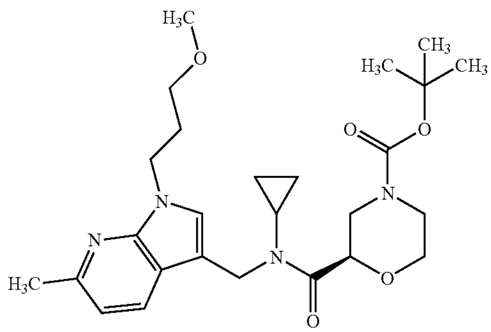 [SMILES: COCCCn1cc(CN(C(=O)[C@H]2CN(C(=O)OC(C)(C)C)CCO2)C2CC2)c2ccc(C)nc21] | Property: purified viscous oil<br>APCI-MS m/z: 487[M + H]+ |
| 560 | 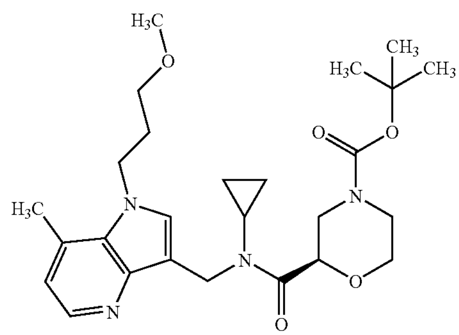 [SMILES: COCCCn1cc(CN(C(=O)[C@H]2CN(C(=O)OC(C)(C)C)CCO2)C2CC2)c2nccc(C)c21] | Property: purified viscous oil<br>APCI-MS m/z: 487[M + H]+ |
| 561 | 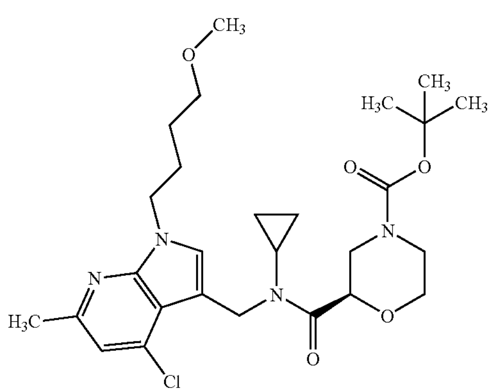 [SMILES: COCCCCn1cc(CN(C(=O)[C@H]2CN(C(=O)OC(C)(C)C)CCO2)C2CC2)c2c(Cl)cc(C)nc21] | Property: purified viscous oil<br>APCI-MS m/z: 535/537[M + H]+ |
| 562 | 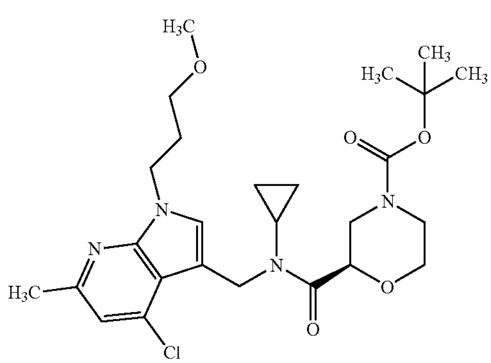 [SMILES: COCCCn1cc(CN(C(=O)[C@H]2CN(C(=O)OC(C)(C)C)CCO2)C2CC2)c2c(Cl)cc(C)nc21] | Property: purified viscous oil<br>APCI-MS m/z: 521/523[M + H]+ |

TABLE 20-continued

| No of Ref. Example | Structure | Properties |
|---|---|---|
| 563 | 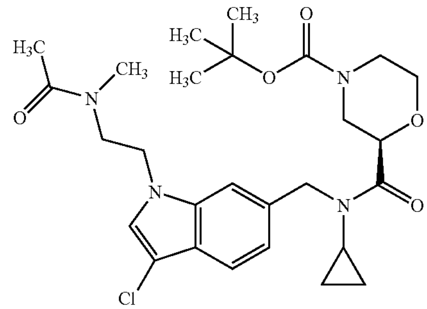 [SMILES: CC(=O)N(C)CCn1cc(Cl)c2ccc(CN(C(=O)[C@H]3CN(C(=O)OC(C)(C)C)CCO3)C3CC3)cc21] | Property: purified viscous oil<br>APCI-MS m/z: 533/536[M + H]⁺ |
| 564 | 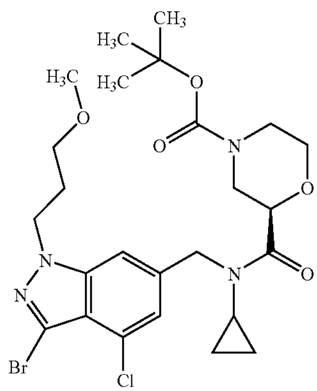 [SMILES: COCCCn1nc(Br)c2c(Cl)cc(CN(C(=O)[C@H]3CN(C(=O)OC(C)(C)C)CCO3)C3CC3)cc21] | Property: purified liquid<br>APCI-MS m/z: 585/587[M + H]⁺ |
| 565 | 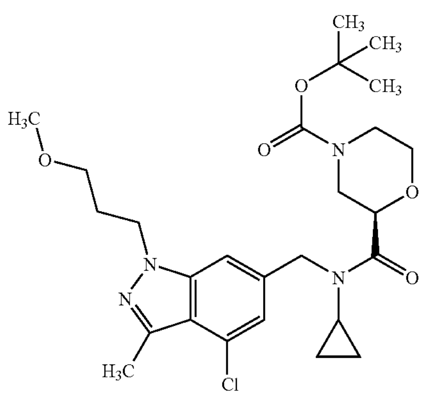 [SMILES: COCCCn1nc(C)c2c(Cl)cc(CN(C(=O)[C@H]3CN(C(=O)OC(C)(C)C)CCO3)C3CC3)cc21] | Property: purified liquid<br>APCI-MS m/z: 521/523[M + H]⁺ |
| 566 | 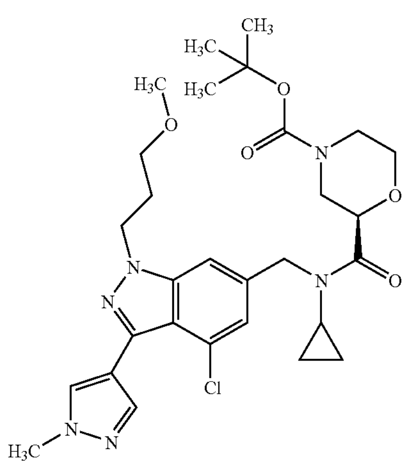 [SMILES: COCCCn1nc(-c2cnn(C)c2)c2c(Cl)cc(CN(C(=O)[C@H]3CN(C(=O)OC(C)(C)C)CCO3)C3CC3)cc21] | Property: purified liquid<br>APCI-MS m/z: 587/589[M + H]⁺ |

TABLE 20-continued
| No of Ref. Example | Structure | Properties |
|---|---|---|
| 567 | 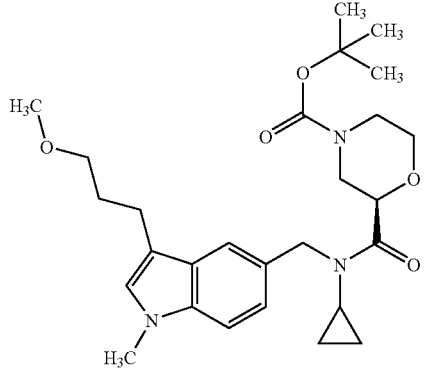 [SMILES: COCCCc1cn(C)c2ccc(CN(C(=O)[C@H]3CN(C(=O)OC(C)(C)C)CCO3)C3CC3)cc12] | Property: purified liquid<br>APCI-MS m/z: 486[M + H]$^+$ |
| 568 | 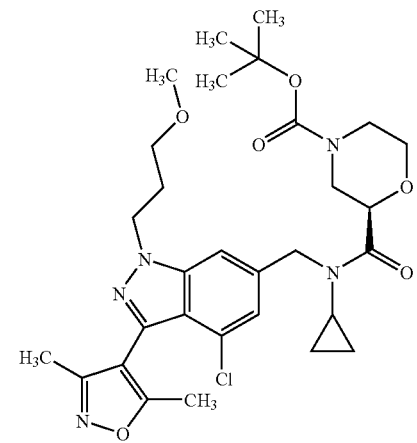 [SMILES: COCCCn1nc(-c2c(C)noc2C)c2c(Cl)cc(CN(C(=O)[C@H]3CN(C(=O)OC(C)(C)C)CCO3)C3CC3)cc21] | Property: purified liquid<br>APCI-MS m/z: 602/604[M + H]$^+$ |
| 569 | 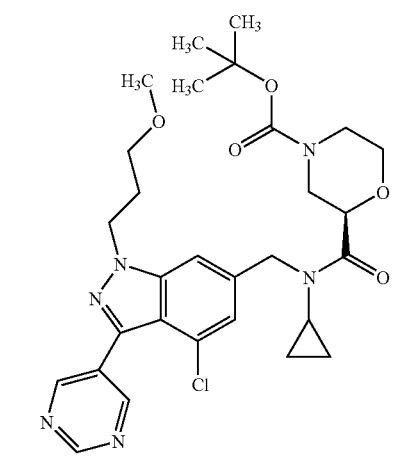 [SMILES: COCCCn1nc(-c2cncnc2)c2c(Cl)cc(CN(C(=O)[C@H]3CN(C(=O)OC(C)(C)C)CCO3)C3CC3)cc21] | Property: purified liquid<br>APCI-MS m/z: 585/587[M + H]$^+$ |

TABLE 20-continued
| No of Ref. Example | Structure | Properties |
|---|---|---|
| 570 | 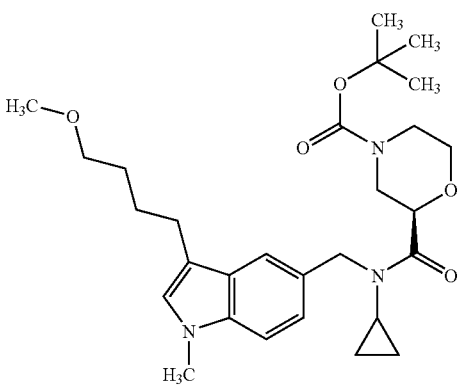 [SMILES: COCCCCc1cn(C)c2ccc(CN(C(=O)[C@H]3CN(C(=O)OC(C)(C)C)CCO3)C3CC3)cc12] | Property: purified liquid<br>APCI-MS m/z: 500[M + H]+ |
| 571 | 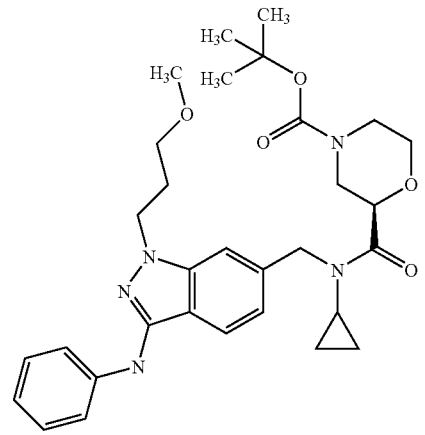 [SMILES: COCCCn1nc(Nc2ccccc2)c2ccc(CN(C(=O)[C@H]3CN(C(=O)OC(C)(C)C)CCO3)C3CC3)cc21] | Property: purified liquid<br>APCI-MS m/z: 564[M + H]+ |
| 572 | 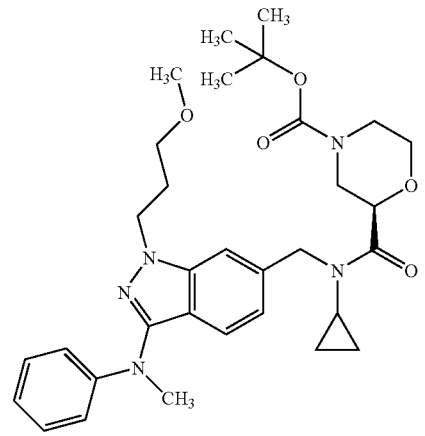 [SMILES: COCCCn1nc(N(C)c2ccccc2)c2ccc(CN(C(=O)[C@H]3CN(C(=O)OC(C)(C)C)CCO3)C3CC3)cc21] | Property: purified liquid<br>APCI-MS m/z: 578[M + H]+ |

| No of Ref. Example | Structure | Properties |
|---|---|---|
| 573 | 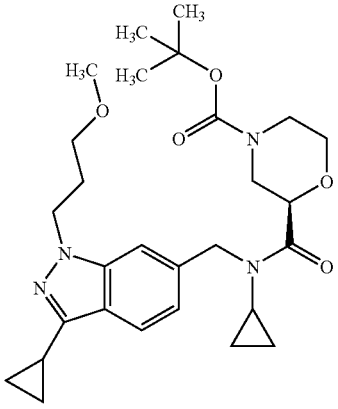 [SMILES: COCCCn1nc(C2CC2)c2ccc(CN(C(=O)[C@H]3CN(C(=O)OC(C)(C)C)CCO3)C3CC3)cc21] | Property: purified liquid<br>APCI-MS m/z: 513[M + H]$^+$ |
| 574 | 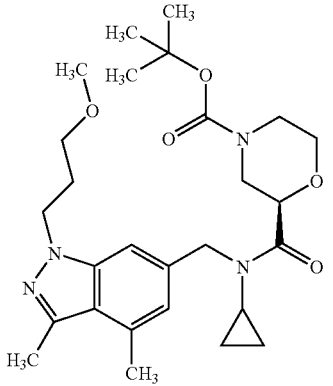 [SMILES: COCCCn1nc(C)c2c(C)cc(CN(C(=O)[C@H]3CN(C(=O)OC(C)(C)C)CCO3)C3CC3)cc21] | Property: purified liquid<br>APCI-MS m/z: 501[M + H]$^+$ |
| 575 | 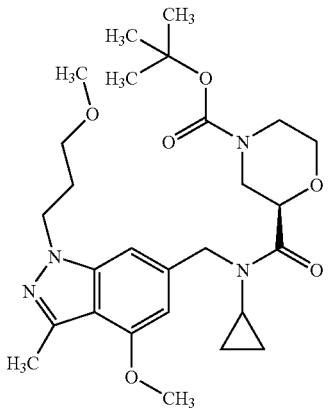 [SMILES: COCCCn1nc(C)c2c(OC)cc(CN(C(=O)[C@H]3CN(C(=O)OC(C)(C)C)CCO3)C3CC3)cc21] | Property: purified liquid<br>APCI-MS m/z: 517[M + H]$^+$ |

| No of Ref. Example | Structure | Properties |
|---|---|---|
| 576 | 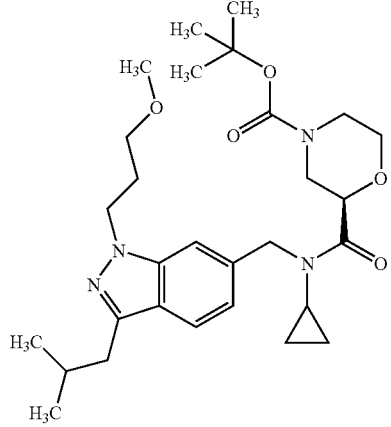 [SMILES: COCCCn1nc(CC(C)C)c2ccc(CN(C(=O)[C@H]3CN(C(=O)OC(C)(C)C)CCO3)C3CC3)cc21] | Property: purified liquid<br>APCI-MS m/z: 529[M + H]$^+$ |
| 577 | 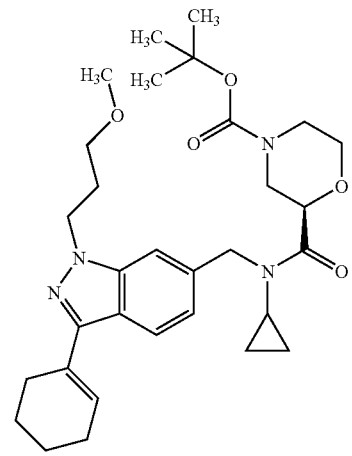 | Property: purified liquid<br>APCI-MS m/z: 533[M + H]$^+$ |
| 578 | 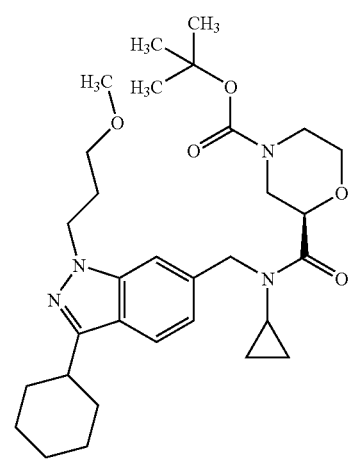 | Property: purified liquid<br>APCI-MS m/z: 555[M + H]$^+$ |

| No of Ref. Example | Structure | Properties |
|---|---|---|
| 579 | 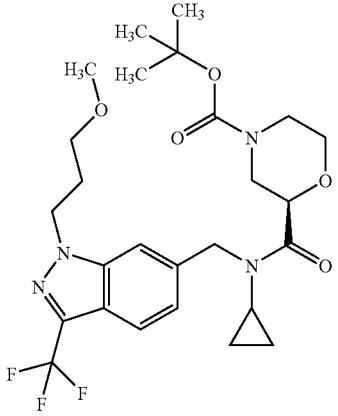 [SMILES: COCCCn1nc(C(F)(F)F)c2ccc(CN(C(=O)[C@H]3CN(C(=O)OC(C)(C)C)CCO3)C3CC3)cc21] | Property: purified liquid<br>APCI-MS m/z: 558[M + NH4]+ |
| 580 | 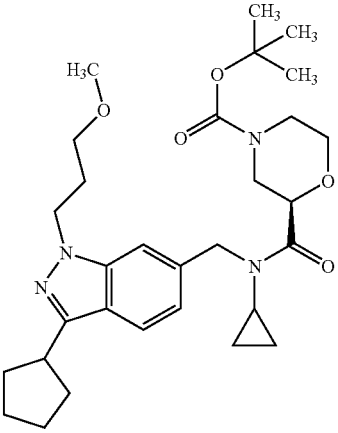 [SMILES: COCCCn1nc(C2CCCC2)c2ccc(CN(C(=O)[C@H]3CN(C(=O)OC(C)(C)C)CCO3)C3CC3)cc21] | Property: purified liquid<br>APCI-MS m/z: 541[M + H]+ |
| 581 | 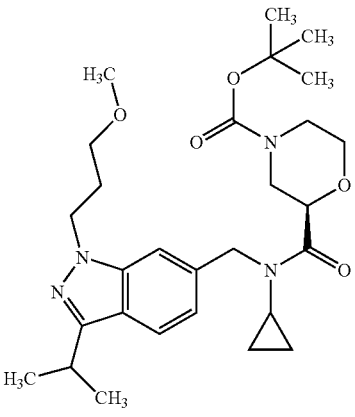 [SMILES: COCCCn1nc(C(C)C)c2ccc(CN(C(=O)[C@H]3CN(C(=O)OC(C)(C)C)CCO3)C3CC3)cc21] | Property: purified liquid<br>APCI-MS m/z: 515[M + H]+ |

TABLE 20-continued

| No of Ref. Example | Structure | Properties |
| --- | --- | --- |
| 582 | 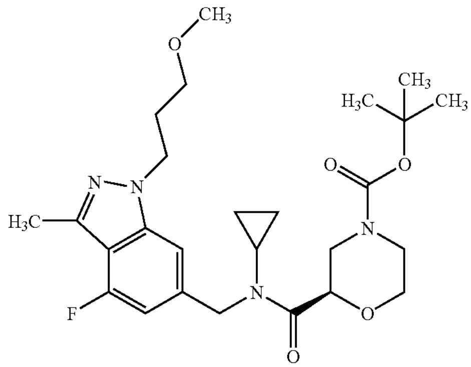 [SMILES: COCCCn1nc(C)c2c(F)cc(CN(C(=O)[C@H]3CN(C(=O)OC(C)(C)C)CCO3)C3CC3)cc21] | Property: purified liquid<br>APCI-MS m/z: 505[M + H]+ |
| 583 | 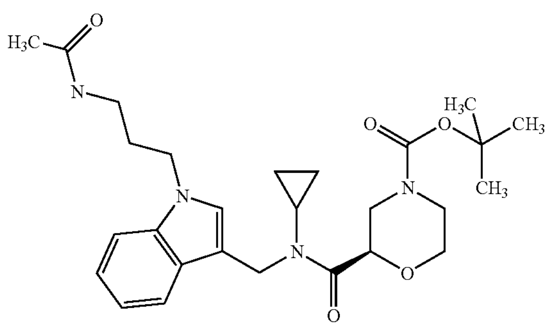 [SMILES: CC(=O)NCCCn1cc(CN(C(=O)[C@H]2CN(C(=O)OC(C)(C)C)CCO2)C2CC2)c2ccccc21] | Property: purified liquid<br>APCI-MS m/z: [M + H]+ |
| 584 | 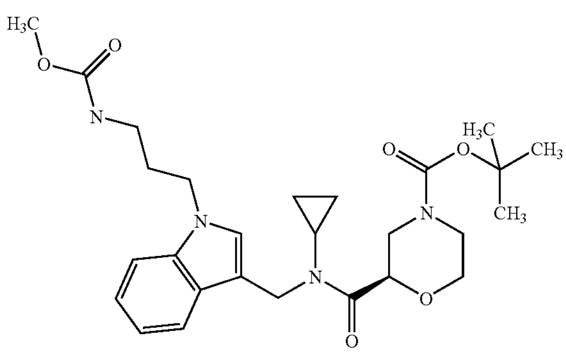 [SMILES: COC(=O)NCCCn1cc(CN(C(=O)[C@H]2CN(C(=O)OC(C)(C)C)CCO2)C2CC2)c2ccccc21] | Property: purified viscous oil<br>APCI-MS m/z: 515[M + H]+ |
| 585 | 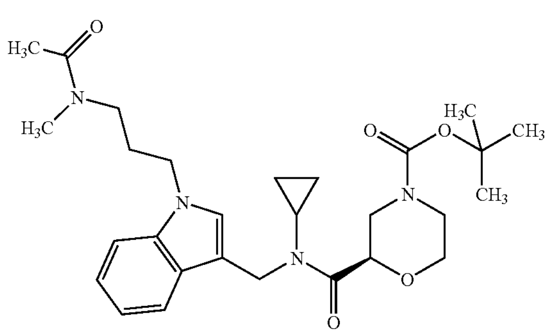 [SMILES: CC(=O)N(C)CCCn1cc(CN(C(=O)[C@H]2CN(C(=O)OC(C)(C)C)CCO2)C2CC2)c2ccccc21] | Property: purified viscous oil<br>APCI-MS m/z: 513[M + H]+ |

TABLE 20-continued

| No of Ref. Example | Structure | Properties |
|---|---|---|
| 586 | 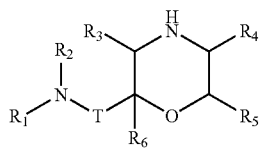 | Property: purified viscous oil<br>APCI-MS m/z: 546[M + NH4]+ |

Test Example

Inhibitory Activity Against Human Renin

A renin substrate of synthetic peptide (Nma-KHPFH LVIHK(Dnp)-$NH_2$) and test compound were mixed, and fluorescence intensity was assayed using a fluorophotometer before starting an enzymatic reaction (exciting wavelength: 340 nm, measuring wavelength: 460 nm). Recombinant human renin was added and the mixture was incubated at 37° C. for an hour, and the fluorescence intensity was measured after the reaction using using a fluorophotometer (exciting wavelength: 340 nm, measuring wavelength: 460 nm). Renin activity was evaluated on the ground of fluorescence intensity which was obtained by deduction of the intensity before the reaction from the intensity after the reaction, and 50% inhibitory concentration (IC50) was calculated from renin activities under the existence of various concentration of the tested compound.

[Result]

| tested compound | Inhibitory Activity against human Renin($IC_{50}$) |
|---|---|
| compound of example 4 | 30.2 nM |
| compound of example 39 | 13.0 nM |

INDUSTRIAL APPLICABILITY

The compound [I] of the present invention or a pharmaceutically acceptable salt thereof has renin inhibitory activity and may be useful for treatment and/or prophylaxis of hypertension, cardiac failure, diabetical nephropathy and the like. Furthermore, the compound [I] of the present invention also has characteristics as a safe medicine due to its low toxicity.

The invention claimed is:

1. Morpholine derivative of the general formula [I] or a pharmaceutically acceptable salt thereof;

[I]

wherein
  $R^1$ is D) a cycloalkyl group;
  $R^2$ is A) an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group, 13) an optionally substituted pyrrolopyridinyl group, 14) an optionally substituted benzoxazinyl group, 15) an optionally substituted xanthenyl group, 16) an optionally substituted indolinyl group and 17) an optionally substituted imidazopyridinyl group, B) an optionally substituted aryl group, C) an optionally substituted heterocyclo group, E) an optionally substituted arylcarbonyl group, F) a carbonyl group substituted with an optionally substituted heterocyclo group or G) a cycloalkylcarbonyl group;
  T is a methylene group or a carbonyl group; and
  $R^3$, $R^4$, $R^5$ and $R^6$ are same or different and a hydrogen atom, an optionally substituted carbamoyl group or an optionally substituted alkyl group.

2. The morpholine derivative or the pharmaceutically acceptable salt thereof according to claim 1, wherein
  $R^1$ is D) a cycloalkyl group;
  $R^2$ is A) an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group and 13) an optionally substituted pyrrolopyridinyl group, B) an optionally substituted aryl group, C) an optionally substituted heterocyclo group, E) an optionally substituted arylcarbonyl group, F) a carbonyl group substituted with an optionally substituted heterocyclo group or G) a cycloalkylcarbonyl group;

T is a methylene group or a carbonyl group;

$R^5$ is a hydrogen atom, an optionally substituted carbamoyl group or an optionally substituted alkyl group; and $R^3$, $R^4$ and $R^6$ are hydrogen atoms.

3. The morpholine derivative or the pharmaceutically acceptable salt thereof according to claim 2, wherein $R^5$ is a hydrogen atom.

4. The morpholine derivative or the pharmaceutically acceptable salt thereof according to claim 2, wherein T is a carbonyl group.

5. The morpholine derivative or the pharmaceutically acceptable salt thereof according to claim 2, wherein $R^2$ is an alkyl group substituted with a group selected from 1) an optionally substituted alkoxy group, 2) a hydroxy group, 3) a halogen atom, 4) an optionally substituted aryl group, 5) an optionally substituted tetrahydronaphthyl group, 6) an optionally substituted indolyl group, 7) an optionally substituted benzofuranyl group, 8) an optionally substituted benzothienyl group, 9) an optionally substituted quinolyl group, 10) an optionally substituted dihydrocromenyl group, 11) an optionally substituted dihydrobenzofuranyl group, 12) an optionally substituted indazolyl group and 13) an optionally substituted pyrrolopyridinyl group.

6. The morpholine derivative or the pharmaceutically acceptable salt thereof according to claim 1, wherein $R^2$ is an alkyl group substituted with a group selected from
   1) an optionally substituted aryl group,
   2) an optionally substituted tetrahydronaphthyl group
   3) an optionally substituted indolyl group,
   4) an optionally substituted benzofuranyl group,
   5) an optionally substituted benzothienyl group,
   6) an optionally substituted quinolyl group,
   7) an optionally substituted dihydrocromenyl group,
   8) an optionally substituted dihydrobenzofuranyl group
   9) an optionally substituted indazolyl group, and
   10) an optionally substituted pyrrolopyridinyl group,
   T is a carbonyl group, $R^5$ is a hydrogen atom, an optionally substituted carbamoyl group or an optionally substituted alkyl group and $R^3$, $R^4$ and $R^6$ are hydrogen atoms.

7. The morpholine derivative or the pharmaceutically acceptable salt thereof according to claim 6, wherein $R^2$ is selected from
   1) a lower alkyl group substituted with an optionally substituted phenyl group,
   2) a lower alkyl group substituted with an optionally substituted naphthyl group,
   3) a lower alkyl group substituted with an optionally substituted tetrahydronaphthyl group,
   4) a lower alkyl group substituted with an optionally substituted indolyl group,
   5) a lower alkyl group substituted with an optionally substituted benzofuranyl group,
   6) a lower alkyl group substituted with an optionally substituted benzothienyl group,
   7) a lower alkyl group substituted with an optionally substituted quinolyl group,
   8) a lower alkyl group substituted with an optionally substituted dihydrocromenyl group,
   9) a lower alkyl group substituted with an optionally substituted dihydrobenzofuranyl group,
   10) a lower alkyl group substituted with an optionally substituted indazolyl group, and
   11) a lower alkyl group substituted with an optionally substituted pyrrolopyridinyl group, or a pharmaceutically acceptable salt thereof.

8. The morpholine derivative or the pharmaceutically acceptable salt thereof according to claim 6, wherein $R^2$ is selected from
   1) an optionally substituted phenylmethyl group,
   2) an optionally substituted naphthylmethyl group,
   3) an optionally substituted tetrahydronaphthylmethyl group,
   4) an optionally substituted indolylmethyl group,
   5) an optionally substituted benzofuranylmethyl group,
   6) an optionally substituted benzothienylmethyl group,
   7) an optionally substituted quinolylmethyl group,
   8) an optionally substituted dihydrocromenylmethyl group,
   9) an optionally substituted dihydrobenzofuranylmethyl group,
   10) an optionally substituted indazolylmethyl group, and
   11) an optionally substituted pyrrolopyridinylmethyl group.

9. The morpholine derivative or the pharmaceutically acceptable salt thereof according to claim 6, wherein $R^2$ is selected from (1)-(11) described below;
   1) a phenylmethyl group optionally substituted with the same or different, two to four groups selected from a phenyl lower alkoxy group, a halogen atom, a lower alkyl group, a lower alkyl group substituted with a lower alkoxy group, a lower alkoxy group substituted with a lower alkoxy group, an aryl group substituted with a lower alkoxy group, a heterocyclic group, a cyano group, a lower alkoxy group, an alkyl group substituted with an alkoxycarbonylamino group, an alkoxy group substituted with an alkoxycarbonylamino group and a carbonyl group substituted with an alkoxyalkylamino group,
   2) a naphthylmethyl group optionally substituted with the same or different, one to six group(s) selected from a trihalogeno lower alkoxy group, a lower alkanoylamino lower alkoxy group, a halogen atom, a lower alkyl group substituted with a lower alkoxy group, a lower alkyl group, a lower alkoxy group substituted with a lower alkoxy group, an aryl group, an aryl group substituted with a lower alkoxy group, a heterocyclic group, a cyano group, a carbonyl group substituted with an alkoxyalkylamino group and a lower alkoxy group,
   3) a tetrahydronaphthylmethyl group optionally substituted with the same or different, one to six group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, a carbonyl group substituted with an alkoxyalkylamino group and a lower alkoxy group,
   4) a indolylmethyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkyl group substituted with an alkoxycarbonylamino group and a lower alkoxy group,
5) a benzofuranylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group,
6) a benzothienylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group,
7) a quinolylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxyalkylamino group, a carbonyl group substituted with alkoxycarbonylamino group and a lower alkoxy group,
8) a dihydrocromenylmethyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group,
9) a dihydrobenzofuranylmethyl group optionally substituted with the same or different, one to four group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkoxy group substituted with alkoxycarbonylamino group, a carbonyl group substituted with alkoxyalkylamino group and a lower alkoxy group,
10) a indazolylmethyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group and a lower alkoxy group, and
11) a pyrrolopyridinylmethyl group optionally substituted with the same or different, one to three group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkyl group substituted with alkoxycarbonylamino group and a lower alkoxy group.

10. The morpholine derivative or the pharmaceutically acceptable salt thereof according to claim 6, wherein R² is selected from (1)-(11) described below;
1) a phenylmethyl group optionally substituted with the same or different, two or three groups selected from a phenyl lower alkoxy group, a halogen atom, a lower alkyl group, a lower alkoxy group substituted with a lower alkoxy group, an alkoxy group substituted with alkoxycarbonylamino group, a carbonyl group substituted with alkoxyalkylamino group and a lower alkoxy group,
2) a naphthylmethyl group optionally substituted with the same or different, one to three group(s) selected from a trihalogeno lower alkoxy group, a lower alkanoylamino lower alkoxy group, a halogen atom, an aryl group, an aryl group substituted with a lower alkoxy group, a heterocyclic group, a lower alkyl group, an alkoxy group substituted with alkoxycarbonylamino group, a carbonyl group substituted with alkoxyalkylamino group and a lower alkoxy group substituted with a lower alkoxy group,
3) a tetrahydronaphthylmethyl group optionally substituted with one or two group(s) selected from a halogen atom, an alkoxy group substituted with alkoxycarbonylamino group, a carbonyl group substituted with alkoxyalkylamino group and a lower alkoxy group substituted with a lower alkoxy group,
4) a indolylmethyl group optionally substituted with the same or different, one to three group(s) selected from a halogen atom, a cyano group, a lower alkoxy group, a lower alkoxy group substituted with an aryl group, a lower alkyl group, an alkyl group substituted with alkoxycarbonylamino group and a lower alkyl group substituted with a lower alkoxy group,
5) a benzofuranylmethyl group optionally substituted with one or three group(s) selected from a halogen atom and a lower alkoxy group substituted with a lower alkoxy group, a lower alkoxy group, a lower alkyl group, a lower alkoxy group substituted with an aryl group, an alkyl group substituted with alkoxycarbonylamino group and a carbonyl group substituted with an alkoxyalkylamino group,
6) a benzothienylmethyl group optionally substituted with a lower alkoxy group substituted with a lower alkoxy group,
7) a quinolylmethyl group optionally substituted with a halogen atom, a lower alkoxy group, a lower alkyl group and a lower alkoxy group substituted with a lower alkoxy group,
8) a dihydrocromenylmethyl group optionally substituted with a lower alkoxy group substituted with a lower alkoxy group,
9) a dihydrobenzofuranylmethyl group optionally substituted with one or two group(s) selected from a halogen atom, a lower alkoxy group, a lower alkyl group and a lower alkoxy group substituted with a lower alkoxy group,
10) a indazolylmethyl group optionally substituted with one or three group(s) selected from a halogen atom, a lower alkyl group substituted with a lower alkoxy group, a lower alkoxy group, a lower alkyl group, a lower alkoxy group substituted with an aryl group and an alkyl group substituted with an alkoxycarbonylamino group, and 11) a pyrrolopyridinylmethyl group optionally substituted with one or three group(s) selected from a halogen atom, a lower alkyl group substituted with a lower alkoxy group, a lower alkoxy group, a lower alkyl group, a lower alkoxy group substituted with an aryl group and an alkyl group substituted with an alkoxycarbonylamino group.

11. The morpholine derivative or the pharmaceutically acceptable salt thereof according to claim 6, wherein $R^2$ is selected from (1)-(11) described below;
1) a phenylmethyl group optionally substituted with two or three groups selected from a phenyl lower alkoxy group, a fluorine atom, a trihalogeno lower alkyl group, a trihalogeno lower alkoxy group, dihalogeno lower alkoxy group, a bromine atom, a chlorine atom, a lower alkyl group, a lower alkoxy group substituted with a lower alkoxy group and a lower alkoxy group,
2) a naphthylmethyl group optionally substituted with the same or different, one to three group(s) selected from a trihalogeno lower alkoxy group, dihalogeno lower alkoxy group, a lower alkanoylamino lower alkoxy group, a fluorine atom, a bromine atom, a chlorine atom, a phenyl group, a phenyl group substituted with a lower alkoxy group, a pyridyl group, a furyl group, a thienyl group, a lower alkyl group and a lower alkoxy group substituted with a lower alkoxy group,
3) a tetrahydronaphthylmethyl group optionally substituted with one or two group(s) selected from a fluorine atom, a chlorine atom, a bromine atom and a lower alkoxy group substituted with a lower alkoxy group,
4) a indolylmethyl group optionally substituted with the same or different, one to three group(s) selected from a fluorine atom, a chlorine atom, a bromine atom, a cyano group, a lower alkoxy group, a lower alkoxy group substituted with a phenyl group, a lower alkyl group, a lower alkyl group substituted with a lower alkoxy group, an alkyl group substituted with an alkoxycarbonylamino group and an alkyl group substituted with an alkylcarbonylamino group,
5) a benzofuranylmethyl group optionally substituted with one to three group(s) selected from a fluorine atom, a chlorine atom, a bromine atom and a lower alkoxy group substituted with a lower alkoxy group,
6) a benzothienylmethyl group optionally substituted with a fluorine atom, a chlorine atom, a bromine atom and a lower alkoxy group substituted with a lower alkoxy group,
7) a quinolylmethyl group optionally substituted with the same or different, one to three group(s) selected from a fluorine atom, a chlorine atom, a lower alkyl group, a lower alkoxy group, an alkoxy group substituted with a lower alkoxycarbonylamino group and a lower alkoxy group substituted with a lower alkoxy group,
8) a dihydrocromenylmethyl group optionally substituted with a lower alkoxy group substituted with a lower alkoxy group,
9) a dihydrobenzofuranylmethyl group optionally substituted with one to three group(s) selected from a chlorine atom a bromine atom and a lower alkoxy group substituted with a lower alkoxy group,
10) a indazolylmethyl group optionally substituted with one to three group(s) selected from a fluorine atom, a chlorine atom, a bromine atom, a lower alkyl group, a trihalogeno lower alkyl group, an alkyl group substituted with an alkoxycarbonylamino group and a lower alkyl group substituted with a lower alkoxy group, and
11) a pyrrolopyridinylmethyl group optionally substituted with one to three group(s) selected from a fluorine atom, a chlorine atom, a bromine atom, a lower alkyl group, a trihalogeno lower alkyl group, an alkyl group substituted with an alkoxycarbonylamino group and a lower alkyl group substituted with a lower alkoxy group.

12. The morpholine derivative or the pharmaceutically acceptable salt thereof according to claim 6, wherein the indolyl group in $R^2$ is any of the next formulae:

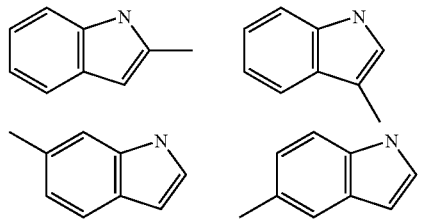

the benzofuranyl group in $R^2$ is any of the next formulae:

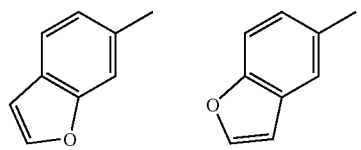

the benzothienyl group in $R^2$ is any of the next formulae:

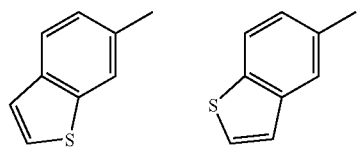

the quinolyl group in $R^2$ is the next formula:

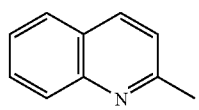

the naphthyl group in $R^2$ is any of the next formulae:

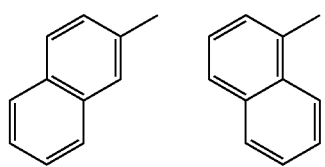

the tetrahydronaphthyl group in $R^2$ is any of the next formulae:

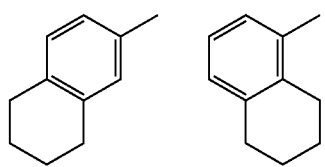

the dihydrocromenyl group in R² is any of the next formulae:

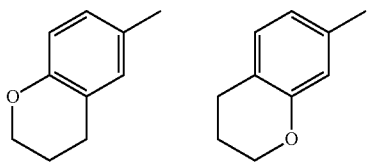

the dihydrobenzofuranyl group in R² is any of the next formulae:

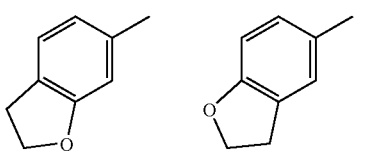

the indazolyl group in R² is any of the next formulae:

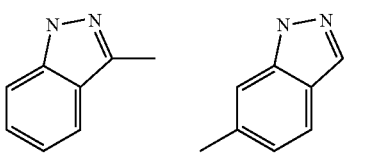

and the pyrrolopyridinyl group in R² is any of the next formulae:

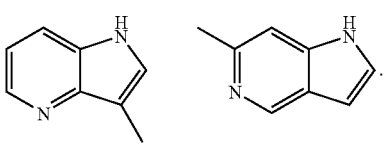

13. The morpholine derivative or the pharmaceutically acceptable salt thereof according to claim 6, wherein the indolyl group in R² is any of the next formulae:

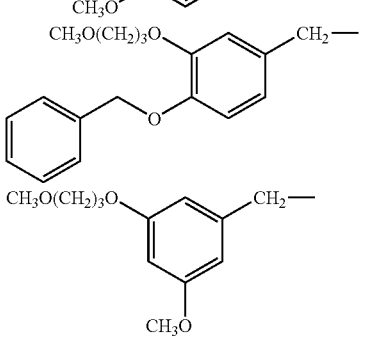

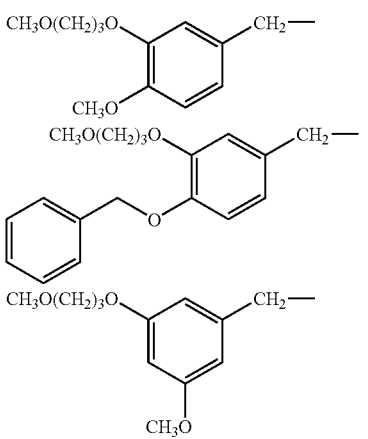

-continued

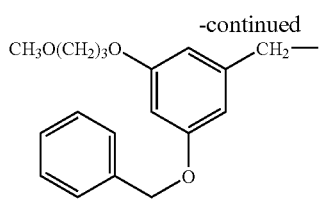

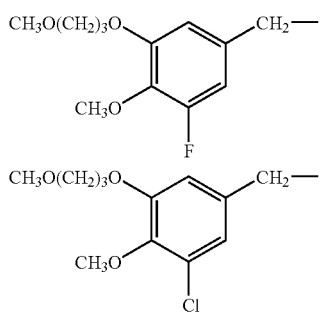

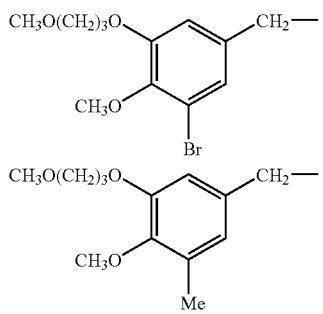

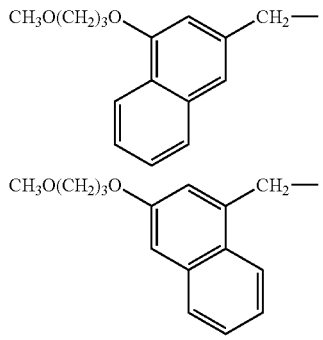

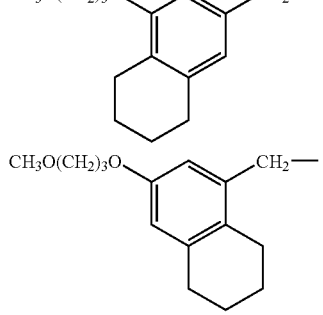

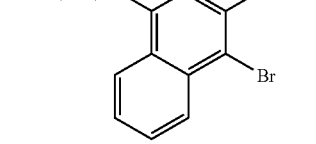

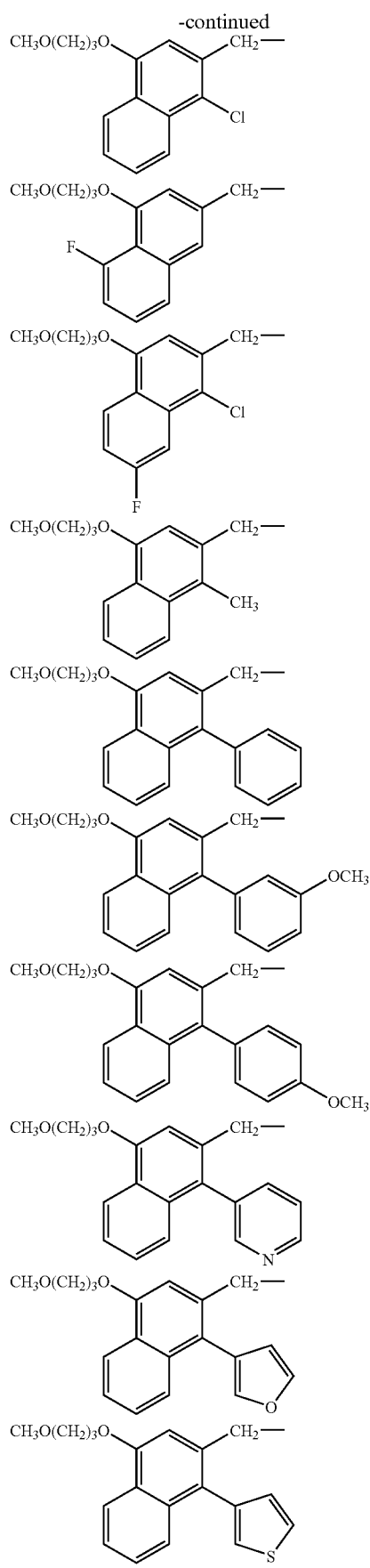
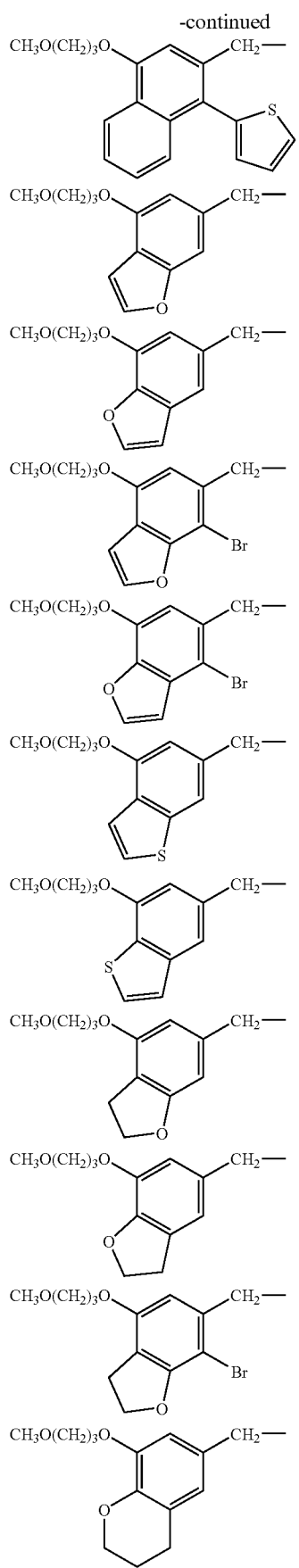

511
-continued
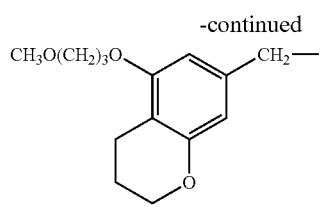
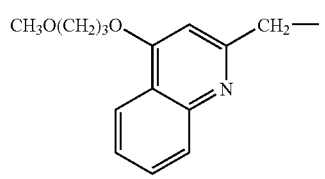
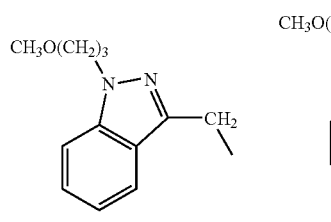
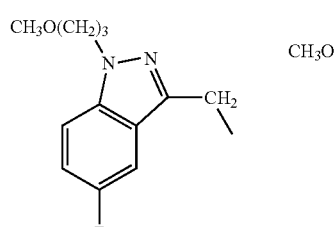
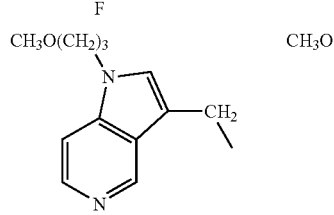
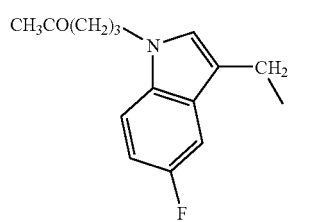
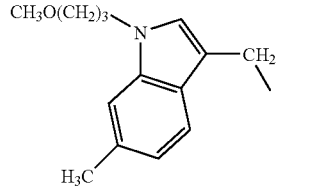
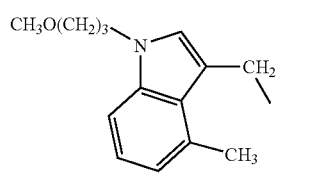
512
-continued
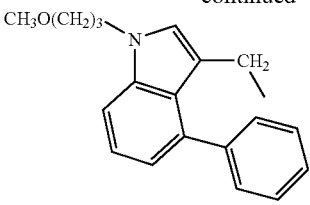
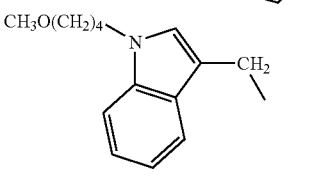
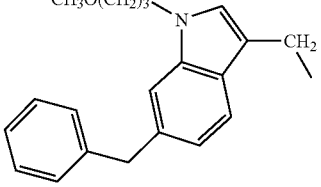
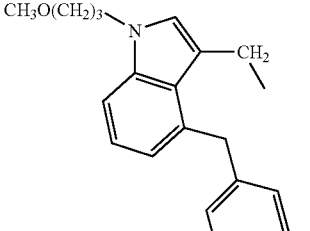
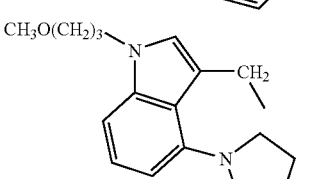
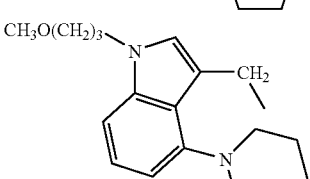
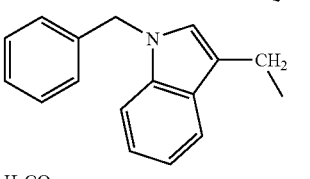
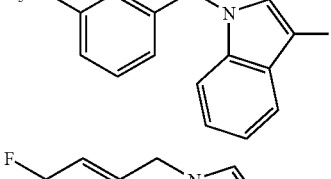
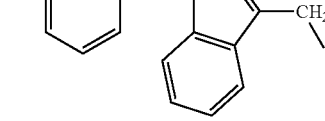

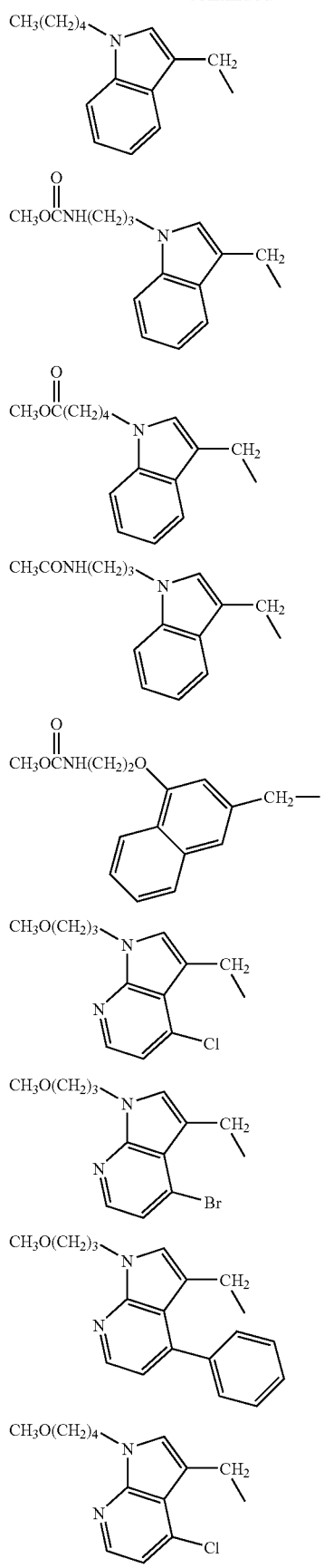
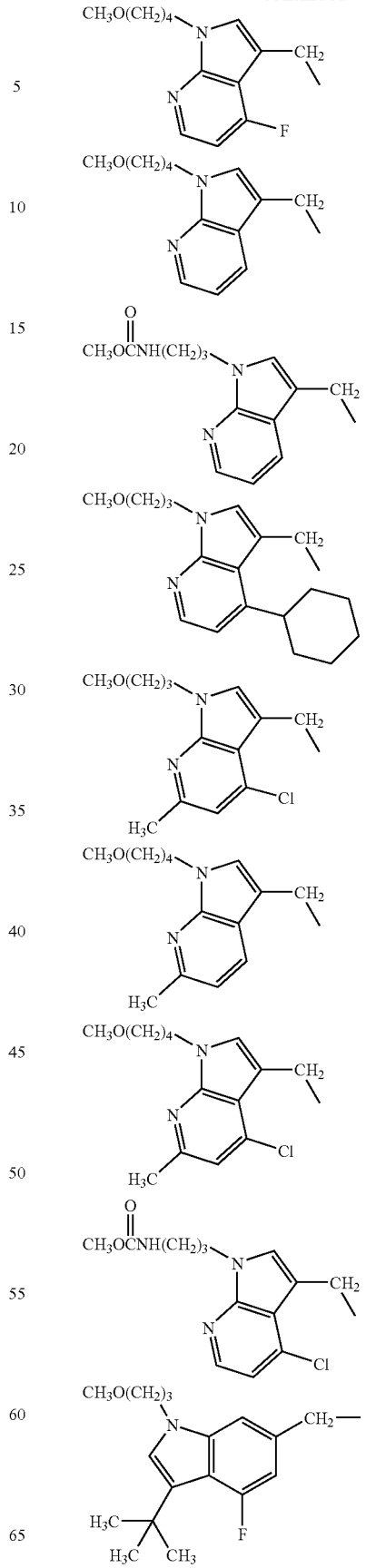

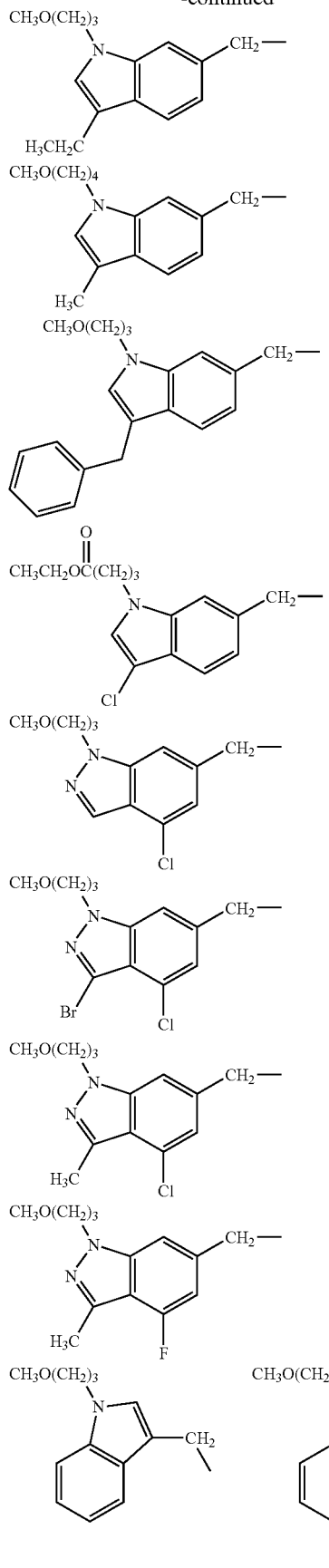
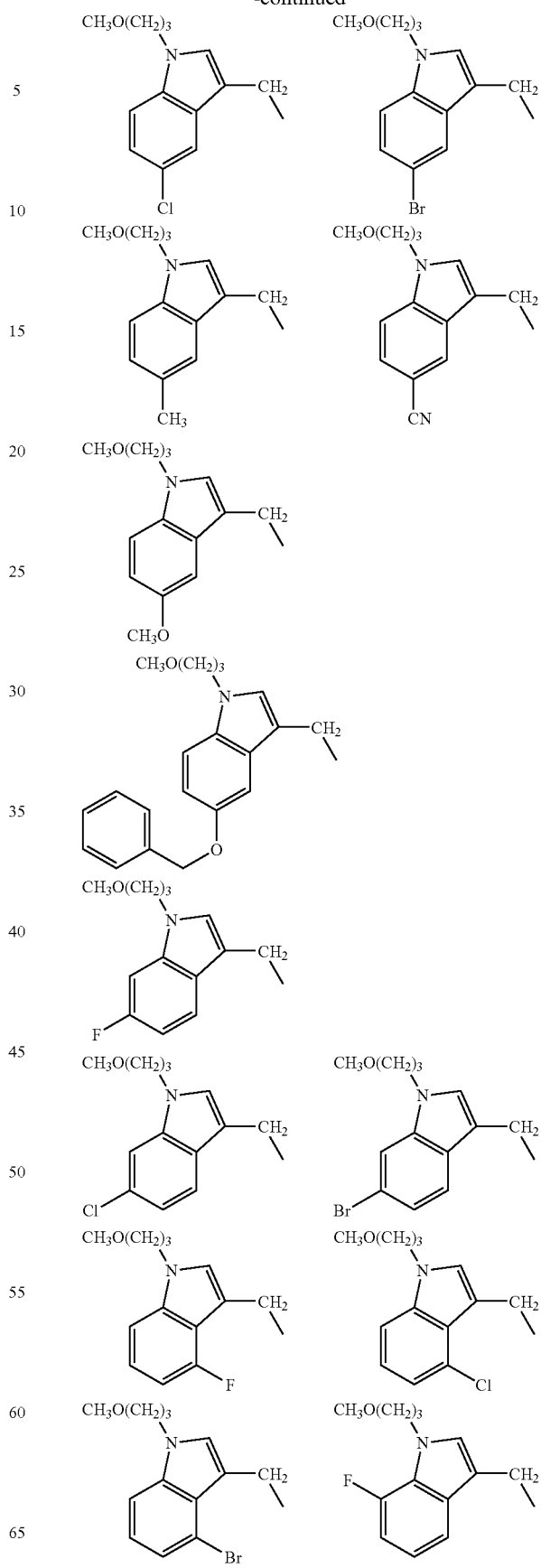

-continued

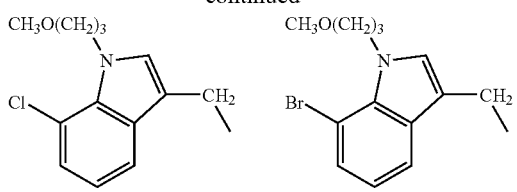
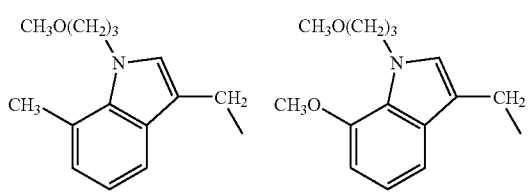
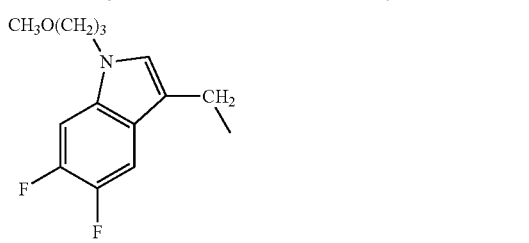
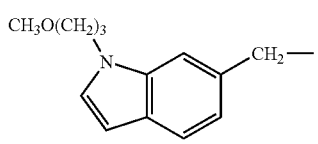
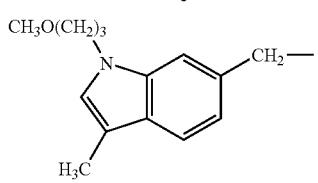
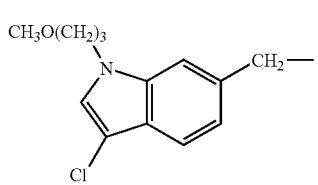
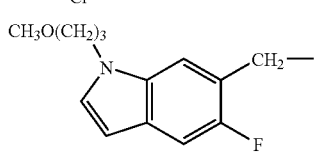
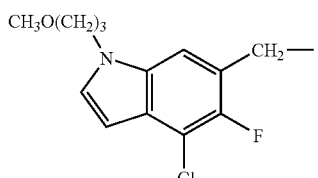
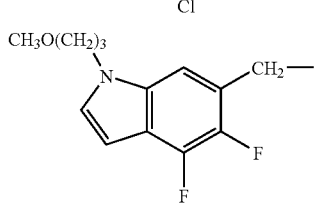

-continued

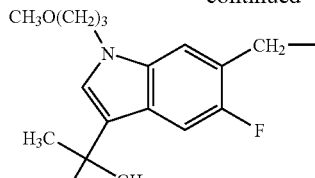
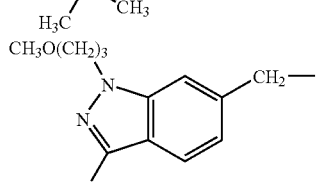

or a pharmaceutically acceptable salt thereof.

14. The morpholine derivative or the pharmaceutically acceptable salt thereof according to claim 6, wherein $R^1$ is a C3-8 cycloalkyl group.

15. The morpholine derivative or the pharmaceutically acceptable salt thereof according to claim 6, wherein $R^1$ is a cyclopropyl group.

16. The morpholine derivative or the pharmaceutically acceptable salt thereof according to claim 6, wherein $R^3$ to $R^6$ are any of
   1) a hydrogen atom,
   2) a carbamoyl group optionally substituted with one or two lower alkyl groups, and
   3) a lower alkyl group optionally substituted with a group selected from an amino group optionally substituted with one or two lower alkyl groups, a lower alkanoyl group, a hydroxyl group and a lower alkoxy group.

17. The morpholine derivative or the pharmaceutically acceptable salt thereof according to claim 6, wherein $R^3$ to $R^6$ are any of
   1) a hydrogen atom,
   2) a carbamoyl group optionally substituted with one or two methyl groups, and
   3) a lower alkyl group optionally substituted with a group selected from an amino group optionally substituted with one or two methyl groups, an acetylamino group, a hydroxyl group and a methoxy group.

18. The morpholine derivative or the pharmaceutically acceptable salt thereof according to claim 6, wherein $R^3$ to $R^6$ are any of
   1) a hydrogen atom,
   2) a carbamoyl group optionally substituted with one or two methyl groups, and
   3) a methyl group optionally substituted with a group selected from an amino group optionally substituted with one or two methyl group(s), an acetylamino group, a hydroxyl group and a methoxy group.

19. The morpholine derivative or the pharmaceutically acceptable salt thereof according to claim 6, wherein $R^3$ to $R^6$ are hydrogen atoms.

20. The morpholine derivative or the pharmaceutically acceptable salt thereof according to claim 6, wherein $R^5$ is any of:
   1) a hydrogen atom,
   2) a carbamoyl group optionally substituted with one or two lower alkyl groups, and
   3) a lower alkyl group optionally substituted with a group selected from an amino group optionally substituted with one or two lower alkyl groups, a lower alkanoylamino group, a hydroxyl group and a lower alkoxy group.

21. The morpholine derivative or the pharmaceutically acceptable salt thereof according to claim 6, wherein $R^5$ is any of:
1) a hydrogen atom,
2) a carbamoyl group optionally substituted with one or two methyl groups, and
3) a lower alkyl group optionally substituted with a group selected from an amino group optionally substituted with one or two methyl groups, an acetylamino group, a hydroxyl group and a methoxy group.

22. The morpholine derivative or the pharmaceutically acceptable salt thereof according to claim 6, wherein $R^5$ is any of:
1) a hydrogen atom,
2) a carbamoyl group optionally substituted with one or two methyl groups, and
3) a methyl group optionally substituted with a group selected from an amino group optionally substituted with one or two methyl groups, an acetylamino group, a hydroxyl group and a methoxy group.

23. The morpholine derivative or the pharmaceutically acceptable salt thereof according to claim 6, wherein $R^5$ is a hydrogen atom.

24. The morpholine derivative or the pharmaceutically acceptable salt thereof according to claim 1, wherein $R^2$ is
(1) optionally substituted phenyl lower alkyl group,
(2) optionally substituted indazolyl lower alkyl group, or
(3) optionally substituted pyrrolopyridinyl lower alkyl group;
T is a carbonyl group and
R3-R6 are hydrogen atoms.

25. The morpholine derivative or the pharmaceutically acceptable salt thereof according to claim 1, wherein $R^2$ is
1) a phenyl lower alkyl group optionally substituted with the same or different, two to four groups selected from a phenyl lower alkoxy group, a halogen atom, a lower alkyl group, a lower alkyl group substituted with a lower alkoxy group, a lower alkoxy group substituted with a lower alkoxy group, an aryl group substituted with a lower alkoxy group, a heterocyclic group, a cyano group, a lower alkoxy group, an alkyl group substituted with an alkoxycarbonylamino group, an alkoxy group substituted with an alkoxycarbonylamino group and a carbonyl group substituted with an alkoxyalkylamino group,
2) a indazolyl lower alkyl group optionally substituted with the same or different, one to five group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group and a lower alkoxy group, or
3) a pyrrolopyridinylmethyl group optionally substituted with the same or different, one to three group(s) selected from a halogen atom, a lower alkyl group substituted with a lower alkoxy group, a lower alkyl group, a lower alkoxy group substituted with a lower alkoxy group, an aryl group substituted with a lower alkoxy group, a heterocyclic group, a cyano group, an alkyl group substituted with alkoxycarbonylamino group and a lower alkoxy group;
T is a carbonyl group; and
$R^3$-$R^6$ are hydrogen atoms.

26. A pharmaceutical composition comprising the compound or the pharmaceutically acceptable salt thereof according to claim 1 or claim 6 as an active ingredient.

* * * * *